United States Patent [19]

Burk et al.

[11] Patent Number: 5,506,262
[45] Date of Patent: Apr. 9, 1996

[54] CHOLESTEROL LOWERING COMPOUNDS

[75] Inventors: Robert M. Burk, Laguna Beach, Calif.; William H. Parsons, Edison, N.J.; John J. Acton, III, Cranford, N.J.; Gregory D. Berger, Belle Mead, N.J.; Tesfaye Biftu, Westfield, N.J.; Robert L. Bugianesi, Colonia, N.J.; Yuan-Ching P. Chiang, Scotch Plains, N.J.; Claude Dufresne, East Brunswick, N.J.; Narindar N. Girotra, Old Bridge, N.J.; Robert W. Marquis, Jr., Iselin, N.J.; Chan-Hwa Kuo, South Plainfield, N.J.; Sandra P. Plevyak, Edison, N.J.; Mitree M. Ponpipom, Branchburg, N.J.; Lori L. Whiting, West Carrollton, Ohio; James D. Bergstrom, Neshanic, N.J.; Conrad Santini, Warren, N.J.

[73] Assignee: Merck & Co., Inc., Rahway, N.J.

[*] Notice: The term of this patent shall not extend beyond the expiration date of Pat. No. 5,256,689.

[21] Appl. No.: 146,100
[22] PCT Filed: May 8, 1992
[86] PCT No.: PCT/US92/03941
  § 371 Date: Nov. 10, 1993
  § 102(e) Date: Nov. 10, 1993
[87] PCT Pub. No.: WO92/20336
  PCT Pub. Date: Nov. 26, 1992

Related U.S. Application Data

[63] Continuation-in-part of Ser. No. 805,602, Dec. 9, 1991, abandoned, which is a continuation-in-part of Ser. No. 698,766, May 10, 1991, abandoned.

[51] Int. Cl.$^6$ .................. A61K 31/335; A61K 31/365; C07D 405/06; C07D 319/04
[52] U.S. Cl. .......... 514/452; 514/422; 514/414; 514/406; 514/397; 514/382; 514/365; 514/338; 514/333; 514/321; 549/363; 549/60; 549/58; 549/28; 549/13; 549/310; 548/518; 548/517; 548/468; 548/467; 548/455; 548/454; 548/253; 548/197; 544/377; 544/357; 544/336; 544/335; 544/296; 544/295; 544/238; 544/151; 544/61; 544/58.4
[58] Field of Search .............. 549/363, 60, 58, 549/28, 13, 310; 548/468, 467, 517, 518, 197, 454, 455, 253; 514/452, 422, 414, 406, 397, 382, 365, 338, 333, 321; 544/58.4, 61, 151, 238, 295, 296, 335, 336, 357, 377

[56] References Cited

U.S. PATENT DOCUMENTS 5,053,425 10/1991 Bartizal et al. .
5,055,487 10/1991 Bartizal et al. .
5,096,923 3/1992 Bergstrom et al. .
5,102,907 4/1992 Bergstrom et al. .
5,132,320 7/1992 Bergstrom et al. .
5,254,727 10/1993 DuFresne et al. .
5,256,689 10/1993 Chiang et al. .
5,258,401 11/1993 Berger et al. .
5,260,332 11/1993 DuFresne .
5,270,332 12/1993 Chen et al. .
5,283,256 2/1994 DuFresne et al. .
5,294,627 3/1994 Arison et al. .
5,302,604 4/1994 Byrne et al. .

FOREIGN PATENT DOCUMENTS 0259087 3/1988 European Pat. Off. .
0409181 1/1991 European Pat. Off. .
0448393 9/1991 European Pat. Off. .
0450812 10/1991 European Pat. Off. .
0475706 3/1992 European Pat. Off. .
0494622 7/1992 European Pat. Off. .
0503520 9/1992 European Pat. Off. .
524677 1/1993 European Pat. Off. .
568946 11/1993 European Pat. Off. .
WO92/12157 7/1992 WIPO .
WO92/12158 7/1992 WIPO .
WO92/12159 7/1992 WIPO .
WO92/12160 7/1992 WIPO .
WO92/12156 7/1992 WIPO .
WO93/07151 4/1993 WIPO .
WO93/18040 9/1993 WIPO .
WO93/18039 9/1993 WIPO .
WO93/17557 9/1993 WIPO .

OTHER PUBLICATIONS

Baxter et al., "Squalestatin 1, a Potent Inhibitor of Squalene Synthase, which Lowers Serum Cholesterol in Vivo", J. Biol. Chem. vol. 267, pp. 11705–11708 (1992).
Sidebottom et al., "The Squalestatins, Novel Inhibitors of Squalene Synthase Produced by a Species of Phoma" J. of Antibiotics, vol. 45, pp. 648–658 (1992).
Dawson et al., "The Squalestatins, Novel Inhibitors of Squalene Synthase Produced by a Species of Phoma", J. Antibiotics, vol. 45, pp. 639–647 (1992).

*Primary Examiner*—Nicky Chan
*Attorney, Agent, or Firm*—Catherine D. Fitch; Carol S. Quagliato; Melvin Winokur

[57] ABSTRACT

Disclosed herein are compounds of structural formula (I)

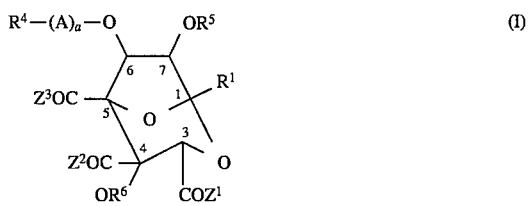

which are useful as cholesterol lowering agents. These compounds are also useful as inhibitors of squalene synthetase, inhibitors of fungal growth, inhibitors of farnesyl-protein transferase and farnesylation of the oncogene protein Ras. These compounds are also useful in the treatment of cancer.

20 Claims, No Drawings

CHOLESTEROL LOWERING COMPOUNDS

RELATED APPLICATION

According to 35 U.S.C. 371, this is the U.S. national phase application from PCT/US92/03941, filed May 8, 1992, which itself was a continuation-in-part of U.S. Ser. No. 07/805,602, filed Dec. 9, 1991 (now abandoned), which itself was a continuation-in-part of U.S. Ser. No. 07/698,766, filed May 10, 1991 (now abandoned).

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time and they are not very palatable.

MEVACOR® (lovastatin), now commercially available, is one of a group of very active antihypercholesterolemic agents that function by limiting cholesterol biosynthesis by inhibiting the enzyme, HMG-CoA reductase.

Squalene synthetase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthetase have employed pyrophosphate or pyrophosphate analogs containing compounds such as those described in P. Ortiz de Montellano et al, J. Med Chem. 20, 243 (1977) and E. J. Corey and R. Volante, J. Am. Chem. Soc., 98, 1291 (1976). S. Billet (U.S. Pat. No. 4,871,721) describes isoprenoid (phosphinylmethyl)phosphonates as inhibitors of squalene synthetase.

Recently certain nonphosphorous containing inhibitors of squalene synthetase have been isolated as natural products. These natural product inhibitors are described in European Patent Publications EP 0 448 393 published Sep. 25, 1991, EP 0 450 812 published Oct. 9, 1991, and EP 0 475 706 published Mar. 18, 1992. Application U.S. Ser. No. 07/741,699 filled Aug. 7, 1991, discloses squalene synthetase inhibitors produced by biotransformation of the natural Zaragozic Acid. A need still remains for a more effective squalene synthetase inhibitor, i.e. one that provides a greater antihypercholesterolemic effect and exhibits a good safety profile.

The present invention is directed to semi-synthetic analogs of the above-noted natural products, and the use of these analogs as cholesterol lowering agents.

Also recently it has been disclosed that certain nonphosphorous containing semi-synthetic compounds are inhibitors of squalene synthetase.

Recently it has been shown that certain natural product nonphosphorous containing inhibitors of squalene synthetase and their esters are useful in inhibiting fungal growth. This utility is described in U.S. Pat. No. 5,026,554.

The present invention is also directed to the use of semi-synthetic analogs of the above-noted natural products which are squalene synthetase inhibitors for the inhibition of fungal growth.

The Ras gene is found activated in many human cancers, including colorectal carcinoma, exocrine pancreatic carcinoma, and myeloid leukemias. Biological and biochemical studies of Ras action indicate that Ras functions like a G-regulatory protein, since Ras must be localized in the plasma membrane and must bind with GTP in order to transform cells (Gibbs, J. et al., Microbiol. Rev. 53:171–286 (1989). Forms of Ras in cancer cells have mutations that distinguish the protein from Ras in normal cells.

At least 3 post-translational modifications are involved with Ras membrane localization, and all 3 modifications occur at the C-terminus of Ras. The Ras C-terminus contains a sequence motif termed a "CAAX" or "Cys-Aaa[1]-Aaa[2]-Xaa" box (Aaa is an aliphatic amino acid, the Xaa is any amino acid) (Willumsen et al., Nature 310:583–586 (1984)). Other proteins having this motif include the Ras-related GTP-binding proteins such as Rho, fungal mating factors, the nuclear lamins, and the gamma subunit of transducin.

Farnesylation of Ras by the isoprenoid farnesyl pyrophosphate (FPP) occurs in vivo on Cys to form a thioether linkage (Hancock et al., Cell 57:1167 (1989); Casey et al., Proc. Natl. Acad. Sci. USA 86:8323 (1989)). In addition, Ha-Ras and N-Ras are palmitoylated via formation of a thioester on a Cys residue near a C-terminal Cys farnesyl acceptor (Gutierrez et al., EMBO J. 8:1093–1098 (1989); Hancock et al., Cell. 57:1167–1177 (1989)). Ki-Ras lacks the palmitate acceptor Cys. The last 3 amino acids at the Ras C-terminal end are removed proteolytically, and methyl esterification occurs at the new C-terminus (Hancock et al., ibid). Fungal mating factor and mammalian nuclear lamins undergo identical modification steps (Anderegg et al., J. Biol. Chem. 263:18236 (1988); Farnsworth et al., J. Biol. Chem. 264:20422 (1989)).

Inhibition of Ras farnesylation in vivo has been demonstrated with lovastatin (Merck & Co., Rahway, N.J.) and compactin (Hancock et al., ibid; Casey et al., ibid; Schafer et al., Science 245:379 (1989)). These drugs inhibit HMG-CoA reductase, the rate limiting enzyme for the production of polyisoprenoids and the farnesyl pyrophosphate precursor. It has been shown that a farnesyl-protein transferase using farnesyl pyrophosphate as a precursor is responsible for Ras farnesylation. (Reiss et al., Cell, 62: 81–88 (1990); Schaber et al., J. Biol. Chem., 265:14701–14704 (1990); Schafer et al., Science, 249: 1133–1139 (1990); Manne et al., Proc. Natl. Acad. Sci USA, 87: 7541–7545 (1990)).

Inhibition of farnesyl-protein transferase and, thereby, of farnesylation of the Ras protein, blocks the ability of Ras to transform normal cells to cancer cells. Surprisingly, the compounds of the invention inhibit Ras farnesylation and, thereby, generate soluble Ras which, as indicated infra, can act as a dominant negative inhibitor of Ras function. While soluble Ras in cancer cells can become a dominant negative inhibitor, soluble Ras in normal cells would not be an inhibitor.

A cytosol-localized (no Cys-Aaa[1]-Aaa[2]-Xaa box membrane domain present) and activated (impaired GTPase activity, staying bound to GTP) form of Ras acts as a dominant negative Ras inhibitor of membrane-bound Ras function (Gibbs et al., Proc. Natl. Acad. Sci. USA 86:6630–6634(1989)). Cytosol-localized forms of Ras with normal GTPase activity do not act as inhibitors. Gibbs et al., ibid, showed this effect in Xenopus oocytes and in mammalian cells.

Administration of compounds of the invention to block Ras farnesylation not only decreases the amount of Ras in the membrane but also generates a cytosolic pool of Ras. In tumor cells having activated Ras, the cytosolic pool acts as another antagonist of membrane-bound Ras function. In normal cells having normal Ras, the cytosolic pool of Ras does not act as an antagonist. In the absence of complete inhibition of farnesylation, other farnesylated proteins are able to continue with their functions.

Farnesyl-protein transferase activity may be reduced or completely inhibited by adjusting the compound dose. Reduction of farnesyl-protein transferase enzyme activity by adjusting the compound dose would be useful for avoiding possible undesirable side effects such as interference with other metabolic processes which utilize the enzyme.

These compounds are inhibitors of farnesyl-protein transferase. Farnesyl-protein transferase utilizes farnesyl pyrophosphate to covalently modify the Cys thiol group of the Ras CAAX box with a farnesyl group. Inhibition of farnesyl pyrophosphate biosynthesis by inhibiting HMG-CoA reductase blocks Ras membrane localization in vivo and inhibits Ras function. Inhibition of farnesyl-protein transferase is more specific and is attended by fewer side effects than is the case for a general inhibitor of isoprene biosynthesis.

Previously, it has been demonstrated that tetrapeptides with the CAAX sequence inhibit Ras farnesylation (Schaber et al., ibid; Reiss et. al., ibid; Reiss et al., *PNAS*, 88:732–736 (1991)). However, the reported inhibitors of farnesyl-transferase are metabolically unstable or inactive in cells.

Pharmaceutical compositions containing the compounds of this invention and methods of treatment utilizing these compositions for use in inhibiting farnesyl-protein transferase and farnesylation of the oncogene protein Ras.

DETAILED DESCRIPTION OF THE INVENTION

This invention relates to compounds of structural formula (I) which are useful as cholesterol lowering agents:

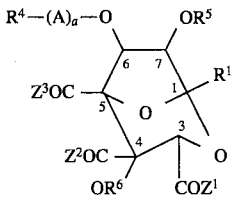

wherein a is 0 or 1;

A is —C(O)—, —NR$^3$—C(O)—, or —OC(O)—;

R$^1$ is selected from the group consisting of:
(1) $C_{1-20}$alkyl,
(2) substituted $C_{1-20}$alkyl in which one or more substituents is selected from:
 (a) halogen,
 (b) hydroxy,
 (c) R$^3$R$^3$N—,
 (d) R$^2$O—,
 (e) R$^2$O—C(O)—,
 (f) R$^3$—C(O)—O—,
 (g) oxo,
 (h) $C_{3-10}$cycloalkyl,
 (i) aryl substituted with X and Y,
 (j) heteroaryl substituted with X and Y,
 (k) heterocycloalkyl,
 (l) arylS(O)$_n$—, wherein aryl is substituted with X and Y,
 (m) R$^3$—C(O)—NR$^3$—,
 (n) R$^3$R$^3$N—C(O)—,
 (o) —CO$_2$H,
 (p) -vinylidene,
 (q) R$^3$—C(O)—,
 (r) R$^2$O—C(O)—O—,
 (s) R$^3$R$^3$N—C(O)—O—, and
 (t) R$^2$O—C(O)—NR$^3$—;
(3) $C_{1-20}$alkyl wherein one or more of the carbons is replaced by —NR$^3$—, —O—, or —S(O)$_n$—;
(4) substituted $C_{1-20}$alkyl wherein one or more of the carbons is replaced by —NR$^3$—, —O— or —S(O)$_n$— and wherein one or more carbon substituents is selected from:
 (a) halogen,
 (b) hydroxy,
 (c) R$^3$R$^3$N—,
 (d) R$^2$O—,
 (e) R$^2$O—C(O)—,
 (f) R$^3$—C(O)—O—,
 (g) oxo,
 (h) $C_{3-10}$cycloalkyl-,
 (i) aryl substituted with X and Y,
 (j) heteroaryl substituted with X and Y,
 (k) heterocycloalkyl,
 (l) arylS(O)$_n$—, wherein aryl is substituted with X and Y,
 (m) R$^3$—C(O)—NR$^3$—,
 (n) R$^3$R$^3$N—C(O)—,
 (o) —CO$_2$H,
 (p) -vinylidene,
 (q) R$^3$—C(O)—,
 (r) R$^2$O—C(O)—O—,
 (s) R$^3$R$^3$N—C(O)—O—, and
 (t) R$^2$O—C(O)—NR$^3$—;
(5) aryl substituted with X and Y;
(6) heteroaryl substituted with X and Y;
(7) $C_{2-20}$alkenyl wherein alkenyl contains one or more double bonds;
(8) substituted $C_{2-20}$alkenyl wherein alkenyl contains one or more double bonds and wherein one or more of the carbons is substituted with:
 (a) halogen,
 (b) hydroxy,
 (c) R$^3$R$^3$N—,
 (d) R$^2$O—,
 (e) R$^2$O—C(O)—,
 (f) R$^3$—C(O)—O—,
 (g) oxo,
 (h) $C_{3-10}$cycloalkyl,
 (i) aryl substituted with X and Y,
 (j) heteroaryl substituted with X and Y,
 (k) heterocycloalkyl,
 (l) arylS(O)$_n$—, wherein aryl is substituted with X and Y,
 (m) R$^3$C(O)—NR$^3$—,
 (n) R$^3$R$^3$N—C(O)—,
 (o) —CO$_2$H,
 (p) -vinylidene,
 (q) R$^3$—C(O)—,
 (r) R$^2$O—C(O)—O—,
 (s) R$^3$R$^3$N—C(O)—O—, and
 (t) R$^2$O—C(O)—NR$^3$—;
(9) $C_{2-20}$alkenyl wherein alkenyl contains one or more double bonds and one or more of the nonolefinic carbons is replaced by —NR$^3$—, —O— or —S(O)$_n$—;
(10) substituted $C_{2-20}$alkenyl wherein alkenyl contains one or more double bonds and one or more of the nonolefinic carbons is replaced by —NR$^3$—, —O— or —S(O)$_n$— and wherein one or more carbon substitutents is selected from:
 (a) halogen,
 (b) hydroxy, (c) $R^3R^3N-$,
(d) $R^2O-$,
(e) $R^2O-C(O)-$,
(f) $R^3-C(O)-O-$,
(g) oxo,
(h) $C_{3-10}$cycloalkyl-,
(i) aryl substituted with X and Y,
(j) heteroaryl substituted with X and Y,
(k) heterocycloalkyl,
(l) arylS(O)$_n-$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;
(11) $C_{3-10}$cycloalkyl;
(12) substituted $C_{3-10}$cycloalkyl in which one or more of the substituents is selected from:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n-$, wherein aryl is substituted with X and Y,
(m) $R^3-C(O)-NR^3-$,
(n) $R^3R^3N-C(O)-$,
(o) $C_{1-10}$alkylS(O)$_n-$,
(p) $C_{1-10}$alkyl,
(q) $-CO_2H$,
(r) -vinylidene,
(s) $R^3-C(O)-$,
(t) $R^2O-C(O)-O-$,
(u) $R^3R^3N-C(O)-O-$, and
(v) $R^2O-C(O)-NR^3-$;

Each $R^2$ is independently selected from:
(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl;
(8) aryl$C_{2-10}$alkenyl wherein aryl is substituted with X and Y; and
(9) $C_{3-10}$alkynyl;

Each $R^3$ is independently selected from:
(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl;
(8) aryl$C_{2-10}$alkenyl wherein aryl is substituted with X and Y;
(9) $C_{3-10}$alkynyl;
(10) hydrogen; and
(11) $C_{1-5}$alkyl substituted with $X^1$;

$R^4$ selected from the group consisting of:
(1) $C_{1-20}$alkyl;
(2) substituted $C_{1-20}$alkyl in which one or more substituents is selected from:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n-$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;
(3) $C_{1-20}$alkyl wherein one or more of the carbons is replaced by $-NR_3-$, $-O-$, or $-S(O)_n-$;
(4) substituted $C_{1-20}$alkyl wherein one or more of the carbons is replaced by $-NR^3-$, $-O-$ or $-S(O)_n-$ and wherein one or more carbon substituents is selected from:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl-,
(i) aryl substituted with X and Y,
(j) heteroaryl substituted with X and Y,
(k) heterocycloalkyl,
(l) arylS(O)$_n-$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;
(5) aryl substituted with X and Y;
(6) heteroaryl substituted with X and Y;
(7) $C_{2-20}$alkenyl wherein alkenyl contains one or more double bonds;
(8) substituted $C_{2-20}$alkenyl wherein alkenyl contains one or more double bonds and wherein one or more of the carbons is substituted with:
(a) halogen, (b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n-$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;
(9) $C_{2-20}$alkenyl wherein alkenyl contains one or more double bonds and one or more of the nonolefinic carbons is replaced by $-NR_3-$, $-O-$ or $-S(O)_n-$;
(10) substituted $C_{2-20}$alkenyl wherein alkenyl contains one or more double bonds and one or more of the nonolefinic carbons is replaced by $-NR^3-$, $-O-$ or $-S(O)_n-$ and wherein one or more carbon substitutents is selected from:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl-,
(i) aryl substituted with X and Y,
(j) heteroaryl substituted with X and Y,
(k) heterocycloalkyl,
(l) arylS(O)$_n-$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;
(11) $C_{3-10}$cycloalkyl;
(12) substituted $C_{3-10}$cycloalkyl in which one or more of the substituents is selected from:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n-$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$; and
(13) hydrogen;

$R^5$ is selected from the group consisting of:
(1) hydrogen;
(2) $C_{1-10}$alkyl;
(3) aryl substituted with X and Y;
(4) aryl$C_{1-4}$alkyl, wherein aryl is substituted with X and Y;
(5) $R^2O-C(O)-$;
(6) $C_{3-10}$cycloalkyl;
(7) $R^3-C(O)-$; and
(8) $R^3R^3N-C(O)-$;

$R^6$ and $R^{6a}$ are each independently selected from the group consisting of:
(1) $C_{1-20}$alkyl;
(2) substituted $C_{1-20}$alkyl in which one or more substituents is selected from:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) aryl S(O)$_n-$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3NOC(O)-O-$, and
(t) $R^2O-C(O)-NR^3-$;
(3) $C_{1-20}$alkyl wherein one or more of the carbons is replaced by $-NR^3-$, $-O-$ or $-s(O)_n-$;
(4) substituted $C_{1-20}$alkyl wherein one or more of the carbons is replaced by $-NR^3-$, $-O-$ or $-S(O)_n-$ and wherein one or more carbon substituents is selected from:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) aryl S(O)$_n-$, wherein aryl is substituted with X and Y,
(m) $R^3-C(O)-NR^3-$,
(n) $R^3R^3N-C(O)-$,
(o) $-CO_2H$,
(p) -vinylidene, (q) $R^3$—C(O)—,
(r) $R^2$O—C(O)—O—,
(s) $R^3R^3$N—C(O)—O—, and
(t) $R^2$O—C(O)—$NR^3$—;
(5) $C_{2-20}$alkenyl wherein alkenyl contains one or more double bonds;
(6) substituted $C_{2-20}$alkenyl wherein alkenyl contains one or more double bonds and wherein one or more of the carbons is substituted with:
(a) halogen
(b) hydroxy,
(c) $R^3R^3$N—,
(d) $R^2$O—,
(e) $R^2$O—C(O)—,
(f) $R^3$—C(O)—O—,
(g) oxo,
(h) $C_{3-10}$cycloalky,
(i) aryl substituted with Z and Y,
(j) heteroaryl substituted with X and Y,
(k) heterocycloalkyl,
(l) aryl S(O)$_n$—, wherein aryl is substituted with X and Y,
(m) $R^3$—C(O)—$NR^3$—,
(n) $R^3R^3$N—C(O)—,
(o) —$CO_2$H,
(p) -vinylidene,
(q) $R^3$—C(O)—,
(r) $R^2$O—C(O)—O—,
(s) $R^3R^3$N—C(O)—O—, and
(t) $R^2$O—C(O)—$NR^3$—;
(7) $C_{2-20}$alkenyl wherein alkenyl contains one or more double bonds and one or more of the nonolefinic carbons is replaced by —$NR^3$—, —O— or —S(O)$_n$—;
(8) substituted $C_{2-20}$alkenyl wherein alkenyl contains one or more double bonds and one or more of the nonolefinic carbons is replaced by —$NR^3$—, —O— or —S(O)$_n$— and wherein one or more carbon substituents is selected from:
(a) halogen
(b) hydroxy,
(c) $R^3R^3$N—,
(d) $R^2$O—,
(e) $R^2$O—C(O)—,
(f) $R^3$—C(O)—O—,
(g) oxo,
(h) $C_{3-10}$cycloalkyl,
(i) aryl substituted with X and Y,
(j) heteroaryl substituted with X and Y,
(k) heterocycloalkyl,
(l) aryl S(O)$_n$—, wherein aryl is substituted with X and Y,
(m) $R^3$—C(O)—$NR^3$—,
(n) $R^3R^3$N—C(O)—,
(o) —$CO_2$H,
(p) -vinylidene,
(q) $R^3$—C(O)—,
(r) $R^2$O—C(O)—O—,
(s) $R^3R^3$N—C(O)—O—, and
(t) $R^2$O—C(O)—$NR^3$—;
(9) $C_{2-20}$alkynyl wherein alkynyl contains one or more triple bonds;
(10) substituted $C_{2-20}$alkynyl wherein alkynyl contains one or more triple bonds and wherein one or more of the carbons is substituted with:
(a) halogen,
(b) hydroxy,
(c) $R^3R^3$N—,
(d) $R^2$O—,
(e) $R^2$O—C(O)—,
(f) $R^3$—C(O)—O—,
(g) oxo,
(h) $C_{3-10}$cycloalkyl,
(i) aryl substituted with X and Y,
(j) heteroaryl substituted with X and Y,
(k) heterocycloalkyl,
(l) arylS(O)$_n$—, wherein aryl is substituted with X and Y,
(m) $R^3$—C(O)—$NR^3$—,
(n) $R^3R^3$N—C(O)—,
(o) —$CO_2$H,
(p) -vinylidene,
(q) $R^3$—C(O)—,
(r) $R^2$O—C(O)—O—,
(s) $R^3R^3$N—C(O)—O—, and
(t) $R^2$O—C(O)—$NR^3$—;
(11) $C_{2-20}$alkynyl wherein alkynyl contains one or more triple bonds and one or more of the saturated carbons is replaced by —$NR^3$—, —O— or —S(O)$_n$—;
(12) substituted $C_{2-20}$alkynyl wherein alkynyl contains one or more double bonds and one or more of the saturated carbons is replaced by —$NR^3$—, —O— or —S(O)$_n$— and wherein one or more carbon substitutents is selected from:
(a) halogen,
(b) hydroxy,
(c) $R^3R^3$N—,
(d) $R^2$O—,
(e) $R^2$O—C(O)—,
(f) $R^3$—C(O)—O—,
(g) oxo,
(h) $C_{3-10}$cycloalkyl-,
(i) aryl substituted with X and Y,
(j) heteroaryl substituted with X and Y,
(k) heterocycloalkyl,
(l) arylS(O)$_n$—, wherein aryl is substituted with X and Y,
(m) $R^3$—C(O)—$NR^3$—,
(n) $R^3R^3$N—C(O)—,
(o) —$CO_2$H,
(p) -vinylidene,
(q) $R^3$—C(O)—,
(r) $R^2$O—C(O)—O—,
(s) $R^3R^3$N—C(O)—O—, and
(t) $R^2$O—C(O)—$NR^3$—;
(13) aryl substituted with X and Y;
(14) Heter oaryl substituted with X and Y;
(15) $C_{3-5}$ cycloalkyl;
(16) substituted $C_{3-5}$ cycloalkyl in which one or more of the substituents is selected from:
(a) $R^3$O—, and
(b) $R^3R^3$N—; and
(17) hydrogen;
aryl including X, Y substitution is:

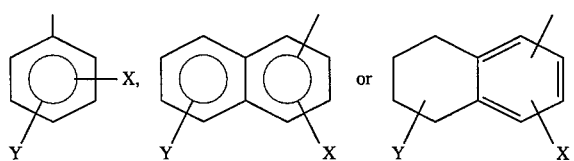

heteroaryl including X, Y substitution is selected from

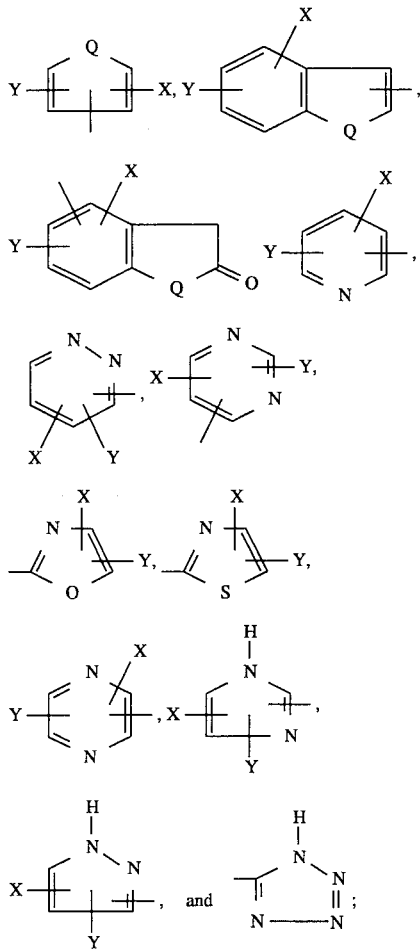

wherein:
Q is —NR³, —O— or —S—;
heterocycloalkyl is selected from:

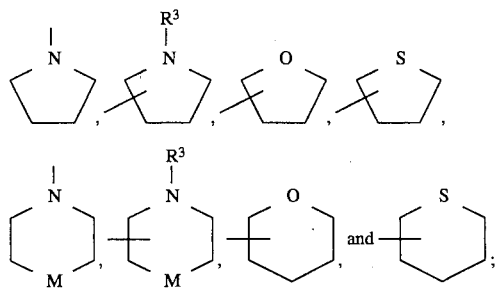

wherein:
M is —NR³, —O—, —S— or —CH₂—
X and Y are each independently selected from:
(1) hydrogen;
(2) hydroxy;
(3) halogen;
(4) trifluoromethyl;
(5) $C_{1-10}$alkyl;
(6) aryl substituted with $X^1$ and $Y^1$;
(7) R²O—;
(8) arylcarbonyloxy-, wherein aryl is substituted with $X^1$ and $Y^1$;
(9) R³—C(O)—O—;
(10) —CO₂R²;
(11) —CO₂H; and
(12) nitro;

$X^1$ and $Y^1$ are each independently selected from:
(1) hydrogen;
(2) hydroxy;
(3) halogen;
(4) trifluoromethyl;
(5) $C_{1-4}$alkyl;
(6) R²O—;
(7) R³—C(O)—O—;
(8) —CO₂R²;
(9) —CO₂H; and
(10) nitro;

n is 0, 1 or 2;

$Z^1$, $Z^2$ and $Z^3$ are each independently selected from:
(1) —OR$^{6a}$;
(2) —SR$^{6a}$; and
(3) —NR$^{6a}$R$^{6a}$;

provided that when R⁵ and R⁶ are H, and $Z^1$, $Z^2$ and $Z^3$ are each OH or OCH₃, then R¹ and R⁴—(A)$_a$— are not both respectively

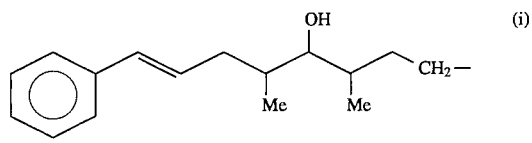

(i)

and

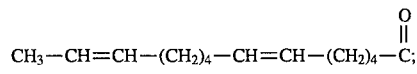

or

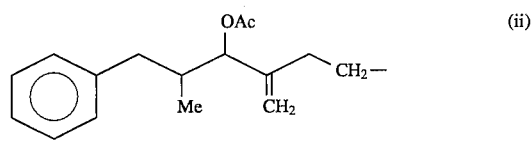

(ii)

and

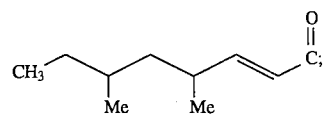

or

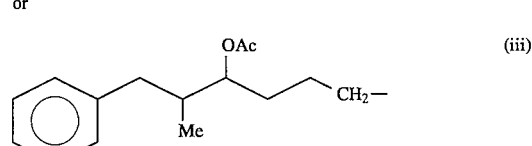

(iii)

and

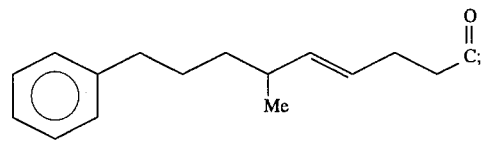

or

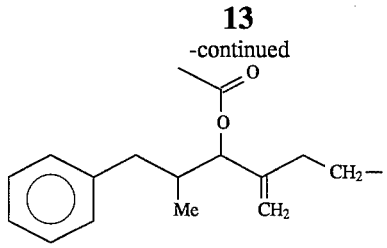

(iv)

and

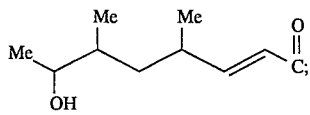

or a pharmaceutically acceptable salt.

One embodiment of this invention is the compounds of formula (I) wherein:

$R^1$ is selected from the group consisting of:
(1) $C_{1-20}$alkyl;
(2) substituted $C_{1-20}$alkyl in which one or more substituents is selected from:
 (a) halogen,
 (b) hydroxy,
 (c) $R^3R^3N$—,
 (d) $R^2O$—,
 (e) $R^2O$—C(O)—,
 (f) $R^3$—C(O)—O—,
 (g) oxo,
 (h) $C_{3-10}$cycloalkyl,
 (i) aryl substituted with X and Y,
 (j) heteroaryl substituted with X and Y,
 (k) heterocycloalkyl,
 (l) arylS(O)$_n$, wherein aryl is substituted with X and Y,
 (m) $R^3$—C(O)—NR$^3$—,
 (n) $R^3R^3N$—C(O)—,
 (o) —CO$_2$H,
 (p) -vinylidene,
 (q) $R^3$—C(O)—,
 (r) $R^2O$—C(O)—O—,
 (s) $R^3R^3N$—C(O)—O—, and
 (t) $R^2O$—C(O)—NR$^3$—;
(3) $C_{1-20}$alkyl wherein one or more of the carbons is replaced by —NR$^3$—, —O—, or —S(O)$_n$—;
(4) substituted $C_{1-20}$alkyl wherein one or more of the carbons is replaced by —NR$^3$—, —O— or —S(O)$_n$— and wherein one or more carbon substituents is selected from:
 (a) halogen,
 (b) hydroxy,
 (c) $R^3R^3N$—,
 (d) $R^2O$—,
 (e) $R^2O$—C(O)—,
 (f) $R^3$—C(O)—O—,
 (g) oxo,
 (h) $C_{3-10}$cycloalkyl,
 (i) aryl substituted with X and Y,
 (j) heteroaryl substituted with X and Y,
 (k) heterocycloalkyl,
 (l) arylS(O)$_n$, wherein aryl is substituted with X and Y,
 (m) $R^3$—C(O)—NR$^3$—,
 (n) $R^3R^3N$—C(O)—,
 (o) —CO$_2$H,
 (p) -vinylidene,
 (q) $R^3$—C(O)—,
 (r) $R^2O$—C(O)—O—,
 (s) $R^3R^3N$—C(O)—O—, and
 (t) $R^2O$—C(O)—NR$^3$—;
(5) aryl substituted with X and Y;
(6) heteroaryl substituted with X and Y;
(7) $C_{2-20}$alkenyl wherein alkenyl contains one, two or three double bonds;
(8) substituted $C_{2-20}$alkenyl wherein alkenyl contains one, two or three double bonds and wherein one or more of the carbons is substituted with:
 (a) halogen,
 (b) hydroxy,
 (c) $R^3R^3N$—,
 (d) $R^2O$—,
 (e) $R^2O$—C(O)—,
 (f) $R^3$—C(O)—O—,
 (g) oxo,
 (h) $C_{3-10}$cycloalkyl,
 (i) aryl substituted with X and Y,
 (j) heteroaryl substituted with X and Y,
 (k) heterocycloalkyl,
 (l) arylS(O)$_n$, wherein aryl is substituted with X and Y,
 (m) $R^3$—C(O)—NR$^3$—,
 (n) $R^3R^3N$—C(O)—,
 (o) —CO$_2$H,
 (p) -vinylidene,
 (q) $R^3$—C(O)—,
 (r) $R^2O$—C(O)—O—,
 (s) $R^3R^3N$—C(O)—O—, and
 (t) $R^2O$—C(O)—NR$^3$—;
(9) $C_{2-20}$alkenyl wherein alkenyl contains one, two or three double bonds and one or more of the non-olefinic carbons is replaced by —NR$^3$—, —O— or —S(O)$_n$—; and
(10) substituted $C_{2-20}$alkenyl wherein alkenyl contains one, two or three double bonds and one or more of the nonolefinic carbons is replaced by —NR$^3$, —O— or —S(O)$_n$— and wherein one or more carbons substituents is selected from:
 (a) halogen,
 (b) hydroxy,
 (c) $R^3R^3N$—,
 (d) $R^2O$—,
 (e) $R^2O$—C(O)—,
 (f) $R^3$—C(O)—O—,
 (g) oxo,
 (h) $C_{3-10}$cycloalkyl,
 (i) aryl substituted with X and Y,
 (j) heteroaryl substituted with X and Y,
 (k) heterocycloalkyl,
 (l) arylS(O)$_n$, wherein aryl is substituted with X and Y,
 (m) $R^3$—C(O)—NR$^3$—,
 (n) $R^3R^3N$—C(O)—,
 (o) —CO$_2$H,
 (p) -vinylidene,
 (q) $R^3$—C(O)—,
 (r) $R^2O$—C(O)—O—,
 (s) $R^3R^3N$—C(O)—O—, and
 (t) $R^2O$—C(O)—NR$^3$—;

Each $R^2$ is independently selected from:
(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;

(5) heteroaryl$C_{1-4}$alkyl- wherein heteroaryl is substituted with X and Y;
(6) heterocycloalkyl$C_{1-4}$alkyl-;
(7) $C_{2-10}$alkenyl;
(8) aryl$C_{2-10}$alkenyl wherein aryl is substituted with X and Y; and
(9) $C_{3-10}$alkynyl;

Each $R^3$ is independently selected from:
(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl;
(8) aryl$C_{2-10}$alkenyl wherein aryl is substituted with X and Y;
(9) $C_{3-10}$alkynyl;
(10) hydrogen; and
(11) $C_{1-5}$alkyl substituted with $X^1$;

$R^4$ is selected from the group consisting of:
(1) $C_{1-20}$alkyl;
(2) substituted $C_{1-20}$alkyl in which one or more substituents is selected from:
  (a) halogen,
  (b) hydroxy,
  (c) $R^3R^3N-$,
  (d) $R^2O-$,
  (e) $R^2O-C(O)-$,
  (f) $R^3-C(O)-O-$,
  (g) oxo,
  (h) $C_{3-10}$cycloalkyl,
  (i) aryl substituted with X and Y,
  (j) heteroaryl substituted with X and Y,
  (k) heterocycloalkyl,
  (l) arylS(O)$_n$, wherein aryl is substituted with X and Y,
  (m) $R^3-C(O)-NR^3-$,
  (n) $R^3R^3N-C(O)-$,
  (o) $-CO_2H$,
  (p) -vinylidene,
  (q) $R^3-C(O)-$,
  (r) $R^2O-C(O)-O-$,
  (s) $R^3R^3N-C(O)-O-$, and
  (t) $R^2O-C(O)-NR^3-$;
(3) $C_{1-20}$alkyl wherein one or more of the carbons is replaced by $-NR^3-$, $-O-$, or $-S(O)n-$;
(4) substituted $C_{1-20}$alkyl wherein one or more of the carbons is replaced by $-NR^3-$, $-O-$ or $-S(O)_n-$ and wherein one or more carbon substituents is selected from:
  (a) halogen,
  (b) hydroxy,
  (c) $R^3R^3N-$,
  (d) $R^2O-$,
  (e) $R^2O-C(O)-$,
  (f) $R^3-C(O)-O-$,
  (g) oxo,
  (h) $C_{3-10}$cycloalkyl,
  (i) aryl substituted with X and Y,
  (j) heteroaryl substituted with X and Y,
  (k) heterocycloalkyl,
  (l) arylS(O)$_n$, wherein aryl is substituted with X and Y,
  (m) $R^3-C(O)-NR^3-$,
  (n) $R^3R^3N-C(O)-$,
  (o) $-CO_2H$,
  (p) -vinylidene,
  (q) $R^3-C(O)-$,
  (r) $R^2O-C(O)-O-$,
  (s) $R^3R^3N-C(O)-O-$, and
  (t) $R^2O-C(O)-NR^3-$;
(5) aryl substituted with X and Y;
(6) heteroaryl substituted with X and Y;
(7) $C_{2-20}$ alkenyl wherein alkenyl contains one, two or three double bonds;
(8) substituted $C_{2-20}$ alkenyl wherein alkenyl contains one, two or three double bonds and wherein one or more of the carbons is substituted with:
  (a) halogen,
  (b) hydroxy,
  (c) $R^3R^3N-$,
  (d) $R^2O-$,
  (e) $R^2O-C(O)-$,
  (f) $R^3-C(O)-O-$,
  (g) oxo,
  (h) $C_{3-10}$cycloalkyl,
  (i) aryl substituted with X and Y,
  (j) heteroaryl substituted with X and Y,
  (k) heterocycloalkyl,
  (l) arylS(O)$_n$, wherein aryl is substituted with X and Y,
  (m) $R^3-C(O)-NR^3-$,
  (n) $R^3R^3N-C(O)-$,
  (o) $-CO_2H$,
  (p) -vinylidene,
  (q) $R^3-C(O)-$,
  (r) $R^2O-C(O)-O-$,
  (s) $R^3R^3N-C(O)-O-$, and
  (t) $R^2O-C(O)-NR^3-$;
(9) $C_{2-20}$alkenyl wherein alkenyl contains one, two or three double bonds and one or more of the non-olefinic carbons is replaced by $-NR^3-$, $-O-$ or $-S(O)_n-$;
(10) substituted $C_{2-20}$alkenyl wherein alkenyl contains one, two or three double bonds and one or more of the nonolefinic carbons is replaced by $-NR^3-$, $-O-$ or $-S(O)_n-$ and wherein one or more carbon substitutents is selected from:
  (a) halogen,
  (b) hydroxy,
  (c) $R^3R^3N-$,
  (d) $R^2O-$,
  (e) $R^2O-C(O)-$,
  (f) $R^3-C(O)-O-$,
  (g) oxo,
  (h) $C_{3-10}$cycloalkyl,
  (i) aryl substituted with X and Y,
  (j) heteroaryl substituted with X and Y,
  (k) heterocycloalkyl,
  (l) arylS(O)$_n$, wherein aryl is substituted with X and Y,
  (m) $R^3-C(O)-NR^3-$,
  (n) $R^3R^3N-C(O)-$,
  (o) $-CO_2H$,
  (p) -vinylidene,
  (q) $R^3-C(O)-$,
  (r) $R^2O-C(O)-O-$,
  (s) $R^3R^3N-C(O)-O-$, and
  (t) $R^2O-C(O)-NR^3-$; and
(11) hydrogen;

$R^5$ is selected from the group consisting of:
(1) hydrogen;
(2) $C_{1-10}$alkyl;
(3) aryl substituted with X and Y;
(4) aryl$C_{1-4}$alkyl, wherein aryl is substituted with X and Y;
(5) $R^2O—C(O)—$;
(6) $C_{3-10}$cycloalkyl;
(7) $R^2—C(O)—$; and
(8) $R^3R^3N—C(O)—$;

$R^6$ and $R^{6a}$ are each independently selected from the group consisting of:
(1) $C_{1-20}$alkyl;
(2) substituted $C_{1-20}$alkyl in which one or more substituents is selected from:
  (a) halogen,
  (b) hydroxy,
  (c) $R^3R^3N—$,
  (d) $R^2O—$,
  (e) $R^2O—C(O)—$,
  (f) $R^3—C(O)—O—$,
  (g) oxo,
  (h) $C_{3-10}$cycloalkyl,
  (i) aryl substituted with X and Y,
  (j) heteroaryl substituted with X and Y,
  (k) heterocycloalkyl,
  (l) aryl S(O)n, wherein aryl is substituted with X and Y,
  (m) $R^3—C(O)—NR^3—$,
  (n) $R^3R^3N—C(O)—$,
  (o) $—CO_2H$,
  (p) -vinylidene,
  (q) $R^3—C(O)—$,
  (r) $R^2O—C(O)—O—$,
  (s) $R^3R^3NC(O)—O—$, and
  (t) $R^2O—C(O)—NR^3—$;
(3) $C_{1-20}$alkyl wherein one or more of the carbons is replaced by $—NR^3—$, $—O—$, or $—S(O)_n—$;
(4) substituted $C_{1-20}$alkyl wherein one or more of the carbons is replaced by $—NR^3—$, $—O—$ or $—S(O)_n—$ and wherein one or more carbon substituents is selected from:
  (a) halogen,
  (b) hydroxy,
  (c) $R^3R^3N—$,
  (d) $R^2O—$,
  (e) $R^2O—C(O)—$,
  (f) $R^3—C(O)—O—$,
  (g) oxo,
  (h) $C_{3-10}$cycloalkyl,
  (i) aryl substituted with X and Y,
  (j) heteroaryl substituted with X and Y,
  (k) heterocycloalkyl,
  (l) aryl $S(O)_n—$, wherein aryl is substituted with X and Y,
  (m) $R^3—C(O)—NR^3—$,
  (n) $R^3R^3N—C(O)—$,
  (o) $—CO_2H$,
  (p) -vinylidene,
  (q) $R^3—C(O)—$,
  (r) $R^2O—C(O)—O—$,
  (s) $R^3R^3N—C(O)—O—$, and
  (t) $R^2O—C(O)—NR^3—$;
(5) $C_{2-20}$alkenyl wherein alkenyl contains one, two or three double bonds;
(6) substituted $C_{2-20}$alkenyl wherein alkenyl contains one, two or three double bonds and wherein one or more of the carbons is substituted with:
  (a) halogen
  (b) hydroxy,
  (c) $R^3R^3N—$,
  (d) $R^2O—$,
  (e) $R^2O—C(O)—$,
  (f) $R^3—C(O)—O—$,
  (g) oxo,
  (h) $C_{3-10}$cycloalkyl,
  (i) aryl substituted with X and Y,
  (j) heteroaryl substituted with X and Y,
  (k) heterocycloalkyl,
  (l) aryl $S(O)_n—$, wherein aryl is substituted with X and Y,
  (m) $R^3—C(O)—NR^3—$,
  (n) $R^3R^3N—C(O)—$,
  (o) $—CO_2H$,
  (p) -vinylidene,
  (q) $R^3—C(O)—$,
  (r) $R^2O—C(O)—O—$,
  (s) $R^3R^3N—C(O)—O—$, and
  (t) $R^2O—C(O)—NR^3—$;
(7) $C_{2-20}$alkenyl wherein alkenyl contains one, two or three double bonds and one or more of the non-olefinic carbons is replaced by $—NR^3—$, $—O—$ or $—S(O)_n—$;
(8) substituted $C_{2-20}$alkenyl wherein alkenyl contains one, two or three double bonds and one or more of the nonolefinic carbons is replaced by $—NR^3—$, $—O—$ or $—S(O)_n—$ and wherein one or more carbon substituents is selected from:
  (a) halogen
  (b) hydroxy,
  (c) $R^3R^3N—$,
  (d) $R^2O—$,
  (e) $R^2O—C(O)—$,
  (f) $R^3—C(O)—O—$,
  (g) oxo,
  (h) $C_{3-10}$cycloalkyl,
  (i) aryl substituted with X and Y,
  (j) heteroaryl substituted with X and Y,
  (k) heterocycloalkyl,
  (l) aryl $S(O)_n—$, wherein aryl is substituted with X and Y,
  (m) $R^3—C(O)—NR^3—$,
  (n) $R^3R^3N—C(O)—$,
  (o) $—CO_2H$,
  (p) -vinylidene,
  (q) $R^3—C(O)—$,
  (r) $R^2O—C(O)—O—$,
  (s) $R^3R^3N—C(O)—O—$, and
  (t) $R^2O—C(O)—NR^3—$;
(9) $C_{2-20}$alkynyl when rein alkynyl contains one or more triple bonds;
(10) substituted $C_{2-20}$alkynyl wherein alkynyl contains one or more triple bonds and wherein one or more of the carbons is substituted with:
  (a) halogen,
  (b) hydroxy,
  (c) $R^3R^3N—$,
  (d) $R^2O—$,
  (e) $R^2O—C(O)—$,
  (f) $R^3—C(O)—O—$,
  (g) oxo,
  (h) $C_{3-10}$cycloalkyl,
  (i) aryl substituted with X and Y,
  (j) heteroaryl substituted with X and Y,
  (k) heterocycloalkyl, (l) arylS(O)$_n$—, wherein aryl is substituted with X and Y,
(m) $R^3$—C(O)—$NR^3$—,
(n) $R^3R^3N$—C(O)—,
(o) —$CO_2H$,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;

(11) $C_{2-20}$alkynyl wherein alkynyl contains one or more triple bonds and one or more of the saturated carbons is replaced by —$NR^3$—, —O— or —S(O)$_n$—;

(12) substituted $C_{2-20}$alkynyl wherein alkynyl contains one or more triple bonds and one or more of the saturated carbons is replaced by —$NR^3$—, —O— or —S(O)$_n$— and wherein one or more carbon substitutents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl-,
(i) aryl substituted with X and Y,
(j) heteroaryl substituted with X and Y,
(k) heterocycloalkyl,
(l) arylS(O)$_n$—, wherein aryl is substituted with X and Y,
(m) $R^3$—C(O)—$NR^3$—,
(n) $R^3R^3N$—C(O)—,
(o) —$CO_2H$,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;

(13) aryl substituted with X and Y;
(14) heteroaryl substituted with X and Y;
(15) $C_{3-5}$ cycloalkyl;
(16) substituted $C_{3-5}$ cycloalkyl in which one or more of the substituents is selected from:
(a) $R^3O$—, and
(b) $R^3R^3N$—; and
(17) hydrogen;

aryl including X, Y substitution is

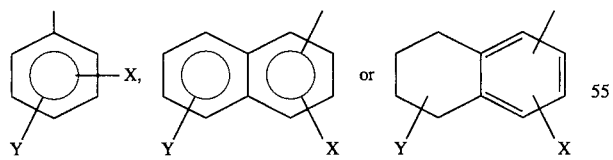

heteroaryl including X, Y substitution is selected from

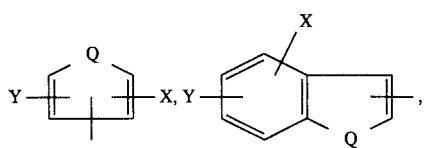

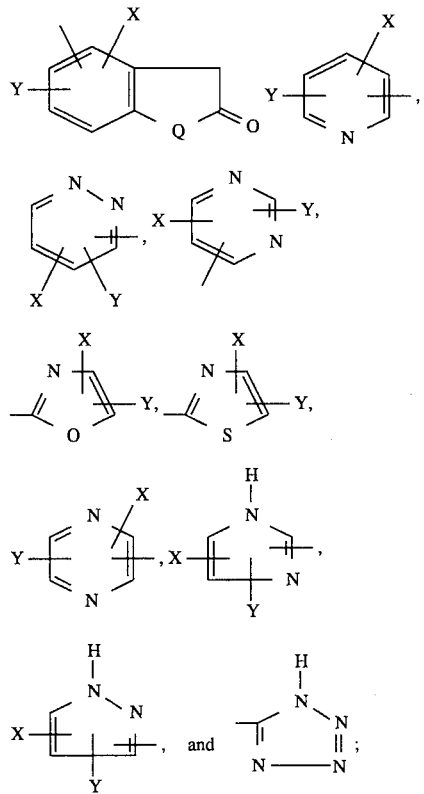

wherein:
Q is —$NR^3$, —O— or —S—;
heterocycloalkyl is selected from:

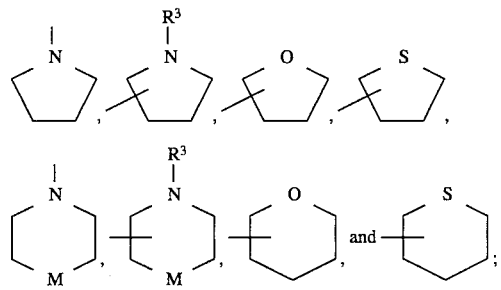

wherein:
M is —$NR^3$, —O—, —S— or —$CH_2$—
X and Y are each independently selected from:
(1) hydrogen;
(2) hydroxy;
(3) halogen;
(4) trifluoromethyl;
(5) $C_{1-10}$alkyl;
(6) aryl substituted with $X^1$ and $Y^1$;
(7) $R^2O$—;
(8) arylcarbonyloxy-, wherein aryl is substituted with $X^1$ and $Y^1$;
(9) $R^3$—C(O)—O—;
(10) —$CO_2R^2$;
(11) —$CO_2H$; and
(2) nitro;
$X^1$ and $Y^1$ are each independently selected from:
(1) hydrogen;
(2) hydroxy;

(3) halogen;
(4) trifluoromethyl;
(5) $C_{1-4}$alkyl;
(6) $R^2O$—;
(7) $R^3$—C(O)—O—;
(8) —$CO_2R^2$;
(10) —$CO_2H$; and
(11) nitro;

n is 0, 1 or 2;

$Z^1$, $Z^2$ and $Z^3$ are each independently selected from:
(1) —$OR^{6a}$;
(2) —$SR^{6a}$; and
(3) —$NR^{6a}R^{6a}$;

provided that when $R^5$ and $R^6$ are H and $Z^1$, $Z^2$ and $Z^3$ are each OH or $OCH_3$, then $R^1$ and $R^4$—$(A)_a$— are not both respectively

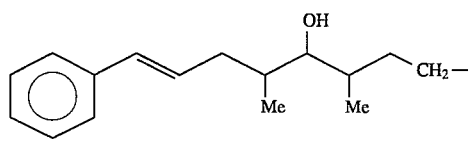

and

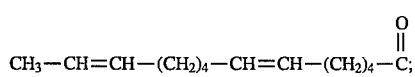

or

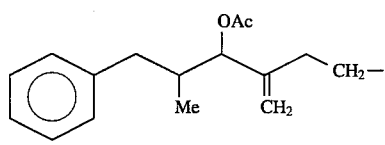

or

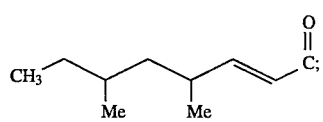

or

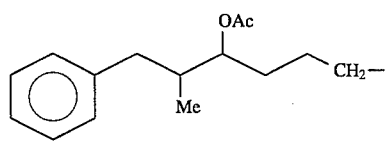

and

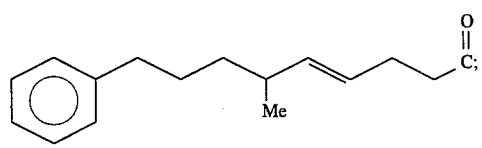

and

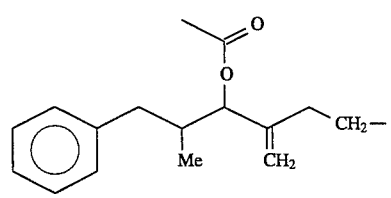

-continued

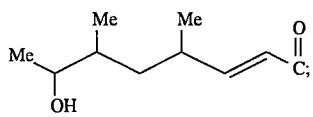

or a pharmaceutically acceptable salt of formula (I).

One class of this embodiment is the compound of formula (I) wherein:

$R^1$ is selected from the group consisting of:
(1) $C_{1-20}$alkyl;
(2) substituted $C_{1-20}$alkyl in which one or more substituents is selected from:
 (a) halogen,
 (b) hydroxy,
 (c) $R^3R^3N$—,
 (d) $R^2O$—,
 (e) $R^2O$—C(O)—,
 (f) $R^3$—C(O)—O—,
 (g) oxo,
 (h) $C_{3-10}$cycloalkyl,
 (i) aryl substituted with X and Y,
 (j) heteroaryl substituted with X and Y,
 (k) heterocycloalkyl,
 (l) arylS(O)$_n$, wherein aryl is substituted with X and Y,
 (m) $R^3$—C(O)—$NR^3$—,
 (n) $R^3R^3N$—C(O)—,
 (o) —$CO_2H$,
 (p) -vinylidene,
 (q) $R^3$—C(O)—,
 (r) $R^2O$—C(O)—O—,
 (s) $R^3R^3N$—C(O)—O—, and
 (t) $R^2O$—C(O)—$NR^3$—;
(3) $C_{1-20}$alkyl wherein one or more of the carbons is replaced by —$NR^3$—, —O—, or —$S(O)_n$—;
(4) substituted $C_{1-20}$alkyl wherein one or more of the carbons is replaced by —$NR^3$—, —O— or —$S(O)_n$— and wherein one or more carbon substituents is selected from:
 (a) halogen,
 (b) hydroxy,
 (c) $R^3R^3N$—,
 (d) $R^2O$—,
 (e) $R^2O$—C(O)—,
 (f) $R^3$—C(O)—O—,
 (g) oxo,
 (h) $C_{3-10}$cycloalkyl,
 (i) aryl substituted with X and Y,
 (j) heteroaryl substituted with X and Y,
 (k) heterocycloalkyl,
 (l) arylS(O)$_n$, wherein aryl is substituted with X and Y,
 (m) $R^3$—C(O)—$NR^3$—,
 (n) $R^3R^3N$—C(O)—,
 (o) —$CO_2H$,
 (p) -vinylidene,
 (q) $R^3$—C(O)—,
 (r) $R^2O$—C(O)—O—,
 (s) $R^3R^3N$—C(O)—O—, and
 (t) $R^2O$—C(O)—$NR^3$—;
(5) aryl substituted with X and Y;
(6) heteroaryl substituted with X and Y;
(7) $C_{2-20}$alkenyl wherein alkenyl contains one, two or three double bonds;
(8) substituted $C_{2-20}$alkenyl wherein alkenyl contains one, two or three double bonds and wherein one or more of the carbons is substituted with:

(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) $arylS(O)_n$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;
(9) $C_{2-20}$alkenyl wherein alkenyl contains one, two or three double bonds and one or more of the non-olefinic carbons is replaced by $-NR^3-$, $-O-$ or $-S(O)_n-$;
(10) substituted $C_{2-20}$alkenyl wherein alkenyl contains one, two or three double bonds and one or more of the nonolefinic carbons is replaced by $-NR^3$, $-O-$ or $-S(O)_n-$ and wherein one or more carbons substituents is selected from:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalky,
(l) $arylS(O)_n$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;

Each $R^2$ is independently selected from:
(1) $C_{1-10}$alkyl;
(2) aryl substituted with X and Y;
(3) $arylC_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl;
(8) aryl$C_{2-10}$alkenyl wherein aryl is substituted with X and Y; and
(9) $C_{3-10}$alkynyl;

Each $R^3$ is independently selected from:
(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl;
(8) aryl$C_{2-10}$alkenyl wherein aryl is substituted with X and Y;
(9) $C_{3-10}$alkynyl;
(10) hydrogen; and
(11) $C_{1-5}$alkyl substituted with $X^1$;

$R^4$ is selected from the group consisting of:
(1) $C_{1-20}$alkyl;
(2) substituted $C_{1-20}$alkyl in which one or more substituents is selected from:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted with X and Y,
(j) heteroaryl substituted with X and Y,
(k) heterocycloalkyl,
(l) $arylS(O)_n$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;
(3) $C_{1-20}$alkyl wherein one or more of the carbons is replaced by $-NR^3-$, $-O-$, or $-S(O)_n-$;
(4) substituted $C_{1-20}$alkyl wherein one or more of the carbons is replaced by $-NR^3-$, $-O-$ or $-S(O)_n-$ and wherein one or more carbon substituents is selected from:
(a) halogen,
(b) hydroxy,
(c) $R^3R^3N-$,
(d) $R^2O-$,
(e) $R^2O-C(O)-$,
(f) $R^3-C(O)-O-$,
(g) oxo,
(h) $C_{3-10}$cycloalkyl,
(i) aryl substituted With X and Y,
(j) heteroaryl substituted with X and Y,
(k) heterocycloalkyl,
(l) $arylS(O)_n$, wherein aryl is substituted with X and Y,
(m) $R^3-C(O)-NR^3-$,
(n) $R^3R^3N-C(O)-$,
(o) $-CO_2H$,
(p) -vinylidene,
(q) $R^3-C(O)-$,
(r) $R^2O-C(O)-O-$,
(s) $R^3R^3N-C(O)-O-$, and
(t) $R^2O-C(O)-NR^3-$;
(5) aryl substituted with X and Y;
(6) heteroaryl substituted with X and Y;

(7) $C_{2-20}$ alkenyl wherein alkenyl contains one, two or three double bonds;
(8) substituted $C_{2-20}$ alkenyl wherein alkenyl contains one, two or three double bonds and wherein one or more of the carbons is substituted with:
  (a) halogen,
  (b) hydroxy,
  (c) $R^3R^3N-$,
  (d) $R^2O-$,
  (e) $R^2O-C(O)-$,
  (f) $R^3-C(O)-O-$,
  (g) oxo,
  (h) $C_{3-10}$cycloalkyl,
  (i) aryl substituted with X and Y,
  (j) heteroaryl substituted with X and Y,
  (k) heterocycloalkyl,
  (l) arylS(O)$_n$, wherein aryl is substituted with X and Y,
  (m) $R^3-C(O)-NR^3-$,
  (n) $R^3R^3N-C(O)-$,
  (o) $-CO_2H$,
  (p) -vinylidene,
  (q) $R^3-C(O)-$,
  (r) $R^2O-C(O)-O-$,
  (s) $R^3R^3N-C(O)-O-$, and
  (t) $R^2O-C(O)-NR^3-$;
(9) $C_{2-20}$alkenyl wherein alkenyl contains one, two or three double bonds and one or more of the non-olefinic carbons is replaced by $-NR^3-$, $-O-$ or $-S(O)_n-$;
(10) substituted $C_{2-20}$alkenyl wherein alkenyl contains one, two or three double bonds and one or more of the nonolefinic carbons is replaced by $-NR^3-$, $-O-$ or $-S(O)_n-$ and wherein one or more carbon substitutents is selected from:
  (a) halogen,
  (b) hydroxy,
  (c) $R^3R^3N-$,
  (d) $R^2O-$,
  (e) $R^2O-C(O)-$,
  (f) $R^3-C(O)-O-$,
  (g) oxo,
  (h) $C_{3-10}$cycloalkyl,
  (i) aryl substituted with X and Y,
  (j) heteroaryl substituted with and Y,
  (k) heterocycloalkyl,
  (l) arylS(O)$_n$, wherein aryl is substituted with X and Y,
  (m) $R^3-C(O)-NR^3-$,
  (n) $R^3R^3N-C(O)-$,
  (o) $-CO_2H$,
  (p) -vinylidene,
  (q) $R^3-C(O)-$,
  (r) $R^2O-C(O)-O-$,
  (s) $R^3R^3N-C(O)-O-$, and
  (t) $R^2O-C(O)-NR^3-$; and
(11) hydrogen;

$R^5$ is selected from the group consisting of:
(1) hydrogen;
(2) $C_{1-10}$alkyl;
(3) aryl substituted with X and Y;
(4) aryl$C_{1-4}$alkyl, wherein aryl is substituted with X and Y;
(5) $R^2O-C(O)-$;
(6) $C_{3-10}$cycloalkyl;
(7) $R^2-C(O)-$; and
(8) $R^3R^3N-C(O)-$;

$R^6$ and $R^{6a}$ are each independently selected from the group consisting of:
(1) $C_{1-20}$alkyl;
(2) substituted $C_{1-20}$alkyl in which one or more substituents is selected from:
  (a) halogen,
  (b) hydroxy,
  (c) $R^3R^3N-$,
  (d) $R^2O-$,
  (e) $R^2O-C(O)-$,
  (f) $R^3-C(O)-O-$,
  (g) oxo,
  (h) $C_{3-10}$cycloalkyl,
  (i) aryl substituted with X and Y,
  (j) heteroaryl substituted with X and Y,
  (k) heterocycloalkyl,
  (l) aryl S(O)$_n$, wherein aryl is substituted with X and Y,
  (m) $R^3-C(O)-NR^3-$,
  (n) $R^3R^3N-C(O)-$,
  (o) $-CO_2H$,
  (p) -vinylidene,
  (q) $R^3-C(O)-$,
  (r) $R^2O-C(O)-O-$,
  (s) $R^3R^3NOC(O)-O-$, and
  (t) $R^2O-C(O)-NR^3-$;
(3) $C_{1-20}$alkyl wherein one or more of the carbons is replaced by $-NR^3-$, $-O-$, or $-S(O)_n-$;
(4) substituted $C_{1-20}$alkyl wherein one or more of the carbons is replaced by $-NR^3-$, $-O-$ or $-S(O)_n-$ and wherein one or more carbon substituents is selected from:
  (a) halogen,
  (b) hydroxy,
  (c) $R^3R^3N-$,
  (d) $R^2O-$,
  (e) $R^2O-C(O)-$,
  (f) $R^3-C(O)-O-$,
  (g) oxo,
  (h) $C_{3-10}$cycloalkyl,
  (i) aryl substituted with X and Y,
  (j) heteroaryl substituted with X and Y,
  (k) heterocycloalkyl,
  (l) arylS(O)$_n-$, wherein aryl is substituted with X and Y,
  (m) $R^3-C(O)-NR^3-$,
  (n) $R^3R^3N-C(O)-$,
  (o) $-CO_2H$,
  (p) -vinylidene,
  (q) $R^3-C(O)-$,
  (r) $R^2O-C(O)-O-$,
  (s) $R^3R^3N-C(O)-O-$, and
  (t) $R^2O-C(O)-NR^3-$;
(5) $C_{2-20}$alkenyl wherein alkenyl contains one, two or three double bonds;
(6) substituted $C_{2-20}$alkenyl wherein alkenyl contains one, two or three double bonds and wherein or more of the carbons is substituted with:
  (a) halogen
  (b) hydroxy,
  (c) $R^3R^3N-$,
  (d) $R^2O-$,
  (e) $R^2O-C(O)-$,
  (f) $R^3-C(O)-O-$,
  (g) oxo,
  (h) $C_{3-10}$cycloalkyl,
  (i) aryl substituted with X and Y, (j) heteroaryl substituted with X and Y,
(k) heterocycloalkyl,
(l) arylS(O)$_n$—, wherein aryl is substituted with X and Y,
(m) R$^3$—C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$N—C(O)—O—, and
(t) R$^2$O—C(O)—NR$^3$—;
(7) C$_{2-20}$alkenyl wherein alkenyl contains one, two or three double bonds and one or more of the non-olefinic carbons is replaced by —NR$^3$—, —O— or —S(O)$_n$—;
(8) substituted C$_{2-20}$alkenyl wherein alkenyl contains one, two or three double bonds and one or more of the nonolefinic carbons is replaced by —NR$^3$—, —O— or —S(O)$_n$— and wherein one or more carbon substituents is selected from:
(a) halogen
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) arylS(O)$_n$—, wherein aryl is substituted with X and Y,
(m) R$^3$—C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$N—C(O)—O—, and
(t) R$^2$O—C(O)—NR$^3$—;
(9) C$_{2-20}$alkynyl 1 wherein alkynyl contains one, two or three triple bonds;
(10) substituted C$_{2-20}$alkynyl wherein alkynyl contains one, two or three triple bond s and wherein one or more of the carbons is substituted with:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) arylS(O)$_n$—, wherein aryl is substituted with X and Y,
(m) R$^3$—C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$N—C(O)—O—, and
(t) R$^2$O—C(O)—NR$^3$—;
(11) C$_{2-20}$alkynyl wherein alkynyl contains one, two or three triple bonds and one or more of the saturated carbons is replaced by —NR$^3$—, —O— or —S(O)$_n$—;
(12) substituted C$_{2-20}$alkynyl wherein alkynyl contains one, two or three triple bonds and one or more of the saturated carbons is replaced by —NR$^3$—, —O— or —S(O)$_n$— and wherein one or more carbon substitutents is selected from:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl-,
(i) aryl substituted with X and Y,
(j) heteroaryl substituted with X and Y,
(k) heterocycloalkyl,
(l) arylS(O)$_n$—, wherein aryl is substituted with X and Y,
(m) R$^3$—C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$N—C(O)—O—, and
(t) R$^2$O—C(O)—NR$^3$—;
(13) aryl substituted with X and Y;
(14) Heteroaryl substituted with X and Y;
(15) C$_{3-5}$ cycloalkyl;
(16) substituted C$_{3-5}$ cycloalkyl in which one or more of the substituents is selected from:
(a) R$^3$O—, and
(b) R$^3$R$^3$N—; and
(17) hydrogen;
aryl is phenyl with X and Y substitution
heteroaryl including X, Y substitution is selected from:

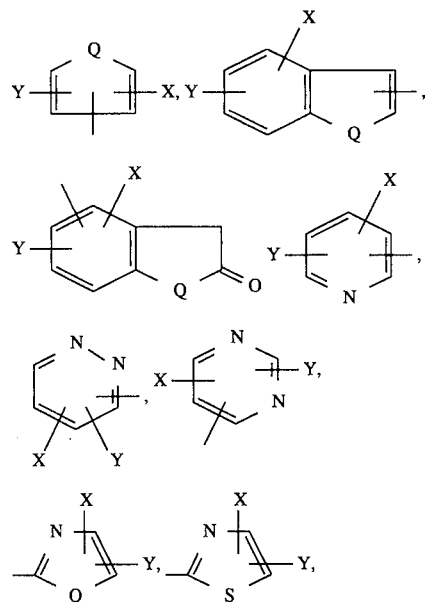

-continued

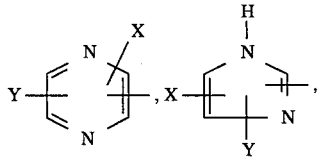

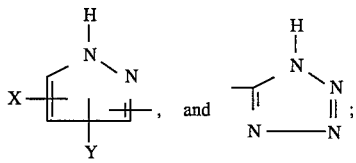

wherein:

Q is —NR$^3$, —O— or —S—;

heterocycloalkyl is selected from:

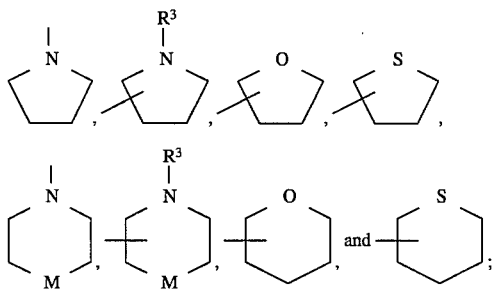

wherein:

M is —NR$^3$, —O—, —S— or —CH$_2$—

X and Y are each independently selected from:
(1) hydrogen;
(2) hydroxy;
(3) halogen;
(4) trifluoromethyl;
(5) C$_{1-10}$alkyl;
(6) aryl substituted with X$^1$ and Y$^1$;
(7) R$^2$O—;
(8) arylcarbonyloxy-, wherein aryl is substituted with X$^1$ and Y$^1$;
(9) R$^3$—C(O)—O—;
(10) —CO$_2$R$^2$;
(11) —CO$_2$H; and
(12) nitro;

X$^1$ and Y$^1$ are each independently selected from:
(1) hydrogen;
(2) hydroxy;
(3) halogen;
(4) trifluoromethyl;
(5) C$_{1-4}$alkyl;
(6) R$^2$O—;
(7) R$^3$—C(O)—O—;
(8) —CO$_2$R$^2$;
(10) —CO$_2$H; and
(11) nitro;

n is 0, 1 or 2;

Z$^1$, Z$^2$ and Z$^3$ are each independently selected from:
(1) —OR$^{6a}$;
(2) —SR$^{6a}$; and
(3) —NR$^{6a}$R$^{6a}$;

provided that when R$^5$ and R$^6$ are H and Z$^1$, Z$^2$ and Z$^3$ are each OH or OCH$_3$, then R$^1$ and R$^4$—(A)$_a$— are not both respectively

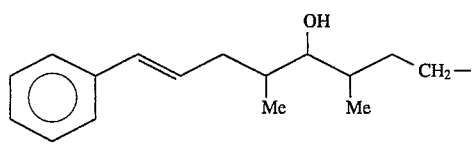 (i)

and

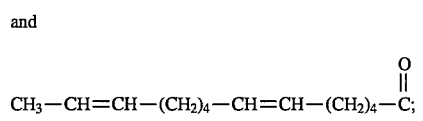

or

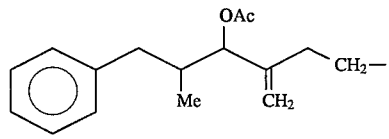 (ii)

and

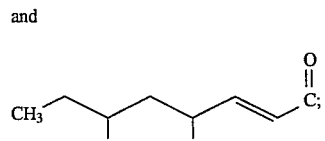

or

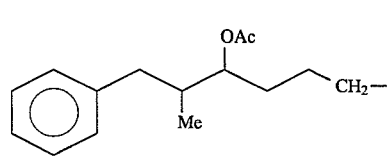 (iii)

and

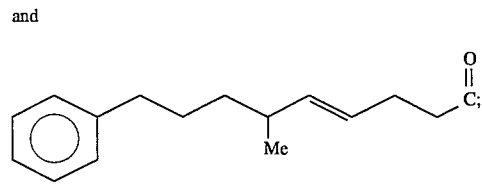

or

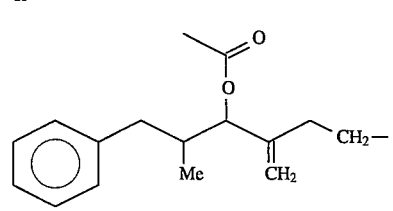 (iv)

and

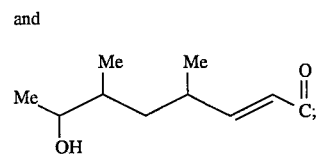

or a pharmaceutically acceptable salt of formula (I).

In a further class of this embodiment are those compounds of formula (I) wherein:

R$^1$ is selected from the group consisting of:
(1) C$_{2-16}$alkyl;
(2) substituted C$_{2-16}$alkyl in which one or more substituents is selected from:
(a) hydroxy,
(b) R$^2$O—,
(c) R$^2$O—C(O)—,
(d) R$^3$—C(O)—O—,
(e) oxo, (f) $C_{3-10}$cycloalkyl,
(g) aryl substituted with X and Y,
(h) $R^3R^3N$—C(O)—,
(i) —$CO_2H$,
(j) -vinylidene,
(k) $R^3$—C(O)—,
(l) $R^2O$—C(O)—O—, and
(m) $R^3R^3N$—C(O)—O—;

(3) $C_{2-16}$alkyl wherein one of the carbons is replaced by —$NR^3$—, —O—, or —$S(O)_n$—;

(4) substituted $C_{2-16}$alkyl wherein one of the carbons is replaced by —$NR^3$—, —O— or —$S(O)_n$— and wherein one or more carbon substituents is selected from:
(a) hydroxy,
(b) $R^2O$—,
(c) $R^2O$—C(O)—,
(d) $R^3$—C(O)—O—,
(e) oxo,
(f) $C_{3-10}$cycloalkyl,
(g) aryl substituted with X and Y,
(h) $R^3R^3N$—C(O)—,
(i) —$CO_2H$,
(j) -vinylidene,
(k) $R^3$—C(O)—,
(l) $R^2O$—C(O)—O—, and
(m) $R^3R^3N$—C(O)—O—;

(5) $C_{2-16}$alkenyl wherein alkenyl contains one, two or three double bonds;

(6) substituted $C_{2-16}$alkenyl wherein alkenyl contains one, two or three double bonds and wherein one or more of the carbons is substituted with:
(a) hydroxy,
(b) $R^2O$—,
(c) $R^2O$—C(O)—,
(d) $R^3$—C(O)—O—,
(e) oxo,
(f) $C_{3-10}$cycloalkyl,
(g) aryl substituted with X and Y,
(h) $R^3R^3N$—C(O)—,
(i) —$CO_2H$,
(j) -vinylidene,
(k) $R^3$—C(O)—,
(l) $R^2O$—C(O)—O—, and
(m) $R^3R^3N$—C(O)—O—;

(7) $C_{2-16}$alkenyl wherein alkenyl contains one, two or three double bonds and one or more of the nonolefinic carbons is replaced by —$NR^3$—, —O— or —$S(O)_n$—; and (8) substituted $C_{2-16}$alkenyl wherein alkenyl contains one, two or three double bonds and one or more of the nonolefinic carbons is replaced by —$NR^3$, —O— or —$S(O)_n$— and wherein one or more carbons substituents is selected from:
(a) hydroxy,
(b) $R^2O$—,
(c) $R^2O$—C(O)—,
(d) $R^3$—C(O)—O—,
(e) oxo,
(f) $C_{3-10}$cycloalkyl,
(g) aryl substituted with X and Y,
(h) $R^3R^3N$—C(O)—,
(i) —$CO_2H$,
(j) -vinylidene,
(k) $R^3$—C(O)—,
(l) $R^2O$—C(O)—O—, and
(m) $R^3R^3N$—C(O)—O—;

Each $R^2$ is independently selected from:
(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl; and
(8) aryl$C_{2-10}$alkenyl wherein aryl is substituted with X and Y;

Each $R^3$ is independently selected from:
(1) $C_{1-10}$alkyl;
(2) aryl substituted with X and Y;
(3) aryl$C_{1-4}$alkyl wherein aryl is substituted with X and Y;
(4) heteroaryl wherein heteroaryl is substituted with X and Y;
(5) heteroaryl$C_{1-4}$alkyl- wherein heteroaryl is substituted with X and Y;
(6) heterocycloalkyl$C_{1-4}$alkyl-;
(7) $C_{2-10}$alkenyl;
(8) aryl$C_{2-10}$alkenyl wherein aryl is substituted with X and Y; and
(9) hydrogen;

$R^4$ is selected from the group consisting of:
(1) $C_{1-20}$alkyl;
(2) substituted $C_{1-20}$alkyl in which one or more substituents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl,
(i) aryl substituted with X and Y,
(j) heteroaryl substituted with X and Y,
(k) heterocycloalkyl,
(l) aryl$S(O)_n$, wherein aryl is substituted with X and Y,
(m) $R^3$—C(O)—$NR^3$—,
(n) $R^3R^3N$—C(O)—,
(o) —$CO_2H$,
(p) -vinylidene,
(q) $R^3$—C(O)—,
(r) $R^2O$—C(O)—O—,
(s) $R^3R^3N$—C(O)—O—, and
(t) $R^2O$—C(O)—$NR^3$—;

(3) $C_{1-20}$alkyl wherein one or more of the carbons is replaced by —$NR^3$—, —O—, or —$S(O)_n$—;

(4) substituted $C_{1-20}$alkyl wherein one or more of the carbons is replaced by —$NR^3$—, —O— or —$S(O)_n$— and wherein one or more carbon substituents is selected from:
(a) halogen,
(b) hydroxy,
(c) $R^3R^3N$—,
(d) $R^2O$—,
(e) $R^2O$—C(O)—,
(f) $R^3$—C(O)—O—,
(g) oxo,
(h) $C_{3-10}$cycloalkyl,
(i) aryl substituted with X and Y, (j) heteroaryl substituted with X and Y,
(k) heterocycloalkyl,
(l) arylS(O)$_n$, wherein aryl is substituted with X and Y,
(m) R$^3$—C(O)—NR$^3$—,
(n) R$^3$R$^3$N—C(O)—;
(o) —CO$_2$H,
(p) -vinylidene,
(q) R$^3$—C(O)—,
(r) R$^2$O—C(O)—O—,
(s) R$^3$R$^3$N—C(O)—O—, and
(t) R$^2$O—C(O)—NR$^3$—;
(5) aryl substituted with X and Y;
(6) C$_{2-20}$ alkenyl wherein alkenyl contains one, two or three double bonds;
(7) substituted C$_{2-20}$ alkenyl wherein alkenyl contains one, two or three double bonds and wherein one or more of the carbons is substituted with:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) R$^3$—C(O)—NR$^3$—,
(n) R$^3$R$^3$N—C(O)—,
(o) —CO$_2$H,
(p) -vinylidene,
(q) R$^3$—C(O)—,
(r) R$^2$O—C(O)—O—,
(s) R$^3$R$^3$N—C(O)—O—, and
(t) R$^2$O—C(O)—NR$^3$—; and
(8) hydrogen;

R$^5$ is selected from the group consisting of:
(1) hydrogen;
(2) C$_{1-3}$alkyl; and
(3) R$^2$—C(O)—;

R$^6$ is selected from the group consisting of:
(1) C$_{1-20}$alkyl;
(2) substituted C$_{1-20}$alkyl in which one or more substituents is selected from:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) R$^3$—C(O)—NR$^3$—,
(m) R$^3$R$^3$N—C(O)—,
(n) —CO$_2$H, and
(o) R$^2$O—C(O)—NR$^3$—;
(3) C$_{1-20}$alkyl wherein one or more of the carbons is replaced by —NR$^3$—, —O—, or —S(O)$_n$—;
(4) substituted C$_{1-20}$alkyl wherein one or more of the carbons is replaced by —NR$^3$—, —O—, or —S(O)$_n$— and wherein one or more carbon substituents is selected from:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) R$^3$—C(O)—NR$^3$—,
(m) R$^3$R$^3$N—C(O)—,
(n) —CO$_2$H, and
(o) R$^2$O—C(O)—NR$^3$—;
(5) C$_{2-20}$alkenyl wherein alkenyl contains one or more double bonds;
(6) substituted C$_{2-20}$alkenyl wherein alkenyl contains one or more double bonds and wherein one or more of the carbons is substituted with:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with and Y,
(k) heterocycloalkyl,
(l) R$^3$—C(O)—NR$^3$—,
(m) R$^3$R$^3$N—C(O)—,
(n) —CO$_2$H, and
(o) R$^2$O—C(O)—NR$^3$—;
(7) C$_{2-20}$alkynyl wherein alkynyl contains one or more triple bonds;
(8) substituted C$_{2-20}$alkynyl wherein alkynyl contains one or more triple bonds and wherein one or more of the carbons is substituted with:
(a) halogen,
(b) hydroxy,
(c) R$^3$R$^3$N—,
(d) R$^2$O—,
(e) R$^2$O—C(O)—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) R$^3$—C(O)—NR$^3$—,
(m) R$^3$R$^3$N—C(O)—;
(n) —CO$_2$H, and
(o) R$^2$O—C(O)—NR$^3$—;
(9) aryl substituted with X and Y;
(10) heteroaryl substituted with X and Y;
(11) C$_{3-5}$ cycloalkyl;
(12) substituted C$_{3-5}$ cycloalkyl in which one or more of the substituents is selected from:
(a) R$^3$O—, and
(b) R$^3$R$^3$N—; and
(13) hydrogen;

aryl is phenyl with X and Y substitution heteroaryl including X, Y substitution is:

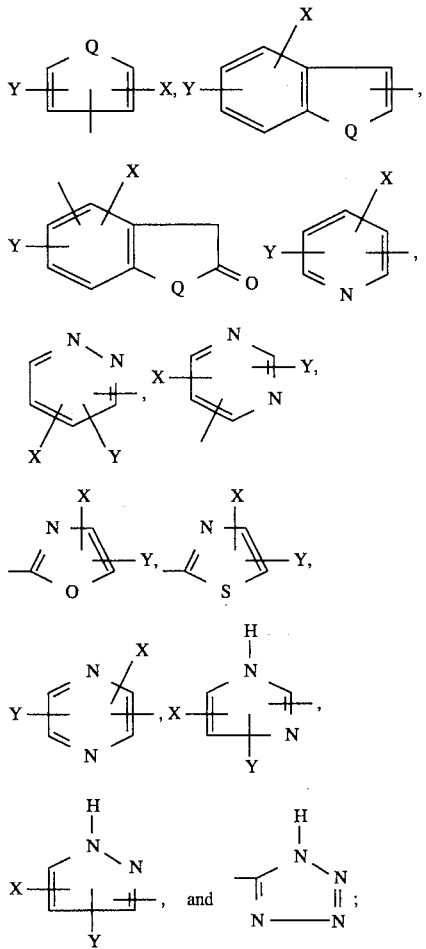

wherein:

Q is —NR³, —O— or —S—;

heterocycloalkyl is:

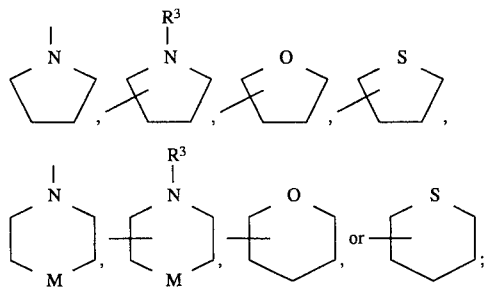

wherein:

M is —NR³, —O—, —S— or —CH₂—

X and Y are each independently selected from:
(1) hydrogen;
(2) hydroxy;
(3) halogen;
(4) trifluoromethyl;
(5) $C_{1-10}$alkyl;
(6) aryl substituted with $X^1$ and $Y^1$;
(7) $R^2O—$;
(8) arylcarbonyloxy-, wherein aryl is substituted with $X^1$ and $Y^1$;
(9) $R^3$—C(O)—O—;
(10) —CO₂R²;
(11) —CO₂H; and
(12) nitro;

$X^1$ and $Y^1$ are each independently selected from:
(1) hydrogen;
(2) hydroxy;
(3) halogen;
(4) trifluoromethyl;
(5) $C_{1-4}$alkyl;
(6) $R^2O—$;
(7) $R^3$—C(O)—O—;
(8) —CO₂R²;
(10) —CO₂H; and
(11) nitro;

n is 0, 1 or 2;

$Z^1$, $Z^2$ and $Z^3$ are each independently selected from:
(1) —OR⁶;
(2) —SR⁶; and
(3) —NR⁶R⁶;

provided that when $Z^1$, $Z^2$ and $Z^3$ are each OH or OCH₃, then $R^1$ and $R^4$—(A)$_a$— are not both respectively

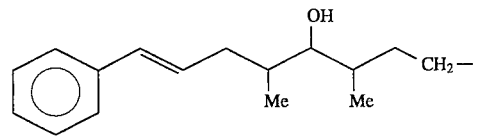

and

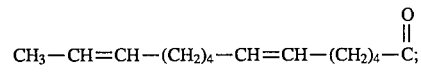

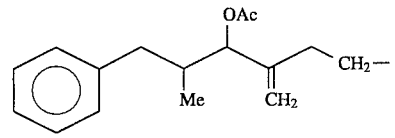

and

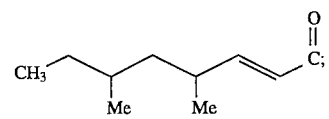

or

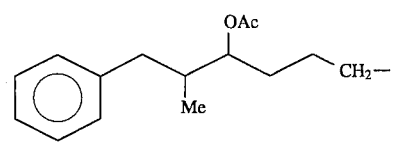

and

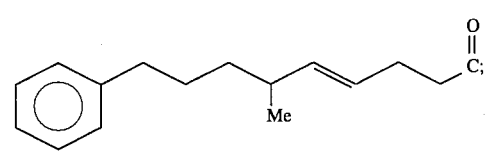

or

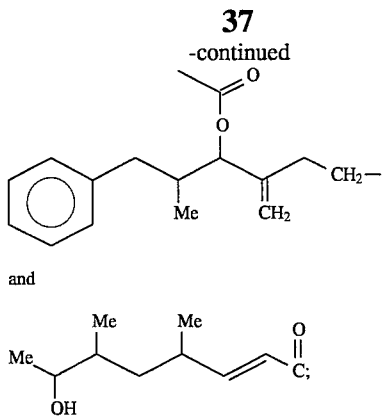

and or a pharmaceutically acceptable salt.

(iv) Except where specifically defined to the contrary the terms alkyl, alkenyl, alkynyl, alkoxy and acyl include both the straight-chain and-branched chain species of the term. The term cycloalkyl includes both monocyclic and polycyclic species. Where two Markush groups are bonded to the same atom, e.g. $R^3R^3N$, these groups may take on the same value e.g. $(CH_3)_2N$ or different values within the markush group, e.g. $CH_3NH$. Similarly each Markush group, such as $R^3$, within a compound of formula (I) is selected independently, e.g. $R^3R^3N-$ may be $NH_2$ while $R^3-C(O)-O-$ is $CH_3-C(O)-O-$.

One subclass of this embodiment is the compounds of formula I with subgeneric formula (II) and wherein $R^4-(A)_a$ and $R^6$ are selected from the group described in Table 1 below:

TABLE 1

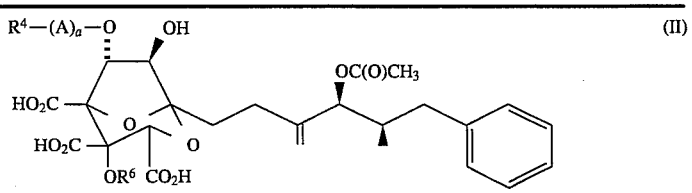

(II)

| Compound # | $R^4-(A)_a-$ | $R^6$ |
|---|---|---|
| 5a | $CH_3(CH_2)_6CO$ | H |
| 5b | $CH_3CO$ | H |
| 5c | $CH_3(CH_2)_{10}CO$ | H |
| 5d | $CH_3(CH_2)_{12}CO$ | H |
| 5e | $CH_3(CH_2)_5-CH=CH(CH_2)_7CO$ | H |
| 5f | $CH_3(CH_2)_{14}CO$ | H |
| 5g | $PhO(CH_2)_{10}CO$ | H |
| 5h | $CH_3(CH_2)_6\text{-}p\text{-}C_6H_4-CO$ | H |
| 5i | $Ph(CH_2)_{10}CO$ | H |
| 5j | $Ph(CH_2)_3CO$ | H |
| 5k | 1-adamantyl$CH_2CO$ | H |
| 5l | $CH_3(CH_2)_7NHCO$ | H |
| 5m | $CH_3(CH_2)_9NHCO$ | H |
| 5n | $CH_3(CH_2)_{10}NHCO$ | H |
| 5o | $CH_3(CH_2)_{11}NHCO$ | H |
| 5p | $CH_3(CH_2)_{12}NHCO$ | H |
| 5q | $CH_3(CH_2)_{13}NHCO$ | H |
| 5r | $CH_3(CH_2)_{15}NHCO$ | H |
| 5s | $PhCH_2NHCO$ | H |
| 5t | $4\text{-}Ph\text{-}Ph-NHCO$ | H |
| 5u | $PhO(CH_2)_{11}NHCO$ | H |
| 5v | $CH_3(CH_2)_{11}N(CH_3)CO$ | H |
| 5w | $CH_3(CH_2)_{15}N(CH_3)CO$ | H |
| 5x | $CH_3(CH_2)_{11}OCO$ | H |
| 5y | $PhO(CH_2)_{11}OCO$ | H |
| 5z | $PhO(CH_2)_8$ | H |
| 5a' | H | $PhO(CH_2)_8$ |
| 5b' | $PhO(CH_2)_8$ | $PhO(CH_2)_8$ |
| 5c' | $PhO(CH_2)_{11}$ | H |
| 5d' | H | $PhO(CH_2)_{11}$ |
| 5e' | $PhO(CH_2)_{11}$ | $PhO(CH_2)_{11}$ |
| 5f' | $CH_3(CH_2)_{13}$ | H |
| 5g' | $CH_3(CH_2)_{15}$ | H |
| 5h' | $2\text{-}Ph-C_6H_4-CH_2$ | H |
| 5p' | $CH_3CH_2CO$ | H |
| 5q' | $CH_3(CH_2)_2CO$ | H |
| 5r' | $(CH_3)_2CHCO$ | H |
| 5s' | $(S)\text{-}CH_3CH_2CH(CH_3)CO$ | H |
| 5t' | $CH_3O(CH_2)_3CO$ | H |
| 5u' | $CH_3(CH_2)_3CO$ | H |
| 5v' | $(CH_3)_2CHCH_2CO$ | H |
| 5w' | $(CH_3)_2CH(CH_2)_2CO$ | H |
| 5x' | $CH_3CH_2CH_2CH(CH_3)CO$ | H |
| 5y' | $CH_3CH_2CH(CH_3)CH_2CO$ | H |
| 5z' | $H_2N(CH_2)_5CO$ | H |
| 5a" | $CH_3(CH_2)_8CH(CH_3)CO$ | H |
| 5b" | cyclohexyl-$CH_2CO$ | H |
| 5c" | $C_6H_5CH_2CO$ | H |

TABLE 1-continued $$R^4-(A)_a-O \quad\text{structure (II)}$$

| Compound # | $R^4-(A)_a-$ | $R^6$ |
|---|---|---|
| 5d" | $C_6H_5OCH_2CO$ | H |
| 5e" | $C_6H_5CH_2CH_2CO$ | H |
| 5f" | $C_6H_5OCH_2CH_2CO$ | H |
| 5g" | $C_6H_5O(CH_2)_3CO$ | H |
| 5h" | $4\text{-}(CH_3CO)\text{-}C_6H_4(CH_2)_{10}CO$ | H |
| 5i" | $\underline{E}\text{-}C_6H_5CH=CHCO$ | H |
| 5j" | $\underline{E}\text{-}(3\text{-}CH_3O)C_6H_4CH=CHCO$ | H |
| 5k" | $4\text{-}(C_6H_5)\text{-}C_6H_4CO$ | H |
| 5l" | $4\text{-}(C_6H_5)\text{-}C_6H_4CH_2CO$ | H |
| 5m" | $4\text{-}(C_6H_5\text{-}O)\text{-}C_6H_4CH_2CO$ | H |
| 5n" | $3\text{-}(C_6H_5\text{-}O)\text{-}C_6H_4CH_2CO$ | H |
| 5o" | $C_6H_5\text{-}CH_2CH(NH_2)CO$ | H |
| 5p" | $Br(CH_2)_{10}CO$ | H |
| 5q" | $4\text{-}(CH_3O)C_6H_4O(CH_2)_{10}CO$ | H |
| 5r" | $3\text{-}((CH_3)_2N)C_6H_5O(CH_2)_{10}CO$ | H |
| 5s" | $4\text{-}((CH_3)_2N)C_6H_4S(CH_2)_{10}CO$ | H |
| 5t" | $CH_3NHCO$ | H |
| 5u" | $(CH_3)_2NCO$ | H |
| 5v" | $CH_3CH_2NHCO$ | H |
| 5w" | $(CH_3)_2NCH_2CH_2NHCO$ | H |
| 5x" | $(CH_3)_2CHNHCH_2CH_2NHCO$ | H |
| 5y" | $CH_3CH_2CH_2NHCO$ | H |
| 5z" | $(CH_3)_2CHNHCO$ | H |
| 5a''' | cyclopropyl-NHCO | H |
| 5b''' | $CH_3CH_2CH_2CH_2NHCO$ | H |
| 5c''' | $(CH_3)_2CHCH_2NHCO$ | H |
| 5d''' | $(R)\text{-}CH_3CH_2CH(CH_3)NHCO$ | H |
| 5e''' | $(S)\text{-}CH_3CH_2CH(CH_3)NHCO$ | H |
| 5f''' | $(CH_3(CH_2)_3)(CH_3(CH_2)_6)CHO(CH_2)_3NHCO$ | H |
| 5g''' | $CH_3(CH_2)_{11}O(CH_2)_3NHCO$ | H |
| 5h''' | $4\text{-}(CH_3O)C_6H_4CH_2NHCO$ | H |
| 5i''' | $4\text{-}(CH_3SO_2)C_6H_4CH_2NHCO$ | H |
| 5j''' | $C_6H_5CH_2CH_2NHCO$ | H |
| 5k''' | $C_6H_5OCH_2CH_2NHCO$ | H |
| 5l''' | $C_6H_5(CH_2)_8NHCO$ | H |
| 5m''' | adamantyl-$CH_2NHCO$ | H |
| 5n''' | $(CH_3)_2CHOCO$ | H |
| 5o''' | $CH_3(CH_2)_9OCO$ | H |
| 5p''' | $CH_2(CH_2)_3O(CH_2)_2O(CH_2)_2O(CH_2)_2OCO$ | H |
| 5q''' | $3,4\text{-}(CH_3O)_2C_6H_3O(CH_2)_{10}$ | H |
| 5r''' | $CH_3(CH_2)_2$ | H |
| 5s''' | H | $CH_3(CH_2)_2$ |
| 5t''' | $CH_3(CH_2)_2$ | $CH_3(CH_2)_2$ |
| 5aa | cyclopropyl-CO— | H |
| 5ab | 1-methylcyclopropyl-CO— | H |
| 5ac | $(3\text{-}CF_3)\text{-}PhCH_2CO$— | H |
| 5ad | 4-pyridylthio-$CH_2CO$— | H |
| 5ae | 3-indolyl-$CH_2CO$— | H |
| 5af | furyl-$CH_2CO$— | H |
| 5ag | $Ph(CH_2)_4CO$— | H |
| 5ah | $(Ph)_2CHCH_2CO$ | H |
| 5ai | $CH_3(CH_2)_{11}\text{-}o\text{-}C_6H_4\text{-}CH_2CO$— | H |
| 5aj | PhCO— | H |
| 5ak | $PhO(CH_2)_{11}CO$— | H |
| 5al | $PhS(CH_2)_{10}CO$— | H |
| 5am | $PhS(O)(CH_2)_{10}CO$— | H |
| 5an | $PhS(O)_2(CH_2)_{10}CO$— | H |
| 5ao | $CH_3(CH_2)_4CO$— | H |
| 5ap | $CH_3C(O)(CH_2)_2CO$— | H |
| 5aq | $HO_2C\text{-}(CH_2)_2CO$— | H |
| 5ar | $H_2C=CHCO$— | H |
| 5as | $H_2C=C(CH_3)CO$— | H |
| 5at | $H_2N\text{-}(CH_2)_{10}CO$— | H |
| 5au | $H_2N\text{-}CH_2CO$— | H |
| 5av | $CH_3C(O)NHCH_2CO$— | H |
| 5aw | $CH_2=C(CH_3)CH_2CO$— | H |
| 5ax | $(CH_3)_2C=CHCO$— | H |
| 5ay | $CH_3CH=CHCO$— | H |

TABLE 1-continued (II) Structure with $R^4-(A)_a-O$, OH, $HO_2C$, $HO_2C$, $OR^6$, $CO_2H$, O, $OC(O)CH_3$, phenyl group.

| Compound # | $R^4-(A)_a-$ | $R^6$ |
|---|---|---|
| 5az | $CH_2=CH-CH_2CO-$ | H |
| 5ba | $(CH_3)_2CHCH(NH_2)CO-$ | H |
| 5bb | $(CH_3)(NH_2)CHCO-$ | H |
| 5bc | $CH_3C(O)-NH-CH(CH_3)CO-$ | H |
| 5bd | cyclobutyl-CO— | H |
| 5be | $(CH_3)_3C-CO-$ | H |
| 5bf | $CH_3-O-CO-$ | H |
| 5ca | cyclopropyl-$CH_2$NHCO— | H |
| 5cb | 3-pyridinyl-$CH_2$NHCO— | H |
| 5cc | 1-imidazolyl-$(CH_2)_3$NHCO— | H |
| 5cd | N-morpholinyl-$(CH_2)_2$NHCO— | H |
| 5ce | 4-piperidinyl-$CH_2$NHCO— | H |
| 5cf | 2-tetrahydropyranyl-$CH_2$NHCO— | H |
| 5cg | cyclobutyl-NHCO— | H |
| 5ch | $CH_3-O-NHCO-$ | H |
| 5ci | $CH_2=CHCH_2NHCO-$ | H |
| 5cj | PhNHCO— | H |
| 5ck | furfuryl-NHCO— | H |
| 5cl | $(CH_3)CH-NHCS-$ | H |
| 5da | H | $CH_3(CH_2)_{13}-$ |
| 5db | $CH_3(CH_2)_{13}-$ | $CH_3(CH_2)_{13}-$ |
| 5dc | $CH_3(CH_2)_{11}-$ | H |
| 5dd | H | $CH_3(CH_2)_{11}-$ |
| 5de | $CH_3(CH_2)_{11}-$ | $CH_3(CH_2)_{11}-$ |
| 5df | $CH_3(CH_2)_9-$ | H |
| 5dg | H | $CH_3(CH_2)_9-$ |
| 5dh | $CH_3(CH_2)_9-$ | $CH_3(CH_2)_9-$ |
| 5di | $HO_2C-(CH_2)_{10}-$ | H |
| 5dj | H | $HO_2C-(CH_2)_{10}-$ |
| 5dk | $HO_2C-(CH_2)_{10}-$ | $HO_2C-(CH_2)_{10}-$ |
| 5dl | $CH_3(CH_2)_3-$ | H |
| 5dm | $(CH_3)_2CHCH_2-$ | H |
| 5dn | $CH_3(CH_2)_4-$ | H |
| 5do | $(CH_3)_2CH(CH_2)_2-$ | H |

Further exemplifying this subclass are those compounds of formula (II), which may be prepared following Schemes A, G, H and I and analogous procedures to those of Compounds 5a to 5y and 5p' to 5p''' and 5aa to 5cl and wherein $R^6$ is H and $R^4-(A)_a-$ is selected from the group consisting of:

$HO_2C(CH_2)_{15}-CO$
$HO_2C-(CH_2)_{10}CO$
$HO_2C(CH_2)_5CO$
$HO_2C(CH_2)_{15}-NHCO$
$HO_2C(CH_2)_{10}-NHCO$
$HO_2C(CH_2)_5NHCO$
$HO_2C(CH_2)_{15}-OCO$
$HO_2C-(CH_2)_{10}-OCO$
$HO_2C(CH_2)_5-OCO$
$HO(CH_2)_{15}-CO$
$HO-(CH_2)_{10}CO$
$HO(CH_2)_5CO$
$HO-(CH_2)_{15}-NHCO$
$HO-(CH_2)_{10}NHCO$
$HO(CH_2)_5NHCO$
$HO(CH_2)_{15}-OCO$
$HO-(CH_2)_{10}-OCO$
$HO(CH_2)_5-OCO$
$CH_3O(CH_2)_{15}-CO$
$CH_3O-(CH_2)_{10}CO$
$CH_3O(CH_2)_5CO$
$CH_3O-(CH_2)_{15}-NHCO$
$CH_3O-(CH_2)_{10}NHCO$
$CH_3O(CH_2)_5NHCO$
$CH_3O(CH_2)_{15}-OCO$
$CH_3O-(CH_2)_{10}-OCO$
$CH_3O(CH_2)_5-OCO$
$CH_3CH_2O(CH_2)_{15}-CO$
$CH_3CH_2O-(CH_2)_{10}CO$
$CH_3CH_2O(CH_2)_5CO$
$CH_3CH_2O-(CH_2)_{15}-NHCO$
$CH_3CH_2O-(CH_2)_{10}NHCO$
$CH_3CH_2O(CH_2)_5NHCO$
$CH_3CH_2O(CH_2)_{15}-OCO$
$CH_3CH_2O-(CH_2)_{10}-OCO$
$CH_3CH_2O(CH_2)_5-OCO$
$C_6H_5O(CH_2)_{15}-CO$
$C_6H_5O(CH_2)_5CO$
$C_6H_5O-(CH_2)_{15}-NHCO$
$C_6H_5O-(CH_2)_{10}NHCO$ $C_6H_5O(CH_2)_5NHCO$
$C_6H_5O(CH_2)_{15}-OCO$
$C_6H_5O-(CH_2)_{10}-OCO$
$C_6H_5O(CH_2)_5-OCO$
$4-Cl-C_6H_4O(CH_2)_{15}-CO$
$4-Cl-C_6H_4O-(CH_2)_{10}CO$
$4-Cl-C_6H_4O(CH_2)_5CO$
$4-Cl-C_6H_4O-(CH_2)_{15}-NHCO$
$4-Cl-C_6H_4O-(CH_2)_{10}NHCO$
$4-Cl-C_6H_4O(CH_2)_5NHCO$
$4-Cl-C_6H_4O(CH_2)_{15}-OCO$
$4-Cl-C_6H_4O-(CH_2)_{10}-OCO$
$4-Cl-C_6H_4O(CH_2)_5-OCO$
$4-CH_3OC_6H_4O(CH_2)_{15}-CO$
$4-CH_3OC_6H_4O(CH_2)_5CO$
$4-CH_3OC_6H_4O-(CH_2)_{15}-NHCO$
$4-CH_3OC_6H_4O-(CH_2)_{10}NHCO$
$4-CH_3OC_6H_4O(CH_2)_5NHCO$
$4-CH_3OC_6H_4O(CH_2)_{15}-OCO$
$4-CH_3OC_6H_4O-(CH_2)_{10}-OCO$
$4-CH_3OC_6H_4O-(CH_2)_5-OCO$
$3-Cl-C_6H_4O-(CH_2)_{15}-CO$
$3-Cl-C_6H_4O-(CH_2)_5CO$
$3-Cl-C_6H_4O-(CH_2)_{10}CO$
$3-Cl-C_6H_4O-(CH_2)_{15}-NHCO$
$3-Cl-C_6H_4O-(CH_2)_{10}NHCO$
$3-Cl-C_6H_4O-(CH_2)_5NHCO$
$3-Cl-C_6H_4O-(CH_2)_{15}-OCO$
$3-Cl-C_6H_4O-(CH_2)_{10}-OCO$
$3-Cl-C_6H_4O-(CH_2)_5-OCO$
$3-CH_3OC_6H_4O-(CH_2)_{15}-CO$
$3-CH_3OC_6H_4O-(CH_2)_{10}CO$
$3-CH_3OC_6H_4O-(CH_2)_5CO$
$3-CH_3OC_6H_4O-(CH_2)_{15}-NHCO$
$3-CH_3OC_6H_4O-(CH_2)_{10}NHCO$
$3-CH_3OC_6H_4O-(CH_2)_5NHCO$
$3-CH_3OC_6H_4O-(CH_2)_{15}-OCO$
$3-CH_3OC_6H_4O-(CH_2)_{10}-OCO$
$3-CH_3OC_6H_4O-(CH_2)_5-OCO$
$C_6H_5S-(CH_2)_{15}CO$
$C_6H_5S-(CH_2)_5CO$
$C_6H_5S-(CH_2)_{15}-NHCO$
$C_6H_5S-(CH_2)_{10}NHCO$
$C_6H_5S-(CH_2)_5NHCO$
$C_6H_5S-(CH_2)_{15}-OCO$
$C_6H_5S-(CH_2)_{10}-OCO$
$C_6H_5S-(CH_2)_5-OCO$
$4-Cl-C_6H_4S-(CH_2)_{15}-CO$
$4-Cl-C_6H_4S-(CH_2)_{10}CO$
$4-Cl-C_6H_4S-(CH_2)_5CO$
$4-Cl-C_6H_4S-(CH_2)_{15}-NHCO$
$4-Cl-C_6H_4S-(CH_2)_{10}NHCO$
$4-Cl-C_6H_4S-(CH_2)_5NHCO$
$4-Cl-C_6H_4S-(CH_2)_{15}-OCO$
$4-Cl-C_6H_4S-(CH_2)_{10}-OCO$
$4-Cl-C_6H_4S-(CH_2)_5-OCO$
$4-CH_3OC_6H_4S-(CH_2)_{15}-CO$
$4-CH_3OC_6H_4S-(CH_2)_{10}CO$
$4-CH_3OC_6H_4S-(CH_2)_5CO$
$4-CH_3OC_6H_4S-(CH_2)_{15}-NHCO$
$4-CH_3OC_6H_4S-(CH_2)_{10}NHCO$
$4-CH_3OC_6H_4S-(CH_2)_5NHCO$
$4-CH_3OC_6H_4S-(CH_2)_{15}-OCO$
$4-CH_3OC_6H_4S-(CH_2)_{10}-OCO$
$4-CH_3OC_6H_4S-(CH_2)_5-OCO$
$3-Cl-C_6H_4S-(CH_2)_{15}-CO$
$3-Cl-C_6H_4S-(CH_2)_5CO$
$3-Cl-C_6H_4S-(CH_2)_{15}-NHCO$
$3-Cl-C_6H_4S-(CH_2)_{10}NHCO$
$3-Cl-C_6H_4S-(CH_2)_5NHCO$
$3-Cl-C_6H_4S-(CH_2)_{15}-OCO$
$3-Cl-C_6H_4S-(CH_2)_{10}-OCO$
$3-Cl-C_6H_4S-(CH_2)_5-OCO$
$3-CH_3OC_6H_4S-(CH_2)_{15}-CO$
$3-CH_3OC_6H_4S-(CH_2)_{10}CO$
$3-CH_3OC_6H_4S-(CH_2)_5CO$
$3-CH_3OC_6H_4S-(CH_2)_{15}-NHCO$
$3-CH_3OC_6H_4S-(CH_2)_{10}NHCO$
$3-CH_3OC_6H_4S-(CH_2)_5NHCO$
$3-CH_3OC_6H_4S-(CH_2)_{15}-OCO$
$3-CH_3OC_6H_4S-(CH_2)_{10}-OCO$
$3-CH_3OC_6H_4S-(CH_2)_5-OCO$
$O[(CH_2)_2]_2N(CH_2)_{15}-CO$
$O[(CH_2)_2]_2N-(CH_2)_{10}CO$
$O[(CH_2)_2]_2N(CH_2)_5CO$
$O[(CH_2)_2]_2N-(CH_2)_{10}NHCO$
$O[(CH_2)_2]_2N(CH_2)_5NHCO$
$O[(CH_2)_2]_2N(CH_2)_{15}-OCO$
$O[(CH_2)_2]_2N-(CH_2)_{10}-OCO$
$O[(CH_2)_2]_2N-(CH_2)_5-OCO$
$C_5H_{10}N(CH_2)_{15}-CO$
$C_5H_{10}N-(CH_2)_{10}CO$
$C_5H_{10}N(CH_2)_5CO$
$C_5H_{10}N-(CH_2)_{15}-NHCO$
$C_5H_{10}N-(CH_2)_{10}NHCO$
$C_5H_{10}N(CH_2)_5NHCO$
$C_5H_{10}N(CH_2)_{15}-OCO$
$C_5H_{10}N-(CH_2)_{10}-OCO$
$C_5H_{10}N(CH_2)_5-OCO$
$HN[(CH_2)_2]_2N(CH_2)_{15}-CO$
$HN[(CH_2)_2]_2N-(CH_2)_{10}CO$
$HN[(CH_2)_2]_2N(CH_2)_5CO$
$HN[(CH_2)_2]_2N-(CH_2)_{15}-NHCO$
$HN[(CH_2)_2]_2N-(CH_2)_{10}NHCO$
$HN[(CH_2)_2]_2N(CH_2)_5NHCO$
$HN[(CH_2)_2]_2N(CH_2)_{15}-OCO$
$HN[(CH_2)_2]_2N-(CH_2)_{10}-OCO$
$HN[(CH_2)_2]_2N(CH_2)_5-OCO$
$CH_3N[(CH_2)_2]_2N(CH_2)_{15}-CO$
$CH_3N[(CH_2)_2]_2N-(CH_2)_{10}CO$
$CH_3N[(CH_2)_2]_2N(CH_2)_5CO$
$CH_3N[(CH_2)_2]_2N-(CH_2)_{15}-NHCO$ $CH_3N[(CH_2)_2]_2N—(CH_2)_{10}NHCO$
$CH_3N[(CH_2)_2]_2N(CH_2)_5NHCO$
$CH_3N[(CH_2)_2]_2N(CH_2)_{15}—OCO$
$CH_3N[(CH_2)_2]_2N—(CH_2)_{10}—OCO$
$CH_3N[(CH_2)_2]_2N(CH_2)_5—OCO$
1-imidazolyl$(CH_2)_{15}$—CO
1-imidazolyl-$(CH_2)_{10}$CO
1-imidazolyl$(CH_2)_5$CO
1-imidazolyl-$(CH_2)_{15}$—NHCO
1-imidazolyl-$(CH_2)_{10}$NHCO
1-imidazolyl$(CH_2)_5$NHCO
1-imidazolyl$(CH_2)_{15}$—OCO
1-imidazolyl-$(CH_2)_{10}$—OCO
1-imidazolyl$(CH_2)_5$—OCO
2-imidazolyl$(CH_2)_{15}$—CO
2-imidazolyl-$(CH_2)_{10}$CO
2-imidazolyl$(CH_2)_5$CO
2-imidazolyl-$(CH_2)_{15}$—NHCO
2-imidazolyl-$(CH_2)_{10}$NHCO
2-imidazolyl$(CH_2)_5$NHCO
2-imidazolyl$(CH_2)_{15}$—OCO
2-imidazolyl-$(CH_2)_{10}$—OCO
2-imidazolyl$(CH_2)_5$—OCO Further illustrating this subclass are those compounds of the formula (II), which may be prepared following Schemes A, G, H and I and analogous procedures to those of Compounds 5z to 5h' and 5q''' to 5t''' and 5da to 5do and wherein $R^4$—$(A)_a$— is selected from the group listed below and $R^6$ is H, or $R^4$—$(A)_a$— is H and $R^6$ is selected from the group listed below, or $R^4$—$(A)_a$— and $R^6$ are the same and are selected from the group listed below.

$HO_2C(CH_2)_{15}$—
$HO_2C(CH_2)_5$—
$HO(CH_2)_{15}$—
$HO—(CH_2)_{10}$—
$HO(CH_2)_5$—
$CH_3O(CH_2)_{15}$—
$CH_3O—(CH_2)_{10}$—
$CH_3O(CH_2)_5$—
$CH_3CH_2O(CH_2)_{15}$—
$CH_3CH_2O—(CH_2)_{10}$—
$CH_3CH_2O(CH_2)_5$—
$C_6H_5O(CH_2)_{15}$—
$C_6H_5O—(CH_2)_{10}$—
$C_6H_5O(CH_2)_5$—
4-Cl—$C_6H_4O(CH_2)_{15}$—
4-Cl—$C_6H_4O—(CH_2)_{10}$—
4-Cl—$C_6H_4O(CH_2)_5$—
4-$CH_3OC_6H_4O(CH_2)_{15}$—
4-$CH_3OC_6H_4O—(CH_2)_{10}$—
4-$CH_3OC_6H_4O(CH_2)_5$—
3-Cl—$C_6H_4O(CH_2)_{15}$—
3-Cl—$C_6H_4O—(CH_2)_{10}$—
3-Cl—$C_6H_4O(CH_2)_5$—
3-$CH_3OC_6H_4O(CH_2)_{15}$—
3-$CH_3OC_6H_4O—(CH_2)_{10}$—
3-$CH_3OC_6H_4O(CH_2)_5$—
$C_6H_5S(CH_2)_{15}$—
$C_6H_5S—(CH_2)_{10}$—
$C_6H_5S(CH_2)_5$—
4-Cl—$C_6H_4S(CH_2)_{15}$—
4-Cl—$C_6H_4S—(CH_2)_{10}$—
4-Cl—$C_6H_4S(CH_2)_5$—
4-$CH_3OC_6H_4S(CH_2)_{15}$—
4-$CH_3OC_6H_4S—(CH_2)_{10}$—
4-$CH_3OC_6H_4S(CH_2)_5$—
3-Cl—$C_6H_4S(CH_2)_{15}$—
3-Cl—$C_6H_4S—(CH_2)_{10}$—
3-Cl—$C_6H_4S(CH_2)_5$—
3-$CH_3OC_6H_4S(CH_2)_{15}$—
3-$CH_3OC_6H_4S—(CH_2)_{10}$—
3-$CH_3OC_6H_4S(CH_2)_5$—
$O[(CH_2)_2]_2N(CH_2)_{15}$—
$O[(CH_2)_2]_2N—(CH_2)_{10}$—
$O[(CH_2)_2]_2N(CH_2)_5$—
$C_5H_{10}N(CH_2)_{15}$—
$C_5H_{10}N—(CH_2)_{10}$—
$C_5H_{10}N(CH_2)_5$—
$HN[(CH_2)_2]_2N(CH_2)_{15}$—
$HN[(CH_2)_2]_2N—(CH_2)_{10}$—
$HN[(CH_2)_2]_2N(CH_2)_5$—
$CH_3N[(CH_2)_2]_2N(CH_2)_{15}$—
$CH_3N[(CH_2)_2]_2N—(CH_2)_{10}$—
$CH_3N[(CH_2)_2]_2N(CH_2)_5$—
1-imidazolyl$(CH_2)_{15}$—
1-imidazolyl-$(CH_2)_{10}$—
1-imidazolyl$(CH_2)_5$—
2-imidazolyl$(CH_2)_{15}$—
2-imidazolyl-$(CH_2)_{10}$—
2-imidazolyl$(CH_2)_5$—

In a second subclass Of this embodiment are the compounds of formula (I), with subgeneric formula (III) and wherein $R^5$ and $R^6$ are selected from the group described in Table 2 below: (where $R^5$ is not associated with a particular compound number that compound may be prepared following the procedures of Schemes A to G.)

TABLE 2

(III)

[Structure of compound III shown with OR⁵, OR⁶, CO₂H, HO₂C groups, and OC(O)CH₃ substituent on a side chain ending in phenyl]

| Compound # | R⁵ | R⁶ |
|---|---|---|
| 5i' | COCH$_3$ | H |
| 5j' | COCH$_2$CH$_3$ | H |
|  | COCH(CH$_3$)$_2$ | H |
|  | CO(CH$_2$)$_3$CH$_3$ | H |
|  | COCH$_2$CH(CH$_3$)$_2$ | H |
| 5k' | COC(CH$_3$)$_3$ | H |
| 5l' | COPh | H |
| 5m' | COCH$_2$CH$_2$CH$_3$ | H |
|  | COC$_6$H$_4$-4-CH$_3$ | H |
|  | COC$_6$H$_4$-3-CH$_3$ | H |
|  | COC$_6$H$_4$-4-Cl | H |
|  | COC$_6$H$_4$-3-Cl | H |
|  | COC$_6$H$_4$-4-OCH$_3$ | H |
|  | COC$_6$H$_4$-3-OCH$_3$ | H |
|  | COC$_6$H$_4$-4-OH | H |
|  | COC$_6$H$_4$-3-OH | H |
| 5n' | CH$_3$ | H |
|  | CH$_2$CH$_3$ | H |
|  | CH$_2$CH$_2$OH | H |
|  | CH$_2$CH$_2$OCH$_3$ | H |
|  | CH$_2$CH$_2$OCH$_2$CH$_3$ | H |
|  | CH$_2$CH$_2$CH$_3$ | H |
|  | CH(CH$_3$)$_2$ | H |
|  | —(CH$_2$)$_3$CH$_3$ | H |
|  | C(CH$_3$)$_3$ | H |
| 5o' | CH$_3$ | CH$_3$ |
| 5ea | H | CH$_2$CH$_3$ |
| 5eb | H | CH$_3$ |

In a third subclass of this embodiment are the compounds of formula (I) with subgeneric formula (IV) and wherein $Z^1$, $Z^2$ and $Z^3$ are as described below: (where $Z^1$, $Z^2$ and $Z^3$ are not associated with a particular compound number; that compound may be prepared following the procedures of Schemes B and C).

TABLE 3

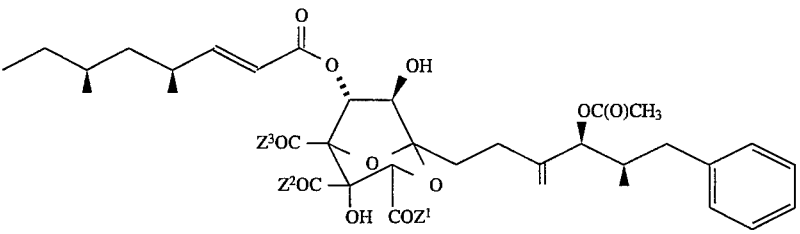

| Compound # | $Z^1$ | $Z^2$ | $Z^3$ |
|---|---|---|---|
| 8a | PhCH$_2$O | OH | OH |
| 8b | CH$_3$O | OH | OH |
| 8c | CH$_3$CH$_2$O | OH | OH |
| 8d | Ph—(CH$_2$)$_2$O | OH | OH |
| 8e | CH$_2$=CH—CH$_2$O— | OH | OH |
| 8f | C$_5$H$_9$CH$_2$CH$_2$CH$_2$O | OH | OH |
| 8g | CH$_3$CH$_2$CH$_2$CH$_2$O— | OH | OH |
| 8h | HC≡CCH$_2$O | OH | OH |
| 8i | (CH$_3$)$_2$CHO— | OH | OH |
| 8j | CH$_3$CH$_2$CH$_2$O | OH | OH |
| 8k | (CH$_3$)$_2$CHCH$_2$O | OH | OH |
| 8l | C$_6$H$_{11}$O— | OH | OH |
| 8m | PhCH$_2$CH$_2$CH$_2$O | OH | OH |
| 8n | CH$_3$CH(CH$_3$)CH$_2$CH$_2$O | OH | OH |
| 8o | PhOCH$_2$CH$_2$O | OH | OH |
| 8p | CH$_3$(CH$_2$)$_4$O | OH | OH |
| 8q | CH$_3$CH=CHCH$_2$O | OH | OH |
| 9a | PhCH$_2$O | tBuO | tBuO |
| 10a | OH | tBuO | tBuO |
| 10b | OH | CH$_3$O | CH$_3$O |
| 10c | OH | PhCH$_2$O | PhCH$_2$O |
| 11a | NH$_2$ | tBuO | tBuO |
| 12a | NH$_2$ | OH | OH |
|  | NH$_2$ | CH$_3$O | OH |
|  | NH$_2$ | CH$_3$CH$_2$O | OH |
|  | NH$_2$ | CH$_3$CH$_2$CH$_2$O | OH |
|  | NH$_2$ | HOCH$_2$CH$_2$O | OH |
|  | NH$_2$ | CH$_3$OCH$_2$CH$_2$ | OH |
|  | NH$_2$ | HO | CH$_3$O |
|  | NH$_2$ | HO | CH$_3$CH$_2$O |
|  | NH$_2$ | HO | CH$_3$CH$_2$CH$_2$O |
|  | NH$_2$ | HO | HOCH$_2$CH$_2$O |
|  | NH$_2$ | HO | CH$_3$OCH$_2$CH$_2$ |
| 12b | PhCH$_2$NH | OH | OH |
| 12c | CH$_3$(CH$_2$)$_6$NH | OH | OH |
| 12d | CH$_3$CH$_2$NH | OH | OH |
|  | CH$_3$CH$_2$NH | CH$_3$O | OH |
|  | CH$_3$CH$_2$NH | CH$_3$CH$_2$O | OH |
|  | CH$_3$CH$_2$NH | CH$_3$CH$_2$CH$_2$O | OH |
|  | CH$_3$CH$_2$NH | HOCH$_2$CH$_2$O | OH |
|  | CH$_3$CH$_2$NH | CH$_3$OCH$_2$CH$_2$ | OH |
|  | CH$_3$CH$_2$NH | HO | CH$_3$O |
|  | CH$_3$CH$_2$NH | HO | CH$_3$CH$_2$O |
|  | CH$_3$CH$_2$NH | HO | CH$_3$CH$_2$CH$_2$O |
|  | CH$_3$CH$_2$NH | HO | HOCH$_2$CH$_2$O |
|  | CH$_3$CH$_2$NH | HO | CH$_3$OCH$_2$CH$_2$ |
| 12e | (CH$_3$)$_2$N | OH | OH |
|  | (CH$_3$)$_2$N | CH$_3$O | OH |
|  | (CH$_3$)$_2$N | CH$_3$CH$_2$O | OH |
|  | (CH$_3$)$_2$N | CH$_3$CH$_2$CH$_2$O | OH |
|  | (CH$_3$)$_2$N | HOCH$_2$CH$_2$O | OH |
|  | (CH$_3$)$_2$N | CH$_3$OCH$_2$CH$_2$ | OH |
|  | (CH$_3$)$_2$N | HO | CH$_3$O |
|  | (CH$_3$)$_2$N | HO | CH$_3$CH$_2$O |
|  | (CH$_3$)$_2$N | HO | CH$_3$CH$_2$CH$_2$O |
|  | (CH$_3$)$_2$N | HO | HOCH$_2$CH$_2$O |
|  | (CH$_3$)$_2$N | HO | CH$_3$OCH$_2$CH$_2$ |
| 12f | Ph(CH$_3$)N | OH | OH |
| 12g | O(CH$_2$CH$_2$)$_2$N | OH | OH |
| 13a | PhCH$_2$O | HO | PhCH$_2$O |
| 14a | PhCH$_2$O | PhCH$_2$O | HO |
| 18a | OH | OH | CH$_3$O |
| 18b | OH | OH | NH$_2$ |
| 16a | OH | CH$_3$O | OH |
| 16b | OH | CH$_3$CH$_2$O | OH |

TABLE 3-continued (IV)

| Compound # | $Z^1$ | $Z^2$ | $Z^3$ |
|---|---|---|---|
| 19a | PhCH$_2$O | OH | tBuO |
| 19b | PhCH$_2$O | OH | CH$_3$O |
| 22a | PhCH$_2$O | NH$_2$ | OH |
| 8r | (CH$_3$)CHOCH$_2$CH$_2$O | OH | OH |
| 8s | CH$_2$=C(CH$_3$)CH$_2$CH$_2$O | OH | OH |
| 8t | (CH$_3$)$_2$CH(CH$_2$)$_2$CH(CH$_3$)O | OH | OH |
| 8u | CH$_3$CH$_2$CH(CH$_3$)CH$_2$CH$_2$O | OH | OH |
| 8v | (CH$_3$)$_2$CH(CH$_2$)$_3$CH(CH$_3$)O | OH | OH |
| 8w | (CH$_3$CH$_2$CH$_2$)(CH$_3$CH$_2$)CHO | OH | OH |
| 8x | CH$_3$OCH$_2$CH(CH$_3$)O | OH | OH |
| 12h | (CH$_3$)$_2$CHO(CH$_2$)$_3$NH— | OH | OH |
| 12i | [(CH$_2$)$_3$N]— | OH | OH |
| 12j | CH$_3$OCH$_2$CH$_2$NH— | OH | OH |
| 12k | (CH$_3$)$_2$NHCH$_2$CH$_2$NH— | OH | OH |
| 8y | (CH$_3$)$_2$NHCH$_2$CH$_2$O | OH | OH |
| 8z | 3-(CF$_3$)C$_6$H$_4$CH$_2$O | OH | OH |
| 8a' | 3-(Cl)C$_6$H$_4$CH$_2$O | OH | OH |
| 8b' | 3-(CH$_3$)C$_6$H$_4$CH$_2$O | OH | OH |
| 8c' | 3-pyrrolidinyl-O | OH | OH |
| 12l | 2-pyridinyl-NH— | OH | OH |
| 12m | 3-pyridinyl-NH— | OH | OH |
| 12n | 4-pyrimidinyl-NH— | OH | OH |
| 12o | 5-quinolinyl-NH— | OH | OH |
| 8d' | C$_6$H$_5$CH$_2$S— | OH | OH |
| 8e' | 4-(Cl)C$_6$H$_4$S— | OH | OH |
| 8f' | (CH$_3$)$_2$CHCH$_2$CH$_2$S— | OH | OH |
| 8h' | (CH$_3$)$_3$CCO$_2$CH$_2$O | OH | OH |
| 8i' | (CH$_3$)$_3$C—O(CO)CH$_2$O | OH | OH |
| 8j' | HO$_2$CCH$_2$O | OH | OH |
| 9b | (CH$_3$)$_3$CCO$_2$CH$_2$O | (CH$_3$)$_3$CCO$_2$CH$_2$O | (CH$_3$)$_3$CCO$_2$CH$_2$O |
| 9c | (CH$_3$)$_2$CHCH$_2$CH$_2$O | (CH$_3$)$_3$CCO$_2$CH$_2$O | (CH$_3$)$_3$CCO$_2$CH$_2$O |
| 9d | (CH$_3$)$_2$CHCH$_2$CH$_2$O | CH$_3$CH$_2$O | CH$_3$CH$_2$O |
| 9e | (CH$_3$)$_2$CHCH$_2$CH$_2$O | (CH$_3$)$_2$CHCH$_2$CH$_2$O | (CH$_3$)$_2$CHCH$_2$CH$_2$O |
| 9f | (CH$_3$)$_3$CO(CO)CH$_2$O | C$_6$H$_5$CH$_2$O | C$_6$H$_5$CH$_2$O |
| 9g | HO$_2$CCH$_2$O | C$_6$H$_5$CH$_2$O | C$_6$H$_5$CH$_2$O |
| 19c | C$_6$H$_5$CH$_2$O | OH | (CH$_3$)$_3$CCO$_2$CH$_2$O |
| 19h | (CH$_3$)$_2$CHCH$_2$CH$_2$O | OH | CH$_3$O |
| 18c | OH | OH | (CH$_3$)$_3$CCO$_2$CH$_2$O |
| 14b | C$_6$H$_5$CH$_2$O | (CH$_3$)$_3$CCO$_2$CH$_2$O | OH |
| 16c | OH | (CH$_3$)$_3$CCO$_2$CH$_2$O | OH |
| 10e | OH | (CH$_3$)$_3$CCO$_2$CH$_2$O | (CH$_3$)$_3$CCO$_2$CH$_2$O |
| 19d | (CH$_3$)$_3$CCO$_2$CH$_2$O | OH | (CH$_3$)$_3$CCO$_2$CH$_2$O |
| 19e | (CH$_3$)$_2$CHCH$_2$CH$_2$O | OH | (CH$_3$)$_3$CCO$_2$CH$_2$O |
| 19f | (CH$_3$)$_2$CHCH$_2$CH$_2$O | OH | CH$_3$CH$_2$O |
| 19g | (CH$_3$)$_2$CHCH$_2$CH$_2$O | OH | (CH$_3$)$_2$CHCH$_2$CH$_2$O |
| 14c | (CH$_3$)$_3$CCO$_2$CH$_2$O | (CH$_3$)$_3$CCO$_2$CH$_2$O | OH |
| 8k' | CH$_3$(CO)NHCH$_2$CH$_2$O | OH | OH |
| 8l' | 1-piperidinyl-(CO)CH$_2$O | OH | OH |
| 12p | 1-pyrrolidinyl | OH | OH |
| 8m' | 1-morpholinyl-(CO)CH$_2$O | OH | OH |
| 8n' | H$_2$N(CO)CH$_2$O | OH | OH |
| 8o' | 1-pyrrolidinyl(CO)CH$_2$O | OH | OH |
| 12q | 1-piperidinyl | OH | OH |
| 14d | (CH$_3$)$_2$CHCH$_2$CH$_2$O | (CH$_3$)$_3$CO(CO)CH$_2$O | OH |
| 14e | (CH$_3$)$_2$CHCH$_2$CH$_2$O | HO$_2$CCH$_2$O | OH |
| 14f | (CH$_3$)$_2$CHCH$_2$CH$_2$O | (CH$_3$)$_3$C(CO)OCH$_2$O | OH |
| 14g | (CH$_3$)$_2$CHCH$_2$CH$_2$O | C$_6$H$_5$CH$_2$O | OH |
| 14h | (CH$_3$)$_2$CHCH$_2$CH$_2$O | (CH$_3$)$_3$CHCH$_2$CH$_2$O | OH |
| 14i | (CH$_3$)$_2$CHCH$_2$CH$_2$O | 4-(Br)—C$_6$H$_4$(CO)CH$_2$O | OH |
| 14j | (CH$_3$)$_2$CHCH$_2$CH$_2$O | allyl-O— | OH |
| 14k | (CH$_3$)$_2$CHCH$_2$CH$_2$O | CH$_3$OCH$_2$CH$_2$O | OH |
| 14l | (CH$_3$)$_2$CHCH$_2$CH$_2$O | C$_6$H$_5$OCH$_2$CH$_2$O | OH |
| 14m | (CH$_3$)$_2$CHCH$_2$CH$_2$O | CH$_3$(CH$_2$)$_5$O | OH |
| 14n | (CH$_3$)$_2$CHCH$_2$CH$_2$O | 4-(F)—C$_6$H$_4$CH$_2$O | OH |
| 14o | (CH$_3$)$_2$CHCH$_2$CH$_2$O | CH$_3$CO$_2$CH$_2$O | OH |
| 14p | (CH$_3$)$_2$CHCH$_2$CH$_2$O | CH$_3$O | OH |

TABLE 3-continued

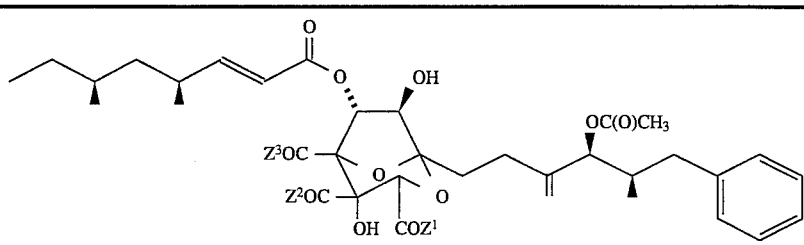

(IV)

| Compound # | $Z^1$ | $Z^2$ | $Z^3$ |
|---|---|---|---|
| 16d | OH | $CH_3OCH_2CH_2O$ | OH |
| 16e | OH | $(CH_3)_2NCH_2CH_2O$ | OH |
| 8aa | $(CH_3)_3CCH_2CH(CH_3)O$ | OH | OH |
| 8ab | $(CH_3)_3C(CH_2)_2O$ | OH | OH |
| 8ac | p-Cl—$C_6H_4$—$CH_2O$ | OH | OH |
| 8ad | $HO(CH_2)_6O$ | OH | OH |
| 8ae | $(CH_3)_2CHCH_2CH(CH_3)O$ | OH | OH |
| 8af | $(CH_3)_3CCH_2CH(CH_3)CH_2O$ | OH | OH |
| 8ag | m-$CH_3$—$C_6H_4$—$CH_2O$ | OH | OH |
| 8ah | m,p-diCl—$C_6H_3$—$CH_2O$ | OH | OH |
| 8ai | m,m__diCl—$C_6H_3$—$CH_2O$ | OH | OH |
| 8aj | p-$(CH_3O)$—$C_6H_4$—$CH_2O$ | OH | OH |
| 8ak | m-$(CH_3O)$—$C_6H_4$—$CH_2O$ | $CH_3O$ | OH |
| 8al | m-Cl—$C_6H_4$—O | OH | OH |
| 8am | m-$(CH_3O)$—$C_6H_4$—O | OH | OH |
| 8an | m-$(CH_3)$—$C_6H_4$—O | OH | OH |
| 8ao | N-morpholino-$(CH_2)_2O$ | OH | OH |
| 8ba | $(CH_3)_2CH(CH_2)_2O$ | pyrrolidinyl-$C(O)CH_2O$ | OH |
| 8bb | $(CH_3)_2CH(CH_2)_2O$ | piperidinyl-$C(O)CH_2O$ | OH |
| 8bc | $(CH_3)_2CH(CH_2)_2O$ | OH | piperidinyl-$C(O)CH_2O$ |
| 8bd | $(CH_3)_2CH(CH_2)_2O$ | $(CH_3)_2NC(O)CH_2O$ | OH |
| 8be | $(CH_3)_2CH(CH_2)_2O$ | OH | $(CH_3)_2NC(O)CH_2O$ |
| 8bf | $(CH_3)_2CH(CH_2)_2O$ | morpholinyl-$C(O)CH_2O$ | OH |
| 8bg | $(CH_3)_2CH(CH_2)_2O$ | $[(CH_3)_2CH]_2NC(O)CH_2O$ | OH |
| 8bh | $(CH_3)_2CH(CH_2)_2O$ | $(CH_3)C(O)OCH_2O$ | OH |
| 8bi | $(CH_3)_2CH(CH_2)_2O$ | OH | $(CH_3)C(O)OCH_2O$ |
| 8bj | $(CH_3)_2CH(CH_2)_2O$ | p-Br—$C_6H_4$—$C(O)CH_2O$ | p-Br—$C_6H_4$—$C(O)CH_2O$ |
| 8ca | $HO(CH_2)_2NH$ | OH | OH |
| 8cb | furfuryl-NH | OH | OH |
| 8cc | 4-imidazolyl-$(CH_2)_2NH$ | OH | OH |
| 8cd | Ph—$CH_2CH(CO_2H)NH$ | OH | OH |
| 8ce | 3-indolyl-$CH_2CH(CO_2H)NH$ | OH | OH |
| 8cf | $(CH_3)_3COC(O)CH(CH_3)NH$ | OH | OH |
| 8cg | $(CH_3)CH(OH)CH(CO_2H)NH$ | OH | OH |
| 8ch | $H_2N(CH_2)_4CH(CO_2H)NH$ | OH | OH |
| 8ci | 1-(2-$CO_2Bzl$)-pyrrolidinyl | OH | OH |
| 8cj | Bzl-$OC(O)NHC(O)(CH_2)_2CH(CO_2Bzl)NH$ | OH | OH |
| 8ck | $H_2NC(O)(CH_2)_2CH(CO_2Bzl)NH$ | OH | OH |
| 8cl | $HO_2C$-$CH(CH_3)NH$ | OH | OH |
| 8g' | (tetrahydronaphthalenyl-O—) | OH | OH |
| 8p' | (methoxy-benzofuranone-O—) | OH | OH |

In a fourth subclass of this embodiment are compounds of formula (I) with subgeneric formula (V) and wherein $R^1$ and $R^4$—$(A)_a$ are as described below.

TABLE 4

(V) structure: $R_4-(A)_a-O$, $OH$, $HO_2C$, $HO_2C$, $OH$, $CO_2H$, $R^1$ substituent on cyclohexane with O bridge; $p^1$ = $-(CH_2)_2CH(CH_3)CH(CH_3)CH=CHC(O)-$ (enone chain); $p^2$ = saturated ketone chain.

| Compound | $R^1$ | $R^4-(A)_a$ |
|---|---|---|
| 7a | $-(CH_2)_2C(CH_2)CH(CH_3CH_2CO_2)CH(CH_3)CH_2C_6H_5$ | $p^1$ |
| 7b | $-(CH_2)_2C(CH_2)CH(CH_3CH_2CH_2CO_2)CH(CH_3)CH_2C_6H_5$ | $p^1$ |
| 7c | $-(CH_2)_2C(CH_2)CH((CH_3)_3CCO_2)CH(CH_3)CH_2C_6H_5$ | $p^1$ |
| 7d | $-(CH_2)_2C(CH_2)CH(PhCO_2)CH(CH_3)CH_2C_6H_5$ | $p^1$ |
| 7f | $-(CH_2)_2C(CH_2)CH(CH_3CH_2CH_2NHCO_2)CH(CH_3)CH_2C_6H_5$ | $p^1$ |
| 7g | $-(CH_2)_2C(CH_2)CH(PhCH_2NHCO_2)CH(CH_3)CH_2C_6H_5$ | $p^1$ |
| 7h | $-(CH_2)_2C(CH_2)CH(PhNHCO_2)CH(CH_3)CH_2C_6H_5$ | $p^1$ |
| 24b | $-(CH_2)_2CH(CH_3)CH(OAc)CH(CH_3)CH_2Ph$ | $p^2$ |
| 25b | $-(CH_2)_2CH(CH_3)CH_2CH(CH_3)CH_2Ph$ | $p^2$ |
| 26b | $-(CH_2)_2CH(CH_3)CH(OAc)CH(CH_3)CH_2C_6H_{11}$ | $p^2$ |
| 26c | $-(CH_2)_2CH(CH_3)CH(OCH_3)CH(CH_3)CH_2C_6H_5$ | $p^2$ |
| 28b | $-(CH_2)_2C(CH_2)CH(epi\text{-}OAc)CH(CH_3)CH_2C_6H_5$ | $p^1$ |
| 29a | $-(CH_2)_2COH(CH_2OH)CH(OH)CH(CH_3)CH_2Ph$ | $p^1$ |
| 30a | $-(CH_2)_2CO_2H$ | $p^1$ |
| 31c | $-(CH_2)_2C(=O)CH(OH)CH(CH_3)CH_2Ph$ | $p^1$ |
| 31d | $-(CH_2)_2COCH_2OH$ | $p^1$ |
| 33a | $-(CH_2)_2CH_2OH$ | $p^1$ |
| 39a | $-(CH_2)_2CH_2OCOC(CH_3)_3$ | $p^1$ |
| 39b | $-(CH_2)_2CH_2OCOC(CH_3)_3$ | $p^1$ |
| 39c | $-(CH_2)_2CH_2OCO(CH_2)_3CH_3$ | $p^1$ |
| 39d | $-(CH_2)_2CH_2OCOCH_3$ | $p^1$ |
| 39e | $-(CH_2)_2CH_2OCO(CH_2)_3Ph$ | $p^1$ |
| 39f | $-(CH_2)_2CH_2OCOPh$ | $p^1$ |
| 39h | $-(CH_2)_2CH_2OCONHPh$ | $p^1$ |
| 39i | $-(CH_2)_2CH_2OCONHPh(2'\text{-}Et)$ | $p^1$ |
| 39j | $-(CH_2)_2CH_2OCONH(CH_2)_7CH_3$ | $p^1$ |
| 7aa | $-(CH_2)_2CH(CH_3)CH(OAc)CH(CH_3)CH_2C_6H_5$ | $p^2$ |
| 7ab | $-(CH_2)_2CH(CH_2OAc)CH_2CH(CH_3)CH_2C_6H_5$ | $p^2$ |
| 7ac | $-(CH_2)_2C(CH_2)CH(OH)CH(CH_3)CH_2C_6H_5$ | $p^1$ |
| 7ad | $-(CH_2)_2CH(OH)(CH_2)_3Ph$ | $p^1$ |
| 7ae | $-(CH_2)_2CH(OH)(CH_2)_5Ph$ | $p^1$ |
| 7af | $-(CH_2)_2CH(OAc)(CH_2)_5Ph$ | $p^1$ |
| 7ag | $-(CH_2)_2CH(OAc)(CH_2)_3Ph$ | $p^1$ |
| 7ah | $-(CH_2)_2C(O)(CH_2)_3Ph$ | $p^1$ |
| 7ai | $-(CH_2)_2C(O)(CH_2)_5Ph$ | $p^1$ |
| 7aj | $-(CH_2)_2(2\text{-methyl-}1,2,3,4\text{-tetrahydronaphthyl})$ | $p^1$ |
| 7ak | $-(CH_2)_2C(CH_2)C(O)CH(CH_3)CH_2Ph$ | $p^1$ |
| 7al | $-(CH_2)_2CH[(CH_2)_4CH_3]C(O)CH(CH_3)CH_2Ph$ | $p^1$ |
| 7am | $-(CH_2)_2CH(CH_2Ph)C(O)CH(CH_3)CH_2Ph$ | $p^1$ |
| 7an | $-(CH_2)_2C(O)OCH_2Ph$ | $p^1$ |
| 7ao | $-(CH_2)_2C(O)OCH_3$ | $p^1$ |

Further exemplifying this subclass are those compounds of formula (V) which may be prepared following Schemes D to F and analogous procedures to those of Compounds 7a to 7h and 24b to 39j and 7aa to 7ao wherein $R^4-(A)_a$ is $p^1$ and $R^1$ is selected from the group consisting of:

$R^1$

—$(CH_2)_2CH_2CH(OAc)CH(CH_3)CH_2Ph$
—$(CH_2)_2CH_2CH(OAc)CH_2CH_2Ph$
—$(CH_2)_6Ph$
—$(CH_2)_2C(=CH_2)CH(OH)CH(CH_3)CH_2Ph$
—$(CH_2)_2CH(CH_3)CH(OH)CH(CH_3)CH_2Ph$
—$(CH_2)_2CH(OH)CH(CH_3)CH_2Ph$
—$(CH_2)_2CH(OH)CH_2CH_2Ph$
—$(CH_2)_2CH(CH_3)CH(OAc)CH(CH_3)CH_2CH=CHPh$
—$(CH_2)_2CH(OAc)CH(CH_3)CH_2CH=CHPh$
—$(CH_2)_2CH(OAc)CH(CH_3)(CH_2)_3Ph$
—$(CH_2)_2CH(OAc)CH_2CH_2CH=CHPh$
—$(CH_2)_2CH(OAc)CH(CH_3)(CH_2)_3Ph$

-continued $R^1$

—$(CH_2)_2CH(CH_3)CH(OH)CH(CH_3)CH_2CH=CHPh$
—$(CH_2)_2CH(OH)CH(CH_3)CH_2CH=CHPh$
—$(CH_2)_2(CH_2)_3CH(OH)CH_2CH_2CH=CHPh$
—$(CH_2)_2CH(CH_3)CH(OH)CH(CH_3)(CH_2)_3Ph$
—$(CH_2)_2CH(OH)CH(CH_3)(CH_2)_3Ph$
—$(CH_2)_2CH(CH_3)CH(OH)CH(CH_3)(CH_2)_3Ph$
—$(CH_2)_2CH(OH)(CH_2)_4Ph$
—$(CH_2)_5$—$OH$
—$(CH_2)_8$—$OH$
—$(CH_2)_{10}$—$OH$
—$(CH_2)_2$—$OH$
—$(CH_2)_3$—$OCH_3$
—$(CH_2)_5$—$OCH_3$
—$(CH_2)_8$—$OCH_3$
—$(CH_2)_{10}$—$OCH_3$
—$(CH_2)_5OAc$
—$(CH_2)_8OAc$
—$(CH_2)_2$—$NHCH_3$

-continued

| $R^1$ |
|---|
| —(CH$_2$)$_3$NHCH$_3$ |
| —(CH$_2$)$_5$—NHCH$_3$ |
| —(CH$_2$)$_8$—NHCH$_3$ |
| —(CH$_2$)$_{10}$—NHCH$_3$ |
| —(CH$_2$)$_2$—N(CH$_3$)$_2$ |
| —(CH$_2$)$_3$N(CH$_3$)$_2$ |
| —(CH$_2$)$_5$N(CH$_3$)$_2$ |
| —(CH$_2$)$_8$—N(CH$_3$)$_2$ |
| —(CH$_2$)$_{10}$—N(CH$_3$)$_2$ |
| —(CH$_2$)$_2$—N(CH$_2$CH$_2$)$_2$O |
| —(CH$_2$)$_3$N(CH$_2$CH$_2$)$_2$O |
| —(CH$_2$)$_5$—N(CH$_2$CH$_2$)$_2$O |
| —(CH$_2$)$_8$—N(CH$_2$CH$_2$)$_2$O |
| —(CH$_2$)$_{10}$—N(CH$_2$CH$_2$)$_2$O |
| —(CH$_2$)$_2$—N(CH$_2$CH$_2$)$_2$NH |
| —(CH$_2$)$_3$N(CH$_2$CH$_2$)$_2$NH |
| —(CH$_2$)$_5$N(CH$_2$CH$_2$)$_2$NH |
| —(CH$_2$)$_8$—N(CH$_2$CH$_2$)$_2$NH |
| —(CH$_2$)$_{10}$—N(CH$_2$CH$_2$)$_2$NH |
| —(CH$_2$)$_2$—OPh |
| —(CH$_2$)$_3$OPh |
| —(CH$_2$)$_5$—OPh |
| —(CH$_2$)$_8$—OPh |
| —(CH$_2$)$_{10}$—OPh |
| —(CH$_2$)$_2$—OC$_6$H$_4$-4-CH$_3$ |
| —(CH$_2$)$_3$OC$_6$H$_4$-4-CH$_3$ |
| —(CH$_2$)$_5$2OC$_6$H$_4$-4-CH$_3$ |
| —(CH$_2$)$_8$—OC$_6$H$_4$-4-CH$_3$ |
| —(CH$_2$)$_{10}$—OC$_6$H$_4$-4-CH$_3$ |
| —(CH$_2$)$_2$—OC$_6$H$_4$-4-OH |
| —(CH$_2$)$_3$OC$_6$H$_4$-4-OH |
| —(CH$_2$)$_5$—OC$_6$H$_4$-4-OH |
| —(CH$_2$)$_8$—OC$_6$H$_4$-4-OH |
| —(CH$_2$)$_{10}$—OC$_6$H$_4$-4-OH |
| —(CH$_2$)$_2$—OC$_6$H$_4$-4-OCH$_3$ |
| —(CH$_2$)$_3$OC$_6$H$_4$-4-OCH$_3$ |
| —(CH$_2$)$_5$—OC$_6$H$_4$-4-OCH$_3$ |
| —(CH$_2$)$_8$—OC$_6$H$_4$-4-OCH$_3$ |
| —(CH$_2$)$_{10}$—OC$_6$H$_4$-4-OCH$_3$ |
| —(CH$_2$)$_2$—OC$_6$H$_4$-4-Cl |
| —(CH$_2$)$_3$OC$_6$H$_4$-4-Cl |
| —(CH$_2$)$_5$—OC$_6$H$_4$-4-Cl |
| —(CH$_2$)$_8$—OC$_6$H$_4$-4-Cl |
| —(CH$_2$)$_{10}$—OC$_6$H$_4$-4-Cl |
| —(CH$_2$)$_2$—OC$_6$H$_4$-3-CH$_3$ |
| —(CH$_2$)$_3$OC$_6$H$_4$-3-CH$_3$ |
| —(CH$_2$)$_5$OC$_6$H$_4$-3-CH$_3$ |
| —(CH$_2$)$_8$—OC$_6$H$_4$-3-CH$_3$ |
| —(CH$_2$)$_{10}$—OC$_6$H$_4$-3-CH$_3$ |
| —(CH$_2$)$_2$—OC$_6$H$_4$-3-OH |
| —(CH$_2$)$_3$OC$_6$H$_4$-3-OH |
| —(CH$_2$)$_5$—OC$_6$H$_4$-3-OH |
| —(CH$_2$)$_8$—OC$_6$H$_4$-3-OH |
| —(CH$_2$)$_{10}$—OC$_6$H$_4$-3-OH |
| —(CH$_2$)$_2$—OC$_6$H$_4$-3-OCH$_3$ |
| —(CH$_2$)$_3$OC$_6$H$_4$-3-OCH$_3$ |
| —(CH$_2$)$_5$—OC$_6$H$_4$-3-OCH$_3$ |
| —(CH$_2$)$_8$—OC$_6$H$_4$-3-OCH$_3$ |
| —(CH$_2$)$_{10}$—OC$_6$H$_4$-3-OCH$_3$ |
| —(CH$_2$)$_2$—OC$_6$H$_4$-3-Cl |
| —(CH$_2$)$_3$OC$_6$H$_4$-3-Cl |
| —(CH$_2$)$_5$—OC$_6$H$_4$-3-Cl |
| —(CH$_2$)$_8$—OC$_6$H$_4$-3-Cl |
| —(CH$_2$)$_{10}$—OC$_6$H$_4$-3-Cl |
| —(CH$_2$)$_2$CH(OH)—(CH$_2$)$_2$—OH |
| —(CH$_2$)$_2$CH(OH)—(CH$_2$)$_3$OH |
| —(CH$_2$)$_2$CH(OH)—(CH$_2$)$_5$—OH |
| —(CH$_2$)$_2$CH(OH)—(CH$_2$)$_8$—OH |
| —(CH$_2$)$_2$CH(OH)—(CH$_2$)$_{10}$—OH |
| —(CH$_2$)$_2$CH(OH)—(CH$_2$)$_2$—OCH$_3$ |
| —(CH$_2$)$_2$CH(OH)—(CH$_2$)$_3$—OCH$_3$ |
| —(CH$_2$)$_2$CH(OH)—(CH$_2$)$_5$—OCH$_3$ |
| —(CH$_2$)$_2$CH(OH)—(CH$_2$)$_8$—OCH$_3$ |
| —(CH$_2$)$_2$CH(OH)—(CH$_2$)$_{10}$—OCH$_3$ |
| —(CH$_2$)$_2$CH(OH)—(CH$_2$)$_3$OAc |
| —(CH$_2$)$_2$CH(OH)—(CH$_2$)$_5$OAc |
| —(CH$_2$)$_2$CH(OH)—(CH$_2$)$_8$OAc |
| —(CH$_2$)$_2$CH(OH)—(CH$_2$)$_2$—NHCH$_3$ |

-continued

| $R^1$ |
|---|
| —(CH$_2$)$_2$CH(OH)—(CH$_2$)$_3$NHCH$_3$ |
| —(CH$_2$)$_2$CH(OH)—(CH$_2$)$_5$—NHCH$_3$ |
| —(CH$_2$)$_2$CH(OH)—(CH$_2$)$_8$—NHCH$_3$ |
| —(CH$_2$)$_2$CH(OH)—(CH$_2$)$_{10}$—NHCH$_3$ |
| —(CH$_2$)$_2$CH(OH)—(CH$_2$)$_2$—N(CH$_3$)$_2$ |
| —(CH$_2$)$_2$CH(OH)—(CH$_2$)$_3$N(CH$_3$)$_2$ |
| —(CH$_2$)$_2$CH(OH)—(CH$_2$)$_5$—N(CH$_3$)$_2$ |
| —(CH$_2$)$_2$CH(OH)—(CH$_2$)$_8$—N(CH$_3$)$_2$ |
| —(CH$_2$)$_2$CH(OH)—(CH$_2$)$_{10}$—N(CH$_3$)$_2$ |
| —(CH$_2$)$_2$CH(OH)—(CH$_2$)$_2$—N(CH$_2$CH$_2$)$_2$O |
| —(CH$_2$)$_2$CH(OH)—(CH$_2$)$_3$N(CH$_2$CH$_2$)$_2$O |
| —(CH$_2$)$_2$CH(OH)—(CH$_2$)$_5$—N(CH$_2$CH$_2$)$_2$O |
| —(CH$_2$)$_2$CH(OH)—(CH$_2$)$_8$—N(CH$_2$CH$_2$)$_2$O |
| —(CH$_2$)$_2$CH(OH)—(CH$_2$)$_{10}$—N(CH$_2$CH$_2$)$_2$O |
| —(CH$_2$)$_2$CH(OH)—(CH$_2$)$_2$—N(CH$_2$CH$_2$)$_2$NH |
| —(CH$_2$)$_2$CH(OH)—(CH$_2$)$_3$N(CH$_2$CH$_2$)$_2$NH |
| —(CH$_2$)$_2$CH(OH)—(CH$_2$)$_5$—N(CH$_2$CH$_2$)$_2$NH |
| —(CH$_2$)$_2$CH(OH)—(CH$_2$)$_8$—N(CH$_2$CH$_2$)$_2$NH |
| —(CH$_2$)$_2$CH(OH)—(CH$_2$)$_{10}$—N(CH$_2$CH$_2$)$_2$NH |
| —(CH$_2$)$_2$CH(OH)—(CH$_2$)$_2$—OPh |
| —(CH$_2$)$_2$CH(OH)—(CH$_2$)$_3$OPh |
| —(CH$_2$)$_2$CH(OH)—(CH$_2$)$_5$—OPh |
| —(CH$_2$)$_2$CH(OH)—(CH$_2$)$_8$—OPh |
| —(CH$_2$)$_2$CH(OH)—(CH$_2$)$_{10}$—OPh |
| —(CH$_2$)$_2$CH(OH)—(CH$_2$)$_2$—OC$_6$H$_4$-4-CH$_3$ |
| —(CH$_2$)$_2$CH(OH)—(CH$_2$)$_3$OC$_6$H$_4$-4-CH$_3$ |
| —(CH$_2$)$_2$CH(OH)—(CH$_2$)$_5$OC$_6$H$_4$-4-CH$_3$ |
| —(CH$_2$)$_2$CH(OH)—(CH$_2$)$_8$—OC$_6$H$_4$-4-CH$_3$ |
| —(CH$_2$)$_2$CH(OH)—(CH$_2$)$_{10}$—OC$_6$H$_4$-4-CH$_3$ |
| —(CH$_2$)$_2$CH(OH)—(CH$_2$)$_2$—OC$_6$H$_4$-4-OH |
| —(CH$_2$)$_2$CH(OH)—(CH$_2$)$_3$OC$_6$H$_4$-4-OH |
| —(CH$_2$)$_2$CH(OH)—(CH$_2$)$_5$—OC$_6$H$_4$-4-OH |
| —(CH$_2$)$_2$CH(OH)—(CH$_2$)$_8$—OC$_6$H$_4$-4-OH |
| —(CH$_2$)$_2$CH(OH)—(CH$_2$)$_{10}$—OC$_6$H$_4$-4-OH |
| —(CH$_2$)$_2$CH(OH)—(CH$_2$)$_2$—OC$_6$H$_4$-4-OCH$_3$ |
| —(CH$_2$)$_2$CH(OH)—(CH$_2$)$_3$OC$_6$H$_4$-4-OCH$_3$ |
| —(CH$_2$)$_2$CH(OH)—(CH$_2$)$_5$—OC$_6$H$_4$-4-OCH$_3$ |
| —(CH$_2$)$_2$CH(OH)—(CH$_2$)$_8$—OC$_6$H$_4$-4-OCH$_3$ |
| —(CH$_2$)$_2$CH(OH)—(CH$_2$)$_{10}$—OC$_6$H$_4$-4-OCH$_3$ |
| —(CH$_2$)$_2$CH(OH)—(CH$_2$)$_2$—OC$_6$H$_4$-4-Cl |
| —(CH$_2$)$_2$CH(OH)—(CH$_2$)$_3$OC$_6$H$_4$-4-Cl |
| —(CH$_2$)$_2$CH(OH)—(CH$_2$)$_5$—OC$_6$H$_4$-4-Cl |
| —(CH$_2$)$_2$CH(OH)—(CH$_2$)$_8$—OC$_6$H$_4$-4-Cl |
| —(CH$_2$)$_2$CH(OH)—(CH$_2$)$_{10}$—OC$_6$H$_4$-4-Cl |
| —(CH$_2$)$_2$CH(OH)—(CH$_2$)$_2$—OC$_6$H$_4$-3-CH$_3$ |
| —(CH$_2$)$_2$CH(OH)—(CH$_2$)$_3$OC$_6$H$_4$-3-CH$_3$ |
| —(CH$_2$)$_2$CH(OH)—(CH$_2$)$_5$OC$_6$H$_4$-3-CH$_3$ |
| —(CH$_2$)$_2$CH(OH)—(CH$_2$)$_8$—OC$_6$H$_4$-3-CH$_3$ |
| —(CH$_2$)$_2$CH(OH)—(CH$_2$)$_{10}$—OC$_6$H$_4$-3-CH$_3$ |
| —(CH$_2$)$_2$CH(OH)—(CH$_2$)$_2$—OC$_6$H$_4$-3-OH |
| —(CH$_2$)$_2$CH(OH)—(CH$_2$)$_3$OC$_6$H$_4$-3-OH |
| —(CH$_2$)$_2$CH(OH)—(CH$_2$)$_5$—OC$_6$H$_4$-3-OH |
| —(CH$_2$)$_2$CH(OH)—(CH$_2$)$_8$—OC$_6$H$_4$-3-OH |
| —(CH$_2$)$_2$CH(OH)—(CH$_2$)$_{10}$—OC$_6$H$_4$-3-OH |
| —(CH$_2$)$_2$CH(OH)—(CH$_2$)$_2$—OC$_6$H$_4$-3-OCH$_3$ |
| —(CH$_2$)$_2$CH(OH)—(CH$_2$)$_3$OC$_6$H$_4$-3-OCH$_3$ |
| —(CH$_2$)$_2$CH(OH)—(CH$_2$)$_5$—OC$_6$H$_4$-3-OCH$_3$ |
| —(CH$_2$)$_2$CH(OH)—(CH$_2$)$_8$—OC$_6$H$_4$-3-OCH$_3$ |
| —(CH$_2$)$_2$CH(OH)—(CH$_2$)$_{10}$—OC$_6$H$_4$-3-OCH$_3$ |
| —(CH$_2$)$_2$CH(OH)—(CH$_2$)$_2$—OC$_6$H$_4$-3-Cl |
| —(CH$_2$)$_2$CH(OH)—(CH$_2$)$_3$OC$_6$H$_4$-3-Cl |
| —(CH$_2$)$_2$CH(OH)—(CH$_2$)$_5$—OC$_6$H$_4$-3-Cl |
| —(CH$_2$)$_2$CH(OH)—(CH$_2$)$_8$—OC$_6$H$_4$-3-Cl |
| —(CH$_2$)$_2$CH(OH)—(CH$_2$)$_{10}$—OC$_6$H$_4$-3-Cl |
| —(CH$_2$)$_2$CH(OR$_2$)—(CH$_2$)$_2$—OH |
| —(CH$_2$)$_2$CH(OR$_2$)—(CH$_2$)$_3$OH |
| —(CH$_2$)$_2$CH(OR$_2$)—(CH$_2$)$_5$—OH |
| —(CH$_2$)$_2$CH(OR$_2$)—(CH$_2$)$_8$—OH |
| —(CH$_2$)$_2$CH(OR$_2$)—(CH$_2$)$_{10}$—OH |
| —(CH$_2$)$_2$CH(OR$_2$)—(CH$_2$)$_2$—OCH$_3$ |
| —(CH$_2$)$_2$CH(OR$_2$)—(CH$_2$)$_3$—OCH$_3$ |
| —(CH$_2$)$_2$CH(OR$_2$)—(CH$_2$)$_5$—OCH$_3$ |
| —(CH$_2$)$_2$CH(OR$_2$)—(CH$_2$)$_8$—OCH$_3$ |
| —(CH$_2$)$_2$CH(OR$_2$)—(CH$_2$)$_{10}$—OCH$_3$ |
| —(CH$_2$)$_2$CH(OR$_2$)—(CH$_2$)$_3$OAc |
| —(CH$_2$)$_2$CH(OR$_2$)—(CH$_2$)$_5$OAc |
| —(CH$_2$)$_2$CH(OR$_2$)—(CH$_2$)$_8$OAc |
| —(CH$_2$)$_2$CH(OR$_2$)—(CH$_2$)$_2$—NHCH$_3$ |

-continued

| R¹ |
|---|
| —(CH₂)₂CH(OR₂)—(CH₂)₃NHCH₃ |
| —(CH₂)₂CH(OR₂)—(CH₂)₅—NHCH₃ |
| —(CH₂)₂CH(OR₂)—(CH₂)₈—NHCH₃ |
| —(CH₂)₂CH(OR₂)—(CH₂)₁₀—NHCH₃ |
| —(CH₂)₂CH(OR₂)—(CH₂)₂—N(CH₃)₂ |
| —(CH₂)₂CH(OR₂)—(CH₂)₃N(CH₃)₂ |
| —(CH₂)₂CH(OR₂)—(CH₂)₅—N(CH₃)₂ |
| —(CH₂)₂CH(OR₂)—(CH₂)₈—N(CH₃)₂ |
| —(CH₂)₂CH(OR₂)—(CH₂)₁₀—N(CH₃)₂ |
| —(CH₂)₂CH(OR₂)—(CH₂)₂—N(CH₂CH₂)₂O |
| —(CH₂)₂CH(OR₂)—(CH₂)₃N(CH₂CH₂)₂O |
| —(CH₂)₂CH(OR₂)-(CH₂)₅—N(CH₂CH₂)₂O |
| —(CH₂)₂CH(OR₂)—(CH₂)₈—N(CH₂CH₂)₂O |
| —(CH₂)₂CH(OR₂)—(CH₂)₁₀—N(CH₂CH₂)₂O |
| —(CH₂)₂CH(OR₂)—(CH₂)₂—N(CH₂CH₂)₂NH |
| —(CH₂)₂CH(OR₂)—(CH₂)₃N(CH₂CH₂)₂NH |
| —(CH₂)₂CH(OR₂)—(CH₂)₅—N(CH₂CH₂)₂NH |
| —(CH₂)₂CH(OR₂)—(CH₂)₈—N(CH₂CH₂)₂NH |
| —(CH₂)₂CH(OR₂)—(CH₂)₁₀—N(CH₂CH₂)₂NH |
| —(CH₂)₂CH(OR₂)—(CH₂)₃CH(OH)—(CH₂)₂—OPh |
| —(CH₂)₂CH(OR₂)—(CH₂)₃CH(OH)—(CH₂)₃OPh |
| —(CH₂)₂CH(OR₂)—(CH₂)₃CH(OH)—(CH₂)₅—OPh |
| —(CH₂)₂CH(OR₂)—(CH₂)₈—OPh |
| —(CH₂)₂CH(OR₂)—(CH₂)₁₀—OPh |
| —(CH₂)₂CH(OR₂)—(CH₂)₂—OC₆H₄-4-CH₃ |
| —(CH₂)₂CH(OR₂)—(CH₂)₃OC₆H₄-4-CH₃ |
| —(CH₂)₂CH(OR₂)—(CH₂)₅OC₆H₄-4-CH₃ |
| —(CH₂)₂CH(OR₂)—(CH₂)₈—OC₆H₄-4-CH₃ |
| —(CH₂)₂CH(OR₂)—(CH₂)₁₀—OC₆H₄-4-CH₃ |
| —(CH₂)₂CH(OR₂)—(CH₂)₂—OC₆H₄-4-OH |
| —(CH₂)₂CH(OR₂)—(CH₂)₃OC₆H₄-4-OH |
| —(CH₂)₂CH(OR₂)—(CH₂)₅—OC₆H₄-4-OH |
| —(CH₂)₂CH(OR₂)—(CH₂)₈—OC₆H₄-4-OH |
| —(CH₂)₂CH(OR₂)—(CH₂)₁₀—OC₆H₄-4-OH |
| —(CH₂)₂CH(OR₂)—(CH₂)₂—OC₆H₄-4-OCH₃ |
| —(CH₂)₂CH(OR₂)—(CH₂)₃OC₆H₄-4-OCH₃ |
| —(CH₂)₂CH(OR₂)—(CH₂)₅—OC₆H₄-4-OCH₃ |
| —(CH₂)₂CH(OR₂)—(CH₂)₈—OC₆H₄-4-OCH₃ |
| —(CH₂)₂CH(OR₂)—(CH₂)₁₀—OC₆H₄-4-OCH₃ |
| —(CH₂)₂CH(OR₂)—(CH₂)₂—OC₆H₄-4-Cl |
| —(CH₂)₂CH(OR₂)—(CH₂)₃OC₆H₄-4-Cl |
| —(CH₂)₂CH(OR₂)—(CH₂)₅—OC₆H₄-4-Cl |
| —(CH₂)₂CH(OR₂)—(CH₂)₈—OC₆H₄-4-Cl |
| —(CH₂)₂CH(OR₂)—(CH₂)₁₀—OC₆H₄-4-Cl |
| —(CH₂)₂CH(OR₂)—(CH₂)₂—OC₆H₄-3-CH₃ |
| —(CH₂)₂CH(OR₂)—(CH₂)₃OC₆H₄-3-CH₃ |
| —(CH₂)₂CH(OR₂)—(CH₂)₅OC₆H₄-3-CH₃ |
| —(CH₂)₂CH(OR₂)—(CH₂)₈—OC₆H₄-3-CH₃ |
| —(CH₂)₂CH(OR₂)—(CH₂)₁₀—OC₆H₄-3-CH₃ |
| —(CH₂)₂CH(OR₂)—(CH₂)₂—OC₆H₄-3-OH |
| —(CH₂)₂CH(OR₂)—(CH₂)₃OC₆H₄-3-OH |
| —(CH₂)₂CH(OR₂)—(CH₂)₅—OC₆H₄-3-OH |
| —(CH₂)₂CH(OR₂)—(CH₂)₈—OC₆H₄-3-OH |
| —(CH₂)₂CH(OR₂)—(CH₂)₁₀—OC₆H₄-3-OH |
| —(CH₂)₂CH(OR₂)—(CH₂)₂—OC₆H₄-3-OCH₃ |
| —(CH₂)₂CH(OR₂)—(CH₂)₃OC₆H₄-3-OCH₃ |
| —(CH₂)₂CH(OR₂)—(CH₂)₅—OC₆H₄-3-OCH₃ |
| —(CH₂)₂CH(OR₂)—(CH₂)₈—OC₆H₄-3-OCH₃ |
| —(CH₂)₂CH(OR₂)—(CH₂)₁₀—OC₆H₄-3-OCH₃ |
| —(CH₂)₂CH(OR₂)—(CH₂)₂—OC₆H₄-3-Cl |
| —(CH₂)₂CH(OR₂)—(CH₂)₃OC₆H₄-3-Cl |
| —(CH₂)₂CH(OR₂)—(CH₂)₅—OC₆H₄-3-Cl |
| —(CH₂)₂CH(OR₂)—(CH₂)₈—OC₆H₄-3-Cl |
| —(CH₂)₂CH(OR₂)—(CH₂)₁₀—OC₆H₄-3-Cl |
| —(CH₂)₈Ph |
| —(CH₂)₂CH₂CH(OAc)CH₂CH₂C₆H₁₁ |
| —(CH₂)₂CH(CH₃)CH₂CH(CH₃)CH₂Ph |
| —(CH₂)₁₀OAc |

In a fifth subclass of this embodiment are those compounds of formula (I) with subgeneric formula (VI), which are prepared following Schemes A to I and the exemplified procedures of 5a to 5z, 5c', 5f' to 5r''', 7a to 7h and 24b to 39j.

TABLE 5

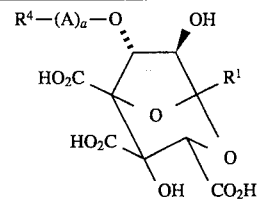

(VI)

and wherein R¹ is selected from the group consisting of:

| R¹ |
|---|
| —(CH₂)₂C(CH₂)CH(CH₃CH₂CO₂)CH(CH₃)CH₂C₆H₅ |
| —(CH₂)₂C(CH₂)CH(CH₃CH₂CH₂CO₂)CH(CH₃)CH₂C₆H₅ |
| —(CH₂)₂C(CH₂)CH((CH₃)₃CCO₂)CH(CH₃)CH₂C₆H₅ |
| —(CH₂)₂C(CH₂)CH(PhCO₂)CH(CH₃)CH₂C₆H₅ |
| —(CH₂)₂C(CH₂)CH(Imidazole-CO₂)CH(CH₃)CH₂C₆H₅ |
| —(CH₂)₂C(CH₂)CH(CH₃CH₂CH₂NHCO₂)CH(CH₃)CH₂C₆H₅ |
| —(CH₂)₂C(CH₂)CH(PhCH₂NHCO₂)CH(CH₃)CH₂C₆H₅ |
| —(CH₂)₂C(CH₂)CH(PhNHCO₂)CH(CH₃)CH₂C₆H₅ |
| —(CH₂)₂CH₂CH(OAc)CH(CH₃)CH₂Ph |
| —(CH₂)₂CH₂CH(OAc)CH₂CH₂Ph |
| —(CH₂)₆Ph |
| —(CH₂)₂C(=CH₂)CH(OH)CH(CH₃)CH₂Ph |
| —(CH₂)₂CH(CH₃)CH(OH)CH(CH₃)CH₂Ph |
| —(CH₂)₂CH(OH)CH(CH₃)CH₂Ph |
| —(CH₂)₂CH(OH)CH₂CH₂Ph |
| —(CH₂)₂CH(CH₃)CH(OAc)CH(CH₃)CH₂CH=CHPh |
| —(CH₂)₂CH(OAc)CH(CH₃)CH₂CH=CHPh |
| —(CH₂)₂CH(OAc)CH(CH₃)(CH₂)₃Ph |
| —(CH₂)₂CH(OAc)CH₂CH₂CH=CHPh |
| —(CH₂)₂CH(OAc)CH(CH₃)(CH₂)₃Ph |
| —(CH₂)₂CH(CH₃)CH(OH)CH(CH₃)CH₂CH=CHPh |
| —(CH₂)₂CH(OH)CH(CH₃)CH₂CH=CHPh |
| —(CH₂)₂(CH₂)₃CH(OH)CH₂CH₂CH=CHPh |
| —(CH₂)₂CH(CH₃)CH(OH)CH(CH₃)(CH₂)₃Ph |
| —(CH₂)₂CH(OH)CH(CH₃)(CH₂)₃Ph |
| —(CH₂)₂CH(CH₃)CH(OH)CH(CH₃)(CH₂)₃Ph |
| —(CH₂)₂CH(OH)(CH₂)₄Ph |
| —(CH₂)₂—OH |
| —(CH₂)₃OH |
| —(CH₂)₅—OH |
| —(CH₂)₈—OH |
| —(CH₂)₁₀—OH |
| —(CH₂)₂—OH |
| —(CH₂)₃—OCH₃ |
| —(CH₂)₅—OCH₃ |
| —(CH₂)₈—OCH₃ |
| —(CH₂)₁₀—OCH₃ |
| —(CH₂)₃OAc |
| —(CH₂)₅OAc |
| —(CH₂)₈OAc |
| —(CH₂)₂—NHCH₃ |
| —(CH₂)₃NHCH₃ |
| —(CH₂)₅—NHCH₃ |
| —(CH₂)₈—NHCH |
| —(CH₂)₁₀—NHCH₃ |
| —(CH₂)₂—N(CH₃)₂ |
| —(CH₂)₃N(CH₃)₂ |
| —(CH₂)₅—N(CH₃)₂ |
| —(CH₂)₈—N(CH₃)₂ |
| —(CH₂)₁₀—N(CH₃)₂ |
| —(CH₂)₂—N(CH₂CH₂)₂O |
| —(CH₂)₃N(CH₂CH₂)₂O |
| —(CH₂)₅—N(CH₂CH₂)₂O |
| —(CH₂)₈—N(CH₂CH₂)₂O |
| —(CH₂)₁₀—N(CH₂CH₂)₂O |
| —(CH₂)₂—N(CH₂CH₂)₂NH |
| —(CH₂)₃N(CH₂CH₂)₂NH |
| —(CH₂)₅—N(CH₂CH₂)₂NH |
| —(CH₂)₈—N(CH₂CH₂)₂NH |
| —(CH₂)₁₀—N(CH₂CH₂)₂NH |
| —(CH₂)₂—OPh |
| —(CH₂)₃OPh |
| —(CH₂)₅—OPh |

| R¹ |
|---|
| —(CH₂)₈—OPh |
| —(CH₂)₁₀—OPh |
| —(CH₂)₂—OC₆H₄-4-CH₃ |
| —(CH₂)₃OC₆H₄-4-CH₃ |
| —(CH₂)₅OC₆H₄-4-CH₃ |
| —(CH₂)₈—OC₆H₄-4-CH₃ |
| —(CH₂)₁₀—OC₆H₄-4-CH₃ |
| —(CH₂)₂—OC₆H₄-4-OH |
| —(CH₂)₃OC₆H₄-4-OH |
| —(CH₂)₅—OC₆H₄-4-OH |
| —(CH₂)₈—OC₆H₄-4-OH |
| —(CH₂)₁₀—OC₆H₄-4-OH |
| —(CH₂)₂—OC₆H₄-4-OCH₃ |
| —(CH₂)₃OC₆H₄-4-OCH₃ |
| —(CH₂)₅—OC₆H₄-4-OCH₃ |
| —(CH₂)₈—OC₆H₄-4-OCH₃ |
| —(CH₂)₁₀—OC₆H₄-4-OCH₃ |
| —(CH₂)₂—OC₆H₄-4-Cl |
| —(CH₂)₃OC₆H₄-4-Cl |
| —(CH₂)₅—OC₆H₄-4-Cl |
| —(CH₂)₈—OC₆H₄-4-Cl |
| —(CH₂)₁₀—OC₆H₄-4-Cl |
| —(CH₂)₂—OC₆H₄-3-CH₃ |
| —(CH₂)₃OC₆H₄-3-CH₃ |
| —(CH₂)₅OC₆H₄-3-CH₃ |
| —(CH₂)₈—OC₆H₄-3-CH₃ |
| —(CH₂)₁₀—OC₆H₄-3-CH₃ |
| —(CH₂)₂—OC₆H₄-3-OH |
| —(CH₂)₃OC₆H₄-3-OH |
| —(CH₂)₅—OC₆H₄-3-OH |
| —(CH₂)₈—OC₆H₄-3-OH |
| —(CH₂)₁₀—OC₆H₄-3-OH |
| —(CH₂)₂—OC₆H₄-3-OCH₃ |
| —(CH₂)₃OC₆H₄-3-OCH₃ |
| —(CH₂)₅—OC₆H₄-3-OCH₃ |
| —(CH₂)₈—OC₆H₄-3-OCH₃ |
| —(CH₂)₁₀—OC₆H₄-3-OCH₃ |
| —(CH₂)₂—OC₆H₄-3-Cl |
| —(CH₂)₃OC₆H₄-3-Cl |
| —(CH₂)₅—OC₆H₄-3-Cl |
| —(CH₂)₈—OC₆H₄-3-Cl |
| —(CH₂)₁₀—OC₆H₄-3-Cl |
| —(CH₂)₂CH(OH)—(CH₂)₂—OH |
| —(CH₂)₂CH(OH)—(CH₂)₃OH |
| —(CH₂)₂CH(OH)—(CH₂)₅—OH |
| —(CH₂)₂CH(OH)—(CH₂)₈—OH |
| —(CH₂)₂CH(OH)—(CH₂)₁₀—OH |
| —(CH₂)₂CH(OH)—(CH₂)₂—OCH₃ |
| —(CH₂)₂CH(OH)—(CH₂)₃—OCH₃ |
| —(CH₂)₂CH(OH)—(CH₂)₅—OCH₃ |
| —(CH₂)₂CH(OH)—(CH₂)₈—OCH₃ |
| —(CH₂)₂CH(OH)—(CH₂)₁₀—OCH₃ |
| —(CH₂)₂CH(OH)—(CH₂)₃OAc |
| —(CH₂)₂CH(OH)—(CH₂)₅OAc |
| —(CH₂)₂CH(OH)—(CH₂)₈OAc |
| —(CH₂)₂CH(OH)—(CH₂)₂—NHCH₃ |
| —(CH₂)₂CH(OH)—(CH₂)₃NHCH₃ |
| —(CH₂)₂CH(OH)—(CH₂)₅—NHCH₃ |
| —(CH₂)₂CH(OH)—(CH₂)₈—NHCH₃ |
| —(CH₂)₂CH(OH)—(CH₂)₁₀—NHCH₃ |
| —(CH₂)₂CH(OH)—(CH₂)₂—N(CH₃)₂ |
| —(CH₂)₂CH(OH)—(CH₂)₃N(CH₃)₂ |
| —(CH₂)₂CH(OH)—(CH₂)₅—N(CH₃)₂ |
| —(CH₂)₂CH(OH)—(CH₂)₈—N(CH₃)₂ |
| —(CH₂)₂CH(OH)—(CH₂)₁₀—N(CH₃)₂ |
| —(CH₂)₂CH(OH)—(CH₂)₂—N(CH₂CH₂)₂O |
| —(CH₂)₂CH(OH)—(CH₂)₃N(CH₂CH₂)₂O |
| —(CH₂)₂CH(OH)—(CH₂)₅—N(CH₂CH₂)₂O |
| —(CH₂)₂CH(OH)—(CH₂)₈—N(CH₂CH₂)₂O |
| —(CH₂)₂CH(OH)—(CH₂)₁₀—N(CH₂CH₂)₂O |
| —(CH₂)₂CH(OH)—(CH₂)₂—N(CH₂CH₂)₂NH |
| —(CH₂)₂CH(OH)—(CH₂)₃N(CH₂CH₂)₂NH |
| —(CH₂)₂CH(OH)—(CH₂)₅—N(CH₂CH₂)₂NH |
| —(CH₂)₂CH(OH)—(CH₂)₈—N(CH₂CH₂)₂NH |
| —(CH₂)₂CH(OH)—(CH₂)₁₀—N(CH₂CH₂)₂NH |
| —(CH₂)₂CH(OH)—(CH₂)₂—OPh |
| —(CH₂)₂CH(OH)—(CH₂)₃OPh |
| —(CH₂)₂CH(OH)—(CH₂)₅—OPh |
| —(CH₂)₂CH(OH)—(CH₂)₈—OPh |
| —(CH₂)₂CH(OH)—(CH₂)₁₀—OPh |
| —(CH₂)₂CH(OH)—(CH₂)₂—OC₆H₄-4-CH₃ |
| —(CH₂)₂CH(OH)—(CH₂)₃OC₆H₄-4-CH₃ |
| —(CH₂)₂CH(OH)—(CH₂)₅OC₆H₄-4-CH₃ |
| —(CH₂)₂CH(OH)—(CH₂)₈—OC₆H₄-4-CH₃ |
| —(CH₂)₂CH(OH)—(CH₂)₁₀—OC₆H₄-4-CH₃ |
| —(CH₂)₂CH(OH)—(CH₂)₂—OC₆H₄-4-OH |
| —(CH₂)₂CH(OH)—(CH₂)₃OC₆H₄-4-OH |
| —(CH₂)₂CH(OH)—(CH₂)₅—CO₆H₄-4-OH |
| —(CH₂)₂CH(OH)—(CH₂)₈—OC₆H₄-4-OH |
| —(CH₂)₂CH(OH)—(CH₂)₁₀—OC₆H₄-4-OH |
| —(CH₂)₂CH(OH)—(CH₂)₂—OC₆H₄-4-OCH₃ |
| —(CH₂)₂CH(OH)—(CH₂)₃OC₆H₄-4-OCH₃ |
| —(CH₂)₂CH(OH)—(CH₂)₅—OC₆H₄-4-OCH₃ |
| —(CH₂)₂CH(OH)—(CH₂)₈—OC₆H₄-4-OCH₃ |
| —(CH₂)₂CH(OH)—(CH₂)₁₀—OC₆H₄-4-OCH₃ |
| —(CH₂)₂CH(OH)—(CH₂)₂—OC₆H₄-4-Cl |
| —(CH₂)₂CH(OH)—(CH₂)₃OC₆H₄-4-Cl |
| —(CH₂)₂CH(OH)—(CH₂)₅—OC₆H₄-4-Cl |
| —(CH₂)₂CH(OH)—(CH₂)₈—OC₆H₄-4-Cl |
| —(CH₂)₂CH(OH)—(CH₂)₁₀—OC₆H₄-4-Cl |
| —(CH₂)₂CH(OH)—(CH₂)₂—OC₆H₄-3-CH₃ |
| —(CH₂)₂CH(OH)—(CH₂)₃OC₆H₄-3-CH₃ |
| —(CH₂)₂CH(OH)—(CH₂)₅OC₆H₄-3-CH₃ |
| —(CH₂)₂CH(OH)—(CH₂)₈—OC₆H₄-3-CH₃ |
| —(CH₂)₂CH(OH)—(CH₂)₁₀—OC₆H₄-3-CH₃ |
| —(CH₂)₂CH(OH)—(CH₂)₂—OC₆H₄-3-OH |
| —(CH₂)₂CH(OH)—(CH₂)₃OC₆H₄-3-OH |
| —(CH₂)₂CH(OH)—(CH₂)₅—OC₆H₄-3-OH |
| —(CH₂)₂CH(OH)—(CH₂)₈—OC₆H₄-3-OH |
| —(CH₂)₂CH(OH)—(CH₂)₁₀—OC₆H₄-3-OH |
| —(CH₂)₂CH(OH)—(CH₂)₂—OC₆H₄-3-OCH₃ |
| —(CH₂)₂CH(OH)—(CH₂)₃OC₆H₄-3-OCH₃ |
| —(CH₂)₂CH(OH)—(CH₂)₅—OC₆H₄-3-OCH₃ |
| —(CH₂)₂CH(OH)—(CH₂)₈—OC₆H₄-3-OCH₃ |
| —(CH₂)₂CH(OH)—(CH₂)₁₀—OC₆H₄-3-OCH₃ |
| —(CH₂)₂CH(OH)—(CH₂)₂—OC₆H₄-3-Cl |
| —(CH₂)₂CH(OH)—(CH₂)₃OC₆H₄-3-Cl |
| —(CH₂)₂CH(OH)—(CH₂)₅—OC₆H₄-3-Cl |
| —(CH₂)₂CH(OH)—(CH₂)₈—OC₆H₄-3-Cl |
| —(CH₂)₂CH(OH)—(CH₂)₁₀—OC₆H₄-3-Cl |
| —(CH₂)₂CH(OR₂)—(CH₂)₂—OH |
| —(CH₂)₂CH(OR₂)—(CH₂)₃OH |
| —(CH₂)₂CH(OR₂)—(CH₂)₅—OH |
| —(CH₂)₂CH(OR₂)—(CH₂)₈—OH |
| —(CH₂)₂CH(OR₂)—(CH₂)₁₀—OH |
| —(CH₂)₂CH(OR₂)—(CH₂)₂—OCH₃ |
| —(CH₂)₂CH(OR₂)—(CH₂)₃—OCH₃ |
| —(CH₂)₂CH(OR₂)—(CH₂)₅—OCH₃ |
| —(CH₂)₂CH(OR₂)—(CH₂)₈—OCH₃ |
| —(CH₂)₂CH(OR₂)—(CH₂)₁₀—OCH₃ |
| —(CH₂)₂CH(OR₂)—(CH₂)₃OAc |
| —(CH₂)₂CH(OR₂)—(CH₂)₅OAc |
| —(CH₂)₂CH(OR₂)—(CH₂)₈OAc |
| —(CH₂)₂CH(OR₂)—(CH₂)₂—NHCH₃ |
| —(CH₂)₂CH(OR₂)—(CH₂)₃NHCH₃ |
| —(CH₂)₂CH(OR₂)—(CH₂)₅—NHCH₃ |
| —(CH₂)₂CH(OR₂)—(CH₂)8-NHCH₃ |
| —(CH₂)₂CH(OR₂)—(CH₂)₁₀—NHCH₃ |
| —(CH₂)₂CH(OR —(CH)₂—N(CH₃)₂ |
| —(CH₂)₂CH(OR₂)—(CH₂)₃N(CH₃)₂ |
| —(CH₂)₂CH(OR₂)—(CH₂)₅—N(CH₃)₂ |
| —(CH₂)₂CH(OR₂)—(CH₂)₈—N(CH₃)₂ |
| —(CH₂)₂CH(OR₂)—(CH₂)₁₀—N(CH₃)₂ |
| —(CH₂)₂CH(OR₂)—(CH₂)₂—N(CH₂CH₂)₂O |
| —(CH₂)₂CH(OR₂)—(CH₂)₃N(CH₂CH₂)₂O |
| —(CH₂)₂CH(OR₂)—(CH₂)₅—N(CH₂CH₂)₂O |
| —(CH₂)₂CH(OR₂)—(CH₂)₈—N(CH₂CH₂)₂O |
| —(CH₂)₂CH(OR₂)—(CH₂)₁₀—N(CH₂CH₂)₂O |
| —(CH₂)₂CH(OR₂)—(CH₂)₂—N(CH₂CH₂)₂NH |
| —(CH₂)₂CH(OR₂)—(CH₂)₃N(CH₂CH₂)₂NH |
| —(CH₂)₂CH(OR₂)—(CH₂)₅—N(CH₂CH₂)₂NH |
| —(CH₂)₂CH(OR₂)—(CH₂)₈—N(CH₂CH₂)₂NH |
| —(CH₂)₂CH(OR₂)—(CH₂)₁₀—N(CH₂CH₂)₂NH |
| —(CH₂)₂CH(OR₂)—(CH₂)₃CH(OH)—(CH₂)₂—OPh |
| —(CH₂)₂CH(OR₂)—(CH₂)₃CH(OH)—(CH₂)₃OPh |
| —(CH₂)₂CH(OR₂)—(CH₂)₃CH(OH)—(CH₂)₅—OPh |

-continued

| $R^1$ |
| --- |
| —(CH$_2$)$_2$CH(OR$_2$)—(CH$_2$)$_8$—OPh |
| —(CH$_2$)$_2$CH(OR$_2$)—(CH$_2$)$_{10}$—OPh |
| —(CH$_2$)$_2$CH(OR$_2$)—(CH$_2$)$_2$—OC$_6$H$_4$-4-CH$_3$ |
| —(CH$_2$)$_2$CH(OR$_2$)—(CH$_2$)$_3$OC$_6$H$_4$-4-CH$_3$ |
| —(CH$_2$)$_2$CH(OR$_2$)—(CH$_2$)$_5$OC$_6$H$_4$-4-CH$_3$ |
| —(CH$_2$)$_2$CH(OR$_2$)—(CH$_2$)$_8$—OC$_6$H$_4$-4-CH$_3$ |
| —(CH$_2$)$_2$CH(OR$_2$)—(CH$_2$)$_{10}$—OC$_6$H$_4$-4-CH$_3$ |
| —(CH$_2$)$_2$CH(OR$_2$)—(CH$_2$)$_2$—OC$_6$H$_4$-4-OH |
| —(CH$_2$)$_2$CH(OR$_2$)—(CH$_2$)$_3$OC$_6$H$_4$-4-OH |
| —(CH$_2$)$_2$CH(OR$_2$)—(CH$_2$)$_5$—OC$_6$H$_4$-4-OH |
| —(CH$_2$)$_2$CH(OR$_2$)—(CH$_2$)$_8$—OC$_6$H$_4$-4-OH |
| —(CH$_2$)$_2$CH(OR$_2$)—(CH$_2$)$_{10}$—OC$_6$H$_4$-4-OH |
| —(CH$_2$)$_2$CH(OR$_2$)—(CH$_2$)$_2$—OC$_6$H$_4$-4-OCH$_3$ |
| —(CH$_2$)$_2$CH(OR$_2$)—(CH$_2$)$_3$—OC$_6$H$_4$-4-OCH$_3$ |
| —(CH$_2$)$_2$CH(OR$_2$)—(CH$_2$)$_5$—OC$_6$H$_4$-4-OCH$_3$ |
| —(CH$_2$)$_2$CH(OR$_2$)—(CH$_2$)$_8$—OC$_6$H$_4$-4-OCH$_3$ |
| —(CH$_2$)$_2$CH(OR$_2$)—(CH$_2$)$_{10}$—OC$_6$H$_4$-4-OCH$_3$ |
| —(CH$_2$)$_2$CH(OR$_2$)—(CH$_2$)$_2$—OC$_6$H$_4$-4-Cl |
| —(CH$_2$)$_2$CH(OR$_2$)—(CH$_2$)$_3$OC$_6$H$_4$-4-Cl |
| —(CH$_2$)$_2$CH(OR$_2$)—(CH$_2$)$_5$—OC$_6$H$_4$-4-Cl |
| —(CH$_2$)$_2$CH(OR$_2$)—(CH$_2$)$_3$OC$_6$H$_4$-3-OCH$_3$ |
| —(CH$_2$)$_2$CH(OR$_2$)—(CH$_2$)$_5$—OC$_6$H$_4$-3-OCH$_3$ |
| —(CH$_2$)$_2$CH(OR$_2$)—(CH$_2$)$_8$—OC$_6$H$_4$-3-OCH$_3$ |
| —(CH$_2$)$_2$CH(OR$_2$)—(CH$_2$)$_{10}$—OC$_6$H$_4$-3-OCH$_3$ |
| —(CH$_2$)$_2$CH(OR$_2$)—(CH$_2$)$_2$—OC$_6$H$_4$-3-Cl |
| —(CH$_2$)$_2$CH(OR$_2$)—(CH$_2$)$_3$OC$_6$H$_4$-3-Cl |
| —(CH$_2$)$_2$CH(OR$_2$)—(CH$_2$)$_5$—OC$_6$H$_4$-3-Cl |
| —(CH$_2$)$_2$CH(OR$_2$)—(CH$_2$)$_8$—OC$_6$H$_4$-3-Cl |
| —(CH$_2$)$_2$CH(OR$_2$)—(CH$_2$)$_{10}$—OC$_6$H$_4$-3-Cl |
| —(CH$_2$)$_8$Ph |
| —(CH$_2$)$_2$CH$_2$CH(OAc)CH$_2$CH$_2$C$_6$H$_{11}$ |
| —(CH$_2$)$_2$CH(CH$_3$)CH$_2$CH(CH$_3$)CH$_2$Ph |
| —(CH$_2$)$_2$COCH$_2$OH |
| —(CH$_2$)$_2$CO$_2$H |
| —CH$_2$CO$_2$H |
| —(CH$_2$)$_2$OCOC(CH$_3$)$_3$ |
| —(CH$_2$)$_3$OCO—(CH$_2$)$_3$CH$_3$ |
| —(CH$_2$)$_3$OCOPh |
| —(CH$_2$)$_3$OCO(CH$_2$)$_3$Ph |
| —(CH$_2$)$_2$CH(OR$_2$)—(CH$_2$)$_8$—OC$_6$H$_4$-4-Cl |
| —(CH$_2$)$_2$CH(OR$_2$)—(CH$_2$)$_{10}$—OC$_6$H$_4$-4-Cl |
| —(CH$_2$)$_2$CH(OR$_2$)—(CH$_2$)$_2$—OC$_6$H$_4$-3-CH$_3$ |
| —(CH$_2$)$_2$CH(OR$_2$)—(CH$_2$)$_3$OC$_6$H$_4$-3-CH$_3$ |
| —(CH$_2$)$_2$CH(OR$_2$)—(CH$_2$)$_5$OC$_6$H$_4$-3-CH$_3$ |
| —(CH$_2$)$_2$CH(OR$_2$)—(CH$_2$)$_8$—OC$_6$H$_4$-3-CH$_3$ |
| —(CH$_2$)$_2$CH(OR$_2$)—(CH$_2$)$_{10}$—OC$_6$H$_4$-3-CH$_3$ |
| —(CH$_2$)$_2$CH(OR$_2$)—(CH$_2$)$_2$—OC$_6$H$_4$-3-OH |
| —(CH$_2$)$_2$CH(OR$_2$)—(CH$_2$)$_3$OC$_6$H$_4$-3-OH |
| —(CH$_2$)$_2$CH(OR$_2$)—(CH$_2$)$_5$—OC$_6$H$_4$-3-OH |
| —(CH$_2$)$_2$CH(OR$_2$)—(CH$_2$)$_8$—OC$_6$H$_4$-3-OH |
| —(CH$_2$)$_2$CH(OR$_2$)—(CH$_2$)$_{10}$—OC$_6$H$_4$-3-OH |
| —(CH$_2$)$_2$CH(OR$_2$)—(CH$_2$)$_2$—OC$_6$H$_4$-3-OCH$_3$ |
| —(CH$_2$)$_3$OCO(CH$_2$)$_{10}$CH$_3$ |
| —(CH$_2$)$_3$OCONHPh |
| —(CH$_2$)$_2$COCH(OH)CH(CH$_3$)CH$_2$Ph |
| —(CH$_2$)$_2$C(OH)(CH$_2$OH)CH(OH)CH(CH$_3$)CH$_2$Ph |
| —(CH$_2$)$_2$CH(CH$_3$)CH(OAc)CH(CH$_3$)CH$_2$C$_6$H$_5$ |
| —(CH$_2$)$_2$CH(CH$_2$OAc)CH$_2$CH(CH$_3$)CH$_2$C$_6$H$_5$ |
| —(CH$_2$)$_2$C(CH$_2$OH)CH(CH$_3$)CH$_2$C$_6$H$_5$ |
| —(CH$_2$)$_2$CH(OH)(CH$_2$)$_3$Ph |
| —(CH$_2$)$_2$CH(OH)(CH$_2$)$_5$Ph |
| —(CH$_2$)$_2$CH(OAc)(CH$_2$)$_5$Ph |
| —(CH$_2$)$_2$CH(OAc)(CH$_2$)$_3$Ph |
| —(CH$_2$)$_2$C(O)(CH$_2$)$_3$Ph |
| —(CH$_2$)$_2$C(O)(CH$_2$)$_5$Ph |
| —(CH$_2$)$_2$(1-methyl-1,2,3,4-tetrahydronaphthyl) |
| —(CH$_2$)$_2$C(CH$_2$)C(O)CH(CH$_3$)CH$_2$Ph |
| —(CH$_2$)$_2$CH[(CH$_2$)$_4$CH$_3$]C(O)CH(CH$_3$)CH$_2$Ph |
| —(CH$_2$)$_2$CH(CH$_2$Ph)C(O)CH(CH$_3$)CH$_2$Ph |
| —(CH$_2$)$_2$C(O)OCH$_2$Ph |
| —(CH$_2$)$_2$C(O)OCH$_3$ | and wherein $R^4$—(A)$_a$— is selected from the group consisting of:

| $R^4$—(A)$_a$— |
| --- |
| CH$_3$(CH$_2$)$_6$CO |
| CH$_3$CO |
| CH$_3$(CH$_2$)$_{10}$CO |
| CH$_3$(CH$_2$)$_{12}$CO |
| CH$_3$(CH$_2$)$_5$—CH=CH(cis)(CH$_2$)$_7$CO |
| CH$_3$(CH$_2$)$_{14}$CO |
| PhO(CH$_2$)$_{10}$CO |
| CH$_3$(CH$_2$)$_6$—p-C$_6$H$_4$—CO |
| Ph(CH$_2$)$_{10}$CO |
| Ph(CH$_2$)$_3$CO |
| 1-adamantylCH$_2$CO |
| CH$_3$(CH$_2$)$_7$NHCO |
| CH$_3$(CH$_2$)$_9$NHCO |
| CH$_3$(CH$_2$)$_{10}$NHCO |
| CH$_3$(CH$_2$)$_{11}$NHCO |
| CH$_3$(CH$_2$)$_{12}$NHCO |
| CH$_3$(CH$_2$)$_{13}$NHCO |
| CH$_3$(CH$_2$)$_{15}$NHCO |
| PhCH$_2$NHCO |
| 4-Ph—Ph—NHCO |
| PhO(CH$_2$)$_{11}$NHCO |
| CH$_3$(CH$_2$)$_9$N(CH$_3$)CO |
| CH$_3$(CH$_2$)$_{15}$N(CH$_3$)CO |
| CH$_3$(CH$_2$)$_{11}$OCO |
| PhO(CH$_2$)$_{11}$OCO |
| PhO(CH$_2$)$_8$ |
| PhO(CH$_2$)$_{11}$ |
| CH$_3$(CH$_2$)$_{13}$ |
| CH$_3$(CH$_2$)$_{15}$ |
| 2-Ph—C$_6$H$_4$—CH$_2$ |
| CH$_3$CH$_2$CO |
| CH$_3$(CH$_2$)$_2$CO |
| (CH$_3$)$_2$CHCO |
| S—CH$_3$CH$_2$CH(CH$_3$)CO |
| CH$_3$O(CH$_2$)$_3$CO |
| CH$_3$(CH$_2$)$_3$CO |
| (CH$_3$)$_2$CHCH$_2$CO |
| (CH$_3$)$_2$CH(CH$_2$)$_2$CO |
| CH$_3$CH$_2$CH$_2$CH(CH$_3$)CO |
| CH$_3$CH$_2$CH(CH$_3$)CH$_2$CO |
| H$_2$N(CH$_2$)$_5$CO |
| CH$_3$(CH$_2$)$_8$CH(CH$_3$)CO |
| cyclohexyl-CH$_2$CO |
| C$_6$H$_5$CH$_2$CO |
| C$_6$H$_5$OCH$_2$CO |
| C$_6$H$_5$CH$_2$CH$_2$CO |
| C$_6$H$_5$OCH$_2$CH$_2$CO |
| C$_6$H$_5$O(CH$_2$)$_3$CO |
| 4-(CH$_3$CO)—C$_6$H$_4$(CH$_2$)$_{10}$CO |
| E-C$_6$H$_5$CH=CHCO |
| E-(3-CH$_3$O)C$_6$H$_4$CH=CHCO |
| 4-(C$_6$H$_5$)—C$_6$H$_4$CO |
| 4-(C$_6$H$_5$)—C$_6$H$_4$CH$_2$CO |
| 4-(C$_6$H$_5$—O)—C$_6$H$_4$CH$_2$CO |
| 3-(C$_6$H$_5$—O)—C$_6$H$_4$CH$_2$CO |
| C$_6$H$_5$—CH$_2$CH(NH$_2$)CO |
| Br(CH$_2$)$_{10}$CO |
| 4-(CH$_3$O)C$_6$H$_4$O(CH$_2$)$_{10}$CO |
| 3-((CH$_3$)$_2$N)C$_6$H$_5$O(CH$_2$)$_{10}$CO |
| 4-((CH$_3$)$_2$N)C$_6$H$_4$S(CH$_2$)$_{10}$CO |
| CH$_3$NHCO |
| (CH$_3$)$_2$NCO |
| CH$_3$CH$_2$NHCO |
| (CH$_3$)$_2$NCH$_2$CH$_2$NHCO |
| (CH$_3$)$_2$CHNHCH$_2$CH$_2$NHCO |
| CH$_3$CH$_2$CH$_2$NHCO |
| (CH$_3$)$_2$CHNHCO |
| cyclopropyl-NHCO |
| CH$_3$CH$_2$CH$_2$CH$_2$NHCO |
| (CH$_3$)$_2$CHCH$_2$NHCO |
| (R)—CH$_3$CH$_2$CH(CH$_3$)NHCO |
| (S)—CH$_3$CH$_2$CH(CH$_3$)NHCO |
| (CH$_3$(CH$_2$)$_3$)(CH$_3$(CH$_2$)$_6$)CHO(CH$_2$)$_3$NHCO |
| CH$_3$(CH$_2$)$_{11}$O(CH$_2$)$_3$NHCO |
| 4-(CH$_3$O)C$_6$H$_4$CH$_2$NHCO |
| 4-(CH$_3$SO$_2$)C$_6$H$_4$CH$_2$NHCO |
| C$_6$H$_5$CH$_2$CH$_2$NHCO |
| C$_6$H$_5$OCH$_2$CH$_2$NHCO |

| $R^4-(A)_a-$ |
|---|
| $C_6H_5O(CH_2)_8NHCO$ |
| adamantyl-$CH_2NHCO$ |
| $(CH_3)_2CHOCO$ |
| $CH_3(CH_2)_9OCO$ |
| $CH_2(CH_2)_3O(CH_2)_2O(CH_2)_2OCO$ |
| $3,4-(CH_3O)_2C_6H_3O(CH_2)_{10}$ |
| $CH_3(CH_2)_2$ |
| $HO_2C(CH_2)_{15}-CO$ |
| $HO_2C-(CH_2)_{10}CO$ |
| $HO_2C(CH_2)_5CO$ |
| $HO_2C(CH_2)_{15}-NHCO$ |
| $HO_2C(CH_2)_{10}-NHCO$ |
| $HO_2C(CH_2)_5NHCO$ |
| $HO_2C(CH_2)_{15}-OCO$ |
| $HO_2C-(CH_2)_{10}-OCO$ |
| $HO_2C(CH_2)_5-OCO$ |
| $HO(CH_2)_{15}-CO$ |
| $HO-(CH_2)_{10}CO$ |
| $HO(CH_2)_5CO$ |
| $HO-(CH_2)_{15}-NHCO$ |
| $HO-(CH_2)_{10}NHCO$ |
| $HO(CH_2)_5NHCO$ |
| $HO(CH_2)_{15}-OCO$ |
| $HO-(CH_2)_{10}-OCO$ |
| $HO(CH_2)_5-OCO$ |
| $CH_3O(CH_2)_{15}-CO$ |
| $CH_3O-(CH_2)_{10}CO$ |
| $CH_3O(CH_2)_5CO$ |
| $CH_3O-(CH_2)_{15}-NHCO$ |
| $CH_3O-(CH_2)_{10}NHCO$ |
| $CH_3O(CH_2)_5NHCO$ |
| $CH_3O(CH_2)_{15}-OCO$ |
| $CH_3O-(CH_2)_{10}-OCO$ |
| $CH_3O(CH_2)_5-OCO$ |
| $CH_3CH_2O(CH_2)_{15}-CO$ |
| $CH_3CH_2O-(CH_2)_{10}CO$ |
| $CH_3CH_2O(CH_2)_5CO$ |
| $CH_3CH_2O-(CH_2)_{15}-NHCO$ |
| $CH_3CH_2O-(CH_2)_{10}NHCO$ |
| $CH_3CH_2O(CH_2)_5NHCO$ |
| $CH_3CH_2O(CH_2)_{15}-OCO$ |
| $CH_3CH_2O-(CH_2)_{10}-OCO$ |
| $CH_3CH_2O(CH_2)_5-OCO$ |
| $C_6H_5O(CH_2)_{15}-CO$ |
| $C_6H_5O-(CH_2)_{10}CO$ |
| $C_6H_5O(CH_2)_5CO$ |
| $C_6H_5O-(CH_2)_{15}-NHCO$ |
| $C_6H_5O-(CH_2)_{10}NHCO$ |
| $C_6H_5O(CH_2)_5NHCO$ |
| $C_6H_5O(CH_2)_{15}-OCO$ |
| $C_6H_5O-(CH_2)_{10}-OCO$ |
| $C_6H_5O(CH_2)_5-OCO$ |
| $4-Cl-C_6H_4O(CH_2)_{15}-CO$ |
| $4-Cl-C_6H_4O-(CH_2)_{10}CO$ |
| $4-Cl-C_6H_4O(CH_2)_5CO$ |
| $4-Cl-C_6H_4O-(CH_2)_{15}-NHCO$ |
| $4-Cl-C_6H_4O-(CH_2)_{10}NHCO$ |
| $4-Cl-C_6H_4O(CH_2)_5NHCO$ |
| $4-Cl-C_6H_4O-(CH_2)_{15}-OCO$ |
| $4-Cl-C_6H_4O-(CH_2)_{10}-OCO$ |
| $4-Cl-C_6H_4O(CH_2)_5-OCO$ |
| $4-CH_3OC_6H_4O(CH_2)_{15}-CO$ |
| $4-CH_3OC_6H_4O-(CH_2)_{10}CO$ |
| $4-CH_3OC_6H_4O(CH_2)_5CO$ |
| $4-CH_3OC_6H_4O-(CH_2)_{10}-NHCO$ |
| $4-CH_3OC_6H_4O-(CH_2)_{10}NHCO$ |
| $4-CH_3OC_6H_4O(CH_2)_5NHCO$ |
| $4-CH_3OC_6H_4O-(CH_2)_{15}-OCO$ |
| $4-CH_3OC_6H_4O-(CH_2)_{10}-OCO$ |
| $4-CH_3OC_6H_4O(CH_2)_5-OCO$ |
| $3-Cl-C_6H_4O-(CH_2)_{15}-CO$ |
| $3-Cl-C_6H_4O-(CH_2)_{10}CO$ |
| $3-Cl-C_6H_4O-(CH_2)_5CO$ |
| $3-Cl-C_6H_4O-(CH_2)_{15}-NHCO$ |
| $3-Cl-C_6H_4O-(CH_2)_{10}NHCO$ |
| $3-Cl-C_6H_4O-(CH_2)_5NHCO$ |
| $3-Cl-C_6H_4O-(CH_2)_{15}-OCO$ |
| $3-Cl-C_6H_4O-(CH_2)_{10}-OCO$ |
| $3-Cl-C_6H_4O-(CH_2)_5-OCO$ |
| $3-CH_3OC_6H_4O-(CH_2)_{15}-CO$ |
| $3-CH_3OC_6H_4O-(CH_2)_{10}CO$ |
| $3-CH_3OC_6H_4O-(CH_2)_5CO$ |
| $3-CH_3OC_6H_4O-(CH_2)_{15}-NHCO$ |
| $3-CH_3OC_6H_4O-(CH_2)_{10}NHCO$ |
| $3-CH_3OC_6H_4O-(CH_2)_5NHCO$ |
| $3-CH_3OC_6H_4O-(CH_2)_{15}-OCO$ |
| $3-CH_3OC_6H_4O-(CH_2)_{10}-OCO$ |
| $3-CH_3OC_6H_4O-(CH_2)_5-OCO$ |
| $C_6H_5S-(CH_2)_{15}CO$ |
| $C_6H_5S-(CH_2)_{10}CO$ |
| $C_6H_5S-(CH_2)_5CO$ |
| $C_6H_5S-(CH_2)_{15}-NHCO$ |
| $C_6H_5S-(CH_2)_{10}NHCO$ |
| $C_6H_5S-(CH_2)_5NHCO$ |
| $C_6H_5S-(CH_2)_{15}-OCO$ |
| $C_6H_5S-(CH_2)_{10}-OCO$ |
| $C_6H_5S-(CH_2)_5-OCO$ |
| $4-Cl-C_6H_4S-(CH_2)_{15}-CO$ |
| $4-Cl-C_6H_4S-(CH_2)_{10}CO$ |
| $4-Cl-C_6H_4S-(CH_2)_5CO$ |
| $4-Cl-C_6H_4S-(CH_2)_{15}-NHCO$ |
| $4-Cl-C_6H_4S-(CH_2)_{10}NHCO$ |
| $4-Cl-C_6H_4S-(CH_2)_5NHCO$ |
| $4-Cl-C_6H_4S-(CH_2)_{15}-OCO$ |
| $4-Cl-C_6H_4S-(CH_2)_{10}-OCO$ |
| $4-Cl-C_6H_4S-(CH_2)_5-OCO$ |
| $4-CH_3OC_6H_4S-(CH_2)_{15}-CO$ |
| $4-CH_3OC_6H_4S-(CH_2)_{10}CO$ |
| $4-CH_3OC_6H_4S-(CH_2)_5CO$ |
| $4-CH_3OC_6H_4S-(CH_2)_{15}-NHCO$ |
| $4-CH_3OC_6H_4S-(CH_2)_{10}NHCO$ |
| $4-CH_3OC_6H_4S-(CH_2)_5NHCO$ |
| $4-CH_3OC_6H_4S-(CH_2)_{15}-OCO$ |
| $4-CH_3OC_6H_4S-(CH_2)_{10}-OCO$ |
| $4-CH_3OC_6H_4S-(CH_2)_5-OCO$ |
| $3-Cl-C_6H_4S-(CH_2)_{15}-CO$ |
| $3-Cl-C_6H_4S-(CH_2)_{10}CO$ |
| $3-Cl-C_6H_4S-(CH_2)_5CO$ |
| $3-Cl-C_6H_4S-(CH_2)_{15}-NHCO$ |
| $3-Cl-C_6H_4S-(CH_2)_{10}NHCO$ |
| $3-Cl-C_6H_4S-(CH_2)_5NHCO$ |
| $3-Cl-C_6H_4S-(CH_2)_{15}-OCO$ |
| $3-Cl-C_6H_4S-(CH_2)_{10}-OCO$ |
| $3-Cl-C_6H_4S-(CH_2)_5-OCO$ |
| $3-CH_3OC_6H_4S-(CH_2)_{15}-CO$ |
| $3-CH_3OC_6H_4S-(CH_2)_{10}CO$ |
| $3-CH_3OC_6H_4S-(CH_2)_5CO$ |
| $3-CH_3OC_6H_4S-(CH_2)_{15}-NHCO$ |
| $3-CH_3OC_6H_4S-(CH_2)_{10}NHCO$ |
| $3-CH_3OC_6H_4S-(CH_2)_5NHCO$ |
| $3-CH_3OC_6H_4S-(CH_2)_{15}-OCO$ |
| $3-CH_3OC_6H_4S-(CH_2)_{10}-OCO$ |
| $3-CH_3OC_6H_4S-(CH_2)_5-OCO$ |
| $O[(CH_2)_2]_2N(CH_2)_{15}-CO$ |
| $O[(CH_2)_2]_2N(CH_2)_5CO$ |
| $O[(CH_2)_2]_2N-(CH_2)_{10}NHCO$ |
| $O[(CH_2)_2]_2N(CH_2)_5NHCO$ |
| $O[(CH_2)_2]_2N(CH_2)_{15}-OCO$ |
| $O[(CH_2)_2]_2N-(CH_2)_{10}-OCO$ |
| $O[(CH_2)_2]_2N(CH_2)_5-OCO$ |
| $C_5H_{10}N(CH_2)_{15}-CO$ |
| $C_5H_{10}N-(CH_2)_{10}CO$ |
| $C_5H_{10}N(CH_2)_5CO$ |
| $C_5H_{10}N(CH_2)_{15}-NHCO$ |
| $C_5H_{10}N-(CH_2)_{10}NHCO$ |
| $C_5H_{10}N(CH_2)_5NHCO$ |
| $C_5H_{10}N(CH_2)_{15}-OCO$ |
| $C_5H_{10}N-(CH_2)_{10}-OCO$ |
| $C_5H_{10}N(CH_2)_5-OCO$ |
| $HN[(CH_2)_2]_2N(CH_2)_{15}-CO$ |
| $HN[(CH_2)_2]_2N-(CH_2)_{10}CO$ |
| $HN[(CH_2)_2]_2N(CH_2)_5CO$ |
| $HN[(CH_2)_2]_2N-(CH_2)_{15}-NHCO$ |
| $HN[(CH_2)_2]_2N-(CH_2)_{10}NHCO$ |
| $HN[(CH_2)_2]_2N(CH_2)_5NHCO$ |
| $HN[(CH_2)_2]_2N(CH_2)_{15}-OCO$ |

-continued

| $R^4$—$(A)_a$— |
|---|
| $HN[(CH_2)_2]_2N$—$(CH_2)_{10}$—OCO |
| $HN[(CH_2)_2]_2N(CH_2)_5$—OCO |
| $CH_3N[(CH_2)_2]_2N(CH_2)_{15}$—CO |
| $CH_3N[(CH_2)_2]_2N$—$(CH_2)_{10}CO$ |
| $CH_3N[(CH_2)_2]_2N(CH_2)_5CO$ |
| $CH_3N[(CH_2)_2]_2N$—$(CH_2)_{15}$—NHCO |
| $CH_3N[(CH_2)_2]_2N$—$(CH_2)_{10}NHCO$ |
| $CH_3N[(CH_2)_2]_2N(CH_2)_5NHCO$ |
| $CH_3N[(CH_2)_2]_2N(CH_2)_{15}$—OCO |
| $CH_3N[(CH_2)_2]_2N$—$(CH_2)_{10}$—OCO |
| $CH_3N[(CH_2)_2]_2N(CH_2)_5$—OCO |
| 1-imidazolyl$(CH_2)_{15}$—CO |
| 1-imidazolyl-$(CH_2)_{10}CO$ |
| 1-imidazolyl$(CH_2)_5CO$ |
| 1-imidazolyl-$(CH_2)_{15}$—NHCO |
| 1-imidazolyl-$(CH_2)_{10}NHCO$ |
| 1-imidazolyl$(CH_2)_5NHCO$ |
| 1-imidazolyl$(CH_2)_{15}$—OCO |
| 1-imidazolyl-$(CH_2)_{10}$—OCO |
| 1-imidazolyl$(CH_2)_5$—OCO |
| 2-imidazolyl$(CH_2)_{15}$—CO |
| 2-imidazolyl-$(CH_2)_{10}CO$ |
| 2-imidazolyl$(CH_2)_5CO$ |
| 2-imidazolyl-$(CH_2)_{15}$—NHCO |
| 2-imidazolyl-$(CH_2)_{10}NHCO$ |
| 2-imidazolyl$(CH_2)_5NHCO$ |
| 2-imidazolyl$(CH_2)_{15}$—OCO |
| 2-imidazolyl-$(CH_2)_{10}$—OCO |
| 2-imidazolyl$(CH_2)_5$—OCO |
| $HO_2C(CH_2)_{15}$— |
| $HO_2C$—$(CH_2)_{10}$— |
| $HO_2C(CH_2)_5$— |
| $HO(CH_2)_{15}$— |
| $HO$—$(CH_2)_{10}$— |
| $HO(CH_2)_5$— |
| $CH_3O(CH_2)_{15}$— |
| $CH_3O$—$(CH_2)_{10}$— |
| $CH_3O(CH_2)_5$— |
| $CH_3CH_2O(CH_2)_{15}$— |
| $CH_3CH_2O$—$(CH_2)_{10}$— |
| $CH_3CH_2O(CH_2)_5$— |
| $C_6H_5O(CH_2)_{15}$— |
| $C_6H_5O$—$(CH_2)_{10}$— |
| $C_6H_5O(CH_2)_5$— |
| 4-Cl—$C_6H_4O(CH_2)_{15}$— |
| 4-Cl—$C_6H_4O$—$(CH_2)_{10}$— |
| 4-Cl—$C_6H_4O(CH_2)_5$— |
| 4-$CH_3OC_6H_4O(CH_2)_{15}$— |
| 4-$CH_3OC_6H_4O$—$(CH_2)_{10}$— |
| 4-$CH_3OC_6H_4O(CH_2)_5$— |
| 3-Cl—$C_6H_4O(CH_2)_{15}$— |
| 3-Cl—$C_6H_4O$—$(CH_2)_{10}$— |
| 3-Cl—$C_6H_4O(CH_2)_5$— |
| 3-$CH_3OC_6H_4O(CH_2)_{15}$— |
| 3-$CH_3OC_6H_4O$—$(CH_2)_{10}$— |
| 3-$CH_3OC_6H_4O(CH_2)_5$— |
| $C_6H_5S(CH_2)_{15}$— |
| $C_6H_5S$—$(CH_2)_{10}$— |
| $C_6H_5S(CH_2)_5$— |
| 4-Cl—$C_6H_4S(CH_2)_{15}$— |
| 4-Cl—$C_6H_4S$—$(CH_2)_{10}$— |
| 4-Cl—$C_6H_4S(CH_2)_5$— |
| 4-$CH_3OC_6H_4S(CH_2)_{15}$— |
| 4-$CH_3OC_6H_4S$—$(CH_2)_{10}$— |
| 4-$CH_3OC_6H_4S(CH_2)_5$— |
| 3-Cl—$C_6H_4S(CH_2)_{15}$— |
| 3-Cl—$C_6H_4S$—$(CH_2)_{10}$— |
| 3-Cl—$C_6H_4S(CH_2)_5$— |
| 3-$CH_3OC_6H_4S(CH_2)_{15}$— |
| 3-$CH_3OC_6H_4S$—$(CH_2)_{10}$— |
| 3-$CH_3OC_6H_4S(CH_2)_5$— |
| $O[(CH_2)_2]_2N(CH_2)_{15}$— |
| $O[(CH_2)_2]_2N$—$(CH_2)_{10}$— |
| $O[(CH_2)_2]_2N(CH_2)_5$— |
| $C_5H_{10}N(CH_2)_{15}$— |
| $C_5H_{10}N$—$(CH_2)_{10}$— |
| $C_5H_{10}N(CH_2)_5$— |
| $HN[(CH_2)_2]_2N(CH_2)_{15}$— |

-continued

| $R^4$—$(A)_a$— |
|---|
| $HN[(CH_2)_2]_2N$—$(CH_2)_{10}$— |
| $HN[(CH_2)_2]_2N(CH_2)_5$— |
| $CH_3N[(CH_2)_2]_2N(CH_2)_{15}$— |
| $CH_3N[(CH_2)_2]_2N$—$(CH_2)_{10}$— |
| $CH_3N[(CH_2)_2]_2N(CH_2)_5$— |
| 1-imidazolyl$(CH_2)_{15}$— |
| 1-imidazolyl-$(CH_2)_{10}$— |
| 1-imidazolyl$(CH_2)_5$— |
| 2-imidazolyl$(CH_2)_{15}$— |
| 2-imidazolyl-$(CH_2)_{10}$— |
| 2-imidazolyl$(CH_2)_5$— |

In a sixth subclass are those compounds of formula (I) with subgeneric formula (VII) prepared following Schemes A to I.

TABLE 6

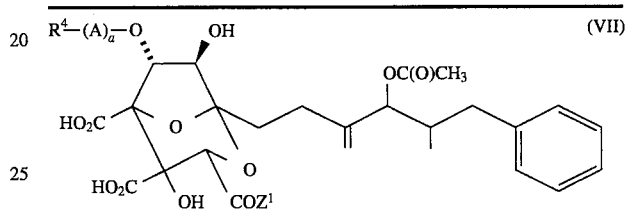

and wherein $R^4$—$(A)_a$— and $Z^1$ are selected from:

| Compound # | $R^4$—$(A)_a$— | $Z^1$ |
|---|---|---|
| 40aa | $CH_3O(CH_2)_3(CO)$— | $(CH_3)_2CHCH_2CH_2O$ |
| 40ab | $(CH_3)_2CHCH_2(CO)$— | $(CH_3)_2CHCH_2CH_2O$ |
| 40ac | $CH_3(CH_2)_{10}(CO)$— | $(CH_3)_2CHCH_2CH_2O$ |
| 40ad | $C_6H_5(CH_2)_3(CO)$— | $(CH_3)_2CHCH_2CH_2O$ |
| 40ae | $C_6H_5O(CH_2)_{10}(CO)$— | $(CH_3)_2CHCH_2CH_2O$ |
| 40af | $(CH_3)CH$—$NH(CO)$— | $(CH_3)_2CHCH_2CH_2O$ |
| 40ag | $CH_3(CH_2)_9NH(CO)$— | $(CH_3)_2CHCH_2CH_2O$ |
| 40ah | $C_6H_5O(CH_2)_8NH(CO)$— | $(CH_3)_2CHCH_2CH_2O$ |
| 40ai | adamantyl-$CH_2NH(CO)$— | $(CH_3)_2CHCH_2CH_2O$ |
| 40aj | $CH_3(CH_2)_9O(CO)$— | $(CH_3)_2CHCH_2CH_2O$ |

The compounds of formula I can be prepared from (1S,3S, 4S,5R,6R,7R)-1-[(4S)-acetoxy-3-methylene-5-methyl-6-phenyl]hexyl-4,6,7-trihydroxy-6-O-(4,6-dimethyl-2-octenoyl)-2,8-dioxabicyclo[3.2.1]octane-3,4,5-tricarboxylic acid (IA), (1S,3S,4S,5R,6R,7R)-1-[(4)-hydroxy-3,5-dimethyl-8-phenyl]oct-7-enyl-4,6,7-trihydroxy-6-O-(tetradeca-6,12-dienoyl)-2,8-dioxabicyclo[3.2.1]octane-3,4,5-tricarboxylic acid (IB), or (1S,3S, 4S,5R,6R,7R)-1-[(4)-acetoxy-5-methyl-6-phenyl]hexyl-4,6,7-trihydroxy-6-O-(6-methyl-9-phenyl-4-nonenoyl)-2,8-dioxabicyclo[3.2.1]octane-3,4,5-tricarboxlic acid (IC) according to sequences described in Schemes A-I and the detailed descriptions below. The preparations of compounds IA, IB and IC have been described in EPO Appl. Nos. 0 450 812 and 0 448 393 and U.S. Pat. No. 5,026,554 respectively and are described below:

Preparation of
(1S,3S,4S,5R,6R,7R)-1-[(4S)-acetoxy-3-methylene-(5R )-methyl-6-phenyl]hexyl-4,6,7-trihydroxy-6-0-((4S), (6S )-dimethyl-2-octenoyl)-2,8-dioxabicyclo[3.2.1]-octane-3,4-5-tricarboxylic acid (IA)

A. Culturing MF5453

Culture MF5453 (ATCC 20986) was inoculated into KF seed medium using one glass scoop of the original soil tube. The KF seed flask was incubated for 73 hours at 25° C., 220 rpm, 85% humidity. At the end of this incubation, 2.0 mls aliquots were aseptically transferred to each of 75 MBM production medium flasks. These production flasks were then incubated at 25° C., 220 rpm, 85% humidity, with a fermentation cycle of 14 days. Flasks were harvested as follows: mycelial growth was homogenized for 20 seconds at high speed using a Biohomogenizer/mixer (Biospec Products Inc. Bartlesville, Okla.); and then 45 mls methanol was added to each flask (final methanol concentration was approximately 50%). Flasks were then returned to he shaker and agitated at 220 rpm for 30 minutes. Subsequently, the contents of the flasks were pooled.

B. Isolation of Compound (IA)

A 6 liter 50% methanol homogenized fungal extract exhibiting a pH of 4.5 was employed in the following isolation procedure. The mycelia was filtered through celits and the recovered mycelia was extracted again by stirring overnight with 3 L of 50% methanol and again filtered.

The combined extract (9 L) of 50% methanol was diluted to 25% methanol with water (total volume 18 L) and applied to a Mitsubishi HP-20 column (750 ml) at a flow rate of 80 ml/minute. The column was washed with water (1 L) and eluted with a stepwise gradient of methanol consisting of 50/50 methanol/$H_2O$ (1 L), 60/40, methanol/$H_2O$ (1 L), 80/20 methanol/$H_2O$ (2 L,) 90/10 methanol/$H_2O$ (1 L), 100% methanol (2 L), and 100% acetone (1L). The fractions from 50/50 to 90/10 methanol/$H_2O$ were combined and diluted with water to 35/65 methanol/$H_2O$ (total volume 10 L).

The 10 L of 35/65 methanol/$H_2O$ was acidified with 1.0N HCl (20 ml) to pH 3.0 and extracted into EtOAc (4 L). The EtOAc layer was separated and the solvent removed in vacuo to yield 260 mg of an orange oil.

A portion (10%) of the orange oil was dissolved in 1 ml methanol and diluted with 0.8 ml 10 mM potassium phosphate (pH 6.5) with some precipitation. The suspension was applied to a preparative HPLC column (Whatman Magnum 20 $C_{18}$, 22 mm ID×25 cm, 8 ml/minute. The initial mobile phase was 60/40 methanol/10 mM $K_3PO_4$, pH 6.5, and after 20 minutes the mobile phase was changed to 80/20 methanol/10 mM potassium phosphate, pH 6.5. Fractions of 8 ml each were collected, and the fractions from 31 to 33 minutes (2) were combined, diluted with water to 35% methanol, acidified with 10% HCl to pH 3, and extracted into EtOAc. The solvent was removed in vacuo and a clear slightly yellow oil identified as the titled compound was obtained.

| KF SEED MEDIUM | per liter | Trace Elements Mix | g/L |
|---|---|---|---|
| Corn Steep Liquor | 5 g | $FeSO_4.7H_2O$ | 1.0 |
| Tomato Paste | 40 g | $MnSO_4.4H_2O$ | 1.0 |
| Oat Flour | 10 g | $CuCl_2.2H_2O$ | 0.025 |
| Glucose | 10 g | $CaCl_2.2H_2O$ | 0.1 |
| Trace Element Mix | 10 ml | $H_3BO_3$ | 0.056 |
| pH adjusted to 6.8 | | $(NH_4)_6Mo_7O_{24}.4H_2O$ | 0.019 |
| (presterile) | | $ZnSO4.7H_2O$ | 0.2 |
| 50 mls/nonbaffled Erlenmeyer flask | 250 mls | | |
| autoclave 20 minutes (121° C., 15 psi) | | dissolved in 1L 0.6 N HCl | |

| MBM Products Medium | g/L |
|---|---|
| Malt extract (Difco) | 5.0 |
| Glucose | 15.0 |
| Peptone | 1.0 |
| $KH_2PO_4$ | 1.0 |
| $MgSO_4$ | 0.5 |
| distilled $H_2O$ (no pH adjustment) | 1000.0 mls |

| | |
|---|---|
| 45 mls/nonbaffled 250 mls Erlenmeyer flask | |
| autoclave 15 minutes (121° C., 15 psi) | |

Preparation of
(1S,3S,4S,5R,6R,7R)-1-[(4)-hydroxy-3,5-dimethyl-
8-phenyl]oct-7-enyl-4,6-7-trihydroxy-6-O-
(tetradeca-6,12-dienoyl)-2,8-dioxabicyclo[3.2.1]-
octane-3,4-5-tricarboxlylic acid (IB)

A. Culturine MF5447

Culture MF5447 (ATCC 20985), inoculated from a soil tube using one glass scoop of soil, was grown in KF seed medium for 72 hours at 25° C., 220 rpm, 85% humidity. At the end of this incubation period, 2.0 mls aliquots were aseptically transferred to each of 45 F204 250 ml Erlenmeyer production flasks. Production flasks were incubated at 25° C. statically for 21 days and then harvested. At harvest 40 mls of methyl ethyl ketone were added to each flask and the solid growth was manually broken apart into smaller pieces. Flasks were then placed onto a gyrotory shaker and shaken at 220 rpm for 30 minutes in order to further break up the mycelial mass as well as to improve contact of the solvent with the cells. After shaking, the contents of the individual flasks were pooled by pouring the entire contents of the flasks (solids and all) into a 4 L beaker.

B. Isolation of Compound (IB)

The methyl ethyl ketone liquid from approximately 2 liters of fermentation extract, cultured for 21 days as described in Example 1A was filtered off. A mixture of ethyl acetate and methanol (1:1, 2 L) was then added to the solid residue. This was stirred for 18 hours using a mechanical stirrer. The mixture was filtered and the filtrate concentrated (Rotovap; 40° C.) to approximately 700 mL. Ethyl acetate (700 mL) was added followed by 500 mL of 5% sodium chloride/water. After stirring for 15 minutes, the aqueous layer was removed and discarded. The ethyl acetate layer was concentrated (Rotovap; 40° C.) to approximately 150 mL. Hexane (500 mL) and methanol (500 mL) were added and the mixture stirred for 15 minutes. The hexane layer was removed and discarded. The methanol layer was dried (Rotovap; 40+ C.) to afford a crude extract.

The crude extract (1.4 g) was dissolved in 25 mL of 3:1:1 hexane/toluene/methanol and applied to a Sephadex LH-20 chromatography column (1 L resin) eluting with the same solvent mixture and with a flow rate approximately 3 mL/minute. The first 1600 mL of eluant was discarded. The following 3600 mL eluant was concentrated to dryness to afford LH-20 eluate. Approximately 310 mg of the LH-20 Eluate was dissolved in 5 mL of 5% methanol/chloroform. This was applied to a silica gel chromatography column (50 mL of E. Merck Kieselgel 40–63 um). The column was eluted stepwise as shown below. Fractions 4–6 were combined and dried to afford an oily residue. The residue (115 mg) was dissolved in 4 mL of tetrahydrofuran and 5 mL of 0.005N hydrochloric acid was added. The resulting suspension was centrifuged (10,000 rpm; 20 minutes). The supernatant was removed and discarded to yield a precipitate.

Twenty-four milligrams of this precipitate was dissolved in 0.2 mL of tetrahydrofuran and 0.2 mL of dimethylsulfoxide was added. This was then adsorbed on the resin bed of an open RP-18 chromatography column (30 mL of Bakerbond 40 µm RP-18), equilibrated with 10% tetrahydrofuran/water. Stepwise solution was followed by HPLC analysis and bioassay of the fractions. Fractions 2–7 were combined and concentrated to approximately 50 mL. The aqueous solution was extracted with 50 mL of ethyl acetate. The ethyl acetate extract was dried and dissolved in 0.3 mL of methanol, followed by the addition of 0.4 mL dimethylsulfoxide, 0.1 mL water, and 0.05 mL 43% acetonitrile/10 mM potassium phosphate buffer (pH 7). This solution was injected on an HPLC column (Amicon Martex Silica MC-100A C8 15 um, 4.6 mm ID×25 cm) eluting with 43% acetonitrile/10 mM potassium phosphate buffer (pH 7) at 1 mL/minute. Fractions 9–12 were combined and 0.05 mL of 0.5N hydrochloric acid was added, followed by 10 mL of ethyl acetate. The ethyl acetate layer was dried to afford Compound (IB).

YME Plating Medium

| Component | Amount |
| --- | --- |
| Yeast Extract | 4.0 g |
| Malt Extract | 10.0 g |
| Glucose | 4.0 g |
| Distilled $H_2O$ | 1000 ml |
| Agar | 25.0 g |

| KF SEED MEDIUM | per liter | Trace Elements Mix | g/L |
| --- | --- | --- | --- |
| Corn Steep Liquor | 5 g | $FeSO_4.7H_2O$ | 1.0 |
| Tomato Paste | 40 g | $MnSO_4.4H_2O$ | 1.0 |
| Oat Flour | 10 g | $CuCl_2.2H_2O$ | 0.025 |
| Glucose | 10 g | $CaCl_2.2H_2O$ | 0.1 |
| Trace Element Mix | 10 ml | $H_3BO_3$ | 0.056 |
| pH adjusted to 6.8 (presterile) | | $(NH_4)_6Mo_7O_{24}.4H_2O$ | 0.019 |
| | | $ZnSO4.7H_2O$ | 0.2 |
| 50 mls/nonbaffled Erlenmeyer flask | 250 mls | | |
| autoclave 20 minutes (121° C., 15 psi) | | dissolved in 1L 0.6 N HCl | |

Production Media

| F204 | | BRF | |
| --- | --- | --- | --- |
| Millet | 15.0 g/flask | Brown rice | 5.0 g/flask |
| Base liquid #1 | 10.0 mls/flask | Base liquid #2 | 20.0 mls/flask |

| Base Liquid #1 | g/L | Trace Elements Mix | g/L |
| --- | --- | --- | --- |
| Yeast extract | 50.0 | $FeSO_4.7H_2O$ | 1.0 |
| Monosodium glutamate | 10.0 | $MnSO_4.4H_2O$ | 1.0 |
| Corn oil | 10.0 mls | $CuCl_2.2H_2O$ | 0.025 |
| Sodium tartrate | 10.0 | $CaCl_2.2H_2O$ | 0.1 |
| $FeSO_4.7H_2O$ | 1.0 | $H_3BO_3$ | 0.056 |
| distilled water (no pH adjustment) | 1000.0 mls | (no pH adjustment) autoclave 20 minutes (121° C., 15 psi) add 15.0 mls distilled $H_2O$/flask | |
| autoclave 15 minutes (121° C., 15 psi) add 15.0 mls distilled $H_2O$/flask autoclave 20 minutes (121° C., 15 psi) | | autoclave 20 minutes (121° C., 15 psi) | |

Solvent composition for silica gel chromatography of the LH-20 Eluate.

TABLE 1b

| Fraction | Solvent % (methanol/water/acetic acid 10:1:1) in chloroform | Volume |
| --- | --- | --- |
| 1 | 5 | 50 mL/fraction |
| 2–3 | 10 | 50 mL/fraction |
| 4–5 | 20 | 50 mL/fraction |
| 6–7 | 30 | 50 mL/fraction |

TABLE 1b-continued

| Fraction | Solvent % (methanol/water/acetic acid 10:1:1) in chloroform | Volume |
| --- | --- | --- |
| 8–9 | 50 | 50 mL/fraction |
| 10–11 | 75 | 50 mL/fraction |
| 12 | 100 | 50 mL/fraction |

Solvent composition for chromatography of the precipitate on Bakerbond RP-18.

| Fraction | Solvent % tetrahydrofuran in water | Volume |
| --- | --- | --- |
| 1 | 10 | 25 mL/fraction |
| 2–3 | 25 | 25 mL/fraction |
| 4–5 | 50 | 25 mL/fraction |
| 6–7 | 75 | 25 mL/fraction |
| 8 | 100 | 25 mL/fraction |

Preparation of
(1S,3S,4S,5R,6R,7R)-1-[(4)-acetoxy-5-methyl-6-phenyl]hexyl-4,6,7-trihydroxy-6-O-(6-methyl-9-phenyl-4-nonenoyl
)-2,8-dioxabicyclo[3.2.1]-octane-3,4,5-tricarboxylic acid (IC)

A. Culturing MF5465

Culture MF5465, (ATCC 74011) inoculated from a soil tube using one glass scoop of soil, was grown in 3 KF seed medium flasks for 74 hours at 25° C., 220 rpm, 85% humidity. The flasks were then pooled, and sterile glycerol added to obtain a final concentration of 10%. The contents were mixed and 2.0 ml aliquots were dispensed aseptically into sterile cryotubes. The vials were frozen and maintained at −80° C.

Three vials contains frozen vegetative mycelia were defrosted and transferred, one to each of three KF seed medium flasks. These seed flasks were incubated for 71 hours at 25° C., 220 rpm, 85% humidity. At completion of the incubation, the three KF flasks were pooled and the seed was used to inoculate 56 Fl production medium flasks. Care was taken to manually distribute seed growth throughout the solid production medium. Production flasks were incubated statically at 25° C. for 21 days. Flasks were harvested as follows: 45 mls 75% methanol was added to each production flask; growth was manually broken apart into small fragments by use of a glass pipette; flasks were re-stoppered and placed onto a gyrotory shaker and agitated for 30 minutes at 220 rpm while the extraction proceeded. After shaking, the contents of the individual flasks were pooled by pouring the solvent-extract off the mycelial covered corn and into a 2 liter Erlenmeyer flask. Contents of each flask were then subjected to a second extraction with another 45 mls 75% methanol. Extraction proceeded as above with the resultant extracts being pooled into a second 2 liter Erlenmeyer flask.

B. Isolation of Compound (IC)

The extracts from above (4800 mL) were loaded onto a DOWEX-1 column (500 mL resin) at a rate of 20 mL/min. The column was then washed with 50% methanol/water (300 mL), and 90% methanol/water (500 mL), and then eluted with 3% ammonium chloride in 90% methanol/water. Six fractions (500 mL) were collected. The first 3 fractions were combined, diluted with water (1 L), and adjusted to pH 2.5 with conc. hydrochloric acid. The acidified eluate was extracted with dichloromethane (2×500 mL). Evaporation of the dichloromethane extract afforded an oily residue (402 mg). The residue was dissolved in methanol (1.2 ml) and loaded on a prep HPLC column (Dynamax 60A, 8 um C8, 24.6×250 mm with guard column). The column was eluted with 72% acetonitrile/28% (0.1% phosphoric acid in water) with a 10 mL/min flow rate. Collecting 5 mL fractions, the desired compound eluted in fractions 29–34. Fractions 29–34 were combined and ethyl acetate (30 mL) was added.

After washing with water (10 mL), the organic layer was evaporated to give Compound (IC) as an oil.

The composition of media employed in the above preparation are:

| KF SEED MEDIUM | per liter | Trace Elements Mix | g/L |
|---|---|---|---|
| Corn Steep Liquor | 5 g | $FeSO_4.7H_2O$ | 1.0 |
| Tomato Paste | 40 g | $MnSO_4.4H_2O$ | 1.0 |
| Oat Flour | 10 g | $CuCl_2.2H_2O$ | 0.025 |
| Glucose | 10 g | $CaCl_2.2H_2O$ | 0.1 |
| Trace Element Mix #2 | 10 ml | $H_3BO_3$ | 0.056 |
| | | $(NH4)6Mo_7O_{24}.4H_2O$ | |
| Distilled water pH adjusted to 6.8 (presterile) | 1000 ml | $ZnSO_4.7H_2O$ | 0.2 |
| 50 mls/nonbaffled Erlenmeyer flask autoclave 20 minutes (121° C., 15 psi) | 250 mls | dissolved in 1L 0.6 N HCl | |

Production Media

| F1 | | BRF | |
|---|---|---|---|
| Cracked corn | 10.0 g/flask | Brown rice | 5.0 g/flask |
| Base liquid #3 | 10.0 mls/flask | Base liquid #2 | 20.0 mls/flask |

| Base Liquid #3 | g/L | Base liquid #2 | g/L |
|---|---|---|---|
| Ardamine PH | 0.2 | Yeast extract | 1.0 |
| $KH_2PO_4$ | 0.1 | Sodium tartrate | 0.5 |
| $MgSO_4.7H_2O$ | 0.1 | $KH_2PO_4$ | 0.5 |
| Sodium tartrate | 0.1 | distilled $H_2O$ | 1000.0mls |
| $FeSO_4.7H_2O$ | 0.01 | | |
| $ZnSO_4.7H_2O$ | 0.01 | (no pH adjustment) | |
| distilled $H_2O$ | 1000.0 mls | | |
| (no pH adjustment) | | autoclave 15 minutes (121° C., 15 psi) add 15.0 mls distilled $H_2O$/flask | |
| autoclave 15 minutes (121° C., 15 psi) | | autoclave 20 minutes (121° C., 15 psi) | |
| | | add 15.0 mls distilled $H_2O$/flask autoclave 20 minutes (121° C., 15 psi) | |

Table 7 below indicates a number of intermediates useful in preparing the final products of this invention.

TABLE 7

$Me_3Si(CH_2)_2$ = P

| # | $Z^1$ | $Z^2$ | $Z^3$ | $R^4$—$(A)_a$— | $R^5$ |
|---|---|---|---|---|---|
| 1a | tBuO | tBuO | tBuO | $P^1$ | H |
| 1b | PO | PO | PO | $P^1$ | H |
| 1c | $CH_3O$ | $CH_3O$ | $CH_3O$ | $P^1$ | H |
| 1d | $CH_3CH_2O$ | $CH_3CH_2O$ | $CH_3CH_2O$ | $P^1$ | H |
| 1e | benzyl-O | benzyl-O | benzyl-O | $P^1$ | H |
| 2a | tBuO | tBuO | tBuO | $P^1$ | $C(CH_3)_2OCH_3$ |
| 2b | PO | PO | PO | $P^1$ | $P-O-CH_2-$ |
| 3a | tBuO | tBuO | tBuO | H | $C(CH_3)_2OCH_3$ |
| 3b | PO | PO | PO | H | $P-O-CH_2-$ |

SCHEME A:

For substitution at position 6 [$R^4$—$(A)_a$—O—] and for the preparation of compounds (4) and (5), compounds IA, IB or IC can be converted to triester (1) by stirring with a $R^2O$—N,N'-dialkylisourea in a solution such as toluene, benzene, acetonitrile, tetrahydrofuran (TEF) and/or dimethoxyethane (DME). [Mathias, L. J., Synthesis, 561–576 (1979)]. $R^2$ may be t-butyl, benzyl, 4-methoxybenzyl, trimethylsilylethyl or any other ester group that is normally selected as an ester protecting group. The rate of tris-esterification utilizing this methodology can be accelerated with gentle heating. An alternative method for the preparation of triester analogs of I(A-C) is to react I(A-C) and a diazoorgano reagent ($R^2N_2$) such as diazomethane or diazoethane in an organic solvent normally used for this reaction such as methanol, TEF or diethylether. A third method involves stirring a solution of I(A-C) with excess $R^2$-halide (chloride, bromide or iodide) in a standard organic solvent in the presence of a base such as triethylamine ($Et_3N$), pyridine or DBU. It may be reasonable at this point to modify or to protect the C-7 hydroxyl group as compound (2). This position may be modified or protected with any number of the commonly utilized protecting groups including the t-butyldimethylsilyl, triethylsilyl, trimethylsilyl, 2-(trialkylsilyl)ethyl, methoxymethyl, and 1-methyl-1-methoxyethyl (MME) ethers. These may be easily appended by methods commonly reported in the literature. Removal of the existing natural product $R^4$—$(A)_a$— acyl group to provide compound (3) can be selectively achieved in the presence of other acyl substituents or esters contained in (2) by use of an alkali metal hydroxide such as lithium hydroxide in the presence of 30% hydrogen peroxide. Employment of titanium (IV)alkoxide reagents in the alcohol corresponding to the triester will also selectively de-acylate at position 6, provided that the $R^1$ moiety does not contain an ester grouping. A third mode of selective deacylation can be achieved with hydroxylamine hydrochloride. Alternatively, the deacylated IB and IC analoguss may be prepared according to the procedures in Schemes H and I, respectively.

Derivatization of compound (3) at the 6 position with $R^4$—$(A)_a$— as an ester, carbamate, carbonate or ether can be accomplished in high yield utilizing a number of procedures. For esterification, employment of an acid chloride or anhydride (symmetrical or mixed) in a dried aprotic solvent such as dichloromethane, THF, DME, diethyl ether with a base such as $Et_3N$, dimethylminopyridine (DMAP) or pyridine are two normally used methods. Another method utilizes the requisite carboxylic acid in an aprotic solvent with any of the standard carbodiimide coupling reagents, such as dicyclohexylcarbodiimide (DCC), 2-ethoxy-1-ethoxycarbonyl-1,2-dihydroquinolone (EEDQ), benzotriazol-1-yloxytris(dimethylamino)phosphoniumhexafluorophosphate (BOP reagent). Carbamate derivatives can be prepared by reacting (3) with an isocyanate, that is commercially available or that can be prepared, in an aprotic solvent such as toluene, pyridine, benzene, acetonitrile, tetrahydrofuran (THF) and/or dimethoxyethane (DME). An alternate method involves first reacting alcohol (3) with carbonyldiimidazole in an anhydrous aprotic solvent such as toluene, benzene, acetonitrile, tetrahydrofuran (TEF) and/or dimethoxyethane (DME) followed by the addition of the appropriate amine. Normally, the intermediate 1-imidazocarbonyl analog (4) can be isolated and purified by standard chromatographic methods. Carbonate analogs can be prepared by the second procedure described for the preparation of carbamates, with an alcohol being used in place of the amine. Ether analogs can be prepared by standard alkylation reactions with the appropriate organohalide (Cl, Br, I) in an anhydrous solvent such as toluene, benzene, acetonitrile, tetrahydrofuran (THF), dimethoxyethane (DME), or dimethylformamide (DMF) and a base such as sodium or potassium hydride. If an organoiodide is not employed, the reaction rate can be accelerated with a catalytic amount of tetra-n-butylammonium iodide. Any of these derivatives (4) can be purified by standard chromatographic methods using silica gel as the solid phase.

Deprotection of the tris ester of (4) or (4') to provide analogs (5) of I can be achieved in high yield by commonly used methods t-Butyl esters are removed in an aprotic solvent with trifluoroacetic acid (TFA), trialkylethylsilyl esters can be removed with standard fluoride reagents such as tri-n-butyl-ammonium fluoride, and benzyl or substituted benzyl esters can be selectively removed by standard methodology including hydrogenation or more selectively via transfer hydrogenation.

SCHEME B:

Where the starting material is compound (IA) that is (1S,3S,4S,5R,6R,7R)-1-[(4S)-acetoxy-3-methylene-(5R)-methyl-6-phenyl]hexyl-4,6,7-trihydroxy-6-O-((4S),(6S)-dimethyl-2-octenoyl)-2,8-dioxabicyclo-[3.2.1]octane-3,4,5-tricarboxylic acid, the 4'-[S]-acetoxy group at $R^1$ can be modified in a variety of ways to provide the compounds of subgeneric formula V as described in Table 4. The acetyl group of tris-t-butylester-7-(1-methyl-1-methoxyethyl) ether (2a, Table 6) can be selectively removed by a reagent composed of cerium (III) chloride and a Grignard reagent such as methyl or ethyl magnesium chloride in THF. The alcohol product (4'a) can be derivatized as an ester, carbamate, carbonate or ether utilizing procedures similar to those used for the preparation of analogs (4). Deprotection of compounds from (4'a) is carried out in a manner similar to that for preparation of compounds (5) to produce derivatives (7).

Any of the carboxyl groups C3, C4 and/or C5 of compounds I(A-C),(5) and (7) may be selectively derivatized by procedures described in the following Schemes B and C.

Compounds of general structure (7) can be selectively converted to mono C3 esters (8) ($CO_2R^2$) by stirring a solution of (5) or (7) in the appropriate alcohol in the presence of an acid catalyst such as hydrochloric (HCl) or sulfuric acid ($H_2SO_4$) that can be added or generated in situ by the addition of acetylchloride to the alcohol solvent used. The crude products can be purified by liquid chromatography. The C4 and C5 carboxyl groups of (8) can subsequently be differentially eterified by use of $R^2O$—N,N'-dialkylisoureas to produce differentially tris-esterified analog (9). For further elaboration at C3, compound (9) can be selectively deprotected to produce compound (10). For example, when $R^2$ is benzyl, it can be selectively removed by hydrogenolysis when $R^{2'}$ is t-butyl, triorganosilylethyl, triorganosilyl or some other nonhydrogenalizable group. Compound (10) can be derivatized as $COZ^1$ by any number of methods. Conversion of (10) to an intermediate mixed anhydride is accomplished by stirring (10) in an anhydrous aprotic solvent such as diethylether, TEF, DME or dichloromethane with an alkyl chloroformate such as isobutyl, isopropyl, methyl or ethyl chloroformate and a base such as N-methylmorpholine pyridine, DBU, DMAP or $Et_3N$. To this mixed anhydride is then added an amine for making amides, an alcohol for making esters or a mercaptan for making thioesters. The resultant compound (11) can then be selectively deprotected at C4 and C5 by methods that have been previously described to give compound (12). Thus, in one step one can selectively prepare a C3 ester of (7); in three steps one can produce a C4, C5-diester of (7); and in 5 steps one could produce C3 amide analogs of (7).

SCHEME C:

C3-monoester (8) can also be selectively esterified at C5 by stirring compound (8) in an anhydrous aprotic solvent such as benzene, toluene, THF, or DME with an isourea reagent such as O-t-butyl-N,N'-diisopropylisourea to give compound (19) as the major product. This may also be accomplished by stirring compound (8) with trifluoroacetic acid anhydride (TFAA) followed by addition of an alcohol. C5 mercaptoesters or amides can be prepared if a mercaptan or amine is used in place of an alcohol.

In the case where (13) is the 3,5-dibenzyl ester, one can selectively derivatize the C4-carboxyl group as an ester, amide or mercaptoester (15) by the same methods described above for derivatization of compound (10). Similarly, when (14) is a 3,4-dibenzyl ester, the C5 position may be similarly derivatized to produce (17). Both (15) or (17) may be selectively deprotected by hydrogenolysis to provide diacids (16) or (18).

Differentially bis-esterified (19) can be derivatized at C4 by procedures previously described to produce (20). Strategic selection of C3 and C5 esters permit differential deprotection to produce compounds (21), (22) or (23).

Triesters of I could be prepared by several procedures. Stirring I with $R^2O$—N,N'-dialkylurea in a solvent such as methylene chloride, toluene, benzene, acetonitrile, dioxane, tetrahydrofuran, and/or dimethoxyethane gives I-triesters in good yield. Also, stirring I with a diazoorgano reagent ($R^2N_2$) such as diazomethane in organic solvents such as tetrahydrofuran, diethyl ether or methanol gives the triesters in excellent yield. An alternative procedure to prepare triesters of I is to stir I with 1,8-diazabicyclo[5.4.0]undec-7-ene (DBU) and alkyl halide in solvents such as acetonitrile, THF and dimethoxyethane.

C-3 monoesters of I could be prepared by several procedures. Stirring I in an alcohol in the presence of an acid such as hydrochloric acid or sulfuric acid gives selective esterification at C-3. When this reaction is carried out in benzyl alcohol the C-3 benzyl ester formed could be used as a C-3 protecting group. This allows modification of he C-4 and C-5 carboxyl groups by forming esters or amides in this positions by any of the reactions described above for triester formation. As such, one can prepare I-4,5-di-t-butyl ester from I-3-benzyl-4,5-di-t-butyl ester by removing the benzyl group by hydzogenolysis with Pd/C and hydrogen gas or transfer hydrogenolysis with Pd/C and methyl cycohexadiene.

I-4,5-dibenzyl ester, I-4,5-di-t-butyl ester or other 4,5-diesters could be modified at the C-3 position by several procdures. For example I-4,5-di-t-butyl ester could be treated with N-methyl morpholine followed by isobutylchloroformate to form a mixed anhydride which reacts well with various alcohols and amines to form the corresponding esters and amides. I-4,5-di-t-butyl ester could also be treated with carbonyl diimidazle or thionyl chloride or BOP-Cl followed by alcohol, thioalcohols or amines to form esters, thioesters or aides respectively. The 4-5-di-t-butyl ester groups could be removed later by stirring the triester formed with trifluoroacetic acid (TFA) in methylene chloride.

I-3,4-diesters or I-3,5-diesters could be prepared from C-3 monoesters by stirring C-3 esters with a base such as DBU and appropriate alkyl halide in solvents such as benzene, TEF and acetonitrile. In this reaction, using one equivalent of base to substrate ratio mainly gives the 3,4-diesters, while a base to substrate ratio of two or more gives mainly the 3,5-diesters as the major product. In the above diester formation if the C-3 substituent is a benzyl group, debenzylation of the resulting 3,4- and 3,5-diesters gives C-4 and C-5 monesters selectively, thereby allowing selective modification of each of the three carboxyl groups.

SCHEME D:

Compounds (4) or (6) can be further derivatized by hydrogenation/hydrogenolysis. For example, when (4) or (6) is stirred in ethyl acetate with a catalytic amount of Pd/C or rhodium-aluminate in an atmosphere of hydrogen gas, a mixture of compounds (24) and (25) can be produced. Further hydrogenation can produce compound (26). When (4) or (6) is a derivative of IA, the [S]-hydroxyl group at position 4 of Cl can be inverted to compound (27) by the Mitsunobu reaction [O. Mitsunobu, Bull. Chem. Soc. Japan, 44, 3427 (1971)]. Compound (27) can be further derivatized by procedures analogous to those employed to produce compounds (6) as described in Scheme B.

SCHEME E:

The Cl side chain of compound (4') can be selectively degraded to intermediates (30), (32) and (33) which can be synthetic starting points for broad synthetic modification. One procedure involves the selective osmylation of (4') to produce penta-ol compound (29). Selective oxidative cleavage of (29) with periodate provides a mixture of hydroxyketones (31a) and (31b). Compound (31a) can also be produced by reacting the appropriate compound (4') with ozone. Reduction followed by oxidative cleavage of hydroxy-ketones (31) gives aldehyde (32) which can be reduced to alcohol (33) by several standard procedures which may include sodium borohydride, in an appropriate solvent. Exhaustive periodate cleavage of (29) produces carboylic acid analog (30). Acid (30) can be reduced to (33).

SCHEME F:

Transformations of intermediates (30), (32) and (33) for derivatization of the Cl-side chain are of standard procedures. Ester derivatives of (30) can be prepared by stirring with a $R^2O$—N,N'-dialkylisourea in a solution such as toluene, benzene, acetonitrile, tetrahydrofuran (THF) and/or dimetoxyethane (DME). [Mathias, L. J., Synthesis, 561–576 (1979)]. Ester derivatives may also be prepared by stirring a solution of (30) with excess $R^2$-halide (chloride, bromide or iodide) in a standard organic solvent in the presence of a base such as triethylamine ($Et_3N$), pyridine or DBU. For ester or amide derivatives, employment of an acid chloride or anhydride (symmetrical or mixed) of (30) in a dried aprotic solvent such as dichloromethane, THF, DME, diethyl ether with a base such as $Et_3N$, dimethylaminopyridine (DMAP) or pyridine are two normally used methods. Another method utilizes the reaction of (30) and the requisite alcohol or amine in an aprotic solvent with any of the standard carbodiimide coupling reagents, such as dicyclohexylcarbodiimide (DCC), 2-ethoxy-1-ethoxycarbonyl-1,2-dihydroquinolone (EEDQ), benzotriazol-1-yloxytris-(dimethylamino)phosphoniumhexafluorophosphate (BOP reagent). Ketone derivatives (34) can be prepared by reacting (30) with an alkyl chloroformate such as methyl chloroformate to form the intermediate mixed anhydride. Subsequent reaction of the mixed anhydride with an alkyl lithium reagent or Grignard reagent provides ketone derivatives (34). Ketone derivatives (34) can be reduced to an alcohol group by stirring the ketone in a solvent such as methanol or ethanol with sodium borohydride. Any of the above derivatives can be deprotected to the triacid or selectively esterified or amidated analogs using procedures previously described.

Aldehyde analog (32) can be converted to olefinic derivatives (35) utilizing well known reactions such as the Witrig or Peterson olefinations. By these methods, both cis and trans olefins can be prepared. These olefinic derivatives can be converted to saturated derivatives (35) by hydrogenation. Alcohol derivatives of (32) can be prepared by the addition of an organometallic reagent such an alkyl lithium or a Grignard reagent. The alcohol derivative can be further derivatized by conversion to an ether, ester or carbamate by procedures described in Scheme B. Alternatively, alcohol (36) can be oxidized to ketone derivative (37) utilizing any one of a variety of commonly used oxidation reagents.

Hydroxy-derivative (33) can be derivatized as a sulfide, ether, unsubstituted or substituted amine, amide, ester, alkyl, or carbamate derivative. (33) can be derivatized as its p-toldenesulfonate, methanesulfonate, chloride, bromide or iodide by commonly used procedures. With any of these reagents can be reacted a metalalkoxide, metalmercaptide, amine to form ethers, sulfides or amines. Amines can be converted to amides by coupling with carboxylic acids via standard peptide coupling reagents. Alkyl derivatives can be prepared by reacting tosylate, methanesulfonate or halide derivatives with the appropriate organometallic reagent. Carbamate and Ester derivatives of (33) can be prepared by procedures described in Scheme A.

SCHEME G:

The 6-position side chains which contain a heteroatom, Y, such as O, S, SO, $SO_2$, NH or $NR^3$ can be readily prepared. One general synthetic strategy to prepare side chains for the preparation of esters, carbamates, carbonates or ethers containing a heteroatom involves a Williamson-type alkyation of a haloorganoester (41) such as t-butyl-3-bromo-propionate with an alcohol (Patai, "The Chemistry of the Ether Linkage", pp 446–450, 460–468, Interscience, New York, 1967), a mercaptan (Peach, in Patai, "The Chemistry of the Thiol Group", Wiley, N.Y., 1974) or an amine such a n-decylamine (40) in the presence of the appropriate base to give ester (42). Compound (42) may also be prepared in the reverse manner with organohalide (40') and aminoester, hydroxyester or mercaptoester (41'). Esters of type (42) can also be prepared by conjugate addition of (40) to 2,3- unsaturated esters (44) in the presence of an appropriate base. In the case where Y is NH or NR, it is more convenient to prepare compounds (42) by reductive alkylation with amine (40) or (41') with an aldehyde (41) or (40') where in these special cases, X=CHO. (Klyuev and Khidekel, Russ. Chem. Rev., 49, 14–27, 1980, Rylander, "Catalytic Hydrogenation over Platinum Metals", Acedemic Press, New York, 1967, Botch et. al., J. Am. Chem, Soc., 93, 2897, 1971) Ester (42). can be hydrolyzed to carboxylic acid (43), a substrate for acylation at C6 of I (A-C). Alternatively, (42) or (43) can be reduced to the corresponding alcohol (45), which can act as substrates for carbonate preparation. Alcohol (45) may be prepared by reaction of (46) with (47) or (46') with (47') by methods similar to those for (40) and (41) or (40') and (41'). In this case a protected alcohol (47) or (47') reacts to form a protected form of (45)which can then be deprotected. Alcohol (45) can be coverted to a leaving group such as a methansulfonate, paratoluenesulfonate, bromide or iodide by standard procedures. Thus, compound (48) would act as a substrate for the preparation of ether derivatives. Alternatively, (48) can be converted to amino analogs (49) which would act as substrates for the preparation of carbamate analogs.

SCHEME H:

Further exemplifying the derivatization of these natural products, in the case of IB, protection of the three acid functionalities as t-butyl esters (1B) is accomplished using the O-t-butyl-N,N'-diisopropylisourea method described in Scheme A. Selective protection of the $C_7$ alcohol proceeds with 2-methoxypropene giving (2B), also described in Scheme A. The C4' alcohol is protected using 5,6-dihydro-4-methoxy-2H-pyran giving the C4' enol ether product of vinyl ether exchange, (2B'). The ester at C6 is removed using sodium hydroxide with concomitant loss of the t-butyl ester at C3. The crude product is re-esterified at C3 using O-t-butyl-N,N'-diisopropylisourea to give the C6-hydroxy-7-MME-tris-t-butyl ester (3B'). The 6-hydroxy group can be functionalized using the previously described procedures (Scheme A) to provide 4B' which was deprotected with trifluoroacetic acid in an aprotic solvent to give the C6 analogs of IB.

SCHEME I:

As an additional means of derivatizing the natural products, in the case of IC, the 7-MME-tris-t-butyl ester (2C) is synthesized according to the procedures described in Scheme A. The olefin of the C6 ester provides a derivatization site allowing for selective C6 deacylation while maintaining the C4' acetate. Oxidation, for example with osmium tetroxide, provides a mixture of diastereomeric C6-derived diols (2C'). These diol intermediates are unstable to basic conditions such as potassium t-butoxide or DBU in DMF. The resulting C6-hydroxy-7-MME-tris-t-butyl ester (3C) is then functionalized as described in Scheme A to give the protected derivative (4C). All protecting groups are removed using the trifluoroacetic acid method to give the target IC-C6 analogs.

SCHEME A

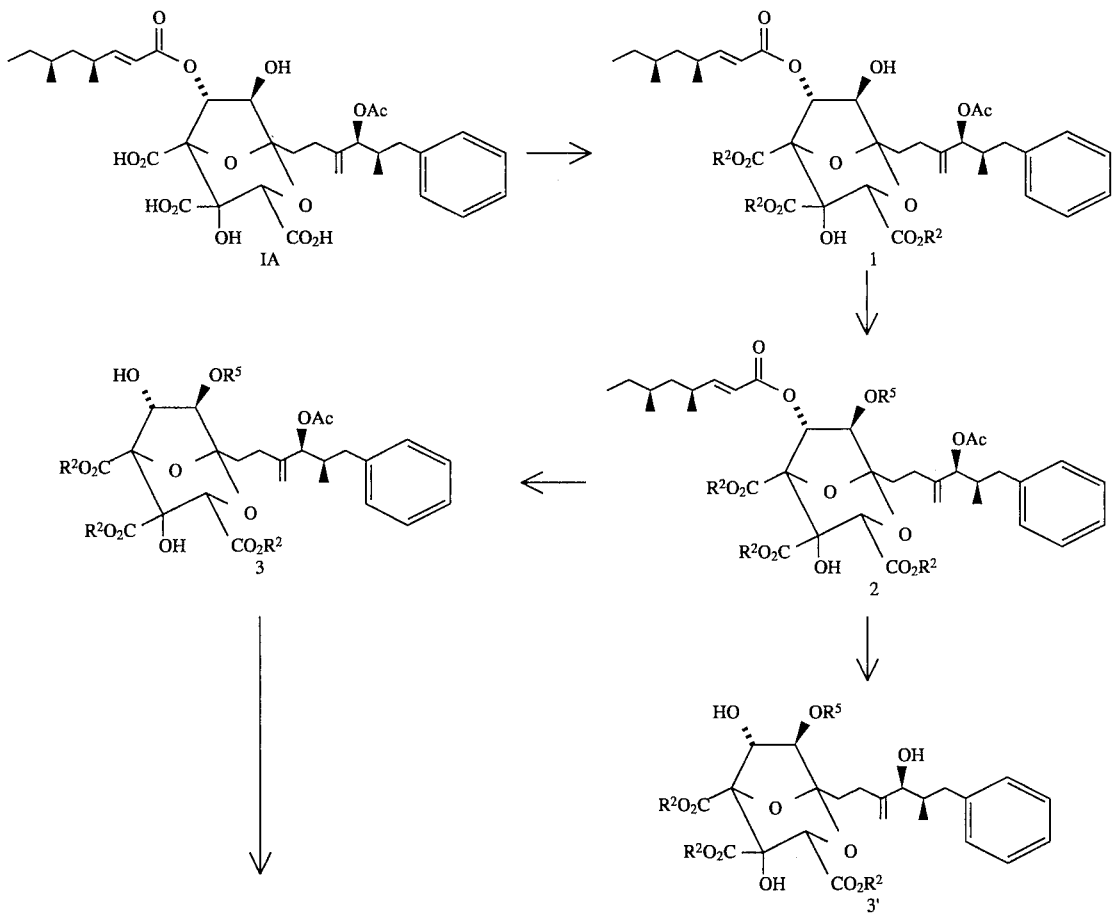

-continued
SCHEME A
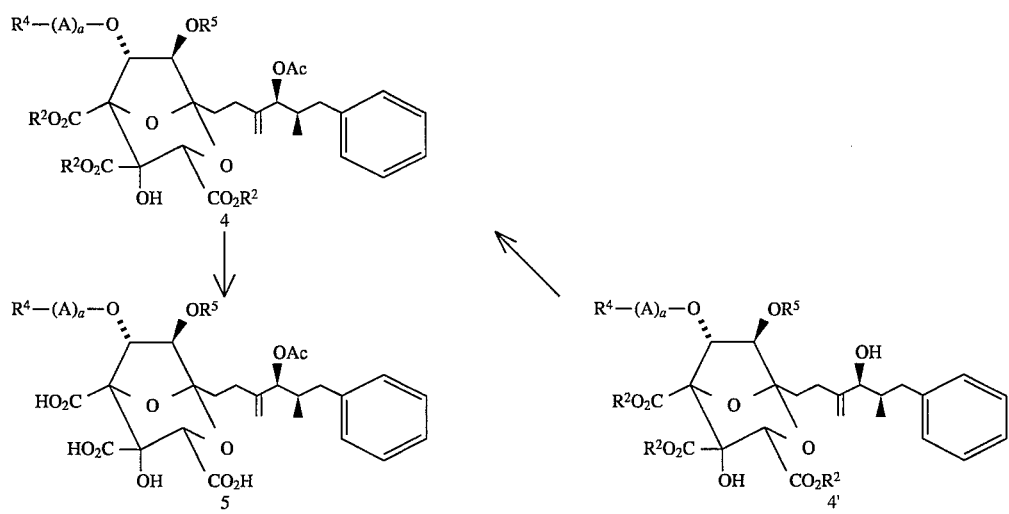
SCHEME B
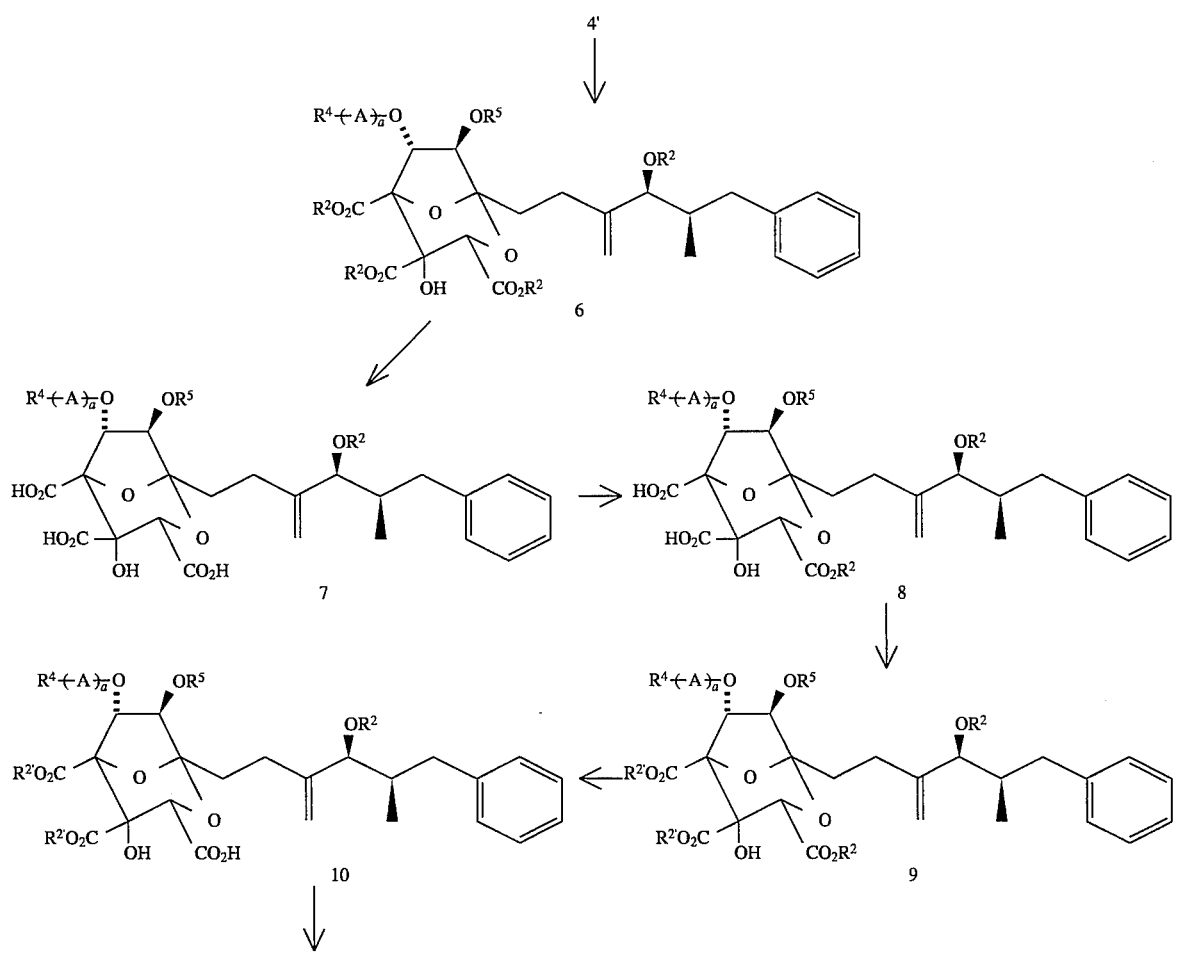

-continued
SCHEME B
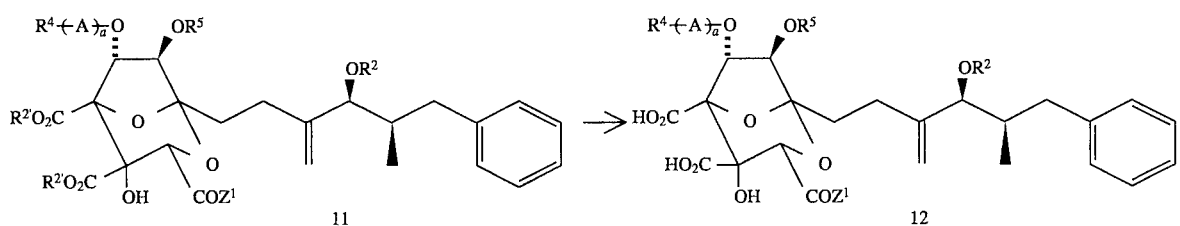
SCHEME C
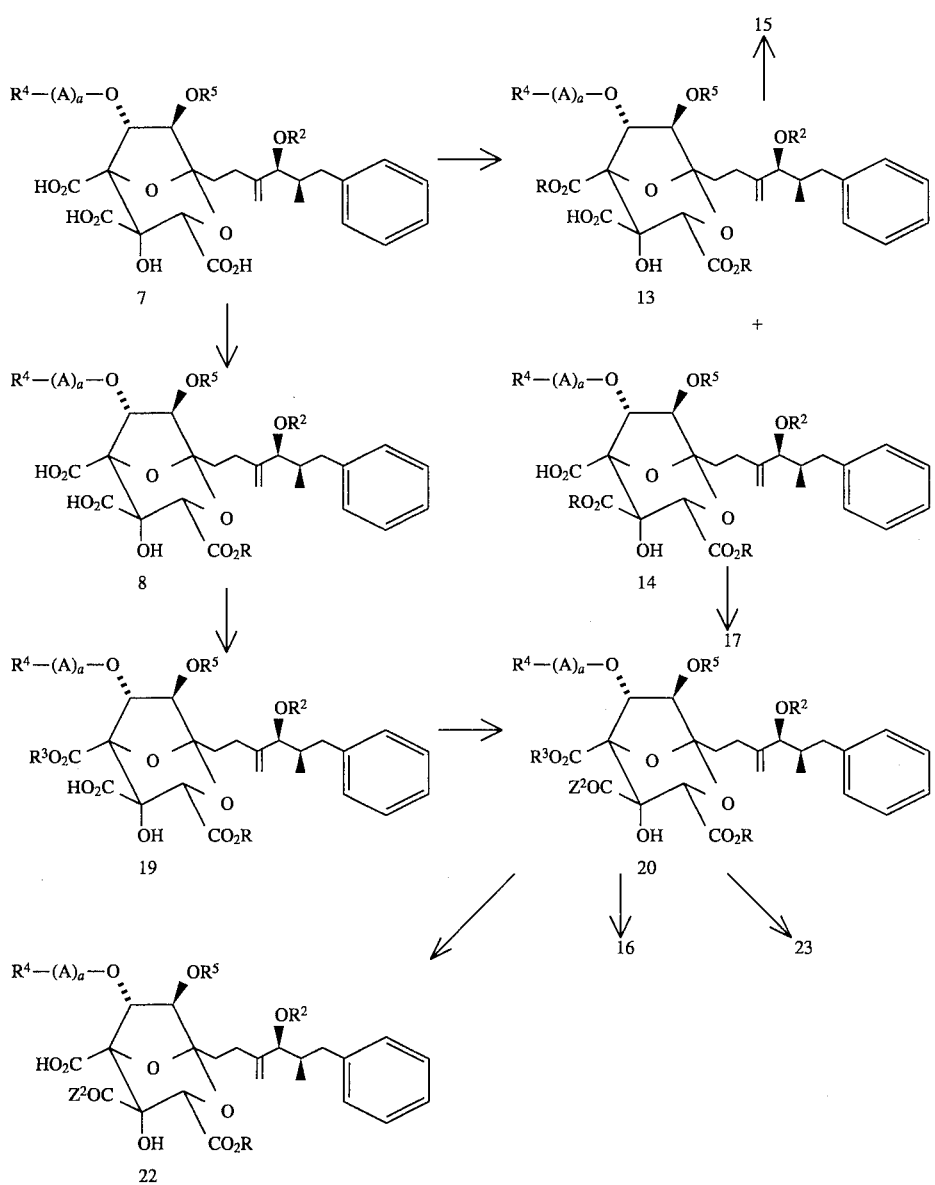

-continued
SCHEME C
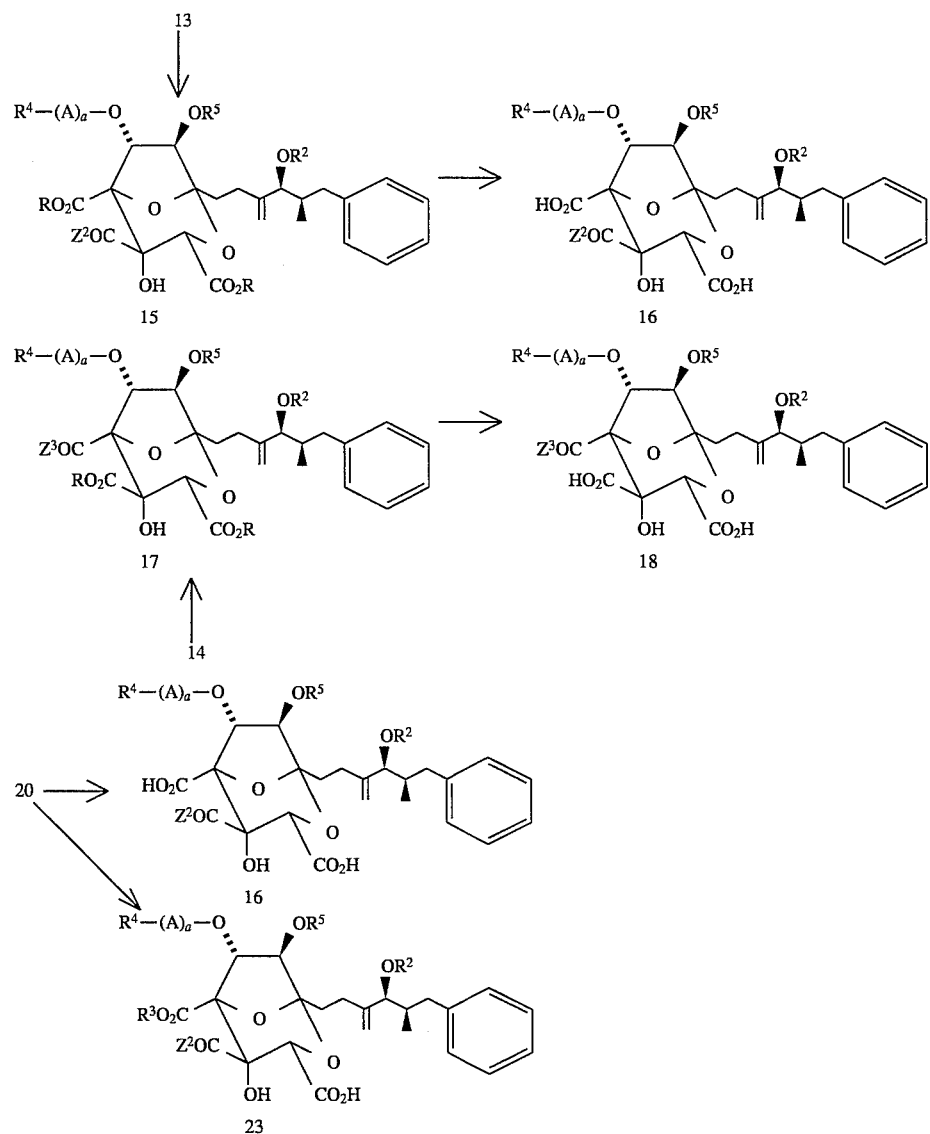

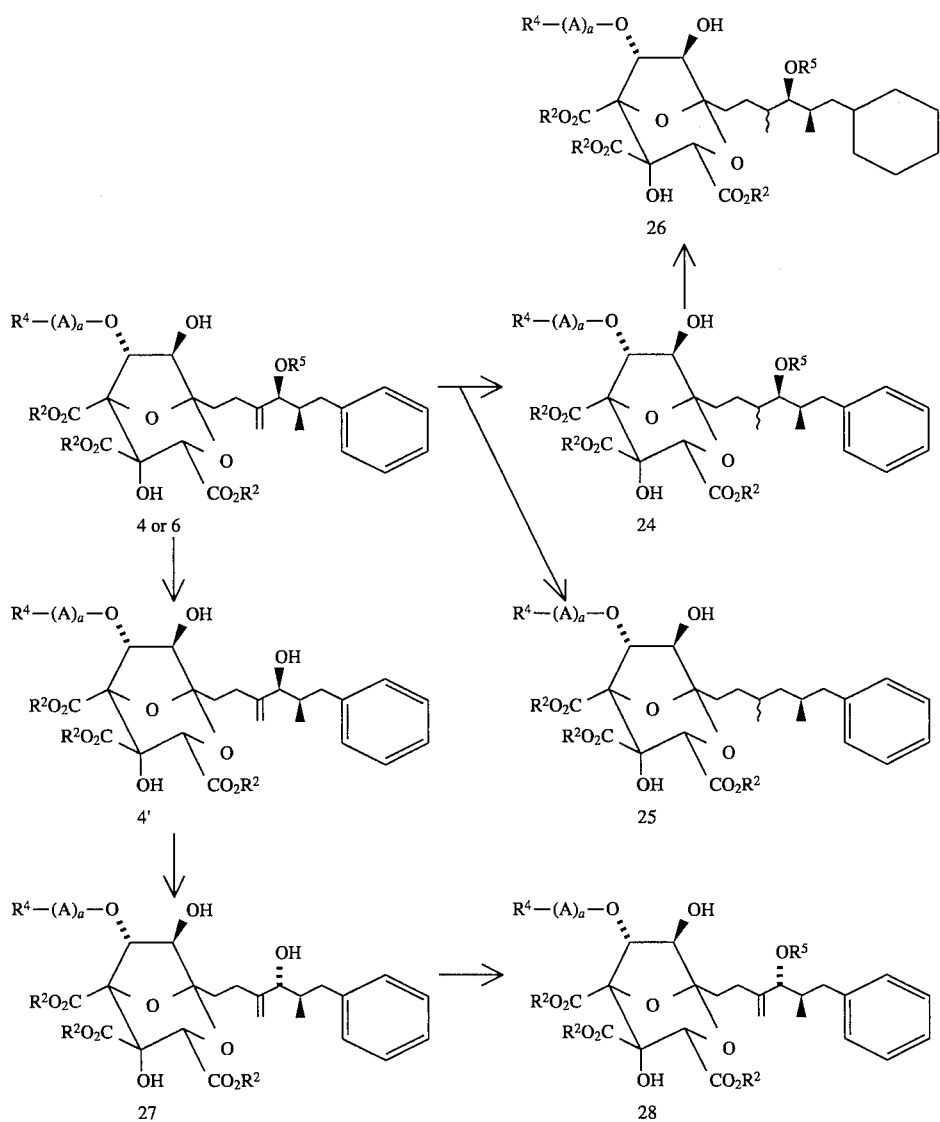
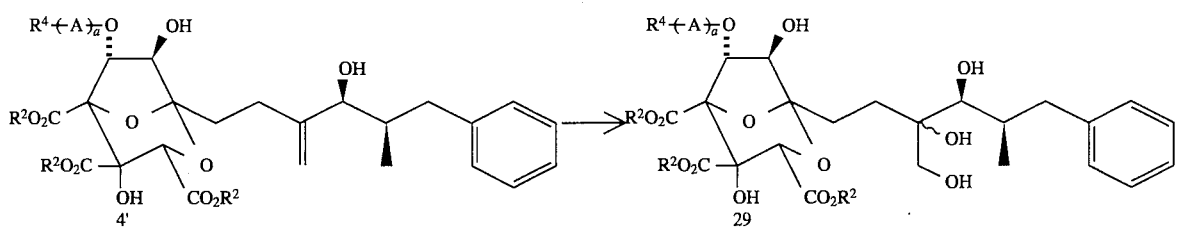

-continued
SCHEME E
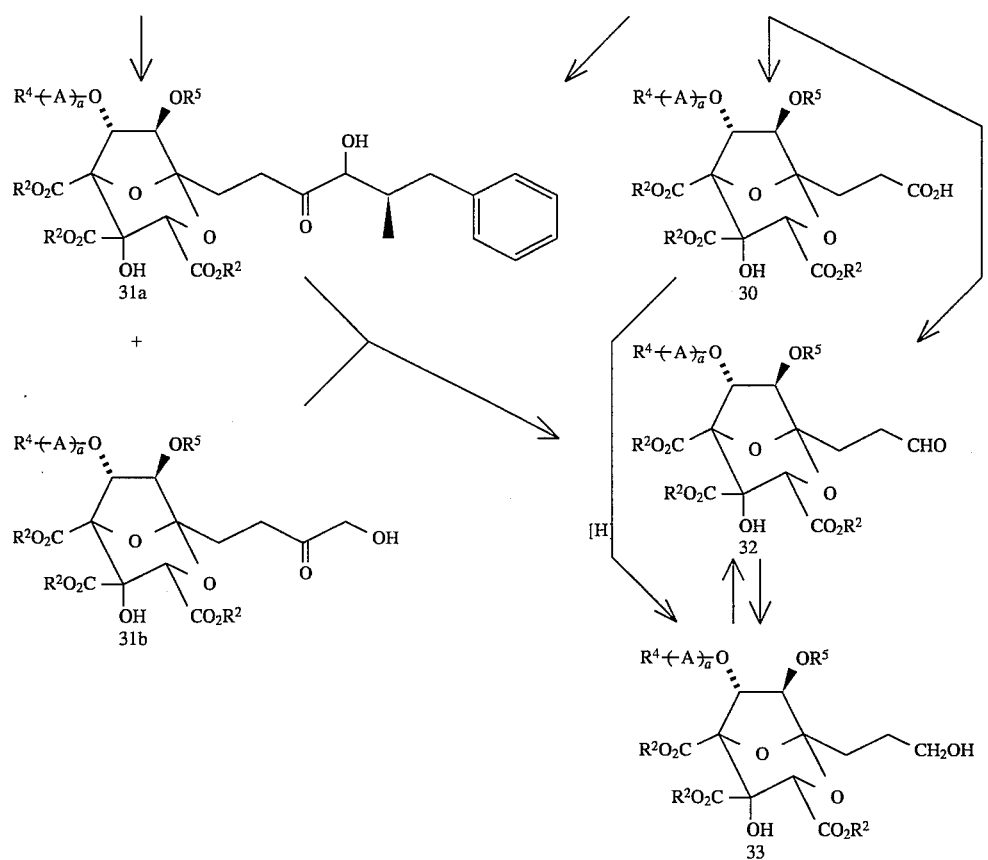
SCHEME F
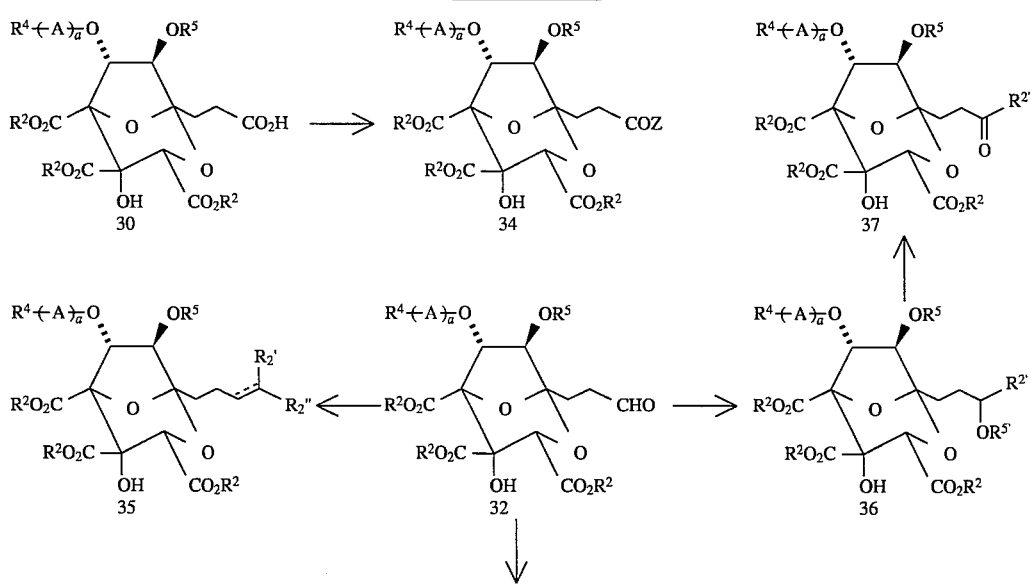

-continued
SCHEME F
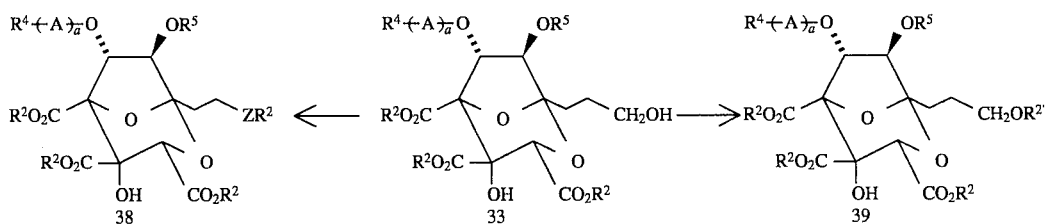
SCHEME G
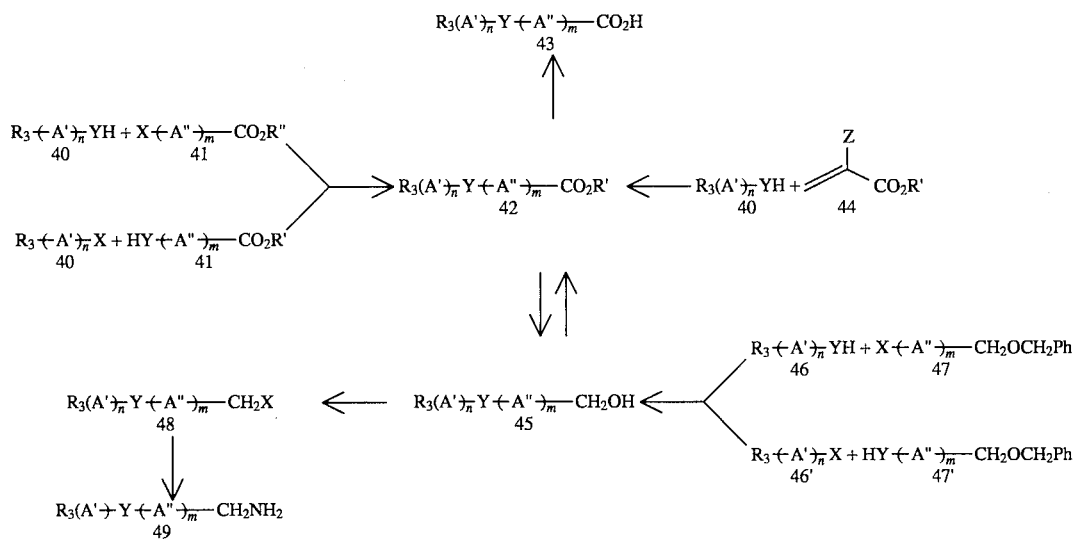
SCHEME H
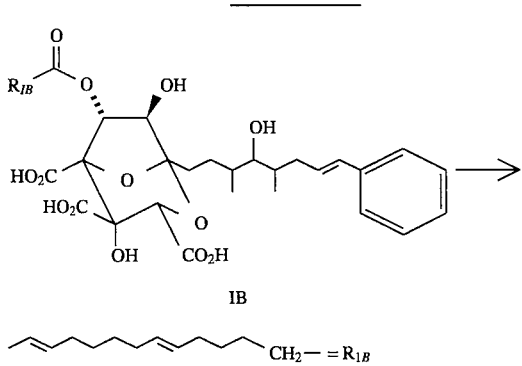
-continued
SCHEME H
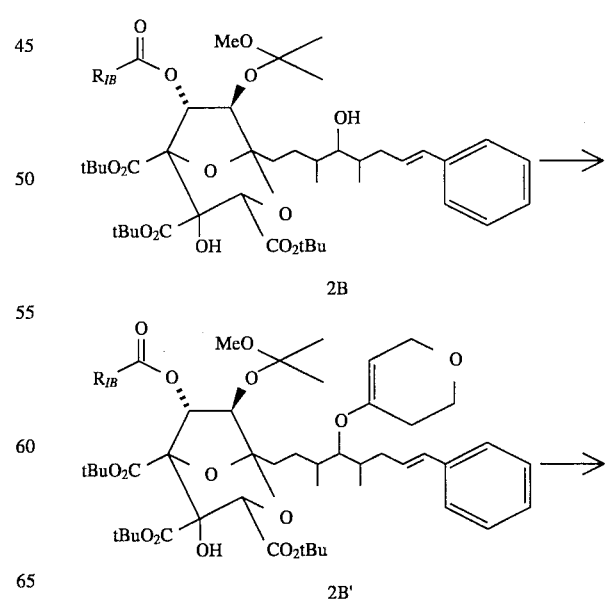

93
-continued
SCHEME H

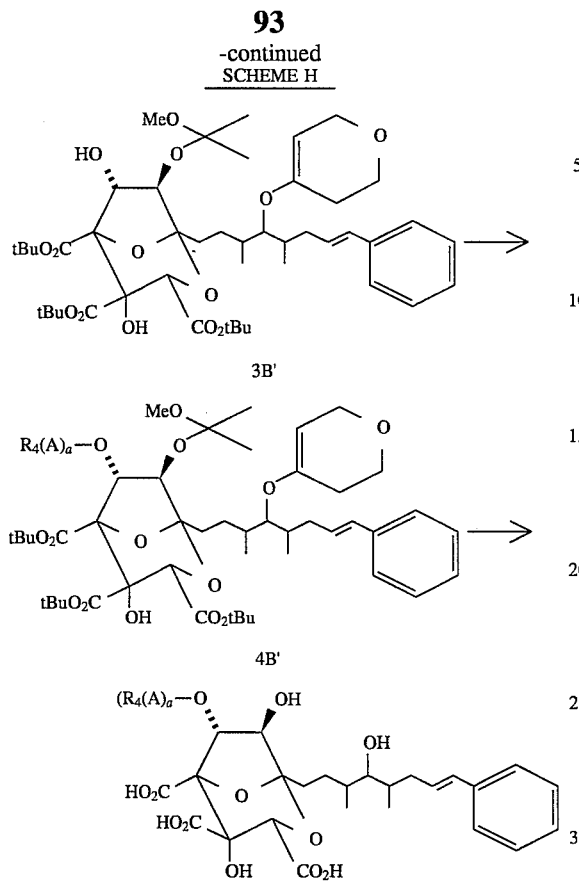

SCHEME I

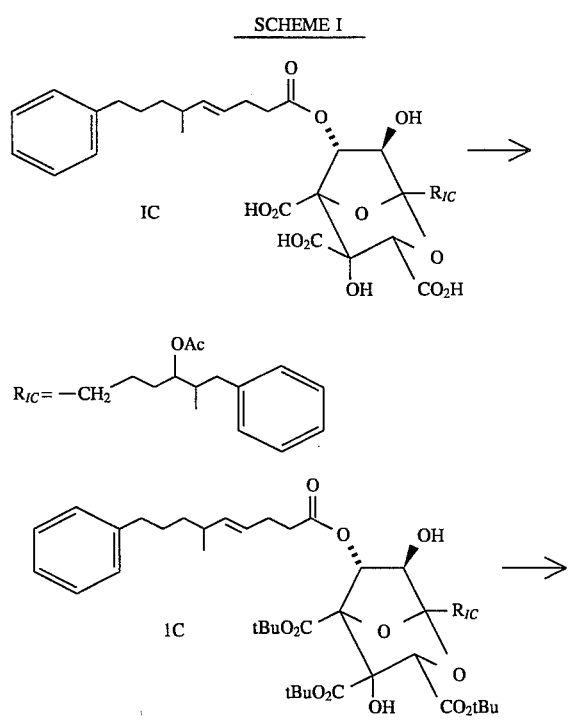

94
-continued
SCHEME I

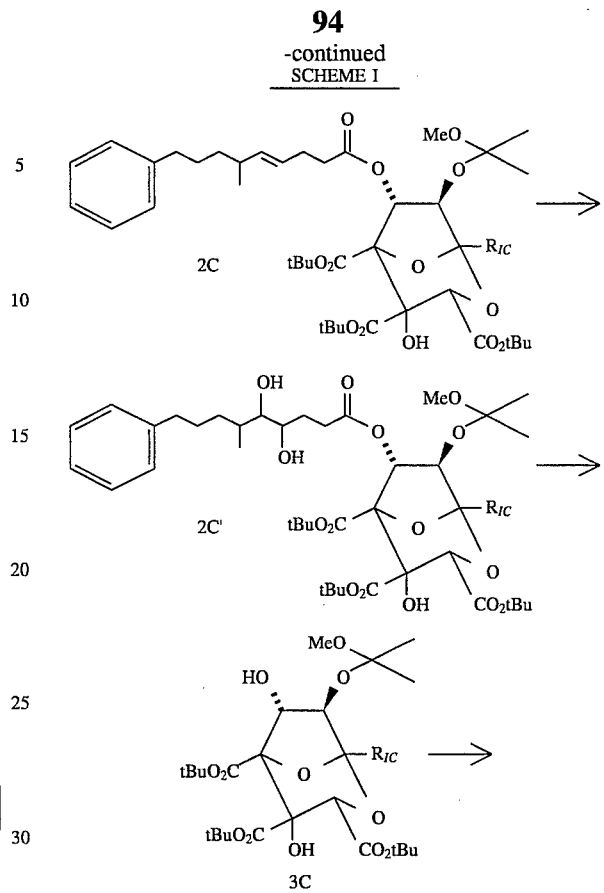

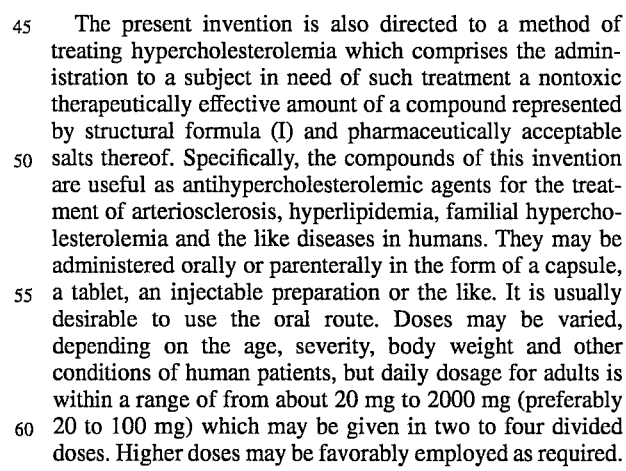

The present invention is also directed to a method of treating hypercholesterolemia which comprises the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The present invention is also directed to a method of inhibiting squalene synthetase which comprises the administration to a subject in need of such treatment a nontoxic therapeutically effective amount of a compound represented by structural formula (I) and pharmaceutically acceptable salts thereof. Specifically, the compounds of this invention are useful in treating disease conditions such as, but not limited to, hypercholesterolemia which result from the action of the enzyme squalene synthetase. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloxoprocaine, diethanolamine, procaine, N-benzylphenethylamine, diethylamine, piperazine, tris(hydroxymethyl)aminomethane, and tetramethylammonium hydroxide. The salts included herein encompass those wherein one, two or all three of the carboxyl groups are in the salt form.

The compounds of this invention may also be administered in combination with other cholesterol lowering agents such as those which inhibit an enzymatic pathway in the biosynthesis of cholesterol. Example of such agents would include-but are not limited to MMG-CoA reductase inhibitors, HMG-COA synthase inhibitors, and squalene expoxidase inhibitors. Illustrative of such inhibitors are lovastatin, simvastatin, pravastatin and fluvastatin. Other cholesterol lowering agents that may be administered include niacin, probucol, and the fibtic acids, clofibrate and gemfibrozil. Appropriate daily dosages for adults are niacin (2–8 gm), probucol (up to 1000 mg), clofibrate (up to 2 gm) and gemfibrozil (800–1500 mg).

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-tri-methylaminopropyl)imino-trimethylene dihalide]. The relative amounts of the compounds of this invention and these polymers is between 1:100 and 1:15,000.

The intrinsic squalene synthetase inhibitory activity of representative compounds of this invention was measured by the standard in vitro protocol described below:

Preparation of Microsomes:

Male, Charles River CD rats (120 to 150 g) were fed a diet containing 0.1% lovastatin for 4 days. The livers from these rats were homogenized in 5 volumes (ml/g) of ice cold 50 mM HEPES (4-(2-hydroxyethyl)-1-piperazine-ethanesulfonic acid), 5 mM EDTA(ethylenediaminetetraacetic acid) pH 7.5 with a Potter-Elvehjem type tissue grinder. The homogenate was centrifuged twice at 20,000× g for 15 minutes at 4° C. discarding the pellet each time. The supernatant was then centrifuged at 100,000× g for 1 hour at 4° C. The resulting microsomal pellet was resuspended in a volume of the above homogenizing buffer equal to one-fifth the volume of the original homogenate. This microsomal preparation has a protein concentration of about 7 mg/ml. The microsomal suspensions were stored in aliquots at −70° C. Squalene synthetase activity in these aliquots is stable for at least several months.

Partial Purification of Prenyl Transferase

Prenyl transferase was purified to use in the enzymatic synthesis of radiolabelled farnesyl pyrophosphate. Prenyl transferase was assayed by the method of Rilling (Methods in Enzymology 110, 125–129 (1985)) and a unit of activity is defined as the amount of enzyme that will produce 1 μmole of farnesyl pyrophosphate per minute at 30° C. in the standard assay.

The livers of 23 forty-day old male rats that had been fed 5% cholestyramine plus 0.1% lovastatin were homogenized in a Waring blender in 1 liter of 10 mM mercaptoethanol, 2 mM EDTA, 25 μM leupeptin, 0.005% phenylmethyl sulfonyl fluoride pH 7.0 containing 0.1 trypsin inhibitor units of aprotinin/ml. The homogenate was centrifuged at 20,000× g for 20 minutes. The supernatant was adjusted to pH 5.5. with 6N HOAc and centrifuged at 100,000× g for 1 hour. This supernatant was adjusted to pH 7.0 with 3N KOH and a 35–60% ammonium sulfate fraction taken. The 60% pellet was redissolved in 60 ml of 10 mM potassium phosphate, 10 mM mercaptoethanol, 1 mM EDTA pH 7.0 (Buffer A) and dialyzed against two 1 liter changes of Buffer A. This dialyzed fraction was applied to a 12.5×5 cm column of DEAE-sepharose 4B equilibrated with Buffer A. The column was washed with 700 ml of Buffer A and a 1 liter gradient from Buffer A to 100 mM potassium phosphate, 10 mM mercaptoethanol, 1 mM EDTA pH 7.0. Fractions having a specific activity greater than 0.20 units/mg were combined, solid ammonium sulfate was added to bring to 60% saturation and pelleted. The pellet was dissolved in 8 ml of 10 mM Tris, 10 mM β-mercaptoethanol pH 7.0 (Buffer B). The redissolved pellet was taken to 60% saturation with ammonium sulfate by adding 1.5 volumes of saturated ammonium sulfate in Buffer B. This ammonium sulfate suspension contained 3.5 units/ml with a specific activity of 0.23 units/mg and was free of isopentenyl pyrophosphate isomerase activity. This ammonium sulfate suspension was used for the synthesis of [4-$^{14}$C]farnesyl-pyrophosphate and its activity was stable stored at 4° C. for at least 6 months.

Enzymatic Synthesis of [4-$^{14}$C]farnesyl-pyrophosphate

The solvent (ethanol: 0.15N NH$_4$OH, 1:1) was removed from 55 μCi of [4-$^{14}$C]isopentenyl pyrophosphate(47.9 μCi/μmole) by rotary evaporation. Six hundred microliters of 100 mM Tris, 10 mM MgCl$_2$, 4 mM dithiothreitol pH 7.5 was added and the solution was transferred to a 1.5 ml Eppendorf centrifuge tube. Geranyl-pyrophosphate, 250 μl of a 20 mM solution, and 50 μl of the ammonium sulfate suspension of prenyl transferase were added to initiate the reaction. This incubation contained 5 μmoles of geranyl pyrophosphate, 1.15 μmoles of isopentenyl pyrophosphate, 6 μmoles of MgCl$_2$ of 0.18 units of prenyl transferase in a volume of 900 μl. The incubation was conducted at 37° C. During the incubation, the mix turned cloudy white as the newly formed magnesium complex of farnesyl pyrophosphate precipitated out of solution. The [4-$^{14}$C]farnesyl pyrophosphate was collected by centrifugation for 3 minutes at 14,000 rpm in an Eppendorf centrifuge tube, the supernatant removed, and the pellet was dissolved in 1.0 ml of 50 mM HEPES, 5 mM EDTA, pH 7.5 The yield was 50.7 μi (92%) of [4-$^{14}$C]farnesyl pyrophosphate. The [4-$^{14}$C]farnesyl pyrophosphate was stored in aliquots at −70° C.

Squalene Synthetase Assay

Reactions were performed in 16×125 mm screw cap test tubes. A batch assay mix was prepared from the following solution:

| | µl per assay | volume for 50 assays |
|---|---|---|
| 1. 250 mM Hepes pH 7.5 | 20 | 1000 |
| 2. NaF 110 mM | 10 | 500 |
| 3. MgCl$_2$ 55 mM | 10 | 500 |
| 4. Dithiothreitol 30 mM | 10 | 500 |
| 5. NADPH 10 mM (made fresh) | 10 | 500 |
| 6. [4-$^{14}$C]farnesyl-pyrophosphate 47.9 µCi/µmole, and 0.025 µCi/3.0 µl | 3.0 | 150 |
| 7. H$_2$O | 24 | 1200 |

This assay mix was degassed under a vacuum and flushed with N$_2$. Solutions of the squalene synthetase inhibitors were prepared either in DMSO or MeOH and a 1:120 dilution of the microsomal protein was made with the original homogenizing buffer. For each reaction, 87 µl of the assay mix was taken with 3 µl of an inhibitor solution (DMSO or MeOH in the controls), warmed to 30° C. in a water bath and then the reaction was initiated by the addition of 10 µl of the 1:120 dilution of microsomal protein (0.6 µg protein total in the assay). The reactions were stopped after 20 minutes by the addition of 100 µl of a 1:1 mix of 40% KOH with 95% EtOH. The stopped mix was heated at 65° C. for 30 minutes, cooled, 10 ml of heptane was added and the mix was vortexed. Two g of activated alumina was then added, the mix vortexed again, the alumina allowed to settle and 5 ml of the heptane layer was removed. Ten ml of scintillation fluid was added to the heptane solution and radioactivity was determined by liquid scintillation counting.

Percent inhibition is calculated by the formula:

$$1 - \frac{[\text{Sample} - \text{Blank}]}{[\text{Control} - \text{Blank}]} \times 100$$

IC$_{50}$ values were determined by plotting the log of the concentration of the test compound versus the percentage inhibition. The IC$_{50}$ is the concentration of inhibitor that gives 50% inhibition as determined from these plots.

Representative compounds of this invention exhibited IC$_{50}$ values which were all <500 µM.

Representative of the intrinsic squalene synthetase inhibitory activities of the compounds of this invention is the IC$_{50}$ data tabulated below:

| Compound | Squalene Synthetase IC$_{50}$ |
|---|---|
| 5u | 0.24 |
| 5m' | 1.21 |
| 7g | 0.99 |
| 8a | 0.62 |
| 28b | 0.79 |

The intrinsic farnesyl-protein transferase (FTase) activity of representative compounds of this invention was measured by the assays described below:

RASIT ASSAY I

Farnesyl-protein transferase (Ftase) from bovine brain was chromatographed on DEAE-Sephacel (Pharmacia, 0–0.8M NaCl gradient elution), N-octyl agarose (Sigma, 0–0.6M Nacl gradient elution), and a mono Q HPLC column (Pharmacia, 0–0.3M NaCl gradient). Ras-CVLS at 3.5 µM, 0.25 µM [$^3$H]FPP, and the indicated compounds were incubated with this partially purified enzyme preparation. The Ftase data presented below is a measurement of the ability of the test compound to inhibit Ras farnesylation in vitro.

RASIT ASSAY II

Farnesyl-protein transferase (Ftase) from bovine brain was chromatographed on DEAE-Sephacel (Pharmacia, 0–0.8M NaCl gradient elution), N-octyl agarose (Sigma, 0–0.6M Nacl gradient elution), and a mono Q HPLC column (Pharmacia, 0–0.3M NaCl gradient). Ras-CVLS at 1.0 µM, 0.5 µM [$^3$H]FPP, and the indicated compounds were incubated with this partially purified enzyme preparation. The Ftase data presented below is a measurement of the ability of the test compound to inhibit Ras farnesylation in vitro.

Table 8 lists IC$_{50}$ data which is representative of the intrinsic Ras inhibitory activity of the compounds of this invention. Data of representative compounds from each embodiment and class of the invention is provided. When an inhibitory value is not provided for a given assay, the compound was not tested in that protocol.

TABLE 8

Inhibition of Ras farnesylation by compounds of this invention

| Compound | Assay I IC$_{50}$ (µM) | Assay II IC$_{50}$ (µM) |
|---|---|---|
| 5u | 0.5 | 0.027 |
| 5y | 0.5 | 0.027 |
| 5n' | 4 | — |
| 7d | 1.7 | 0.052 |
| 24b | 1.3 | — |
| 39e | 0.12 | 0.019 |

The pharmaceutical compositions containing the compounds of structural formula I inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The compounds of this invention may be administered to mammals, preferably humans, either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal, subcutaneous and topical administration.

For oral use of a chemotherapeutic compound according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The present invention also encompasses a method of the treatment of cancer, comprising the administration of a pharmaceutical composition comprising a therapeutically effective amount of the compounds of this invention, with or without pharmaceutically acceptable carriers or diluents.

Suitable compositions of this invention include aqueous solutions comprising compounds of this invention and pharmacologically acceptable carriers, e.g. saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in an amount between about 0.1 mg/kg of body weight to about 20 mg/kg of body weight of a mammal per day, preferably of between 0.5 mg/kg of body weight to about 10 mg/kg of body weight of a mammal per day.

The present compounds also demonstrate broad spectrum antifungal activity as determined by broth and agar dilution methods. The compounds are particularly active towards filamentous fungi and yeasts including *Candida albicans* and *Cryptococcus neoformans*. The sensitivity of filamentous fungi and yeast was determined using inhibitor dilution assays in microtiter format. The compounds were dissolved in DMSO at 2 mg/ml and serially diluted in 0.1M phosphate buffer, pH 7.0 in the microtiter dish from 100 to 0.006 µg/ml. A standardized spore suspension for testing the filamentous fungi was prepared by inoculating Antibiotic Medium #3 containing 1.5% agar with spores such that $1.5 \times 10^3$ colony forming units were added per well. The microtiter wells were filled with 50 µl of buffer containing compound and 50 µl of inoculated medium.

The sensitivity of yeasts was determined by inoculating yeast nitrogen base containing 1% dextrose (YNB/G) with aliquots of an overnight yeast culture grown in Yeast Morphology (YM) media at 35° C. and diluting in YNB/G to yield a final concentration of $1.5-7.5 \times 10^3$ colony forming units/well. To test the sensitivity of yeast, compound was solubilized in 10 percent aqueous DMSO at 2.56 mg/ml. The compound was diluted serially in YNB/G from 128 to 0.06 µg/ml and further diluted 1:10 in YNB/G. The wells were filled with 150 µl of media containing drug. The minimum inhibitory concentration (MIC) is defined as the lowest concentration to prevent growth after an incubation for 42 hours, at 28° C. for the filamentous fungi and 24 to 48 hours, at 35° C. for the yeasts. Representative of the antifungal activity are the minimum inhibitory concentration data shown below for representative compounds from the various embodiments and classes described hereinabove.

Assay Organisms and their designation numbers:

Filamentous Fungi

*Aspergillus flavus* MF383

Yeast

*Candida albicans* MY1055

*C. tropicalis* MY1012

*C. parapsilosis* MY1010

*Crypt. neoformans* MY1051

| | Minimum Inhibitory Concentration (mcg/ml) | | | | |
|---|---|---|---|---|---|
| | ORGANISM | | | | |
| Compound # | MF383 | MY1055 | MY1012 | MY1010 | MY1051 |
| 5s | — | 1 | >128 | >128 | 32 |
| 5t | 0.5 | 8 | 0.5 | >128 | >128 |
| 5n' | 4 | 4 | 1 | 16 | 1 |
| 5q''' | 1 | 8 | 128 | 1 | 0.25 |
| 7b | 2 | 2 | 2 | 2 | 0.5 |
| 8n' | 0.5 | 64 | 8 | 64 | >128 |
| 12a | 2 | 8 | 2 | 8 | 1 |
| 12n | 2 | 16 | 8 | 32 | 0.25 |
| 25b | 4 | 8 | 8 | >128 | 2 |

Thus the present invention is also directed to a method of treating fungus infections which comprises the administration to an organism in need of such treatment a nontoxic therapeutically effective amount of a compound represented by the structural formula (I) and pharmaceutically acceptable salts thereof. Based on the above MIC data it is determined that generally from 2 to about 20 mg/kg should be employed as a unit dosage in an antifungal treatment.

The compounds of this invention are adaptable to being utilized in various applications of antifungal compositions. In such use, compounds may be admixed with a biologically inert carrier, generally with the aid of a surface active dispersing agent, the nature of which would vary depending on whether the use is for the control of pathogens infecting mammals such as man, or birds or reptiles, or for control of fungi in agriculture such as in soil or plant parts, or for the control of fungi in inanimate objects.

In compositions for medical applications, the compounds may be admixed with a pharmaceutically acceptable carrier, the nature of which will vary depending on whether the composition is to be topical, parenteral or oral.

If said application is to be topical, the drug may be formulated in conventional creams and ointments such as white petroleum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by intimately mixing the component drugs with any of the usual pharmaceutical media, including, for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricant such as calcium stearate, together with binders, disintegrating agents and the like.

These compositions are then administered in amounts sufficient to obtain the desired antifungal effect. For medical application, the method comprises administering to a subject in need of treatment a therapeutically effective antifungal amount of a compound of Formula I. The appropriate doses will vary depending on age, severity, body weight and other conditions. For topical application the compositions are applied directly to the area where control is desired. For internal administration, the composition may be applied by injection or may be administered orally.

For non-medical application, the product of the present invention, either singly or as a mixture, may be employed in compositions in an inert-carrier which includes finely divided dry or liquid diluents, extenders, fillers, conditioners and excipients, including various clays, diatomaceous earth, talc, and the like, or water and various organic liquids such a lower alkanols, for example ethanol and isopropanol, or kerosene, benzene, toluene and other petroleum distillate fractions or mixtures thereof to inhibit fungal growth.

These compositions may be employed by applying to the surface of or incorporating in the medium to be protected. For the control of rice blast, tomato late blight, tomato early blight, wheat leaf rust, bean powdery mildew and tomato Fusarium wilt, the compositions may be applied directly to the plant in topical application or administered to the soil for systemic application. The method comprises administering to the affected plant, soil or medium to be protected an antifungally effective amount of the compound of Formula I.

The following Examples illustrate the preparation of the compounds of formula (I) and their incorporation into pharmaceutical compositions and as such are not to be considered as limiting the invention set forth in the claims appended hereto.

Compound IA is (1S,3S,4S,5R,6R,7R)-1-[(4S)-acetoxy-3-methylene-5-methyl-6-phenyl]hexyl-4,6,7-trihydroxy-6-O-(4,6-dimethyl-2-octenoyl)-2,8-dioxabicyclo [3.2.1]octane-3,4,5-tricarboxylic acid. Compound IB is (1S,3S,4S,5R,6R,7R)-1-[(4-hydroxy-3,5-dimethyl-8-phenyl)oct-7-enyl]-4,6,7-trihydroxy-6-O-(tetradeca-6,12-dienoyl)-2,8-dioxabicyclo[3.2.1]octane-3,4,5-tricarboxylic acid. Compound IC is (1S,3S,4S,5R,6R,7R)-1-[(4)-acetoxy-5-methyl-6-phenyl]hexyl-4,6,7-trihydroxy-6-O-(6-methyl-9-phenyl-4-nonenoyl)-2,8-dioxabicyclo[3.2.1]octane-3,4,5-tricarboxylic acid.

EXAMPLE 1

I. Esterification Methods:

Preparation of (1S,3S,4S,5R,6R,7R)-1-[(4S)-acetoxy-3-methylene-5-methyl-6-phenyl]hexyl-4,6,7-trihydroxy-6-O-(4,6-dimethyl-2-octenoyl)-2,8-dioxabicyclo[3.2.1]octane 3,4,5-tris-t-butyl ester (1a)

A solution of IA (40.0 g, 0.058 mol, 61% pure) and O-t-butyl-N,N'-diisopropylisourea (116 g, 0.58 mol) in toluene (45 mL) was heated to 65° C. for 16 h. The reaction was allowed to cool to room temperature and concentrated in vacuo. Purification of the residue by flash column chromatography (silica gel, 2:1 hexane/EtOAc) afforded the tri-t-butyl ester 1a as a white solid: $^1$H NMR (300 MHz, CDCl$_3$) d 7.26–7.10 (m, 5H), 6.88 (dd, J=8.5, 15.6 Hz, 1H), 5.98 (d, 1.8 Hz, 1H), 5.75 (d, J=15.6 Hz, 1H), 5.09 (d, J=4.8 Hz, 1H), 5.03 (s, 1H), 4.94 (br s, 2H), 4.06 (s, 1H), 4.00–3.99 (m, 1H), 2.91 (d, J=3.3 Hz, 1H), 2.71–2.63 (m, 1H), 2.50–2.02 (m, 7H), 2.07 (s, 3H), 1.57 (s, 9H), 1.46 (s, 9H), 1.42 (s, 9H), 1.50–1.09 (m, 5), 1.01 (d, J=6.6 Hz, 3H), 0.84–0.78 (m, 9H); $^{13}$C NMR (100 MHz, CDCl$_3$) δ170.20, 168.61, 166.58, 165.52, 163.98, 157.26, 145.72, 140.31, 129.09, 128.17, 125.79, 118.16, 111.15, 104.28, 88.85, 85.61, 83.73, 82.98, 82.29, 80.77, 78.90, 75.29, 74.14, 43.10, 39.93, 36.52, 34.42, 34.15, 31.77, 29.63, 28.07, 27.93, 25.42, 21.02, 20.18, 18.75, 13.52, 11.04 ppm; MS (FAB), m/e 865 [M+Li]$^+$.

EXAMPLE 2

Preparation of IA-tis-2-(trimethylsilyl)ethyl ester (1b)

A solution of IA (0.75 g, 1.08 mmol) and O-2-(trimethylsilyl)ethyl-N,N'-diisopropylisourea (2.64 g, 14.5 mmol) in benzene (40 mL) was heated to 65° C. for 16 h. The reaction was allowed to cool to room temperature and concentrated in vacuo. Purification of the residue by flash column chromatography (silica gel, 3:1 hexane/EtOAc) afforded tri-ester 1b as a greenish-yellow oil: $^1$H NMR (400 MHz, CDCl$_3$) δ7.26–7.11 (m, 5H), 6.85 (dd, J=15.6, 8.5 Hz, 1H), 5.84 (d, J=1.8 Hz, 1H), 5.73 (d, J=15.6 Hz, 1H), 5.17 (s, 1H), 5.08 (d, J=4.8 Hz, 1H), 4.96 (br s, 1H), 4.95 (br s, 1H), 4.40–4.18 (m, 6H), 4.01 (m, 1H), 3.81 (s, 1H), 3.11 (d, J=2.4 Hz, 1H), 2.67 (dd, J=13.6, 5.2 Hz, 1H), 2.41–2.07 (m, 7H), 2.07 (s, 3H), 1.35–0.91 (m, 11H), 1.01 (d, J=6.9 Hz, 3H), 0.85–0.79 (m, 9H), 0.046 (s, 9H), 0.016 (s, 9H), −0.005 (s, 9H); $^{13}$C NMR (100 MHz, CDCl$_3$) δ170.1, 169.4, 166.9, 166.4, 164.9, 157.6, 145.5, 140.2, 129.0, 128.2, 125.8, 117.9, 111.5, 105.4, 88.4, 81.9, 81.6, 79.0, 75.2, 74.3, 65.8, 64.7, 64.2, 43.0, 39.8, 36.6, 34.3, 34.0, 31.7, 29.5, 25.2, 21.0, 20.0, 18.8, 17.4, 17.2, 17.1, 13.7, 11.0, −1.7 (3X) ppm; MS (FAB), m/e 997 [M+Li]$^+$.

EXAMPLE 3

Preparation of IA-trimethyl ester (1c)

To a stirred solution of IA (2.1 g) in benzene (15 mL) was added O-methyl-N,N'-diisopropylisourea (2.5 g) and the reaction mixture was heated at 60° C. for 16 hr. The reaction mixture was cooled to room temperature, concentrated in vacuo and purified by chromatography (silica, 6:4 hexane/ethyl acetate) to yield 1c. $^1$H NMR (400 MHz, CD$_3$OD) δ7.3–7.1(m, 5H), 6.88(dd, J=8, 15 Hz, 1H), 6.29(d, J=2 Hz, 1H), 5.68(d, J=15.5 Hz, 1H), 5.28(s, 1H), 5.07(d, J=5 Hz, 1H), 5.07(d, J=5 Hz, 1H), 5.02(brs, 1H), 4.98(brs, 1H), 4.05(d, J=2 Hz, 1H), 3.69, 3.72 and 3.86(ea s, ea 3H).

EXAMPLE 4

Preparation of the IA-triethyl ester (1d) an of the IA-tribenzyl ester (1e)

To a solution of IA (17.5 mg) in acetonitrile (0.5 mL) was added ethyl bromide (80 mg) and DBU (80 mg). The reaction was stirred overnight at room temperature. The mixture was concentrated in vacuo and purified by HPLC (silica, 1:1 hexane/ethyl acetate) to yield 1d. MS (FAB), m/e 781 [M+Li]$^+$ By using a similar procedure to the one described above for compound (1d) in EXAMPLE 4, the following triester was prepared from IA and the appropriate halide. 3,4,5-tribenzyl ester (1e) MS (FAB), m/e 961 [M]$^+$. Derivatization of C7

EXAMPLE 5

Preparation of IA-tris-t-butyl ester-7-(1-methyl-1-methoxyethyl ether (2a)

A solution of diol (1a) (13.34 g, 15.63 mmol) and 2-methoxypropene (15 mL, 0.156 mol) in CH$_2$Cl$_2$ (120 mL) was cooled to 0° C. and pyridinium p-tolenesulfonate (196 mg, 0.78 mmol) was added. After stirring for 2 h at 0° C. the reaction solution was neutralized with saturated aqueous NaHCO$_3$ and extracted with Et$_2$O. The organic portion was separated and washed with brine, dried (MgSO$_4$), filtered and the filtrate concentrated in vacuo. Purification of the residue by flash column chromatography (silica gel, 4:1 hexane/EtOAc) yielded the ketal (2a): $^1$H NMR (300 MHz, CDCl$_3$) δ7.26–7.13 (m, 5H), 6.88 (dd, J=8.0, 15.6 Hz, 1H), 6.41 (d, 1.6 Hz, 1), 5.76 (d, J=15.6 Hz, 1H), 5.12 (d, J=4.8 Hz, 1H), 5.02 (s, 1H), 4.94 (br s, 1H), 4.93 (br s, 1H), 4.20 (d, J=1.2 Hz, 1H), 4.04 (s, 1H), 3.19 (s, 3H), 2.71 (dd, J=5.2, 13.2 Hz, 1H), 2.60–1.91 (m, 7H), 2.07 (s, 3H), 1.66 (s, 9H), 1.43 (s, 9H), 1.42–1.22 (m, 3H), 1.36 (s, 9H), 1.34 (s, 3H), 1.26 (s, 3H), 1.09–1.05 (m, 2H), 0.97 (d, J=6.4 Hz, 3H), 0.83–0.77 (m, 9H); $^{13}$C NMR (100 MHz, CDCl$_3$) δ170.06, 168.98, 166.06, 164.48, 156.46, 146.11, 140.33, 129.13, 128.14, 125.77, 118.64, 110.91, 104.24, 101.22, 90.58, 85.75, 83.74, 83.02, 79.99, 79.26, 77.30, 75.39,. 73.78, 49.69, 43.13, 39.95, 36.41, 34.31, 34.21, 31.68, 29.52, 28.03, 27.93, 27.90, 25.86, 25.36, 24.40, 21.03, 19.96, 18.81, 13.45, 11.00 ppm. Anal. Calc. for C$_{51}$H$_{78}$O$_{15}$.0.5 H$_2$O: C, 65.15; H, 8.47. Found: C, 65.38; H, 8.25.

EXAMPLE 6

Preparation of IA-tri-2-(trimethylsilyl)ethyl ester-C7-SEM ether (2b)

A solution of diol (1b) (0.58 g, 0.586 mmol), N,N'-diisopropylethylamine 2.4 mL, 14.07 mmol), and 2-(trimethylsilyl)ethoxymethyl chloride (2.0 mL, 11.73 mmol) in CH$_2$Cl$_2$ (16.0 mL) was heated to reflux for 24 h. The reaction was cooled to room temperature and washed with 1N HCl, 5% aqueous NaHCO$_3$ and brine. The organic portion was dried (Na$_2$SO$_4$), filtered and the filtrate concentrated in vacuo. Purification of the residue by flash column chromatography (silica gel, 4:1 hexane/EtOAc) yielded the SEM-ether (2b) as a clear yellow oil: $^1$H NMR (400 MHz, CDCl$_3$) δ7.26–7.12 (m, 5H), 6.84 (dd, J=15.6, 8.0 Hz, 1H), 6.41 (d, J=1.6 Hz, 1H), 5.70 (d, J=15.6 Hz, 1H), 5.13 (s, 1H), 5.10 (d, J=4.8 Hz, 1H), 4.97 (br s, 1H), 4.94 (br s, 1H), 4.77 (ABq, J=6.8 Hz, Dn=42.2 Hz, 2H), 4.40–4.34 (m, 2H), 4.22–4.11 (m, 4H), 4.09 (d, J=2.0 Hz, 1H), 3.84 (s, 1H), 3.65–3.56 (m, 2H), 2.70 (dd, J=13.6, 5.2 Hz, 1H), 2.50–2.05 (m, 7H), 2.07 (s, 3H), 1.33–0.91 (m, 11H), 0.99 (d, J=6.4 Hz, 3H), 0.90–0.78 (m, 11H), 0.05 (s, 9), −0.01 (s, 9), −0.02 (s, 9H), −0.05 (s, 9H); $^{13}$C NMR (100 MHz, CDCl$_3$) δ169.9, 169.4, 166.5, 164.8, 164.1, 156.7, 145.7, 140.2, 129.0, 128.2, 125.8, 118.1, 111.2, 105.3, 94.6, 89.9, 84.6, 79.0, 75.1, 75.0, 74.1, 66.1, 66.0, 64.4, 64.1, 43.0, 39.9, 36.5, 34.2, 33.9, 31.6, 29.4, 25.2, 21.0, 19.9, 18.9, 17.7, 17.3, 17.2, 16.9, 13.6, 11.0, −1.5, −1.6, −1.7 (2×) ppm; MS (FAB), m/e 1127 [M+Li]$^+$.

Deacylation Reactions:

EXAMPLE 7

IA-tris-t-butyl ester-6-hydroxy-7-(1-methyl-1-methoxyethyl)ether (3a)

Method A:

A biphasic solution of (2a) (10 g, 10.7 mmol), lithium hydroxide monohydrate (4.50 g, 107 mmol) in THF (152 mL) and 30% by wt. hydrogen peroxide (6.0 mL) was vigorously stirred at 23° C. for 48 h. The reaction was quenched with saturated aqueous NH$_4$Cl and extracted twice with CH$_2$Cl$_2$. The combined organic fractions were dried (Na$_2$SO$_4$), filtered and the filtrate concentrated in vacuo. The residue was purified by PrepPak 500/silica on a Waters Associates Prep LC/System 500 at 250 mL/min using hexanes-EtOAc (2:1, v/v) as a liquid phase to yield the deacylated product (3a).

Method B:

To a mixture of 2a (9.31 g, 10 mmol) and NaOAc.3H$_2$O (30 g, 220 mmol) in methanol (100 mL) is added hydroxylamine hydrochloride (6.95 g, 100 mmol). The reaction is stirred at ambient temperature for 20 hr, filtered and concentrated to dryness. The residue is partitioned between Et$_2$O and brine and the organic layer is dried (Na$_2$SO$_4$), filtered and the filtrate is concentrated in vacuo. The residue is purified by column chromatography (silica gel, 2:1 hexane/EtOAc) to afford the deacylated product 3a: $^1$H NMR of 3a (400 MHz, CDCl$_3$) δ7.25–7.10 (m, 5H), 5.10 (d, J=5.2 Hz, 1H), 4.94 (br s, 3H), 4.83 (s, 1H), 4.04 (d, J=2.0 Hz, 1H), 3.89 (s, 1H), 3.24 (s, 3H), 2.69 (dd, J=5.2, 13.6 Hz, 1H), 2.51–1.88 (m, 7H), 2.06 (s, 3H), 1.57 (s, 9H), 1.47 (s, 9H), 1.44 (s, 3H), 1.43 (s, 9H), 1.37 (s, 3H), 0.78 (d, J=6.8 Hz, 3H); $^{13}$C NMR (100 MHz, CDCl$_3$) δ170.09, 168.67, 166.25, 166.13, 145.80, 140.29, 129.07, 128.17, 125.85, 111.04, 104.74, 1.1.49, 84.69, 83.86, 82.96, 80.85, 79.26, 77.54, 75.27, 74.13, 49.50, 39.92, 36.53, 33.60, 28.13, 27.99, 27.89, 25.72, 25.33, 24.52, 21.01, 13.56 ppm; MS (FAB), m/e 785 [M+Li]$^+$.

EXAMPLE 8

IA-tris-trimethylsilyl-6-hydroxy-7-SEM ether (3b).

A biphasic solution of 2b (120 mg, 0.107 mmol), lithium hydroxide monohydrate (9.0 mg, 0.214 mmol) in THF (0.76 mL), 30% by wt. hydrogen peroxide (0.29 mL), and H$_2$O (0.06 mL) was stirred at 23° C. for 48 h. The reaction mixtures was acidified to pH1 with 1N HCl and extracted with C$_2$Cl$_2$ (2×). The combined organic fractions were dried (Na$_2$SO$_4$), filtered and the filtrate concentrated in vacuo. A solution of the residue and O-2-(trimethylsilyl)-ethyl-N,N'-diisopropylisourea (0.40 g, 1.64 mmol) in benzene (2.0 mL) was heated to 65° C. for 16 h. The solution was cooled to room temperature and concentrated in vacuo. Flash column chromatography (silica gel, 6:1 hex/EtOAc) of the residue gave the deacylated product (3b) as a white solid: $^1$H NMR (300 MHz, CDCl$_3$) δ7.27–7.16 (m, 5H), 5.20 (dd, J=2.1, 4.8 Hz, 1H), 5.09 (d, J=5.1 Hz, 1H), 4.99 (s, 1H), 4.97 (br s, 2H), 4.79 (ABq, J=6.9 Hz, Dn=37.5 Hz, 2H), 4.39–4.17 (m, 6H), 3.93 (d, J=2.1 Hz, 1H), 3.80–3.59 (m, 2H), 3.69 (s, 1), 2.70 (dd, J=5.2, 13.6 Hz, 1H), 2.53 (d, J=4.5 Hz, 1H), 2.37–2.07 (m, 5H), 2.08 (s, 3H), 1.17–0.93 (m, 8H), 0.81 (d, J=6.6 Hz, 3H), 0.054 (s, 9H), 0.011 (s, 9H), 0.003 (s, 9H), −0.004 (s, 9H).

EXAMPLE 9

Bis-deacylation of IA-tri-2-(trimethylsilyl)ethyl ester-C7-SEM ether to triol (3'a).

A solution of (2b) (0.56 g, 0.504 mmol) and titanium (IV) ethoxide (100 μL, 0.476 mmol) in 2-(trimethylsilyl)ethanol (1.0 mL) was heated to 100° C. for 24 h. The reaction was cooled to room temperature and quenched with 1N HCl. After stirring for 1 h the mixture was extracted with EtOAc (2×). The combined organic fractions were washed with brine, dried (MgSO$_4$), filtered and the filtrate concentrated in vacuo. Purification of the residue by flash column chromatography (silica gel, 4:1 hexane/EtOAc) afforded triol (3'a) as a white solid: $^1$H NMR (300 MHz, CDCl$_3$)δ7.27–7.15 (m, 5H), 5.18 (dd, J=1.8, 5.4 Hz, 1H), 5.15 (br s, 1H), 5.03 (br s, 1H), 4.98 (s, 1H), 4.78 (ABq, J=6.9 Hz, Dn=33.9 Hz, 2H), 4.36–4.17 (m, 6H), 4.11 (br m, 1H), 3.96 (d, J=1.8 Hz, 1H), 3.75 (s, 1H), 3.73–3.60 (m, 2H), 2.85 (d, J=3.0 Hz, 1H), 2.78 (dd, J=5.6, 13.2 Hz, 1H), 2.52–1.86 (m, 8H), 1.55–0.93 (m, 8H), 0.83 (d, J=6.6 Hz, 3H); 0.050 (s, 9H), 0.013 (s, 18H), −0.004 (s, 9H); $^{13}$C NMR (100 MHz, CDCl$_3$)δ168.7, 166.8, 166.1, 151.8, 141.3, 129.1, 128.1, 125.6, 111.1, 105.6, 95.2, 90.9, 87.8, 76.8, 76.6, 75.5, 74.4, 66.1, 65.1, 64.9, 64.3, 40.3, 38.1, 33.4, 26.8, 17.9, 17.3 (2×), 17.2, 13.3, −1.50, −1.66 (2×), −1.71 ppm.

Derivatization at C$_6$:

EXAMPLE 10

General Procedures for Preparation of C6 Esters. Method A.

A solution of 3a (100 mg, 0.128 mmol), the appropriate carboxylic acid (0.256 mmol), dicyclohexylcarbodiimide (DCC; 53 mg, 0.257 mmol), and 4-(N,N-dimethylamino)pyridine (DMAP; 6–12 mg, 0.05–1.0 mmol) in dichloromethane (1 mL) is stirred at room temperature overnight. In most cases, the reaction is found to be complete; otherwise more carboxylic acid (0.256 mmol), DCC (53 mg, 0.257 mmol), and DMAP (6 mg, 0.05 mmol) are added and stirring is continued until the reaction is complete as shown by TLC. The reaction mixture is diluted with hexanes, filtered, and the filtrate is evaporated to dryness. The residue is purified by preparative TLC (hexanes-ethyl acetate; 4:1, v/v) to provide ester (4).

Method B.

The appropriate acid chloride (0.256 mmol) is added to a solution of (3a) (100 mg, 0.128 mmol), triethylamine (71 µL, 0.52 mmol), and DMAP (2 mg, 0.016 mmol) in dry dichloromethane (1 mL). The mixture is stirred at room temperature overnight and then diluted with dichloromethane. The solution is washed with 1N HCl, 5% aq. NaHCO$_3$, and brine, dried, and evaporated to dryness. The product is purified by preparative TLC (hexanes-ethyl acetate; 4:1, v/v) to provide ester (4).

EXAMPLE 11

General Procedure for Deprotection of tris-t-butyl ester analogs (4).

A solution of (4) (100 mg) in dry dichloromethane (3 mL) is treated with trifluoroacetic acid (1 mL) at room temperature overnight. The solution is evaporated to a residue, which is redissolved in toluene and concentrated to dryness. This process is repeated twice, and the product is dissolved in benzene and freeze-dried to give a white solid. The purity of the products is monitored by reversed-phase HPLC.

EXAMPLE 12

Preparation of IA-tris-t-butylester-6-octanoyl-7-(1-methyl-1-methoxyethyl)ether (4a).

A solution of diol (3a) (45.5 mg, 0.058 mmol), Et$_3$N (32.5 µL, 0.233 mmol), and DMAP (1.0 mg, 0.008 mmol) in CH$_2$Cl$_2$ (0.5 mL) was cooled to 0° C. Octanoyl chloride (50.0 µL, 0.292 mmol) was added and the solution was warmed to 23° C. for 24 h. The reaction solution was diluted with CH$_2$Cl$_2$ and washed with 1N HCl, 5% aqueous NaHCO$_3$, and saturated aqueous NaCl. The organic portion was dried (Na$_2$SO$_4$), filtered and the filtrate concentrated in vacuo. Purification of the residue by flash column chromatography (silica gel, 3:1 hexane/EtOAc) provided (4a) as a colorless oil: $^1$H NMR (300 MHz, CDCl$_3$) δ7.25–7.10 (m, 5H), 5.89 (d, J=1.8 Hz, 1H), 5.08 (d, J=4.5 Hz, 1H), 4.98 (s, 1H), 4.94 (br s, 2H), 4.07 (br s, 1H), 3.94 (d, J=1.8 Hz, 1H), 2.72–2.64 (m, 1H), 2.50–2.04 (m, 9H), 2.08 (s, 3H), 1.62–1.50 (m, 2H), 1.56 (s, 9H), 1.47 (s, 9H), 1.42 (s, 9H), 1.37–1.20 (m, 8H), 0.86–0.83 (m, 3H), 0.79 (d, J=6.9 Hz, 3H).

EXAMPLE 13

Preparation of IA-C6-octanoyl ester (5a)

A solution of (4a) (38.1 mg, 0.0421 mmol) in CH$_2$Cl$_2$ (1.2 mL) was cooled to 0° C. and trifluoroacetic acid (0.3 mL) was added. The solution was then allowed to warm to room temperature, stirred an additional 16 h, and concentrated in vacuo. The residue was diluted with toluene and reconcentrated (2×). The glassy solid was diluted with CH$_3$CN and filtered through a Sep-Pak C-18 plug. The filtrate was concentrated, rediluted with benzene, and lyophilized to give (5a) as a white solid: $^1$H NMR (300 MHz, CD$_3$OD) δ7.33–7.19 (m, 5H), 6.32 (d, J=1.8 Hz, 1H), 5.30 (s, 1H), 5.12 (d, J=4.8 Hz, 1H), 5.06 (br s, 1H), 5.02 (br s, 1H), 4.06 (d, J=1.8 Hz, 1H), 2.76–2.70 (m, 1H), 2.50–2.06 (m, 8H), 2.14 (s, 3H), 1.70–1.58 (m, 2H), 1.41–1.26 (m, 8H), 0.95–0.88 (m, 6H); MS (FAB), m/e 683 [M/Li3+H]$^+$.

EXAMPLE 14

Preparation of IA-C6-acetyl ester (5b)

A solution of diol (3a) (66.0 mg, 0.0848 mmol), Et$_3$N (47.3 µL, 0.339 mmol), DMAP (10.3 mg, 0.0848 mmol) and acetic anhydride (12.0 µL, 0.127 mmol) in CH$_2$Cl$_2$ (0.84 mL) was allowed to stir at 23° C. for 16 h. The reaction solution was diluted with CH$_2$Cl$_2$ and washed with 1N HCl, 5% aqueous NaHCO$_3$, and saturated aqueous NaCl. The organic portion was separated, dried (Na$_2$SO$_4$), filtered and the filtrate concentrated in vacuo. Purification of the residue by flash column chromatography (silica gel, 3:1 hexane/EtOAc) provided (4b) as a colorless oil:
$^1$H NMR (400 MHz, CDCl$_3$) δ7.26–7.13 (m, 5H), 6.34 (d, J=1.6 Hz, 1H), 5.11 (d, J=4.8 Hz, 1H), 4.97 (s, 1H), 4.94 (br s, 1H), 4.93 (br s, 1H), 4.16 (d, J=1.6 Hz, 1H), 4.06 (s, 1H), 3.19 (s, 3H), 2.70 (dd, J=5.0, 13.6 Hz, 1H), 2.58–2.47 (m, 1H), 2.36–2.29 (m, 2H), 2.17–2.11 (m, 2H), 2.07 (s, 3H), 2.04 (s, 3H), 1.94–1.89 (m, 1H), 1.64 (s, 9H), 1.43 (s, 18H), 1.34 (s, 3H), 1.27 (s, 3H), 0.79 (d, J=6.8 Hz, 3H). In a manner similar as described above for (4a), 53.9 mg of diacetate (4b) was deprotected to provide (5b)
$^1$H NMR (400 MHz, CD$_3$OD)δ7.27–7.13 (m, 5H), 6.27 (d, J=2.0 Hz, 1H), 5.24 (s, 1H), 5.07 (d, J=4.4 Hz, 1H), 5.01 (br s, 1H), 4.97 (br s, 1H), 4.03 (d, J=2.0 Hz, 1H), 2.69 (dd, J=6.4, 13.2 Hz, 1H), 2.45–2.02 (m, 6H), 2.09 (s, 3H), 2.02 (s, 3H), 0.85 (d, J=6.8 Hz, 3H); MS (FAB), m/e 603 [M+Na].

EXAMPLE 15

Selective acylation of triol 3'a with an acid chloride. (4'a')

To a solution of triol 3'a (24.5 mg, 0.0264 mmol), triethylamine (11.0 µL, 0.0793 mmol) and 4-dimethylaminopyridine (0.5 mg, 0.004 mmol) in CH$_3$CN (0.5 mL) cooled to 0° C. was added octanoyl chloride (9.0 µL, 0.0528 mmol). The reaction was then warmed to 23° C. and stirred for 4 h. The solution was diluted with CH$_2$Cl$_2$ and washed with 1N HCl, 5% aqueous NaHCO$_3$, and saturated aqueous NaCl. The organic portion was dried (Na$_2$SO$_4$), filtered and the filtrate concentrated in vacuo. Flash column chromatography (silica gel, 6:1 hexane/EtOAc) of the residue yielded (4'a') as a colorless oil: $^1$H NMR (300 MHz, CDCl$_3$) δ7.24–7.15 (m, 5H), 6.33 (d, J=1.8 Hz, 1H), 5.14 (br s, 1H), 5.09 (s, 1H), 5.07 (br s, 1), 4.73 (ABq, J=6.9 Hz, Dn=30.8 Hz, 2H), 4.37–4.10 (m, 7H), 4.03 (d, J=1.8 Hz, 1H), 3.85 (s, 1H), 3.70–3.52 (m, 2H), 2.82–1.89 (m, 10H), 1.26–1.22 (m, 10H), 1.20–0.82 (m, 14H), 0.050 (s, 9H), 0.007 (s, 9H), −0.005 (s, 9H), −0.009 (s, 9H).

EXAMPLE 16

Acylation of IA-tris-trimethylsilylethyl ester-6-hydroxy-7-SEM ether (3b).

A solution of diol (3b) (15.8 mg, 0.0163 mmol), triethylamine (6.8 µL, 0.0489 mmol), and DMAP (0.5 mg, 0.004 mmol) in CH$_2$Cl$_2$ (0.25 mL) was cooled to 0° C. Octanoyl chloride (50.0 µL, 0.292 mmol) was added and the solution was warmed to 23° C. for 16 h. The reaction solution was diluted with CH$_2$Cl$_2$ and washed with 1N HCl, 5% aqueous NaHCO$_3$, and saturated aqueous NaCl. The organic portion was dried (Na$_2$SO$_4$), filtered and the filtrate concentrated in vacuo. Purification of the residue by flash column chromatography (silica gel, 3:1 hexane/EtOAc) provided (4b) as a colorless oil:

$^1$NMR (300 MHz, CDCl$_3$) δ7.24–7.15 (m, 5), 6.33 (d, J=1.8 Hz, 1H), 5.14 (s, 1H), 5.10 (d, J=4.8 Hz, 1H), 4.97 (br s, 1H), 4.94 (br s, 1H), 4.73 (ABq, J=6.9 Hz, Dn=30.8 Hz,

2H), 4.37–4.10 (m, 6H), 4.03 (d, J=1.8 Hz, 1H), 3.85 (s, 1H), 3.70–3.52 (m, 2H), 2.82–1.89 (m, 9H), 2.09 (s, 3H), 1.26–1.22 (m, 10H), 1.20–0.82 (m, 14H), 0.050 (s, 9H), 0.007 (s, 9H), –0.005 (s, 9H), –0.009 (s, 9H).

By procedures described above for Examples 10A, 10B, 11 and 14, the following 6-position esters of (1S,3S,4S,5R,6R,7R)-1-[(4S)-acetoxy-3-methylene-5(R)-methyl-6-phenyl]hexyl-4,6,7-trihydroxy-6-O-(4(S), 6(S)-dimethyl-2-octenoyl)-2,8-dioxabicyclo-[3.2.1]octane 3,4,5-tricarboxylic acid (IA) were prepared.

EXAMPLE 17

IA-6-Dodecanoyl Ester(5c).

NMR (CD$_3$OD) δ0.88–0.95 (m, 6H), 1.26–1.41 (m, 18H), 1.58–1.70 (m, 2H), 2.14 (s, 3H), 2.06–2.50 (m, 8H), 2.70–2.76 (m, 1H), 4.06 (d, J=1.8 Hz, 1H), 5.02 (br s, 1H), 5.06 (br s, 1H), 5.12 (d, J=4.8 Hz, 1H), 5.30 (s, 1H), 6.32 (d, J=1.8 Hz, 1H), 7.19–7.33 (m, 5H); MS (FAB) m/z 743 (M+Na)$^+$.

EXAMPLE 18

IA6-Tetradecanoyl Ester (5d).

NMR (CD$_3$OD) δ0.86 (m, 6-H), 1.26 [br s, (CH$_2$)x], 2.08 (s, OAc), 4.00 (br s, H-7), 4.96 & 5.01 (2 s, =CH$_2$), 5.07 (d, J=5.0 Hz, C$\underline{H}$OAc), 5.24 (s, H-3), 6.28 (br s, H-6), 7.06–7.30 (m, ArH); MS (FAB) m/z 771 (M+Na)$^+$, 793 (M+2Na–1)$^+$ 816 (M+3 Na–1)$^+$.

EXAMPLE 19

IA-6-Palmitoleoyl Ester (5e).

(CD$_3$OD) δ0.80–0.91 (m, 6-H), 1.30 [br s, (CH$_2$)x], 2.10 (s, OAc), 4.00 (br s, H-7), 4.99 & 5.01 (2 s, =CH$_2$), 5.07 (d, J=5.0 Hz, C$\underline{H}$OAc), 5.24 (s, H-3), 5.33 (br t, CH=CH), 6.26 (br s, H-6), 7.02–7.32 (m, ArH); MS (FAB) m/z 797 (M+Na)$^+$, 820 (M+2 Na)$^+$.

EXAMPLE 20

IA-6-Hexadecanoyl Ester (5f).

NMR (CD$_3$OD) δ0.85 (d, J=6.5 Hz, CHC$\underline{H}_3$), 0.89 (t, J=7.0 Hz, CH$_2$C$\underline{H}_3$), 1.27 [br s, (CH$_2$)$_n$], 2.11 (s, OAc), 4.02 (br s, H-7), 4.98 & 5.02 (2 s, =CH$_2$), 5.07 (d, J=5.5 Hz, C$\underline{H}$OAc), 5.26 (s, H-3), 6.27 (br s, H-6), 7.08–7.29 (m, ArH); MS (FAB) m/z 799 (M+Na)$^+$, 821 (M+2 Na)$^+$, 843 (M+3 Na)$^+$. Anal. Calc. for C$_{41}$H$_{60}$O$_{14}$. 1.14 H$_2$O: C, 61.75; H, 7.87. Found: C, 61.78; H, 7.90.

EXAMPLE 21

IA-6-(11-Phenoxy)undecanoyl Ester (5g).

NMR (CD$_3$OD) δ0.86 (d, J=7.0 Hz, CHC$\underline{H}_3$), 2.10 (s, OAc), 3.94 (t, J=6.2 Hz, PhOCH$_2$), 4.02 (d, J=1.5 Hz, H-7), 4.87 & 5.02 (2 s, =CH$_2$), 5.07 (d, J=6.5 Hz, C$\underline{H}$OAc), 5.27 (s, H-3), 6.28 (d, J=1.5 Hz, H-6), 6.79–6.93 & 7.03–7.30 (2 m, ArH); MS (FAB) m/z 821 (M+Na)$^+$. Anal. Calc. for C$_{42}$H$_{54}$O$_{15}$. 1.02H$_2$O: C, 61.73; H, 6.91. Found: C, 61.60; H, 7.21.

EXAMPLE 22

IA-6-(4-Heptyl)benzoyl Ester(5h).

NMR (CD$_3$OD) δ0.90–0.98 (m, 6H), 1.32 (br s, , 10H), 1.66 (m, 2 H), 2.14 (s, 3H), 2.07–2.77 (m, 13H), 4.18 (d, J=1.5 1H), 5.0 (br s, 1H), 5.06 (br s, 1H), 5.1 (d, J=4.8 Hz, 1H), 5.36 (s, 1H), 6.52 (d, J=1.5 Hz, 1H), 7.1–7.3 (m, 5H), 7.34 & 7.97 (2 d, 4H).

EXAMPLE 23

IA-6-(11-Phenyl)undecanoyl Ester (5i).

NMR (CD$_3$OD) δ0.92 (d, 3H), 1.30 (br s, 14H), 1.62 (m, 8H), 2.14 (s, 3H), 2.07–2.77 (m, 13H), 4.07 (d, J=1.5 1H), 5.0 (br s, 1H), 5.06 (br s, 1H), 5.1 (d, J=4.8 Hz, 1H), 5.32 (s, 1H), 6.33 (d, J=1.5 Hz, 1H), 7.14–7.35 (m, 10H); MS (FAB) m/z 804 (M+Na)+.

EXAMPLE 24

IA-6-(4-Phenyl)butanoyl Ester (5j).

$^1$NMR (CD$_3$OD) δ0.90–0.98 (m, 6H), 1.32 (br s, 10H), 1.66 (m, 2H), 2.14 (s, 3H), 2.07–2.77 (m, 13H), 4.18 (d, J=1.5, 1H), 5.0 (br s, 1H), 5.06 (br s, 1H), 5.1 (d, J=4.8 Hz, 1H), 5.36 (s, 1H), 6.52 (d, J=1.5 Hz, 1H), 7.1–7.3 (m, 5H), 7.34 & 7.97 (2 d, 4H); MS (FAB) m/z 728 (M+2Na)$^+$.

EXAMPLE 25

IA-6-Adamantylacetyl Ester (5k).

NMR (CD$_3$OD) δ0.85 (d, 3H), 1.6–1.75 (m, 14H), 1.62 (m, 8H), 1.95 (m, 3H), 2.12 (s, 3H), 2.07–2.77 (m, 13H), 4.06 (d, J=1.5, 1H), 5.00–5.10 (m, 3H), 5.28 (s, 1H), 6.24 (d, J=1.5 Hz, 1H), 7.16–7.30 (m, 5H); MS (FAB) m/z 759 (M+2 Na)+.

EXAMPLE 26

IA-C6-Propionyl-7-MME-tris-t-butyl ester (4p').

NMR (CDCl$_3$) δ0.81 (d, J=7.0 Hz, CHC$\underline{H}_3$), 1.15 (t, J=7.0 Hz, CH$_2$C$\underline{H}_3$), 1.29 & 1.36 [2 s, (CH$_3$)$_2$C], 1.45, 1.47 & 1.67 (3 s tBu), 2.10. (s, OAc), 3.23 (s, CH$_3$O), 4.08 (s, C$_4$ OH), 4.18 (d, J=2.0 Hz, H-7), 4.97 (b s, =CH$_2$), 5.02 (s, H-3), 5.14 (d, J=5.0 Hz, C$\underline{H}$OAc), 6.38 (d, J=2.0 Hz, H-6), 7.10–7.32 (m, ArH).

EXAMPLE 27

IA-C6-Propionyl Ester (5p').

NMR (CD$_3$OD) δ0.86 (d, J=7.0 Hz, CHC$\underline{H}_3$), 1.12 (t, J=7.0 Hz, CH$_2$C$\underline{H}_3$), 2.11. (s, OAc), 4.04 (d, J=2.0 Hz, H-7), 4.98 & 5.03 (2 s, 2H), 5.09 (d, J=5.0 Hz, C$\underline{H}$OAc), 5.26 (s, H-3), 6.30 (d, J=2.0 Hz, H-6), 7.05–7.36 (m, ArH). MS (Neg. FAB) m/z 593.

EXAMPLE 28

IA-C6-Butyryl-7-MME-tris-t-butyl Ester (4q').

NMR (CDCl$_3$) δ0.80 (d, J=7.0 Hz, CHC$\underline{H}_3$), 0.95 (t, J=7.0 Hz, CH$_2$C$\underline{H}_3$), 1.30 & 1.37 [2 s, (CH$_3$)$_2$C], 1.45, 1.47 & 1.68 (3 s tBu), 2.10. (s, OAc), 3.22 (s, CH$_3$O), 4.08 (s, C$_4$ OH), 4.16 (d, J=2.0 Hz, H-7 ), 4.96 (br s, =CH$_2$) 5.01 (s, H-3), 5.14 (d, .J=5.0 Hz, C$\underline{H}$OAc), 6.37 (d, J=2.0 Hz, H-6), 7.09–7.31 (m, ArH).

EXAMPLE 29

IA-C6-Butyryl Ester (5q').

NMR (CD$_3$OD) δ0.87 (d, J=7.0 Hz, CHC$\underline{H}_3$), 0.96 (t, J=7.0 Hz, CH$_2$C$\underline{H}_3$), 1.64 (m, CH$_2$CH$_2$CH$_3$), 2.12 (s, OAc), 4.04 (d, J=2.0 Hz, H-7), 4.99 & 5.03 (2 s, 2H), 5.08 (d, J=5.0 Hz, C$\underline{H}$OAc), 5.26 (s, H-3), 6.30 (d, J=2.0 Hz, H-6), 7.06–7.38 (m, ArH). MS (Neg. FAB) m/z 607.

EXAMPLE 30

IA-C6-Isobutyryl-7-MME-tris-t-butyl Ester (4r').

NMR (CDCl$_3$) δ0.82 (d, J=7.0 Hz, CHC$\underline{H}_3$), 1.15.& 1.22 [2 d, J=7.0 Hz, CH(C$\underline{H}_3$)$_2$], 1.29 & 1.37 [2 s, (CH$_3$)$_2$C], 1.45, 1.47 & 1.68 (3 s tBu), 2.10. (s, OAc), 3.22 (s, C$_3$O), 4.09 (s, C$_4$OH), 4.17 (d, J=2 0 Hz, H-7), 4.98 (br s, =CH$_2$), 5.02 (s, H-3), 5.15 (d, J=5.0 Hz, C<u>H</u>OAc), 6.37 (d, J=2.0 Hz, H-6), 7.12–7.34 (m, ArH).

EXAMPLE 31

IA-C6-Isobutyryl Ester (5r').
NMR (CD$_3$OD) δ0.87 (d, J=7.0 Hz, CHC<u>H</u>$_3$), 1.17 [d, J=7.0 Hz, CH(C<u>H</u>$_3$)$_2$], 2.12. (s, OAc), 4.02 (d, J=2.0 Hz, H-7), 4.99 & 5.04 (2 s, 2H), 5.09 (d, J=5.0 Hz, C<u>H</u>OAc), 5.27 (s, H-3), 6.29 (d, J=2.0 Hz, H-6), 7.06–7.38 (m, ArH). MS (Neg. FAB) m/z 607.

EXAMPLE 32

IA-C6-(2(S)-Methyl)butyryl-7-MME-tris-t-butyl Ester (4s').
NMR (CDCl$_3$) δ0.82 (d, J=7.0 Hz, CHC<u>H</u>$_3$), 0.95 (t, J=7.0 Hz, CH$_2$C<u>H</u>$_3$), 1.13 (d, J=7.0 Hz, COCHC<u>H</u>$_3$), 1.32 & 1.38 [2 s, (CH$_3$)$_2$C], 1.48 & 1.68 (2 s, tBu), 2.11 (s, OAc), 3.23 (s, CH$_3$O), 4.09 (s, C$_4$ OH), 4.17 (d, J=2 0 Hz, H-7), 4.99 (br s, =CH$_2$) 5.04 (s, H-3), 5.15 (d, J=5.0 C<u>H</u>OAc), 6.37 (d, J=2 0 Hz, H-6), 7.12–7.34 (m, ArH).

EXAMPLE 33

IA-C6-(2(S)-Methyl)butyryl Ester (5s').
NMR (CD$_3$OD) δ0.86 (d, J=7.0 Hz, CHC<u>H</u>$_3$), 0.91 (t, J=7.0 Hz, CH$_2$C<u>H</u>$_3$), 1.13 (d, J=7.0 Hz, COCHC<u>H</u>$_3$), 2.10 (s, OAc), 4.0 (d, J=2.0 Hz, H-7), 4.98 & 5.02 (2 s, 2 H), 5.08 (d, J=5.0 Hz, C<u>H</u>OAc), 5.26 (s, H-3), 6.28 (d, J=2.0 Hz, H-6) 7.01–7.38 (m, ArH). MS (Neg. FAB) m/z 621.

EXAMPLE 34

IA-C6-(4-Methoxy)butyryl-7-MME-tris-t-butyl Ester (4t').
This compound was prepared from 3a and 4-methoxybutyric acid: NMR (CDCl$_3$) δ0.82 (d, CHC<u>H</u>$_3$), 1.30 & 1.37 [2s, C(OCH$_3$)(CH$_3$)$_2$], 1.46, 1.47 & 1.67 (3 s, tBu), 2.10 (s, OAc), 3.22 [s, C(OC<u>H</u>$_3$)(CH$_3$)$_2$], 3.31 (s, CH$_3$OCH$_2$), 3.38 (t, CH$_3$OC<u>H</u>$_2$), 4.08 (s, C$_4$—OH), 4.16 (d, J=2.0 Hz, H-7), 4.95 (br s, =CH$_2$), 4.99 (s, H-3), 5.14 (d, J=5.0 Hz, C<u>H</u>OAc), 6.38 (d, J=2.0 Hz, H-6), 7.14–7.30 (m, ArH).

EXAMPLE 35

IA-C6-(4-Methoxy)butyryl Ester (5t').
This compound was obtained as a white fluffy material from its precursor, 4t'. Purification by reversed-phase HPLC provided the title compound: NMR (CD$_3$OD) δ0.86 (d, J=6.5 Hz, CHC<u>H</u>$_3$), 2.10 (s, OAc), 3.30 (s, OCH$_3$), 3.39 (t, CH$_3$OC<u>H</u>$_2$), 4.05 (d, J=2.0 Hz, H-7), 4.98–5.02 (=CH$_2$), 5.08 (d, J=5.0 Hz, C<u>H</u>OAc), 5.26 (s, H-3), 6.28 (d, J=2.0 Hz, H-6,), 7.14–7.30 (m, ArH); MS (Neg. FAB) m/z 637 (M–H)$^+$.
Anal. Calc. for C$_{30}$H$_{38}$O$_{15}$·0.6H$_2$O: C, 55.45; H, 6.09. Found: C, 55.44; H, 6.12.

EXAMPLE 36

IA-C6-Valeryl-7-MME-tris-t-butyl Ester (4u').
120 Mg (0.154 mmol) of 3a afforded the blocked C$_6$-valeryl ester as a white solid: NMR (200 MHz, CDCl$_3$) δ0.80 (d, 3H), 0.89 (t, 3H), 2.08 (s, 3H C<u>H</u>$_3$CO), 2.02–2.75 (m, 9H), 4.07 (s, C$_4$OH), 4.16 (d, J=2 Hz, H-7), 4.96 (br s, =CH$_2$), 5.05 (s, H-3), 5.12 (d, J=5 Hz, 1H), 6.37 (d, J=2 Hz, 1H), 7.15–7.27 (m, 5H).

EXAMPLE 37

IA-C6-Valeryl Ester (5u').
NMR (400 MHz, CD$_3$OD) δ0.84 (d, 6H), 2.1 (s, 3H C<u>H</u>$_3$CO), 2.02–2.75 (m, 9H), 4.04 (d, J=2 Hz, 1H), , 5.01 (d, =CH$_2$), 5.10 (d, J=5 Hz 1H), 5.27 (s, C-3H), 6.20 (d, J=2 Hz, C-6H), 7.15–7.27 (m, 5H). MS (FAB-neg), m/e 622 [M-H].

EXAMPLE 38

IA-C6-Isovaleryl-7-MME-tris-t-butyl Ester (4v').
According to the procedures described above, 120 mg (0.154 mM) of 3a afforded the blocked ester as a white solid: NMR (200 MHz, CDCl$_3$) δ0.82 (d, 3H), 0.97 (m, 6H), 1.24, 1.30, 1.58 (3s, tBu), 2.1 (s, 3H C<u>H</u>$_3$CO), 2.02–2.75 (m, 9H), 3.49 (d, J=2 Hz, C-7H), 3.70 (m, 1H (CH$_3$)$_2$C<u>H</u>NH), 4.06 (d, J=2 Hz, 1H), 4.96 (m, 3H), 5.06 (d, J=3 Hz, 1H), 6.19 (d, J=2 Hz, 1H), 7.15–7.27 (m, 5H).

EXAMPLE 39

IA-C6-Isovaleryl Ester (5v').
A solution of 114 mg (0.132 mmol) of the blocked ester 4v' in CH$_2$Cl$_2$ (0.9 mL) was cooled to 0° C. and trifluoroacetic acid (0.25 mL) was added, affording the title compound as a white solid: NMR (400 MHz, CD$_3$OD) δ0.84 (d, 3H), 1.1 (m, 6H), 2.1 (s, 3H C<u>H</u>$_3$CO), 2.02–2.75 (m, 9H), 3.70 (m, 1H (CH$_3$)$_2$C<u>H</u>NH), 4.06 (d, J=2 Hz, 1H), 4.96 (m, 3H), 5.06 (d, J=3Hz, 1H), 6.19 (d, J=2Hz, 1H), 7.15–7.27 (m, 5H). MS (FAB-neg), m/e 621 [M–H].

EXAMPLE 40

IA-C6-(4-Methyl)valeryl-7-MME-tris-t-butyl Ester (4w').
This compound was prepared from 3a and 4-methylvaleric acid: NMR (CDCl$_3$) δ0.82 (d, J=6.5 Hz, CHC<u>H</u>$_3$), 0.88 & 0.89 [2 d, J=6.0 Hz, CH(CH$_3$)$_2$], 1.30 & 1.36 [2 s, C(OCH$_3$)(CH$_3$)$_2$], 1.46, 1.47 & 1.67 (3 s, tBu), 2.10 (s, OAc), 3.22 (s, OCH$_3$), 4.07 (s, C$_4$—OH), 4.17 (d, J=3.0 Hz, H-7), 4.99 (br s, =CH$_2$), 5.04 (s, H-3), 5.15 (d, J=5.0 Hz, C<u>H</u>OAc), 6.39 (d, J=3.0 Hz, H-6), 7.15–7.28 (m, ArH).

EXAMPLE 41

IA-C6-(4-Methyl)valeryl Ester (5w').
This compound was obtained as a white fluffy material from 4w'. Purification by reverse-phase HPLC gave the title compound: NMR (CD$_3$OD) δ0.85 (d, J=6.5 Hz, CHC<u>H</u>$_3$), 0.89 [d, J=6.0 Hz, CH(CH$_3$)$_2$], 2.10 (s, OAc), 4.04 (d, H-7), 5.08 (d, J=5.5 Hz, C<u>H</u>OAc), 5.28 (s, H-3), 6.28 (d, H-6,), 7.14–7.29 (m, ArH); MS (Neg. FAB) m/z 635 (M–H)$^+$.
Anal. Calc. for C$_{31}$H$_{40}$O$_{14}$·H$_2$O: C, 56.87; H, 6.47. Found: C, 56.84; H, 6.53.

EXAMPLE 42

IA-C6-(2-Methyl)valeryl Ester (5x').
The blocked ester compound was prepared from 3a and deblocked to give the title compound: NMR (400 MHz, CD$_3$OD) δ0.88 (m, C<u>H</u>$_3$), 1.00–1.80 (m, 5H), 2.08 (s, OOCC<u>H</u>$_3$), 3.98 (t, J=2Hz, C$_7$-H), 4.98 & 5.01 (2s, =CH$_2$), 5.08 (d, C<u>H</u>OAc), 5.25 (s, C$_3$-H), 6.25 (d, J=2 Hz, C$_6$-H), 7.12–7.28 (m, 5 ArH).
Anal. Calc. for C$_{31}$H$_{40}$O$_{14}$·2.0H$_2$O: C,55.35; H,6.59; Found: C,55.34; H,6.51; MS (FAB-neg), m/e 635 [M–H]

EXAMPLE 43

IA-C6-(3-Methyl)valeryl Ester (5y').
The blocked compound was prepared from 3a and deblocked to provide the title compound: NMR (400 MHz, CD$_3$OD) δ0.90 (m, C<u>H</u>$_3$), 2.10 (s, OOCC<u>H</u>$_3$), 4.00 (d, C$_7$-H), 4.95 & 5.00 (2s, =C<u>H</u>$_2$), 5.05 (d, <u>H</u>OAc), 5.25 (s, C$_3$-H), 6.28 (d, C$_6$-H), 7.12–7.28 (m, 5ArH); MS (FAB-neg), m/e 635 [M–H].

EXAMPLE 44

IA-C6-(Boc-6-Aminocaproyl)-7-MME-tris-t-butyl Ester (4z').

This compound was prepared from 3a and Boc-6-aminocaproic acid: NMR (CDCl$_3$) δ0.82 (d, CHCH$_3$), 1.36 & 1.36 [2 s, C(OCH$_3$(CH$_3$)$_2$], 1.45, 1.46, 1.48 & 1.68 (4 s, tBu), 2.10 (s, OAc), 3.22 (s, OCH$_3$), 4.08 (s, C$_4$—OH), 4.16 (d, H-7), 4.62 (m, NH), 4.97 (br s, =CH$_2$), 5.0 (s, H-3), 5.14 (d, J=5.0 Hz, CHOAc), 6.37 (d, H-6), 7.12–7.30 (m, ArH).

EXAMPLE 45

IA-C6-(6-Aminocaproyl) Ester (5z').

This compound was obtained as a white fluffy material from 4z'. The product was further purified by reversed-phase HPLC: NMR (CD$_3$OD) δ0.85 (d, J=6.5 Hz, CHCH$_3$), 2.10 (s, OAc), 2.91 (br t, CH$_2$NH$_2$), 3.98 (s, C$_4$—OH), 4.03 (d, H-7), 5.06 (d, CHOAc), 5.26 (s, H-3), 6.29 (d, H-6,), 7.13–7.30 (m, ArH); MS (Neg. FAB) m/z 650 (M–H)$^+$.

Anal. Calc. for C$_{31}$H$_{41}$O$_{14}$·CF$_3$CO$_2$H: C, 51.7; H, 5.53; N, 1.83. Found.: C, 51.60; H, 5.62, N, 1.74.

EXAMPLE 46

IA-C6-(2-Methyl)undecanoyl-7-MME-tris-t-butyl Ester (4a").

NMR (CDCl$_3$) δ0.82 (d, J=7.0 Hz, CHCH$_3$), 0.88 (t, J=7.0 Hz, CH$_2$CH$_3$), 1.11 & 1.19 (2 d, J=7 Hz, COCHCH$_3$), 1.26 [b s, (CH$_2$)$_x$], 1.30 & 1.37 [2 s,(CH$_3$)$_2$C],.1.46, 1.48 & 1.68 (3 s tBu), 2.10. (s, OAc), 3.22 (s, CH$_{30}$), 4.07 (s, C$_4$ OH), 4.15 (b d, H-7), 4.98 (b s, =CH$_2$) 5.02 (s, H-3), 5.15 (d,.J=5.0 Hz CHOAc), 6.38 (b d, H-6), 7.10–7.32 (m, ArH).

EXAMPLE 47

IA-C6-(2-Methyl)undecanoyl Ester (5a"). NMR (CD$_3$OD) δ0.80–0.94 (m, 6H), 1.14 (m, COCHCH$_3$), 1.29 [b s,(CH$_2$)$_x$], 2.11 (s, OAc), 4.00 (m, H-7), 4.99 & 5.02 (2 s, 2H), 5.09 (d, J=5.0 Hz, CHOAc), 5.27 (s, H-3), 6.26 (m, H-6) 7.06–7.38 (m, ArH). MS (FAB–) m/z 719.

EXAMPLE 48

IA-C6-Cyclohexaneacetyl-7-MME-tris-t-butyl Ester (4b").

NMR (CDCl$_3$) δ0.80 (d, J=7.0 Hz, CHCH$_3$), 1.28 & 1.36 [2 s,(CH$_3$)$_2$C], 1.45, 1.47 & 1.67 (3 s tBu), 2.10 (s, OAc), 3.23 (s, CH$_3$O), 4.08 (s, C$_4$ OH), 4.16 (d, J=20 Hz, H-7), 4.97 (b s, =CH$_2$)$_{5.02}$ (s, H-3), 5.14 (d, J=5.0 Hz, C HOAc), 6.36 (d, J=2.0 Hz, H-6), 7.11–7.33 (m, ArH).

EXAMPLE 49

IA-C6-Cyclohexaneacetyl Ester (5b").

NMR (CD$_3$OD) δ0.87 (d, J=7.0 Hz, CHCH$_3$), 2.12 (s, OAc), 4.03 (d, J=2.0 Hz, H-7), 4.99 & 5.03 (2 s, 2H), 5.09 (d, J=5.0 Hz, CHOAc), 5.26 (s, H-3), 6.26 (d, J=2.0 Hz, H-6 ) 7.08–7.36 (m, ArH). MS (FAB–) m/z 662

EXAMPLE 50

IA-C6-Phenylacetyl-tris-t-butyl Ester (4c").

IA-C6-Phenylacetyl-7-MME-tris-t-butyl ester was produced as described above. The 7-MME protecting group was removed by dissolving 200 mg of the fully blocked compound in 2 mL THF and adding 0.1 mL 2N HCl. After stirring for 1 hour, the product was isolated by flash chromatography.

NMR (CDCl$_3$) δ0.83 (d, J=7.0 Hz, CHCH$_3$), 1.44, 1.51 & 1.54 (3 s tBu), 2.10 (s, OAc ), 3.66 (s, COCH$_2$), 3.95 (m, H-7), 4.10 (s, C$_4$ OH), 5.0 (b s, =CH$_2$ & H-3), 5.11 (d, J=5.0 Hz CHOAc), 5.93 (d, J=2.0 Hz, H-6), 7.08–7.40 (m, ArH).

EXAMPLE 51

IA-C6-Phenylacetyl Ester (5c").

NMR (CD$_3$OD) δ0.86 (d, J=7.0 Hz, CHCH$_3$), 2.10 (s, OAc ), 3.62 (m, COCH$_2$), 3.98 (d, J=2.0 Hz, H-7), 4.99 & 5.02 (2 s, 2H), 5.07 (d, J=5.0 Hz, CHOAc), 5.28 (s, H-3), 6.29 (b d, H-6) 7.06–7.38 (m, ArH). MS (FAB–) m/z 655.

EXAMPLE 52

IA-C6-Phenoxyacetyl-7-MME-tris-t-butyl Ester (44d").

This compound was prepared from 3a and phenoxyacetic acid: NMR (CDCl$_3$) δ0.83 (d, J=6.5 Hz, CHCH$_3$), 1.32 & 1.37 [2 s, C(OCH$_3$)(CH$_3$)$_2$], 1.48, 1.49 & 1.66 (3 s, tBu), 2.10 (s, OAc), 3.22 (s, OCH$_3$), 4.09 (s, C$_4$—OH), 4.19 (d, J=1.5 Hz, H-7), 4.61 (q, PhOCH$_2$), 4.99 (br s, =CH$_2$), 5.01 (s, H-3), 5.15 (d, J=5.0 Hz, CHOAc), 6.48 (d, J=2.0 Hz, H-6), 6.90–7.03 (m, OPh), 7.15–7.32 (m, ArH).

EXAMPLE 53

IA-C6-Phenoxyacetyl Ester (5d").

This compound was obtained as a white fluffy material from 4d". The product was further purified by reversed-phase HPLC: NMR (CD$_3$OD) δ0.86 (d, J=6.5 Hz, CHCH$_3$), 2.10 (s, OAc), 4.09 (d, J=2.0 Hz, H-7), 4.66 (q, PhOCH$_2$), 5.0–5.03 (=CH$_2$), 5.08 (d, J=5.0 Hz, CHOAc), 5.28 (s, H-3), 6.46 (d, J=2.0 Hz, H-6,), 6.88–6.99 (m, OPh), 7.14–7.31 (m, ArH); MS (Neg. FAB) m/z 671 (M–H)$^+$.

Anal. Calc. for C$_{33}$H$_{36}$O$_{15}$·0.7 H$_2$O: C, 57.84; H, 5.50. Found: C, 57.79; H, 5.63.

EXAMPLE 54

IA-C6-Phenylpropionyl-7-MME-tris-t-butyl Ester (4e").

NMR (CDCl$_3$) δ0.82 (d, J=7.0 Hz, CHCH$_3$), 1.21 & 1.35 [2 s, (CH$_3$)$_2$C], 1.44, 1.47 & 1.69 (3 s tBu), 2.10 (s, OAc), 3.19 (s, CH$_3$O), 4.07 (s, C$_4$ OH), 4.14 (d, J=2 0 Hz, H-7), 4.97 (b s, =CH$_2$), 5.02 (s, H-3), 5.14 (d, J=5.0 Hz C HOAc), 6.39 (d, J=2 0 Hz, H-6), 7.09–7.35 (m, ArH).

EXAMPLE 55

IA-C6-Phenylpropionyl Ester (5e").

NMR (CD$_3$OD) δ0.86 (d, J=7.0 Hz, CHCH$_3$), 2.11 (s, OAc), 3.89 (d, J=2.0 Hz, H-7), 4.99 & 5.03 (2 s, 2H), 5.09 (d, J=5.0 Hz, CHOAc), 5.26 (s, H-3), 6.23 (b d, H-6), 7.04–7.38 (m, ArH). MS (FAB–) m/z 670.

EXAMPLE 56

IA-C6-(2-Phenoxy)propionyl-7-MME-tris-t-butyl Ester (4f"). NMR (CDCl$_3$) δ0.81 (d, J=7.0 Hz, CHCH$_3$), 1.31 & 1.36 [2 s, (CH$_3$)$_2$C], 1.47, 1.49 & 1.67 (3 s tBu), 2.10 (s, OAc), 3.22 (s, CH$_3$O), 4.09 (s, C$_4$ OH), 4.21 (d, J=2.0 Hz, H-7), 4.24 (m, CH$_2$OAr), 4.98 (b s, =CH$_2$), 5.02 (s, H-3), 5.15 (d, J=5.0 Hz CHOAc), 6.44 (d, J=2.0 Hz, H-6), 6.84–7.38 (m, ArH).

EXAMPLE 57

IA-C6-(2-Phenoxy)propionyl Ester (5f").

NMR (CD$_3$OD) δ0.85 (d, J=7.0 Hz, CHCH$_3$), 2.11 (s, OAc), 2.79 (b t, COCH$_2$), 4.07 (b s, H-7), 4.24 (b d, CH$_2$OAr), 4.99 & 5.01 (2 s, 2H), 5.09 (d, J=5.0 Hz, C HOAc), 5.28 (s, H-3), 6.32 (b s, H-6), 6.82–7.38 (m, ArH). MS (FAB–) m/z 685

EXAMPLE 58

IA-C6-Phenoxybutyryl Ester (5g").

The blocked compound was prepared from 3a and deblocked to provide the title compound: NMR (300 MHz, CD$_3$OD) δ0.86 (d, CHCH$_3$), 2.10 (s, OOCCH$_3$), 4.00 (t, PhOCH$_2$), 4.05 (d, C$_7$-H), 4.98 & 5.05 (2s, =CH$_2$), 5.08 (d, CHOAc), 5.27 (s, H$_3$), 6.31 (s, C$_6$-H), 6.84–6.96 (m, 7ArH), 7.12–7.31 (m, 3ArH); MS (FAB), m/e 723 [M+Na]$^+$.

EXAMPLE 59

IA-C6-[11-(4-Acetylphenoxy)]undecanoyl-7-MME-tris-t-butyl Ester (4h").

This compound was prepared from 3a and 11-(4-acetylphenoxy)undecanoic acid: NMR (CDCl$_3$) δ0.81 (d, J=6.5 Hz, CHCH$_3$), 1.30 [br s, (CH$_2$)$_n$], 1.46, 1.47 & 1.67 (3 s, tBu), 2.10 (s, OAc), 2.55 (s CH$_3$COC$_6$H$_4$), 3.21 (s, OCH$_3$), 4.0 (t, J=6.5 Hz, PhOCH$_2$), 4.06 (s, C$_4$—OH), 4.16 (d, J=2.0 Hz, H-7), 4.96 (br s, =CH$_2$), 5.0 (s, H-3), 5.13 (d, J=5.0 Hz, CHOAc), 6.35 (d, J=2.0 Hz, H-6), 6.90 & 7.90 (2 d, CH$_3$COArH), 7.13–7.30 (m, ArH).

EXAMPLE 60

IA-C6-[11-(4-Acetylphenoxy)]undecanoyl Ester (5h").

This compound was obtained as a white solid from its precursor, 4h": NMR (CD$_3$OD) δ0.85 (d, CHCH$_3$), 1.32 [br s, (CH$_2$)$_n$], 2.10 (s, OAc), 2.54 (s, CH$_3$COC$_6$H$_4$), 4.03 (d, H-7), 4.04 (t, J=6.5 Hz, PhOCH$_2$), 4.97–5.02 (=CH$_2$), 5.07 (d, J=5.0 Hz, CHOAc), 5.27 (s, H-3), 6.28 (d, H-6), 6.97 & 7.93 (2 d, CH$_3$COArH), 7.13–7.29 (m, ArH); MS (FAB) m/z 859 (M+3 Li)$^+$.

EXAMPLE 61

IA-C6-trans-Cinnamyl Ester (5i").

The blocked compound was prepared from 3a and deblocked to provide the title compound: NMR (400 MHz, CD$_3$OD) δ0.85 (d, CHCH$_3$), 2.09 (s, OOCCH$_3$), 4.10 (d, J=2 Hz, C$_7$-H), 4.97 & 5.02 (2s, =CH$_2$), 5.08 (d, HOAc), 5.29 (s, C3-H), 6.39 (s, C6-H), 6.49 & 7.69 (2d, J=16 Hz, —CH=CH—), 7.18 (m, 5 ArH), 7.40 & 7.58 (2m, 5 ArH).

Anal. Calc. for C$_{34}$H$_{36}$O$_{14}$·2.5 H$_2$O: C,57.22; H,5.79; Found: C,57.34; H,5.65; MS (FAB-neg), m/e 667 [M–H].

EXAMPLE 62

IA-C6-(3-Methoxy)cinnamyl Ester (5j").

The blocked compound was prepared from 3a and deblocked to provide the title compound: NMR (400 MHz, CD$_3$OD) δ0.85 (d, CHCH$_3$), 2.09 (s, OOCCH$_3$), 3.80 (s, PhOCH$_3$), 4.10 (d, J=2 Hz, C$_7$-H), 4.97 & 5.02 (2S, =CH$_2$), 5.07 (d, CHOAc), 5.29 (S, C$_3$-H), 6.40 (S, C$_6$-H), 6.49 & 7.66 (2d, J=16 Hz, —CH=CH—), 6.97–7.33 (m, 9ArH);

Anal. Calc. for C$_{35}$H$_{38}$O$_{15}$: C,60.17; H,5.48; Found: C, 60.02; H, 5.77; MS (FAB), m/e 717 [M+3Li]$^+$

EXAMPLE 63

Ia-C6-(4-phenyl)benzoyl Ester (5k").

The blocked compound was prepared from 3a and deblocked to provide the title compound: NMR (200 MHz, CD$_3$OD) δ0.86 (d, CHCH$_3$), 2.09 (S, OOCCH$_3$), 4.19 (d, C$_7$-H), 4.80 & 5.00 (2S, =CH$_2$), 5.40 (d, HOAc), 5.33 (s, C$_3$-H), 6.50 (d, C$_6$-H), 7.10–8.12 (m, 14ArH); MS (FAB-neg), m/e 717 [M–H]

EXAMPLE 64

IA-C6-(4-Biphenyl)acetyl Ester (5l").

According to the procedures described above, a solution of 3a (276 mg, 0.354 mmol), dicyclohexylcarbodiimide (146 mg, 0.708 mmol), 4-dimethylaminopyridine (45 mg, 0.354 mmol) and 4-biphenylacetic acid (154 mg, 0.708 mmol) in CH$_2$Cl$_2$ (1.0 ml) was allowed to stir for 16 hours at 25° C. providing a colorless oil. This oil, in CH$_2$Cl$_2$ (1.8 ml), was cooled to 0° C. and trifluoroacetic acid (0.6 ml) was added, affording the title compound as a white solid: NMR (200 MHz, CD$_3$OD) δ0.85 (d, CHCH$_3$), 2.10 (s, OOCCH$_3$), 3.65 (d, CH$_2$-Ph-Ph), 4.00 (d, C$_7$-H), 4.95 & 5.00 (2S, =CH$_2$), 5.05 (d, HOAc), 5.25 (s, C$_3$-H), 6.30 (d, C$_6$-H), 7.12–7.60 (m, 14ArH).

Anal. Calc. for C$_{39}$H$_{40}$O$_{14}$·2.5 H$_2$O: C,60.23; H,5.83; Found: C,60.37; H,5.68; MS (FAB-neg), m/e 731 [M–H]

EXAMPLE 65

IA-C6-(4-Phenoxy)phenylacetyl-tris-t-butyl Ester (4m").

IA-C6-(4-Phenoxy)phenylacetyl-7-MME-tris-t-butyl ester was produced as described above. The 7-MME protecting group was removed as described for 4c". NMR (CDCl$_3$) δ0.81 (d, J=7.0 Hz, CHCH$_3$), 1.43, 1.50 & 1.53 (3 s tBu), 2.09 (s, OAc), 3.63 (s, COCH$_2$), 3.98 (m, H-7), 4.07 (s, C$_4$ OH), 4.97 (b s, =CH$_2$ & H-3), 5.10 (d, J=5.0 Hz C HOAc), 5.93 (d, J=2 0 Hz, H-6), 6.93–7.39 (m, ArH).

EXAMPLE 66

IA-C6-(4-Phenoxy)phenylacetyl Ester (5m").

NMR (CD$_3$OD) δ0.86 (d, J=7.0 Hz, CHCH$_3$), 2.12 (s, OAc), 3.62 (m, COCH$_2$), 4.02 (d, J=2.0 Hz, H-7), 4.98 & 5.02 (2 s, 2H), 5.07 (d, J=5.0 Hz, CHOAc), 5.25 (s, H-3), 6.30 (d, J=2.0 Hz, H-6)$_{6.84–7.42}$ (m, ArH). MS (FAB–) m/z 747.

EXAMPLE 67

IA-C6-(3-Phenoxy)phenylacetyl-tris-t-butyl Ester (4n").

NMR (CDCl$_3$) δ0.82 (d, J=7.0 Hz, CHCH$_3$), 1.45, 1.48 & 1.55 (3 s tBu), 2.15 (s, OAc),3.63. (m, COCH$_2$), 3.97 (d, J=2.0 Hz, H-7), 4.99 (b s, =CH$_2$ & H-3), 5.11 (d, J=5.0 Hz CHOAc), 5.95 (d, J=2 0 Hz, H-6), 6.87–7.41 (m, ArH).

EXAMPLE 68

IA-C6-(3-Phenoxy)phenylacetyl Ester (5n").

NMR (CD$_3$OD) δ0.85 (d, J=7.0 Hz, CHCH$_3$), 2.10 (s, OAc), 3.61 (m, COCH$_2$), 4.00 (d, J=2.0 Hz, H-7), 4.99 & 5.02 (2 s, 2H), 5.08 (d, J=5.0 Hz, CHOAc), 5.25 (s, H-3), 6.30 (b s, H-6)$_{6.79–7.43}$ (m, ArH). MS (FAB–) m/z 748.

EXAMPLE 69

IA-C6-Phenylalanine-7-MME-tris-t-butyl Ester (4o").

According to the procedures described above, 100 mg of the 3a afforded blocked C6-phenylalanine ester as a white solid: NMR (200 MHz, CDCl$_3$) δ0.82 (d, J=6.5 Hz, 3H), 1.42 (s, 3tBu), 1.64 (s, 2tBu), 2.08 (s, 3H CH$_3$CO), 2.02–2.75 (m, 9H), 4.04 (d, J=2 Hz, C-7), 4.96 (m, C-3H), 5.06 (d, J=5 Hz, 1H), 6.41 (d, J=2 Hz, 1H), 7.15–7.27 (m, 5H).

EXAMPLE 70

IA-C6-Phenylalanine Ester (5o").

According to the procedures described above, 70 mg of the diol afforded the title compound as a white solid: NMR (200 MHz, CD$_3$OD) δ0.84 (d, 6H), 2.1 (s, 3H CH$_3$CO), 4.04 (d, J=2 Hz, 1H), 5.00 (m, 3H), 5.10 (d, J=5 Hz, 1H), 6.40 (d, J=2 Hz, 1H), 7.15–7.27 (m, 10ArH). MS (FAB-neg), m/e 684 [M–H].

EXAMPLE 71

IA-C6-(11-Bromo)undecanoyl-7-MME-tris-t-butyl Ester (4p").

According to the procedures described above, a solution of 3a (600 mg, 0.770 mmol), dicyclohexylcarbodiimide (318 mg, 1.54 mmol), 4-dimethylaminopyridine (94 mg, 0.770 mmol) and 11-bromoundecanoic acid (408.5 mg, 1.54 mmol) in $CH_2Cl_2$ (6.0 ml) was allowed to stir at 23° C. for 16 hours. The reaction product was chromatographed on a flash column using 3:1 Hexane:Ethyl Acetate to provide the blocked ester as a colorless oil: NMR (300 MHz, $CDCl_3$) δ0.84 (d, $CHCH_3$), 1.47 & 1.67 (2s, 3tBu), 2.12 (s, $OOCCH_3$), 3.24 (s, $OCH_3$), 3.42 (t, $CH_2$-Br), 4.09 (s, $C_4$—OH), 4.20 (s, C7-H), 5.00 (br s, =$CH_2$), 5.04 (s, $C_3$-H), 5.17 (d, $C$HOAc), 6.40 (s, C6-H), 7.16–7.36 (m, 5ArH).

EXAMPLE 72

IA-C6-(11-Bromo)undecanoyl Ester (5p").

According to the deblocking procedures above, a solution of blocked 11-bromoundecanoic acid, 5p" (101 mg, 0.098 mmol) in $CH_2Cl_2$ (0.9 ml) was cooled to 0° C. and trifluoroacetic acid (0.3 ml) was added, affording the title compound as a white solid. $^1H$ NMR (400 MHz, $CD_3OD$) δ0.84 (d, $CHCH_3$), 2.09 (s, $OOCCH_3$), 2.25 (t, $CH_2COO$), 3.42 (m, $CH_2$-Br), 4.01 (s, C7-H), 5.00 & 5.01 (2s, =$CH_2$), 5.07 (d, $C$HOAc), 6.28 (s, $C_6$-H), 7.14–7.27 (m, 5ArH); MS (FAB), m/e 807 $[M+Na]^+$

EXAMPLE 73

IA-C6-(4-Methoxy)phenoxyundecanoyl Ester (5q").

A solution of sodium 4-methoxyphenolate was made by dissolving 4-methoxyphenol (145 mg, 1.12 mmol) in dimethylformamide (5.0 ml) and adding sodium hydride (38 mg, 0.936 mmol) which was stirred until all hydrogen evolution had ceased. In a separate flask, blocked C6-(11-bromo)undecanoyl ester, 4p"(96 mg, 0.0936 mmol) was dissolved in dimethylformamide (1.0 ml) then an aliquot (1.0 ml) of the sodium 4-methoxyphenolate was added. This reaction was allowed to stir for 16 hours at 23° C. The reaction product was chromatographed on 500 micron prep TLC plates using 4:1 Hexane:Ethyl Acetate which provided a colorless oil. This oil was dissolved in $CH_2Cl_2$ (0.9 ml) and cooled to 0° C. and trifluoroacetic acid (0.3 ml) was added, affording the title compound as a white solid: NMR (200 MHz, $CD_3OD$) δ0.84 (d, $CHCH_3$), 1.3 (br s, 16H), 2.09 (s, $OOCCH_3$), 3.72 (s, $CH_3OPh$), 3.88 (t, $OCH_2$), 4.02 (s, C7-H), 4.98 & 5.03 (2s, =$CH_2$), 5.08 (d, $C$HOAc), 5.25 (s, $C_3$-H), 6.28 (s, $C_6$-H), 6.81 (s, 4ArH), 7.05–7.28 (m, 5ArH); MS (FAB-neg), m/e 827 [M–H]

EXAMPLE 74

IA-C6-(3-Dimethylamino)phenoxyundecanoyl Ester (5t").

According to the procedure used for 3-methoxyphenoxyundecanoic acid analog, sodium 3-dimethylaminophenolate was made from 3-dimethylaminophenol (119 mg, 0.865 mmol), sodium hydride (28 mg, 0.692 mmol) in dimethylformamide (4 ml). An aliquot (1.0 ml) of the sodium 3-dimethylphenolate was added to a stirred solution of blocked C6-(11-bromo)undecanoyl ester, 4p", (89 mg, 0.0865 mmol) in dimethylformamide (1.0 ml). The reaction was allowed to run at 23° C. for 16 hours. The reaction product was chromatographed on 500 micron TLC plates using 3:1 Hexane:Ethyl Acetate which provided a colorless oil. This oil was dissolved in $CH_2Cl_2$ (0.6 ml) then cooled to 0° C. and trifluoroacetic acid (0.2 ml) was added, affording the title compound as a white solid: NMR (400 MHz, $CD_3OD$) δ0.84 (d, $CHCH_3$), 2.09 (s, $OOCCH_3$), 2.92 (d, J=7 Hz, $N(CH_3)_2$), 3.93 (t, J=6.5 Hz, $OCH2$), 4.01 (s, $C_7$-H), 4.96 & 5.01 (2s, =$CH_2$), 5.06 (d, J=5 Hz, C$H$OAc), 5.25 (s, $C_3$-H), 6.32 (s, $C_6$-H), 6.28–7.25 (m, 9ArH); MS (FAB-neg), m/e 840 [M–H].

EXAMPLE 75

IA-C6-(4-dimethylamino)thiophenoxyundecanoyl Ester (5s").

According to the previously described procedures, sodium 4-dimethylaminothiophenolate was made using 4-dimethylaminothiophenol (182 mg, 1.19 mmol), sodium hydride (36 mg, 0.951 mmol) in dimethylformamide (2 ml). An aliquot (0.5 ml) of sodium 4-dimethylaminothiophenolate was added to a stirred solution of blocked C6-(11-bromo)undecanoyl ester, 4p", (122 mg, 0.119 mmol) in dimethylformamide (0.5 ml). The reaction was allowed to run at 23° C. for 16 hours. The reaction product was chromatographed on a flash column using 4:1 Hexane:Ethyl Acetate which provided 24 mg of colorless oil. This oil was dissolved in $CH_2Cl_2$ (0.9 ml) then cooled to 0° C. and trifluoroacetic acid (0.3 ml) was added, affording the title compound as a grey solid: NMR (400 MHz, $CD_3OD$) δ0.84 (d, $CHCH_3$), 1.25 (m, 16H), 2.09 (s, $OOCCH_3$), 2.93 (d, N($CH_3)_2$), 4.01 (s, $C_7$-H), 4.96 & 5.01 (2s, =$CH_2$), 5.06 (d, C$H$OAc), 5.25 (s, $C_3$-H), 6.29 (s, $C_6$-H), 6.78–7.28 (m, 9ArH); MS (FAB-neg), m/e 856 [M–H].

EXAMPLE 76

General Procedure for Preparation of C6 Carbamates.
Method A.

The appropriate isocyanate (0.192 mmol) is added to a solution of general structure (3) (100 mg, 0.128 mmol) in pyridine (1 mL) or toluene (1 mL) containing triethylamine (90 μL) and the mixture is heated at 90° C. for 2 h. The solution is cooled and more isocyanate (0.192 mmol) is added and heating is continued for another 1 h. If the reaction is not complete as shown by TLC, more isocyanate (0.192 mmol) is added. The reaction mixture is cooled and the solid is filtered off and washed with dichloromethane. The combined filtrates are evaporated to a residue, which is purified by preparative TLC (hexanes-ethyl acetate; 4:1, v/v).
Method B.

A solution of-(3a) (100 mg, 0.128 mmol) and 1,1'-carbonyldiimidazole (42 mg, 0.256 mmol) in dry toluene (0.5 mL) is stirred at room temperature for 5 h. The appropriate amine (1.28 mmol) is added and the mixture is stirred at room temperature for 3 h. The reaction mixture is diluted with hexanes, filtered, and the filtrate is evaporated to dryness. The residue is purified by preparative TLC (hexanes-ethyl acetate; 4:1 or 3:1, v/v).

EXAMPLE 77

General Procedure for Deprotection of carbamates (4).

A solution of (4) (100 mg) in dry dichloromethane (3 mL) is treated with trifluoroacetic acid (1 mL) at room temperature overnight. The solution is evaporated to a residue, which is redissolved in toluene and concentrated to dryness. This process is repeated twice, and the product is dissolved in benzene and freeze-dried to give a white solid. The purity of the products is monitored by reversed-phase HPLC.

EXAMPLE 78

Preparation IA-6-(1-Imidazolylcarbonyl)-7-MME-tris-t-butyl ester (4A).

This compound was prepared following EXAMPLE 76: NMR (CDCl$_3$) δ0.84 (d, J=7.5 Hz, CHCH$_3$), 1.27, 1.47 & 1.69 (3 s, tBu), 1.36 & 1.39 [2 s, C(OCH$_3$)(CH$_3$)$_2$], 2.12 (s, OAc), 3.25 (s, OCH$_3$), 4.11 (s, C$_4$-H), 4.34 (d, H-7), 5.0 (br s, =CH$_2$), 5.03 (s, H-3), 5.16 (d, J=7.0 Hz, C$\underline{H}$OAc), 6.54 (d, J=2.5, H-6), 7.10, 7.43 & 8.15 (2 br s & s, imidazole), 7.13–7.31 (m, ArH).

By procedures described for Examples 76A or 76H and 77, the following 6-position carbamates of (1S,3S,4S,5R, 6R,7R)-1-[(4S)-acetoxy-3-methylene-5(R)-methyl- 6-phenyl]hexyl-4,6,7-trihydroxy-6-O-(4(S), 6(S)-dimethyl-2-octenoyl)-2,8-dioxabicyclo[3.2.1]octane 3,4,5-tricarboxylic acid (IA) were prepared.

EXAMPLE 79

IA-6-Octylaminocarbonyl Carbamate (5ll).

NMR (CD$_3$OD) δ0.80–0.92 (m, 6-H)$_{1.28}$ [br s, (CH$_2$)x], 2.08 (s, OAc), 3.07 (br t, C$\underline{H_2}$NH),.4.06 (br s, H-7), 4.98 & 5.01 (2 s, =CH$_2$), 5.07 (d, J=5.0 Hz, C$\underline{H}$OAc), 5.25 (s, H-3), 6.16 (br s, H-6), 7.04–7.36 (m, ArH); MS (FAB) m/z 716 (M+Na)$^+$, 739 (M+2 Na)$^+$.

EXAMPLE 80

IA-6-Decylaminocarbonyl Carbamate (5m).

NMR (CD$_3$OD) δ0.81–0.90 (m, 6H), 1.28 (s, 16H), 1.53 (m), 2.1 (s, C$\underline{H_3}$CO), 2.03–2.52 (m, 9H), 2.7 (2 d, J=6.3 & 13.2 Hz, 1H), 3.08 (m, 2H), 4.06 (d, J=1.8 Hz, 1H), 5.00 (br s, 1H), 5.06 (br s, 1H), 5.14 (t, 1H), 7.18–7.33 (m, 5H); MS (FAB) m/z 728 (M+Li)$^+$.

Anal. Calc. for C$_{36}$H$_{51}$O$_{14}$N. 2 H$_2$O: C, 57.06; H, 7.32; N, 1.85. Found: C; 57.37; H, 7.49; N, 1.90.

EXAMPLE 81

IA-6-Undecylaminocarbonyl Carbamate (5n).

NMR (CD$_3$OD) δ0.85 (d, J=6.5 Hz, CHC$\underline{H_3}$), 0.88 (t, J=6.5 Hz, CH$_2$CH$_3$), 2.09 (s, OAc), 3.07 (t, J=6.5 Hz, C$\underline{H_2}$NHCO), 4.05 (d, J=2.5 Hz, H-7), 4.98 & 5.02 (2 s, =CH$_2$), 5.08 (d, J=5.0 Hz, C$\underline{H}$OAc), 5.26 (s, H-3), 6.17 (br s, H-6), 7.14–7.30 (m, ArH); MS (FAB) m/z 758 (M+Na)$^+$, 780 (M+2 Na)$^+$, 802 (M+3 Na)$^+$.

EXAMPLE 82

IA-6-Dodecylaminocarbonyl Carbamate (5o).

NMR (CD$_3$OD) δ0.82–0.94 (m, 6H), 1.28 [br s, (CH$_2$)$_x$], 2.08 (s, OAc), 3.07 (br t, C$\underline{H_2}$NH),.4.04 (br s, H-7), 4.97 &.5.01 (2 s, =CH$_2$), 5.07 (d, J=5.0 Hz, C$\underline{H}$OAc), 5.25 (s, H-3), 6.17 (br s, H-6), 7.12–7.25 (m, ArH); MS (FAB) m/z 772 (M+Na)$^+$, 795 (M+2 Na)$^+$.

EXAMPLE 83

IA-6-tridecylaminocarbonyl Carbamate (5p).

NMR (CD$_3$OD) δ0.85 (d, J=6.5 Hz, CHCH$_3$), 0.88 (t, J=6.5 Hz, CH$_2$CH$_3$), 2.09 (s, OAc), 3.07 (t, J=6.5 Hz, C$\underline{H_2}$NHCO), 4.05 (d, J=2.5 Hz, H-7), 4.98 & 5.02 (2 s, =CH$_2$), 5.08 (d, J=5.0 Hz, C$\underline{H}$OAc), 5.26 (s, H-3), 6.16 (br s, H-6), 7.12–7.30 (m, ArH); MS (FAB) m/z 786 (M+Na)$^+$.

EXAMPLE 84

IA-6-tetradecylaminocarbonyl Carbamate (5q).

NMR (CD$_3$OD) δ0.81–0.90 (m, 6H), 1.28 (s, 24H), 1.45 (m, 2H), 2.1 (s, CH$_3$CO), 2.03–2.52 (m, 9H), 2.7 (2 d, J=6.3 & 13.2 Hz, 1H), 3.05 (m, 2H), 4.06 (d, J=1.8 Hz, 1H), 5.00 (br s, 1H), 5.06 (br s, 1H), 5.14 (t, 1 H), 7.33–7.18 (m, 5H); MS (FAB) m/z 800 (M+Na)$^+$.

EXAMPLE 85

IA-6-hexadecylaminocarbonyl Carbamate (5r).

NMR (CD$_3$OD) δ0.86 (d, J=6.5 Hz, CHCH$_3$), 0.90 (t, J=6.5 Hz, CH$_2$CH$_3$), 2.12 (s, OAc), 3.08 (m, C$\underline{H_2}$NHCO), 4.06 (br s, H-7), 4.98 & 5.02 (2 br s, =CH$_2$), 5.08 (d, J=5.5 Hz, C$\underline{H}$OAc), 5.26 (s, H-3), 6.17 (br s, H-6); MS (FAB) m/z 828 (M+Na)$^+$, 850 (M+2 Na)$^+$, 872 (M+3 Na)$^+$. Anal. Calc. for C$_{42}$H$_{63}$O$_{14}$. 2.29 H$_2$O: C, 59.54; H, 8.04; N, 1.65. Found: C, 59.51; H, 7.89; N, 1.85.

EXAMPLE 86

IA-6-benzylaminocarbonyl Carbamate (5s).

NMR (CD$_3$OD) δ0.94 (d, J=7.0 Hz, C$\underline{H_3}$CH), 2.10 (s, OAc), 4.17 (br s, H-7), 5.13 (d, J=5.0 Hz, C$\underline{H}$OAc), 5.28 (s, H-3), 6.28 (br s, H-6), 7.0–7.50 (m, ArH); MS (FAB) m/z 694 (M+Na)$^+$, 717 (M+2 Na)$^+$.

EXAMPLE 87

IA-6-(4-phenylaminocarbonyl Carbamate (5t).

NMR (CD$_3$OD) δ0.81 (d, J=6.5 Hz, CHCH$_3$), 2.09 (s, OAc), 4.17 (d, H-7), 4.99 & 5.03 (2 s, =CH$_2$), 5.07 (d, J=5.5 Hz, C$\underline{H}$OAc), 5.32 (s, H-3), 6.37 (d, H-6), 9.40 (br s, NH); MS (FAB) m/Z 756 (M+Na)$^+$, 778 (M+2 Na)$^+$, 800 (M+3 Na)$^+$. Anal. Calc. for C$_{38}$H$_{39}$NO$_{14}$ 1.36 H$_2$O: C, 60.20; H, 5.55; N, 1.85. Found: C, 60.26; H, 5.55; N, 1.72.

EXAMPLE 88

IA-6-(11-phenoxy)undecylaminocarbonyl Carbamate (5u).

NMR (CD$_3$OD) δ0.87 (d, J=7.5 Hz, CHCH$_3$), 2.10 (s, OAc), 3.10 (m, CH$_2$NHCO), 3.97 (t, J=6.5 Hz, PhOCH$_2$), 4.09 (d, J=1.5 Hz, H-7), 5.01 & 5.05 (2 s, =CH$_2$), 5.11 (d, J=5.0 Hz, C$\underline{H}$OAc), 5.29 (s, H-3), 6.20 (d, J=1.5 Hz, H-6), 6.87–6.94 & 7.15–7.32 (2 m, ArH); MS (FAB) m/z 849 (M+Na)$^+$, 871 (M+2 Na)$^+$, 893 (M+3 Na)$^+$. Anal. Calc. for C$_{43}$H$_{57}$NO$_{15}$. 2.27 H$_2$O: C, 59.45; H, 7.14, N, 1.61. Found: C, 59.52; H, 6.82; N, 1.76.

EXAMPLE 89

IA-6-(N-methyl)Dodecylaminocarbonyl Carbamate (5v).

NMR (CD$_3$OD) δ0.82–0.94 (m, 6H), 1.28 (s, 20H), 1.45 (m, 2H), 2.1 (s, CH$_3$CO), 2.7 (m, 1H), 2.04–2.50 (m, 9H), 2.84 & 2.90 (2 s, CH$_3$N), 3.08 (m, 1H), 4.06 (d, J=1.8 Hz, 1H), 5.00 (br s, 1H), 5.06 (br s, 1H), 5.14 (t, 1H), 7.18–7.33 (m, 5H).

EXAMPLE 90

IA-6-(N-methyl)Hexadecylaminocarbonyl Carbamate (5w).

NMR (CD$_3$OD) δ0.82–0.94 (m, 6H), 1.28 (s, 28H), 1.45 (m, 2H), 2.1 (s, CH$_3$CO), 2.04–2.50 (m, 9H), 2.7 (m, 1H), 2.84 & 2.90 (2 s, CH$_3$N), 3.08 (m, 1H) 4.06 (d, J=1.8 Hz, 1H), 5.00 (br s, 1H), 5.06 (br s, 1H), 5.14 (t, 1H), 7.18–7.33 (m, 5H).

EXAMPLE 91

IA-C6-Methylaminocarbonyl Carbamate-7-MME-tris-t-butyl ester (4t").

This compound was prepared from 4A and 40% aq. methylamine: NMR (CDCl$_3$) δ0.80 (d, J=6.5 Hz, CHCH$_3$), 1.36 & 1.39 [2 s, C(OCH$_3$)(CH$_3$)$_2$], 1.46, 1.48 & 1.70 (3 s, tBu), 2.10 (s, OAc), 2.78 (d, C$\underline{H_3}$NH), 3.24 (s, OCH$_3$), 4.05 (s, C$_4$—OH), 4.21 (br s, H-7), 4.66 (m, NH), 4.98 (br s, =CH$_2$), 5.06 (s, H-3), 5.14 (d, C$\underline{H}$OAc), 6.24 (br s, H-6), 7.14–7.30 (m, ArH).

EXAMPLE 92

IA-C6-Methylaminocarbonyl Carbamate (5t").

This compound was obtained as a white fluffy material from its precursor, 4t", and was purified by reversed-phase HPLC: NMR (CD$_3$OD) δ0.86 (d, J=6.5 Hz, CHC$\underline{H}_3$), 2.10 (s, OAc), 2.69 (s, CH$_3$NH), 4.06 (d, H-7), 5.08 (d, C$\underline{H}$OAc), 5.26 (s, H-3), 6.17 (d, H-6), 7.13–7.30 (m, ArH); MS (Neg. FAB) m/z 594 (M–H)$^+$.

Anal. Calc. for C$_{27}$H$_{33}$NO$_{14}$.1.2 H$_2$O: C, 52.55; H, 5.78; N, 2.27. Found: C, 52.69; H, 5.77; N, 2.01.

EXAMPLE 93

IA-C6-N,N-Dimethylaminocarbonyl Carbamate-7-MME-tris-t-butyl ester (4u").

This compound was prepared from 4A and 40% aq. dimethylamine: NMR (CDCl$_3$) δ0.81 (d, J=6.5 Hz, CHC$\underline{H}_3$), 1.34 & 1.39 [2 s, C(OCH$_3$)(CH$_3$)$_2$], 1.44, 1.48 & 1.70 (3 s, tBu), 2.10 (s, OAc), 2.87 & 2.91 [2 s, (CH$_3$)$_2$N], 3.24 (s, OCH$_3$), 4.06 (s, C$_4$—OH), 4.21 (d, H-7), 4.98 (br s, =CH$_2$), 5.08 (s, H-3), 5.15 (d, C$\underline{H}$OAc), 6.28 (d, H-6), 7.14–7.30 (m, ArH).

IA-C6-N,N-Dimethylaminocarbonyl Carbamate (5u").

This compound was obtained as a white fluffy material from its precursor, 4u", and was purified by reversed-phase HPLC: NMR (CD$_3$OD) δ0.86 (d, J=6.5 Hz, CHC$\underline{H}_3$), 2.10 (s, OAc), 2.86 & 2.90 [2 s, (CH$_3$)$_2$N], 4.06 (d, J=2.5 Hz, H-7), 5.08 (d, J=5.0 Hz, C$\underline{H}$OAc), 5.24 (s, H-3), 6.07 (d, J=2.5 Hz, H-6), 7.13–7.30 (m, ArH); MS (Neg. FAB) m/z 608 (M–H)$^+$.

Anal. Calc. for C$_{28}$H$_{35}$NO$_{14}$.1.6 H$_2$O: C, 52.71; H, 6.03; N, 2.20. Found: C,.53.00; H, 5.69; N, 1.92.

EXAMPLE 94

IA-C6-Ethylaminocarbonyl Carbamate-7-MME-tris-t-butyl ester (4v").

This compound was prepared from 4A and 70% aq. ethylamine: NMR (CDCl$_3$) δ0.81 (d, J=6.5 Hz, CHCH$_3$), 1.12 (t, J=7.0 Hz, CH$_3$CH$_2$), 1.36 & 1.38 [2 s, C(OC$\underline{H}_3$)(CH$_3$)$_2$], 1.46, 1.47 & 1.69 (3 s, tBu), 2.09 (s, OAc), 3.25 (s, OC$\underline{H}_3$), 4.05 (s, C$_4$—OH), 4.21 (br s, H-7), 4.68 (m, NH), 4.98 (br s, =CH$_2$), 5.06 (s, H-3), 5.14 (d, C$\underline{H}$OAc), 6.24 (br s, H-6), 7.14–7.32 (m, ArH).

EXAMPLE 95

IA-C6-Ethylaminocarbonyl Carbamate (5v").

This compound was obtained as a white fluffy material from its precursor and was purified by reversed-phase HPLC: NMR (CD$_3$OD) δ0.86 (d, J=6.5 Hz, CHCH$_3$), 1.10 (t, J=7.0 Hz, CH$_3$CH$_2$), 2.09 (s, OAc), 3.12 (m, CH$_3$CH$_2$NH), 4.06 (br s, H-7), 5.08 (d, C$\underline{H}$OAc), 5.26 (s, H-3), 6.19 (d, H-6), 7.14–7.31 (m, ArH); MS (Neg. FAB) m/z 608 (M–H)$^+$.

Anal. Calc. for C$_{28}$H$_{35}$NO$_{14}$.1.6 H$_2$O: C, 52.69; H, 6.03; N, 2.20. Found: C, 52.85; 11, 5.83; N, 2.06.

EXAMPLE 96

IA-C6-(2-Dimethylamino)ethylaminocarbonyl Carbamate-7-MME-tris-t-butyl ester (4w")

NMR (CDCl$_3$) δ0.80 (d, J=7.0 Hz, CHC$\underline{H}_3$), 1.36 & 1.38 [2 s,(CH$_3$)$_2$C], 1.47, 1.48 & 1.69 (3 s, tBu), 2.09 (s, OAc), 2.17 [s, NH(CH$_3$)$_2$], 3.24 (s, CH$_3$O), 4.04 (s, C$_4$ OH), 4.20 (b d, H-7), 4.96 (b s, =CH$_2$) 5.04 (s, H-3), 5.14 (d, J=5.0 Hz, C$\underline{H}$OAc), 5.28 (m, NH), 6.22 (b d, H-6), 7.11–7.33 (m, ArH).

EXAMPLE 97

IA-C6-(2-Dimethylamino)ethylaminocarbonyl Carbamate (5w").

NMR (CD$_3$OD) δ0.87 (d, J=7.0 Hz CHCH$_3$), 2.12 (s, OAc), 2.92 [s, N(CH$_3$)$_2$], 4.14 (d, J=2.0 Hz, H-7), 4.99 & 5.03 (2 s, 2H), 5.08 (d, J=5.0 Hz, C$\underline{H}$OAc), 5.24 (s, H-3), 6.21 (b d, H-6)$_{7.08–7.40}$ (m, ArH). MS (FAB–) m/z 651.

EXAMPLE 98

IA-C6-(2-Isopropylamino)ethylaminocarbonyl Carbamate-7-MME-tris-t-butyl ester (4x").

NMR (CDCl$_3$) δ0.80 (d, J=7.0 Hz, CHC$\underline{H}_3$), 1.02 [m, CH(CH$_3$)$_2$], 1.36 & 1.39 [2 s,(CH$_3$)$_2$C], 1.46, 1.48 & 1.69 (3 s, tBu), 2.09.(s, OAc), 3.24 (s, CH$_3$O), 4.05 (s, C$_4$ OH), 4.21 (d, J=2.0 Hz H-7), 4.98 (b s, =CH$_2$)$_{5.05}$ (s, H-3), 5.15 (d, J=5.0 Hz, C$\underline{H}$OAc), 6.24 (b d, H-6), 7.13–7.32 (m, ArH).

EXAMPLE 99

IA-C6-(2-Isopropylamino)ethylaminocarbonyl Carbamate (5x").

NMR (CD$_3$OD) δ0.87 (d, J=7.0 Hz CHCH$_3$), 1.36 [d, J=7.0 Hz CH(CH$_3$)$_2$], 2.13 (s, OAc), 4.12 (d, J=2.0 Hz, H-7), 4.99 & 5.03 (2 s, 2H), 5.10 (d, J=5.0 Hz, C$\underline{H}$OAc), 5.25 (s, H-3), 6.20 (b d, H-6) 7.07–7.37 (m, ArH). MS (FAB–) m/z 665.

EXAMPLE 100

IA-C6-n-Propylaminocarbonyl Carbamate-7-MME-tris-t-butyl ester (4y").

A solution of diol, 3a, (280 mg, 0.359 mM), 1,1 carbonyl diimidazole (120 mg, 0.76 mM) in toluene (1 mL) was stirred at 25° C. for 3.5 h. then propylamine (287 mg, 4.86 mM) was added. After 24 h. the mixture was filtered and concentrated to dryness and chromatographed on a prepTLC (3:1 hexane/ethylacetate) to afford the blocked carbamate: NMR (400 MHz, CD$_3$OD) δ0.86 (d, J=6.5 Hz, CHC$\underline{H}_3$), 1.5 (m, 2H), 1.53 (s, tBu), 1.75 (s, 2tBu), 2.16 (s, 3H C$\underline{H}_3$CO), 2.02–2.85 (m, 9H), 3.04 (t, C$\underline{H}_2$NH), 4.11 (s, C4—OH), 4.26 (bs, C7-H), 4.61 (d, J=8 Hz, NH), 4,96, 5.04 (2s, =CH$_2$), 5.13 (s, C-3H), 5.20 (d, J=5 Hz, C$\underline{H}$OAc), 6.29 (bs, C6-H), 7.15–7.27 (m, 5H).

EXAMPLE 101

IA-C6-n-Propylaminocarbonyl Carbamate (5y").

To a solution of the blocked carbamate, 4y", (270 mg, 0.312 mM) in CH$_2$Cl$_2$ (3 mL) was added trifluoroacetic acid (1 mL) and the mixture was allowed to stand at room temperature for 16 h. The solvent was removed in vacuo and the residue was diluted with toluene and concentrated in vacuo. The solid residue was lyophilized from benzene to afford the title compound as a white solid: NMR (400 MHz, CDCl$_3$) δ0.84 (d, 3H), 0.89 (t, 3H), 1.48 (m, 2H), 2.1 (s, 3H CH$_3$CO), 2.02–2.75 (m, 9H), 3.04 (t, C$\underline{H}_2$NH), 4.06 (d, J=2 Hz, 1H), 4.96, 5.02 (2s, =CH$\underline{H}_2$), 5.06 (d, J=5 Hz, C$\underline{H}$OAc), 6.19 (d, J=2 Hz, 1H), 7.15–7.27 (m, 5H). MS (FAB-neg), m/e 622 [M–H].

EXAMPLE 102

IA-C6-Isopropylaminocarbonyl Carbamate-7-MME-tris-t-butyl ester (4z").

A solution of diol, 3a, (125 mg, 0.160 mM), 1,1 carbonyl diimidazole (52 mg, 0.32 mM) in toluene (1 mL) was stirred at 25° C. for 3.5 h. then isopropylamine (95 mg, 1.6 mM) was added. After 96 h. the mixture was filtered and concentrated to dryness and chromatographed on a prepTLC (3:1 hexane/ethylacetate) affording the blocked carbamate m.p. 165°–168° C. ($CH_2Cl_2$/hexane): NMR (400 MHz, $CD_3OD$) δ0.86 (d, J=6.5 Hz, CHC$\underline{H}_3$), 1.2 (m, 6H), 1.53 (s, tBu), 1.75 (s, 2tBu), 2.16 (s, 3H C$\underline{H}_3$CO), 2.02–2.85 (m, 9H), 3.30 (s, C$\underline{H}_3$O), 3.85 (m, $(CH_3)_2$C$\underline{H}$NH), 4.11 (s, $C_4$—OH), 4.26 (bs, C-7H), 4.61 (d, J=8 Hz, NH), 5.03, 5.05 (2s, =C$\underline{H}_2$), 5.13 (s, C3-H), 5.20 (d, J=5 Hz, C$\underline{H}$OAc), 6.29 (bs, C6-H), 7.15–7.27 (m, 5H).

Anal. Calc. for $C_{45}H_{69}O_{15}N$: C,62.55; H,8.05 N,1,62; Found: C,62.37; H,7.89; N,1.90.

EXAMPLE 103

IA-C6-Isopropylaminocarbonyl Carbamate (5z″).

To a solution of the blocked carbamate, 4z″, (820 mg, 0.964 mM) in $CH_2Cl_2$ (10 mL) was added trifluoroacetic acid (3 mL) and the mixture was allowed to stand at room temperature for 16 h. The solvent was removed in vacuo and the residue was diluted with toluene and concentrated in vacuo. The solid residue was lyophilized from benzene to afford the title compound as a white solid: NMR (400 MHz, $CD_3OD$) δ0.84 (d, 3H), 1.1 (m, 6H), 2.1 (s, 3H $CD_3CO$), 2.02–2.75 (m, 9H), 3.70 (m, 1H $(CH_3)_2$C$\underline{H}$NH), 4.06 (d, J=2 Hz, 1H), 4.96, 5.02 (2s, =C$\underline{H}_2$), 5.06 (d, J=5 Hz, C$\underline{H}$OAc), 5.25 (s, C-3H), 6.19 (d, J=2 Hz, 1H), 7.15–7.27 (m, 5H). MS (FAB-neg), m/e 622 [M–H]. $[a]_D$=+5.1 (c=1, $CH_3OH$).

Anal. Calc. for $C_{29}H_{37}O_{14}N.0.5\ H_2O$: C,55.06; H,6.05; N,2.21; Found: C,54.91; H,5.80; N2.05.

EXAMPLE 104

IA-C6-Cyclopropylaminocarbonyl Carbamate-7-MME-tris-t-butyl ester (4a‴).

This compound was prepared from 4A and cyclopropylamine: NMR ($CDCl_3$) δ0.39–0.56 & 0.69–0.78 (2 m, $CH_2CH_2$ cyclic), 0.80 (d, J=6.5 Hz, CHC$\underline{H}_3$), 1.35 & 1.38 [2 s C($OCH_3$)$(CH_3)_2$], 1.45, 1.46 & 1.69 (3 s, tBu), 2.09 (s, OAc), 3.24 (s, $OCH_3$), 4.04 (s, $C_4$—OH), 4.19 (br s, H-7), 4.89 (br s, NH), 4.86–4.88 (=C$\underline{H}_2$), 5.05 (s H-3), 5.14 (d, C$\underline{H}$OAc), 6.22 (br s, H-6), 7.12–7.32 (m, ArH).

EXAMPLE 105

IA-$C_6$-Cyclopropylaminocarbonyl Carbamate (5a‴)

This compound was obtained as a white fluffy material from its precursor, 4a‴, and was purified by reversed-phase HPLC: NMR ($CD_3OD$) δ0.38–0.50 & 0.58–0.69 (2 m, $CH_2CH_2$ cyclic), 0.84 (d, J=6.5 Hz, CHC$\underline{H}_3$), 2.10 (s, OAc), 3.97 (s, $C_4$—OH), 4.05 (br s, H-7), 5.06 (d, C$\underline{H}$OAc), 5.25 (s, H-3), 6.19 (br s, H-6), 7.15–7.30 (m, ArH); MS (Neg. FAB) m/z 620 (M–H)$^+$.

Anal. Calc. for $C_{29}H_{35}NO_{14}.1.1\ H_2O$: C, 54.29; H, 5.85; N, 2.18. Found: C, 54.44; H, 5.67; N, 2.03.

EXAMPLE 106

IA-C6-Butylaminocarbonyl Carbamate-7-MME-tris-t-butyl ester (4b‴).

NMR ($CDCl_3$) δ0.79 (d, J=7.0 Hz, CHC$\underline{H}_3$), 0.90 (t, J=7.0 Hz, $CH_2CH_3$), 1.34 & 1.38 [2 s,$(CH_3)_2$C], 1.45, 1.47 & 1.68 (3 s, tBu), 2.09 (s, OAc), 3.14 (m, C$\underline{H}_2$NH), 3.24 (s, $CH_3O$), 4.04 (s, $C_4$ OH), 4.19 (b d, H-7),4.66 (m, NH), 4.97 (b s, =C$\underline{H}_2$), 5.04 (s, H-3), 5.13 (d, J=5.0 Hz, C$\underline{H}$OAc), 6.21 (b d, H-6), 7.10–7.30 (m, ArH).

EXAMPLE 107

IA-C6-Butylaminocarbonyl Carbamate (5b‴).

NMR ($CD_3OD$) δ0.86 (d, J=7.0 Hz CHC$\underline{H}_3$),0.92 (t, J=7.0 Hz $CH_2CH_3$), 1.40 (m,4H), 2.10 (s, OAc), 3.09 (b t, $CH_2$NH), 4.07 (d, J=2.0 Hz, H-7), 4.99 & 5.03 (2 s, 2H), 5.09 (d, J=5.0 Hz, C$\underline{H}$OAc), 5.26 (s, H-3), 6.18 (b d, H-6), 7.04–7.36 (m, ArH). MS (FAB–) m/z 636.

EXAMPLE 108

IA-C6-Isobutylaminocarbonyl Carbamate-7-MME-tris-t-butyl ester (4c‴).

This compound was prepared from 4A and isobutylamine: NMR ($CDCl_3$) δ0.80 (d, J=6.5 Hz, CHC$\underline{H}_3$), 0.90 [d, J=6.5 Hz, $(CH_3)_2$CH], 1.36 & 1.39 [2 s, C($OCH_3$)$(CH_3)_2$], 1.47, 1.48 & 1.70 (3 s, tBu), 2.10 (s, OAc), 3.25 (s, $OCH_3$), 4.06 (s, $C_4$—OH), 4.23 (br s, H-7), 4.75 (t, J=5.5 Hz, NH), 4.99 (br s, =C$\underline{H}_2$), 5.06 (s, H-3), 5.16 (d, J=5.0 Hz, C$\underline{H}$OAc), 6.24 (br s, H-6), 7.13–7.33 (m, ArH).

EXAMPLE 109

IA-C6-Isobutylaminocarbonyl Carbamate (5c‴).

This compound was obtained as a white fluffy material from its precursor, 4c‴, and was purified by reversed-phase HPLC: NMR ($CD_3OD$) δ0.85 (d, J=6.5 Hz, CHC$\underline{H}_3$), 0.89 [d, J=6.5 Hz, $(CH_3)_2$CH], 2.10 (s, OAc), 4.07 (d, J=1.0 Hz, H-7), 5.07 (d, J=5.0 Hz, C$\underline{H}$OAc), 5.26 (s, H-3), 6.19 (d, J=1.0 Hz, H-6), 7.06–7.30 (m, ArH); MS (Neg. FAB)m/z 636 (M–H)$^+$.

EXAMPLE 110

IA-C6-(R)-sec-Butylaminocarbonyl Carbamate-7-MME-tris-t-butyl ester (4d‴).

This compound was prepared from 4A and (R)-(–)-sec-butylamine: NMR ($CDCl_3$) δ0.80 (d, J=6.5 Hz, CHC$\underline{H}_3$), 0.88 (t, J=7.0 Hz, $CH_3CH_2$), 1.08 (d, J=6.5 Hz, C$\underline{H}_3$CHNH), 1.35 & 1.38 [2 s, C($OCH_3$)$(CH_3)_2$], 1.46 (6H) & 1.69 (3H) (2 s, tBu), 2.09 (s, OAc), 3.24 (s, $OCH_3$), 3.62 (m, $CH_3$C$\underline{H}$NH), 4.05 (s, $C_4$—OH), 4.21 (br s, H-7), 4.50 (d, NH), 4.98 (br s, =C$\underline{H}_2$), 5.05 (s, H-3), 5.15 (d, J=5.0 Hz, C$\underline{H}$OAc), 6.23 (br s, H-6), 7.12–7.32 (m, ArH).

EXAMPLE 111

IA-C6-(R)-sec-Butylaminocarbonyl Carbamate (5d‴).

This compound was obtained as a white fluffy material from its precursor, 4d‴, and was purified by reversed-phase HPLC: NMR ($CD_3OD$) δ0.84 (d, J=6.5 Hz, CHC$\underline{H}_3$), 0.89 (t, J=7.0 Hz, $(CH_3CH_2)$, 1.08 (d, J=6.5 Hz, C$\underline{H}_3$CHNH), 2.09 (s, OAc), 3.49 (m, $CH_3$C$\underline{H}$NH), 4.06 (d, J=2.0 Hz, H-7), 5.07 (d, J=5.0 Hz, C$\underline{H}$OAc), 5.25 (s, H-3), 6.18 (d, J=2.0 Hz, H-6), 7.05–7.30 (m, ArH); MS (Neg. FAB) m/z 636 (M–H)$^+$.

EXAMPLE 112

IA-C6-(S)-sec-Butylaminocarbonyl Carbamate-7-MME-tris-t-butyl ester (4e‴).

This compound was prepared from 4A and (S)-(+)-sec-butylamine: NMR ($CDCl_3$) δ0.81 (d, J=6.5 Hz, CHC$\underline{H}_3$), 0.89 (t, J=7.0 Hz, $CH_3CH_2$), 1.11 (d, J=6.5 Hz, C$\underline{H}_3$CHNH), 1.34 & 1.39 [2 s, C($OCH_3$)$(CH_3)_2$], 1.47 (6H) & 1.70 (3H) (2 s, tBu), 2.10 (s, OAc), 3.25 (s, $OCH_3$), 3.60 (m, $CH_3$C$\underline{H}$NH), 4.07 (s, $C_4$—OH), 4.22 (br s, H-7), 4.54 (d, NH), 4.99 (br s, =C$\underline{H}_2$), 5.06 (s, H-3), 5.15 (d J=5.0 Hz, C$\underline{H}$OAc), 6.24 (br s, H-6), 7.13–7.33 (m, ArH).

EXAMPLE 113

IA-C6-(S)-sec-Butylaminocarbonyl Carbamate (5e''').

This compound was obtained as a white fluffy material from its precursor, 4e''', and was purified by reversed-phase HPLC: NMR (CD$_3$OD) δ0.84 (d, J=6.5 Hz, CHCH$_3$), 0.88 (t, J=7.0 Hz, CH$_3$CH$_2$), 1.09 (d, J=6.5 Hz, CH$_3$CHNH), 2.10 (s, OAc), 3.49 (m, CH$_3$CHNH), 4.06 (d, J=2.0 Hz, H-7), 5.07 (d, J=5.0 Hz, CHOAc), 5.26 (s, H-3), 6.19 (d, J=2.0 Hz, H-6), 7.05–7.30 (m, ArH); MS (Neg. FAB) m/z 636 (M–H)$^+$.

EXAMPLE 114

IA-C6-[3-(α-Butyl)octyloxy]-1-propylaminocarbonyl Carbamate-7-MME-tris-t-butyl ester (4f''').

This compound was prepared from 4A and 3-(α-butyl)octyloxy-1-propylamine: NMR (CDCl$_3$) δ0.80 (d, J=6.5 Hz, CHCH$_3$), 0.88 & 0.89 (2 t, J=7.0 Hz, 2 CH$_2$CH$_3$), 1.35 & 1.38 [2 s, C(OCH$_3$)(CH$_3$)$_2$], 1.45, 1.46 & 1.68 (3 s, tBu), 2.10 (s, OAc), 3.24 (s, OCH$_3$), 4.04 (s, C$_4$—OH), 4.20 (br s, H-7), 4.95 (m, NH), 4.99 (br s, =CH$_2$), 5.16 (d, J=5.0 Hz, CHOAc), 6.25 (br s, H-6), 7.15–7.30 (m, ArH).

EXAMPLE 115

IA-C6-[3-(α-Butyl)octyloxy]-1-propylaminocarbonyl Carbamate (5f''').

This compound was obtained as a white fluffy material from its precursor, 4f''': NMR (CD$_3$OD) δ0.86 (d, J=6.5 Hz, CHCH$_3$), 0.90 (t, J=7.0 Hz, 2 CH$_2$CH$_3$), 2.10 (s, OAc), 3.18 (br t, CH$_2$NHCO), 4.07 (d, H-7), 4.99–5.03 (=CH$_2$), 5.09 (d, J=5.0 Hz, CHOAc), 5.26 (s, H-3), 6.18 (d, H-6), 7.15–7.30 (m, ArH); MS (FAB) m/z 830 (M+Na)$^+$, 852 (M+2 Na)$^+$, 874 (M+3 Na)$^+$.

EXAMPLE 116

IA-C6-(3-Dodecyloxy)propylaminocarbonyl Carbamate-7-MME-tris-t-butyl ester (4g''').

This compound was prepared from 4A and 3-dodecyloxypropylamine: NMR (CDCl$_3$) δ0.80 (d, J=6.5 Hz, CHCH$_3$), 0.88 (t, J=7.0 Hz, CH$_2$CH$_3$), 1.26 [br s, (CH$_2$)$_n$], 1.35 & 1.38 [2 s, C(OCH$_3$)(CH$_3$)$_2$], 1.46, 1.47 & 1.69 (3 s, tBu), 2.10 (s, OAc), 3.24 (s, OCH$_3$), 3.36 & 3.42 (2 t, CH$_2$OCH$_2$), 4.04 (s, C$_4$—OH), 4.19 (br s, H-7), 4.94 (m, NH), 4.97 (br s, =CH$_2$), 5.04 (s, H-3), 5.14 (d, J=5.0 Hz, CHOAc), 6.23 (br s, H-6), 7.14–7.30 (m, ArH).

EXAMPLE 117

IA-C6-(3-Dodecyloxy)propylaminocarbonyl Carbamate (5g''').

This compound was obtained as a white solid from its precursor, 4g''': NMR (CD$_3$OD) δ0.85 (d, J=6.5 Hz, CHCH$_3$), 1.28 [br s, (CH$_2$)$_n$], 2.09 (s, OAc), 3.17 (br t, CH$_2$NHCO), 3.40 & 3.44 (2 t, CH$_2$OCH$_2$), 4.05 (br s, H-7), 4.98–5.02 (=CH$_2$), 5.07 (d, J=5.0 Hz, CHOAc), 5.25 (s, H-3), 6.17 (br s, H-6), 7.14–7.30 (m, ArH); MS (FAB) m/z 830 (M+Na)$^+$, 852 (M+2 Na)$^+$, 874 (M+3 Na)$^+$.

EXAMPLE 118

IA-C6-(4-methoxy)benzylaminocarbonyl Carbamate-7-MME-tris-t-butyl ester (4h''').

A solution of diol, 3a, (100 mg, 0.128 mM), 1,1 carbonyl diimidazole (42 mg, 0.256 mM) in toluene (1 mL) was stirred at 25° C. for 3.5 h., then 4-methoxybenzylamine (100 mg, 0.75 ml) was added. After 24 h. the mixture was filtered and concentrated to dryness and chromatographed on a prepTLC (3:1 hexane/ethyl-acetate) to provide the blocked carbamate: NMR (200 MHz, CDCl$_3$) δ0.82 (d, J=6.5 Hz, CHCH$_3$), 1.4, 1.46, 1.69 (3s, 3t-Bu), 2.09 (s, 3H C$_3$ HCO), 3.80 (s, CH$_3$O), 4.07 (s, C4-OH), 4.23 (bs, C7-H), 4.31 (m, CH$_2$NH), 4.90 (m, NH), 5.01 (brs, =CH$_2$), 5.08 (s C3-H), 5.16 (d, J=5 Hz, CHOAc), 6.32 (bs, C$_6$-H), 6.88 (d, J=9, 2ArH), 7.15–7.27 (m, 7ArH).

EXAMPLE 119

IA-C6-(4-methoxy)benzylaminocarbonyl Carbamate (5h''').

To a solution of the blocked carbamate, 4h''', (60 mg) in CH$_2$Cl$_2$ (3 mL) was added trifluoroacetic acid (1 mL) and the mixture was allowed to stand at room temperature for 16 h. Work up as usual to give the product: NMR (400 MHz, CD$_3$OD) δ0.84 (d, J=6.5, 3H), 2.09 (s, 3H CH$_3$CO), 2.02–2.75 (m, 9H), 3.74 (s, CH$_3$O), 4.15 (d, J=2Hz, C-7H), 4.98 (d, 3H), 5.06 (d, J=5 Hz, CHOAc), 6.22 (d, J=2 Hz, C6-H), 6.83, (d, J=8.5, 2ArH), 7.15–7.24 (m, 7H). MS (EI), m/e 725 [M+Na]$^+$.

EXAMPLE 120

IA-C6-(4-methylsulfonyl)benzylaminocarbonyl Carbamate-7-MME-tris-t-butyl ester (4i''').

A solution of diol, 3a, (100 mg, 0.128 mM), 1,1-carbonyl diimidazole (42 mg, 0.256 mM) in toluene (1 mL) was stirred at 25° C. for 3.5 h., then 4-methoxybenzylamine (200 mg, 0.9 mM) was added. After 24 h. the mixture was filtered and concentrated to dryness and chromatographed on a prepTLC (3:1 hexane/ethylacetate) to provide the blocked carbamate: NMR (200 MHz, CDCl$_3$) δ0.80 (d, J=6.5 Hz, CHCH$_3$), 1.4, 1.46, 1.66 (3s, 3t-Bu), 2.08 (s, 3H C H$_3$CO), 3.02 (s, CH$_3$SO$_2$), 4.05 (s, C4-OH), 4.21 (bs, C7-H), 4.44 (m, CH$_2$NH), 4.97 (brs, =CH$_2$), 5.01 (s, C3-H), 5.12 (d, J=5 Hz, 1H), 5.18 (t, NH), 6.28 (d, J=2 Hz, C6-H), 7.10–7.90 (m, 7ArH).

EXAMPLE 121

IA-C6-(4-methylsulfonyl)benzylaminocarbonyl Carbamate (5i''').

To a solution of the blocked carbamate, 4i''', (90 mg) in CH$_2$Cl$_2$ (1 mL) was added trifluoroacetic acid (350 μL) and the mixture was allowed to stand at room temperature for 16 h. The reaction was worked up as usual to provide the product: NMR (400 MHz, CD$_3$OD) δ0.85 (d, J=6.5, 3H), 2.09 (s, 3H CH$_3$CO), 2.02–2.75 (m, 9H), 3.08 (s, C H$_3$SO$_2$), 4.09 (d, J=2 Hz, 1H), 4.38 (m, CH$_2$NH), 5.05 (d, J=5 Hz, 1H), 6.25 (d, J=2 Hz, 1H), 7.13–7.24 (m, 5ArH), 7.53 (d, J=8 Hz, 2ArH), 7.88 (d, J=8 Hz, 2ArH). MS (FAB-neg), m/e 748 [M–H].

EXAMPLE 122

IA-C6-(2-Phenyl)ethylaminocarbonyl Carbamate-7-MME-tris-t-butyl ester (4j''').

This compound was prepared from 4A and 2-phenethylamine: NMR (CDCl$_3$) δ0.08 (d, CHCH$_3$), 1.35 & 1.39 [2 s, C(OCH$_3$)(CH$_3$)$_2$], 1.42, 1.46 & 1.69 (3 s, tBu), 2.09 (s, OAc), 3.24 (s, OCH$_3$), 4.04 (s, C$_4$—OH), 4.18 (br s, H-7), 4.71 (m, NH), 4.97 (br s, =CH$_2$), 5.05 (s, H-3), 5.14 (d, CHOAc), 6.24 (br s, H-6), 7.14–7.29 (m, ArH).

EXAMPLE 123

IA-C6-(2-Phenyl)ethylaminocarbonyl Carbamate (5j''').

This compound was obtained as a white fluffy material from its precursor, 4j''', and was purified by reversed-phase HPLC: NMR (CD$_3$OD) δ0.85 (d, J=6.5 Hz, CHCH$_3$), 2.09

(s, OAc), 2.75 (t, PhCH$_2$), 3.30 (m, CH$_2$NHCO), 4.02 (bs, H-7), 4.99–5.02 (=CH$_2$), 5.08 (d, J=5.0 Hz, CHOAc), 5.27 (s, H-3), 6.17 (bs, H-6), 7.14–7.29 (m, ArH); MS (Neg. FAB) m/z 684 (M–H)$^+$.

Anal. Calc. for C$_{34}$H$_{39}$NO$_{14}$: C, 59.56; H, 5.73, N, 2.04. Found: C, 59.84; H, 5.96; N, 1.94.

EXAMPLE 124

IA-C6-(2-Phenoxy)ethylaminocarbonyl Carbamate-7-MME-tris-t-butyl ester (4k''').

This compound was prepared from 4A and 2-phenoxyethylamine: NMR (CDCl$_3$) δ0.80 (d, CHCH$_3$), 1.34 & 1.38 [2 s, C(OCH$_3$)(CH$_3$)$_2$], 1.40, 1.47 & 1.69 (3 s, tBu), 2.09 (s, OAc), 3.23 (s, OCH$_3$), 3.57 (m, CH$_2$NHCO), 3.98 (t, PhO CH$_2$), 4.04 (s, C$_4$—OH), 4.21 (br s, H-7), 4.97 (br s, =CH$_2$), 5.04 (s, H-3), 5.14 (d, CHOAc), 5.19 (m, NH), 6.25 (br s, H-6), 6.80–6.99 (m, PhO), 7.13–7.34 (m, ArH).

EXAMPLE 125

IA-C6-(2-Phenoxy)ethylaminocarbonyl Carbamate (5k''').

This compound was obtained as a white fluffy material from its precursor, 4k''', and purified by reversed-phase HPLC: NMR (CD$_3$OD) δ0.84 (d, CHCH$_3$), 2.09 (s, OAc), 3.49 (m, CH$_2$NHCO), 4.01 (br t, PhOCH$_2$), 4.17 (d, H-7), 4.98–5.02 (=CH$_2$), 5.08 (d, J=5.0 Hz, CHOAc), 5.26 (s, H-3), 6.20 (d, H-6), 6.87–6.94 (m, PhO), 7.12–7.29 (m, ArH); MS (Neg. FAB) m/z 700 (M–H)$^+$.

Anal. Calc. for C$_{34}$H$_{39}$NO$_{15}$·2.2 H$_2$O: C, 55.15; H, 5.90, N, 1.89. Found: C, 55.34; H, 5.62; N, 1.76.

EXAMPLE 126

IA-C6-(8-Phenoxy)octylaminocarbonyl Carbamate-tris-t-butyl ester (4l''').

This compound was prepared from 4A and 8-phenoxyoctylamine in the presence of DBU. The crude product was purified by flash column chromatography (silica gel; hexanes-EtOAc, 85:15; v/v). This material (contaminated with an impurity) was treated with 70% HOAc to remove the 7-ketal protecting group. The partially blocked product was again purified by chromatography and had NMR (CDCl$_3$) δ0.81 (d, J=6.5 Hz, CHCH$_3$), 1.45, 1.49 & 1.62 (3 s, tBu), 2.10 (s, OAc), 3.20 (m, CH$_2$NHCO), 3.95 (t, PhOCH$_2$), 4.06 (br s, H-7), 4.07 (s, C$_4$—OH), 4.60 (br t, J=6.5 Hz, NH), 4.99 (br s, =CH$_2$), 5.06 (s, H-3), 5.13 (d, J=5.0 Hz, CHOAc), 5.91 (br s, H-6), 6.87–6.96 (m, PhO), 7.12–7.30 (m, ArH).

EXAMPLE 127

IA-C6-(8-Phenoxy)octylaminocarbonyl Carbamate (5l''').

This compound was obtained as a white fluffy material from its precursor, 4l''', and was purified by reversed-phase HPLC: NMR (CD$_3$OD) δ0.85 (d, CHCH$_3$), 2.10 (s, OAc), 3.08 (m, CH$_2$NHCO), 3.94 (t, PhOCH$_2$), 4.07 (d, J=2.0 Hz, H-7), 4.99–5.02 (=CH$_2$), 5.08 (d, J=5.0 Hz, CHOAc), 5.28 (s, H-3), 6.18 (d, J=2.0 Hz, H-6), 6.85–6.92 (m, PhO), 7.14–7.29 (m, ArH); MS (Neg. FAB)m/z 784 (M–H)$^+$.

Anal. Calc. for C$_{40}$H$_{51}$NO$_{15}$·H$_2$O: C, 59.80; H, 6.64, N, 1.74. Found: C, 59.81; H, 6.67; N, 1.70.

EXAMPLE 128

IA-C6-Adamantylmethylaminocarbonyl Carbamate-7-MME-tris-t-butyl ester (4m''').

According to the procedure described above a solution of diol, 3a, (100 mg, 0.128 mM), 1,1-carbonyl diimidazole (42.0 mg, 0.256 mmol) in toluene (1 mL,) was stirred at 25° C. for 3.5 h. then adamantylmethylamine (165 mg, 1.0 mmol) was added to provide the blocked Carbamate: NMR (200 MHz, CDCl$_3$) δ0.80 (d, 3H), 1.43 (s, adamantyl-C H$_2$), 1.66 (s, 3tBu), 2.07 (s, 3H CH$_3$CO), 3.23 (s, CH$_3$O), 4.05 (s, 1H), 4.21 (d, J=2 Hz, C-7H), 4.73 (t, J=5, NH), 4.99, 5.05 (2s, =CH$_2$), 5.16 (d, CHOAc), 6.24 (d, J=2 Hz, C-6H), 7.2 (m, 5H)

EXAMPLE 129

IA-C6-adamantylmethylaminocarbonyl Carbamate (5m''').

A solution of 4m''' (90 mg, 0.088 mmol) in CH$_2$Cl$_2$ (0.9 mL) was cooled to 0° C. and trifluoroacetic acid (0.25 mL) was added. The solution was then allowed to warm to room temperature and after 16 h the solvent was removed in vacuo. The residue was diluted with toluene and concentrated in vacuo. The solid residue was lyophilized from benzene to afford the title compound as a white solid: NMR (200 MHz, CDCl$_3$) δ0.84 (d, 3H), 1.43 (s, adamantyl-C H$_2$), 2.1 (s, CH$_3$CO), 2.02–2.75 (m, 9H), 4.06 (d, J=2 Hz, 1H), 4.96 (m, 3H), 5.02 (2s, =CH$_2$), 5.06 (d, J=5 Hz, C HOAc), 6.16 (d, J=2 Hz, 1H), 7.15–7.27 (m, 5H). MS (FAB-neg), m/e 728 [M–H].

Anal. Calc. for C$_{36}$H$_{51}$O$_{14}$N.2 H$_2$O: C,57.06; H,7.32; N,25; Found: C,57.37; H,7.49; N,1.90.

EXAMPLE 130

General Procedure for Preparation of C-6 Carbonates.

A solution of compound (3a) (100 m, 0.128 mmol) and 1,1'-carbonyldiimidazole (42 mg, 0.256 mmol) in dry toluene (0.5 mL) is stirred at room temperature for 5 h. The appropriate alcohol (0.64 mmol) and DBU (96 uL, 0.64 mmol) are added and the mixture is stirred at room temperature overnight. The appropriate carbonate (4) is purified by preparative TLC (hexanes-ethyl acetate; 7:3, v/v).

EXAMPLE 131

General Procedure for Deprotection of Carbonate 4.

A solution of C6-carbonate-7-MME-tris-t-butyl ester (4) (100 mg) in dry dichloromethane (3 mL) is treated with trifluoroacetic acid (1 mL) at room temperature overnight. The solution is evaporated to a residue, which is redissolved in toluene and concentrated to dryness. This process is repeated twice, and the product is dissolved in benzene and freeze-dried to give a white solid. The purity of the products is monitored by reversed-phase HPLC.

Examples of C$_6$ carbonates:

By procedures described for Examples 130 and 131, the following 6-position carbonates of (1S,3S,4S,5R,6R,7R)-1-[(4S)-acetoxy-3-methylene-5(R)-methyl-6-phenyl]hexyl-4,6,7-trihydroxy-6-O-(4(S),6(S)-dimethyl-2-octenoyl)-2,8-dioxabicyclo[3.2.1]octane 3,4,5-tricarboxylic acid (IA) were prepared.

EXAMPLE 132

IA-6-dodecyloxycarbonyl Carbonate (5x).

This compound was prepared from (3a) following Examples 130 and 131. NMR (CD$_3$OD) δ0.86 (d, J=6.5 Hz, CHCH$_3$), 0.88 (t, J=6.5 Hz, CH$_2$CH$_3$), 2.10 (s, OAc), 4.09 (d, J=1.5 Hz, H-7), 4.14 (t, J=6.2 Hz, CH$_2$OCOO), 4.96 & 5.01 (2 s, =CH$_2$), 5.08 (d, J=4.5 Hz, CHOAc), 5.22 (s, H-3), 6.18 (d, J=1.5 Hz, H-6), 7.14–7.30 (m, ArH); MS (FAB) m/z 773 (M+Na)$^+$, 795 (M+2 Na)$^+$, 817 (M+3 Na)$^+$ Anal. Calc. for C$_{38}$H$_{54}$O$_{15}$·2.15 H$_2$O: C, 57.81H, 7.44. Found: C, 57.89; H, 7.27.

EXAMPLE 133

IA-6-(11-phenoxy)undecyloxycarbonyl Carbonate (5y).

This compound was prepared from (3a). NMR (CD$_3$OD) δ0.86 (d, J=6.0 Hz, CHCH$_3$), 2.09 (s, OAc), 3.93 (t, J=6.2 Hz, PhOCH$_2$), 4.09–4.17 (m, H-7 & CH$_2$OCOO), 4.95 & 5.01 (2 s, =CH$_2$), 5.07 (d, J=4.5 Hz, CHOAc), 5.23 (s, H-3), 6.18 (br s, H-6), 6.84–6.91 & 7.13–7.29 (2 m, ArH); MS (FAB) m/z 850 (M+Na)$^+$, 872 (M+2 Na)$^+$, 894 (M+3 Na)$^+$. Anal. Calc. for C$_{43}$H$_{56}$O$_{16}$. 1.84 H$_2$O: C, 59.92; H, 6.98. Found: C, 59.76; H, 7.33.

EXAMPLE 134

IA-C6-Isopropyloxycarbonyl Carbonate-7-MME-tris-t-butyl ester (4n''').

This compound was prepared from 4A and isopropanol in the presence of DBU: NMR (CDCl$_3$) δ0.81 (d, J=6.5 Hz, CHCH$_3$), 1.25 & 1.26 [2 d, J=6.5 Hz, (CH$_3$)$_2$CH], 1.36 & 1.38 [2 s, C(OCH$_3$)(CH$_3$)$_2$], 1.46 (6H) & 1.67 (3H) (2 s, tBu), 2.09 (s, OAc), 3.23 (s, OCH$_3$), 4.09 (s, C$_4$—OH), 4.24 (d, H-7), 4.86 [m, (CH$_3$)$_2$CH], 4.96 (s, H-3), 4.96 (br s, =CH$_2$), 5.13 (d, J=5.0 Hz, CHOAc), 6.19 (d, H-6), 7.15–7.29 (m, ArH).

EXAMPLE 135

IA-C6-Isopropyloxycarbonyl Carbonate (5n''').

This compound was obtained as a solid mass from its precursor, 4n''', and was purified by reversed-phase HPLC: NMR (CD$_3$OD) δ0.86 (d, J=6.5 Hz, CHCH$_3$), 1.27 & 1.28 [2 d, J=6.5 Hz, (CH$_3$)$_2$CH], 2.10 (s, OAc), 4.08 (d, J=3.0 Hz, H-7), 5.06 (d, J=5.0 Hz, CHOAc), 5.22 (s, H-3), 6.17 (d, J=3.0 Hz, H-6), 7.12–7.30 (m, ArH); MS (Neg. FAB) m/z 623 (M+H)$^+$.

Anal. Calc. for C$_{29}$H$_{36}$O$_{15}$. 2.2 H$_2$O: C, 52.50; H, 6.13. Found: C, 52.58; H, 5.94.

EXAMPLE 136

IA-C6-Decyloxycarbonyl Carbonate-tris-t-butyl ester (4o''').

This compound was prepared from 4A and 1-decanol in the presence of DBU. The crude product was purified by flash column chromatography (silica gel; hexanes-EtOAc, 85:15; v/v). This material (contaminated with an impurity) was treated with 70% HOAc to remove the 7-ketal protecting group. The partially blocked product was again purified by chromatography: NMR (CDCl$_3$) δ0.83 (d, J=6.5 Hz, CHCH$_3$), 1.46, 1.49 & 1.63 (3 s, tBu), 2.11 (s, OAc), 4.11 (d, J=2.0 Hz, H-7), 4.18 (t, J=6.5 Hz, CH$_2$OCO), 4.97–5.0 (=CH$_2$), 5.01 (s, H-3), 5.11 (d, CHOAc), 5.97 (d, H-6), 7.13–7.31 (m, ArH).

EXAMPLE 137

IA-C6-Decyloxycarbonyl Carbonate (5o''').

This compound was obtained as a white fluffy material from its precursor, 4o''', and purified by reversed-phase HPLC: NMR (CD$_3$OD) δ0.87 (d, J=6.5 Hz, CHCH$_3$), 0.89 (t, CH$_2$CH$_3$), 2.10 (s, OAc), 4.12 (d, H-7), 4.15 (t, CH$_2$OCO), 4.97–5.02 (=CH$_2$), 5.25 (s, H-3), 6.19 (d, H-6), 7.14–7.29 (m, ArH); MS (FAB) m/z 745 (M+Na)$^+$, 767 (M+2 Na)$^+$, 789 (M+3 Na)$^+$ Anal. Calc. for C$_{36}$H$_{50}$O$_{15}$.1.5 H$_2$O: C, 57.63; H, 7.13. Found: C, 57.66; H, 7.06.

EXAMPLE 138

IA-C6-2-(((2-Butoxy)-2-ethoxy)-ethoxy)ethoxycarbonyl Carbonate-7-MME-tris-t-butyl ester (4p''').

This compound was prepared from 4A and triethylene glycol butyl ether in the presence of DBU: NMR (CDCl$_3$) δ0.82 (d, J=6.5 Hz, CHCH$_3$), 0.92 (t, J=7.0 Hz, CH$_3$CH$_2$), 1.36 & 1.38 [2 s, C(OCH$_3$)(CH$_3$)$_2$], 1.48, 1.49 & 1.68 (3 s, tBu), 2.10 (s, OAc), 3.23 (s, OCH$_3$), 3.44 (t, CCHCH$_2$), 4.07 (s, C$_4$-OH), 4.26 (d, J=2.0 Hz, H-7), 4.29 (t, CH$_2$OCO), 4.98 (=CH$_2$), 4.97 (s, H-3), 5.14 (d, CHOAc), 6.19 (d, J=2.0 Hz, H-6), 7.14–7.29 (m, ArH).

EXAMPLE 139

IA-C6-2-(((2-Butoxy)-2-ethoxy)-ethoxy)ethoxycarbonyl Carbonate (5p''').

This compound was obtained as a white fluffy material from its precursor, 4p''': NMR (CD$_3$OD) δ0.86 (d, J=6.5 Hz, CHCH$_3$), 0.92 (t, J=7.0 Hz, CH$_2$CH$_3$), 2.10 (s, OAc), 3.45 (t, CH$_2$O), 4.11 (d, J=2.0 Hz, H-7), 4.29 (m, CH$_2$OCO), 5.08 (d, J=5.0, CHOAc), 5.23 (s, H-3), 6.17 (d, J=2.0 Hz, H-6), 7.14–7.30 (m, ArH); MS (FAB) m/z 793 (M+Na)$^+$, 815 (M+2 Na)$^+$, 837 (M+3 Na)$^+$.

EXAMPLE 140

General Procedure for Preparation of C6 Ethers.

Sodium hydride (60% dispersion in mineral oil; 19.3 mg, 0.48 mmol) is added to a solution of (3a) (300 mg, 0.384 mmol) and the appropriate organic bromide (0.48 mmol) with tetra-n-butylammonium iodide (15 mg, 0.038 mmol) in dry DMF (1.5 mL), and the reaction mixture is stirred at room temperature for 7–16 h. The mixture is partitioned between ethyl ether and water. The aqueous layer is re-extracted twice with ethyl ether, and the combined ethereal extracts are washed with brine, dried, and evaporated to dryness. Two monoalkylated products, C-6 and C-4 ethers, the C-4,6 dialkylated product and the starting material are separated by preparative TLC (hexanes/ethyl acetate, 4:1; v/v). If the appropriate organic iodide was used, tetra-n-butylammonium iodide is omitted in the above reaction.

EXAMPLE 141

General Procedure for Deprotection of (4).

A solution of protected ether (4) (100 mg) in dry dichloromethane (3 mL) is treated with trifluoroacetic acid (1 mL) at room temperature overnight. The solution is evaporated to a residue, which is redissolved in toluene and concentrated to dryness. This process is repeated twice, and the product is dissolved in benzene and freeze-dried to give a white solid. The purity of the products is monitored by reversed-phase HPLC.

Examples of C6 ethers, C4-ethers and C4, C6 diethers: These compounds were prepared following Examples 140 and 141.

EXAMPLE 142

IA-6-(8-phenoxy)octyl Ether (5z).

NMR (CD$_3$OD) δ0.85 (d, J=7.5 Hz, CHCH$_3$), 1.37 [br s, (CH$_2$)$_n$], 2.09 (s, OAc), 3.35 & 3.68 (2 m, CH$_2$O), 3.94 (t, J=6.5 Hz, PhOCH$_2$), 4.08 (d, J=2.0 Hz, H-7), 4.89 (d, J=2.0 Hz, H-6), 4.98 & 5.04 (2 s, =CH$_2$), 5.09 (d, J=4.5 Hz, CHOAc), 5.13 (s, H-3), 6.85–6.91 & 7.12–7.30 (2 m, ArH); MS (FAB) m/z 765 (M+Na)$^+$.

EXAMPLE 143

IA-4-(8-Phenoxy)octyl Ether (5a').

NMR (CD$_3$OD) δ0.85 (d, J=7.0 Hz, CHCH$_3$), 2.08 (s, OAc), 3.81 (t, J=6.5 Hz, PhOCH$_2$), 4.04 (d, J=2.0 Hz, H-7), 5.01 & 5.05 (2 s, =CH$_2$), 5.09 (d, J=5.0 Hz, CHOAc), 5.20 (s, H-3), 5.23 (d, J=2.0 Hz, H-6), 6.85–6.93 & 7.14–7.30 (2 m, ArH); MS (FAB) m/z 765 (M+Na)$^+$.

EXAMPLE 144

C4,6-Bis-(8-Phenoxy)octyl Ether (5b').

NMR (CD$_3$OD) δ0.87 (d, J=7.0 Hz, CHCH$_3$), 2.10 (s, OAc), 3.92 & 3.97 (2 t, J=6.5 Hz, PhOCH$_2$), 4.05 (d, J=2.0 Hz, H-7), 5.00 & 5.06 (2 br s, =CH$_2$), 5.02 (d, J=2.0 Hz, H-6), 5.12 (d, J=5.0 Hz, CHOAc), 5.17 (s, H-3), 6.87–6.94 & 7.14–7.32 (2 m, ArH); MS (FAB) m/z 969 (M+NA)$^+$. Anal. Calc. for C$_{53}$H$_{70}$O$_{15}$: C, 67.21; H, 7.45. Found: C, 66.98; H, 7.54.

EXAMPLE 145

IA-6-(11-Phenoxy)undecyl Ether (5c').

NMR (CD$_3$OD) δ0.84 (d, J=6.0 Hz, CHCH$_3$), 2.08 (s, OAc), 3.54 & 3.66 (2 m, CH$_2$O), 3.92 (t, J=6.5 Hz, PhOCH$_2$), 4.05 (br s, H-7), 4.95 & 5.00 (2 s, =CH$_2$), 5.07 (d, J=4.5 Hz, CHOAc), 6.84–6.90 & 7.12–7.30 (2 m, ArH); MS (FAB) m/z 806 (M+Na)$^+$, 828 (M+2 Na)$^+$.

EXAMPLE 146

IA-4-(11-Phenoxy)undecyl Ether (5d').

NMR (CD$_3$OD) δ0.85 (d, J=6.5 Hz, CHCH$_3$), 2.09 (s, OAc), 3.92 & 4.06 (2 m, CH$_2$O), 3.93 (t, J=6.0 Hz, PhOCH$_2$), 4.02 (d, J=2.0 Hz, H-7), 5.00 & 5.04 (2 s, =CH$_2$), 5.11 (d, J=5.0 Hz, CHOAc), 5.18 (s, H-3), 5.23 (d, J=2.0 Hz, H-6), 6.86–6.93 & 7.14–7.30 (2 m, ArH); MS (FAB) m/z 806 (M+Na)$^+$, 828 (M+2 Na)$^+$, 850 (M+3 Na)$^+$. Anal. Calc. for C$_{42}$H$_{56}$O$_{14}$·1.35 H$_2$O: C, 62.35; H, 7.31. Found: C, 62.41; H, 7.17.

EXAMPLE 147

C4,6-Bis-(11-Phenoxy)undecyl Ether (5e').

MS (FAB) m/z 1052 (M+Na)$^+$, 1074 (M+2 Na)$^+$, 1096 (M+3 Na)$^+$.

EXAMPLE 148

IA-6-Tetradecyl Ether (5f').

NMR (CD$_3$OD) δ0.83–0.91 (m, 6-H), 1.27 [br s, (CH$_2$)$_x$], 2.09 (s, OAc), 3.54 & 3.67 (2 m, CH$_2$O), 4.06 (br s, H-7), 4.97 (s, 1H), 5.06 (s, 1H), 5.09 (m, 2H), 7.11–7.31 (m, ArH); MS (FAB) m/z 757 (M+Na)$^+$, 780 (M+2 Na)$^+$.

EXAMPLE 149

IA-6-Hexadecyl Ether (5g').

NMR (CD$_3$OD) δ0.84–0.96 (m, 6-H), 1.30 [br s, (CH$_2$)$_x$], 2.11 (s, OAc), 3.56 & 3.70 (2 m, CH$_2$O), 4.08 (br s, H-7), 4.98 (s, 1H), 5.04 (s, 1H), 5.12 (m, 2H), 7.12–7.34 (m, ArH); MS (FAB) m/z 785 (M+Na)$^+$, 808 (M+2 Na)$^+$.

EXAMPLE 150

IA-6-(2'-Phenyl)-benzyl Ether (5h')

$^1$H NMR (CD$_3$OD): δ0.85 (d, J=7.0 Hz, CHCH$_3$), 2.10.(s, OAc), 4.00 (br s, H-7), 4.42 & 4.62 (AB q J=10 Hz OCH$_2$Ar), 4.98 (br d 2H), 5.08 (br d 1H), 7.00–7.60 (m, ArH); MS (FAB) m/z 727 (M+Na)$^+$, 750 (M+2 Na)$^+$.

EXAMPLE 151

IA-C6-[10-(3,4-Dimethoxy)phenoxy]decyl Ether-7-MME-tris-t-butyl ester (4q''').

This compound was prepared from 3a and 10-(3,4-dimethoxy)phenoxydecyl bromide in the presence of tetra-n-butylammonium iodide: NMR (CDCl$_3$) δ0.81 (d, CHCH$_3$), 1.47 1.50 & 1.64 (3 s, tBu), 2.09 (s, OAc), 3.27 (s, OCH$_3$), 3.54 & 3.70 (2 m, CH$_2$O), 3.84 & 3.86 (2 s, 2 ArOCH$_3$), 3.89 (q, PhOCH$_2$), 3.98 (s, C$_4$—OH), 4.17 (br d, J=1.5 Hz, H-7), 4.70 (br d, J=1.5 Hz, H-6), 4.84 (s, H-3), 4.96 (br s, =CH$_2$), 5.16 (d, J=5.0 Hz, CHOAc), 6.39 [q, J=2.5 & 9.0 Hz, ArH$_6$ of C$_6$H$_3$(OCH$_3$)$_2$], 6.53 [d, J=2.5 Hz, ArH$_2$ of C$_6$H$_3$(OCH$_3$)$_2$], 6.78 [d, J=9.0 Hz, ArH$_5$ of C$_6$H$_3$(OCH$_3$)$_2$], 7.13–7.30 (m, ArH).

EXAMPLE 152

IA-C6-[10-(3,4-Dimethoxy)phenoxy]decyl Ether (5q''').

This compound was obtained as a white fluffy material from its precursor, 4q''': NMR (CD$_3$OD) δ0.85 (d, CHCH$_3$), 2.10 (s, OAc), 3.54 & 3.68 (2 m, CH$_2$O), 3.76 & 3.79 (2 s, 2 ArOCH$_3$), 3.89 (t, J=6.5 Hz, PhOCH$_2$), 4.07 (d, J=2.0 Hz, H-7), 4.98 & 5.03 (=CH$_2$), 5.09 (d, CHOAc), 5.13 (s, H-3), 6.41 [q, J=2.5 & 9.0 Hz, ArH$_6$ of C$_6$H$_3$(OCH$_3$)$_2$], 6.54 [d, J=2.5 Hz, ArH$_2$ of C$_6$H$_3$(OCH$_3$)$_2$], 6.83 [d, J=9.0 Hz, ArH$_5$ of C$_6$H$_3$(OCH$_3$)$_2$], 7.13–7.30 (m, ArH); MS (FAB) m/z 853 (M+Na)$^+$, 875 (M+2 Na)$^+$, 897 (M+3 Na)$^+$.

EXAMPLE 153

IA-C4-Propyl Ether-7-MME-tris-t-butyl ester (4s''').

NMR (CDCl$_3$) δ0.83 (d, J=7.0 Hz, CHCH$_3$), 0.93 (t, J=7.0 Hz, CH$_2$CH$_3$), 1.40 & 1.46 [2 s, (CH$_3$)$_2$C], 1.48, 1.51 & 1.58 (3 s, tBu) 2.12 (s, OAc), 3.28 (s, CH$_3$O), 3.64 & 3.85 (2 m, CH$_2$O), 4.01 (d, J=2.0 Hz, H-7), 4.84 (s, H-3), 4.95 (b d, =C$_2$), 5.14 (d, J=5.0 Hz, CHOAc), 5.18 (m, H-6), 7.11–7.34 (m, ArH).

EXAMPLE 154

IA-C4-Propyl Ether (5s''').

NMR (CD$_3$OD) δ0.79–0.95 (m, 6H), 1.57 (m, CH$_2$CH$_2$CH$_3$), 2.11 (s, OAc), 3.85 & 4.03 (2 m, CH$_2$O), 4.04 (d, J=2.0 Hz H-7), 4.99 (s, 1H), 5.03 (s, 1H), 5.09 (d, J=5.0 Hz CHOAc), 5.19 (s, H-3), 5.23 (d, J=2.0 Hz, H-6), 7.09–7.37 (m, ArH); MS (FAB–) m/z 579.

EXAMPLE 155

IA-C6-Propyl Ether-7-MME-tris-t-butyl ester (4r''').

NMR (CDCl$_3$) δ0.81 (d, J=7.0 Hz, CHCH$_3$), 0.92 (t, J=7.0 Hz, CH$_2$CH$_3$), 1.40 & 1.43 [2 s, (CH$_3$)$_2$C], 1.47 1.50 & 1.65 (3 s tBu), 2.09 (s, OAc), 3.27 (s, CH$_3$O), 3.52 & 3.70 (2 m, CH$_2$O), 3.99 (s, C$_4$ OH), 4.19 (d, J=2.0 Hz, H-7), 4.71 (d, J=2.0 Hz, H-6), 4.85 (s, H-3), 4.97 (b s, =CH$_2$), 5.13 (d, J=5.0 Hz CHOAc), 7.10–7.34 (m, ArH).

EXAMPLE 156

IA-C6-Propyl Ether (5r''').

NMR (CD$_3$OD) δ0.86 (d, J=7.0 Hz, CHCH$_3$), 0.94 (t, J=7.0 Hz, CH$_2$CH$_3$), 1.58 (m, CH$_2$CH$_2$CH$_3$), 2.11 (s, OAc), 3.52, 3.66 (2 m, CH$_2$O), 4.06 (d, J=2.0 Hz, H-7), 4.98 & 5.02 (2 s, 2 H), 5.09 (d, J=5.0 Hz, CHOAc), 5.12 (s, H-3), 7.04–7.38 (m, ArH). MS (FAB–) m/z 579.

EXAMPLE 157

IA-C4,6-bis-Propyl Ether-7-MME-tris-t-butyl ester (4t''').

NMR (CDCl$_3$) δ0.80–1.0 (m, 9H), 1.41 & 1.43 [2 s, (CH$_3$)$_2$C], 1.48, 1.51 & 1.61 (3 s tBu) 2.12. (s, OAc), 3.27 (s, CH$_3$O), 3.36, 3.46 & 3.64 (3 m, CH$_2$O), 4.13 (d, J=2.0 Hz, H-7), 4.84 (s, H-3), 4.90 (d, J=2.0 Hz, H-6), 4.96 (b s, =CH$_2$), 5.14 (d, J=5.0 Hz, CHOAc), 7.12–7.34 (m, ArH).

EXAMPLE 158

IA-C4,6 bis-Propyl Ether (5t''').

NMR (CD$_3$OD) δ0.82–0.96 (m, 9H), 1.56 (m, CH$_2$CH$_2$CH$_3$), 2.11 (s, OAc), 3.49, 3.64, 3.82 & 4.02 (4 m,

CH₂O), 4.03 (d, J=2.0 Hz H-7), 4.98 (s, 1H), 5.02 (s, 1H), 5.0 (d, J=2.0 Hz, H-6), 5.08 (d, J=5 0 Hz, CHOAc), 5.12 (s, H-3), 7.10–7.37 (m, ArH); MS (FAB–) m/z 621.
Derivatization at C-1 (4')

EXAMPLE 159

Preparation of IA-7-MME-tris-t-butyl ester-Cl(4')-alcohol (4'a)

A suspension of anhydrous cerium (III) chloride (2.0 g, 5.37 mmol) in THF (16.5 mL) was stirred for 1.5 h at 23° C. and cooled to 0° C. Ethylmagnesium chloride (2.4 mL of a 2.0M solution in THF, 4.83 mmol) was added and after 1.5 h the resultant mixture was cooled to –70° C. A solution of tris-t-butylester-7-(1-methyl-1-methoxyethyl) ether (2a) (0.50 g, 0.537 mmol) in THF (3.0 mL) was added and after 0.5 h the reaction was quenched with saturated aqueous ammonium chloride. The resultant mixture was allowed to warm to room temperature, diluted with ethyl ether, and filtered through a plug of celite. The filtrate was transferred to a separatory funnel and washed with brine. The organic portion was dried (MgSO₄), filtered and concentrated in vacuo. Flash column chromatography (4:1 hex/EtOAc, silica gel) afforded the allylic alcohol (4'a) as a white solid: ¹H NMR (300 MHz, CDCl₃) δ7.27–7.14 (m, 5H), 6.88 (dd, J=8.1, 15.6 Hz, 1H), 6.40 (d, J=1.8 Hz, 1H), 5.74 (d, J=15.6 Hz, 1H), 5.11 (br s, 1H), 5.03 (s, 1H), 4.99 (br s, 1H), 4.22 (d, J=1.8 Hz, 1H), 4.14–4.11 (m, 1H), 3.95 (s, 1), 3.19 (s, 3H), 2.81 (dd, J=4.8, 12.9 Hz, 1H), 2.57–1.94 (m, 7H), 1.66 (s, 9H), 1.44–1.05 (m, 6H), 1.44 (s, 9H), 1.36 (s, 9H), 1.35 (s, 3H), 1.26 (s, 3H), 0.98 (d, J=6.6 Hz, 3H), 0.86–0.79 (m, 9H).

EXAMPLE 160

Preparation of IA-7-MME-tris-t-butyl ester-Cl(4')-Propionate (6a).

A solution of (4'a) (30 mg, 0.337 mmol), triethylamine (56.5µL, 0.405 mmol), 4-dimethylamino-pyridine (4.1 mg, 0.0337 mmol) and propionic anhydride (43.3 µL, 0.337 mmol) in CH₂Cl₂ (0.5 mL) was allowed to stir at 23° C. for 2 h. The reaction was diluted with CH₂Cl₂ and washed with 1N HCl, 5% aq. sodium bicarbonate, and saturated aq. NaCl. The organic portion was then dried (Na₂SO₄), filtered and concentrated in vacuo. The residue was purified by flash column chromatography (3:1 hex/EtOAc, silica gel) to provide (6a) as a colorless oil: ¹H NMR (300 MHz, CDCl₃) δ7.27–7.13 (m, 5H), 6.88 (dd, J=8.2, 15.9 Hz, 1H), 6.41 (d, J=1.8 Hz, 1H), 5.77 (d, J=15.9 Hz, 1H), 5.14 (d, J=4.8 Hz, 1H), 5.03 (s, 1H), 4.93 (br s, 2H), 4.20 (d, J=1.8 Hz, 1H), 4.04 (s, 1H), 3.19 (s, 3H), 2.77–1.90 (m, 10H), 1.66 (s, 9H), 1.48–1.05 (m, 5H), 1.45 (s, 9H), 1.37 (s, 9H), 1.34 (s, 3H), 1.26 (s, 3H), 1.15 (t, J=7.5 Hz, 3H ), 0.98 (d, J=6.6 Hz, 3H), 0.86–0.77 (m, 9H).

EXAMPLE 161

Preparation of IA-7-MME-tris-t-butyl ester-Cl(4')-Butyrate (6b).

Prepared according to the procedure described above for (6a) except an equivalent amount of butyric anhydride was substituted for propionic anhydride to afford butyrate (6b): ¹H NMR (300 MHz, CDCl₃) δ7.27–7.13 (m, 5H), 6.88 (dd, J=8.2, 15.6 Hz, 1H), 6.41 (d, J=1.8 Hz, 1H), 5.77 (d, J=15.6 Hz, 1H), 5.14 (d, J=4.8 Hz, 1H), 5.03 (s, 1H), 4.94 (br s, 1H), 4.93 (br s, 1H), 4.19 (d, J=1.8 Hz, 1H), 4.04 (s, 1H), 3.20 (s, 3H), 2.78–1.91 (m, 10H), 1.66 (s, 9H), 1.43–1.05 (m, 7H), 1.43 (s, 9H), 1.37 (s, 9H), 1.34 (s, 3H), 1.26 (s, 3H), 0.99–0.92 (m, 6H), 0.83–0.77 (m, 9H).

EXAMPLE 162

Preparation of IA-7-MME-tris-t-butyl ester-Cl(4')-Pivalate (6c).

¹H NMR (300MHz, CDCl₃) δ7.27–7.13 (m, 5H), 6.88 (dd, J=8.2, 15.6 Hz, 1H), 6.40 (d, J=1.5 Hz, 1H), 5.76 (d, J=15.6 Hz, 1H), 5.11 (d, J=3.6 Hz, 1H ), 5.02 (s, 1H), 4.92 (br s, 2H), 4.19 (d, J=1.5 Hz, 1H), 4.03 (s, 1H), 3.19 (s, 3H), 2.60–1.91 (m, 8H), 1.66 (s, 9H), 1.43–1.06 (m, 5H), 1.43 (s, 9H), 1.37 (s, 9H), 1.34 (s, 3H), 1.26 (s, 3H), 1.25 (s, 9H), 0.98 (d, J=6.6 Hz, 3H), 0.86–0.78 (m, 9H).

EXAMPLE 163

Preparation of IA-7-MME-tris-t-butyl ester-Cl(4')-Benzoate (6d).

¹H NMR (300 MHz, CDCl₃) δ8.13–8.10 (m, 2H), 7.54–7.40 (m, 3H), 7.27–7.14 (m, 5H), 6.89 (dd, J=8.1, 15.6 Hz, 1H), 6.41 (d, J=1.5 Hz, 1H), 5.77 (d, J=15.6 Hz, 1H), 5.39 (d, J=4.5 Hz, 1H), 5.05 (s, 1H), 5.04 (br s, 1H), 4.98 (br s, 1H), 4.18 (d, J=1.5 Hz, 1H), 4.06 (s, 1H), 3.08 (s, 3H), 2.86–1.91 (m, 8H), 1.67 (s, 9H), 1.43–1.06 (m, 5H), 1.43 (s, 9H), 1.38 (s, 9H), 1.27 (s, 3H), 1.23 (s, 3H), 0.98 (d, J=6.6 Hz, 3H ), 0.91 (d, J=6.6 Hz, 3H), 0.86–0.78 (m, 6H).

EXAMPLE 164

Preparation of IA-Cl(4')-propionyl tri-acid (7a)

A solution of (6a) (32.0 mg, 0.0338 mmol) in CH₂Cl₂ (1.6 mL) was cooled to 0° C. and trifluoroacetic acid (0.4 mL) was added. The solution was then allowed to warm to room temperature and after 16 h the solvent was removed in vacuo. The residue was rediluted with toluene and reconcentrated in vacuo. The resultant solid was diluted with CH₃CN, passed through a Sep-Pak (C-18) filter, and again concentrated in vacuo. The solid residue was lyophilized from benzene to afford (7a) as a pale white solid: ¹H NMR (300 MHz, CD₃OD) δ7.33–7.18 (m, 5H), 6.89 (dd, J=8.4, 15.6 Hz, 1H), 6.36 (d, J=1.8 Hz, 1H), 5.84 (d, J=15.6 Hz, 1H), 5.31 (s, 1H), 5.14 (d, J=4.8 Hz, 1H), 5.06 (br s, 1H), 5.00 (br s, 1H), 4.08 (d, J=1.8 Hz, 1H), 2.72 (dd, J=6.3, 13.2 Hz, 1H), 2.52–2.03 (m, 9H), 1.48–1.09 (m, 5H), 1.20 (t, J=7.5 Hz, 3), 1.08 (d, J=6.9 Hz, 3H), 0.99–0.89 (m, 9H).

EXAMPLE 165

Preparation of IA-Cl(4')-Butanoyl tri-acid (7b)

According to the procedure described above for (7a) butyrate (7b) was produced.: ¹H NMR (300 MHz, CD₃OD) δ7.32–7.18 (m, 5H), 6.89 (dd, J=8.4, 15.6 Hz, 1H), 6.35 (d, J=1.8 Hz, 1H), 5.84 (d, J=15.6 Hz, 1H), 5.31 (s, 1H), 5.14 (d, J=4.5 Hz, 1H), 5.06 (br s, 1H), 5.00 (br s, 1H), 4.08 (d, J=1.8 Hz, 1H), 2.72 (dd, J=6.3, 13.5 Hz, 1H), 2.51–2.04 (m, 10H), 1.76–0.98 (m, 12H), 0.92–0.89 (m, 9H).

EXAMPLE 166

Preparation of IA-Cl(4')-Pivaloyl tri-acid (7c).

¹H NMR (300 MHz, CD₃OD) δ7.33–7.18 (m, 5H), 6.89 (dd, J=8.7, 15.6 Hz, 1H), 6.35 (d, J=1.5 Hz, 1H), 5.84 (d, J=15.6 Hz, 1H), 5.30 (s, 1H), 5.09 (d, J=3.9 Hz, 1H), 5.05 (br s, 1H), 4.98 (br s, 1H), 4.07 (d, J=1.5 Hz, 1H), 2.75–2.03 (m, 8H), 1.46–1.15 (m, 5H), 1.31 (s, 9H), 1.08 (d, J=6.6 Hz, 3H), 0.95–0.88 (m, 9H).

EXAMPLE 167

Preparation of IA-Cl(4')-Benzoyl tri-acid (7d).

¹H NMR (300 MHz, CD₃OD) δ8.14–8.10 (m, 2H), 7.67–7.53 (m, 3H), 7.31–7.18 (m, 5H), 6.89 (dd, J=8.6, 15.6

Hz, 1H), 6.36 (d, J=1.8 Hz, 1H), 5.85 (d, J=15.6 Hz, 1H), 5.37 (d, J=4.5 Hz, 1H), 5.32 (s, 1H), 5.09 (br s, 1H), 5.06 (br s, 1H), 4.09 (d, J=1.8 Hz, 1H), 2.84–2.18 (m, 8H), 1.47–1.15 (m, 5H), 1.08–1.02 (m, 6H), 0.92–0.87 (m, 6H).

EXAMPLE 168

Preparation of IA-7-MME-tris-t-butyl ester-Cl(4')-Imidazoyl-carbamate (6e)

A solution of alcohol (4'a) (36.0 mg, 0.0405 mmol) and N,N'-carbonyldiimidazole (9.8 mg, 0.0608 mmol) in $CH_2Cl_2$ (0.4 mL) was stirred at 23° C. for 4 h. The solution was concentrated in vacuo and the residue was purified by flash column chromatography (2:1 hex/EtOAc, silica gel) to provide carbamate 6e as a white solid: $^1H$ NMR (400 MHz, $CDCl_3$) δ.8.19 (s, 1H), 7.47 (d, J=1.2 Hz, 1H), 7.27–7.14 (m, 5H), 7.05 (d, J=1.2 Hz, 1H), 6.87 (dd, J=8.0, 15.6 Hz, 1H), 6.42 (d, J=2.0 Hz, 1H), 5.76 (d, J=15.6 Hz, 1H), 5.30 (d, J=4.8 Hz, 1H), 5.05 (br s, 2H), 5.04 (br s, 1H), 4.18 (d, J=2.0 Hz, 1H), 4.07 (s, 1H), 3.10 (s, 3H), 2.81–1.95 (m, 8H), 1.66 (s, 9H), 1.43 (s, 9H), 1.43–1.05 (m, 5H), 1.37 (s, 9H), 1.30 (s, 3H), 1.24 (s, 3H), 0.98 (d, J=6.8 Hz, 3H), 0.89 (d, J=6.4 Hz, 3H), 0.81–0.78 (m, 6H).

EXAMPLE 169

Preparation of IA-7-MME-tris-t-butyl ester-Cl(4')-N-Propyl carbamate (6f).

A solution of the imidazoyl carbamate (6e) (36.2 mg, 0.0368 mmol) and n-propylamine (30.0 μL, 0.368 mmol) in $CH_2Cl_2$ (0.37 mL) was stirred at 23° C. for 20 h. The resultant solution was concentrated in vacuo and the residue was purified by flash column chromatography (2:1 hex/EtOAc, silica Eel) to yield (6f) as a clear, colorless oil: $^1H$ NMR (400 MHz, $CDCl_3$) δ7.26–7.15 (m, 5H), 6.88 (dd, J=8.4, 15.6 Hz, 1H), 6.41 (d, J=2.0 Hz, 1H), 5.77 (d, J=15.6 Hz, 1H), 5.06 (d, J=4.8 Hz, 1H), 5.04 (s, 1H), 4.97 (br s, 1H), 4.95 (br s, 1H), 4.21 (d, J=2.0 Hz, 1H), 4.04 (s, 1H), 3.21 (s, 3H), 3.17–3.08 (m, 2H), 2.78 (dd, J=4.8, 13.6 Hz, 1H), 2.61–1.96 (m, 7H), 1.67 (s, 9H), 1.64–1.05 (m, 7H), 1.44 (s, 9H), 1.37 (s, 9H), 1.35 (s, 3H), 1.27 (s, 3H), 0.98 (d, J=6.8 Hz, 3H), 0.90 (t, J=7.2 Hz, 3H), 0.83–0.77 (m, 9H).

EXAMPLE 170

Preparation of IA-7-MME-tris-t-butyl ester-Cl(4')-N-Benzyl carbamate (6g).

Prepared according to the procedure described above for (6f) except benzylamine was employed. 43.7 mg of 6e afforded (6g) as a clear, colorless oil: $^1H$ NMR (400 MHz, $CDCl_3$) δ7.31–7.15 (m, 10H), 6.89 (dd, J=8.0, 15.6 Hz, 1H), 6.42 (d, J=1.6 Hz, 1H), 5.77 (d, J=15.6 Hz, 1H), 5.40 (br s, 1H), 5.11 (d, J=5.2 Hz, 1H), 5.05 (s, 1H), 5.00 (br s, 1H), 4.97 (br s, 1H), 4.46–4.28 (m, 2H), 4.23 (d, J=1.6 Hz, 1H), 4.03 (s, 1H), 3.21 (s, 3H), 2.83–1.98 (m, 8H), 1.67 (s, 9H), 1.40–1.14 (m, 5H), 1.40 (s, 9H), 1.37 (s, 9H), 1.35 (s, 3H), 1.25 (s, 3H), 0.97 (d, J=6.4 Hz, 3H), 0.83–0.78 (m, 9H).

EXAMPLE 171

Preparation of IA-tris-t-butyl ester-Cl(4')-N-Phenyl carbamate (6h).

A solution of alcohol (4'a) (40 mg, 0.0450 mmol), phenyl isocyanate (48.9 μL, 0.450 mmol), and triethylamine (31.3 μL, 0.225 mmol) in toluene (1.0 mL) was heated at reflux for 16 h. The resultant mixture was allowed to cool to room temperature and concentrated in vacuo. The residue was purified by flash column chromatography (4:1 hex/EtOAc, silica gel) to afford (6 h) as a clear, colorless oil: $^1H$ NMR (400 MHz, $CDCl_3$) δ7.40–7.16 (m, 10H), 7.02 (t, J=7.2 Hz, 1H), 6.88 (dd, J=8.0, 15.6 Hz, 1H), 6.40 (d, J=1.6 Hz, 1H), 5.76 (d, J=15.6 Hz, 1H), 5.19 (d, J=6.0 Hz, 1H), 5.09 (s, 1H), 5.02 (br s, 1H), 5.01 (br s, 1H), 4.19 (d, J=1.6 Hz, 1H), 4.07 (s, 1H), 3.10 (s, 3H), 2.88–1.98 (m, 8H), 1.67 (s, 9H), 1.46–1.06 (m, 5H), 1.46 (s, 9H), 1.38 (s, 9H), 1.20 (s, 3H), 1.19 (s, 3H ), 0.98 (d, J=6.8 Hz, 3H), 0.85 (d, J=6.8 Hz, 3H), 0.82–0.79 (m, 6H).

EXAMPLE 172

Preparation of IA-Cl(4')-N-Propyl carbemoyltri-acid (7f).

According to the procedures described above for (7a), 30.7 mg of (6f) afforded (7f) as a white solid: $^1H$ NMR (400 MHz, $CD_3OD$) δ7.24–7.13 (m, 5H), 6.84 (dd, J=8.4, 15.6 Hz, 1H), 6.32 (d, J=2.0 Hz, 1H), 5.80 (d, J=15.6 Hz, 1H), 5.26 (s, 1H), 5.00 (br s, 2H), 4.92 (d, J=4.5 Hz, 1H), 4.02 (d, J=2.0 Hz, 1H), 3.05 (t, J=5.2 Hz, 2H), 2.74–1.98 (m, 8H), 1.56–0.95 (m, 7H), 1.02 (d, J=6.8 Hz, 3H), 0.92 (t, J=7.6 Hz, 3H), 0.88–0.84 (m, 9H).

EXAMPLE 173

Preparation of IA-Cl(4')-N-Benzyl carbamoyltri-acid (7g).

According to the procedures described above for (7a), 35.3 mg of (6g) afforded (7g) as a white solid: $^1H$ NMR (300 MHz, $CD_3OD$) δ7.49–7.16 (m, 10H), 6.88 (dd, J=8.4, 15.6 Hz, 1H), 6.35 (d, J=1.8 Hz, 1H), 5.83 (d, J=15.6 Hz, 1H), 5.30 (s, 1H), 5.07 (br s, 2H), 4.99 (d, J=4.5 Hz, 1H), 4.33 (br s, 2H), 4.08 (d, J=1.8 Hz, 1H), 2.78–2.00 (m, 8H), 1.46–1.10 (m, 5H), 1.07 (d, J=6.6 Hz, 3H), 0.93–0.87 (m, 9H).

EXAMPLE 174

Preparation of IA-C4'-N-Phenylcarbamoyltri-acid (7h).

According to the procedures described above for (7a), (6h) afforded (7h) as a white solid: $^1H$ NMR (300 MHz, $CD_3OD$) δ7.50–7.05 (m, 11H), 6.89 (dd, J=8.4, 15.6 Hz, 1H), 6.36 (d, J=1.8 Hz, 1H), 5.83 (d, J=15.6 Hz, 1H), 5.32 (s, 1H), 5.13 (d, J=4.5 Hz, 1H), 5.10 (br s, 2H), 4.11 (d, J=1.8 Hz, 1H), 2.86–2.08 (m, 8H), 1.46–1.00 (m, 5H), 1.07 (d, J=6.6 Hz, 3H), 0.96 (d, J=6.6 Hz, 3H), 0.93–0.88 (m, 6H).

EXAMPLE 175

Preparation of IA-3-benzyl ester (8a).

A solution of acetyl chloride (0.4 ml) in benzyl alcohol (10 ml) was stirred at room temperature for 30 min. To this mixture was added IA (1 g) and the reaction mixture was stirred for an additional 6 hr. The mixture was poured into acetonitrile-water (200 mL, 38%) and purified by chromatography (C-8, acetonitrile-water, 3:2) to give the title compound. $^1$NMR (300 MHz, $CD_3OD$) δ7.46–7.12 (m, 10H), 6.88 (dd, J=8.9,18 Hz, 1H), 6.38 (brs, 1H), 5.84 (d, J=15 Hz, 1H), 5.42 (s, 1H), 5.23 (dd, J=13, 51 Hz), 2H), 5.14 (s, 1H), 5.04 & 5.00 (2s, 2H), 4.06 (br s, 1H), 2.71 (m, 1H), 2.54–2.00 (m, 7H), 2.12 (s, 3H), 1.50–1.1 (m, 6H), 1.07 (d, J=6 Hz, 3H), 0.90 (m, 9H); FAB m/e 793 (M+2Li), 799 (M+3Li).

By methods described for compound 8a, the following compounds were prepared.

EXAMPLE 176

Preparation of IA-3-methyl ester (8b ).

$^1$H-NMR (400 MHz, $CD_3OD$) δ7.29–7.09 (m, 5H), 6.85 (dd, J=15.6, 8.5 Hz, 1H), 6.31 (d, J=1.8 Hz, 1H), 5.80 (d, J=15.6 Hz, 1H), 5.31 (s, 1H), 5.09 (d, J=4.9 Hz, 1H, 5.03 (s, 1H), 4.98 (s, 1H), 4.02 (d, J=1.7 Hz, 1H), 3.72 (s, 3H), 2.70 (m, 1H), 2.45 (m, 3H), 2.36–2.21 (m, 3H), 2.05 (s, 3H), 1.45–1.26 (m, 6H), 1.19–1.10 (m, 3H), 1.05 (d, J=6.4 Hz, 3H), 0.91–0.82 (m, 10H), MS data (FAB) 685 (M+Na)⁺.

EXAMPLE 177

Preparation of IA-3-ethyl ester (8c).

¹H-NMR (400 MHz, CD₃OD) δ7.30–7.10 (m, 5H), 6.88 (dd J=15.66, 8.43 Hz, 1H), 6.30 (d, J=1.8 Hz, 1H), 5.80 (d, J=14.66 Hz, 1H), 5.30 (s, 1H), 5.09 (d, J=4.56 Hz, 1H), 5.01 (s, 1H), 4.95 (s, 1H), 4.22–4.12 (m, 3H), 4.02 (d, J=1.8 Hz, 1H), 2.70 (dd, J=13.3, 6.27 Hz, 1H), 2.10 (s, 3H), 2.02 (m, 2H), 1.42–1.21 (m, 8H), 1.80–1.50 (m, 2H), 1.03 (d, J=6.68 Hz, 2H), 0.92–0.81 (m, 8H).

EXAMPLE 178

Preparation of IA-3-(2-phenylethyl) ester (8d).

¹H NMR (400 MHz, CD₃OD) δ7.35–7.10 (m, 10H), 6.85 (dd, J=8.5, 15.6 Hz, 1H), 6.35 (br s, 1H), 5.82 (d, J=15.6 Hz, 1H), 5.32 (br s, 1H), 5.09 (d, J=4.9 Hz, 1H), 5.00 and 4.95 (ea s, ea 1H), 4.28 (br t, 2H), 4.00 (s, 1H), 2.94 (br t, 2H), 2.69 (m, 1H), 2.50–2.10 (m, 6H), 2.10 (s, 3H), 2.01 (t, 3H), 1.45–1.05 (m, 8H), 1.03 (d, J=6.1 Hz, 3H), 0.86 (m, 10H); MS (FAB), m/e 816, 839 [M+Na, M+2 Na]⁺.

EXAMPLE 179

Preparation of IA-3-allyl ester (8e).

¹H NMR (400 MHz, CD₃OD) δ7.30–7.10(m, 5H), 6.85(dd, J=8.4, 16 Hz, 1H), 6.31(br s, 1H, 5.91(m, 1H), 5.80(d, J=16 Hz, 1H), 5.35(d, 2H), 5.18(d, 1H), 5.06(d, J=6 Hz, 1H), 5.00 and 4.96(ea s, ea 1H), 4.63(m, 2H), 4.01(s, 1H). 2.67(m, 1H), 2.50–2.10(m, 4H), 2.09(s, 3H), 1.55–1.05(m, 1.01(d, J=7 Hz, 3H), 0.86(m, 7H); MS (FAB), m/e 748 [M+2Li]⁺.

EXAMPLE 180

Preparation of IA-3-(3-cyclopentylpropyl) ester (8f).

¹H NMR (400 MHz, CD₃OD) δ7.11–7.27 (m, 5H), 6.84 (dd, J=8.4, 15.6 Hz, 1H), 6.31 (d, J=1.5 Hz, 1H), 5.79 (d, J=15.6 Hz, 1H), 5.29 (s, 1H), 5.08 (d, J=4.6 Hz, 1H), 5.01 (s, 1H), 4.96 (s, 1H), 4.12 (m, 2H), 4.03 (d, J=1.5 Hz, 1H), 2.67 (dd, J=5.2, 13.2 Hz, 1H), 2.44 (m), 2.23 (m,), 2.1 (s, 3H), 2.0 (m), 1.76 (m), 1.63 (m), 1.52 (m), 1.26–1.43 (m), 1.10 (m), 1.02 (d, J=6.5 Hz, 3H), 0.85 (m). HPLC R$_t$ 19.1 min. MS (FAB) m/z 823.8 (M+Na)⁺, 845.3 (M+2 Na)⁺.

EXAMPLE 181

Preparation of IA-3-n-butyl ester (8g).

¹H (400 MHz, CD₃OD) δ7.30–7.10(m, 5H), 6.84(dd, J=8, 16 Hz, 1H), 6.30(s, 1H), 5.80(d, J=16 Hz, 1H), 5.29(s, 1H), 5.08 (d, J=4.4 Hz, 1H), 5.00 and 4.96(ea s, ea 1H), 4.14(t, J=7 Hz, 2H), 4.02(s, 1H), 2.69(m, 2H), 2.52–2.15(m), 2.10(s,3H), 2.05–1.9(m, 2H), 1.65–1.55(m, 2H), 1.4–1.05(m), 1.02(d, J=7 Hz, 3H), 0.94(t, J=7 Hz, 3H), 0.86(m, 9H).

EXAMPLE 182

Preparation of IA-3-propynyl ester (8h).

¹H NMR (400 MHz, CD₃OD) δ7.34–7.10(m, 5H), 6.85(dd, J=8.4, 15.6 Hz, 1H), 6.32(s, 1H), 5.80(d, J=15.6, 1H), 5.36(s, 2H), 5.08(d, J=4 Hz, 1H), 5.03 and 4.96(ea s, ea 1H), 4.75(q, 2H), 4.04(s, 1H), 2.94(s, 1H), 2.12(s, 3H)

EXAMPLE 183

Preparation of IA-3-isopropyl ester (8i).

¹H NMR (200 MHz, CD₃OD) δ7.30–7.10(m, 5H), 6.86(dd, J=8, 16 Hz, 1H), 6.31(d, 1.7 Hz, 1H), 5.80(d, J=16 Hz, 1H), 5.26(s, 1H), 5.10(d, J=4.6 Hz, 1H), 5.04 and 5.00(ea s, ea ¹H), 4.11(t, J=7 Hz, 2H), 4.03(d, J=1.8 Hz, 1H), 2.68(m, 1H), 2.52–2.10(m), 2.10(s, 3H), 1.40–1.10(m), 1.24(d, J=7 Hz, 6H), 1.01(d, J=7 Hz, 3H), 0.90–075(m).

EXAMPLE 184

Preparation of IA-3-n-propyl ester (8j).

¹H NMR (200 MHz, CD₃OD) δ7.30–7.10(m, 5H), 6.84(dd, J=8, 16 Hz, 1H), 6.31(d, 1.7 Hz, 1H), 5.80(d, J=16 Hz, 1H), 5.29(s, 1H), 5.08(d, J=4.6 Hz, 1H), 5.03 and 4.97(ea s, ea 1H), 4.11(t, J=7 Hz, 2H), 4.04(d, J=1.8 Hz, 1H), 2.69(m, 1H), 2.52–2.10(m), 2.10(s, 3H), 1.90–1.12(m), 1.65(q, J=7 Hz, 2H), 1.44–1.06(m), 1.01(d, J=7 Hz, 3H), 0.94(t, J=7 Hz, 3H), 0.86(m).

EXAMPLE 185

Preparation of IA-3-isobutyl ester (8k).

¹H NMR (400 MHz, CD₃OD) δ7.30–7.10(m, 5H), 6.84(dd, J=8, 16 Hz, 1H), 6.31(d, J=1.8 Hz, 1H), 5.78(dd, J=0.4, 16 Hz, 1H), 5.30(s, 1H), 5.08(d, J=4.6 Hz, 1H), 5.01 and 4.96(ea s, ea 1H), 4.02(d, J=1.8 Hz, 1H), 3.93(m, 2H), 2.69(m, 1H), 2.52–2.10(m, 5H), 2.10(s, 3H), 2.08–1.85(m, 2H), 1.40–1.05(m, 3H), 1.05(d, J=7 Hz, 3H), 0.92(m, 6H), 0.86(m, 9H).

EXAMPLE 186

Preparation of IA-3-cyclohexyl ester (8l).

¹H NMR (400 MHz, CD₃OD) δ7.30–7.10(m, 5H), 6.84(dd, J=9, 16 Hz, 1H), 6.31(s, 1H), 5.80(d, J=16 Hz, 1H), 5.26(s, 1H), 5.03 and 4.97(ea s, ea 1H), 4.04(s, 1H), 2.69(m, 1H), 2.52–2.20(m,), 2.10(s, 3H), 1.90–1.12(m,), 1.01 (d, J=7 Hz, 3H), 0.86(m); MS (FAB), m/e 785, 791 [M+2Li, M+3Li]⁺.

EXAMPLE 187

Preparation of IA-3-(3-phenylpropyl) ester (8m).

¹H NMR (400 MHz, CD₃OD) δ7.30–7.10(m, 5H), 6.84(dd, J=8, 16 Hz, 1H), 6.31(s, 1H), 5.78(d, J=16 Hz, 1H), 5.33(s, 1H), 5.08(d, J=4.4 Hz, 1H), 5.02 and 4.95(ea s, ea 1H), 4.13(m, 2H), 4.04(d, J=2 Hz, 1H), 2.68(t, J=7 Hz, 2H), 2.67(m, 1H), 2.52–2.10(m), 2.10(s, 3H), 2.08–1.85(m), 1.55–1.2(m) 1.2–1.08(m), 1.03(d, J=7 Hz, 3H), 0.86(m).

EXAMPLE 188

Preparation of IA-3-(3-methyl-1-butyl) ester (8n).

¹NMR (400 MHz, CD₃OD) δ7.30–7.10(m, 5H), 6.84(dd, J=8, 16 Hz, 1H), 6.31(s, 1H, 5.78(d, J=16 Hz, 1H), 5.27(s, 1H), 5.08(d, J=4.6 Hz, 1H), 5.02 and 4.95(ea s, ea 1H), 4.18(m, 2H), 4.03(d, J=1.8 Hz, 1H), 2.69(m, 1H), 2.52–2.10(m), 2.10(s, 3H), 2.08–1.95(m, 2H), 1.65(m, 1H), 1.44–1.06(m, 6H), 1.01(d, J=7 Hz, 1H), 0.92(m, 6H), 0.86(m).

EXAMPLE 189

Preparation of IA-3-phenoxyethyl) ester (8o).

¹H NMR (400 MHz, CD₃OD) δ7.30–7.10(m, 10H), 6.84(dd, J=8.6, 15.8 Hz, 1H), 6.31(s, 1H), 5.78(d, J=15.8 Hz, 1H), 5.35(s, 1H), 5.06(d, J=4.2 Hz, 1H), 4.99 and 4.95 (ea s, ea 1H ), 4.47 and 4.17 (ea t, J=4.8 Hz, ea 2H), 4.02(s, 1H), 2.09(s, 3H). MS (FAB) m/z 855 (M+2Na)⁺.

EXAMPLE 190

Preparation of IA-3-n-pentyl ester (8p).

¹H NMR (300 MHz, CD₃OD) δ7.40–7.10 (m, 51H, Ar—H), 6.89 (dd, J=9, 17 Hz, 1H, 3"-H), 6.36 (d, J=1 Hz, 1H, 6-

H), 5.86 (d, J=18 Hz, 1H, 2"-H), 5.34 (s, 1H, CHCOOC$_5$H$_{11}$), 5.13 (d, J=6 Hz, 4"-H); 5.06 and 5.00 (2s, 2H, >=CH$_2$), 4.18 (t, 2H, COOCH2(CH$_2$)$_3$CH$_3$), 4.07 (s, 1H, 7-H), 2.73 (m, 1H, 4"-H), 2.55–2.20 (m, 8H), 2.16 (s, 3H, COCH$_3$), 2.06 (m, 3H), 1.69 (m, 3H), 1.50–1.10 (m, 12H), 1.07 (d, J=6 Hz, 3H, 5'-CH$_3$), 0.93 (m, 14H). MS (FAB) 783, 805 (m, Na, 2Na) 827 (M+3Na).

EXAMPLE 191

Preparation of IA-3-(2-butenyl) ester (8q). $^1$H NMR (400 MHz, CD$_3$OD) δ7.30–7.10 (m, 5H, Ar—H), 6.84 (dd, J=8, 16 Hz, 1H, 3'-H), 5.81 (br s, 1H, 6-H)), 5.81 (d, J=16 Hz, 2H, COOCH$_2$CH=CHCH$_3$), 5.60 (m, 1H, COOCH$_2$CH=CHCH$_3$), 5.31 (bs, 1H, CH—COOR), δ5.08 (d, J=6 Hz, 1H, 4'-H), 5.00+4.95 (2s, 2H, =CH$_2$), 4.56 (m, 2H, COOCH$_2$CH=CH—CH$_3$), 4.01 (s, 1H, 7-H), δ2.69 (m, 1H, 4"-H), δ2.50–2.15 (m, 6H), 2.10 (s, 3H, COCH$_3$), 1.69 (d, J=6Hz, 3H, COOCH$_2$CH=CH—CH$_3$), 1.30–1.05 (m, 11H), δ1.02 (d, J=6 Hz, 3H, 5'-CH$_3$), 0.85 (m, 11H). MS (FAB) 767, 789 (M+Na, M+2Na) 810 (M+3Na).

EXAMPLE 192

IA-3-(2-isopropoxyethyl)ester (8t) A mixture of acetyl chloride (0.4 mL) and 2-isopropoxyethanol (10 mL) was stirred for 30 min. at room temperature to which was add ed 1 g IA and the resulting mixture was stirred ore might. The mixture was concentrated in vacuo. An aliquot was purified by HPLC to give IA-3-(2-isopropoxyethyl)ester. (–)FAB MS m/e 775(M$^+$-1)

$^1$H (200 MHz, CDCl$_3$) δ0.72–0.96(m, 9H), 1.01 (d, J=6 Hz, 3H), 1.08–1.481(m, 12H), 1.84–2.22(m+s, 6H) 2.24–2.60(m, 4H), 2.69(dd, J=5 Hz, 13 Hz, 1H), 3.40–3.80(m, 4H), 4.05(brs, 1H), 4.16–4.38(m, 2H), 4.96(s, 2H), 5.08 (s, 1H), 5.24–5.38(m+s, 2H), 5.78 (d, J=15 Hz, 1H), 5.88(s, 1H), 6.89(dd, J=9.15, 1H), 7.04(m, 5H).

EXAMPLE 193

IA-3-(3-methyl-3-butenyl)ester (8s)

At ambient temperature, 3-methyl-3-buten-1-ol (2.5 mL) was stirred and treated with acetyl chloride (100 mL). After 30 min., 500 mg. of I was added and stirring continued at r.t. for 72 hrs. The IA-3-(3-methyl-3-butenyl)ester was isolated by HPLC, HPLC RT=15.8 min. MS(–) FAB m/e=758.2

$^1$H NMR(400 MHz, CD$_3$OD) δ7.27–7.13(m, 5H), 6.84(dd, J=8.4, 15.6 Hz, 1H), 6.30(s, 1H), 6.30(s, 1H) 5.07(d, J=4.65 5.79(d, J=15.7 Hz, 1H), 5.29(brs, 1H), 5.07 (d, J=4.65 Hz, 1H), 5.01 (s, 1H), 4.96(s, 1H), 4.96(s, 1H), 4.79 & 4.74(2S), 4.32–4.16(m, 2H), 4.02 (s, 1H), 3.65–3.4(m), 2.68(dd, J=6.45, 13.7 Hz, 1H), 2.5–2.3(m), 2.3–2.18(m), 2.1(s, 3H), 2.08–1.9(m), 1.45–1.10(m), 1.02(d, J=6.64 Hz, 3H), 0.86(m).

The following compounds were prepared according to the procedure described for IA-3-(2-isopropoxyethyl)ester (8r) and using the appropriate alcohols.

EXAMPLE 194

IA-3-[2-(5-methylhexyl)]ester (8t) $^1$H NMR(400 MHz, CD$_3$OD) δ7.27–7.13(m, 5H), 6.84(dd, J=8.4, 15.6Hz, 1H), 6.30(d, J=1.6 Hz, 1H), 5.79(d, J=15.7 Hz, 1H), 5.24(d, J=2.86Hz, 1H), 5.08(d, J=4.6 Hz, 1H), 5.01(s, 1H), 4.96(s), 4.95(m), 4.02(d, J=1.6 Hz, 1H), 2.68(dd, J=6.45, 13.7 Hz, 1H), 2.5–2.2(m), 2.1(s, 3HO), 2.05–2.0(m), 1.7–1.1(m), 1.22(d, J=5.5 Hz), 1.02(d, J=6.64 Hz, 3H), 0.86(m). HPLC: RT 18 min., MS (–)FAB m/e= 787.8

EXAMPLE 195

IA-3-(3-methylpentyl)ester (8u) $^1$H NMR(400 MHz, CD$_3$OD): δ7.27–7.13(m, 5H), 6.84(dd, J=8.4, 15.6 Hz, 1H), 6.30(brs, 1H), 5.79(d, J=15.8 Hz, 1H), 5.07(d, J=4.8 Hz, 1H), 5.01(s, 1H), 4.96(s, 1H), 4.19(m, 2H), 4.02(s, 1H), 2.68(dd, J=6.45, 13.7 Hz, 1H), 2.5–2.25(m), 2.1(s, 3H), 2.07–1.98(m, 2H), 1.75–1.58(m), 1.55–1.24(m), 1.23–1.05(m), 1.02(d, J=6.64 Hz, 3H), 0.86(m, 15H). MS (–)FAB m/e=773.7

EXAMPLE 196

IA-3-[2-(6-methylheptyl)ester (8v)

$^1$H NMR(400 MHz, CD$_3$OD): δ7.2–7.1(m, 5H), 6.84(dd, J=8.4, 15.6 Hz, 1H), 6.30(d, J=1.6 Hz, 1H), 5.79(d, J=15.6 Hz, 1H), 5.25(d, J=5 Hz, 1H), 5.08(d, J=4.65 Hz, 1H), 5.01(s, 1H), 4.96(s, 1H), 4.02(d, J=1.6 Hz, 1H), 2.67(dd, J=6.45, 13.7 Hz, 1H), 2.44(m), 2.35, 2.24(both m), 2.1(s, 3H), 2.2(m), 2.02(m), 1.69–1.4(m), 1.4–1.25(m), 1.25–1.07(m), 1.22(d, J=6.27 Hz), 1.02(d, J=6.68 Hz, 3H), 0.85(m, 9H). HPLC: RT 19.1 min, MS (–)FAB m/e=801.8

EXAMPLE 197

IA-3-(3-heptyl)ester (8w)

$^1$H NMR(400MHz, CD$_3$OD) δ7.3–7.1(m, 5H), 6.84(dd, J=8.5, 15.6 Hz, 1H), 6.29(d, J=1.66 Hz, 1H), 5.79(d, J=15.77 Hz, 1H), 5.27(d, J=1.66 Hz, 1H), 5.08(d, J=4.37 Hz, 1H), 5.01(s, 1H), 4.96(s, 1H), 4.02(d, J=1.7 Hz, 1H), 2.67(dd, J=6.45, 13.7 Hz, 1H), 2.5–2.2(m), 2.1(s, 3H), 2.03–2.0(m), 1.66–1.47(m), 1.46–1.2(m), 1.2–1.05(m), 1.02(d, J=6.64 Hz, 3H), 0.84(d, J=6.68 Hz, 3H), 0.92–0.84(m, 16H). HPLC: RT 19.07 min, MS (–)FAB m/e=787.5

EXAMPLE 198

IA-3-[2-(3-methoxypropyl)]ester (8x)

$^1$H NMR(400 MHz, CD$_3$OD) δ7.27–7.13(m, 5H), 6.84(dd, J=8.4, 15.6 Hz, 1H), 6.31(d, J=1.8, 1H), 5.79(d J=15.7 Hz, 1H), 5.29(d, J=3.0 Hz, 1H), 5.2–5.09(m), 5.08(d, J=4.65 Hz), 5.01(s), 4.96(s), 4.03(d, J=1.8 Hz, 1H), 3.5–3.4(m), 3.34(s), 2.68(dd, J=6.45, 13.7 Hz, 1H), 2.51–2.15(m), 2.1(S, 3h), 2.05–2.0(m), 1.45–1.26(m), 1.23(m), 1.17–1.07(m), 1.02(d, J=6.64 Hz, 3H), 0.86(m). MS (–)FAB m/e=762

EXAMPLE 199

IA-3-thiobenzyl ester (8d')

A mixture of IA-4,5-di-t-butyl ester, 10a, (0.1 g) and carbonyl di-imidazole (0.022 g) in 3 mL of DMF was stirred for 2 hours at –10° C. To which was added benzyl mercaptan (0.0154 mL). The resulting mixture was stirred for 1 hr at –10° C. 10 mL of EtOAc was added. The solution was extracted with 10 mL of brine. The organic phase was separated, dried and concentrated. The product was purified by prep TLC to afford IA-4,5-t-butyl-3-thiobenzyl ester which was deblocked by TFA in methylene chloride as described earlier to provide the IA-3-thiobenzyl ester. MS (–)FAB m/e 795 (m$^+$–1)

$^1$H NMR(400 MHz, CDCl$_3$) δ0.68–0.92(m, 9H), 1.02(d, J=6 Hz, 3H), 1.0–1.18(m, 3H), 1.20–1.44(m, 3H), 2.0–2.2(s+m, 6H), 2.24–2.52(m, 4H), 2.68(dd, J=5 Hz, 13 Hz, 1H), 4.0–4.21(brs+m, 4H), 5.0(s, 2H), 5.14(d, J=5 Hz, 1H), 5.28(s, 1H), 5.78(d, J=15 Hz, 1H), 5.81(brs, 1H), 6.89(dd, J=9 Hz, 15 Hz, 1H), 7.06–7.38(m, 10H).

EXAMPLE 200

IA-3-(4-chlorothiophenyl) ester (8e')

$^1$H NMR(400 MHz, CDCl$_3$) δ0.68–0.94(m, 9H), 0.96(d, J=6 Hz, 3H), 0.98–1.16(m, 3H), 1.18–1.42(m, 3H), 2.0–2.26(s+m, 6H), 2.26–2.58(m, 4H), 2.72(dd, J=5 Hz, 13 Hz, 1H), 4.09(s, 1H), 5.04(d, J=5 Hz, 1H), 5.31(s, 1H), 5.62–5.86(2 brs, 2H), 6.88(dd, J=9 Hz, 15 Hz, 1H), 7.02–7.40(m, 9H). MS (−)FAB m/e 815 (m$^+$−1)

EXAMPLE 201

IA-3-(3-methylthiobutyl) ester (8f')

$^1$H NMR(400 MHz, CDCl$_3$) δ0.80–0.96(m, 15H), 0.98–1.23(d+m, 6H), 1.2–1.56(m, 5H), 2.04–2.24(s+m, 6H), 26–2.62(m, 4H), 2.66–2.88(m-3H), 4.07(s, 1H), 5.05(s, 2H), 5.21(d, J=5 Hz, 1H), 5.26(s, 1H), 5.82(d, J=15 Hz, 1H), 5.84(s, 1H), 6.91(dd, J=9.15 Hz, 15 Hz, 1H), 7.05–7.40(m, 5H). MS (−)FAB m/e 775 (m$^+$1)

EXAMPLE 202

IA-4,5-di-t-butyl ester 7-MME (10d)

To the C-3 benzyl C-4/C-5 t-butyl triester, 9a, (2.204 mmole, 1.9) in 50 mL CH$_2$Cl$_2$ at 0° C., 1.05 mL of 2-methoxypropene was added, followed by 25 mg of pyridine p-toluene sulfonate (PPTS). The reaction was placed under an N$_2$ atmosphere and stirred for 2 hours. Work-up consisted of diluting the reaction with CH$_2$Cl$_2$ and washing with NaHCO$_3$ and brine. The organic layer was dried over Na$_2$SO$_4$ and the residue purified by chromatography (4.1 Hex:EtOAc, silica gel) to yield the C-7 protected alcohol. The compound was taken-up in 50 mL MeOH and 1-methyl-1,4-cyclo-hexadiene (27.6 mmole, 3.10 ml) and 10% Pd/c (2.5 g) was added. The reaction was heated to 41° C. in a water bath for 10 minutes. Work-up consisted of filtering the reaction through Celite (CH$_2$Cl$_2$ solvent). Concentration and chromatography 5:1 CHCl$_3$:MeOH, silica gel) provided the title diester as a white foam.

$^1$H NMR (400 MHz, CDCl$_3$) δ7.28–7.11 (m, 5H), 6.90 (dd, J=15.70, 8.43 Hz, 1H), 6.51 (s, 1H), 5.85 (d, J=15.67 Hz, 1H), 5.10 (d, J=4.79 Hz, 1H), 5.02 (s, 1H), 4.96 (s, 1H), 4.22(s, 1H), 3.19 (s, 1H), 2.70 (dd, J=13.30, 6.41 Hz, 1H), 2.50–2.42 (m, 3H), 2.30–2.20 (m,2H), 2.10 (s, 3H), 1.95–1.10 (m, 1H), 1.51 (s, 9H), 1.50 (m, 1H), 1.41 (s, 9H), 1.32 (s, 3H), 1.25 (s, 3H), 1.20–1.10 (m, 4H), 1.03 (d, J=6.69 Hz, 3H), 0.90–0.80 (m, 10H). MS (Fab-Neg) 861 (M−1).

EXAMPLE 203

IA-3(2,5-dihydroxyphenylacetic-gamma lactone) ester (8p')

To the C-7 protected IA-4,5-di-t-butyl ester (10d) (0.116 mmole, 100 mg), 2 mL of dry dichloromethane was added and placed under a nitrogen atmosphere. Following, triethylamine (0.58 mmole, 80.8 μL) was added, and the reaction flask was cooled to 0° C. where BOP-Cl (0.232 mmole, 59.1 mg) was added. The reaction was allowed to stir for 1 hour. 2,5-dihydroxyphenyl-acetic gamma lactone (0.580 mmole, 87.1 mg) was added and the reaction was stirred overnight. The following morning, the reaction was diluted with dichloromethane and extracted with sodium bicarbonate and brine. The organic layer was dried over sodium sulfate and concentrated in vacuo. Chromatography (5:1 Hexane:Ethyl Acetate, silica gel) provided the triester as a colorless oil. To the C-7 protected alcohol, IA-3-(2,5-dihydroxyphenylacetic-gamma lactone)-4,5-di-t-butyl-7-MME triester, 2 mL of dry dichloromethane was added and the reaction was placed under a nitrogen atmosphere. 500 μL of TFA was then added and reaction was stirred overnight. The following morning, the reaction was concentrated in vacuo and purified via HPLC to provide the monoester as a colorless oil.

$^1$H NMR (400 MHz, CD$_3$OD): δ7.26–7.09 (m, 8h), 6.85 (dd, J=15.61, 8.30 Hz, 1H), 6.40 (s, 1H), 5.81 (d, J=15.86 Hz, 1H), 5.07 (d, J=4.56 Hz, 1H), 5.02 (s, 1H), 4.97 (s, 1H), 4.08 (s, 1H), 3.83 (s, 2H), 2.69 (dd, J=13.40, 6.31 Hz, 1H), 2.50–2.35 (m, 4H), 2.21 (m, 1H), 2.08 (s, 3H), 1.40–1.25 (m, 6H), 1.15 (m, 2H), 1.04 (d, J=6.64 Hz, 3), 0.90–0.80 (m, 9H). MS (−)FAB m/e 802 (M−2).

EXAMPLE 204

IA-3-(5,6,7,8-tetrahydro-1-naphthol)ester (8g')

Triester (48 mg) was prepared from 1.16 mg of C-7 protected IA-4,5-di-t-butyl ester (10d) and deblocked to provide of IA-3-(5,6,7,8-tetrahydro-1-naphthol)ester by using the procedure shown above except that 5,6,7,8-tetrahydro-1-naphthol was employed.

$^1$H NMR (400 MHz, CD$_3$OD): δ7.20–6.81 (m, 9H), 6.38 (s, 1H), 5.80 (d, J=16.19 Hz, 1H), 5.09 (s, 1), 5.08 (d, J=4.97 Hz, 1H), 5.02 (s, 1H), 4.86 (s, 1H), 4.08 (s, 1H), 2.75 (m, 2H), 2.67 (m, 1H), 2.60 (m, 2H), 2.50–2.35 (m, 5), 2.08 (s, 3H), 1.73 (m, 4H), 1.35–1.25 (m, 6), 1.15 (m, 2H), 1.03 (d, J=6.64 Hz, 3H), 0.90–0.80 (m, 9H). MS (FAB-Neg) m/e 819 (M−1).

EXAMPLE 205

IA-4.5-dibenzyl ester (10c)

To 25 mL of dry TMS-ethanol, 0.382 mL of thionyl chloride was added and allowed to stir for 30 min. To the reaction mixture 5.0 g of I was added and stirred overnight The following day the solution was diluted with water and extracted with ether. The ether layer was dried over anhydrous magnesium sulfate, filtered and evaporated to yield IA-3-(2-trimethylsilyl ethyl)ester which was dissolved in 100 mL of methylene chloride and 16.9 g of benzyl isourea. The following day the methylene chloride was distilled off and the residue dissolved in hexane and filtered over celite. The filtrate was evaporated and chromatographed on silica gel (9:1 hexane:ethyl acetate). The triester obtained as such was dissolved in 25 mL of THF and stirred with tetrabutyl ammonium fluoride (2.47 mL, 1.0M in THF) for four hours. The solution was concentrated and chromatographed on silica gel (8:1 chloroform:methanol) to provide IA-4,5-dibenzyl ester.

$^1$H NMR (400 MHz, CD$_3$OD) δ7.42–7.10(m, 15H), 6.78(dd, J=15.61, 8.8 Hz, 1H), 6.22 (d, J=1.94 Hz, 1H), 5.60 (d, J=0.83 Hz, 1H), 5.05–4.93 (m, 7H), 3.97 (d, J=1.94 Hz, 1H), 2.65(m, 1H), 2.45–2.37(m, 3H), 2.08(s, 3H), 1.35–1.22(m, 4H), 1.10(d, J=6.55 Hz, 5H), 1.03–0.99(m, 4H), 0.86–0.78(m, 10H). MS (−)FAB m/e/869 (M−1)

EXAMPLE 206

IA-3-methyl pivalate ester (8h')

To IA-4,5-dibenzyl ester 10c (0.23 mmole, 200 mg), 2.5 mL of acetonitrile was added, and the solution was stirred at reflux under a nitrogen atmosphere. Following, DBU (2.30 Mole, 0.344 mL) and chloromethyl pivalate (2.30 mmole, 0.332 mL) was added. The solution was stirred at reflux for 3 hours, concentrated in vacuo and chromatographed on silica gel (4:1 Hexane:Ethyl Acetate, silica gel) to provide the triester as a colorless oil.

To IA-4,5-dibenzyl-3 methyl pivalate triester, 3 mL of methanol was added followed by 200 μL of 1-methyl-1,4-cyclohexadiene and 100 mg of 5% Pd/C. The reaction was stirred in a 40° C. water bath for 5 minutes and then filtered through Celite (dichloromethane solvent). The reaction was concentrated in vacuo and purified by HPLC to yield the monoester as a colorless oil. ¹H NMR (400 MHz, CD₃OD): δ7.28–7.10 (m, 5H), 6.85 (dd, J=15.66, 8.53 Hz, 1H), 6.39 (s, 1H), 5.82–5.74 (m, 3H), 5.35 (s, 1H), 5.07 (d, J=4.66 Hz, 1H), 5.02 (s, 1H), 4.95 (s, 1H), 4.02 (s, 1H), 2.69 (dd, J=13.43, 6.55 Hz, 1H), 2.48–2.40 (m, 2H), 2.38–2.30 (m, 1H), 2.24–2.20 (m, 1H), 2.10 (s, 3H), 1.42–1.28 (m, 4H), 1.20 (s, 9H), 1.10 (d, J=6.46 Hz, 3H), 1.03 (d, J=6.69 Hz, 3H), 0.90–0.80 (m, 10H). MS (−)FAB m/e 803 (M−1).

EXAMPLE 207

IA-3-(t-butyl glycolate) ester (8i') and IA-4, 5-dibenzyl-3-t-butyl glycolic acid triester (9f)

IA-3-(t-butyl glycolate) ester (8i) and IA-4, 5-dibenzyl-3-t-butyl glycolic acid triester (9f) were prepared according to the procedure described above from t-butylchloroacetate and 180 mg of IA-4,5-dibenzyl ester, 10c.

IA-3-(t-butyl gylcolate ester) (8i')

¹NMR (400 MHz, CD₃OD): δ7.28–7.12 (m, 5H), 6.85 (dd, J=15.68, 8.48 Hz, 1H), 6.33 (d, J=1.80 Hz, 1H), 5.80 (d, J=1.80 Hz, 1H), 5.43 (s, 1H), 5.07 (d, J=4.57 Hz, 1H), 5.02 (s, 1H), 4.96 (s, 1H), 4.55 (dd, delta v=25.06 Hz, J=14.62 Hz, 2H), 4.02 (d, J=1.80 Hz, 1H), 2.69 (dd, J=12.73, 4.98 Hz, 1H), 2.47–2.30 (m, 5H), 2.10 (s, 3H), 1.60 (m, 4H), 1.47 (s, 9H), 1.30 (m, 2H), 1.03 (d, J=6.69 Hz, 3H), 0.91–0.82 (m, 10H). MS (−)FAB m/e 804 (M).

IA-4,5-dibenzyl-3-t-butyl glycolic acid triester (9f)

¹H NMR (400 MHz, CD₃OD): δ7.38–7.10 (m,15H), 6.80(dd, J=15.67, 8.86 Hz, 1H), 6.32 (d, J=1.41 Hz, 1H), 5.61 (d, J=15.80 Hz, 1H), 5.40 (s, 1H), 5.10–4.95 (m, 8H), 4.20 (s, 2H), 4.03 (d, J=1.91 Hz, 1H), 2.65 (m, 1H), 2.44–2.40 (m, 3H), 2.10 (s, 3H), 1.45(s, 9H), 1.40–1.27 (m, 6H), 1.17–1.10 (m, 4H), 1.03 (d, J=4.58 Hz, 5H), 0.90–0.80 (m, 14H).

EXAMPLE 208

IA-3-glycolic acid ester (8j') and IA-4,5-dibenzyl-3-glycolic acid triester (9g)

To the IA-4,5-dibenzyl-3-t-butylglycolic acid ester (9f) (0.0559 mmole, 55.0 mg) 2 mL of dry dichloromethane was added and stirred under a nitrogen atmosphere. TFA (0.0559 mmole, 4.3 uL) was then added and the reaction was allowed to run overnight. The following morning, the reaction was concentrated in vacuo, and the resulting IA-4,5-dibenzyl-3-glycolic acid triester (9g) (50.1 mg) was debenzylated according to the procedure outlined earlier to provide the monoester as a colorless oil.

IA-3-glycolic acid ester (8j')

¹H NMR (400 MHz, CD₃OD): δ7.28–7.11 (m, 5H), 6.85 (dd, J=15.67, 8.53 Hz, 1H), 6.32 (s, 1H), 5.80 (d, J=15.68 Hz, 1H), 5.43 (s, 1H), 5.08 (d, J=4.88 Hz, 1H), 5.01 (s, 1H), 4.95 (s, 1H), 4.66 (dd, Δv=15.08 Hz, J=16.0 Hz, 2H), 4.02 (s, 1H), 2.68 (dd, J=13.33, 6.32 Hz, 1H), 2.45–2.40 (m, 3H), 2.35 (m, 1H), 2.22 (m, 1H), 2.09 (s, 3H), 1.40–1.25 (m, 4H), 1.20–1.05 (m, 2H), 1.02 (d, J=6.69 Hz, 3H), 0.91–0.80 (m, 10H). MS (−)(FAB m/e 747 (M−1).

IA-4,5-dibenzyl-3-glycolic acid triester (9g)

¹H NMR (400MHz, CD₃OD): δ7.38–7.10 (m, 15H), 6.80 (dd, J=15.60, 8.82 Hz, 1H), 6.32 (d, J=1.42 Hz, 1H), 5.62 (d, J=15.77 Hz, 1H), 5.40 (s, 1H), 5.10–4.95 (m, 8H), 4.29 (s, 2H), 4.03 (d, J=1.93 Hz, 1H), 2.65 (m, 1H), 2.45–2.39 (m, 3H), 2.08 (s, 3H), 1.40–1.23 (m, 6H), 1.16–1.06 (m, 4H), 1.02 (d, J=4.57 Hz, 5H), 0.90–0.79 (m, 14H).

EXAMPLE 209

IA-3-N-Acetyl ethanolamine ester (8k')

To the IA-4,5-dibenzyl ester, 10c, (0.115 mmole, 100 mg) in 3 mL of dichloromethane, oxalyl chloride (2M in dichloromethane, 115 μL) was added, and the system was warmed to reflux under a nitrogen atmosphere. The reaction was stirred overnight and the following morning, excess N-acetylethanolamine was added. Reaction was worked-up by evaporating excess dichloromethane and purified by chromatography on silica gel (1:1 hexane:ethyl acetate, silica gel) to provide the ester which was deprotected as usual to provide the monoester.

¹H NMR (400 MHz, CD₃OD): δ7.28–7.10 (m, 5H), 6.85 (dd, J=15.68, 8.53 Hz, 1H), 6.33 (s, 1H), 5.80 (d, J=15.77 Hz, 1H), 5.32 (s, 1H), 5.07 (d, J=4.98 Hz, 1H), 5.01 (s, 1H), 4.96 (s, 1H), 4.38 (bs, 1H), 4.05 (m, 2H), 3.37 (m, 1H), 2.68 (dd, J=13.37, 6.22 Hz, 1H), 2.30 (m, 1H), 2.20 (m, 1H), 2.08 (s, 3H), 2.05 (m, 2H), 1.95 (s, 3H), 1.41–1.26 (m, 4H), 1.18–1.08 (m, 2H), 1.05 (d, J=6.68 Hz, 3H), 0.90–0.80 (m, 10H). MS (−)FAB m/e 790 (M−1).

EXAMPLE 210

IA-3-piperidinyl glycolamide ester (8l')

To the IA-4,5-dibenzyl-3-glycolic acid triester (9g) (0.083 mmole, 77 mg) in 3 mL of refluxing dichloromethane, oxalyl chloride (0.166 mmole, 83 μL) was added followed by triethylamine (0.083 mmole, 11.6 μL). The reaction was stirred overnight and addition of piperidine ((0.125 mmole, 12.3 μL) gave the triester which was purified by HPLC and debenzylated by the usual procedure to provide the IA-3-piperidinyl glycolamide ester.

¹H NMR (400 MHz, CD₃OD): δ7.28–7.10 (m, 5H), 6.85 (dd, J=15.66, 8.48 Hz, 1H), 6.35 (s, 1H), 5.80 (d, J=15.77 Hz, 1H), 5.48 (s, 1H), 5.09 (d, J=4.79 Hz, 1H), 5.02 (s, 1H), 4.95 (s, 1H), 4.90 (apparent dd, 2H), 4.02 (s, 1H), 3.52 (bt, 2H), 3.37 (bt, 2H), 2.67 (dd, J=13.32, 6.32 Hz, 1H), 2.09 (s, 3H), 1.70–1.46 (m, 10H), 1.40–1.25 (m, 5H), 1.20–1.10 (m, 2H), 1.03 (d, J=6.64 Hz, 3H), 0.90–0.79 (m, 10H). MS (−)FAB m/e 814 (M−1).

EXAMPLE 211

IA-Morpholinyl glycolamide ester (8m')

The blocked title compound was prepared according to the procedure for compound 81' but using a drop of triethylamine followed by one equivalent of morpholine. Isolation of the triester by HPLC and deblocking by the usual procedure provided the monoester as a colorless oil. ¹H NMR (400 MHz, CD₃OD): δ7.28–7.10 (m, 5H), 6.85 (dd; J=15.63, 8.57 Hz, 1H), 6.40 (s, 1H), 5.80 (d, J=15.36 Hz, 1H), 5.48 (s, 1H), 5.02 (s, 1H), 4.85 (apparent dd, 2H), 4.03 (s, 1H), 3.65 (m, 4H), 3.45 (m, 2H), 3.30 (m, 1H), 2.68 (dd, J=13.49, 6.46 Hz, 1H), 2.45 (m, 2H), 2.32 (m, 1H), 2.22 (m, 1H), 2.08 (s, 3H), 1.30 (m, 5H), 1.13 (m, 2H), 1.01 (d, J=6.64 Hz, 3H), 0.90–0.80 (m, 0H). MS (−)FAB m/e 816 (M−1).

EXAMPLE 212

IA-3-glycolamide ester (8n')

The blocked title compound was prepared according to the procedure outlined above except that ammonia gas was bubbled into the reaction mixture. The protected amide was deblocked as usual to provide the monoester as a colorless oil.

¹H NMR (400 MHz, CD₃OD): δ7.30–7.10 (m, 5H), 6.85 (dd, J=15.66, 8.48 Hz, 1H), 6.33 (s, 1H), 5.80 (d, J=1 5.77 Hz, 1H), 5.45 (s, 1), 5.06 (d, J=4.66 Hz, 1H), 5.02 (s, 1H), 4.96 (s, 1H), 4.62 (dd, delta v=100.35 Hz, J=15.59 Hz, 2), 4.03 (s, 1H), 2.69 (dd, J=13.44, 6.31 Hz, 1H), 2.48–2.40 (m, 3H), 2.26–2.19 (m, 1H), 2.10 (s, 3H), 2.05–1.99 (m, 2H), 1.42–1.25 (m, 4H), 1.18–1.10 (m, 2H), 1.02 (d, J=6.73 Hz, 2H), 0.9 0–0.80 (m, 10H). MS (–)FAB m/e 746 (M–1).

EXAMPLE 213

IA-3-pyrrolidinyl glycolamide ester (8o')

Compound prepared according to the procedure described above but using pyrrolidine. The protected amide was deblocked as usual to provide the monoester as a colorless oil.

1H NMR (400 MHz, $CD_3OD$): δ7.28–7.10 (m, 5H), 6.85 (dd, J=15.65, 8.59 Hz, 1H), 6.35 (s, 1H), 5.80 (d, J=15.35 Hz, 1H), 5.48 (s, 1H), 5.07 (d, J=4.56 Hz, 1H), 5.01 (s, 1H), 4.96 (s, 1H), 4.90 (apparent dd, 2H), 4.02 (s, 1H), 3.50–3.40 (m, 4H), 2.68 (dd, J=13.40, 6.55 Hz, 1H), 2.48–2.40 (m, 3H), 2.10 (s, 3H), 2.07–1.95 (m, 5H), 1.90–1.81 (m, 2H), 1.40–1.25 (m, 4H), 1.20–1.10 (m, 3H), 1.03 (d, J=6.69 Hz, 3H), 0.90–0.80 (m, 10H). MS (–)FAB m/e 800 (M–1)

EXAMPLE 214

Preparation of IA-3-benzyl-4,5-di-t-butyl ester (9a)

To a solution of (8a) (100 mg) in methylene chloride (2 mL) was added O-t-butyl-N,N'-diisopropylisourea (300 mg) and the solution was stirred at 40° C. for 2 days. The reaction mixture was then cooled to room temperature, concentrated in vacuo and filtered through silica eluting with ethyl acetate:hexane, 1:4 to yield the title compound. $^1$H NMR (400 MHz, $CDCl_3$) δ7.35–7.08(m, 10H), 6.89(dd, J=16, 8.4 Hz, 1H), 5.97(d, J=1Hz, 1H), 5.75(d, J=16 Hz), 1H), 5.24(s, 1H), 5.16(dd, J=12 Hz, 64 Hz, 2H), 5.06(br s, 1H), 4.94(br s, 2H), 4.00(br s, 1H), 2.96(d, J=2 Hz, 1H), 2.66(m, 1H), 2.5–2.2(m, 5H), 2.15–2.00(m, 4H), 2.05(s, 3H), 1.39(s, 9H), 1.37(s, 9H), 1.40–1.05(m, 6H), 1.02(d, J=6 Hz, 3H), 0.86–0.76(m, 9H).

EXAMPLE 215

I-3,4,5-tris(methyl pivalate)ester (9b)

To IA (0.145 mmole, 100 mg) in 7 mL of acetonitrile, DBU (4.35 mmole, 0.650 mL) and chloromethyl pivalate (4.35 mmole, 0.627 mL) was added. The solution was placed under a nitrogen atmosphere, heated to reflux, and stirred overnight. The following morning, the reaction was diluted with dichloromethane and extracted with sodium bicarbonate and brine. The organic layer was dried over sodium sulfate and concentrated in vacuo. Chromatography (3.5:1 Hexane:Ethyl Acetate) provided the triester as a colorless oil.

$^1$H NMR (400 MHz, $CD_2Cl_2$) δ7.28–7.10 (m, 5H) 6.88 (dd, J-15.69, 8.5 Hz, 1H, 5.98 (d, J-5.41 Hz, 1H), 5.82–5.70 (m, 7H), 5.62 (s, 1H), 5.20 (s, 1H), 5.05 (d, J=4.84 Hz, 1), 4.95 (d, J=6.22 Hz, 2H), 3.98 (s, 1H), 3.78 (s, 1H), 3.27 (d, J=2.28 Hz, 1H), 2.65 (dd, J=13.35, 7.69 Hz, 1H), 2.45–2.30 (m, 4H), 2.08 (s, 3H), 1.63 (s, 1H), 1.32–1.22 (m, 3H), 1.20 (s, 27H), 1.02 (d, J=6.59 Hz, 3H), 0.88–0.78 (m, 10H). MS (–)FAB m/e 1168 (M+dithiothreitol).

EXAMPLE 216 preparation of IA-4,5-di-t-butyl ester (10a).

To a solution of IA-3-benzyl-4,5-di-t-butyl ester (9a) (100 mg) in methanol (4 mL) was added 1-methyl-1,4-cyclohexadiene (200 uL) and Pd/C (50 mg). The reaction mixture was stirred at 30°–35° C. for 1.5 hr and filtered over celite. The filtrate was evaporated in vacuo to give the title compound.

$^1$NMR (400 MHz, $CD_3OD$) δ7.30–7.10(m, 5H), 6.89(dd, J=8,16 Hz, 1), 6.43(d, J=1 Hz, 1H), 5.82(d, J=16 Hz, 1H), 5.06(d, J=5 Hz, 1H), 5.04(s, 1H), 5.01 & 4.96(each s, each 1H), 4.07(s, 1H), 2.69(m, 1H), 2.51–2.20(m, 6H), 2.10(s, 3H), 1.60(s, 9H), 1.42(s, 9H), 1.65–1.05(m, 6H), 1.03(d, J=8.1 Hz, 3H), 0.88(m, 10H).

EXAMPLE 217

Preparation of IA-4,5-dimethyl ester (10b)

A solution of IA-3-benzyl ester (8a) (30.4 mg) in ethyl acetate (1 mL), was cooled to 10° C. and treated with a solution of diazomethane in diethyl ether (0.5 mL) and was stirred for 1 hour. The solvent was subsequently evaporated in vacuo and the residue was purified by chromatography (silica, ethyl acetate-hexane 4:6). The purified IA-3-benzyl-4,5-dimethyl ester (18.6 mg) was dissolved in methanol (1 mL) and debenzylated with 1-methyl-1,4-cyclohexadiene (40 uL) and 10% Pd/C (39 mg) by procedures outlined for example (10a) to yield IA-3,4-dimethyl ester (10b).

$^1$H NMR ($CD_3OD$, 400 MHz) δ7.30–7.12(m, 5H), 6.88(dd, J=9, 16 Hz, 1H), 6.28(d, J=1.5 Hz, 1H), 5.77(d, J=16 Hz, 1H), 5.27(s, 1H), 5.06(d, J=4.8 Hz, 1H), 5.02 and 4.97(ea s, ea 1H), 4.05(d, J=1.6 Hz, 1H), 3.85, 3.67(ea s, ea 3H), 2.68(m, 1H), 2.5–2.15(m,), 2.10(s, 3H), 1.03(d, J=7 Hz, 3H), 0.87(m); MS (FAB) m/e 741, 742 [M+Na]$^+$.

EXAMPLE 218

IA-4,5-bis(methyl pivalate)ester (10e)

The title compound was prepared from IA-3-benzyl ester (8a) (26.3 mg) and debenzylated in the usual way.

$^1$H NMR (400 MHz, $CD_3OD$): δ7.28–7.10 (m, 5H), 6.85 (dd, J=15.63, 8.72 Hz, 1H), 6.12 (d, J=1.84 Hz, 1H), 5.90–5.70 (m, 7H), 5.12 (s, 1H), 5.05 (d, J=4.57 Hz, 1H), 5.01 (s, 1H), 3.99 (d, J=1.89 Hz, 1H), 3.33 (s, 1H), 2.65 (dd, J=6.64 Hz, 1H), 2.45 (m, 3H), 2.32 (m, 1H), 2.21 (m, 1H), 2.09 (s, 3H), 1.40–1.25 (m, 4H), 1.20 (d, J=2.54 Hz, 18H), 1.05 (d, J=6.64 Hz, 3H), 0.90–0.81 (m, 10H). MS (–)FAB m/e 917 (M–1).

EXAMPLE 219

Preparation of IA-3-carboxamide (12a)
Step A.
Preparation of IA-4,5-di-t-butylester-3-carboxamide (11a).

N-methylmorpholine (6.9 ul, 0.063 mmole) was added to a solution of 4,5-di-t-butyl-3-carboxylic acid (10a) (46 mg) dissolved in 1.02 mL of methylene chloride and stirred at room temperature for 20 min. The reaction mixture was cooled to –20° and isobutyl chloroformate (8.17 ul) was added dropwise and stirring continued for an hour. 1.3 mL of tetrahydrofuran was added and the reaction mixture was allowed to warm up to 0° C. Dry ammonia was then bubbled into the reaction mixture for 2 hr at 0° C. and 1 hr at room temperature. Filtration, evaporation and purification by prep TLC (silica, ethyl acetate/hexane 6/4) gave compound 11a.

$^1$NMR(400 MHz, $CD_3OD$) δ7.33–7.12(m, 5H), 6.89(dd, J=8, 15.6 Hz, 1H), 5.83(d, J=15.6 Hz, 1H), 5.43(s, 1H), 5.14(s, 1H), 5.07(d, J=4 Hz, 1H), 5.04(s, 1H), 4.98(s, 1H), 4.10(s, 1H), 2.11(s, 3H), 1.59(s, 9H), 1.42(s, 9H).

EXAMPLE 220

Step B.
Preparation of IA-3-carboxamide (12a).

A solution of trifluoroacetic acid (200 ml) in 0.5 ml of methylene chloride was added to a stirred solution of IA-4,5-di-t-butyl-3-carboxamide (11a, 32 mg) in 1 ml of methylene chloride and the mixture was stirred at room temperature for 3 days whence the total deprotection was realized (monitored by HPLC). On evaporation, trituration twice with toluene, and re-evaporation to dryness yielded the 3-carboxamido-4,5-dicarboxylic acid 12a.

$^1$H NMR (400 MHz, CD$_3$OD) δ7.1–7.3(m, 5H), 6.85(dd, J=8.5, 15.6 Hz 1H), 6.30(br s, 1H), 5.79(d, J=15.6 Hz, 1H), 5.13(br s, 1H), 5.05(d, J=4.6 Hz, 1H), 5.03(s, 1H), 4.05(br s, 1H), 2.67(dd, J=5.2, 13.6 Hz, 1H), 2.55–2.35 (m), 2.34–2.15 (m), 2.10 (s, 3H), 2.03(m, 2H), 1.40–1.25 (m), 1.20–1.05 (m), 1.02 (d, J=6.7 Hz, 3), 0.86–0.84 (m, 9H), MS (FAB-Li sppke ) m/z 702 (m+2Li)$^+$.

EXAMPLE 221

Preparation of IA-3-benzylamide (12b).

By using a similar procedure as shown above, IA-4,5-di-t-butyl-3-benzylamide (11b) was prepared from IA-4,5-di-t-butyl- 3-carboxylic acid (10a) (37.8 mg), methylene chloride (0.84 mL), tetrahydrofuran (1.1 mL), N-methylmorpholine (5.7 uL), isobutyl chloroformate (6.71 uL) and benzylamine (5.66 uL).

$^1$H NMR(400 MHz, CD$_3$OD) δ7.30–7.03(m, 10H), 6.89(dd, J=8.0, 15.6 Hz, 1H), 6.83(br s, 1H), 5.98(d, J=0.8 Hz, 1H), 5.76(d, J=15.6 Hz, 1H), 5.12(s, 1H), 4.99(d, J=4 Hz, 1H), 4.88(br d, J=4.8 Hz, 2H), 4.01(d, J=0.8 Hz, 1H), 2.01(s, 3H), 1.59(s, 9H), 1.46(s, 9H). 26 mg of 4,5-di-t-butyl-3-benzylamide 11b was deprotected with trifluoroacetic acid (300 uL) in methylene chloride (1.6 mL) over a period of 16 hr to give the desired compound 12b. MS FAB m/e 799 (M+3Li); $^1$H NMR (400 MHz, CD$_3$OD) δ2.10(s, 3H), 4.10(s, 1H), 4.46(br s, 2H), 5.04(br s, 1H), 5.07(d, J=5 Hz, 1H)), 5.26(s, 1H), 5.83(d, J=15.6, 1H), 6.36(br s, 1H), 6.88(dd, J=8.4, 15.6, 1H), 7.1–7.4(m, 10H).

EXAMPLE 222

Preparation of IA-3-heptylamide (12c).

By using a procedure analogous to that shown above, IA-4,5-di-t-butyl-3-heptylamide was prepared from IA-4,5-di-t-butyl-3-carboxylicacid (10a) (46 mg), methylene chloride (1.02 mL), tetrahydrofuran (1.3 mL), N-methylmorpholine (6.93 uL) and heptylamine (25.5 uL).

$^1$H-NMR(400 MHz,CD$_3$OD) δ1.42(s, 9H), 1.63(s, 9H), 2.12(s, 3H), 3.16(m, 2H), 4.09(s, 1H), 5.01(d, 2H), 5.14(s, 1H), 5.82(d, 2H), 6.43(s, 1H), 6.89(m, 1H), 7.11–7.30(m, 5H), 7.34(t, 1H). 28 mg of 4,5-di-t-butyl-3-heptylamide was stirred with trifluoroacetic acid (300 uL) in methylene chloride (1.6 mL) over a period of 16 hr to give the desired compound 12c. $^1$H-NMR (400 MHz,CD$_3$OD) δ7.35–7.03(m, 5H), 6.84(dd, J=8.0, 15.6 Hz, 1H), 6.29(br s, 1H), 6.26(br s, 5.78(d, J=15.6, 1H), 5.12(s, 1H), 5.07(d, J=4 Hz, 1H), 5.04(s, 1H), 4.98(s, 1H), 4.07 (br s, 1H), 2.11 (s, 3H); MS FAB m/e 807 (M+3Li).

EXAMPLE 223

Preparation of IA-3-ethylamide (12d).

By a procedure similar to that shown above, IA-4,5-di-t-butyl-3-ethylamide was prepared from IA-4,5-di-t-butyl-3-carboxylic acid (40 mg), methylene chloride (1 mL), tetrahydrofuran (1.3 mL), N-methylmorpholine (5.5 uL), isobutyl chloroformate (7.1 uL) and ethylamine (slowly bubbled in for 1 min). HPLC Rt 24.3 min. 21 mg of di-t-butyl-3-ethylamide was stirred with trifluoroacetic acid (400 uL) in methylene chloride (2.0 mL) over a period of 16 hr to give the title compound. $^1$H-NMR (400 MHz,CD$_3$OD) δ7.30–7.1-(m, 5H), 6.84(dd, 8.0, 16 Hz, 1H), 6.30(s, 1H), 5.79(d, J=16 Hz, 1H), 5.12(s, 1H), 5.10–5.02(m, 2H), 5.05 & 5.00(each s, each 1H), 4.06(d, J=1 Hz, 1H), 3.78(m, 2H), 3.26–3.14(m, 4H), 2.68(m, 1H), 2.50–2.15(m, 7H), 2.11(s, 3H), 1.45–1.06(m, 6H), 1.03(d, J=8 Hz, 3H ), 0.86(m, 12H); MS FAB m/e 739(M+Na).

EXAMPLE 224

Preparation of IA-3-N,N-dimethylamide (12e).

By a procedure similar to that shown above, IA-4,5-di-t-butyl- 3-(N,N-dimethyl)amide was prepared from IA-4,5-di-t-butyl-3-carboxylic acid, 10a, (40 mg), methylene chloride (1 mL), tetrahydrofuran (1.3 mL), N-methylmorpholine (5.5 uL), isobutyl chloroformate (7.1 uL) and dimethylamine (bubbled in for 1 min). HPLC Rt 24.92 min. 30 mg of 4,5-di-t-butyl-3-(N,N-dimethyl)amide was stirred with trifluoroacetic acid (400 uL) in methylene chloride (2.0 mL) over a period of 16 hr to give 14.4 mg of the title compound. MS FAB m/e 740(M+Na), 761(M+2 Na), 783(M+3 Na); $^1$H-NMR (400 MHz, CD$_3$OD) δ7.30–7.10(m, 5H), 6.85(dd, J=8, 15 Hz, 1H), 6.16(d, J=1Hz, 1H), 5.80(d, J=15 Hz, 1H), 5.37(s, 1H), 5.04(d, 1H), 4.98 & 4.96(each s, each 1H), 4.06(d, J=1Hz, 1H), 3.20 & 2.90(each s, each 3H), 2.64(m, 1H), 2.50–2.10(m, 6H), 2.10(s, 3H), 1.40–1.10(m, 10H), 1.03(d, J=8 Hz, 3H), 0.87 (m, 10H).

EXAMPLE 225

Preparation of IA-3-(N-methyl)phenylamide (12f).

By a procedure similar to that shown above, IA-4,5-di-t-butyl- 3-(N-methyl)phenylamide was prepared from IA-4, 5-di-t-butyl-3-carboxylic acid, 10a, (40 mg), methylene chloride (1 mL), tetrahydrofuran (1.3 mL), N-methylmorpholine (5.5 uL), isobutyl chloroformate (7.1 uL) and N-methylaniline (9 uL). 19 mg of 4,5-di-t-butyl-3-(N-methyl)phenylamide was stirred with trifluoroacetic acid (400 uL) in methylene chloride (2.0 mL) over a period of 16 hr to give the title compound. MS FAB m/e 801(M+Na), 824(M+2Na), 846(M+3Na); Characteristic NMR peaks $^1$H-NMR (400 MHz,CD$_3$OD) δ7.40–7.10(m 10H, Ar—H), 3.24(s, 3H N-He), 2.10(s, 3H, COMe).

EXAMPLE 226

Preparation of I-3-morpholino amide (12g)

NMR (400 MHz, CD$_3$OD) δ7.15–7.30 (m, 5H), 6.84 (dd, J=8.4, 15.6 Hz, 1H), 6.13 (bs, 1H), 5.79 (d, J=15.6 Hz, 1H), 5.31 (s, 1H), 5.03 (d, J=4.6 Hz, 1H), 4.98 (d, J=8 Hz, 2H), 4.05 (bs, 1H), 3.5–3.75 (m, 3H), 2.09 (s, 3H). MS (FAB-Li Spike) m/z 778 (M$^+$+3Li)

EXAMPLE 227

IA-3-(3-isopropoxy)propylamide (12h)

IA-4,5-di-t-butyl ester, 10a, (0.2 g, 0.249mmole) and 4-methyl morpholine (30 mL, 0.29 mmole) in 14 mL of THF at −20° C. was added isobutylchloroformate (38 mL, 0.29 mmole). The mixture was stirred for 10 min, at −20° C., then isopropoxypropylamine (50 mL, 0.42 mmole) was added. The resulting mixture was stirred for 1 hr at −20° C. additional 1 hr at r.t. The mixture was concentrated in vacuo and the product was purified by prep. TLC to provide IA-4,5-di-t-butyl-3-isopropoxypropylamide. IA-4,5-di-t-butyl-3-isopropoxypropylamide in 4.5 mL of methylene chloride/TFA (4:1) was stirred at 0° C. was stirred for 17 hrs at r.t. and the solution was concentrated in vacuo. The residue was dissolved in 3 mL of toluene and evaporated. This procedure was repeated two more times to remove the trace amount of TFA. Finally, the residue was dissolved in 3 mL of benzene and freeze-dried to provide the title compound.
MS (–)FAB m/e 788(m⁺–1)

1H NMR (200 MHz, CDCl$_3$) δ0.70–0.92(m, 9H), 1.03 (d, J=6 Hz, 3), 1.18(d, J=6Hz, 6), 1.00–1.23(m, 3H), 1.23–1.48(m, 3H), 1.65–1.91(m, 2H), 1.99–2.23(m, 6), 2.23–2.53(m, 4H), 2.71(dd, J=5.13 Hz, 1H), 3.16–3.41 (m, 1H), 3.41–3.71(M, 5H), 4.07(s, 1H), 5.02 (d, J=6Hz, 2H), 5.13(d, J=5 Hz, 1H), 5.82 (d, J=15 Hz, 1H), 5.94 (s, 1H), 6.92 (dd, J=9.15 Hz, 1H), 7.00–7.09(m, 1), 7.10–7.39 (m, 5H)

The following compounds, 12i through 12q and 8y through 8c' were made by using the procedure described for IA-3-(3-isopropoxy)-propylamide and appropriate reagents.

EXAMPLE 228

IA-3-azetamide (12i)

$^1$NMR(400 MHz, CD$_3$OD) δ7.3–7.16(m, 5H), 6.84(dd, J=8.5, 15.6 Hz, 1H), 6.27(s, 1H), 5.79(d, J=15.6 Hz, 1H), 5.27(s, 1H), 5.50(d, J=4.6 Hz, 1H), 4.98(d, J=6.64 Hz, 2H), 4.621(m, 1H), 4.04(s, 1H), 4.01(m, 2H), 2.67(dd, J=6.45, 13.7 Hz, 1H), 2.5–2.13(m), 2.1(s, 3H), 2.06–1.98(m, 2H), 1.4–1.22(m), 1.2–1.06(m), 1.02(d, J=6.68 Hz, 3H), 0.86(m, 9H).

EXAMPLE 229

IA-3-(2-methoxyethyl)amide (12j)

$^1$H NMR (200 MHz, CDCl$_3$) δ0.70–0.92(m, 9H), 1.03 (d, J=6 Hz, 3H), 1.04–1.20(m, 3H), 1.20–1.42(m, 3H), 2.11 (s, 3H), 1.98–2.20 (m, 3H), 2.20–2.48(m, 4H), 2.62(dd, 1H), 3.27 (s, 3H), 3.36–3.62(m, 5H), 4.05(br, s, 1H), 5.02 (s, 2H), 5.10 (d, $^1$H, J=5H), 5.21(s, 1H), 5.82 (d, J=15 Hz, 1H), 5.92 (s, 1H), 6.9(dd, J=9, 15 Hz, 1H), 7.08–7.42(m, 6H). MS (–)FAB m/e 746(m⁺–1)

EXAMPLE 230

IA-3-(2-dimethylaminoethyl)amide (12k )

$^1$H NMR(400 MHz, CD$_3$OD) δ7.27–7.12 (m, 5H), 6.87(dd, J=14.8, 8.8, Hz, 1H), 6.17(s, 1H), 5.82(d, J=16.0 Hz, 1H), 5.03(s, 1H) 5.02 (s, 1H), 4.98 (d, J=12.0 Hz, 1H), 4.90(s, 1H), 4.05 (s, 1H), 3.88–3.80(m, 2H), 3.60–3.39 (m, 3H), 3.22(d, J=2.8 Hz, 1H), 2.97–2.88 (m, 5H), 2.66 (dd, J=13.6, 6.8 Hz, 1H), 2.48–2.40(m, 2H), 2.37, 2.27(m, 2H), 2.09(d, J=4.0 Hz, 3H), 2.02–1.89 (m, 2H), 1.42–1.26 (m, 2H), 1.71–1.10(m, 2H), 1.03(d, 3H), 0.99–0.79(m, 9H).

EXAMPLE 231

IA-3-(2-amidopyridine) (12l)

$^1$H NMR(400 MHz, CD$_3$OD) δ8.57(d, J=6.4 Hz, 2H), 7.25–7.09(m, 7H), 6.88(dd, J=14.8, 7.6 Hz, 1H), 6.35(s, 1H), 5.82(d, J=14.8 Hz, 2H), 5.12(d, J=4.8 Hz, 1H), 5.09(s, 1H), 5.04(s, 1H), 4.89(s, 1H), 4.11(s, 1H), 2.74(dd, J=13.6, 6.0 Hz, 1H), 2.46–2.38(m, 5H), 2.29–2.22(m, 1H), 2.19–2.13(m, 2H), 2.11(s, 3H), 1.41–1.21(m, 2H), 1.20–1.07(m, 2H), 1.04(d, J=6.4 Hz, 3H), 0.99–0.79(m, 9H).

EXAMPLE 232

IA-3-(2-dimethylamino ethyl)ester (8y)

$^1$H NMR(400 MHz, CD$_3$OD) δ7.27–7.12 (m, 5H), 6.87(dd, J=15.6, 8.4, Hz, 1H), 6.34(s, 1H), 5.82(d, J=15.6, 1H), 5.07(d, J=4.8 Hz, 1H), 4.96(s, 1H), 4.89(s, 1H), 4.02(s, 1H), 3.71(s, 2H), 2.70(dd, J=13.6, 6.6 Hz, 1H), 2.46–2.1(m, 6H), 2.09(s, 3H), 2.03–1.99(m, 2H), 1.59–1.20(m, 4H), 1.18–1.11(m, 2H), 1.10(d, J=6.4 Hz, 3H), 1.03 (d, J=6.8 Hz, 3H), 0.99–0.79(m, 12H).

EXAMPLE 233

IA-3-(3-trifluoromethylbenzyl)ester (8z)

$^1$H NMR(400 MHz, CD$_3$OD) δ7.68–7.54 (m, 4H), 7.25–7.05(m, 5H), 6.87(dd, 15.6, 8.8 Hz, 1H), 6.31(d, 1H), 5.81(d, J+15.6 Hz, 1H), 5.38 (s, 1H), 5.37(d, J=12.4 Hz, 1H), 5.30(s, 1H), 5.22(s, 1H), 5.07(d, J=5.2 Hz, 1H), 4.99(s, 1H), 4.03(d, 1H), 2.69 (dd, J=13.2, 6.8 Hz, 1H) 2.47–2.2(m, 5H ), 2.15(s, 3H), 2.09–1.94(m, 2H), 1.42–1.2(m, 3H), 1.17–1.08(m, 2H), 1.03(d, 3H), 0.99–0.80(m, 9H).

EXAMPLE 234

IA-3-(3-chlorobenzyl)ester (8a')

$^1$H NMR(400 MHz, CD$_3$OD) δ7.50–7.12 (m, 9H), 6.87(dd, 15.6, 8.8 Hz, 1H), 6.32(d, J=1.6 Hz, 1H), 5.80(d, J=14.4 Hz, 1H), 5.25(d, J=12.8 Hz, 1H), 5.11(s, 1H), 5.06(d, J=4.8 Hz, 2H), 4.96(s, 2H), 4.04(d, J=2.0 Hz, 1H), 2.66 (dd, J=13.2, 6.8 Hz, 1H) 2.43–2.41(m, 4H), 2.38–2.14(m, 1H), 2.08(s, 3H), 2.0 3–1.99(m, 2H), 1.29–1.25(m-5H), 1.10(d, J=6.4 Hz, 3H), 1.02(d, J=6.8 Hz, 3H), 0.99–0.84(m, 6H).

EXAMPLE 235

IA-3-(3-methylbenzyl)ester (8b')

$^1$H NMR(400 MHz, CD$_3$OD) δ7.28–7.08(m, 8H), 6.87(dd, 15.6, 8 Hz, 1H), 6.32(s, 1H), 5.81(d, J=15.6 Hz, 1H), 5.24(d, J=11.6 Hz, 1H), 5.07(d, J=4.8 Hz, 1H), 4.99(s, 1H), 4.95(s, 1H), 4.82(s, 1H), 2.69(dd, J=10.4, 6.8 Hz, 1H), 2.48–2.34(m, 6), 2.32(s, 3H), 2.29, 2.15(m, 3H), 2.08(s, 8H), 2.06–192(m, 2H), 1.59–1.30(m, 2H), 1.29–1.07(m, 2), 1.03(d, J=6.8 Hz, 3H), 0.99–0.71(m, 9H).

EXAMPLE 235A

IA-3-pyrrolidinyl ester (8c')

$^1$H NMR(400 MHz, CD$_3$OD) δ7.27–7.12(m, 5H), 6.88(dd, 15.6, 8.8 Hz, 1H), 6.22(s, 1H), 5.81(d, J=16.0 Hz, 1H), 5.04(s, 1H), 4.99(d, J=12.4 Hz, 1H), 4.89(s, 1H), 4.84(s, 1H), 4.38–4.35(m, 2H), 4.06–4.05(m, 1H), 3.91–3.90(m, 1H), 2.47–2.01(M, 7H), 2.00(s, 3H), 1.98–1.84(m, 2), 1.42–1.25(m, 3H), 1.24–1.07(m, 2H), 1.03(d, J=6.4 Hz, 3H), 0.99–0.81(m, 9H).

EXAMPLE 236

IA-3-(3-amidopyridine) (12m)

$^1$H NMR(400 MHz, CD$_3$OD) δ8.48(d, J=8.4 Hz, 2H), 7.80(brs, 2H), 7.23–7.09(m, 5H), 6.89(dd, J=15.6, 8.4 Hz, 1H), 6.36(brs, 2H) 5.83(d, J=15.2 Hz, 1H), 5.08(s, 1H), 5.07(d, J=4.8 Hz, 1H), 5.03(s, 1H), 4.91(s, 1H), 3.34(s, 1H), 2.71(dd, J=13.6, 6.8 Hz, 1H), 2.48–2.40(m, 3H), 2.35–2.13(m, 5H), 2.10(s, 3H), 1.49–1.21(m, 4H), 1.04(d, J=6.4 Hz, 3H), 1.01–0.81(m, 9H).

EXAMPLE 237

IA-3-(4-amidopyrimidine) (12n)

$^1$H NMR(400 MHz CD$_3$OD) δ8.55(brs, 1H), 7.29–7.13(m, 7H), 6.95(dd, J=20.8, 11.6 Hz, 1H), 6.41(s, 1H), 5.88(d, J=20.8 Hz, 1H), 5.13(d, J=6.0 Hz, 1H), 5.42(s, 1H), 5.10(s, 1H), 5.08(s, 1H), 4.99(s, 1H), 2.79(dd, J=17.6, 8.8 Hz, 1H), 2.53–2.31(m, 5H), 2.29(m, 1H), 2.20, 2.1(m, 2H), 2.16(s, 3H), 1.49–1.21(m, 2H), 1.19–1.13(m, 2H), 2.16(s, 3H), 1.49–1.21(m, 2H), 1.19–1.13(m, 2H), 1.09(d, J=9.2 Hz, 3H), 1.05–0.89(m, 9H).

EXAMPLE 238

IA-3-(5-amidoquinoline). (12o)

$^1$H NMR(400 MHz, CD$_3$OD) δ9.23(d, J=8.0 Hz, 1HO, 8.96–8.88(m, 1H), 8.62(d, J=8.0 Hz, 1H), 7.99(d, J=8.4 Hz, 1H), 7.88–7.70(m, 2H), 7.66–7.57(m, 1H), 7.29–7.01 (m, 5H), 6.90(dd, J=15.6, 8.8 Hz, 1H), 6.43(d, J=2.0 Hz, 1H), 5.84(d, J=15.6 Hz, 1H), 5.08(s, 1H), 4.99(s, 1H), 4.93(d,

J=4.6 Hz, 1H), 4.88(s, 1H), 4.16(s, 1H), 2.69(dd, J=13.2, 6.4 Hz, 1H), 2.56–2.29(m, 4H), 2.23–2.16(m, 2H), 2.05(s, 3H), 2.04–2.00(m, 2H), 1.47–1.22(m, 5H), 1.19–1.07(m, 2H), 1.05(d, J=6.8 Hz, 3H), 0.99–0.77(m, 6H).

EXAMPLE 239

IA-3-pyrrolidinamide (12p)

The reaction was run according to the procedure above except that the IA-4,5-dibenzyl-3-glycolic acid ester (9g) (0.101 mmole, 100 mg) was used with excess pyrrolidine. Chromatography (1:1 Hexane:Ethyl Acetate, silica gel) provided the diester-amide which was debenzylated by the usual procedure to yield IA-3-pyrrolidinamide as a colorless oil.

$^1$H NMR (400 MHz, CD$_3$OD): δ7.28–7.10 (m, 5H), 6.85 (dd, J=15.63, 8.53 Hz, 1H), 6.20 (s, 1H), 5.80 (d, J=15.77 Hz, 1H), 5.31 (s, 1H), 5.04 (d, J=4.56 Hz, 1H), 4.99 (s, 1H), 4.95 (s, 1H), 4.05 (s, 1H), 3.81 (m, 1H), 3.68 (m, 1H), 3.40 (m, 2H), 2.65 (dd, J=13.44, 6.64 Hz, 1H), 2.45–2.25 (m, 4H), 2.09 (s, 3H), 1.90–1.75 (m, 4H), 1.40–1.25 (m, 5H), 1.20–1.10 (m, 2H), 1.02 (d, J=6.63 Hz, 3H), 0.90–0.80 (m, 10H). MS (−)FAB m/e

EXAMPLE 240

IA-3-piperidinylamide (12q)

Triester (60 mg) was prepared according to the procedure outlined above from IA-4,5-dibenzyl ester, 10c, (80 mg) and piperidine and deblocked as usual to provide the monoester as a colorless oil.

$^1$H NMR (400 MHz, CD$_3$OD): δ7.28–7.11 (m, 5H), 6.85 (dd, J=15.66, 8.48 Hz, 1H), 6.15 (s, 1H), 5.80 (d, J=15.35 Hz, 1H), 5.32 (s, 1H), 5.03 (d, J=4.47 Hz, 1H), 4.96 (s, 1H), 4.95 (s, 1H), 4.06 (s, 1H), 3.73 (m, 3H), 3.50 (m, 2H), 2.65 (m, 1H), 2.45 (m, 2H), 2.08 (s, 3H), 1.65–1.50 (m, 13H), 1.40–1.30 (m, 2H), 1.03 (d, J=6.68 Hz, 3H), 0.91–0.79 (m, 10H). MS(−)FAB–m/e 756 (M−1).

EXAMPLE 241

Preparation of IA-3,5-dibenzyl ester (13a) and IA-3,4-dibenzyl ester (14a).

DBU (900 mg) was added to a solution of 3-benzyl IA (900 mg) in THF (25 mL), and to the reaction mixture benzyl chloride (250 uL) was added dropwise. After stirring for 3 days at room temperature, the resulting salt was filtered off through a bed of silica, then eluted with 1:1 ethyl acetate hexane first and the desired products eluted with acetone containing acetic acid (1%). The acetone fraction was concentrated in vacuo and separated by flash column chromatography (silica, methylene chloride: acetone: acetic acid 46/3/1) to yield IA-3,5-dibenzyl ester (13a) (fast moving band) and IA-3,4-dibenzyl ester (14a) (slow moving band).

$^1$H NMR (14a) (CD$_3$OD, 400 MHz) d 7.4–7.15(m, 15H), 6.85(m, 1H), 6.23(brs, 1H), 5.78(br d, J=16 Hz, 1H), 5.28(s, 1H), 5.06(d, J=4.6 Hz, 1H), 5.03(m, 4H), 5.00 and 4.95(ea s, ea 1H), 4.07(s, 1H), 2.68(m, 1H), 2.5–2.15(m, 5H), 2.10(s, 3H), 1.4–1.1(m, 7H), 1.03(d, J=6 Hz, 3H), 0.86(m, 9H). $^1$H NMR (13a) (CD$_3$OD, 400 MHz) d 7.45–7.05(m, 15H), 6.68(dd, J=9, 16 Hz, 1H), 6.32(brs, 1H), 5.47(d, J=16 Hz, 1H), 5.4–5.1(m, 3H), 5.06(d, J=4.8 Hz, 1H), 4.98 and 4.92(ea s, ea 1H), 3.97(s, 1H), 2.68(m, 1H), 2.5–2.15(m, 5H), 2.10(s, 3H), 1.4–1.02(m, 7H), 0.97(d, J=7 Hz, 3H), 0.87(m, 9H)

EXAMPLE 242

IA-3-benzyl-4-methyl pivalate ester (14b)

IA-3-benzyl-4-methyl pivalate ester was prepared from IA-3-benzyl ester, 8a (160 mg) and purified according to the procedure outlined for IA-3-benzyl-5-methyl pivalate ester, 19c, by using one equivalent of DBU.

$^1$H NMR (400 MHz, CD$_3$OD): δ7.40–7.10 (m, 10H), 6.82 (dd, J=15.65, 8.58 Hz, 1H), 6.26 (s, 1H), 5.82 (m, 3H), 5.15 (m, 1H), 5.05 (d, J=4.88 Hz, 1H), 4.99 (s, 1H), 4.94 (s, 1H), 4.90 (s, 2H), 3.99 (s, 1H), 2.65 (dd, J=13.32, 6.54 Hz, 1H), 2.50–2.40 (m, 3H), 3.32 (m, 1H), 2.20 (m, 1H), 2.10 (s, 3H), 1.35–1.25 (m, 4H), 1.19 (s, 9H), 1.15 (m, 2H), 1.04 (d, J=6.64 Hz, 1H), 0.90–0.81 (m, 10H). MS (−)FAB m/e 893 (M−1).

EXAMPLE 243

IA-3,4-bis-(methyl pivalate)ester (14c)

The title compound was prepared according to procedure outlined for IA-3,5-bis(methyl pivalate)ester, 19d, from IA-3-methyl pivalate ester, 8h', (78.3 mg) and one equivalent of DBU. $^1$H NMR (400 MHz, CD$_3$OD): δ7.30–7.10 (m, 5H), 6.85 (dd, J=15.67, 8.67 Hz, 1H), 6.29 (s, 1H), 5.86–5.70 (m, 6H), 5.35 (s, 1H), 5.05 (d, J=4.24 Hz, 1H), 5.01 (s, 1H), 4.97 (s, 1H), 2.65 (m, 1H), 2.50–2.40 (m, 3H), 2.31 (m, 1H), 2.20 (m, 1H), 1.40–1.30 (m, 5H), 1.20 (s, 18H), 1.05 (d, J=6.64 Hz, 3H), 0.90–0.80 (m, 10H). MS (−)FAB m/e 917 (m−1).

EXAMPLE 244

IA-3-isoamyl-4-t-butylglycolate ester (14d)

A solution of IA-3-isoamyl ester (0.342 mmol, 260 mg), in 5 mL of dry toluene was heated to 50° C. under a nitrogen atmosphere. Following, DBU (0.369 mmole, 55 mL) and t-butylchloroacetate (0.684 mmole, 98 mL) was added. Solution was stirred overnight and concentrated in vacuo the following morning. Purification by HPLC provide the diester as a colorless oil.

$^1$H NMR (400 MHz, CD$_3$OD) δ7.28–7.10 (m, 5H), 6.85(dd, J=15.67, 8.53 Hz, 1H), 6.30 (s, 1H), 5.95(d, J=0.96 Hz, 1H), 5.30(s, 1H), 5.07(d, J=4.56 Hz, 1H), 5.01(s, 1H), 4.95(s, 1H), 4.55 (dd, DV=26.67 Hz, J=15.59 Hz, 2H), 4.18(t, J=6.76 Hz, 2H), 4.01(s, 1H), 2.65(dd, J=13.32, 6.64 Hz, 1H), 2.50–2.40(m, 3H), 2.10(s, 3H), 1.71(s, 1H), 1.54(m, 3H), 1.48(s, 9H), 1.32–1.29(m, 3H), 1.20–1.10(m, 2H), 1.03(d, J=6.69 Hz, 3H), 0.95–0.84(m, 18H). MS(EI) m/e 874.

EXAMPLE 245

IA-3-isoamyl-4-glycolic acid ester (14e)

56.6 mg of the IA-3-isoamyl-4-t-butylglycolate ester, 14d, in 5 mL of dry dichloromethane at 0° C. was treated with 500 µL of TFA. The reaction was placed under a nitrogen atmosphere and warmed to room temperature, where it was stirred overnight. The following morning, an additional 100 µL of TFA was added to ensure complete removal of the t-butyl group. After 1 hour, the reaction was concentrated in vacuo and provided the diester as a colorless oil.

$^1$H NMR (400 MHz, CD$_3$OD) δ7.28–7.10 (m, 5H), 6.80(dd, J=15.68, 8.76 Hz, 1H), 6.30(s, 1H), 5.90(d, J=14.71 Hz, 1H), 5.30(s, 1H), 5.08(d, J=4.56 Hz, 1H), 5.01(s, 1H), 4.95(s, 1H), 4.63(dd, DV=26.31 Hz, J=15.91 Hz, 2H), 4.18(t, J=6.64 Hz, 2H), 4.01(s, 1H), 2.45(m, 3H), 2.10(s, 3H), 1.55–1.50(m, 3H), 1.40–0.35(m, 3H), 1.29–1.20(m, 2H), 1.03(d, J=6.68 Hz, 3H), 0.94–0.81(m, 18H). MS(EI) m/e 818.

EXAMPLE 246

IA-3-isopentyl-4-methylester (14p) and IA-3-isopentyl-5-methylester (19h)

150 mg of IA-3-isopentyl ester, 8n, in 2 mL of acetonitrile was stirred with 66 µL of DBU and after 30 minutes 12.3 µL of methyl iodide was added and stirring continued for 16 hrs. The following day, purification of the two diesters by prep TLC (silica, methylene chloride:acetone:acetic acid 46:3:1) gave a mixture of IA-3-isopentyl-4-methylester (Rf 0.23) and IA-3-isopentyl-5-methylester (Rf 0.36). The above reaction when carried out in tetrahydrofuran with 33 uL of DBU gave a 4:1 ratio of IA-3-isopentyl-4-methylester and IA-3-isopentyl-5-methylester. IA-3-isopentyl-4-methylester(14p)

$^1$H 400 MHz (CD$_3$OD) δ7.1–7.27(m, 5H), 6.64(dd, J=15.6, 8 Hz, 1H), 6.28(d, 1.9 Hz, 1H), 5.80(d, J=15.6 Hz, 1H), 5.24(s, 1H), 5.07(d, J=4.4 Hz, 1H), 5.00 and 4.96(ea s, ea 1H), 4.16(m, 2H), 4.04(d, J=1.9 Hz, 1H), 2.67 (m, 2H), 2.4–2.5(m, 2H), 2.10(s, 3H), 1.1–1.7(m, 5H), 1.03(d, J=7.1 HZ), 0.85–0.95(m, 9H).

IA-3-isopentyl-5-methylester (19h)

$^1$H 400 MHz (CD$_3$OD), δ7.12–7.28(m, 5H), 6.77 (dd, J=15.6, 8 Hz, 1H), 6.30(d, 1.9 Hz, 1H), 5.76(d, J=15.6 Hz, 1H), 5.29(s, 1H), 5.07(d, J=4 Hz, 1H), 5.00 and 4.96(ea s, ea 1H), 4.18(m, 2H), 4.02(d, J=1.9 Hz, 1H), 2.67 (m, 2H), 2.4–2.5(m, 2H), 2.10(s, 3H), 1.1–1.7(m, 5H), 1.03(d, J=7.1HZ), 0.83–0.95(m, 9H)

EXAMPLE 247

IA-3-isopentyl-4-pivaloyloxymethyl (POM) ester (14f) and IA-3-isopentyl-5-pivaloxyloxymethyl ester (19e)

A mixture of IA-3-isopentyl ester, 8n, (1.56 g, 0.00205 mole), DBU (0.33 mL, 0.0022 mole) and chloromethyl pivalate (0.59 mL, 0.0041 mole) in 20 mL of benzene was heated for 40 hours at 65° C. The solution was concentrated and the products were purified by prep TLC (CH$_2$Cl$_2$/acetone/HOAc=43:5:1) to afford the 3,4-diester, the 3,5-diester and the 3,4,5-triester.

3,4-diester (14f):

$^1$H NMR (200MHz, CDCl$_3$) δ0.68–0.96(m, 15H), 0.96–1.42(d+s+m, 18H), 1.42–1.74(m, 3H), 1.88–2.22(s+m, 6H), 2.22–2.54(m, 4H), 2.60–2.78(dd, 1H), 4.01(brs, 1H), 4.08–4.28(m, 2H), 4.98(brs, 2H), 5.29(brs, 2H), 5.56–6.08(3brs, 4H), 6.82–7.02(dd, 1H), 7.06–7.42(m, 5H). (−)FAB MS m/e 873(m$^+$−1)

IA-3-isopentyl-5-pivaloxyloxymethyl ester (19e)

$^1$H NMR (400 MHz, CD$_3$OD) δ0.74–0.96 (m, 15H), 1.03 (d, 3H), 1.08–1.44 (s+m, 15H), 1.45–1.62 (m, 2H), 1.63–1.80 (m, 1H), 1.86–2.12 (s+m, 5H), 2.15–2.25 (m, 1H), 2.26–2.35 (m, 1H), 2.35–2.52 (m, 3H), 2.68 (dd, 1H), 3.96 (s, 1H), 4.08–4.33 (m, 2H), 4.99 (s, 2H), 5.04 (s, 1H), 5.10 (s, 1H), 5.76–5.95 (m, 3H), 6.86 (dd, 1H), 7.10–7.33 (m, 5H). Mass spec.: FAB (−) 873.

The following diesters were made according to the procedure described for IA-3-isopentyl-4-POM ester, 14f, and using appropriate alkyl halides.

EXAMPLE 248

IA-3-isopentyl-4-benzyl ester (14g)

$^1$H NMR (200 MHz, CDCl$_3$) δ0.65–0.96(m, 15H), 0.98–1.19(d+m, 5H), 1.20–1.64(m, 7H), 1.88–2.16(s+m, 6H), 2.16–2.50(m, 4H), 2.60–2.78(dd, 1H), 3.17–3.40(brs, 1H), 3.76–4.20(brs+m, 3H), 4.96(brs, 2H), 5.10(brs, 2H), 5.21(s, 1H), 5.38(brs, 1H), 5.68(s, 1H), 5.93(d, 1H), 6.89(dd, 1H), 7.03–7.51(m, 10H). (−)FAB MS m/e 849(m$^+$−1)

EXAMPLE 249

IA-3,4-diisopentyl ester (14h)

$^1$H NMR (200 MHz, CDCl$_3$) δ0.66–0.96(m, 15H), 0.96–1.19(d+m, 5H), 1.20–1.70(m, 10H), 1.88–2.20(s+m, 6H), 2.20–2.50(m, 4H), 2.70(dd, 1H), 3.24(brs, 1H), 3.92–4.48(s+m, 5H), 5.00 (s, 5H), 5.07(s, 2H), 5.07 (brs, 1H), 5.19(s, 1H), 5.70(s, 1H), 5.83(d, 1H), 6.88(dd, 1H), 7.06–7.42(m, 5H). (−)FAB MSp m/e 787 (m+−1)

EXAMPLE 250

IA-3-isopentyl-4-methylene(4-bromobenzoyl)ester (14i)

$^1$H NMR (200 MHz, CDCl$_3$): δ0.62–0.96(m, 15H), 0.96–1.19(d+m, 5H), 1.20–1.66(m, 7H), 1.84–2.20(s+m, 6H), 2.20–2.56(m, 4H), 2.56–2.80(dd, 1H), 3.90–4.36(m, 3H), 4.98–5.20(m, 3H), 5.20–5.98(m, 5H), 6.76–7.00(m, 1H), 7.00–7.37(m, 5H), 7.44–7.70(m, 2H), 7.70–7.98(m, 2H). (−)FAB MS m/e 956(m+−1)

EXAMPLE 251

IA-3-isopentyl-4-allyl ester (14j)

$^1$H NMR (200 MHz, CDCl$_3$): δ0.64–0.97(m, 15H), 0.98–1.20(d+m, 5H), 1.20–1.72(m, 7H), 1.84–2.20(s+m, 6H), 2.20–2.58(m, 4H), 2.60–2.82(dd, 1H), 3.30(brs, 1H), 3.86–4.34(m, 3H), 4.62–4.8(m, 2H), 5.00(brs, 2H), 5.09(brs, 1H), 5.16–5.50(m, 3H), 5.70(brs, 1H), 5.80–6.18(m, 2H), 6.78–7.00(m, 1H), 7.02–7.42(m, 5H). (−)FAB MS m/e 799(m$^+$−1)

EXAMPLE 252

IA-3-isopentyl-4-(2-methoxyethyl)ester (14k)

$^1$H NMR (200 MHz, CDCl$_3$): δ0.66–0.96(m, 15H), 0.98–1.98(d+m, 5H), 1.20–1.68(m, 7H), 1.86–2.18(s+m, 6H), 2.20–2.52(m, 4H), 2.60–2.78(dd, 1H), 3.31(s, 3H) 3.55–3.77(m, 2H), 3.90–4.36(s+m, 6H), 4.90(brs, 2H), 5.09(brs, 1H), 5.25(brs, 1H), 5.62–5.69(brs+d, 2H), 6.80–7.00(dd, 1H), 7.04–7.36(m, 5H). (−)FAB MS m/e 817(m+−1)

EXAMPLE 253

IA-3-isopentyl-4-(2-phenoxyethyl)ester (14l) FAB(neg) Mass Spectrum m/e 879(m+−1)

$^1$H NMR (200 MHz, CDCl$_3$): δ0.63–0.95 (m, 15H), 0.96–1.19(d+m, 5H), 1.20–1.65(m, 7H), 1.83–2.17(s+m, 6H), 2.21–2.53(m, 4H), 2.60–2.78(dd, 1H), 3.33(brs, 1H), 3.85–4.37(s+m, 5H), 4.47–4.76(s+m, 5H), 4.47–4.76(m, 2H), 4.98(brs, 2H), 5.06(brs, 1H), 5.25(brs, 1H), 5.63–5.89(m, 2H), 6.69–7.03(m, 6H), 7.05–7.43(m, 5H). (−)FAB MS m/e 879(m+−1)

EXAMPLE 254

IA-3-isopentyl-4-heptyl ester (14m)

$^1$H NMR (200 MHz, CDCl$_3$): δ0.63–0.98(m, 18H), 0.98–1.82(m, 24H), 1.84–2.20(s+m, 6H), 2.20–2.54(m, 4H), 2.62–2. (dd, 1H), 3.84–4.44(s+m, 5H), 4.84–5.32(m, 4H), 5.54–5.92(m, 2H), 6.76–7.00(m, 1H), 7.02–7.54(m, 5H). (−)FAB MS m/e 871(m$^+$−1)

EXAMPLE 255

IA-3-isopentyl-4-p-fluorobenzyl ester (14n)

$^1$H NMR (200 MHz, CDCl$_3$): δ0.64–0.96(m, 15H), 0.96–1.19(d+m, 5H), 1.20–1.68(m, 7H), 1.82–2.14(s+m, 6H), 2.18–2.56(m, 4H), 2.60–2.78(dd, 1H), 3.30(brs, 1H), 3.80–4.22(brs+m, 3H), 4.80–5.23(2brs+m, 5H), 5.36–5.68(s+d, 2H), 5.78–6.02(d, 1H), 6.76–7.56(m, 10H). (−)FAB MS m/e 875(Li spike)

EXAMPLE 256

IA-3-isopentyl-4-acetoxymethyl ester (14o)

$^1$H NMR (200MHz, CD$_3$OD) δ0.84–1.01 (m, 15H), 1.02–1.26 (m, 6H), 1.28–1.46 (m, 3H), 1.50–1.64 (m, 2H), 1.64–1.80 (m, 1H), 1.98–2.16 (s+m, 8H), 2.20–2.34 (m, 1H), 2.34–2.60 (m, 3H), 2.72 (dd, 1H), 4.08 (s, 1H), 4.16–4.30 (m, 2H), 5.03 (d, 2H), 5.11 (d, 1H), 5.25 (s, 1H), 5.78–6.04 (m, 3H), 6.17 (s, 1H), 6.89 (dd, 1H), 7.14–7.36 (m, 5H). mass spec.: FAB (−) m/e 831 (M$^+$−1)

EXAMPLE 257

IA-3-isopentyl-4,5-dipivaloyloxymethyl ester (9c)

$^1$H NMR (200 MHz, CDCl$_3$) δ0.76–0.92 (m, 15H), 1.04 (d, 3H), 1.07–1.26 (s+m, 21H), 1.26–1.40 (m, 2H), 1.40–1.72 (m, 4H). 2.00–2.18 (s+m, 6H), 2.24–2.52 (m, 3H), 2.67 (dd, 1H), 3.22 (d, 1H), 3.77 (s, 1H), 3.99 (s, 1H), 4.08–4.26 (m, 2H), 4.96 (d, 2H), 5.08 (d, 1H), 5.16 (s, 1H), 5.66 (d, 1H), 5.74–6.06 (m, 5H), 6.89 (dd, 1H), 7.08–7.30 (m, 5H). Mass spec.: FAB (−) m/e 818.2 (M$^+$−3-t-butyl).

EXAMPLE 258

IA-3-isopentyl-4,5-diethyl ester (9d)

$^1$H NMR (400 MHz, CDCl$_3$) δ0.73–0.90 (m, 15H), 0.99 (d, 3H), 1.03–1.74 (m, 15H), 2.00–217 (s+m, 6H), 2.25–2.50 (m, 4H), 2.66 (dd, 1H), 3.82 (brs, 1H), 4.00 (d, 1H), 4.05–4.40 (m, 6H), 4.94 (s, 2H), 5.08 (d, 1H), 5.18 (s, 1H), 5.72 (d, 1H), 5.88 (d, 1H), 6.82 (dd, 1H), 7.06–7.28 (m, 5H). Mass spec.: FAB (−) 815 (M$^+$−1).

EXAMPLE 259

IA-3,4,5-triisopentyl ester (9e)

$^1$H NMR (200 MHz, CDCl$_3$) δ0.74–0.98 (m, 27H), 1.04 (d, 3H), 1.08–1.80 (m, 15H), 2.02–2.20 (s+m, 6H), 2.27–2.54 (m, 4H), 3.10 (dd, 1H), 4.03 (d, 1H), 4.08–4.42 (m, 6H), 4.99 (s, 2H), 5.10 (d, 1H), 5.19 (s, 1H), 5.76 (d, 1H), 5.84 (d, 1H), 6.88 (dd, 1H), 7.08–7.32 (m, 5H). Mass spec.: FAB (−) m/e 900 (M$^+$−1). M$^+$−1).

EXAMPLE 260

IA-3-isopentyl-5-ethyl ester (19f)

$^1$H NMR (400 MHz, CDCl$_3$) δ0.62–0.90 (m, 15H), 0.90–1.04 (brs, 3H), 1.04–1.78 (m, 12H), 1.84–2.18 (s+m, 6H), 2.18–2.52 (m, 4H), 2.59–2.77 (dd, 1H) 3.80–4.40 (m, 6H), 4.92 (s, 2H), 5.08 (d, 1H) 5.26 (s, 1H), 5.40 (brs, 1H), 5.58–5.83 (d, 1H), 6.70–6.96 (m, 1H), 7.00–7.30 (m, 5H). Mass spec.: FAB (−) 787 (M$^+$−1).

EXAMPLE 261

IA-3,5-diisopentyl ester (19g)

$^1$H NMR (400, CDCl$_3$) δ0.70–0.95 (m, 21H), 0.95–1.78 (m, 15HO, 1.96–2.22 (s+m, 6H), 2.22–2.52 (m, 4H), 2.70 (d, 1H), 3.94–4.12 (brs, 2H), 4.12–4.46 (m, 4H), 4.90–5.06 (brs, 3H), 5.15 (s, 1H), 5.65 (s, 1H) 5.72–5.90 (d, 1H), 6.78–7.00 (m, 1H), 7.06–7.36 (m, 5H). Mass spec.; FAB (−) 829 (M$^+$−1).

EXAMPLE 262

Preparation of IA-C5-methyl ester (18a).

To a solution of IA-3,4-dibenzyl ester (14a) (40 mg) in methylene chloride (1 mL) was added O-methyl-N,N'-diisopropylisourea and the mixture was stirred at 40° C. overnight. The resulting IA-3,4-dibenzyl-5-methyl triester was purified by prep TLC (silica, ethyl acetate-hexane 3:7) and the colorless gum (23.6 mg) was dissolved in methanol (1 mL) and stirred for 3 hr at room temperature with 1-methyl-1,4-cyclohexadiene (20 uL) and 10% Pd/C (15 mg). Filtration over celite and evaporation gave IA-C5-methyl ester (18a). $^1$H NMR (CD$_3$OD, 400 MHz) δ7.3–7.1(m, 5H), 6.77(dd, J=8, 16 Hz, 1H), 6.36(s, 1H), 5.75(d, J=16 Hz, 1H), 5.33(s, 1H), 5.06(d, J=5.2 Hz, 1H), 5.07 and 4.96(ea s, ea 1H), 4.02(s, 1H), 3.68(s, 3H), 2.68(m, 1H), 2.5–2.15(m, 5H), 2.10(s, 3H), 1.4–1.1(m, 3H), 1.03(d, J=6 Hz, 3H), 0.86(m, 9H)

EXAMPLE 263

Preparation of IA-C5-carboxamide (18b)

This compound was prepared by using a procedure similar to that used for compound (12e) and using IA-3,4-dibenzyl ester (14a), N-ethyl morpholine (6.5 uL), isobutyl chloroformate (8.5 uL), and dry ammonia bubbled in for 1 min. Debenzylation was carried out with 1-methyl-1,4-cyclohexadiene and Pd/C as described in Example 262.

$^1$H NMR (CD$_3$OD, 400 MHz ): δ7.3–7.1(m, 5H), 6.83(dd, J=8, 16 Hz, 1H), 6.32(br s, 1H), 5.77(d, J=16 Hz, 1H), 5.23(m, 2H), 5.07(d, J=4.4 Hz, 1H), 5.02 and 4.97(ea s, ea 1H), 4.02(s, 1H), 2.68(m, 1H), 2.5–2.15(m, 5H), 2.10(s, 3H), 1.03–0.7(m, 12H)

EXAMPLE 264

IA-5-methyl pivalate ester (18c)

IA-3-benzyl-5-methyl pivalate ester, 19c, was debenzylated according to the procedure outlined earlier to provide the monoester as a colorless oil.

$^1$H NMR (400 MHz, CD$_3$OD): δ7.29–7.10 (m, 5H), 6.85 (dd, J=15.63, 8.58 Hz, 1H), 6.12 (s, 1H), 5.90–5.78 (m, 4H), 5.15 (s, 1H), 5.07 (d, J=4.66 Hz, 1H), 5.00 (s, 1H), 4.00 (s, 1H), 3.30 (s, 1H), 2.68 (m, 1H), 2.48–2.38 (m, 3H), 2.08 (s, 3H), 1.35–1.25 (m, 4H), 1.20 (s, 9H), 1.12 (m, 3H), 1.00 (d, J=6.64 Hz, 3H), 0.89–0.80 (m, 10H). MS (−)FAB m/e 803 (M−1).

EXAMPLE 265

Preparation of
IA-C4-Methyl ester (16a).

To a solution of IA-3,5-dibenzyl ester (13a) (35 mg), in benzene (0.5 mL), was added O-methyl-N,N'-diisopropylisourea (35 uL) and the mixture was heated with stirring for 16 hr. The triester was purified by prep TLC (40% ethyl acetate in hexane), and was then dissolved in methanol (1 mL). To this mixture was added Pd/C (30 mg) and 1-methyl-1,4-cyclohexadiene (50 mg), and the reaction mixture was then stirred at 30°–35° C. for 30 min. The reaction mixture was then filtered through celite and evaporated under vacuum to yield IA-4-methyl ester (16a). $^1$H NMR (CD$_3$OD, 400 MHz) δ7.3–7.1(m, 5H), 6.81(dd, J=8, 16 Hz, 1H), 6.22(s, 1H), 5.79(d, J=16 Hz, 1H), 5.17(s, 1H), 5.07(d, J=4.4 Hz, 1H), 5.01 and 4.97(ea s, ea 1H), 4.02(s, 1H), 3.82(s, 3H), 2.68(m, 1H), 2.5–2.15(m, 5H), 2.10(s, 3H), 1.4–1.1(m, 3H), 1.03–0.86(m, 12H)

EXAMPLE 266

Preparation of
IA-C4-n-propyl ester (16b).

This compound was prepared by procedures analogous to those used in the preparation of compound (16a).

$^1$H NMR (CD$_3$OD, 400 MHz) δ7.3–7.1(m, 5H), 6.83(dd, J=8, 16 Hz, 1H), 6.22(s, 1H), 5.79(d, J=16 Hz, 1H), 5.21(s, 1H), 5.07(d, J=4.4 Hz, 1H), 5.02 and 4.97(ea s, ea 1H), 4.20(m, 2), 4.02(s, 1H), 2.68(m, 1H), 2.5–2.15(m, 3H), 2.10(s, 3H), 1.4–1.1(m, 2H), 1.03–0.86(m, 15H)

EXAMPLE 267

IA-4-methyl pivalate ester (16c)

IA-3-benzyl-4-methyl pivalate ester (22.2 mg) was debenzylated to IA-4-methyl pivalate ester according to the procedure outlined earlier.

$^1$H NMR (400 MHz, CD$_3$OD): δ7.28–7.10 (m, 5H), 6.85 (dd, J=15.7, 8.72 Hz, 1H), 6.40 (s, 1H), 5.85–5.22 (m, 3H, 5.25 (s, 1H), 5.05 (d, J=4.57 Hz, 1H), 5.00 (s, 1H), 4.90 (s, 1H), 3.95 (s, 1H), 2.65 (dd, J=13.37, 6.64 Hz, 1H), 2.50–2.40 (m, 3H), 2.10 (s, 3H), 2.00–1.90 (m, 1H), 1.35–1.25 (m, 4H), 1.20 (s, 9H), 1.03 (d, J=6.64 Hz, 3H), 0.90–0.80 (m, 10H). MS (–)FAB m/e 804 (M).

EXAMPLE 268

IA-4-(2-methoxyethyl) ester (16d)

$^1$H NMR (400 MHz, CD$_3$OD): δ7.30–7.10 (m, 5H), 6.86 (dd, J=15.6, 8.4 Hz, 1H), 6.29(d, J=2.0 Hz, 1H), 5.79(d, J=15.6 Hz, 1H), 5.23 (s, 1H), 5.06 (d, J=4.0 Hz, 1H), 5.01 and 4.95(ea s, ea 1H), 4.4–4.26(m, 2H), 4.04(d, J=2.0 Hz, 1H), 3.69(m, 2H), 2.68(m, 2H), 2.5–2.18(m, 4H), 2.10(s, 3H), 1.08–1.45(m, 4H), 1.03 (d, J=7 Hz, 3H), 0.90–0.80 (m, 9H).

EXAMPLE 269

IA-4-(2-dimethylaminoethyl)ester (16e)

$^1$H NMR (400 MHz, CD$_3$OD): δ7.30–7.10 (m, 5H), 6.87 (dd, J=16.0, 8.4 Hz, 1H), 6.29(d, J=2.08 Hz, 1H), 5.83(d, J=16 Hz, 1H), 5.20(s, 1H), 5.07 (d, J=4 Hz, 1H), 5.02 and 4.97(ea s, ea 1H), 4.13 (d, J=2.08 Hz, 1H), 3.30(s, 6H), 2.7(m, 2H), 2.45–2.15(m, 4H), 2.10(s, 3H), 1.4–1.05(m, 3H), 1.03(d, J=6.8 Hz, 3H), 0.90–0.80 (m, 9H).

EXAMPLE 270

Preparation of IA-3-benzyl-5-t-butyl ester (19a).

A solution of IA-3-benzyl ester (8a) (156 mg) dissolved in benzene (2.5 mL) was treated with O-t-butyl-N,N'-diisopropylisourea, (50 uL, 1.4 eq.) and heated at 40° C. for 16 hr. MPLC separation (C-8 column, 59% acetonitrile in water containing 0.005% TFA) gave 3-benzyl-5-t-butyl ester (19a). $^1$H-NMR (400 MHz, CD$_3$OD) δ7.40–7.10(m, 5H), 6.88(dd, J=8.1,16 Hz, 1H), 6.36(br s, 1H), 5.82(d, J=16 Hz, 1H), 5.29(br s, 1H), 5.27(brs, 1H), 5.07(d, J=12 Hz, 1H), 4.98 & 5.00(each s, each 1H), 4.02(d, J=1 Hz), 1H), 2.67(m, 2H), 2.5–2.15(m, 6H), 2.10(s, 3H), 2.05–1.90(m, 2H), 1.47(s, 9H), 1.02(d, J=7 Hz, 3H), 0.9–0.8(m, 9H).

EXAMPLE 271

Preparation of IA-3-Benzyl-5-methyl ester (19b).

To a solution of IA-3-benzyl ester (8a) (30 mg) in methylene chloride (200 uL), was added trifluoroacetic anhydride (10 uL) and the solution was stirred at room temperature for 15 minutes. The reaction mixture was then treated with excess methanol (1 mL), stirred for an additional 15 min. and then evaporated in vacuo. The product was purified by MPLC (60% acetonitrile in water with 0.005% trifluoroacetic acid) to yield the diester (19b). $^1$H NMR (CD$_3$OD, 200 MHz) δ7.40–7.10(m, 10H), 6.88(dd, J=8, 16 Hz, 1H), 6.28(d, J=2 Hz, 1H), 5.77(d, J=16 Hz, 1H), 5.29(s, 1H), 5.20(dd, J=12, 28 Hz, 2H), 5.06(d, J=4.8 Hz, 1H), 5.02 and 4.98(ea s, ea 1H), 4.04(d, J=1.6 Hz, 1H), 3.70(s, 3H), 2.66(m, 1H), 2.58–2.12(m, 5H), 2.10(s, 3H), 1.03(d, J=7 Hz, 3H), 0.87(m, 9H).

EXAMPLE 272

IA-3-benzyl-5-methyl pivalate ester (19c)

To the IA-3-benzyl ester, 8a, (0.205 mmole, 160 mg), 5 mL of acetonitrile was added and placed under a nitrogen atmosphere. DBU (0.410 mmole, 61.3 uL) and chloromethyl pivalate (0.205 mmole, 29.5 uL) was added. The reaction was stirred at reflux for 2 days then concentrated in vacuo. The compound was purified via HPLC to provide the diester as a colorless oil.

$^1$H NMR (400 MHz, CD$_3$OD): δ7.40–7.10 (m, 10H), 6.82 (dd, J=15.66, 8.57 Hz, 1H), 6.10 (s, 1H), 5.78 (d, J=15.54 Hz, 1H), 5.88 (m, 2H), 5.30 (s, 1H), 5.16 (dd, delta ν=35.67, J=12.03 Hz, 2H), 5.06 (d, J=4.98 Hz, 1H), 5.00 (s, 1H), 4.96 (s, 1H), 4.02 (s, 1H), 2.64 (m, 1H), 2.45–2.36 (m, 4H), 2.20 (m, 1H), 2.09 (s, 3H), 2.00 (m, 1H), 1.40–1.28 (m, 4H), 1.15 (s, 9H), 1.02 (d, J=6.64 Hz, 3H), 0.90–0.80 (m, 10H). MS (–)FAB m/e 893 (M–1).

EXAMPLE 273

IA-3,5-bis(methyl pivalate)ester (19d)

To the IA-3-methyl pivalate ester, 8h', (0.097 mmole, 78.3 mg), 3 mL of acetonitrile was added and placed under a nitrogen atmosphere. DBU (0.194 mmole, 29 υL) and chloromethyl pivalate (0.097 mmole, 14 υL) was added and stirred at reflux overnight. The following morning, the reaction was concentrated in vacuo and purified via HPLC to provide the C-3, C-5 methyl pivalate diester as a colorless oil.

$^1$H NMR (400 MHz, CD$_3$OD): δ7.30–7.10 (m, 5H), 6.85 (dd, J=15.65, 8.57 Hz, 1H), 6.10 (s, 1H), 5.90–5.71 (m, 6H), 5.28 (s, 1H), 5.06 (d, J=4.66 Hz, 1H), 5.01 (s, 1H), 4.95 (s, 1H), 4.02 (s, 1H), 2.69 (m, 1H), 2.42 (m, 3H), 2.22 (m, 1H), 2.10 (s, 3H), 1.35–1.27 (m, 4H), 1.04 (s, 9H), 1.03 (s, 9H), 1.15 (m, 2H), 1.02 (d, J=6.64 Hz, 3H), 0.92–0.82 (m, 9H). MS (FAB-Neg) m/e 917 (M–1).

EXAMPLE 274

Preparation of IA-4-carboxamide-3-benzyl ester (22a).

By using a procedure similar to that used in example (11a) 12 mg of 3-benzyl-5-t-butyl-4-carboxamide (20a) was prepared from 3-benzyl-5-t-butyl-4-carboxylic acid (19a) (30 mg), methylene chloride (0.64 mL), tetrahydrofuran (0.85 mL), N-methylmorpholine (4.34 uL), and isobutyl chloroformate (5.1 uL). $^1$H NMR (300 MHz, CD$_3$OD) δ1.50(s, 9H), 2.15(s, 3H), 4.09(d, 1.2 Hz, 1H), 5.01(br s, 1H), 5.04(br s, 1H), 5.12(d, J=4.8 Hz, 1H), 5.14(d, J=12 Hz, 1H), 5.31(d, J=12 Hz, 1H), 5.33(s, 1H), 5.82(d, J=15.6 Hz, 1H), 6.38(d, 1.2 Hz, 1H), 6.88(dd, J=8.4, 15.6 Hz, 1H), 7.17–7.50(m, 10H). 12 mg of 3-benzyl-5-t-butyl-4-carboxamide (20a) was deprotected with trifluoroacetic acid (150 uL) in methylene chloride (0.8 mL) over a period of 16 hr. MS (FAB) m/z 786(M+Li)$^+$ $^1$H NMR (400 MHz, CD$_3$OD), diagnostic peaks δ7.45–7.08(m, 10H), 6.84(dd, J=8, 15.6 Hz, 1H), 6.26(br s, 1H), 5.76(d, J=15.6 Hz, 1H), 5.27(d, J=12 Hz, 1H), 5.09(d, J=12 Hz, 1H), 5.07(d, J=4.8 Hz, 1H), 4.99 & 4.96(each br s, each 1H).

EXAMPLE 275

Preparation of (1S,3S,4S,5R,6R,7R)-1-[(4S)-acetoxy-3,5(R)-dimethyl-6-phenyl]hexyl-4,6,7-trihydroxy-6-O-(4(S),6(S)-dimethyl-2-octanoyl)-2,8-dioxabicyclo-[3,2,1]octane-3,4,5-tricarboxylic acid (24b) and (1S,3S,4S, 5R,6R,7R)-1-[3,5(R)-dimethyl-6-phenyl]hexyl-4,6,7trihydroxy-6-O-(4(S),6(S)-dimethyl-2-octanoyl)-2,8-dioxabicyclo[3.2.1]octane-3,4,5-tricarboxylic acid (25b)

Step A.

A mixture of tris-t-butyl ester 1a (100 mg, 0.116 mmol) and 10% Pd-C (45 mg) in EtOAc (3.0 mL) was evacuated and purged under an atmosphere of hydrogen gas. The reaction was stirred for 36h at 23° C., filtered through a plug of celite and the filtrate was concentrated in vacuo. Purification of the residue by flash column chromatography (4:1 hex/EtOAc, silica gel) gave a diastereomeric mixture of deacetoxy products (25a) and a diastereomeric mixture of acetoxy products (24a): $^1$H NMR of (25a) (300 MHz, $CDCl_3$) δ7.26–7.10 (m, 10H), 6.33 (m, 2H), 4.98 (s, 2H), 4.17 (m, 2H), 4.01 (s, 1H), 3.98 (s, 1H), 2.72–1.78 (m, 14H), 1.64 (s, 18H), 1.43 (s, 18H), 1.41 (s, 18H), 1.57–0.77 (m, 56H); $^1$H NMR of (24a) (300 MHz, $CDCl_3$) δ7.24–7.14 (m, 10H), 6.32 (m, 2H), 4.96 (s, 2H), 4.81–4.70 (m, 2H), 4.14–4.11 (m, 2H), 4.00 (s, 1H), 3.95 (s, 1H), 2.78–2.65 (m, 2H), 2.28–1.75 (m, 10H), 2.09 (s, 3H), 2.08 (s, 3H), 1.63 (s, 18H), 1.43–1.40 (m, 36H), 1.35–0.76 (m, 56H).

EXAMPLE 276

STEP B:
Deprotection of (24a) and (25a) to produce triacid analogs (24b) and 25b).

According to the usual procedures 54.4 mg (0.0631 mmol) of (24a) was deprotected to afford (24b), as a white solid: $^1$H NMR (300 MHz, $CD_3OD$) δ7.32–7.21 (m, 10H), 6.30–6.28 (m, 2H), 5.29–5.27 (m, 2H), 4.95–4.81 (m, 2H), 4.07–4.05 (m, 2H), 2.80–2.72 (m, 2H), 2.36–0.86 (m, 64H), 2.16 (s, 3H), 2.14 (s, 3H). According to the usual procedures 41.7 mg (0.0518 mmol) of product (25a) was deprotected to afford (25b) as a white solid: $^1$H NMR (300 MHz, $CD_3OD$) δ7.31–7.15 (m, 10H), 6.30–6.28 (m, 2H), 5.28 (m, 2H), 4.09–4.08 (m, 2H), 2.78–2.32 (m, 10H), 2.00–0.86 (m, 60H).

EXAMPLE 277

Preparation of (1S,3S,4S,5R,6R,7R)-1-[(4S)-acetoxy-3,5(R)-dimethyl-6-cyclohexyl]hexyl-4,6,7-trihydroxy-6-O-(4(S),6(S)-dimethyl-2-octenoyl)-2,8-dioxabicyclo-[3.2.1]-octane-3,4,5-tricarboxylic acid (26b)
Step A.

A mixture of tris-t-butylester-7-(1-methyl-1-methoxyethyl ether (2a) (100 mg, 0.1075 mmol) and 5% Rh-$Al_2O_3$ (20 mg) in EtOAc (3.0 mL) was evacuated and purged under and atmosphere of hydrogen gas. The reaction was stirred for 48h at 23° C., filtered through a plug of celite and the filtrate was concentrated in vacuo. Purification of the residue by flash column chromatography (6:1 hex/EtOAc, silica gel) gave a diastereomeric mixture of saturated tris-t-butylester product (26a): $^1$H NMR (300 MHz, $CDCl_3$) δ 6.31 (m, 1H), 4.97 and 4.96 (ea s, 1H), 4.70–4.65 (m, 1H), 4.16 and 4.14 (ea d, J=1.2 Hz, 1H), 4.00 and 3.94 (ea s, 1H), 3.22 and 3.21 (ea s, 3H), 2.2–2.3 (m, 2H), 2.04 and 2.03 (ea s, 3H), 1.63 (s, 9H), 1.43–1.40 (m, 18H), 0.86–0.79 (m, 12H).
Step B.

According to the usual procedures 65.0 mg (0.0691 mmol) of (26a) was deprotected to afford (26b) as a white solid: $^1$H NMR (300 MHz, $CD_3OD$) δ6.23–6.21 (m, 1H), 5.23 (s, 1H), 4.75–4.69 (m, 1H), 4.02–4.01 (m, 1H), 2.72–2.32 (m, 2H), 2.07 (s, 3H), 2.06 (s, 3H), 0.90–0.82 (m, 15H).

EXAMPLE 278

Synthesis of (1S,3S,4S,5R,6R,7R)-1-[(4R)-acetoxy-3-methylene-5(R)-methyl-6-phenyl]hexyl-4,6,7-trihydroxy-6-O-(4(S),6(S)-dimethyl-2-octenoyl)-2,8-dioxabicyclo[3,2,1]= octane-3,4,5-tricarboxylic acid (28b). To a solution of IA-tris-t-butyl ester Cl(4') alcohol (4'a) (100.0 mg, 0.112 mmol), triphenylphosphine (153.6 mg, 0.585 mmol) and p-nitrobenzoic acid (97.7 mg, 0.585 mmol) in THF (2.9 mL) was added diethyl azidodicarboxylate (98.0 mg, 0.563 mmol) at 23° C. After 24 h the reaction was concentrated in vacuo and the residue was purified by flash column chromatography (3:1 hex/EtOAc, silica gel) to give a 1:1 mixture of regioisomeric p-nitrobenzoates. The mixture was inseparable by TLC so it was hydrolyzed prior to purification as described below. A solution of the p-nitrobenzoates (70.0 mg, 0.0675 mmol) and potassium carbonate (13.9 mg, 0.101 mmol) in MeOH (1.75 mL) was stirred at 23° C. for 1 h. The reaction was quenched with saturated aqueous ammonium chloride and concentrated in vacuo. The residue was extracted with EtOAc and the organic portion was dried ($MgSO_4$), filtered and concentrated in vacuo. Flash column chromatography (3:1 hex/EtOAc, silica gel) gave epimeric $C_4$'-allylic alcohol (1S,3S,4S,5R,6R,7R)-1-[(4R)-hydroxy-3-methylene-5(R)-methyl-6-phenyl]hexyl-4,6,7-trihydroxy-6-O-(4(S),6(S)-dimethyl-2-octenoyl)-2,8-dioxabicyclo [3.2.1]octane-3,4,5-tri-t-butyl ester (27a) as a white solid: $^1$H NMR (300 MHz, $CDCl_3$) δ7.26–7.15 (m, 5H), 6.88 (dd, J=8.4, 15.6 Hz, 1H), 6.40 (d, J=1.6 Hz, 1H), 5.76 (d, J=15.6 Hz, 1H), 5.10 (br s, 1H), 5.04 (s, 1H), 5.02 (br s, 1H), 4.25 (d, J=1.6 Hz, 1H), 3.96 (br s, 1H), 3.93 (s, 1H), 3.23 (s, 3H), 3.16–3.12 (m, 1), 2.60–1.96 (m, 8H), 1.66 (s, 9H), 1.45 (s, 9H), 1.42–1.06 (m, 6H), 1.37 (s, 12H), 1.28 (s, 3H), 0.98 (d, J=6.4 Hz, 3H), 0.83–0.79 (m, 6H), 0.74 (d, J=6.8 Hz, 3H), and the allylically rearranged C3' alcohol (27c): $^1$H NMR (400 MHz, $CDCl_3$) δ7.25–7.13 (m, 5H), 6.89 (dd, J=15.6, 8.4 Hz, 1H), 6.39 (d, J=1.6 Hz, 1H), 5.77 (dd, J=15.6, 0.80 Hz, 1H), 5.21 (d, J=10.0 Hz, 1H), 5.01 (s, 1H), 4.09 (d, J=1.6 Hz, 1H ), 4.05–3.89 (m, 2H), 3.17 (s, 3H), 2.72–2.64 (m, 1H ), 2.56–2.53 (m, 2H), 2.40–2.37 (m, 3H), 2.30–2.22 (m, 1H), 1.92–1.84 (m, 1H), 1.66 (s, 9H), 1.44 (s, 9H), 1.39 (s, 9H), 1.33 (s, 3H), 1.26 (s, 3H), 1.21–1.49 (m, 4H), 1.10–1.06 (m, 2H), 0.99–0.95 (m, 6H), 0.83–0.79 (m, 6H). A solution of (27a) (25.8 mg, 0.0295 mmol), triethylamine (12.1 μL, 0.0871 mmol), 4-dimethylaminopyridine (3.5 m, 0.0295 mmol) and acetic anhydride (4.1 μL, 0.0435 mmol) in $CH_2Cl_2$ (0.25 mL) was stirred at 23° C. for 16 h. The solution was diluted with $CH_2Cl_2$ and washed with 1N HCl, 5% aqueous $NaHCO_3$, brine, dried ($Na_2SO_4$), filtered and concentrated in vacuo. Purification of the residue by flash column chromatography (3:1 hex/EtOAc, silica gel) gave 4'-epiacetate-7-MME-tris-t-butyl ester (28a): $^1$H NMR (400 MHz, $CDCl_3$) δ7.26–7.12 (m, 5H), 6.88 (dd, J=15.6, 8.0 Hz, 1H), 6.43 (s, 1H), 5.76 (d, J=15.6 Hz, 1H), 5.11 (d, J=6.4 Hz, 1H), 5.05 (s, 1H), 5.03 (s, 1H), 4.97 (s, 1H), 4.24 (s, 1H), 4.06 (s, 1H), 3.23 (s, 3H), 2.91 (d, J=10.4 Hz, 1H), 2.55–2.48 (m, 2H), 2.42–2.34 (m, 1H), 2.23–2.18 (m, 3H), 2.05 (s, 3H), 2.03–1.95 (m, 1H), 1.67 (s, 9H), 1.42 (s, 9H), 1.37 (s, 9H), 1.34–1.23 (m, 6H), 1.15–1.06 (m, 4H), 0.98 (d, J=6.8 Hz, 2H), 0.83–0.77 (m, 3H), 0.76–0.70 (m, 6H). According to the usual procedures epimeric C4'-acetate (28a) (27.1 mg, 0.0291 mmol) was deprotected to provide triacid (28b) as a white solid: $^1$H NMR (400 MHz, $CD_3OD$) δ7.26–7.14 (m, 5H), 6.82 (dd, J=8.4, 15.6 Hz, 1H), 6.31 (d, J=1.6 Hz, 1H), 5.77 (d, J=15.6 Hz, 1H), 5.27 (s, 1H), 5.12 (d, J=6.4 Hz, 1H), 5.05 (br s, 1H), 5.04 (br s, 1H), 4.10 (d, J=1.6 Hz, 1H), 2.92–2.89 (m, 1H), 2.46–2.07 (m, 6H), 2.06 (s, 3H), 1.41–1.09 (m, 6H), 1.02 (d, J=6.8 Hz, 3H), 0.88–0.84 (m, 6H), 0.77 (d, J=6.4 Hz, 3H).

EXAMPLE 279

Synthesis of (1S,3S,4S,5R,6R,7R)-1-[(4S)-methoxy-3-methylene-5(R)-methyl-6-phenyl]hexyl-4,6,7-trihydroxy-6-O-

(4(S),6(S)-dimethyl-2-octenoyl)-2,8-dioxabicyclo[3.2.1]-octane-3,4,5-tris-t-butyl ester To a solution of IA-tris-t-butyl ester-7-1-methyl-1-methoxyethyl ether-Cl(4')-alcohol (4'a) (0.075 g, 0.083 mmol) in chloroform (1.5 ml) was added silver oxide (0.120 g, 0.498 mmol) and methyl iodide (0.071 g, 0.498 mmol) and the reaction mixture was stirred overnight at rt. At completion, the reaction mixture was filtered through celite and washed with hexanes. The filtrate was concentrated in vacuo. Purification of the residue by flash column chromatography (silica gel, 3:1 hexane/EtOAc) yielded of the title compound as a light yellow solid.

EXAMPLE 280

Synthesis of (1S,3S,4S,5R,7R)-1-[(4S)-methoxy-3,5(R)-dimethyl-6-phenyl]hexyl-4,6,7-dihydroxy-6-O-(4(S),6(S)-dimethyl-2-octanoyl)-2,8-dioxabicyclo-[3.2.1]octane-3,4,5-triacid (26c)

To a solution of the methyl ether prepared in Example 279 (0.080 g, 0.0889 mmol) in ethyl acetate (1.6 ml), was added 10% palladium on carbon (0.0365 g) and the mixture was stirred overnight under an atmosphere of hydrogen gas at room temperature. The reaction mixture was filtered through a plug of celite and washed with EtOAc. The filtrate was concentrated in vacuo and then purified by flash column chromatography (silica gel, 4:1 hexane/EtOAc). The resulting yellow oil was then deprotected by standard methods (TFA) to provide the title compound.

$^1$H NMR (300 MHz, CD$_3$OD): δ7.321–7.195 (m, 10H), 6.338 (s, 2H), 5.292(s, 2H), 4.00 (s, 2H), 3.9449 (s, 2H), 3.722 (s, 6H), 3.249–2.929 (m, 10H), 2.584–2.320 (m, 10H), 1.940–1.232 (m, 20H), 1.154–0.781 (m, 15H).

EXAMPLE 281

Synthesis of (1S,3S,4S,5R,6R,7R)-1-[(4S)-acetoxy-3,5(R)-dimethyl-6-phenyl]hexyl-4,6-dihydroxy-6-O-(4(S),6(S)-dimethyl-2-octenoyl)-7-trimethylacetoxy-2,8-dioxabicyclo[3.2.1]octane-3,4,5-triacid (IA-7-trimethyl-acetyl ester) (5k')

To a solution of the 3,4,5tris t-butyl ester (1a) (50 mg, 0.0583 mmol) in methylene chloride 0.5 ml) was added triethylamine (24 μl, 0.1749 mmol) and 4-dimethylaminopyridine (7 mg, 0.0583 mmol). The solution was stirred at room temperature for five minutes and trimethylacetic anhydride (0.0130g, 0.0699 mmol) was added. The reaction was capped under nitrogen for sixteen hours and was then concentrated in vacuo. Purification of the residue by flash column chromatography (silica gel, 3:1 hexane/EtoAc) afforded the pivalyl triester as a white solid. This solid was then deprotected by the general method using triflouroacetic acid to give the title compound.

$^1$H NMR (300 MHz, CD$_3$OD): δ7.32–7.12 (m, 5H), 6.90 (dd, J=8.4, 15.6 Hz, 1H), 6.45 (d, J=2.1 Hz, 1H), 5.83 (d, J=15.6 Hz, 1H), 5.25 (d, J=2.1 Hz, 1H), 5.22 (s, 1H), 5.13 (d, J=5.4 Hz, 1H), 5.06 (brs, 1H), 5.03 (brs, 1H), 2.65 (dd, J=5.6, 13.4 Hz, 1H), 2.52–2.05 (m, 6H), 2.14 (s, 3H), 1.60–1.10 (m, 6H), 1.30 (s, 9H), 1.07 (d, J=6.6 Hz, 3H), 0.93–0.86 (m, 9H).

By procedures described above, the following IA-7-esters were prepared:

EXAMPLE 282

7-Benzoyl Ester (5l')

$^1$H NMR (300 MHz, CD$_3$OD): δ8.10–8.07 (m, 2H), 7.73–7.68 (m, 1), 7.59–7.54 (m, 2H), 7.28–7.08 (m, 5H), 6.91 (dd, J=8.4, 15.9 Hz, 1H), 6.64 (d, J=2.1 Hz, 1H), 5.86 (d, J=15.9 Hz, 1H), 5.51 (d, J=1.8 Hz, 1H), 5.34 (s, 1H), 5.08 (d, J=5.1 Hz, 1H), 5.06 (brs, 2H), 2.68 (dd, J=5.8, 13.5 Hz, 1H), 2.51–2.13 (m, 6H), 2.09 (s, 3H), 1.48–1.32 (m, 4H), 1.20–1.13 (m, 2H), 1.08–1.01 (m, 3H), 0.93–0.83 (m, 9H).

EXAMPLE 283

7-n-Butanoyl Ester (5m')

$^1$H NMR (300 MHz, CD$_3$OD): δ7.32–7.12 (m, 5H), 6.89 (dd, J=8.6, 15.6 Hz, 1H), 6.47 (d, J=1.8 Hz, 1H), 5.85 (d, J=15.6Hz, 1H), 5.28 (d, J=2.1Hz, 1H), 5.18 (s, 1H), 5.13 (d, J=4.8 Hz, 1H), 5.05 (brs, 1H), 5.01 (brs, 1H), 2.74 (dd, J=5.6, 13.5 Hz, 1H), 2.50–2.07 (m, 8H), 2.14 (s, 3H), 1.76–1.689 (m, 2H), 1.67–1.13 (m, 6H), 1.08–0.99 (m, 9H), 0.93–0.87 (m, 6H).

EXAMPLE 284

7-Acetate (5i')

$^1$H NMR (300 MHz, CD$_3$OD): δ7.32–7.18 (m, 5H), 6.91 (dd, J=8.6, 15.6 Hz, 1H), 6.49 (d, J=2.1 Hz, 1H), 5.84 (d, J=15.6 Hz, 1H), 5.25 (d, J=2.1 Hz, 1H), 5.16 (s, 1H), 5.12 (d, J=4.8 Hz, 1H), 5.05 (brs, 1H), 5.01 (brs, 1H), 2.74 (dd, J=5.4, 13.5 Hz, 1H), 2.47–2.02 (m, 6H), 2.21 (s, 3H), 2.14 (s, 3H), 1.43–1.14 (m, 6H), 1.07 (d, J=6.6 Hz, 3H), 0.93–0.84 (m, 9H).

EXAMPLE 285

7-Propionate (5j')

$^1$H NMR (300 MHz, CD$_3$OD): δ7.32–7.19 (m, 5H), 6.91 (dd, J=8.6, 15.6 Hz, 1H), 6.47 (d, J=2.1 Hz, 1H), 5.83 (d, J=15.6 Hz, 1H), 5.27 (d, J=1.8 Hz, 1H), 5.17 (s, 1H), 5.12 (d, J=5.4 Hz, 1H), 5.06 (brs, 1H), 5.02 (brs, 1H), 2.75 (dd, J=5.7, 13.2 Hz, 1H), 2.54–2.03 (m, 8H), 2.14 (s, 3H), 1.47–1.02 (m, 12H), 0.93–0.79 (m, 9H).

EXAMPLE 286 AND 287

Syntheses of (1S,3S,4S,5R,6R,7R)-1-[(4S)-acetoxy-3,5(R)-dimethyl-6-phenyl]hexyl-4,6-dihydroxy-6-O-(4(S),6(S)-dimethyl-2-octenoyl)-7-methoxy-2,8-dioxabicyclo-[3.2.1]octane-3,4,5-triacid (5n') and (1S,3S,4S,5R,6R,7R)-1-[(4S)-acetoxy-3,5(R)-dimethyl-6-phenyl]hexyl-4,7-dimethoxy-6-hydroxy-6-O-(4(S),6(S)-dimethyl-2-octenoyl)-2,8-dioxabicyclo[3.2.1]octane-3,4,5-triacid (5o')

To a stirred solution of tris-t-butyl ester (0.05 g, 0.0583 mmol) in anhydrous dimethylsulfoxide (0.148 g, 1.892 mmol) was added barium oxide (0.083 g, 0.5435 mmol). TO this stirred solution was added methyl iodide (0.637 g, 4.488 mmol) and the reaction mixture was stirred for 16 hours at room temperature. The reaction mixture was filtered through a sintered glass funnel and washed with chloroform. The organic solution was then diluted with water and extracted. The organic layer was dried over MgSO$_4$ and concentrated in vacuo. Purification of the residue by flash column chromatography (silica gel, 3:1 hexane/EtOAc) afforded the 7-monomethyl, and 4,7-dimethylether analogs as white solids. These compounds were then deprotected by the general method (TFA). Mono ethyl ether (5n') $^1$H NMR (300 MHz, CD$_3$OD): δ7.317–7.211 (m, 5H), 6.907 (dd, J=20.8, 11.6 Hz, 1H), 6.47 (s, 1H), 5.875 (d, J=21.2 Hz, 1H), 5.298 (s, 1H), 5.095 (d, J=14.4 Hz, 1H), 5.017 (s, 1H), 5.003 (s, 1H), 4.067 (d, J=2 Hz, 1H), 3.65 (s, 3H), 2.747 (dd, J=18, 7.4 Hz, 1H), 2.492–2.431 (m, 4H), 2.140 (s, 3H), 2.119–2.035 (m, 2H), 1.484–1.126 (m, 8H), 1.089 (d, J=7.2 Hz, 3H), 1.059–0.830 (m, 9H). Dimethyl ether (5o') $^1$H NMR (300 MHz, CD$_3$OD): δ7.327–7.187 (m, 5H), 6.93 (dd, J=20.4, 10.8 Hz, 1H), 6.634

(s, 1H), 5.832 (d, J=20.8 Hz, 1H), 5.535 (s, 1H), 5.279 (s, 1H), 5.101–5.017 (m, 3H), 3.768–3.721 (m, 3H), 3.574–3.519 (m, 3H), 2,504 (dd, J=17.6, 5.2 Hz, 1H), 2.182–2.093 (m, 6H), 2.075 (s, 3H), 1.427–1.329 (m, 3H), 1.204–1.117 (m, 2H), 1.077 (d, J=8.8 Hz, 3H), 0.951–0.847 (m, 9H).

EXAMPLE 288

Preparation of IA-tris-t-butyl ester-Cl(4')-alcohol (4')

A solution of IA-tris-t-butyl ester-7-(1-methyl-1-methoxyethyl ether-Cl(4')-alcohol (4'a) (200 mg, 0.23 mmol) in THF (6 mL), water, (2 mL) and acetic acid (2 mL) was heated a 45° C. for 16 hours. The reaction was cooled to room temperature, diluted with dichloromethane (50 mL), washed with sat. sodium bicarbonate (10 mL), brine (10 mL), dried ($Na_2SO_4$) and concentrated in vacuo. Column chromatography of the residue (silica gel, 3:1 hexanes: ethyl acetate) gave 4' as a white solid.

$^1$H NMR (400 MHz, $CDCl_3$): δ7.34–7.12 (m, 5H), 6.86 (dd, J=15.6, 8.5 Hz, 1H), 5.97 (app s, 1H), 5.73 (dd, J=15.7, 1.06 Hz, 1H), 5.1 (s, 1H), 5.04 (s, 1H), 4.03 (d, J=5.4 Hz, 1H), 4.01 (d, J=1.87 Hz, 1H), 2.75 (dd, J=13.5, 5.41 Hz, 1H), 2.47–2.30 (m, 4H), 2.12 (t, J=7.24 Hz, 2H), 1.96 (m, 1H), 1.57 (s, 9H), 1.46 (s, 9H), 1.44 (s, 9H), 1.41–1.24(m, 3H, 1.1 (m, 2H), 1.01 (d, J=6.6 Hz, 3H), 0.81 (m, 9H); MS (FAB) m/z 823 (M+Li)+.

EXAMPLE 289

Preparation of (1S,3S,4S,5R,6R,7R)-1-[(4S)-hydroxy-3-hydroxy-3-hydroxymethyl-5(R)-methyl-6-phenyl]hexyl-4,6,7-trihydroxy-6-O-((S),(4S), 6(S)-dimethyl-2-octenoyl)-2,8-dioxa-bicyclo[3.2.1]octane-3,4,5-tris-t-butyl ester (29)

To a solution of allylic alcohol 4'a (1.31 g, 1.60 mmol) was added a solution of osmium tetraoxide (5.2 mL of a 0.36 molar solution of osmium tetraoxide in dioxane) dropwise via syringe pump. The reaction was maintained at room temperature for ca. 8–10 hours whereupon it was diluted with additional dioxane (20 mL). Hydrogen sulphide was bubbled through the mixture for 15 min. The black reaction mixture was then filtered through a short pad of celite eluting with dichloromethane and was then concentrated in vacuo to yield a clear light green oil. Column chromatography of the residue (silica gel, 2:1 ethyl acetate:hexanes) gave of the title compound (29) as a white powder:

$^1$H NMR (400 MHz $CD_3OD$): δ7.26–7.09 (m, 5H), 6.88 (dd, J=15.6, 8.6 Hz, 1H), 5.81 (d, J=14.71 Hz, 1H), 5.15 (s, 1H), 4.00 (d, J=1.71 Hz, 1H), 3.65 (br m, 1H), 3.52 (br m, 2H), 2.78–2.52 (m, 2H), 2.45 (m, 1H), 2.19 (m, 1H), 1.88 (br m, 3H), 1.62 (s, 9H), 1.46 (s, 9H), 1.43 (s, 9H), 1.41–1.27 (m, 3H), 1.66–1.09 (m, 3H), 1.02 (d, J=6.7 Hz, 3H), 0.97 (d, J=6.6 Hz, 3H), 0.87 (m, 6H); MS (FAB)m/z 857 (M+Li)+

EXAMPLE 290

Preparation of (1S,3S,4S,5R,6R,7R)-1-[(4S)-hydroxy-3-oxo-5(R)-methyl-6-phenyl]hexyl-4,6,7-trihydroxy-6-O-(4(S),6(S)-dimethyl-2-octenoyl)-2,8-dioxabicyclo[3.2.1]octane-3,4,5-tris-t-butyl ester (31a) and (1S,3S,4S,5R,6R,7R)-1-[4-hydroxy-3-oxo-butyl]-4,6,7-trihydroxy-6-O-(4(S),6(S)-dimethyl-2-octenoyl)-2,8-dioxa-bicyclo[3.2.1]octane-3,4,5-tris-t-butyl ester (31b)

To a solution of (29) (87 mg, 0.102 mmol) in dioxane:water (5 mL:1 mL) was added sodium periodate (48.73 mg, 0.11 mmol) in a single portion. The reaction mixture was stirred at room temperature for 4 h, whereupon it was diluted with dichloromethane (20 mL). The organic layer was washed with water (10 mL), brine (10 mL), dried ($MgSO_4$) and concentrated. Column chromatography of the residue (silica gel, 1:1 hexanes: ethyl acetate) gave the highest $R_f$ material (31a) and the lower $R_f$ spot (31b):

$^1$H NMR (300 MHz, $CDCl_3$): highest $R_f$ material (31a) δ7.29–7.14 (m, 5H), 6.88 (dd, J=15.75, 8.55 Hz, 1H), 5.98 (d, J=1.9 Hz, 1H), 5.72 (d, J=15.4 Hz, 1H), 5.01 (s, 1H), 4.14 (m, 1H), 4.07 (s, 1H), 3.50 (d, J=4.6 Hz, 1H), 3.03 (d, J=3.12 Hz, 1H), 2.87–2.58 (m, 5H), 1.57 (s, 9H), 1.43 (s, 9H), 1.41 (s, 9H), 1.36–1.12 (m, 6H), 1.07 (d, J=6.7 Hz ), 1.00 (d, J=6.7 Hz, 3H), 0.84–0.81 (m, 6H), 0.68 (d, J=6.7 Hz, 3H). (31b) $^1$H NMR (300 MHz, $CDCl_3$): lower $R_f$ material δ6.85 (dd, J=15.8, 8.5 Hz, 1H), 5.98 (d, J=0.94 Hz, 1H), 5.72 (d, J=16.4 Hz, 1H), 5.02 (s, 1H), 4.29 (br s, 1H), 3.23 (br s, 1H), 3.07 (d, J=2.75 Hz, 1H), 2.84–2.78 (m, 2H), 2.41–2.34 (m, 2H), 2.20 (m, 1), 1.65 (s, 9H), 1.43 (app. s, 18H), 1.36–1.21 (m, 3H), 1.12 (m, 2H), 1.00 (d, J=6.65 Hz, 3H) 0.84–0.79 (m, 6H).

EXAMPLE 291

Preparation of (1S,3S,4S,5R,6R,7R)-1-[2-carboxyethyl]-4,6,7-trihydroxy-6-O-(4(S),6(S)-dimethyl-2-octenoyl)-2,8-dioxabicyclo[3.2.1]octane-3,4,5-tris-t-butyl ester(30).

To a solution of (29) (184 mg, 0.22 mmol) in dioxane (10 mL) and water (2 mL) was added sodium periodate (468 mg, 1.08 mmol). The reaction mixture was stirred at room temperature overnight whereupon it was diluted with dichloromethane (50 mL), washed with water (15 mL), brine (15 mL), dried ($Na_2SO_4$) and concentrated in vacuo. Column chromatography of the residue (silica gel, 5:1 chloroform: methanol) gave the title compound (30) as a white solid:

$^1$H NMR (300 MHz, $CD_3OD$): δ6.92 (dd, J=15.63, 8.47 Hz, 1H), 6.46 (d, J=1.57 Hz, 1H), 5.84 (d, J=15.62 Hz, 1H), 5.24 (s, 1H), 4.17 (d, J=1.63 Hz, 1H), 2.54 (m, 3H), 2.23 (m, 2H), 1.67 (s, 9H), 1.52 (s, 9H), 1.46 (s, 9H), 1.65–1.16 (m, 8H), 1.05 (d, J=6.73 Hz, 2H), 0.91 (m, 4H); MS (FAB) m/z 709 (M+Na)$^+$

EXAMPLE 292

Preparation of (1S,3S,4S,5R,6R,7R)-1-[3-hydroxypropyl]-4,6,7-trihydroxy-6-O-(4(S),6(S)-dimethyl-2-octenoyl)-7-O-(1-methyl-1-methoxyethylether)-2,8-dioxabicyclo[3.2.1]octane-3,4,5-tris-t-butyl ester (33: $R^5$=C($CH_3$)$_2$O$CH_3$)

To a solution of (29) (761.5 mg, 0.895 mmol) in dioxane (25 mL) and water (5 mL) was added sodium metaperiodate (426 mg, 0.98 mmol). The reaction mixture was maintained at room temperature for approximately 3 hours whereupon it was diluted with dichloromethane (100 mL), washed with water (20 mL), brine (20 mL), dried ($Na_2SO_4$) and concentrated in vacuo. The crude material was then dissolved in methanol (10 mL), cooled to 0° C. and sodium borohydride (67 mg, 1.79 mmol) was added in a single portion. The reaction was then stirred for 20 minutes at room temperature then quenched with water (10 mL) and ethyl acetate (50 mL). The organic layer was washed with brine (10 mL), dried ($Na_2SO_4$) and concentrated to give 690 mg of the crude geminal diols. This crude material was dissolved in dioxane:water (10 mL: 2 mL) and sodium periodate (426 mg, 0.98 mmol) was added in a single portion. The reaction was stirred at room temperature for 6 h and worked up as before. Column chromatography of the residue (silica gel, 4:1 hexanes:ethyl acetate) gave 32 as a clear light green viscous oil. To a solution of the aldehyde 32 ($R^5$=H; 100 mg, 0.149 mmol) in dichloromethane (3.0 mL) at 0° C. was added p-PTS (10 mg) and 2-methoxypropene (72 uL, 0.75 mmol). The reaction mixture was maintained at 0° C. for approximately 2 h whereupon it was diluted with dichloromethane (30 mL) and washed with sat. sodium bicarbonate (10 mL), brine (10 mL), dried ($Na_2SO_4$) and concentrated in vacuo. Column chromatography of the residue (silica gel, 2:1 hexanes:ethyl acetate) gave the protected compound (32) [$R^5$=C($CH_3$)$_2$O$CH_3$] as a clear colorless oil:

$^1$H NMR (400 MHz, $CDCl_3$): δ9.86 (apparent s, 1H), 6.85 (dd, J=15.81, 8.24 Hz, 1H), 6.39 (s, 1H), 5.72 (d, J=15.8 Hz, 1H), 5.02 (s, 1H), 4.20 (br s, 1H), 4.01 (br s, 1H), 3.22 (s, 3H), 3.02–2.81 (m, 2H), 2.40–2.33 (m, 1H), 2.07 (m, 1H), 1.65 (s, 9H), 1.43 (s, 9H), 1.35 (s, 2H), 1.34 (s, 9H), 1.25 (s, 3H), 1.22 (s, 3H), 1.05 (m, 3H), 0.96 (d, J=6.7, 3H), 0.78 (m, 6H); MS (FAB) m/z 755 (M+Li2)$^+$.

To a solution of the protected aldehyde (32; $R^5$=C($CH_3$)$_2$O$CH_3$) (56 mg, 0.074 mmol) in methanol (3.0 mL) at 0° C. was added sodium borohydride (8.4 mg, 0.22 mmol) in a single portion. The reaction was stirred at 0° C. for 10 mins. and workup was performed in the usual fashion. Column chromatography of the residue (silica gel, 1:1 hexanes ethyl acetate) gave alcohol (33; $R^5$=C($CH_3$)$_2$O$CH_3$) as a clear light green oil: $^1$H NMR (400 MHz, $CD_3OD$): δ6.88 (dd, J=15.7, 8.3 Hz, 1H), 6.47 (s, 1H), 5.81 (d, J=15.7 Hz, 1H), 5.09 (s, 1H), 4.27 (s, 1H), 3.66 (m, 2H), 3.23 (br s, 3H), 2.46 (m, 1H), 2.05 (m, 1H), 1.9–1.82 (m, 3H), 1.66 (s, 9H), 1.47 (s, 9H), 1.38 (s, 12H), 1.38–1.28 (m, 4H), 1.28 (s, 3H), 1.15–1.02 (m, 3H), 1.02 (d, J=6.7 Hz, 3H), 0.86 (m, 6H); MS (FAB) m/z 767 (M+Na)$^+$.

EXAMPLE 293

Preparation of (1S,3S,4S,5R,6R,7R)-1-[3'-hydroxypropyl]-4,6,7-trihydroxy-6-O-(4(S),6(S)-dimethyl-2-octenoyl)-2,8-dioxabicyclo[3,2,1]octane-3,4,5-tris-t-butyl ester (33: $R^5$=H)

To a solution of the aldehyde (32; $R^5$=H) (142 mg, 0.19 mmol) in methanol (5.0 mL) was added sodium borohydride (21.5 mg, 0.57 mmol) in a single portion. The reaction was maintained at room temperature for approximately 15 mins. whereupon the reaction was diluted with dichloromethane (50 mL). The organic layer was washed with sat. sodium bicarbonate (10 mL), water (10 mL), brine (10 mL), dried ($Na_2SO_4$) ad concentrated in vacuo to yield 33; $R^5$=H. This material was of sufficient purity to be used in the following step:

$^1$H NMR (400 MHz, $CDCl_3$): δ6.86 (dd, J=15.7, 8.4 Hz, 1H), 6.01 (d J=1.9 Hz, 1H), 5.72 (d, J=15.7 Hz, 1H), 5.06 (s, 1H), 4.08 (br s, 2H), 3.75 (br s, 2H), 3.3 (br s, 1H), 2.66 (br s, 1H), 2.39 (m, 1H), 2.07 (t, J=6.6 Hz, 2H), 1.86 (m, 2H), 1.57 (s, 9H ), 1.44 (s, 9H), 1.43 (s, 9H), 1.39–1.21 (m, 4H), 1.09 (m, 2H), 1.00 (d, J=6.7 Hz, 2H), 0.82 (m, 6H).

EXAMPLE 294

The preparation of (1S,3S,4S,5R,6R,7R)-1-[(4S)-hydroxy-3-hydroxy-3-hydroxymethyl-5(R)-methyl-6-phenyl]-hexyl-4,6,7-trihydroxy-6-O-(4(S),6(S)-dimethyl-2-octenoyl)-2,8-dioxabicyclo[3.2.1]octane-3,4,5-triacid (29a)

To a room temperature of 3% HCl in methanol (21 mL generated from 20 mL of methanol and 1.1 mL of $SOCl_2$) was added the tribenzyl ester 1e(1.00 gm, 1.01 mmol). The solution was maintained at room temperature for ca. 5.5 hr whereupon one half of the methanol was removed in vacuo. The remaining organics were diluted with methylene chloride and washed with sat. $NaHCO_3$, brine, dried ($Na_2SO_4$), concentrated and the residue was chromatographed to give the tribenzyl $C_4'$-alcohol and the C3-monomethyl ester-C4, C5-dibenzyl $C_4'$-alcohol.

To the tribenzyl $C_4'$-alcohol (388 mg, 0.42 mmol) in dioxane (10 mL) and pyridine (0.5 mL) was added a solution of osmium tetraoxide (1.35 mL of a 95 mg/mL solution of osmium tetraoxide in dioxane). The reaction was maintained at room temperature for 1 hr whereupon hydrogen sulfide was bubbled through the reaction. The black solution was filtered through celite with ethyl acetate and the organics were concentrated in vacuo. The residue was chromatographed (2:1 ethyl acetate:hexane, silica gel) and gave the tribenzyl pentaol.

Deprotection of the tribenzyl pentaol (31.2 mg, 0.032 mmol) according to the procedure of Example 90 gave the triacid-pentaol, 29a, as a white solid. MS (FAB) m/z 705 (M+Na).

EXAMPLE 295

General Procedure of Deprotection

The fully protected or partially protected derivatives (t-Bu) are dissolved in dry dichloromethane and trifluoroacetic acid is added. The reaction mixture is stirred at room temperature overnight whereupon the solvent is removed in vacuo. The residue is dissolved in dry toluene and concentrated (2×). The residue is then dissolved in dry benzene and lyophilized to yield a white to off white solid.

EXAMPLE 296

Preparation of (1S,3S,4S,5R,6R,7R)-1-[2-carboxyethyl]-4,6,7-trihydroxy-6-O-(4(S),6(S)-dimethyl-2-octenoyl)-2,8-dioxabicyclo[3.2.1]octane-3,4,5-triacid (30a)

Deprotection of the acid (30) (50 mg, 0.073 mmol) gave (30a) as a white solid:

$^1$H NMR (400 MHz, $CD_3OD$): δ6.82 (dd, J=15.7, 8.6 Hz, 1H), 6.29 (d, J=1.7 Hz, 1H), 5.75 (d, J=15.7 Hz, 1H), 5.25 (s, 1H), 4.50 (app. t, J=5.9, 2H), 4.07 (d, J=1.9 Hz, 1H), 2.44 (m, 1H), 2.13–1.99 (m, 3H), 1.40–1.26 (m, 6H), 1.17–1.10 (m, 2H), 1.02 (d, J=6.7 Hz, 3H ), 0.86 (m, 8H); MS (FAB) m/z 584 [M+Na3+H]+

EXAMPLE 297

Preparation of (1S,3S,4S,5R,6R,7R)-1-[3-hydroxypropyl]-4,6,7-trihydroxy-6-O-(4(S),6(S)-dimethyl-2-octenoyl)-2,8-dioxabicyclo[3.2.1]octane-3,4,5-triacid (33a)

Deprotection of (33; $R^5$=H) (43.7 mg, 0.065 mmol) gave 33a as a white solid:

$^1$H NMR (400 MHz, $CD_3OD$): δ6.82 (dd, J=15.4, 8.3 Hz, 1H), 6.30 (s, 1H), 5.77 (d, J=15.6 Hz, 1H), 5.24 (s, 1H), 4.08 (s, 1H), 2.73–2.66 (m, 2H), 2.43 (m, 1H), 2.24–2.17 (m, 2H), 1.47–1.28 (m, 6H), 1.17–1.09 (m, 3H), 1.02 (d, J=6.6 Hz, 3H), 0.85 (m, 8H); MS (FAB) m/z 529 [M+Li4+H]$^+$

EXAMPLE 298

Preparation of (1S,3S,4S,5R,6R,7R)-1-[4-hydroxy-3-oxobutyl]-4,6,7-trihydroxy-6-O-(4(S),6-(S)-dimethyl-2-octenoyl)-2,8-dioxabicyclo[3.2.1]octane-3,4,5-triacid (31d)

Deprotection of (31b) gave (31d):

$^1$H NMR (400 MHz, $CD_3OD$): δ6.80 (dd, J=15.66, 8.53 Hz, 1H), 6.30 (d, J=1.5 Hz, 1H), 5.75 (d, J=14.8 Hz, 1H), 5.20 (s, 1H), 3.37 (m, 2H), 2.80–2.60 (m, 1H), 2.50–2.10 (m, 3H), 1.35 (m, 3H), 1.14 (m, 1H), 1.0 (m, 3H), 0.92–0.80 (m, 6H). FAB m/e 555 (M+Na ).

EXAMPLE 299

Preparation of (1S,3S,4S,5R,6R,7R)-1-[(4S)-hydroxy-3-oxo-5(R)-methyl-6-phenyl]hexyl-4,6,7-trihydroxy-6-O-(4(S),6(S)-dimethyl-2-octenoyl)-2,8-dioxabicyclo[3.2.1]-octane-3,4,5-triacid (31c)

Deprotection of (31a) gave (31c):

$^1$H NMR (400 MHz, $CD_3OD$): δ7.30–7.11 (m, 5H), 6.82 (dd, J=15.6, 8.62 Hz, 1H), 6.29 (d, J=1.9 Hz, 1H), 5.78 (d, J=14.6 Hz, 1H), 5.25 (s, 1H), 4.29 (d, J=3.7 Hz, 2H), 4.05

(d, J=2.03 Hz, 2H), 2.98 (m, 1), 2.80 2H), 2.60 (m, 1H), 1.34–1.28 (m, 5H), 1.15 (m, 2H), 1.01 (d, J=6.64 Hz, 2H), 0.90 (m, 7H). FAB m/e 673 (M+Na).

EXAMPLE 300

Synthesis of Esters of C-1 Sidechain

1. Preparation of Esters

The esters are prepared according to known literature procedures through either acylation of the alcohol 33 ($R^5$=C(CH$_3$)$_2$OCH$_3$) with the appropriate acid chloride or coupling of the alcohol with the appropriate acid and DCC. Deprotection of the t-butyl esters is performed in the usual manner with trifluoroacetic acid in dichloromethane.

EXAMPLE 301

Preparation of 39-dodecoylester (39a)

$^1$H NMR (300 MHz, CD$_3$OD): δ6.82 (dd, J=15.6, 8.4 Hz, 1H), 6.29 (d, J=1.8 Hz, 1H), 5.79 (dd, J=15.6, 1.0 Hz, 1H), 5.25 (s, 1H), 4.16 (br s, 2H), 4.07 (d, J=1.8 Hz, 1H), 2.43 (m, 1H), 2.32 (t, J=4.2 Hz, 2H), 1.97 (m, 3H), 1.55 (m, 3H) 1.28 (m, 28H), 1.16 (m, 2H), 1.13 (d, J=6.1 Hz, 3H), 0.91–0.85 (m, 9H). MS (FAB) m/e 709 (M+Na).

EXAMPLE 302

Preparation of 39-pivaloyl ester (39b )

This compound was a white solid.

$^1$H NMR (400 MHz, CD$_3$OD): δ6.82 (dd, J=15.59, 8.39 Hz, 1H), 6.30 (d, J=1.8 Hz, 1H), 5.80 (d, J=15.58 Hz, 1H), 5.25 (d, J=5.24 Hz, 1H), 4.15 (m, 2H), 4.07 (d, J=1.75 Hz, 1H), 2.04–1.95 (m, 3H), 1.41–1.25 (m, 6H), 1.20 (s, 9H), 1.05 (d, J=6.69 Hz, 2H), 0.90–0.82 (m, 8H). MS (FAB) m/e 611 (M+Na).

EXAMPLE 303

Preparation of 39-pentanoate ester (39c)

Compound prepared was a white solid.

$^1$H NMR (400 MHz, CD$_3$OD): δ6.80 (dd, J=15.61, 8.62 Hz, 1H), 6.30 (s, 1H), 5.77 (d, J=15.67 Hz, 1H), 5.25 (s, 1H), 4.15 (m, 2H), 4.06 (s, 1H), 2.50–2.40 (m, 1H), 2.33 (t, J=7.47 Hz, 3H), 2.00 (m, 4H), 1.63–1.55 (m, 2H) 1.41–1.22 (m, 7H), 1.20–1.10 (m, 2H), 1.05 (d, J=6.64 Hz, 2H), 0.95–0.81 (m, 8H). MS (FAB) m/e 611 (M+Na).

EXAMPLE 304

Preparation of 39-acetate ester (39d)

Compound (39d) was isolated as a white solid.

$^1$H NMR (400 MHz, CD$_3$OD): δ6.80 (dd, J=15.68, 8.53 Hz, 1H), 6.30 (d, J=1.94 Hz, 1H), 5.79 (d, J=14.8 Hz, 1H), 5.25 (s, 1H), 4.15 (m, 1H), 4.09 (d, J=1.98 Hz, 1H), 2.45 (m, 1H), 2.03 (s, 1H), 1.95 (m, 4H), 1.40–1.25 (m, 5H), 1.20–1.10 (m, 2H), 1.03 (d, J=6.68 Hz, 2H), 0.87 (m, 5H). MS (FAB) m/e 569 (M+Na).

EXAMPLE 305

Preparation of 39-4-phenylbutyrate ester (39e)

Compound (39e) was isolated an off-white solid.

$^1$H NMR (400 MHz, CD$_3$OD): δ7.30–7.10 (m, 5H), 6.82 (dd, J=15.66, 8.48 Hz, 1H), 6.30 (d, J=1.80 Hz, 1H), 5.76 (d, J=14.61 Hz, 1H), 5.25 (s, 1H), 4.15 (m, 1H), 4.07 (d, J=1.84 Hz, 1H), 2.62 (t, J=7.33 Hz, 2H), 2.40 (m, 1H), 2.30 (t, J=7.37 Hz, 1H), 2.0–1.88 (m, 6H), 1.40–1.25 (m, 5H), 1.20–1.10 (m, 2H), 1.01 (dd, J=6.55 Hz, 2H), 0.92–0.82 (m, 5H). MS (FAB) m/e 673 (M+Na).

EXAMPLE 306

Preparation of 39-benzoate ester (39f)

Compound (39f) was isolated as an off-white solid. $^1$H NMR (CD$_3$OD): δ8.05 (d, J=7.06, 2H), 7.60 (m, 1H), 7.45 (m, 2H), 6.82 (dd, J=15.60, 8.57 Hz, 2H), 6.31 (d, J=1.8 Hz, 1H), 5.80 (d, J=15.77, 1H), 5.27 (s, 1H), 4.45–4.37 (m, 2H), 4.12 (d, J=1.89, 1H), 2.48–2.40 (m, 1H), 2.12–2.05 (m, 3H), 1.40–1.25 (m, 6H), 1.20–1.10 (m, 2H), 1.15 (d, J=5.81, 2H), 0.92–0.80 (m, 5H). MS (FAB) m/e 631 (m+Na ).

EXAMPLE 307

Synthesis of Carbamates of C-1 Sidechain

1. Preparation of Carbamates.

Carbamates of the C-1 sidechain are synthesized by acylation of the alcohol 33 ($R^5$=C(CH$_3$)$_2$OCH$_3$) with the appropriate isocyanate. Deprotection of these intermediates is performed with trifluoroacetic acid in dichloromethane solvent.

EXAMPLE 308

Preparation of 39-phenylcarbamate (39h)

$^1$H NMR (400 MHz, CD$_3$OD): δ7.42 (m, 2H), 7.29 (m, 2H), 7.01 (m, 1H), 6.82 (dd, 15.7, 8.5 Hz, 1H), 6.30 (s, 1H) 5.77 (d, J=15.5 Hz, 1H), 5.26 (s, 1H), 4.21 (br s, 2H), 4.09 (d, J=6.8 Hz, 1H), 2.43 (m, 1H), 2.15–1.98 (m, 4H), 1.40–1.21 (m, 5H), 1.17 (m, 2H), 1.01 (d, J=6.7 Hz, 3H), 0.91–0.89 (m, 7H); MS (FAB) m/z 624 (M+)

EXAMPLE 309

Preparation of 39-o-ethylphenyl carbamate (39i)

Compound (39i) was isolated as a white solid.

$^1$H NMR (400 MHz, CD$_3$OD): δ7.37 (d, 7.47 Hz, 1H), 7.23–7.07 (m, 3H), 6.82 (dd, J=15.65, 8.48, 1H), 6.30 (d, J=1.70 Hz, 1H), 5.77 (d, J=14.93 Hz, 1H), 5.25 (s, 1H), 4.22 (s, 1H), 4.10 (s, 1H), 2.70–2.60 (m, 3H), 2.50–2.40 (m, 1H), 2.10 (m, 3H), 1.40–1.28 (m, 5H), 1.23–1.10 (m, 5H), 1.05 (d, J=6.68 Hz, 2H), 0.90 (m, 5H). MS (FAB) m/e 674 (M+Na ).

EXAMPLE 310

Preparation of 39-n-octylcarbamate (39j)

Compound (39j) was isolated as a white solid.

$^1$H NMR (400 MHz, CD$_3$OD): δ6.82 (dd, J=15.63, 8.48 Hz, 1H), 6.29 (d, J=1.6 Hz, 1H), 5.75 (d, J=15.77 Hz, 1H), 5.25 (d, J=1.61 Hz, 1H), 4.10 (m, 2H), 3.10 (m, 5H), 2.45 (m, 1H, 2.00–1.90 (b m, 3H), 1.50–1.40 (m, 3H), 1.38–1.22 (m, 1.7H), 1.05 (d, J=6.68 Hz, 2H), 0.92–0.82 (m, 6H). FAB m/e 682 (M+Na).

EXAMPLE 311

Preparation of (1S,3S,4S,5R,6R,7R)-1-[(4-hydroxy-3,5-dimethyl-8-phenyl]oct-7-enyl-4,6,7-trihydroxy-6-O-(tetradeca-6,12-dienoyl)-2,8-dioxabicyclo[3.2.1]-octane-3.4,5-tris-t-butyl ester (1B)

A solution of (1S,3S,4S,5R,6R,7R)-1-[(4)-hydroxy-3,5-dimethyl-8-phenyl]oct-7-enyl-4,6,7-trihydroxy-6-(O-(tetradeca-6,12-dienoyl)-2,8-dioxabicylo[3.2.1]octane-3,4,5-tricarboxylic acid (IB) (68 mg, 0.0931 mmol) and O-t-butyl-N,N′-diisopropylisourea (0.56 g, 2.794 mmol) in benzene (2.9 mL) was heated to 65° C. for 16 hours. The resultant mixture was cooled to room temperature and concentrated in vacuo. Purification of the residue (silica gel, 3:1, hexanes: ethyl acetate) provided the title compound as a viscous oil.

$^1$H NMR (CDCl$_3$, 400 MHz): δ7.33–7.17 (m, 5H), 6.37 (d, J=16.0 Hz, 1H), 6.17 (dt, J=7.6, 16 Hz, 1H), 5.87 (d, J=2.0 Hz, 1H), 5.39–5.34 (m, 4H), 4.98 (s, 1H), 4.05 (s, 1H), 3.95 (d, J=2.0 Hz, 1H), 3.31–3.29 (m, 1H), 2.87 (br s, 1H), 2.34–2.27 (m, 3H), 2.08–1.62 (m, 13H), 1.61–1.23 (m, 12H), 1.55 (s, 9H), 1.46 (s, 9H), 1.42 (s, 9H), 0.94 (d, J=6.4 Hz, 3H), 0.93 (d, J=6.4 Hz, 3H).

EXAMPLE 312

Preparation of (1S,3S,4S,5R,6R,7R)-1-[(4-oxo-3,5-dimethyl-8-phenyl]oct-7-enyl-4,6,7-trihydroxy-6-O-(tetradeca-6,12-dienoyl)-2,8-dioxabicylo[3.2.1]octane-3,4,5-tris-t-butyl ester A mixture of (1S,3S,4S,5R,6R,7R)-1-[(4-hydroxy-3,5-dimethyl-8-phenyl]oct-7-enyl-4,6,7-trihydroxy-6-O-(tetradeca-6,12-dienoyl)-2,8-dioxabicylo[3.2.1]octane-3,4,5-tris-t-butyl ester (10 mg, 0.011 mmol), pyridinium dichromate (21 mg, 0.0556 mmol), magnesium sulfate (21 mg) and 4 Å sieves (21 mg) in C$_2$Cl$_2$ (0.5 mL) was stirred at 23° C. for 16 hours. The mixture was diluted with ether (3.0 mL), stirred for 1 hour, and filtered through a plug of celite. The filtrate was concentrated in vacuo and the residue was purified (silica gel, 3:1, hexanes: ethyl acetate) to provide the title compound. $^1$H NMR (CDCl$_3$, 400 MHz): δ7.32–7.15 (m, 5H), 6.37 (d, J=16.0 Hz, 1H ), 6.10 (dt, J=7.6, 16 Hz, 1H), 5.85 (d J=2.0 Hz, 1H), 5.39–5.33 (m, 4H), 4.96 (s, 1H), 4.01 (s, 1H), 3.91–3.89 (m, 1H), 2.83–2.76 (m, 3H), 2.56–2.48 (m, 1H), 2.31–2.27 (m, 2H), 2.19–2.12 (m, 1H), 1.99–1.78 (m, 9H), 1.62–1.23 (m, 12H), 1.55 (s, 9H) 1.44 (s, 9H), 1.09 (d, J=6.8 Hz, 3H), MS (FAB), m/e 903 [M+Li]$^+$.

EXAMPLE 313

Preparation of (1S,3S,4S,5R,6R,7R)-1-[(4R,S)-hydroxy-3,5-dimethyl-8-phenyl]oct-7-enyl-4,6,7-trihydroxy-6-O-(tetradeca-6,12-dienoyl)-2,8-dioxabicylo[3.2.1]octane-3,4,5-tri-acid Sodium tetrahydridoborate (NaBH$_4$) (1 mg, 0.0264 mmol) was added to a solution of (1S,3S,4S,5R,6R,7R)-1-[(4-oxo-3,5-dimethyl-8-phenyl]-oct-7-enyl-4,6,7-trihydroxy-6-O-(tetradeca-6,12-dienoyl)-2,8-dioxabicylo[3.2.1]octane-3,4,5-tris-t-butyl ester (13.0 mg, 0.0145 mmol) in methanol (0.20 mL) at 23° C. After 0.25 hour, TLC indicated two lower R$_f$ spots. The reaction was quenched with saturated aqueous ammonium chloride and extracted with CH$_2$Cl$_2$. The combined organic extracts were dried (Na$_2$SO$_4$), filtered and concentrated in vacuo. Chromatography (silica gel, 4:1 hexanes:ethyl acetate) gave the title compound as an apparent 2:1 mixture of alcohols as evidenced by NMR. The mixture of alcohols (13 mg, 0.0144 mmol) in CH$_2$Cl$_2$ (0.5 mL) was cooled to 0° C. and trifluoroacetic acid (0.1 mL) was added. The solution was allowed to warm to 23° C. and stirred for 12 hours. The solution was concentrated in vacuo and the residue was diluted with toluene and concentrated again in vacuo to provide the title compound as a 2:1 mixture of the 4'-alcohols based upon HPLC analysis MS (FAB) m/e 749 [M.Li$_2$+Li]$^+$.

EXAMPLE 314

Preparation of IB-C3-Methyl Ester

Compound IB free acid (20 mg) was stirred for 18 hours at room temperature in 3 mL of 3% methanolic HCl. The reaction solution was concentrated to a residue that was chromatographed by HPLC using a C$_8$ reverse phase column and acetonitrile/20 mM phosphate buffer pH 2.5 as eluting eluate. Appropriate HPLC fractions were pooled, diluted with two volumes of water and extracted with dichloromethane. The organic extract was washed with water, dried over anhydrous Na$_2$SO$_4$, and concentrated to afford the title compound as an oil in essentially pure form.

$^{13}$C NMR (CD$_3$OD, 75 MHz) δ173.54, 172.40, 169.08, 168.44, 139.22, 132.60, 132.53, 131.86, 130.95, 130.16, 129.48 (2), 127.85, 126.99 (2), 125.69, 107.52, 90.97, 81.93, 80.93, 78.43, 76.98, 75.75, 52.58, 38.62, 36.88, 36.62, 34.80, 33.86, 33.47 (2), 33.19, 30.24 (2), 30.22, 27.48, 25.28, 18.11, 15.07, 14.84.

EXAMPLE 315

Preparation of (1S,3S,4S,5R,6R,7R)-1-[(4S)-hydroxy-3-methylene-5(R)-methyl-6-phenyl]hexyl-4,6,7-trihydroxy-2.8-dioxabicyclo[3.2.1]-octane-3.4.5-tricarboxylic acid trisodium salt.

To 120 mg of compound IA dissolved in 12 mL of methanol was added 8 mL water, followed by 5.2 mL of 0.2N aqueous NaOH solution. After stirring for 8 hours at room temperature, the reaction mixture was acidified to pH 7.5 with 0.5N hydrochloric acid. The solution was concentrated by rotary evaporation to remove the methanol and the concentrate was applied to a 15 mL open column of Bakerbond C$_{18}$ resin. The resin was eluted with a stepwise gradient of methanol/water. The title compound eluted with 2/8 methanol/water and concentration afforded the trisodium salt.

$^1$H NMR (CD$_3$OD) δ7.32 (m, 5H), 5.26 (s, 1H), 5.13 (s, 1H), 5.09 (s, 1H), 4.10 (s, 1H), 3.97 (d, J=5 Hz, 1H), 2.76 (dd, J=14, 6 Hz, 1H), 2.4 (m, 2H, 2.2 (m), 2.1 (m, 3H), 0.82 (d, J=7 Hz, 3H).

EXAMPLE 316

As a specific embodiment of an oral composition of a compound of this invention, 20 mg of the compound 5z" from Example 103 is formulated with sufficient finely divided lactose to provide a total amount of 580 to 590 mg to fill a size 0 hard gelatin capsule.

EXAMPLE 317

Preparation of an Ammonium Salt

A 0.1 mmol sample of the free acid of a compound of formula (I) is dissolved in 10 mL of ethyl acetate. The resulting solution is saturated with gaseous ammonia upon which the ammonium salt precipitates from solution.

EXAMPLE 318

Preparation of a Potassium Salt

A solution of 0.1 mmol of the free acid of a compound of formula (I) in 10 mL of methanol is treated with an aqueous or methanolic solution containing 0.3 mmol of potassium hydroxide. Evaporation of the solvent affords the tri-potassium salt. Addition of between 0.1 and 0.3 mmol of potassium hydroxide yields analogously mixtures of the mono-potassium, di-potassium and tri-potassium salts whose composition depends upon the exact amount of potassium hydroxide added.

In a similar fashion the sodium and lithium salts can be formed.

EXAMPLE 319

Preparation of a Calcium Salt

A solution of 0.1 mmol of the free acid of a compound of formula (I) in 20 mL 6:4 methanol/water is treated with an aqueous solution of 0.1 mmol of calcium hydroxide. The solvents are evaporated to give the corresponding calcium salt.

EXAMPLE 320

Preparation of a Ethylenediamine Salt

A solution of 0.1 mmol of the free acid of a compound of formula (I) in 10 mL 6:4 methanol is treated with 0.1 mmol of ethylenediamine. Evaporation of the solvent affords the ethylenediamine salt.

EXAMPLE 321

Preparation of a Tris(hydroxymethyl)aminomethane Salt

To a solution of 0.1 mmol of the free acid of a compound of formula (I)in 10 mL of methanol is added from 0.1 to 0.3 mmol of tris(hydroxymethyl)aminomethane dissolved in 10 mL of methanol. Evaporation of the solvent gives a corresponding salt form of the exact composition of which is determined by the molar ratio of amine added. Similarly prepared are the salts of L-ornithine, L-lysine, and N-methylglucamine.

EXAMPLE 322

Preparation of an L-arginine Salt

A solution of 0.1 mmol of the free acid of a compound of formula (I) in 10 mL of 6:4 methanol/water is treated with an aqueous solution of 0.1 to 0.3 mmol of L-arginine. Evaporation of the solvent affords the title salt, the exact composition of which is determined by the molar ratio of amino acid to the free acid of formula (I) used.

Similarly prepared are the salts of L-ornithine, L-lysine and N-methylglucamine.

By Procedures described above for Examples 10A and 11, the following 6-positions esters of (1S,3S,4S,5R,6R,7R)-1-[(4S)-acetoxy-3-methylene-(5R)-methyl- 6-phenyl]hexyl-4,6,7-trihydroxy-6-O-(4S,6S-dimethyl-2-octenoyl)-2,8-dioxabicyclo[3.2.1]octane 3,4,5-tricarboxylic acid (IA) were prepared.

EXAMPLE 323

IA-6-Cyclopropanecarbonyl Ester (5aa).

NMR (CD$_3$OD) d 0.86 (d, J=6.7 Hz, CHCH$_3$), 0.90–0.97 (2 m, CH$_2$CH$_2$ cyclic), 2.10 (s, OAc), 4.0 (d, J=2.0 Hz, H-7), 4.97 & 5.02 (=CH$_2$), 5.08 (d, J=4.7 Hz, CHOAc), 5.24 (s, H-3), 6.25 (d, J=1.9 Hz, H-6), 7.13–7.29 (m, ArH); MS (Neg. FAB) m/z 605 (M–H)$^+$.

EXAMPLE 324

IA-6-(1-Methylcyclopropane)carbonyl Ester (5ab).

NMR (CD$_3$OD) d~0.73 (m, CH$_2$CH$_2$ cyclic), 0.86 (d, J=6.5 Hz, CHCH$_3$), 1.27 [s, (CH$_2$)$_3$CH$_{3+b}$], 2.10(s, OAc), 3.97 (d, J=1.5 Hz, H-7), 5.07 (d, J=4.5 Hz, CHOAc), 5.23 (s, H-3), 6.17 (d, J=1.5 Hz, H-6), 7.14–7.29 (m, ArH); MS (Neg. FAB) m/z 619 (M–H)$^+$.

EXAMPLE 325

IA-6-(m-Trifluoromethylphenyl)acetyl Ester (5ac)

NMR (CD$_3$OD) d 0.86 (d, J=6.7 Hz, CHCH$_3$), 2.10 (s, OAc), 3.74 (q, CH$_2$CO), 4.03 (d, J=1.9 Hz, H-7), 4.98 & 5.01 (=CH$_2$), 5.07 (d, J=4.9 Hz, CHOAc), 5.24 (s, H-3), 6.32 (d, J=1.9 Hz, H-6,), 7.14–7.26 & 7.51–7.59 (2 m, ArH); MS (Neg. FAB) m/z 723 (M–H)$^+$.

EXAMPLE 326

IA-6-(4-Pyridylthio)acetyl Ester (5ad).

NMR (CD$_3$OD) d 0.85 (d, J=6.7 Hz, CHCH$_3$), 2.10 (s, OAc), 4.08 (q, SCH$_2$CO), 4.09 (s, H-7), 4.98 & 5.0 (=CH$_2$), 5.05 (d, J=4.6 Hz, CHOAc), 5.25 (s, H-3), 6.38 (s, H-6,), 7.16–7.32 (m, ArH), 7.61 & 8.44 (2 br s, PyrH); MS (Neg. FAB) m/z 688 (M–H)$^+$.

EXAMPLE 327

IA-6-(3-Indolyl )acetyl (5ae).

NMR (CD$_3$OD) d 0.85 (d, J=6.6 Hz, CHCH$_3$), 2.09 (s, OAc), 3.75 (q, CH$_2$CO), 3.91 (d, J=1.5 Hz, H-7), 4.96 & 4.98 (=CH$_2$), 5.04 (d, J=5.0 Hz, CHOAc), 5.24 (s, H-3), 6.29 (d, J=1.6 Hz, H-6,), 7.0–7.56 (m, ArH); MS (Neg. FAB) m/z 694 (M–H)$^+$.

EXAMPLE 328

IA-6-Furylacetic Ester (5af)

$^1$H NMR (400 MHZ, CD$_3$OD) d 3.70 (d, CH$_2$—C=CO), 6.25 (s, 1H), 6.35 (s, 1H), 7.35 (s, 1H). FAB-MS [M+Na]$^+$ 669, [M+2Na]$^+$ 691, [M+3Na]$^+$ 713.

EXAMPLE 329

IA-6-(5-Phenyl)pentanoyl Ester (5ag)

NMR (CD$_3$OD) d 0.85 (d, J=7.0 Hz, CHCH$_3$), 2.08.(s, OAc), 4.04 (d, J=2.0 Hz, H-7), 4.98 & 5.03 (2 s, 2 H), 5.09 (d, J=5.0 Hz, CHOAc), 5.27 (s, H-3), 6.30 (d, J=2.0 Hz, H-6) 7.02–7.36 (m, ArH). MS (FAB) m/z 721 (M+Na).

EXAMPLE 330

IA-6-(3.3-Diphenyl)propionyl Ester (5ah)

NMR (CD$_3$OD) d 0.88 (d, J=7.0 Hz, CHCH$_3$), 2.12.(s, OAc), 3.08 (d, J=8.0 Hz, CH$_2$CO), 3.50 (bs, H-7), 4.50 [t, J=8.0 CH(C$_6$H$_5$)$_2$], 5.04 (s, 2H), 5.13 (d, J=5.0 Hz, CHOAc), 5.23 (s, H-3), 6.28 (bs, H-6) 7.04–7.40 (m, ArH). MS (FAB) m/z 769 (M+Na).

EXAMPLE 331

IA-6-(4-Dodecyloxy)benzoyl Ester (5ai)

NMR (CD$_3$OD) d 0.82–0.94 (m, 6H), 1.30 [bs, (CH$_2$)$_n$], 2.10.(s, OAc), 4.06 (t, J=7.0 Hz, CH$_2$O), 4.15 (bs, H-7), 5.00 & 5.05 (2 s, 2H), 5.09 (d, J=5.0 Hz, CHOAc), 5.34 (s, H-3), 6.44 (bs, H-6) 7.06–7.25 (m, C6H5),.6.98, 7.84 (2 m COC$_6$H$_4$O), MS (FAB) m/z 849 (M+Na).

EXAMPLE 332

IA-6-Benzoyl Ester (5aj)

NMR (CD$_3$OD) d 0.86 (d, J=7.0 Hz, CHCH$_3$), 2.10.(s, OAc), 4.18 (d, J=2.0 Hz, H-7), 4.98 & 5.04 (2 s, 2 H), 5.06 (d, J=5.0 Hz, CHOAc), 5.34 (s, H-3), 6.49 (d, J=2.0 Hz, H-6) 7.04–7.32 (m, C$_6$H$_5$CH$_2$) 7.49 7.65 & 8.01 (3 m C6H5CO) MS (FAB–) m/z 641 (M–1).

EXAMPLE 333

IA-6-(12-Phenoxy)Dodecanoyl Ester (5ak)

NMR (CD$_3$OD) d 0.85 (d, J=7.0 Hz, CHCH$_3$), 1.33 [bs (CH$_2$)$_n$], 2.11.(s, OAc), 3.96 (t, J=7.0 Hz, CH$_2$O), 4.04 (bs, H-7), 4.99 & 5.04 (2 s, 2H), 5.09 (d, J=5.0 Hz, CHOAc), 5.28 (s, H-3), 6.29 (bs, H-6) 6.77–6.97 & 7.04–7.37 (2 m, ArH). MS (FAB) m/z 835 (M+Na).

EXAMPLE 334

IA-6-(11-Phenylthio)undecanoyl Ester (5al)

NMR (CD$_3$OD) d 0.86 (d, J=7.0 Hz, CHCH$_3$), 1.29 [bs (CH$_2$)$_n$], 2.11.(s, OAc), 2.90 (t, J=7.0 Hz, CH$_2$S), 4.03 (bs,

H-7), 4.98 & 5.03 (2 s, 2H), 5.08 (d, J=5.0 Hz, CHOAc), 5.27 (s, H-3), 6.28 (bs, H-6), 7.07–7.35 (m, ArH). MS (FAB) m/z 837 (M+Na).

EXAMPLE 335

IA-6-(11-Phenylsulfoxido)undecanoyl Ester (5am)

NMR (CD$_3$OD) d 0.86 (d, J=7.0 Hz, CHCH$_3$), 1.30 [bs (CH$_2$)$_n$], 2.11.(s, OAc), 2.90 (m C$_2$SO), 4.03 (d, J=2.0 Hz, H-7), 4.97 & 5.03 (2 s, 2H), 5.09 (d, J=5.0 Hz, CHOAc), 5.27 (s, H-3H), 6.29 (d, J=2.0 Hz, H-6), 7.06–7.36 & 7.54–7.74(2 m, ArH). MS (FAB) m/z 853 (M+Na).

EXAMPLE 336

IA-6-(11-Phenylsulfonyl)undecanoyl Ester (5an)

NMR (CD$_3$OD) d 0.86 (d, J=7.0 Hz, CHCH$_3$), 1.27 [bs (CH$_2$)$_n$], 2.10.(s, OAc), 3.18 (m C$_2$SO$_2$), 4.03 (d, J=2.0 Hz, H-7), 5.00 & 5.04 (2 s, 2H), 5.09 (d, J=5.0 Hz, CHOAc), 5.28 (s, H-3), 6.30 (d, J=2.0 Hz, H-6), 7.06–7.36 7.58–7.78 & 7.86–7.98 (3 m, ArH). MS (FAB) m/z 869 (M+Na).

EXAMPLE 337

IA-6-Hexanoyl Ester (5ao)

NMR (CD$_3$OD) d 0.84–0.94 (m, 6H), 1.62 (m, 2H), 2.11.(s, OAc), 4.03 (d, J=2.0 Hz, H-7), 4.98 & 5.03 (2 s, 2H), 5.09 (d, J=5.0 Hz, CHOAc), 5.27 (s, H-3), 6.28 (d, J=2.0 Hz, H-6) 7.02–7.32 (m, ArH). MS (FAB–) m/z 635 (M–1).

EXAMPLE 338

IA-6-(3-Acetyl)Propionyl Ester (5ap)

NMR (CD$_3$OD) d 0.86 (d, J=7.0 Hz, CHCH$_3$), 2.12.(s, OAc), 2.16 (s, COCH$_3$), 4.06 (d, J=2.0 Hz, H-7), 4.99 & 5.03 (2 s, 2H), 5.08 (d, J=5.0 Hz, CHOAc), 5.25 (s, H-3H), 6.20 (d, J=2.0 Hz, H-6) 7.11–7.33 (m, ArH). MS (FAB–) m/z 635 (M–1).

EXAMPLE 339

IA-6-(3-Carboxy)propionyl Ester (5aq)

The blocked IA-6-(3-carboxy)propionyl-3,4,5-tris-t-butyl ester was prepared according to method B Example 10 with the exceptions that the diol, 3a, was reacted with succinic anhydride, rather than an acid chloride, and the protected product was purified by PrepTLC eluting with methylene chloride/methanol (95:5). The blocked compound was deprotected by the usual trifluoroacetic acid procedure to give the title compound.

NMR (CD$_3$OD) d 0.86 (d, J=7.0 Hz, CHCH$_3$), 2.11.(s, OAc), 2.59 (m, COCH$_2$CH2CO$_2$H), 4.09 (d, J=2.0 Hz, H-7), 4.98 & 5.03 (2 s, 2H), 5.07 (d, J=5.0 Hz, CHOAc), 5.25 (s, H-3), 6.27 (d, J=2.0 Hz, H-6) 7.06–7.33 (m, ArH). MS (FAB–) m/z 637 (M–1).

EXAMPLE 340

IA-6-Acrylic Ester (5ar)

NMR (CD$_3$OD) d 0.86 (d, J=7.0 Hz, CHCH$_3$), 2.10.(s, OAc), 4.06 (d, J=2.0 Hz, H-7), 4.97 & 5.02 (2 s, 2H), 5.08 (d, J=5.0 Hz, CHOAc), 5.26 (s, H-3), 5.92 6.13 & 6.28 (3 m CH=CH$_2$), 7.06–7.31 (m, ArH). MS (FAB–) m/z 591 (M–1).

EXAMPLE 341

IA-6-Methacrylic Ester (5as)

NMR (CD$_3$OD) d 0.83 (d, J=7.0 Hz, CHCH$_3$), 1.92 (s, CH$_2$=CCH$_3$), 2.09.(s, OAc), 4.04 (d, J=2.0 Hz, H-7), 4.95 & 5.00 (2 s, 2H), 5.06 (d, J=5.0 Hz, CHOAc), 5.25 (s, H-3), 5.65 & 6.08 (2 m C=CH$_2$), 6.27 (d, J=2.0 Hz, H-6), 7.04–7.30 (m, ArH). MS (FAB–) m/z 605 (M–1).

EXAMPLE 342

IA-6-(11-Amino)undecanoyl Ester (5at)

NMR (CD$_3$OD) d 0.86 (d, J=7.0 Hz, CHCH$_3$), 1.33 [bs, (CH$_2$)n], 2.10.(s, OAc), 2.91 (m, 2H), 4.01 (bs, H-7), 4.97 & 5.01 (2 s, 2H), 5.08 (d, J=5.0 Hz, CHOAc), 5.27 (bs, H-3), 6.29 (bs, H-6)7.03–7.33 (m, ArH ); MS (FAB–) m/z 720 (M–1).

EXAMPLE 343

IA-6-Aminoacetyl Ester (5au)

NMR (CD$_3$OD) d 0.86 (d, J=7.0 Hz, CHCH$_3$), 2.11.(s, OAc), 3.82 (m, CH2CO), 4.16 (bs, H-7), 5.00 & 5.04 (2 s, 2H), 5.07 (d, J=5.0 Hz, CHOAc), 5.26 (s, H-3), 6.45 (bs, H-6), 7.10–7.38 (m, ArH); MS (FAB–) m/z 594 (M–1).

EXAMPLE 344

IA-6-Acetamidoacetyl Ester (5av)

NMR (CD$_3$OD) d 0.86 (d, J=7.0 Hz, CHCH$_3$), 2.00 (s, CH$_3$CO), 2.11.(s, OAc), 3.92 (m, CH2CO), 4.09 (s, J=2.0 Hz, H-7), 4.99 & 5.03 (2 s, 2H), 5.08 (d, J=5.0 Hz, CHOAc), 5.25 (s, H-3), 6.30 (d, J=2.0 Hz, H-6), 7.08–7.35 (m, ArH); MS (FAB–) m/z 636 (M–1).

EXAMPLE 345

IA-6-(3-Methyl)3-butenoic Ester (5aw)

NMR (CD$_3$OD) d 0.86 (d, J=7.0 Hz, CHCH$_3$), 1.80 (s, CH$_3$C=CH$_2$), 2.13.(s, OAc), 3.06 (bs, CH$_2$CO), 4.04 (d, J=2.0 Hz, H-7), 4.98 & 5.03 (2 s, 2H), 5.09 (d, J=5.0 Hz, CHOAc), 5.26 (s, H-3), 6.31 (d, J=2.0 Hz, H-6), 7.06–7.34 (m, ArH); MS (FAB–) m/z 619 (M–1). The nmr spectrum also indicates the presence of the isomeric IA-6-(3,3-dimethyl)acrylic ester (5ax) (ca 20%) as shown by the following peaks: 1.92 [bs, =C(CH$_3$)], & 5.66 (bs, (=CHCO).

EXAMPLE 346

IA-6-Crotyl Ester (5ay)

NMR (CD$_3$OD) d 0.86 (d, J=7.0 Hz, CHCH$_3$), 1.88 (m, CH$_3$CH=CH), 2.10.(s, OAc), 4.03 (d, J=2.0 Hz, H-7), 4.98 & 5.02 (2 s, 2H), 5.09 (d, J=5.0 Hz, CHOAc), 5.26 (s, H-3), 5.84 (m, CH$_3$CH=CH), 6.29 (d, J=2.0 Hz, H-6), 6.92–7.34 (m, ArH & CH$_3$CH=); MS (FAB) m/z 629 (M+Na).

The nmr spectrum also indicates the presence of the isomeric IA-6-(3-butenoyl) ester (ca 15%) as shown by the following peak: 3.09 (m,CH2=CHCH$_2$).

EXAMPLE 347

IA-6-(2-Amino-3-methyl)butanoic Ester (5az)

This compound was obtained as a mixture of two diastereomers arising due to the C$_6$ side-chain. The chemical shifts of the major isomer are described below.

NMR (CD$_3$OD) d 0.86 (d, J=7.0 Hz, CHCH$_3$), 1.05 [m, CH(C$_3$)$_2$], 2.10.(s, OAc), 3.86 (bd, CHCHCO), 4.10 (d, J=2.0 Hz, H-7), 4.98 & 5.04 (2 s, 2H), 5.07 (d, J=5.0 Hz, CHOAc), 5.24 (s, H-3), 6.45 (d, J=2.0 Hz, H-6), 7.07–7.34 (m, ArH), MS (FAB–) m/z 636 (M–1).

EXAMPLE 348

IA-6-(2-Amino)propyl Ester (5ba)

This compound was obtained as a mixture of two diasteriomers arising due to the C$_6$ side-chain. The chemical shifts of the major isomer are described below.

NMR (CD$_3$OD) d 0.86 (d, J=7.0 Hz, CHCH$_3$), 1.52 (m, 3 H), 2.10.(s, OAc), 4.04 (m, C$_3$CHCO), 4.08 (d, J=2.0 Hz, H-7), 4.98 & 5.03 (2 s, 2H), 5.06 (d, J=5.0 Hz, CHOAc), 5.26 (s, H-3), 6.44 (d, J=2.0 Hz, H-6), 7.06–7.36 (m, ArH), MS (FAB–) m/z 608 (M–1).

EXAMPLE 349

IA-6-(2-Acetamido)propyl Ester (5bc)

This compound was obtained as a mixture of two diasteriomers arising due to the C$_6$ side-chain. The chemical shifts of the major isomer are described below.

NMR (CD$_3$OD) d 0.85 (d, J=7.0 Hz, CHCH$_3$), 1.36 (m, 3 H), 1.98 (s, C$_3$CONH), 2.11.(s, OAc), 4.13 (d, J=2.0 Hz, H-7), 4.36 (m, C$_3$CHCO), 5.00 & 5.04 (2 s, 2 H), 5.10 (d, J=5.0 Hz, CHOAc), 5.26 (s, H-3), 6.34 (d, J=2.0 Hz, H-6), 7.04–7.37 (m, ArH), MS (FAB–) m/z 650 (M–1).

EXAMPLE 350

IA-6-Cyclobutyl Ester (5bd)

NMR (CD$_3$OD) d 0.86.(d, J=7.0 Hz, CHCH$_3$), 2.10.(s, OAc), 3.16 (m, CHCO) 4.02 (d, J=2.0 Hz, H-7), 4.98 & 5.63 (2 s, 2H), 5.08 (d, J=5.0 Hz, CHOAc), 5.26 (s, H-3), 6.32 (d, J=2.0 Hz, H-6) 7.05–7.35 (m, ArH). MS (FAB) m/z 643 (M+Na).

EXAMPLE 351

IA-6-Trimethylacetyl Ester (5be)

NMR (CD$_3$OD) d 0.86.(d, J=7.0 Hz, CHCH$_3$), 1.19 [s, C(CH$_3$H)$_3$]2.10.(s, OAc), 3.98 (d, J=2.0 Hz, H-7), 4.98 & 5.03 (2 s, 2H), 5.08 (d, J=5.0 Hz, CHOAc), 5.27 (s, H-3), 6.25 (d, J=2.0 Hz, H-6) 7.05–7.33 (m, ArH). MS (FAB) m/z 645 (M+Na).

EXAMPLE 352

IA-6-Methyl Carbonate (5bf)

A solution of diol 3a (250 mg, 0.32 mM), 1,1 carbonyl diimidazole (120 mg, 0.7 mmol) in toluene (2 mL) was stirred at 25° C. or 3.5 h. then methanol (100 mg) and DBU (100 mg) was added. After 24 h. the mixture was filtered and concentrated to dryness and chromatographed on a prepTLC (3:1 hexane/ethyl acetate) affording the blocked carbonate.

NMR (400 MHz, CDCl$_3$) d 0.78 (d, J=6.5 Hz, CHCH$_3$), 1.4, 1.43, 1.64 (3s, 3tbu), 2.06(s, 3H CH$_3$CO), 3.75 (s, CH$_3$O), 4.05 (s, C4—OH), 4.23 (s br, C7-H), 4.93(s br, C3—OH, =CH$_2$), 5.08 (s, CHOAc), , 6.15 (s br, C6-H), 7.15–7.27 (m, 7ArH).

According to the procedures described above (Example 11), 60 mg of the blocked carbonate afforded IA-6-methylcarbonate (5bf) as a white solid.

NMR (400 MHz, CD$_3$OD) d 0.84 (d, J=6.5, 3H), 2.09 (s, 3H CH$_3$CO), 2.02–2.75 (m, 9H), 3.78(s, CH$_3$O), 4.09(d, J=2 Hz, C-7H), 4.98 (d, 3H), 5.06 (d, J=5 Hz, CHOAc), 6.17(d, J=2 Hz, C6-H), 7.15–7.24 (m, 7H). MS (FAB-neg), m/e 595 [M–H].

By Procedures described for Examples 76B and 77, the following 6-positions carbamates of (1S,3S,4S,5R, 6R,7R)-1-[(4S)-acetoxy-3-methylene-(5R)-methyl-6phenyl]hexyl-4,6,7-trihydroxy-6-O-(4S,6S-dimethyl-2-octenoyl)-2,8-dioxabicyclo[3.2.1]octane 3,4,5-tricarboxylic acid (IA) were prepared.

EXAMPLE 353

IA-6-Cyclopropylmethylaminocarbonyl Carbamate (5ca)

NMR (CD$_3$OD) d 0.12–0.21 & 0.40–0.48 (2 m, CH$_2$CH$_2$ cyclic), 0.85 (d, J=6.5 Hz, CHCH$_3$), 2.10 (s, OAc), 2.95 (m, CH$_2$NHCO), 3.97 (s, C$_4$—OH), 4.07 (d, J=1.0 Hz, H-7), 5.08 (d, J=4.5 Hz, CHOAc), 5.26 (s, H-3), 6.18 (d, J=1.0 Hz, H-6), 7.14–7.29 (m, ArH); MS (Neg. FAB) m/z 634 (M–H)$^+$.

EXAMPLE 354

IA-6-(3-Pyridinyl)methylaminocarbonyl Carbamate (5cb)

NMR (CD$_3$OD) d 0.85 (d, J=6.6 Hz, CHCH$_3$), 2.10 (s, OAc), 4.11 (s, H-7), 4.47 (q, CH$_2$NHCO), 4.98 & 5.0 (=CH$_2$), 5.06 (d, J=4.2 Hz, CHOAc), 5.26 (s, H-3), 6.28 (s, H-6), 7.15–7.28 (m, ArH), 7.90, 8.37–8.39 & 8.70–8.73 (PyrH); MS (Neg. FAB) m/z 671 (M–H)$^+$.

EXAMPLE 355

IA-6-(1-Imidazolyl)propylaminocarbonyl Carbamate (5cc)

NMR (CD$_3$OD) d 0.85 (d, J=6.6 Hz, CHCH$_3$), 2.10 (s, OAc), 4.09 (s, H-7), 4.97 & 5.0 (=CH$_2$), 5.05 (br s, CHOAc), 5.25 (s, H-3), 6.30 (s, H-6), 7.15–7.28 (m, ArH), 7.55, 7.63 & 8.92 (3 br s, ImidH); MS (Neg. FAB) m/z 688 (M–H)$^+$.

EXAMPLE 356

IA-6-(N-Morpholinyl)ethylaminocarbonyl Carbamate (5cd)

NMR (CD$_3$OD) d 0.86 (d, J=6.7 Hz, CHCH$_3$), 2.11 (s, OAc), 3.20–3.30 (m, NCH$_2$CH$_2$N), 3.96 (br s, CH$_2$OCH$_2$), 4.12 (d, J=2.1 Hz, H-7), 4.98 & 5.01 (=CH$_2$), 5.06 (d, J=4.9 Hz, CHOAc), 5.22 (s, H-3), 6.26 (d, J=1.9 Hz, H-6), 7.16–7.27 (m, ArH); MS (Neg. FAB) m/z 693 (M–H)$^+$.

EXAMPLE 357

IA-6-(4-Piperidinyl)methylaminocarbonyl Carbamate (5ce).

NMR (CD$_3$OD) d 0.86 (d, J=6.7 Hz, CHCH$_3$), 2.10 (s, OAc), 2.79–2.83 (br m, CH$_2$NHCO), 4.04 (s, H-7), 4.98 & 5.02 (=CH$_2$), 5.08 (d, J=4.9 Hz, CHOAc), 5.24 (s, H-3), 6.10 (s, H-6), 7.15–7.28 (m, ArH); MS (Neg. FAB) m/z 677 (M–H)$^+$.

EXAMPLE 358

IA-6-(2-Tetrahydropyran)methylaminocarbonyl Carbamate, (5cf).

NMR (CD$_3$OD) d 0.85 (d, J=6.6 Hz, CHCH$_3$), 2.10 (s, OAc), 3.04–3.19 (m, CH$_2$NHCO), 3.34–3.45 (m, tetrahyCH$_2$O), 3.90–3.93 (tetrahyCHO), 4.07 (d, J=1.7 Hz, H-7), 4.98 & 5.02 (=CH$_2$), 5.08 (d, J=5.0 Hz, CHOAc), 5.25 (s, H-3), 6.17 (s, J=2.0 Hz,H-6), 7.14–7.28 (m, ArH); MS (Neg. FAB) m/z 678 (M–H)$^+$.

EXAMPLE 359

IA-6-Cyclobutylaminocarbonyl Carbamate (5cg)

NMR (CD$_3$OD) d 0:86. (d, J=7.0 Hz, CHCH$_3$), 2.10.(s, OAc), 4.05 (m, CHNH), 4.05 (d, J=2.0 Hz, H-7), 4.99 & 5.03 (2 s, 2H), 5.07 (d, J=5.0 Hz, CHOAc), 5.25 (s, H-3), 6.17 (d, J=2.0 Hz, H-6) 7.06–7.34 (m, ArH). MS (FAB) m/z 658 (M+Na).

EXAMPLE 360

IA-6-Methoxyaminocarbonyl Carbamate (5ch)

NMR (CD$_3$OD) d 0.85.(d, J=7.0 Hz, CHCH$_3$), 2.10.(s, OAc), 3.64 (s, OCH$_3$), 4.07 (d, J=2.0 Hz, H-7), 4.97 & 5.01 (2 s, 2H), 5.07 (d, J=5.0 Hz, CHOAc), 5.24 (s, H-3), 6.26 (d, J=2.0 Hz, H-6) 7.12–7.30 (m, ArH). MS (FAB–) m/z 610 (M–1).

EXAMPLE 361

IA-6-Allylaminocarbonyl Carbamate (5ci)

NMR (CD₃OD) d 0.84.(d, J=7.0 Hz, CHCH₃), 2.09.(s, OAc), 3.72 (m, NHCH₂CH=CH₂), 4.08 (d, J=2.0 Hz, H-7), 5.22 (s, H-3), 5.80 (m, CH2=CH) 6.20 (bs, H-6) 7.04–7.30 (m, ArH). MS (FAB–) m/z 620 (M–1).

EXAMPLE 362

IA-C6-Phenyl Carbamate (5cj)

This compound was made following examples 76A and 77: ¹H NMR (400 MHz, CD₃OD) d 7.0 (t, 2H), 7.43–7.40 (m, 3H). FAB–MS [M–1]656.

EXAMPLE 363

IA-6-Furfurylamine Carbamate (5ck)

This compound was made following examples 76A and 77: ¹H NMR (400 MHz, CD₃OD) d 4.25 (dd, CH₂), 6.31 (s, 1H), 6.22 (s, 1H), 7.39 (s, 1H). FAB-MS [M+Na]⁺684, [M+2Na]⁺706, [M+3Na]⁺728.

EXAMPLE 364

IA-6-Isopropyl Thiocarbamate (5cl)

A solution of diol (210 mg, 0.27 mmol), 1,1 thiocarbonyl diimidazole (200 mg, 1.15 mmol) in toluene (1.5 mL) was stirred at 70° C. for 1 h then isopropylamine (200 mg, 3.4 mmol) was added. After 96 h. the mixture was filtered and concentrated to dryness and chromatographed on a prepTLC (3:1 hexane/ethylacetate) affording the blocked carbamate.

NMR (400 MHz, CD₃OD) d 0.76 (d, J=6.5 Hz, CHCH₃), 1.14, 1.18 (2d, 6H), 1.40, 1.43, 1.68 (s, 3tBu), 2.07 (s, 3H CH₃CO), 2.02–2.85 (m, 9H), 3.23 (s, CH₃O), 4.08 (s, C4—OH), 4.19(s br, C-7H), 4.23 (m, (CH₃)₂CHNH), 4.61 (d, J=8 Hz, NH), 4.94, 4.95(2s, =CH₂), 5.13 (d, J=5 Hz, CHOAc), 5.15(s, C3-H), 6.20(d, NH), 6.79 (s br, C6-H), 7.15–7.27 (m, 5H).

According to the procedures described above (Example 77), 100 mg of the blocked carbamate afforded IA-6-isopropylthiocarbamate as a white solid.

NMR (400 MHz, CD₃OD) d 0.86(d, 3H), 1.18 (m, 6H), 2.07 (s, 3H C₃CO), 2.02–2.75 (m, 9H), 4.05 (d, J=2 Hz, 1H), 4,13 (m, 1H (CH₃)₂CHNH), 4.96, 5.02 (2s, =CH₂), 5.08 (d, J=5 Hz, CHOAc), 5.27 (s, C-3H), 6.65(d, J=2 Hz, 1H), 7.15–7.27 (m, 5H). MS (FAB-neg), m/e 638 [M–H].

By methods described for compound 8a (Example 175), the following compounds were prepared.

EXAMPLE 365

IA-3-(4,4-dimethyl-2-pentyl) Ester (8aa)

IA (200 mg) in 1 mL, of 4,4-dimethyl-2-pentanol and 40 uL of acetyl chloride gave, after mplc'(RP-X8 column, 62% CH₃CN in H2O), IA-3-(4,4-dimethyl-2-pentyl) ester. ¹H NMR (400 MHz, CD₃OD) d 7.27–7.12 (m, 5H), 6.84 (d, J=8.5, 15.6 Hz, 1H), 6.29 and 6.27(each d, each J=1.89 Hz, 1H), 5.78 (d, J=15.6 Hz, 1H), 5.23 (s, 1H), 5.09 (m, 2H), 5.01 (d, J=4.57 Hz, 1H), 4.95 (d, J=6.32 Hz, 1H), 4.02 (d, J=1.89 Hz, 1H), 2.69 (dd, J=6.3, 13.5 Hz, 1H), 2.5–2.16 (m), 2.10 (s, 3H), 2.06–1.95 (m), 1.75–1.53 (m, 1H), 1.41–1.22 (m), 1.24 (d, J=6.3 Hz, 3H), 1.21 (d, J=6.3 Hz, 3H), 0.94–0.86 (m), MS FAB-neg m/z 787.

EXAMPLE 366

IA-3-(3,3-dimethylbutyl) Ester (8ab)

HPLC Rt 17 min ¹H NMR (400 MHz, CD₃OD) characteristic resonances: d 4.20 (m, 2H), 1.58 (t, 2H), MS FAB-neg m/z 773

EXAMPLE 367

IA-3-p-Chlorobenzyl Ester (8ac)

¹H NMR (400 MHz, CD₃OD) characteristic resonances: d 7.4–7.06 (m, 9H), 6.84 (dd, J=8.4, 15.6 Hz, 1H), 6.30 (br s, 1H), 5.78 (d, J=15.7 Hz, 1H), 5.36 (br s, 1H), 5.23 (AB, J=12 Hz, 1H), 5.14 (AB, J=12 Hz, 1H), 5.06 (d, J=4.8 Hz, 1H), 5.0 and 4.97 (each s, each 1H), 4.01 (br s, 1H), 2.09 (s, 3H), MS FAB m/z 861 (m+2Na)

EXAMPLE 368

IA-3-(6-Hydroxyhexyl) Ester (8ad)

¹H NMR (400 Hz, CD₃OD) characteristic resonances: d 4.15 (t, C₃—COOCH₂—(CH₂)₄—CH₂—OH), 3.55 (t, C₃—COO—CH₂—(CH₂)₄—CH₂—OH)

EXAMPLE 369

IA-3-(4-Methyl-2-pentyl) Ester (8ae)

¹H NMR (400 MHz, CD₃OD) diagnostic resonances: d 7.28–7.1 (m, 5H), 6.84 (dd, 1H), 4.02 (s, 1H), 2.1 (s, 3H), 1.23 (d, 3H), 1.03 (d, 3H), 0.94–0.73 (m, 15H), MS FAB-neg m/z 773.

EXAMPLE 370

I-3-(2,4,4-Trimethyl-1-pentanoyl) Ester (8af)

HPLC Rt 19.2 min ¹H NMR (400 MHz, CD₃OD) diagnostic resonances: d 7.29–7.11 (m, 5H), 6.84 (dd, 1H), 4.03 (br s, 1H), 4.2–4.13 and 4.0–3.7 (m, 3H), 2.1 (s, 3H), 1.03 (d, 3H), 0.98 (2d, 3H), 0.91 (s, 9H), 0.88–0.81 (m, 9H), MS FAB-neg 801.9

EXAMPLE 371

IA-3-(3-methylbenzyl) Ester (8ag)

¹H NMR (400 MHz, CD₃OD) d 7.28–7.08 (m, 8H), 6.87 (dd, J=15.6, 8 Hz, 1H), 6.32 (s, 1H), 5.81 (d, J=15.6 Hz, 1H), 5.07 (d, J=4.8Hz, 1H), 4.99 (s, 1H), 4.95 (s, 1H), 4.82 (s, 1H), 4.01 (s, 1H), 2.69 (dd, J=10.4, 6.8 Hz, 1H), 2.48–2.34 (m, 6H), 2.32 (m, 3H), 2.29–2.15 (m, 3H), 2.08 (m, 3H), 2.06–1.92 (m, 2H), 1.59–1.30 (m, 2H), 1.29–1.07 (m, 2H), 1.03 (d, J=9.6 Hz, 6H), 0.99–0.71 (m, 9H) ppm.

EXAMPLE 372

IA-3-(3,4-dichlorobenzyl) Ester (8ah)

¹H NMR (400 MHz, CD₃OD) d 7.56–7.11 (m, 8H), 6.84 (dd, J=15.6, 8.4 Hz, 1H), 6.30 (d, J=2 Hz, 1H), 5.79 (dd, J=16.0, 1.2 Hz, 1H), 5.37 (s, 1H), 5.16 (dd, J=35.6, 13.2 Hz, 2H), 5.06 (d, J=5.6 Hz, 1H), 5.00 (s, 1H), 4.96 (s, 1H), 4.92 (s, 1H), 4.04 (d, J=2.0 Hz, 1H), 2.75 (dd, J=13.2, 6.4 Hz, 1H), 2.45–2.34 (m, 5H), 2.22–2.15 (m, 1H), 2.08 (s, 3H), 2.05–1.98 (m, 2H), 1.40–1.21 (m, 2H), 1.15–1.04 (m, 2H), 1.02 (d, J=6.8 Hz, 3H), 0.87–0.81 (m, 9H) ppm.

EXAMPLE 373

IA-3-(3,5-dichlorobenzyl) Ester (8ai)

¹H NMR (400 MHz, CD₃OD) d 7.55–7.10 (m, 8H), 6.81 (dd, J=15.6, 8.4 Hz, 1H), 6.30 (d, J=2 Hz, 1H), 5.77 (dd, J=16, 1.2 Hz, 1H), 5.37 (s, 1H), 5.16 (dd, J=35.6, 13.2 Hz, 2H), 5.06 (d, J=5.6 Hz, 1H), 5.00 (s, 1H), 4.95 (s, 1H), 4.91 (s, 1H), 4.04 (d, J=2.0 Hz, 1H), 2.66 (dd, J=13.2, 6.4 Hz, 1H) 2.44–2.34 (m, 5H), 2.22–2.14 (m, 1H), 2.06 (s, 3H), 2.05–1.99 (m, 2H), 1.41–1.22 (m, 2H), 1.15–1.04 (m, 2H), 1.01 (d, J=6.8 Hz, 3H), 0.87–0.81 (m, 9H) ppm.

EXAMPLE 374

IA-3-(4-methoxybenzyl) Ester (8aj)

$^1$H NMR (400 MHz, CD$_3$OD) d 7.31–7.11 (m, 9H), 6.87 (d, J=8.8 Hz, 1H), 6.84–6.80 (m, 1H), 6.30 (d, J=5.6 Hz, 1H), 5.78 (d, J=15.6 Hz, 1H), 5.34–5.15 (m, 2H), 5.06 (d, J=6.8 Hz, 1H), 5.02 (s, 1H), 5.00 (s, 1H), 4.95 (s, 1H), 4.02 (d, J=2.0 Hz, 1H), 3.76 (s, 3H), 2.66 (dd, J=13.2, 6.8 Hz, 1H), 2.46–2.33 (m, 5H), 2.21–2.09 (m, 1H), 2.09 (s, 3H), 2.05–1.97 (m, 2H), 1.43–1.23 (m, 2H), 1.19–1.09 (m, 2H), 1.04–0.99 (m, 3H), 0.99–0.79 (m, 9H) ppm.

EXAMPLE 375

IA-3-(3-methoxybenzyl) Ester (8ak)

$^1$H NMR (400 MHz, CD$_3$OD) d 7.26–7.11 (m, 7H), 6.96–6.93 (m, 2H), 6.87–6.81 (m, 1H), 6.31 (s, 1H), 5.79 (d, J=16.0 Hz, 1H), 5.37 (s, 1H), 5.24 (d, J=2.8 Hz, 1H), 5.15 (d, J=46.4 Hz, 1H), 5.09 (s, 1H), 5.07 (s, 1H), 4.95 (s, 1H), 4.04 (d, J=1.6 Hz, 1H), 3.78 (s, 3H), 2.65 (dd, J=1.36, 6.4 Hz, 1H), 2.45–2.35 (m, 4H), 2.24–2.19 (m, 2H), 2.08 (s, 3H), 2.05–1.98 (m, 2H), 1.40–1.28 (m, 2H), 1.15–1.08 (m, 2H), 1.02 (d, J=6.4 Hz, 3H), 0.87–0.84 (m, 9H) ppm.

EXAMPLE 376

IA-3-(3-chlorophenyl) Ester (8al)

$^1$H NMR (400 MHz, CD$_3$OD) d 7.40–7.10 (m, 10H), 6.86 (dd, J=15.6, 8.4 Hz, 1H), 6.38 (d, J=1.6 Hz, 1H), 5.81 (dd, J=15.6, 0.8 Hz, 1H), 5.06 (d, J=4.8 Hz, 1H), 2.67 (dd, J=13.2, 6.4 Hz, 1H), 2.49–2.37 (m, 5H), 2.23–2.20 (m, 1H), 2.09 (s, 3H), 2.08–2.01 (m, 2H), 1.41–1.27 (m, 2H), 1.17–1.10 (m, 2H), 1.03 (d, J=6.8 Hz, 3H), 1.01.–0.82 (m, 9H)

EXAMPLE 377

IA-3-(3-methoxyphenyl) Ester (8am)

$^1$H NMR (400 MHz, CD$_3$OD) d 7.24–7.04 (m, 9H), 6.92–6.83 (m, 2H), 6.38 (d, J=2.0 Hz, 1H), 4.97 (s, 1H), 4.96 (s, 1H), 4.08 (d, J=2.0 Hz, 1H), 3.78 (s, 3H), 2.65 (dd, J=13.2, 6.4 Hz, 1H), 2.47–2.32 (m, 5H), 2.24–2.20 (m, 1H), 2.08 (s, 3H), 2.07–2.02 (m, 2H), 1.43–1.27 (m, 2H), 1.16–1.10 (m, 2H), 1.04–1.01 (m, 3H), 0.99–0.82 (m, 9H) ppm.

EXAMPLE 378

IA-3-(3-methylphenyl) Ester (8an)

$^1$H NMR (400 MHz; CD$_3$OD) d 7.27–6.93 (m, 9H), 6.86 (dd, J=15.6, 8.8 Hz, 1H), 6.54 (d, J=2.0 Hz, 1H), 5.81 (dd, J=15.6, 4.4 Hz, 1H), 5.54 (s, 1H), 5.08 (d, J=4.4 Hz, 1H), 5.02 (s, 1H), 4.96 (s, 1H), 4.89 (s, 1H), 4.09 (d, J=2.0 Hz, 1H), 2.67 (dd, J=13.6, 6.0 Hz, 1H), 2.47–2.37 (m, 5H), 2.34 (s, 3H), 2.28–2.15 (m, 1H), 2.09 (s, 3H), 2.07–1.98 (m, 2H), 1.42–1.29 (m, 2H), 1.27–1.10 (m, 2H), 1.04 (d, 3H), 0.99–0.75 (m, 9H) ppm.

EXAMPLE 379

IA-3-(2-(N-Morpholino))ethyl Ester (8ao)

This compound was prepared from 60 mg of IA-4,5-di-t-butyl ester, 10a, 1.33 mL of methylene chloride, 9.04 uL N-methylmorpholine, 10.68 uL of isobutyl chloroformate, 1.7 mL of THF, 27.14 uL of 4-(2-hydroxyethyl)morpholine following the usual conditions to give after preparative tlc IA-3-(2-(N-morpholino))ethyl-4,5-di-t-butyl ester. $^1$H NMR (400 MHz, CD$_3$OD) significant resonances d 3.68 and 3.75 (2 multiplets). This was deblocked in 2 mL of CH$_2$Cl$_2$ with 300 uL of TFA in the usual manner to give the title compound upon evaporation. $^1$H NMR (400 MHz, CD$_3$OD) with multiplets at d 3.68, 3.75 and 3.90. MS FAB m/z 804 (M$^+$+1)

EXAMPLE 380

IA-3-Isoamyl-4-pyrrolidinylglycolamide Ester (8ba)

To the IA-3-isoamyl ester ((8n) (0.197 mmole, 150 mg) in 3 ml of refluxing acetonitrile, DBU (0.212 mmole, 32 μl) was added followed by 3 drops of the chloromethyl pyrrolidinamide. The reaction was stirred overnight and concentrated in vacuo the following morning. Purification by HPLC yielded the diester as a colorless oil. $^1$H NMR (400 MHz, CD$_3$OD): d 7.28–7.12 (m, 5H), 6.82 (dd, J=15.66, 8.53 Hz, 1H), 6.27 (d, J=1.89 Hz, 1H), 5.79 (d, J=15.76 Hz, 1H), 5.29 (s, 1H), 5.08 (d, J=4.65 Hz, 1H), 5.01 (s, 1H), 4.97 (s, 1H), 4.85 (apparent dd, 2H), 4.20 (m, 2H), 4.02 (d, J=1.99 Hz, 1H), 3.57 (m, 2H), 3.50 (t, J=7.97 Hz, 2H), 2.60 (dd, J=13.35, 6.45 Hz, 1H), 2.49–2.40 (m, 4H), 2.10 (s, 3H), 2.15–1.95 (m, 2H), 1.90 (m, 2H), 1.65 (m, 1H), 1.50 (m, 2H), 1.40–1.25 (m, 4H), 1.20–1.12 (m, 2H), 1.03 (d, J=6.68 Hz, 2H), 0.92–0.80 (m, 16H). MS (–)FAB m/e 870 (m–1).

EXAMPLE 381

IA-3-Isoamyl-4-piperidinylglycolamide Ester (8bb) and IA-3-Isoamyl-5-piperidinylglycolamide Ester (8bc)

A mixture of these compounds was prepared according to the procedure outlined for the IA-3-isoamyl-4-pyrrolidinylglycolamine ester (8ba). The diesters were purified by HPLC; 4-piperidinylglycolamide ester $^1$H NMR (400 MHz, DMSO): d 4.65 (d, J=6.22 Hz, 2H), 4.10–3.91 (m, 4H), 2.45–2.37 (m, 4H), 1.98 (m, 2H). MS (–)FAB m/e 884 (m–1); 5-piperidinylglycolamide ester $^1$H NMR (400 MHz, CD$_3$OD): d 4.87 (apparent dd, 2H), 3.51 (m, 2H), 3.35 (m, 2H), 2.48–2.40 (m, 4H), 1.90 (m, 2H). MS (–)FAB m/e 884 (m–1).

EXAMPLE 382

IA-3-Isoamyl-4-dimethylglycolamide Ester (8bd) and IA-3-Isoamyl-5-dimethylglycolamide Ester (8be)

Compound prepared according to the procedure of Example 380. The diesters were purified by HPLC; 4-dimethylglycolamide ester $^1$H NMR (400 MHz, CD$_3$OD): d 4.91 (apparent dd, 2H), 3.07 (s, 3H), 2.98 (s, 3H). MS (–)FAB m/e 844 (m–1); 5-dimethylglycolamide ester $^1$H NMR (400 MHz, CD$_3$OD): d 4.82 (apparent dd, 2H), 2.99 (s, 3H), 3.92 (s, 3H). MS (–)FAB m/e 844 (m–1).

EXAMPLE 383

IA-3-Isoamyl-4-morpholinylglycolamide Ester (8bf)

Compound prepared according to the procedure of Example 380. $^1$H NMR (400 MHz, CD$_3$OD): d 4.85 (apparent dd, 2H), 3.70 (m, 2H), 3.61 (m, 2H), 3.55 (m, 2H). MS (–)FAB m/e 886 (m–1).

EXAMPLE 384

IA-3-Isoamyl-4-diisopropylglycolamide Ester (8ba)

Compound prepared according to the procedure of Example 380. $^1$H NMR (400 MHz, CD$_3$OD): d 4.83 (apparent dd, 2H), 3.68 (m, 2H), 1.40 (d, J=6.64 Hz, 6H), 1.24 (d, J=6.55 Hz, 6H). MS (–)FAB 914 (m+2 Li).

The following diesters and triesters were prepared according to the procedure described for IA-3-isopentyl-4-pivaloyloxymethyl ester (14f) and using appropriate alkyl halides.

EXAMPLE 385

IA-3-Isopentyl-4-acetoxymethyl Ester (8bh) (L-731, 148) and IA-3-Isopentyl-5-acetoxymethyl Ester (8bi)

4-Acetoxymethyl ester $^1$H NMR (200 MHz, CDCl$_3$) d 4.48–5.02 (s+m, 3H), 3.72 (s, 3H). MS, FAB(−) m/e 831 (m$^+$−1); 5-acetoxymethyl ester $^1$H NMR (200 MHz, CD$_3$OD) d 5.70–5.81 (m, 2H), 2.05 (s, 3H), 2.10 (s, 3H). MS, EI m/e 832.2 (m$^+$).

EXAMPLE 386

IA-3-Isopentyl-4,5-di-(4'-bromobenzoyl)methyl Ester (8bj)
$^1$H NMR (200 MHz, CDCl$_3$) d 7.52–7.66 (m, 4H), 7.66–7.80 (m, 4H), 5.44 (s, 4H). MS, FAB(−) m/e 1153 (m$^+$−1).

EXAMPLE 387

I-3-(2-Hydroxyethyl) Amide (8ca)

IA-7-MME-4,5-di-t-butyl ester, 10d, (80 mg) was dissolved in DMF (0.53 ml) and cooled to −10° C. Carbonyldiimidazole (17.79 mg) was added and stained at −10° for 2 h. 2-aminoethanol (11.03 ml) was added and the mixture was stirred for an additional 16h. IA-7-MME-3-(2-hydroxyethyl) amide-4,5-di-t-butyl ester was isolated by evaporation and preparive tlc. (Rt 0.67; EtOAc/hex 7/3). $^1$H NMR (400 MHz, CD$_3$OD) diagnostic resonance: d 7.3–7.15 (m, 5H), 6.91 (dd, 1H), 4.26 (br s, 1H), 3.59 (t, 2H), 3.31 (m, 2H). The compound above was deprotected in 2 mL of CH$_2$Cl$_2$ with 300 uL of TFA in the usual manner to give IA-3-(2-hydroxyethyl)amide. $^1$H NMR (400 MHz, CD$_3$OD) characteristic resonance: d 7.4 (t, 1H), 7.28–7.11 (m, 5H ), 6.84 (dd, 1H), 4.41 (t, 2H), 4.04 (br s, 1H), 3.54 and 3.60 (2m, 2H), 2.1 (s, 3H). MS FAB-neg m/z733

EXAMPLE 388

IA-3-(furfuryl) Amide (8cb)

Utilizing the procedure for the formation of IA-3-(3-isopropoxy)-propylamide (12h, Example 227) and furfurylamine, the title compound was prepared.

$^1$H NMR (200 MHz, CD$_3$OD) d 7.35–7.06 (m, 8H), 6.84 (dd, J=31.6 17.2 Hz, 1H), 6.30 (s, 1H), 5.78 (d, J=30.4 Hz, 1H), 5.47 (s, 1H), 5.18 (s, 1H), 5.052 (d, J=9.6 Hz, 1H), 5.018 (s, 1H), 4.48–4.27 (m, 2H), 4.051 (s, 1H), 2.66 (dd, J=26.4, 12.4 Hz, 1H), 2.46–2.36 (m, 3H), 2.31 (s, 1H), 2.25–2.14 (m, 3H) 2.077 (s, 3H), 2.037–1.97 (m, 2H), 1.41–1.28 (m, 2H), 1.24–1.073 (m, 2H), 1.014 (d, J=13.2 Hz, 3H), 0.96–0.76 (m, 9H) ppm.

EXAMPLE 389

IA-3-(histamine) Amide(8cc)

Utilizing the procedure for the formation of IA-3-(3-isopropoxy)-propylamide (12h, Example 227) and histamine, the title compound was prepared. $^1$H NMR (200 MHz, CD$_3$OD) d 9.19 (s, 1H), 7.70 (s, 1H), 7.39–7.054 (m, 5H), 6.83 (dd, J=31.6, 17.2 Hz, 1H), 6.30 (s, 1H), 5.79 (d, J=30.4 Hz, 1H), 5.04 (s, 1H), 5.03 (d, J=9.6 Hz, 1H), 4.91 (s, 1H), 4.91 (s, 1H), 4.28 (d, J=17.2 Hz, 1H), 4.03–4.02 (s, 1H), 3.70–3.50 (m, 1H), 3.49–3.25 (m, 1H), 2.90–2.76 (m, 2H), 2.66 (dd, J=26.4, 12.4 Hz, 1H) 2.50–2.31 (m, 4H), 2.38–2.15 (m, 2H), 2.08 (m, 3H), 2.06–1.91 (m, 2H), 1.49–1.22 (m, 2H), 1.18 (d, J=13.2 Hz, 3H), 0.99–0.77 (m; 9H) ppm.

EXAMPLE 390

IA-3-(L-phenylalanine) Amide (8cd)

To IA-4,5-di-t-butyl ester (10a, Example 216) (0.20, 10 mmol) was added dichloromethane (3.5 mL) and L-phenylalanine-t-butyl ester (0.45 g, 20 mmol) followed by dicyclohexylcarbodiimide (0.206 g, 10 mmol) at ambient temperature while stirring. A precipitate was noted ca. 2 h after beginning of the reaction. After 8 h, the reaction was filtered and the filtrate was washed with 1N HCl, 1N potassium bicarbonate, water, dried (MgSO$_4$), and concentrated in vacuo. The residue was purified by flash column chromatography in 3:1 hex/EtOAc. This compound was then deprotected by the standard TFA deprotection to afford the title compound. $^1$H NMR (200 MHz, CD$_3$OD) d 7.37–7.06 (m, 10H), 6.85 (dd, J=31.6, 17.2 Hz, 1H), 6.31 (s, 1H), 5.80 (d, J=9.6 Hz, 1H), 5.17 (s, 1H), 5.05 (d, J=9.6 Hz, 1H), 4.99 (s, 1H), 4.93 (s, 1H), 4.74–4.70 (m, 1H), 3.99 (s, 1H), 3.12 (d, J=10.4 Hz, 2H), 2.65 (dd, J=25.6, 12.0 Hz, 1H), 2.47–2.36 (m, 3H), 2.31 (s, 1H), 2.28–2.10 (m, 3H), 2.06 (s, 3H), 2.00–1.81(m, 2H), 1.45–1.090 (m, 4H), 1.03 (d, J=13.2 Hz, 3H), 0.96–0.78 (m, 9H) ppm.

General Procedure for Tryptophan, t-butyl-L-alaninate, Lysine and Threonine Amides To the IA-4,5-dibenzyl ester (10c, Example 205) (ca. 0.18 mmol) is added dichloromethane (4.5 mL) at room temperature while stirring followed by the addition of freshly distilled oxalyl chloride (2 eq.). The reaction is stirred at reflux overnight. In the morning, the amino ester (20 eq.) is added. The reaction is allowed to stir for 30 minutes and is then concentrated in vacuo. Purification is by flash column chromatography in 3:1 hex/EtOAc. The title compounds are obtained by the standard debenzylation procedure.

Utilizing the above procedure the following compounds were prepared:

EXAMPLE 391

IA-3-(L-tryptophan) Amide (8ce)

$^1$H NMR (400 MHz, CD$_3$OD) d 7.63 (d, J=12.8 Hz, 1H), 7.59–6.96 (m, 10H), 6.85 (dd, J=15.6, 8.4 Hz, 1H), 6.29 (d, J=1.6 Hz, 1H), 5.79 (dd, J=15.6, 0.8 Hz, 1H), 5.48 (s, 1H), 5.17 (d, J=4.0 Hz, 1H), 5.00–4.99 (s, 1H), 4.98 (s, 1H), 4.72–4.70 (m, 1H), 4.01 (d, J=2.0 Hz, 1H), 3.42–3.25 (m, 2H), 3.08 (m, 1H), 2.59 (dd, J=13.2, 6.8 Hz, 1H), 2.40–2.35 (m, 5H), 2.26–2.22 (m, 2H), 2.05 (s, 1H), 2.02–1.90 (m, 2H), 1.42–1.24 (m, 2H), 1.16–1.09 (m, 2H), 1.03 (d, J=6.4 Hz, 3H), 0.99–0.80 (m, 9H) ppm.

EXAMPLE 392

IA-3-(L-alanine-t-butyl ester) Amide (8cf)

$^1$H NMR (400 MHz, CD$_3$OD) d 7.27–7.13 (m, 5H), 6.85 (dd, J=15.6, 8.8 Hz, 1H), 6.29 (d, J=10.8 Hz, 1H), 5.79 (d, J=16.0 Hz, 1H), 5.16 (s, 1H), 5.09 (d, J=4.4 Hz, 1H), 5.05 (s, 1H), 4.99 (s, 1H), 4.31–4.29 (m, 1H), 4.04 (d, J=8.4 Hz, 1H), 3.08–3.03 (m, 1H), 2.70 (dd, J=13.6, 6.8 Hz, 1H), 2.48–2.38 (m, 5H), 2.28–2.24 (m, 1H), 2.15 (s, 3H), 2.11 (s, 3H), 2.10–2.02 (m, 2H), 1.43 (s, 9H), 1.41–1.24 (m, 2H), 1.16–1.09 (m, 2H), 1.03 (d, J=6.8 Hz, 3H), 0.91–0.80 (m, 9H) ppm.

EXAMPLE 393

IA-3-(L-threonine) Amide (8c)

$^1$H NMR (400 MHz, CD$_3$OD) d 7.28–7.11 (m, 5H), 6,86 (dd, J=15.6, 8.8 Hz, 1H), 6.31 (d, J=6.0 Hz, 1H), 5.80 (dd, J=15.6, 1.2 Hz, 1H), 5.24 (s, 1H), 5.06 (s, 1H), 5.05 (d, J=4.0 Hz, 1H), 4.91 (s, 1H), 4.57–4.40 (m, 1H), 4.24–4.21 (m, 1H), 4.01 (d, J=2.0 Hz, 1H), 3.31–3.04 (m, 2H), 2.63 (dd, J=13.6, 6.0 Hz, 1H), 2.45–2.35 (m, 4H), 2.20–2.17 (m, 2H), 2.15 (s, 3H), 2.07 (s, 3H), 2.05–1.94 (m, 2H), 1.39–1.09 (m, 4H), 1.03 (d, J=6.4 Hz, 3H), 0.91–0.79 (m, 9H) ppm.

EXAMPLE 394

IA-3-(L-lysine) Amide (8ch)

$^1$H NMR (400 MHz, CD$_3$OD) d 7.27–7.11 (m, 5H), 6.85 (dd, J=15.6, 8.8 Hz, 1H), 6.14 (s, 1H), 5.88–5.74 (m, 5H), 5.03 (d, J=4.8 Hz, 1H), 4.96 (s, 1H), 4.93 (s, 1H), 4.88 (s, 1H), 4.57 (d, J=12.4 Hz, 1H), 3.97 (d, J=2.0 Hz, 1H), 3.74 (d, J=12.4 Hz, 1H), 2.64 (dd, J=13.2, 6.8 Hz, 1H), 2.48–2.43 (m, 3H), 2.33–2.17 (m, 3H), 2.15 (s, 3H), 2.09 (s, 3H), 2.07–1.84 (m, 2H), 1.48–1.22 (m, 4H), 1.21 (d, J=2.0 Hz, 3H), 1.05 (d, J=6.8 Hz, 3H), 1.03–0.82 (m, 9H) ppm.

General Procedures for Glutamines, Alanine, Proline

To the IA-4,5-di-t-butyl ester (10a, Example 216) (ca. 12 mmol) is added dichloromethane (1 mL) and a,a-dichloromethylmethylether (2 eq.) at room temperature while stirring. The reaction is heated to 35° C. and allowed to stir overnight. In the morning, triethylamine (10 eq.) is added to scavenge any excess HCl followed by the amino ester (20 eq.). The reaction is stirred for 1 hour and is then concentrated in vacuo. Purification is by flash column chromatography in 3:1 hex/EtOAc. Deprotection with TFA affords the title compounds.

Utilizing the above procedure the following compounds were prepared:

EXAMPLE 395

IA-3-(L-proline benzyl ester) Amide (8ci)

$^1$H NMR (400 MHz, CD$_3$OD) d 7.36–7.11 (m, 10H), 6.85 (dd, J=15.6, 8.4 Hz, 1H), 6.20 (d, J=46.0 Hz, 1H), 5.80 (d, J=16.8 Hz, 1H), 5.42–4.86 (m, 6H), 4.46–4.40 (m, 1H), 4.08 (d, J=1.6 Hz, ½H), 3.99 (d, J=2.0 Hz, ½H), 3.85–3.75 (m, 1H), 3.60–3.45 (m, 1H), 2.64 (dd, J=13.6, 6.4 Hz, 1H), 2.44–2.30 (m, 4H), 2.17–2.12 (m, 2H), 2.10 (s, 2H), 2.08 (s, 2H), 2.02 (s, 3H), 2.00–1.84 (m, 2H), 1.39–1.21 (m, 2H), 1.15–1.10 (m, 2H), 1.07 (d, J=6.8 Hz, 3H), 0.99–0.81 (m, 9H) ppm.

EXAMPLE 396

IA-3-(L-glutamine, benzyl ester, N-CBZ) Amide (8ci)

$^1$H NMR (400 MHz, CD$_3$OD) d 7.33–7.08 (m, 15H), 6.85 (dd, J=15.6, 8.4 Hz, 1H), 6.34 (s, 1H), 5.79 (d, J=14.8 Hz, 1H), 5.20–4.91 (m, 10H), 4.59–4.56 (m, 1H), 4.06 (d, J=1.6 Hz, 1H), 2.68 (dd, J=13.2, 6.0 Hz, 1H), 2.49–2.36 (m, 4H), 2.27–2.19 (m, 2H), 2.08 (s, 4H), 2.03 (s, 3H), 2.01–1.97 (m, 2H), 1.42–1.27 (m, 2H), 1.17–1.10 (m, 2H), 1.03(d, J=6.4 Hz, 3H), 0.99–0.82 (m, 9H) ppm.

EXAMPLE 397

IA-3-(L-glutamine benzyl ester) Amide (8ck)

$^1$H NMR (400 MHz, CD$_3$OD) d 7.39–7.11 (m, 10H), 6.85 (dd, J=16.0, 8.8 Hz, 1H), 6.30 (d, J=2.0 Hz, 1H), 5.79 (dd, J=15.6, 1.2 Hz, 1H), 5.35–4.91 (m, 8H), 4.03 (d, J=2.0 Hz, 1H), 2.66 (dd, J=13.6, 6.4 Hz, 1H), 2.47–2.25 (m, 4H), 2.23–2.11 (m, 2H), 2.08 (s, 4H), 2.03 (s, 3H), 1.42–1.24 (m, 2H), 1.17–1.06 (m, 2H), 1.02 (d, J=6.8 Hz, 3H), 0.99–0.81 (m, 9H) ppm.

EXAMPLE 398

IA-3-(L-alanine) Amide (8cl)

$^1$H NMR (400 MHz, CD$_3$OD) d 7.26–7.12 (m, 5H), 6.84 (dd, J=16.0, 8.0 Hz, 1H), 6.33 (s, 1H), 5.80 (dd, J=15.6, 4.0 Hz, 1H), 5.17 (s, 1H), 5.05 (s, 1H), 5.02 (d, J=2.4 Hz, 1H), 4.98 (s, 1H), 4.94 (s, 1H), 4.4 (d, J=6.4 Hz, 1H), 4.04 (s, 1H), 3.30 (s, 3H), 2.69 (dd, J=13.6, 6.4 Hz, 1H), 2.48–2.31 (m, 4H), 2.30–2.20 (m, 2H), 2.03 (s, 3H), 2.02–1.98 (m, 2H), 1.61–1.26 (m, 2H), 1.18–1.11 (m, 2H), 1.03 (d, J=6.4 Hz, 3H), 0.99–0.81 (m, 9H) ppm.

The following C6 and C4 ethers and C4,6-diethers were prepared according to the procedures in Examples 140 and 141.

EXAMPLE 399

IA-4-Tetradecyl Ether (5da)

NMR (CD$_3$OD) d 0.81–0.93 (m, 6H), 1.21 (bs, (CH$_2$)$_n$), 2.10.(s, OAc), 3.78–4.14 (m, CH$_2$O), 4.01 (bs, H-7), 5.00 (s, 1H), 5.04 (s, 1H), 5.10 (d, J=5.0 Hz CHOAc), 5.18 (s, 1H), 5.23 (bs 1H) 7.08–7.34 (m, ArH); MS (FAB) m/z 757 (M+Na)

EXAMPLE 400

IA-4,6-Ditetradecyl Ether :(5db)

NMR (CD$_3$OD) d 0.84–0.96 (m, 9H), 1.30 (bs,(CH$_2$)$_n$), 2.12.(s, OAc), 3.56, 3.66, 3.90 & 4.06 (4 m, CH$_2$O), 4.02 (bs, H-7), 5.01 (s, 2H), 5.06 (s, 1H), 5.12 (m, 2H) 7.10–7.36 (m, ArH); MS (FAB) m/z 953 (M+Na)

EXAMPLE 401

IA-6-Dodecyl Ether (5dc)

NMR (CD$_3$OD) d 0.83–0.93 (m, 6H), 1.29 (bs, (CH$_2$)$_n$), 2.11.(s, OAc), 3.53 & 3.69 (2 m, CH$_2$O), 4.06 (s, J=2.0 Hz, H-7), 4.98 (s, 1H), 5.03 (s, 1H), 5.09 (d, J=5.0 Hz, CHOAc), 5.12 (s, 1H), 7.05–7.33 (m, ArH); MS (FAB) m/z 729 (M+Na).

EXAMPLE 402

IA-4-Dodecyl Ether (5dd)

NMR (CD$_3$OD) d 0.84–0.93 (m, 6H), 1.23 (bs, (CH$_2$)n), 2.10.(s, OAc), 3.89 & 4.05 (2 m, CH$_2$O), 4.00 (d J=2.0 Hz, H-7), 4.98 (s, 1H), 5.03 (s, 1H), 5.09 (d, J=5.0 Hz, CHOAc), 5.17 (s, 1H), 5.22 (s, J=2.0 Hz, H-7) 7.05–7.31 (m, ArH); MS (FAB) m/z 729 (M+Na).

EXAMPLE 403

IA-4,6-Didodecyl Ether (5de)

NMR (CD$_3$OD) d 0.83–0.93 (m, 9H), 1.24–1.30 (m, (CH$_2$)n), 2.11.(s, OAc), 3.52, 3.65, 3.87 & 4.03 (4 m, CH$_2$O), 4.01 (bs, H-7), 4.98 (s, 2H), 5.04 (s, 1H), 5.11 (m, 2H) 7.05–7.33 (m, ArH); MS (FAB–) m/z 874 (M).

EXAMPLE 404

IA-6-Decyl Ether (5df)

NMR (CD$_3$OD) d 0.82–0.91 (m, 6H), 1.28 (bs, (CH$_2$)n), 2.09.(s, OAc), 3.42 & 3.62 (2 m, CH$_2$O), 4.01 (s, J=2.0 Hz, H-7), 4.93 (s, 1H), 4.98 (s, 1H), 5.04 (m, 2H), 7.04–7.30 (m, ArH); MS (FAB) m/z 701 (M+Na).

EXAMPLE 405

IA-4-Decyl Ether (5dg)

NMR (CD$_3$OD) d 0.81–0.89 (m, 6H), 1.23 (bs, (CH$_2$)n), 2.10.(s, OAc), 3.87 & 4.05 (2 m, CH$_2$O), 4.00 (d, J=2.0 Hz, H-7), 4.99 (s, 1H), 5.03 (s, 1H), 5.09 (d, J=5.0 Hz, CHOAc), 5.17 (s, 1H), 5.22 (s, J=2.0 Hz, H-7) 7.09–7.31 (m, ArH); MS (FAB–) m/z 677 (M–1)).

EXAMPLE 406

IA-4,6-Didecyl Ether (5dh)

NMR (CD$_3$OD) d 0.84–0.92 (m, 9H), 1.25, & 1.31 (2 bs, (CH$_2$)n), 2.11.(s, OAc), 3.50, 3.68, 3.86 & 4.06 (4 m, CH$_2$O), 4.02 (bs, H-7), 4.99 (s, 2H), 5.04 (s, 1H), 5.11 (d, J=5.0 Hz, CHOAc), 5.14 (s, 1H), 7.06–7.36 (m, ArH); MS (FAB–) m/z 818 (M).

EXAMPLE 407

IA-6-(10-Carboxy)decyl Ether (5di)
NMR (CD$_3$OD) d 0.86 (d, J=7.0 Hz, CHCH$_3$), 1.32 (bs, (CH$_2$)n), 2.10.(s, OAc), 2.26 (t, J=7.0 Hz, CH$_2$CO$_2$H), 3.54 & 3.68 (2 m, CH$_2$O), 4.08 (bs, H-7), 4.98 (s, 1H), 5.04 (s, 1H), 5.10 (m, 2H), 7.06–7.34 (m, ArH); MS (FAB–) m/z 721 (M–1).

EXAMPLE 408

IA-4-(10-carboxy)decyl Ether (5d)
NMR (CD$_3$OD) d 0.86 (d, J=7.0 Hz, CHCH$_3$), 1.25 (bs, (CH$_2$)n), 2.11.(s, OAc), 2.25 (t, J=7.0 Hz, CH$_2$CO$_2$H) 3.91 & 4.03 (2 m, CH$_2$O), 4.02 (d, J=2.0 Hz, H-7), 5.01 (s, 1H), 5.05 (s, 1H), 5.11 (d, J=5.0 Hz, CHOAc), 5.19 (s, 1H), 5.25 (d, J=2.0 Hz H-7) 7.05–7.36 (m, ArH); MS (FAB–) m/z 722 (M).

EXAMPLE 409

IA-4,6-Bis-(10-carboxy)decyl Ether (5dk)
NMR (CD$_3$OD) d 0.86 (d, J=7.0 Hz, CHCH$_3$), 1.25 & 1.32 (2 bs,(CH$_2$)n), 2.11.(s, OAc), 2.24 (m, CH$_2$CO$_2$H), 3.54, 3.65, 3.86 & 4.04 (4 m, CH$_2$O), 4.00 (s, J=2.0 Hz, H-7), 5.00 (m, 2H), 5.04 (s, 1H), 5.10 (d, J=5.0 Hz, CHOAc), 5.14 (s, 1H) 7.06–7.36 (m, ArH); MS (FAB–) m/z 905 (M–1)

EXAMPLE 410

IA-6-Butyl Ether (5dl)
NMR (CD$_3$OD) d 0.86 (d, J=7.0 Hz, CHCH$_3$), 0.92 (t, J=7.0 Hz, CH$_2$CH$_3$), 1.38 (m, 2H), 1.53 (m, 2H), 2.10.(s, OAc), 3.54, 3.69 (2 m, CH$_2$O), 4.06 (d, J= 2.0 Hz, H-7), 4.87 (d, J=2.0 Hz, H-6), 4.97 & 5.02 (2 s, 2H), 5.08 (d, J=5.0 Hz, CHOAc), 5.11 (s, H-3), 7.13–7.30 (m, ArH). MS (FAB–) m/z 593 (M–1).

EXAMPLE 411

IA-6-Isobutyl Ether (5dm)
NMR (CD$_3$OD) d 0.83–0.98 (m, 9H), 1.83 (m, 1H), 2.11.(s, OAc), 3.29, 3.47 (2 m, CH$_2$O), 4.06 (d, J=2.0 Hz, H-7), 4.86 (d, J=2.0 Hz, H-6), 4.98 & 5.03 (2 s, 2H), 5.08 (d, J=5.0 Hz, CHOAc), 5.10 (s, H-3), 7.07–7.31 (m, ArH). MS (FAB–) m/z 593 (M–1).

EXAMPLE 412

IA-6-Pentyl Ether (5dn)
NMR (CD$_3$OD) d 0.84–0.91 (m, 6H), 1.32 (m, 4H), 1.55 (m, 2H), 2.10.(s, OAc), 3.54, 3.68 (2 m, CH$_2$O), 4.05 (d, J=2.0 Hz, H-7), 4.90 & 4.96 (2 s, 2H), 5.09 (m, 2H), 7.14–7.27 (m, ArH). MS (FAB–) m/z 607 (M–1).

EXAMPLE 413

IA-6-Isoamyl Ether (5do)
NMR (CD$_3$OD) d 0.84–0.90 (m, 9H), 1.44 (m, 2H), 1.71 (m, 1H), 2.10.(s, OAc), 3.56, 3.72 (2 m, CH$_2$O), 4.05 (d, J=2.0 Hz, H-7), 4.86 (d, J=2.0 H-6), 4.96 & 5.01 (2 s, 2H), 5.08 (d, J=5.0 CHOAc), 5.10 (s, H-3), 7.14–7.27 (m, ArH). MS (FAB–) m/z 608 (M).

EXAMPLE 414

IA-[1-(3', 3'a), 6-(3',4')-Tetrahydro-4'-epiacetate (7aa)
To IA-4'-epiacetate-7-MME-tris-t-butyl ester (28a, Example 278) (0.052 g, 0.056 mmol) was added 10% palladium on carbon (0.026 g, 0.24 mmol) while stirring in ethyl acetate (2 mL) under hydrogen gas at room temperature over night. The reaction mixture was filtered, concentrated in vacuo and purified by flash column chromatography (silica gel, 4:1 hexane/EtOAc) yielding the protected, reduced epimeric acetate as a light yellow solid. This compound was deprotected by the standard TFA deprotection. $^1$H NMR (400 MHz, CD$_3$OD) d 7.27–7.00 (m, 10H), 6.25 (d, J=6 Hz, 2H), 5.24 (d, J=5.6 Hz, 2H), 4.84–4.77 (m, 16H), 4.02 (d, J=2 Hz, 1H), 4.00 (d, J=2 Hz, 1H) 2.75–2.67 (m, 2H), 2.34–2.14 (m, 6H), 2.10 (d, J=9.6 Hz, 6H), 2.07–1.03 (m, 24H), 0.98–0.79 (m, 30H).

EXAMPLE 415

IA-[1-(3',3a'), 6-(3',4')-Tetrahydro]-[1-(3a'-acetoxy)-(4'-desacetoxy)]
The protected, allylically rearranged alcohol (27c, Example 278) was acetylated according to the procedure for acetylation of the 4'-epimeric allyl alcohol (27a, Example 278) to provide the corresponding acetate (28c): $^1$H NMR (300 MHz, CDCl$_3$) d 7.26–7.13 (m, 5H), 6.91 (dd, J=21.2, 11.2 Hz, 1H), 6.39 (d, J=2.4 Hz, 1H), 5.80 (d, J=20.4 Hz, 1H), 5.28 (s, 1H), 5.26 (s, 1H), 4.97 (s, 1H), 4.40 (dd, J=40.4, 16.8 Hz, 2H), 4.12–4.02 (m, 2H), 3.15 (s, 3H), 2.94–2.80 (m, 1H), 2.60 (dd, J=12.0, 8.0 Hz, 1H), 2.51 (dd, J=14.0, 11.2 Hz, 1H), 2.39–2.34 (m, 3H), 2.01 (s, 3H), 1.89–1.75 (m, 1H), 1.66 (s, 9H), 1.43 (s, 9H), 1.48–1.22 (m, 3H), 1.40 (s, 9H), 1.31 (s, 3H), 1.26 (s, 3H), 1.10–1.05 (m, 2H), 1.00–0.96 (m, 6H), 0.83–0.78 (m, 6H). To 28c (0.094 g, 0.01 mmol) was added 10% palladium on carbon (0.047 g, 0.44 mmol) while stirring in ethyl acetate (1 mL) under hydrogen gas at room temperature overnight. The reaction mixture was filtered, concentrated in vacuo and purified by flash column chromatography (silica gel, 3:1 hexane/EtOAc) yielding the 7-MME-tris-t-butyl reduced, rearranged acetate as a light yellow solid. This compound was deprotected by the standard TFA deprotection. $^1$H NMR (200 MHz, CD$_3$OD) d 7.27–7.08 (m, 5H), 6.25 (s, 1H), 5.25 (s, 1H), 4.03 (s, 1H), 2.71 (dd, J=10.4, 6.8 Hz, 1H), 2.57 (dd, J=10.4, 6.8 Hz, 1H), 2.10–2.22 (m, 5H), 2.07 (s, 3H), 1.95–1.76 (m, 4H), 1.70–1.02 (m, 7H), 0.98–0.78 (m, 14H).

EXAMPLE 416

IA-4'-desacetate (7ac)
To a solution of 3% HCl/CH$_3$OH (10 mL) was added IA-3,4,5-tribenzyl ester, 1e Example 4, (506.2 mg, 0.53 mmol). The reaction was allowed to stir for ca. 5 h whereupon it was concentrated to ca. ⅓ its original volume, diluted with CH$_2$Cl$_2$ and washed with sat. NaHCO$_3$, brine, dried (Na$_2$SO$_4$) and chromatographed (5:1 hexanes:EtOAc) to yield IA-3,4,5-tribenzyl ester-4'-desacetate and IA-3-methyl ester-4,5-dibenzyl ester-4'-desacetate. IA-3-methyl ester-4,5-dibenzyl ester-4'-desacetate $^1$H NMR (CDCl$_3$, 400 MHz) d 7.35–7.11 (m, 15H), 6.76 (dd, J=15.7, 8.8 Hz, 1H), 5.77 (d, J=2.1 Hz, 1H), 5.37 (d, J=15.6 Hz, 1H), 5.21–4.87 (m, 7H), 4.04 (d, J=4.8 Hz, 1H), 3.97 (br s, 1H), 3.47 (s, 3H), 3.22 (br s, 1H), 2.73 (dd, J=13.2, 5.1 Hz, 1H), 2.49–1.88 (m, 8H), 1.02 (d, J=6.7 Hz, 2H), 0.83–0.72 (m, 9H).

IA-3,4,5-tribenzyl ester-4'-desacetate $^1$H NMR (CDCl$_3$, 400 MHz) d 7.31–7.07 (m, 20H), 6.75 (dd, J=15.6, 8.8 Hz, 1H), 5.72 (d, J=1.9 Hz, 1H), 5.30 (d, J=15.5 Hz, 1H), 5.21–4.87 (m, 8H), 4.74 (ab q, J=19.2, 12.3 Hz, 2H), 4.03 (d, J=5.4 Hz, 1H), 3.95 (br s, 1H), 2.72 (dd, J=13.2, 5.6 Hz, 1H), 2.49–2.04 (m, 5H), 1.01 (d, J=6.6 Hz, 3H), 0.82–0.79 (m, 8H).

To a solution of the IA-3,4,5-tribenzyl ester-4'-desacetate (175 mg, 0.19 mmol) in CH$_3$OH (3.0 mL) was added dihydrotoluene (0.20 mL) and 10% Pd/C (ca. 100 mg). The reaction was stirred with occasional heating until the starting material had been consumed. The reaction was then filtered through celite with CH₃OH, the filtrate was concentrated and the residue was purified by HPLC to give the title compound. ¹H NMR (CD₃OD, 400 MHz) d 7.25–7.09 (m, 5H), 6.83 (dd, J=15.7, 8.6 Hz, 1H), 6.30 (br s, 1H), 5.77 (d, J=15.7 Hz, 1H), 5.26 (br s, 1H), 5.08 (s, 1H), 4.98 (s, 1H), 4.07 (s, 1H), 3.92 (d, J=5.0 Hz, 1H), 2.75 (dd, J=13.4, 5.6 Hz, 1H), 2.48–2.23 (m, 4H), 2.08–2.05 (m, 3H), 1.41–1.23 (m, 4H), 1.16–1.08 (m, 2H), 1.02 (d, J=6.6 Hz, 3H), 0.98–0.81 (m, 10H).

EXAMPLE 417

IA3-Methyl Ester-4'-des-acetate and IA-3-Methyl Ester

To 10 mL of methanol at 0° C., 0.527 mL of acetyl chloride was added. The resulting mixture was stirred for 10 minutes, after which time, IA (0.3067 mmol, 211 mg) was added. The reaction was allowed to run overnight. Analytical HPLC the following morning indicated the formation of two higher retention time products and the absence of starting material. Reaction was worked-up by diluting the reaction with methylene chloride and washing with brine. The organic layer was dried over sodium sulfate and concentrated in vacuo. Purification by HPLC yielded IA-3-methyl ester-4'-desacetate and IA-3-methyl ester.
IA-3-methyl ester ¹H NMR (CD₃OD, 400 MHz) d 7.27–7.12 (m, 5H), 6.84 (dd, J=15.6, 8.5 Hz, 1H), 6.31 (d, J=1.9 Hz, 1H), 5.79 (d, J=15.6 Hz, 1H), 5.31 (s, 1H), 5.07 (d, J=5.0 Hz, 1H), 5.01 (s, 1H), 4.96 (s, 1H), 4.03 (d, J=1.7 Hz, 1H), 3.30 (s, 3H), 2.68 (dd, J=13.4, 6.2 Hz, 1H), 2.47–2.15 (m, 5H), 2.09 (s, 3H), 2.03–1.93 (m, 2H), 1.39–1.27 (m, 7H), 1.17–1.05 (m, 3H), 1.02 (d, J=6.7 Hz, 3H), 0.91–0.84 (m, 9H), IA-3-methyl ester-4'-des-acetate ¹H NMR (CD₃OD, 400 MHz) d 7.29–7.10 (m, 5H), 6.85 (dd, J=15.3, 8.5 Hz, 1H), 6.30 (d, J=1.75 Hz, 1H), 5.77 (d, J=15.6 Hz, 1H), 5.32 (s, 1H), 5.10 (s, 1H), 4.07 (d, J=1.8 Hz, 1H), 3.91 (d, J=4.9 Hz, 1H), 3.72 (s, 3H), 2.75 (dd, J=13.3, 5.9 Hz, 1H), 2.50–2.20 (m, 4H), 2.10–1.97 (m, 3H), 1.40–1.23 (m, 4H), 1.20–1.05 (m, 3H), 1.02 (d, J=6.64 Hz, 1H), 0.90–0.81 (m, 9H).

EXAMPLE 418

IA-4-Methyl Ether (5ea)

To a solution of the IA-7-MME-tris-t-butyl ester, 2a, (50 mg, 0.06 mmol. ) in DMF (1.0 mL) was added iodomethane (0.02 mL, 0.28 mmol) followed by silver oxide (77.8 mg, 0.33 mmol). The reaction was stirred overnight filtered through celite with CH₂Cl₂, concentrated and chromatographed (6:1 hexanes:EtOAc) to give the
IA-4-methyl ether-7-MME-tris-t-butyl ester, ¹H NMR (CDCl₃, 400 MHz) d 7.26–7.12 (m, 5H), 6.87 (dd, J=15.7, 8.2 Hz, 1H), 6.52 (d, J=1.3 Hz, 1H), 5.75 (d, J=15.8 Hz, 1H), 5.10 (d, J=5.1 Hz, 1H), 4.96 (s, 1H), 4.93 (s, 1H), 4.16 (d, J=1.4 Hz, 1H), 3.74 (s, 3H), 3.19 (s, 3H), 2.08 (s, 3H), 1.62 (s, 9H), 1.47 (s, 9H), 0.98 (d, J=6.7 Hz, 3H), which was deprotected using the TFA method to give IA-4-methyl ether, ¹H NMR (CD₃OD, 400 MHz) d 7.26–7.13 (m, 5H), 6.84 (dd, J=15.7, 8.6 Hz, 1H), 6.39 (d, J=1.6 Hz, 1H), 5.78 (d, J=15.7 Hz, 1H), 5.31 (s, 1H), 5.04 (d, 1H), 4.95 (s, 1H), 4.88 (s, 1H), 3.99 (d, J=1.7 Hz, 1H), 3.31 (s, 3H), 2.64 (m, 1H), 2.48–2.42 (m, 3H), 2.09 (s, 3H), 1.43–1.31 (m, 5H), 1.15–1.12 (m, 2H), 1.03 (d, J=6.7 Hz, 3H), 0.88–0.84 (m, 7H).

EXAMPLE 419

IA-4-Ethyl Ether (5eb)

Using the procedure for the synthesis of IA-4-methyl ether (Example 418) and ethyl iodide, IA-4-ethyl ether was produced. ¹H NMR (CD₃OD, 400 MHz) d 7.62–7.11 (m, 5H), 6.36 (br s, 1H), 5.31 (br s, 1H), 2.09 (s, 3H).

EXAMPLE 420

IA-1-[3-(R,S)-hydroxy-6-phenyl]hexane (7ad)

To a solution of CeCl₃ (830 mg, 3.37 mmol) in THF was added a solution of 3-phenylpropyl magnesium bromide (2.7 mL of a 1.0M solution in THF, 2.7 mmol). The reaction was stirred for 1.5 h whereupon a solution of the aldehyde (500 mg, 0.67 mmol) in THF (6 mL) was added dropwise. The reaction was stirred 1 hour whereupon tetramethylethylenediamine:triethylamine (1:1, 1 mL) was added. The reaction was stirred 0.5 h, H₂O (1 mL) was added and the reaction was filtered through celite with ether. The filtrate was washed with sat. NaHCO₃, brine, dried (Na₂SO₄) concentrated and chromatographed (2:1 hexanes:EtOAc) to yield the 3'-hydroxy-7-MME-tris-t-butyl ester, ¹H NMR (CDCl₃, 400 MHz) d 7.25–7.12 (m, 5H), 6.89–6.83 (m, 1H), 6.39 (app s, 1H), 5.76–5.71 (m, 1H), 5.03 (m 1H), 4.23 (m, 1H), 4.01 (app s, 1H), 3.21 & 3.2 (s, 3H), 2.68–2.58 (m, 4H), 2.36–2.34 (m, 3H), 1.99–1.761 (m, 4H), 1.65 (s, 9H), 1.44 &1.43 (s, 9H), 1.41–1.35 (m, 2H), 1.35 (s, 9H), 1.26 (s, 3H), 1.11–1.03 (m, 3H), 0.98–0.95 (m, 3H), 0.86–0.78 (m, 7H), which was deprotected with the usual TFA procedure to give IA-1-(3-(R,S)-hydroxy-6-phenyl)hexane, ¹H NMR (CD₃OD, 400 MHz) d 7.23–7.12 (m, 5H), 6.28 (dd, J=17.1, 1.1 Hz, 1H), 6.28 (app s, 1H), 5.79 (d, J=15.55 Hz, 1H), 5.24 (app s, 2H), 4.05 (m, 1H), 2.66–2.63 (m, 2H), 2.42 (m, 1H), 2.09–1.91 (m, 4H), 1.75–1.55 (m, 4H), 1.38–1.26 (m, 4H), 1.17–1.09 (m, 2H), 1.02 (d, J=6.7 Hz, 3H), 0.88–0.84 (m, 7H).

EXAMPLE 421

IA-1-[3-(R,S)-hydroxy-8-phenyl]octane (7ae)

Using the procedure for synthesizing IA-1-(3-(R,S)-hydroxy-6-phenyl)hexane and 5-phenylpentyl magnesium bromide, the 7-MME-tris-t-butyl protected intermediate was synthesized, ¹H NMR (CDCl₃, 400 MHz) d 7.26–7.13 (m, 5H), 6.86 (m, 1H), 6.05–5.98 (d, J=1.8 Hz, 1H), 5.73 (d, J=15.7 Hz, 1H), 4.07 (s, 3H), which was deprotected to yield the title compound. ¹H NMR (CD₃OD, 400 MHz) d 7.28–7.09 (m, 5H), 6.81 (m, 1H), 6.29 (br s, 1H), 5.75 (d, J=15.5 Hz, 1H), 5.24 (s, 1H), 5.19 (m, 1H).

EXAMPLE 422

IA-1-(3-(R,S)-acetoxy-6-phenyl)octane (7af)

To a solution of the alcohol, IA-1-(3-(R,S)-hydroxy-6-phenyl)hexane-7-MME-tris-t-butyl ester, (107 mg, 0.12 mmol) in CH₂Cl₂ (2.5 mL) was added DMAP (2.0 mg), triethylamine (0.08 mL, 0.60 mmol) and acetic anhydride (0.04 mL, 0.36 mmol). The reaction was stirred until the starting material was consumed (TLC) whereupon the reaction was worked up in the usual manner. Chromatography (3:1 hexanes:EtOAc) gave the protected acetate intermediate, ¹H NMR (CDCl₃, 400 MHz) d 7.26–7.12 (m, 5H), 6.85 (m, 1H), 6.39 (m, 1H), 5.74 (m, 1H), 5.02 (m, 1H), 4.89 (br s, 1H), 4.19 (m, 1H), 4.01 (s, 1H), 3.21 & 3.19 (s, 3H), 2.56 (app t, 2H), 2.37 (m, 1H), 2.06 & 1.67 (m, 3H), 1.99 & 1.97 (s, 3H), 1.65 (s, 9H), 1.63 (s, 3H), 1.44 (s, 9H), 1.35 (s, 9H), 1.25 (s, 3H), 1.11–1.05 (m, 3H), 0.98 (d, 3H), 0.82–0.78 (m, 7H), which was deprotected using the TFA method to produce the title compound, ¹H NMR (CD₃OD, 400 MHz) d 7.24–7.10 (m, 5H), 6.82 (dd, J=15.6, 7.1 Hz, 1H), 5.77 (d, J=15.4 Hz, 1H), 5.24 (s, 1H), 4.05 (m, 1H), 2.59 (t, 2H), 2.43 (m, 1H), 2.03 (s, 3H), 1.99–1.83 (m, 4H), 1.64–1.55 (m, 4H), 1.41–1.28 (m, 9H), 1.15–1.08 (m, 2H), 1.01 (d, J=6.6 Hz, 3H), 0.86 (m, 8H).

EXAMPLE 423

IA-1-[3-(R,S) acetoxy-(8-phenyl)]hexane (7ag)

Using the procedure for synthesizing IA-1-(3-(R,S)-acetoxy-6-phenyl)octane, the intermediate acetoxy-7-MME-tris-t-butyl ester was produced, $^1$H NMR (CDCl$_3$, 400 MHz) d 4.17 (m, 1H), 3.19 & 3.18 (s, 3H), 2.00 & 1.98 (s, 3H), 1.65 (s, 9H), 1.35 (s, 9H), which was deprotected using the TFA procedure to afford IA-1-[3-(R,S) acetoxy-(8-phenyl)]hexane, $^1$H NMR (CD$_3$OD, 400 MHz) d 2.43 (m, 1H), 2.03 (s, 3H). MS FAB(−) 663 (M−1).

EXAMPLE 424

IA-1-(6-phenyl-hex-3-one) (7ah)

To a −78° C. solution of oxalyl chloride (1.75 mL of a 2M solution in CH$_2$CL$_2$, 3.5 mmol) in CH$_2$Cl$_2$ (5.0 mL) was added DMSO (0.49 mL, 7.0 mmol). The reaction was stirred for 20 min whereupon IA-1-(3-(R,S)-hydroxy-6-phenyl-)hexane-7-MME-tris-t-butyl ester (300 mg, 0.35 mmol) in CH$_2$Cl$_2$ (3×2 mL) was added. The reaction was stirred for 20 min then triethylamine (2.0 mL) was added. The reaction was allowed to warm to room temperature and worked up in the usual manner. Chromatography (3:1 hexanes:EtOAc) gave the protected ketone, $^1$H NMR (CDCl$_3$, 400 MHz) d 7.26–7.13 (m, 5H), 6.85 (dd, J=15.7 Hz, 1H), 6.39 (d, J=1.5 Hz, 1H), 5.72 (d, J=15.7 Hz, 1H), 5.02 (s, 1H), 4.19 (d, 1H), 4.04 (s, 1H), 3.23 (s, 3H), 2.94–2.81 (m, 2H), 2.57 (t, J=7.4 Hz, 2H), 2.48–2.44 (m, 2H), 2.36–2.30 (m, 2H), 2.02–1.91 (m, 1H), 1.89–1.86 (m, 2H), 1.65 (s, 9H), 1.43 (s, 9H), 1.35 (s, 3H), 1.34 (s, 9H), 0.97 (d, J=6.7 Hz, 3H), 0.81–0.78 (s, 7H), which was deprotected using the TFA method to provide IA-1-(6-phenyl-hex-3-one), $^1$H NMR (CD$_3$OD, 400 MHz) d 7.26–7.12 (m, 5H), 6.81 (dd, J=15.6 Hz, 1H), 6.28 (d, J=1.8 Hz, 1H), 5.76 (d, J=15.8 Hz, 1H), 5.23 (s, 1H), 4.04 (d, J=1.9 Hz, 1H), 2.88–2.75 (m, 2H), 2.60 (t, J=7.4 Hz, 2H), 2.53 (t, J=7.4 Hz, 2H), 2.43 (m, 1H), 2.25–2.05 (m, 2H), 1.91–1.84 (m, 2H), 1.38–1.25 (m, 5H), 1.17–1.08 (m, 2H), 1.02 (d, J=6.6 Hz, 3H), 0.88–0.84 (m, 7H).

EXAMPLE 425

IA-1-(8-phenyl-oct-3-one) (7ai)

Using the procedure for synthesizing IA-1-(6-phenyl-hex-3-one), IA-1-(8-phenyl-oct-3-one)-7-MME-tris-t-butyl ester was synthesized, $^1$H NMR (CDCl$_3$, 400 MHz) d 7.26–7.12 (m, 5H), 1.58 (s, 9H), 1.43 (s, 9H), 1.42 (s, 9H), and was deprotected to provide the title compound, $^1$H NMR (CD$_3$OD, 400 MHz) d 7.32–7.10 (m, 5H), 2.59 (t, J=7.8 Hz, 2H), 2.51 (t, J=7.3 Hz, 2H). MS FAB 647 (M−1).

EXAMPLE 426

IA-1-[2-(1-(1-Methyl-1,2,3,4-tetrahydronaphthalene))ethane](7aj)

To a −78° C. solution of CeCl$_3$ (107 mg, 0.44 mmol) in THF (5.0 mL) was added trimethylsilylmethyllithium (0.35 mL of a 1.0M solution in pentane, 0.35 mmol). The reaction was stirred for 1 hour at −78° C. whereupon the IA-1-(6-phenyl-hex-3-one)-7-MME-tris-t-butyl ester (75 mg, 0.09 mmol) in THF (3 mL) was added dropwise. The reaction was allowed to stir at −78° C. for ca. 3 hours then quenched with tetramethylethylenediamine (1 mL) and sat. NH$_4$Cl (2 mL). The reaction was then filtered through celite with ether. The filtrate was washed with sat. NaHCO$_3$, brine, dried and concentrated. The crude residue was dissolved in CH$_3$CN (2–3 mL) and several drops of HF were added. The reaction was stirred until the starting material was consumed (TLC). The reaction was then diluted with CH$_2$Cl$_2$ washed with sat. NaHCO$_3$, brine, dried (Na$_2$SO$_4$), concentrated and chromatographed (3:1 hexanes:EtOAc) to yield IA-1-(6-phenyl-hex-3-ene)-7-MME-tris-t-butyl ester, $^1$H NMR (CDCl$_3$, 400 MHz) d 7.25–7.16 (m, 5H), 6.88 (dd, J=15.7, 8.5 Hz, 1H), 6.00 (d, J=1.8 Hz, 1H), 5.75 (d, J=15.6 Hz, 1H), 5.29 (s, 1H), 5.06 (s, 1H), 4.76 (s, 1H), 4.73 (s, 1H), 4.06 (m, 2H), 2.59 (t, J=7.9 Hz, 2H), 2.41–2.39 (m, 3H), 2.06 (t, J=8.1 Hz, 2H), 1.76 (m, 2H), 1.59 (s, 9H), 1.46 (s, 9H), 1.44 (s, 9H), 1.02 (d, J=6.7 Hz, 3H), 0.85–0.82 (m, 5H). During the standard TFA deprotection conditions, the Friedel-Crafts alkylation product, IA-1-[2-(1-(1-Methyl-1,2,3,4-tetrahydronaphthalene))ethane], (7aj) is obtained, $^1$H NMR (400 MHz, CD$_3$OD) d 7.34 (m, 1H), 7.07 (m, 2H), 6.98 (m, 3H), 6.82 (dd, J=18.4, 1.2 Hz, 1H), 6.27 (d, J=1.98 Hz, 1H), 5.77 (d, J=15.6 Hz, 1H), 5.22 (d, J=2.2 Hz, 1H), 4.02 (d, J=1.8 Hz, 1H), 2.73 (m, 2H), 2.42 (m, 1H), 2.17–1.55 (m, 6H), 1.45–1.26 (m, 3H), 1.28 (s, 3H), 1.18–1.08 (m, 2H), 1.02 (d, J=1.5 Hz, 3H), 0.88–0.84 (m, 6H). MS FAB 617 (m−1).

EXAMPLE 427

IA-1-4'-ketone (7ak)

To a −78° C. solution of oxalyl chloride (23.5 uL, 0.27 mmol) in CH$_2$CL$_2$ (5.0 mL) was added DMSO (38.3 uL, 0.54 mmol). The reaction was stirred for 15 mins. whereupon IA-4'-desacetate-7-MME-tris-t-butyl ester, Example 159 (200 mg, 0.23 mmol) in CH$_2$Cl$_2$ (3 mL) was added. The reaction was stirred for 20 mins. then triethylamine (0.62 mL, 4.5 mmol) was added. The reaction was allowed to warm to room temperature and worked up in the usual manner. Chromatography (3:1 hexanes:EtOAc) gave 183 mg of IA-1-4'-ketone-7-MME-tris-t-butyl ester, $^1$H NMR (CDCl$_3$, 400 MHz) d 7.25–7.12 (m, 5H), 6.8 (dd, J=15.7, 8.1 Hz, 1H), 6.39 (d, J=1.5 Hz, 1H), 5.87 (s, 1H), 5.77 (s, 1H), 5.73 (s, 1H), 5.03 (s, 1H), 4.24 (d, J=1.5 Hz, 1H), 3.98 (s, 1H), 3.46–3.44 (m, 1H), 3.21 (s, 3H), 3.00 (dd, J=13.6, 6.6 Hz, 1H), 2.64–2.60 (m, 2H), 2.53 (dd, J=13.6, 7.7 Hz, 1H), 2.37 (m, 1H), 2.03–1.94 (m, 2H), 1.66 (s, 9H), 1.44 (s, 9H), 1.36 (s, 12H), 1.27 (s, 3H), 1.03 (d, J=6.8 Hz, 3H), 0.98 (d, J=6.6 Hz, 3H), 0.82–0.78 (m, 6H), which was deprotected by the standard TFA conditions to give IA-1-4'-ketone, (7ak), $^1$H NMR (CD$_3$OD, 400 MHz) d 7.24–7.13 (m, 5H), 6.83 (dd, J=15.6, 8.5 Hz, 1H), 6.28 (d, J=1.8 Hz, 1H), 6.05 (s, 1H), 5.86 (s, 1H), 5.78 (d, J=15.7 Hz, 8.3 1H), 5.25 (s, 1H), 4.08 (d, J=1.7 Hz, 1H), 3.63 (m, 1H), 2.95 (dd, J=13.5, 7.6 Hz, 1H), 3.62–2.44 (m, 3H), 1.91–1.86 (m, 2H), 1.56–1.28 (m, 6H), 1.16–1.09 (m, 2H), 1.07 (d, J=6.9 Hz, 3H), 1.03 (d, J=6.7 Hz, 3H), 0.96–0.85 (m, 6H).

EXAMPLE 428

IA-1-[3'-(R,S)-pentyl-5(R)-methyl-6-phenyl]hex-4-one (7al)

To a −78° C. solution of copper(I) cyanide (30.7 mg, 0.34 mmol) in diethyl ether (1.0 mL) has added dropwise n-butyllithium (0.42 mL of a 1.6M solution in hexane, 0.67 mmol). The reaction was warmed to −78° C. for approximately 2 mins. then recooled to −78° C. A solution of IA-1-4'-ketone (150 mg, 0.17 mmol) in diethyl ether (1 mL) was added dropwise to the cuprate. The reaction was allowed to stir for 10 mins at −78° C. then quenched with saturated ammonium chloride and diluted with diethyl ether. The organic layer was washed with NaHCO$_3$, brine; dried (Na$_2$SO$_4$) concentrated and chromatographed (3:1 hexane: ethyl acetate) to yield the C3' substituted 7-MME-tris-t-butyl esters as a 1:1 mixture. $^1$H NMR (400 MHz, CDCl$_3$) d 7.26–7.12 (m, 5H), 6.88–6.82 (m, 1H), 6.37 (brs, 1H), 5.74 and 5.69 (d, 1H), 4.99 (s, 1H), 4.19–4.08 (brs, 1H), 3.97–3.96 (s, 1H), 3.20 and 3.17 (s, 3H), 1.65 (s, 9H), 1.63 and 1.54 (s, 3H), 1.43–1.42 (s, 9H), 1.35 (s, 9H), 1.35 (s, 9H), 1.32–0.95 (m, 21H), 0.82 (m, 9H). This compound was deprotected according to the TFA procedure to yield IA-1-[3'-(R, 8) -pentyl-5(R)-methyl-6-phenyl]hex-4-one (7al) as an off-white solid. $^1$H NMR (400 MHz, CD$_3$OD) d 7.24–7.12 (m, 5H), 6.87–6.79 (m, 1H), 5.82–5.75 (m, $^1$H), 5.24 and 5.22 (s, 1H) MS (FAB)$_{704}$

EXAMPLE 429

IA-1-[3'-(R,S)-benzyl-5(R)-methyl-6-phenyl]hex-4-one (7am)

IA-1-[3'-(R,S)-benzyl-5 (R)-methyl-6-phenyl]hex-4-one-7-MME-tris-t-butyl ester was prepared using the previously described procedure for the 3'-pentyl compound. $^1$H NMR (400 MHz, CDCl$_3$) d 7.24–7.08 (m, 9H), 6.89–6.81 (m, H), 6.38 (m, 1H), 5.27, 5.13, 5.02 and 5.00 (s, 2H), 4.20 and 4.19 (b, s, 1H), 3.97 (app. d, 1H), 3.19 and 3.18 (s, 3H), 1.65 (s, 9H), 1.44 and 1.42 (s, 9H), 1.36 and 1.35 (s, 9H). Deprotection with TFA yielded an off-white solid. $^1$H NMR (400 MHz, CD$_3$OD) d 7.24–7.08 (m, 9H), 6.91–6.79 (m, 2H), 6.28 and 6.26 (br s, 1H), 5.78 (2 doublets, 1H), 5.25 and 5.23 (brs, 1H), 4.03 and 3.91 (brs, 1H), 3.3 (m, 2H), 2.97–2.33(m, 5H), 2.12–1.64 (m, 4H), 1.39–1.27 (m, 3H), 1.1 (m, 2H), 1.01 (m, 3H), 0.90–0.82 (m, 8H), 0.55 (app.d., J=6.6 Hz, 2H).

EXAMPLE 430

IA-1-4'-hydroxy-tris-t-butyl ester

A solution of IA-1-4'-hydroxy-7-MME-tris-t-butyl ester, 4'a (200 mg, 0.23 mmol) in THF (6 mL), water, (2 mL) and acetic acid (2 mL) was heated a 45° C. for 16 hours. The reaction was cooled to room temperature and diluted with dichloromethane (50 mL) washed with sat. NaHCO$_3$ (10 mL), brine (10 mL), dried (Na$_2$SO$_4$) and concentrated in vacuo. Column chromatography of the residue (silica gel, 3:1 hexanes:ethyl acetate) gave a white solid; $^1$H NMR (400 MHz, CDCl$_3$) 7.34–7.12 (m, 5H), 6.86 (dd, J=15.6, 8.5 Hz, 1H), 5.97 (app s, 1H, 5.73 (dd, J=15.7, 1.06 Hz, 1H), 5.1 (s, 1H), 5.04 (s, 1H), 4.03 (d, J=5.4 Hz, 1H), 4.01 (d, J=1.87 Hz, 1H), 2.75 (dd, J=13.5, 5.41 Hz, 1H), 2.47–2.30 (m, 4H), 2.12 (t, J=7.24 Hz, 2H), 1.96 (m, 1H), 1.57 (s, 9H), 1.46 (s, 9H), 1.44 (s, 9H), 1.41–1.24 (m, 3H), 1.1 (m, 2H), 1.01 (d, J=6.6 Hz, 3H), 0.81 (m, 9H); MS (FAB) m/z 823 (M+Li)$^+$.

EXAMPLE 431

IA-1-3'-dihydroxy-4'-hydroxy-tris-t-butyl ester

To a solution of IA-1-4'-hydroxy-tris-t-butyl ester (1.31 g, 1.60 mmol) was added a solution of osmium tetraoxide (5.2'mL of a 0.36M solution of osmium. tetraoxide in dioxane) dropwise via syringe pump. The reaction was maintained at room temperature for ca. 8–10 hours whereupon it was diluted with additional dioxane (20 mL) and hydrogen sulphide was bubbled through the mixture for 15 min. The black reaction mixture was then filtered through a short pad of celite with dichloromethane and concentrated in vacuo to yield a clear light green oil. Column chromatography of the residue (silica gel, 2:1 ethyl acetate:hexanes) gave a white powder: $^1$H NMR (400 MHz, CD$_3$OD) 7.26–7.09 (m, 5H), 6.88 (dd, J=15.6, 8.6 Hz, 1H), 5.81 (d, J=14.71 Hz, 1H), 5.15 (s, 1H), 4.00 (d, J=1.71 Hz, 1H), 3.65 (br m, 1H), 3.52 (br m, 2H), 2.78–2.52 (m, 2H), 2.45 (m, 1H), 2.19 (m, 1H), 1.88 (br m, 3H), 1.62 (s, 9H), 1.46 (s, 9H), 1.43 (s, 9H), 1.41–1.27 (m, 3H), 1.66–1.09 (m, 3H), 1.02 (d, J=6.7 Hz, 3H), 0.97 (d, J=6.6 Hz, 3H), 0.87 (m, 6H); MS (FAB) m/z 857 (M+Li)$^+$

EXAMPLE 432

IA-1-(3-propionic acid)-3,4,5-tris-t-butyl ester

To a solution of IA-1-3'-dihydroxy-4'-hydroxy-tris-t-butyl ester (184 mg, 0.22 mmol) in dioxane (10 mL) and water (2 mL) was added sodium periodate (468 mg, 1.08 mmol). The reaction mixture was stirred at room temperature overnight whereupon it was diluted with dichloromethane (50 mL) and washed with water (15 mL), brine (15 mL), dried (Na$_2$SO$_4$) and concentrated in vacuo. Column chromatography of the residue (silica gel, 5:1 chloroform:methanol) gave the acid as a white solid: $^1$H NMR (300 MHz, CD$_3$OD) d 6.92 (dd, J=15.63, 8.47 Hz, 1H), 6.46 (d, J=1.57 Hz, 1H), 5.84 (d, J=15.62 Hz, 1H), 5.24 (s, 1H), 4.17 (d, J=1.63 Hz, 1H), 2.54 (m, 3H), 2.23 (m, 2H), 1.67 (s, 9H), 1.52 (s, 9H), 1.46 (s, 9H), 1.65–1.16 (m, 8H), 1.05 (d, J=6.73, 2H), 0.91 (m, 4H); MS (FAB) m/z 709 (M+Na) $^+$

EXAMPLE 433

IA-1-(3-(Benzyl propionate)) (7an)

To a solution of IA-1-(3-propionic acid)-3,4,5-tris-t-butyl ester (180 mg, 0.33 mmol) in CH$_3$CN (8 mL) was added DBU (0.39 mL, 3.32 mmol) and benzyl bromide (0.45 mL, 3.32 mL). The reaction was allowed to stir overnight whereupon it was diluted with ether, washed with sat. NaHCO$_3$, brine, dried (Na$_2$SO$_4$) concentrated and chromatographed to yield IA-1-(3-(benzyl propionate) )-3,4,5-tris-t-butyl ester, $^1$H NMR (400 MHz, CDCl$_3$) d 7.32–7.23 (m, 5H), 6.85 (dd, J=15.7, 8.1 Hz, 1H), 6.39 (d, J=1.5 Hz, 1H), 5.72 (dd, J=15.8, 1.1 Hz, 1H), 5.09 (dd, J=5.4, 2.5 Hz, 2H), 5.02 (s, 1H), 4.19 (d, J=1.5 Hz, 1H), 3.97 (s, 1H), 3.21 (s, 3H), 2.92–2.81 (m, 2H), 2.41–2.35 (m, 3H), 2.17–2.12 (m, 2H), 1.65 (s, 9H), 1.43 (s, 9H), 1.34 (s, 9H), 1.25 (s, 3H), 1.23 (s, 3H), 1.21–1.07 (m, 3H), 0.96 (d, J=6.6 Hz, 3H), 0.89–0.78 (m, 7H). The tert-butyl esters were deprotected using the standard TFA protocol to give the title compound, $^1$H NMR (400 MHz, CD$_3$OD) d 7.32–7.23 (m, 5H), 6.85 (dd, J=15.7, 8.1 Hz, 1H), 6.39 (d, J=1.5 Hz, 1H), 5.72 (dd, J=15.8, 1.1 Hz, 1H), 5.09 (dd, J=15.4, 2.5 Hz, 2H ), 5.02 (s, 1H), 4.19 (d, J=1.5 Hz, 1H), 3.97 (s, 1H), 3.21 (s, 3H), 2.92–2.81 (m, 2H), 2.41–2.35 (m, 3H), 1.65 (s, 9H), 1.43 (s, 9H), 1.34 (s, 9H), 1.25 (s, 3H), 1.23 (s, 3H), 1.21–1.07 (m, 3H), 0.96 (d, J=6.6 Hz, 3H), 0.89–0.78 (m, 7H), 2.17–2.12 (m, 2H). MS (–)FAB 607.6 (M–1).

EXAMPLE 434

IA-1-(3-(Methyl propionate)) (7ao)
$^1$H NMR (400 MHz, CD$_3$OD) d 6.82 (dd, J=15.7, 8.5 Hz, 1H), 6.30 (d, J=1.8 Hz, 1H), 5.78 (d, J=14.7 Hz, 1H), 5.23 (s, 1H), 4.08 (d, J=1.9 Hz, 1H), 3.68 (s, 3H), 2.70 (m, 2H), 2.45 (m, 1H), 2.30–2.13 (m, 2H), 1.40–1.26 (m, 3H), 1.13 (m, 2H), 1.03 (d, J=6.7 Hz, 3H), 0.87 (m, 7H). MS 9–) FAB 531.5 (M–1).

EXAMPLE 435

IA-1-(3-propionic acid)-7-MME-tris-t-butyl ester

To a 0° C. solution of the IA-1-(3-(benzyl propionate))-tris-t-butyl ester (100 mg, 0.16 mmol) in CH$_2$Cl$_2$ (5.0 mL) was added pyridine p-toluene sulfonate (p-PTS; ca. 3.0 mg) and 2-methoxypropene (0.05 mL, 0.47 mmol). The reaction was stirred 45 mins whereupon it was diluted with CH$_2$Cl$_2$ and washed with sat. NaHCO$_3$, brine, dried and concentrated. The crude ester (ca. 3.0 mg) was then dissolved in CH$_3$OH (2 mL) and dihydrotoluene (0.2 mL) was added followed by 10% Pd/C (ca. 30 mg). The reaction was allowed to stir with occasional gentle heating until TLC analysis indicated that the reaction was complete. The reaction was then filtered through celite with $CH_2Cl_2$ and concentrated to yield the acid as an off white powder. $^1H$ NMR (400 MHz, $CD_3OD$) d 6.89 (dd, J=15.7, 8.4 Hz, 1H), 6.47 (br s, 1H), 5.81 (d, J= 15.8 Hz, 1H), 5.09 (s, 1H), 4.23 (s, 1H), 3.24 (s, 3H), 2.74–2.61 (m, 3H), 2.48–2.44 (m, 2H), 2.87–2.06 (m, 2H), 1.65 (s, 9H), 1.63–1.59 (m, 3H), 1.47 (s, 9H), 1.38 (s, 9H), 1.27 (s, 3H), 1.17–1.11 (m, 3H), 1.02 (d, J=6.7 Hz, 3H), 0.94–0.85 (m, 7H).

EXAMPLE 436

IA-6-hydroxy-1-(3-propanol)

To a 0° C. solution of the alcohol, Example 293 (50 mg, 0.07 mmol) in $CH_3OH$ (1 mL) was added NaOAc (121 mg, 1.48 mmol) followed by hydroxylamine hydrochloride (46.5 mg, 0.67 mmol). The reaction was allowed to warm to room temperature and stirred for 48 hours whereupon it was filtered with $CH_2Cl_2$ and the filtrate was washed with water, brine, dried ($Na_2SO_4$), concentrated and chromatographed (1:1 hexanes:EtOAc) to yield the tetraol. The tetraol was deprotected in the usual fashion to yield the triacid as an off white solid after lyophilization. $^1H$ NMR ($CD_3OD$, 400 MHz) d 5.13 (s, 1H), 5.10 (d, J=2.1 Hz, 1H), 4.51 (t, J=5.5 Hz, 1H), 4.05 (d, J=2.1 Hz, 1H), 2.31–1.96 (m, 5H).

EXAMPLE 437

I-3-Decylcarboxamide-6-Carbamate

IA-6-imidazolylcarbonyl-7-MME-3-benzyl-4,5-di-t-butyl ester (89.2 mg; Example 78) decyclamine (0.8 mL) was treated with DBU (14.71 mL) at room temperature under N2. After 7 days, the product was treated with 0.2 mL of $Ac_2O$ in 0.6 mL of pyridine for 3 h. Upon evaporation and preparative tlc, IA-3-decylcarboxamide- 7-MME-6-decylcarbamate was isolated. After the usual de-t-butylation with TFA (300 uL) in $CH_2Cl_2$ (1.5 mL), yielded IA-3-decylcarboamido-6-decylcarbamate HPLC:$R_t$22.68 mins, 1H NMR (400MHz, $CD_3OD$) characteristic resonances: d 7.38 (t, 1H, 7.3–7.13 (m, 5H), 6.16 (br s, 1H), 4.07 (s, 1H), 2.1 (s, 3H), 1.28 and 1.26 (each s, total 30H), 0.94–0.8 (m, 9H). MS FAB m/z 8.61 (m+)

General Procedures for preparation of C6/C3Hybrids.

A mixture of C-6 ester (carbamate, carbonate or ether; 100 mg), isopentanol (0.65 mL), and acetyl chloride (32 uL) are stirred at room temperature overnight. The mixture is partitioned between dichloromethane and aqueous sodium bicarbonate. The organic layer is dried and concentrated in vacuo. The residue is co-distilled twice with toluene and purified by reversed-phase HPLC. The product is dissolved in benzene and the solution is lyophilized to give a white fluffy material.

EXAMPLE 438

IA-6-(4-Methoxybutyl) Ester-3-Isopentyl Ester (40aa)

This compound was prepared as usual and purified by reversed-phase HPLC: NMR ($CD_3OD$) d 0.86 (d, J=6.5 Hz CH$CH_3$), 0.92 [2 d, J=6.5 Hz, CH($CH_3$)$_2$], 2.10 (s, OAc), 3.29 (s, O$CH_3$), 3.39 (t, $CH_3$O$CH_2$), 4.04 (s, H-7), 4.19 (t, $CO_2CH_2$), 4.98–5.01 (=$CH_2$), 5.08 (d, C$H$OAc), 5.29 (s, H-3), 6.28 (s, H-6,), 7.14–7.31 (m, ArH); (Neg. FAB) m/z 707 (M–H)$^+$.

EXAMPLE 439

IA-6-Isovaleroyl Ester-3-Isopentyl Ester (40ab)

NMR (400 MHz, $CD_3OD$) d 0.89 (m, CH$CH_3$ 16H), 1.52 (m, ($CH_3$)$_2$CHC$H_2$$CH_2$), 1.70 (m, ($CH_3$)$_2$C$H$$CH_2$), 2.09 (s, C$H_3$CO), 4.01 (d, J=2 Hz, H$_7$), 4.19 (m,($CH_3$)$_2$CH$CH_2$CH $H_2$O), 4.96, 5.02 (2s, =$CH_2$), 5.07 (d, J=5, C$H$OAc), 5.27 (s, C-3H), 6.28 (d, J=2 Hz, H$_6$), 7.14–7.26(m, ArH): MS (FAB-neg), m/e 691 [M–H].

EXAMPLE 440

IA-6-Lauroyl Ester-3-Isopentyl Ester (40ac)

NMR (400 MHz, $CD_3OD$) d 0.89 (m, CH$CH_3$ 16H), 1.26 (s, $CH_2$14H), 1.52 (m, ($CH_3$)$_2$CHC$H_2$$CH_2$), 1.70 (m, ($CH_3$)$_2$CHC$H_2$), 2.11 (s, C$H_3$CO), 4.01 (d, J=2 Hz, H7), 4.19 (m,($CH_3$)$_2$CHCH$_2$C$H_2$O ), 4.96, 5.02 (2s, =$CH_2$), 5.07 (s, J=5 Hz, C$H$OAc), 5.27 (s, C-3H), 6.28 (d, J=2 Hz, H6) 7.14–7.26(m, ArH): MS (FAB-neg), m/e 789 [M–H].

EXAMPLE 441

IA-6-Phenylbutyryl Ester-3-Isopentyl Ester (40ad)

NMR (200 MHz, $CD_3OD$) d 0.88 (m, CHC$H_3$), 2.08 (s, C$H_3$CO), 4.05 (br s, H7), 4.19 (t,($CH_3$)$_2$CHCH$_2$C$H_2$O), 4.96, 5.2 (2s, =$C_2$), 5.09 (d, J=5 Hz C$H$OAc), 5.30 (s, C-3H), 6.32 (br s, H6), 7.10–7.30(m, ArH): MS (FAB-neg), m/e 753 [M–H].

EXAMPLE 442

IA-6-(11-Phenoxy)undecanoyl Ester-3-Isopentyl (40ae) Ester

This compound was prepared as usual and purified by reversed-phase HPLC: NMR ($CD_3OD$) d 0.85 (d, J=6.5 Hz, CHC$H_3$), 0.91 [2 d, J=6.5 Hz, CH(C$H_3$) 2], 2.10 (s, OAc), 3.94 (t, J=6.5 Hz, PhOC$H_2$), 4.01 (br s, H-7), 4.18 (t, J=6.5 Hz, $CO_2CH_2$), 4.98 & 5.02 (=$CH_2$), 5.08 (d, J=4.5 Hz, C$H$OAc), 5.29 (s, H-3), 6.30 (br s, H-6), 6.84–6.93 (m, PhO), 7.14–7.32 (m, ArH); MS (Neg. FAB) m/z 867 (M+H)$^+$.

EXAMPLE 443

IA-6-Isopropylaminocarbonyl Carbamate-3-Isopentyl Ester (40af)

NMR (200 MHz, $CD_3OD$) d 0.89 (m, CHC$H_3$ 9H), 1.1 (d, (C$H_3$)$_2$$CH_2$NH), 1.52 (m, ($CH_3$)$_2$CHC$H_2$$CH_2$). 1.70 (m, (C$H_3$)$_2$C$H$$CH_2$), 2.09 (s, C$H_3$CO), 3.68 (m, ($CH_3$)$_2$CHN$H$), 4.04 (d, J=2 Hz, H7), 4.16 (m,($CH_3$)$_2$CHCH$_2$C$H_2$O), 4.96, 5.02 (2s, =C$H_2$), 5.07 (d, J=5 Hz, C$H$OAc), 5.27 (s, C-3H), 6.20 (d, J=2 Hz, H$_6$), 7.14–7.26(m, ArH): MS (FAB-neg), m/e 692 [M–H].

EXAMPLE 444

IA-6-Decylaminocarbonyl Carbamate-3-Isopentyl Ester (40aa)

NMR (400 MHz, $CD_3OD$) d 0.89 (m, CHC$H_3$ 12H), 1.26 (s, $CH_2$ 14H), 1.70 (m, ($CH_3$)$_2$C$H$$CH_2$), 2.08 (s, C$H_3$ CO), 3.08 (m, C$H_2$NH), 4.06 (s, H6), 4.16 (m,($CH_3$)$_2$CHCH$_2$C $H_2$O), 4.96, 5.02 (2s, =$CH_2$), 5.07 (d, J=5 Hz, C$H$OAc), 5.27 (s, C-3H), 6.22 (br H$_6$), 7.10–7.30(m, ArH): MS (FAB), m/e 836 [M=+2 Na]$^+$.

EXAMPLE 445

IA-6-(8-Phenoxy) octylaminocarbonyl Carbamate-3-Isopentyl Ester (40ah)

This compound was prepared as described as above HPLC in 52% yield: NMR ($CD_3OD$) d 0.85 (d, J=6.5 Hz, CHC$H_3$), 0.90 & 0.91 [2d, J=6.5 Hz, CH(C$H_3$)$_2$], 2.09 (s, OAc), 3.08 (m, C$H_2$NHCO), 3.94 (t, J=6.5 Hz, PhOC$H_2$), 4.06 (br s, H-7), 4.18 (t, J=6.5 Hz, $CO_2CH_2$), 4.99–5.02 (=$CH_2$), 5.08 (d, J=4.5 Hz, C$H$OAc), 5.30 (s, H-3), 6.19 (br s, H-6), 6.85–6.91 (m, PhO), 7.14–7.31 (m, ArH); MS (Neg. FAB) m/z 854 (M–H)$^+$.

EXAMPLE 446

IA-6-Adamantanylmethylaminocarbonyl Carbamate-3-Isopentyl Ester (40ai)

NMR (200 MHz, CD$_3$OD) d 0.89 (m, CHC$\underline{H}_3$ 9H), 1.48 (s br, adamantylC$\underline{H}$C$\underline{H}_2$CH), 1.70 (m, (CH$_3$)$_2$C$\underline{H}$CH$_2$), 2.08 (s, C$\underline{H}_3$CO), 4.06 (s br, H7), 4.16 (m,(CH$_3$)$_2$CHCH$_2$C$\underline{H}_2$O), 4.96, 5.02 (2s, =CH$_2$), 5.07 (d, J=5 Hz, C$\underline{H}$OAc), 5.27 (s, H3), 6.28 (s br, H6), 6.97 (t, NH), 7.14–7.26(m, ArH): MS (FAB-neg), m/e 798 [M–H].

EXAMPLE 447

IA-6-Decyloxycarbonyl Carbonate-3-Isopentyl Ester (40ai)

This compound was prepared as usual and purified by reversed-phase HPLC in 54% yield: NMR (CD$_3$OD) d 0.85–0.94 (m, 4 CH$_3$), 2.10 (s, OAc), 4.09 (br s, H-7), 4.12–4.22 (m, 2 CH$_2$OCO), 4.98–5.02 (=CH$_2$), 5.09 (d, C$\underline{H}$OAc), 5.25 (s, H-3), 6.20 (br s,, H-6), 7.14–7.30 (m, ArH); MS (Neg. FAB) m/z 791 (M+H)$^+$.

EXAMPLE 448

IB-3-Isopentyl Ester (45aa)

A mixture of acetyl chloride (0.2 mL) and 3-methyl-1-butanol (5 mL) was stirred for 1 hr at RT to which was added IB (500 mg). The resulting mixture was stirred for 19 h at ambient temperature. The solution was concentrated in vacuo. Half of the crude product was purified by preparative HPLC to the title compound as a white solid. $^1$H NMR (400 MHz, CD$_3$OD) d 7.35 (d, 2H), 7.26 (t, 2H), 7.15 (t, 1H, 6.45 (d, 1H, 6.20–6.31 (s+m, 2H), 5.32–5.46 (m, 4H), 5.27 (s, 1H), 4.10–4.20 (m, 2H), 4.04 (s, 1H), 2.24–2.38 (m, 3H), 2.04–2.15 (m, 1H), 1.82–2.04 (m, 9H), 1.64–1.82 (m, 3H), 1.48–1.64 (m, 7H), 1.26–1.48 (m, 8H), 0.98 (d, 6H), 0.92 (d, 3H), 0.91 (d, 3H). MS, EI m/e 800.4 (m+).

EXAMPLE 449

IB-3-Isopentyl-4-pivaloyloxymethyl Ester (45ab)

A solution of IB-3-isopentyl ester (0.102 g, 0.127 mmol) in 5 mL of benzene was added DBU (0 02 mL, 0.134 mmol) and chloromethylpivalate (0.028 mL, 0.191 mmol) The mixture was heated for 64 h at 50° C. The solution was concentrated in vacuo and the product was purified by preparative HPLC to give the title compound. $^1$H NMR (400 MHz, CD$_3$OD) d 7.36 (d, 2H), 7.28 (t, 2H), 7.18 (t, 1H, 6.44 (d, 1H, 6.24–6.35 (dt, 1H, 6.14 (s, 1H), 5.82–5.92 (q, 2H), 5.34–5.50 (m, 4H), 5.23 (s, 1H), 4.19 (t, 2H), 4.06 (s, 1H), 2.22–2.41 (m, 3H), 2.07–2.18 (m, 1H), 1.84–2.07 (m, 9H), 1.50–1.84 (m, 10H), 1.28–1.50 (m, 8H), 1.25 (s, 9H), 0.99 (d, 6H), 0.94 (d, 6H). MS, EI m/e 915.6 (m+).

EXAMPLE 450

IC-3-Isopentyl Ester (55aa)

A mixture of 3-methyl-1-butanol (2.5 mL) and acetyl chloride (0.076 mL) was stirred for 1 h at ambient temperature to which was added IC (190 mg). The resulting mixture was stirred for 15 h at ambient temperature. The solution was concentrated in vacuo and the product was purified by preparative HPLC to yield the title compound. $^1$H NMR (200 MHz, CD$_3$OD) d 7.04–7.30 (m, 10H), 6.23 (d, 1H, 5.28–5.42 (m, 2H), 5.26 (s, 1H, 4.18 (t, 2H), 4.01 (d, 1H, 2.73 (dd, 1H), 2.55 (t, 2H), 2.18–2.51 (m, 5H), 1.80–2.16 (m+s, 7H), 1.45–1.79 (m, 9H), 1.19–1.39 (m, 3H), 0.78–1.06 (m, 12H). MS, EI m/e 824.3 (m$^+$)

EXAMPLE 451

IC-3-Isopentyl-4-pivaloyloxymethyl Ester (55ab)

A solution of IC-3-isopentyl ester (48 mg, 0.058 mmol) in 4 mL of benzene was added DBU (0.0092 mL, 0.061 mmol) and chloromethylpivalate (0.0125 mL, 0.087 mmol). The mixture was heated at 50° C. for 72 hrs. The solution was concentrated in vacuo and the product was purified by preparative HPLC to afford the title compound. $^1$H NMR (200 MHz, CD$_3$OD) d 7.06–7.34 (m, 10H), 6.07 (s, 1H), 5.83 (q, 2H), 5.30–5.44 (m, 2H), 5.18 (s, 1H), 4.17 (t, 2H), 4.00 (s, 1H), 2.74 (dd, 1H), 2.56 (t, 2H), 2.18–2.42 (m, 5H), 1.80–2.16 (s+m, 7H), 1.44–1.80 (m, 9H), 1.16–1.40 (s+m, 12H), 0.82–1.10 (m, 12H). MS, EI m/e 938.7 (m$^+$).

EXAMPLE 452

Preparation of (1S,3S,4S,5R,6R,7R)-1-[(4-hydroxy-3,5-dimethyl-8-phenyl)oct-7-enyl]-4,6,7-trihydroxy-6-0-(tetradeca-6,12-dienoyl)-7-(1-methoxy-1-methyl)-ethyl- 2,8-dioxabicyclo[3.2.1]octane 3,4,5-tris-t-butyl ester (2H)

A solution of the IB-tris-t-butyl ester (1B, Example 311) (400 mg) and 2-methoxypropene (400 mg) in CH$_2$Cl$_2$ (5 mL) was cooled to 0° C. and pyridinium p-toluenesulfonate (10 mg) was added. After stirring for 2 h at 0° C., the reaction mixture was diluted CH$_2$Cl$_2$ and washed with aq. NaHCO$_3$, dried, and evaporated to dryness. NMR (400 MHz, CDCl$_3$) d 0.95 (m, 6H), 1.25, 1.33 [2 s,(CH$_3$)$_2$C], 1.33, 1.40, 1.63 (3 s, tBu), 3.19 (s, CH$_3$O), 3.32 (m, OH), 4.03 (s, C$_4$—OH), 4.16 (d, J=2.0 Hz, H-7), 4.96 (s, H-3), 5.33–5.39 (m, 4H), 6.17 (d,t, J=7.6,16 Hz, 1H), 6.32 (d, J=2 Hz, H-6), 6.37 (d, J=16 Hz, 1H), 7.13–7.33 (m, 5H).

EXAMPLE 453

Preparation of (1S,3S,4S,5R,6R,7R)-1-{[4-(5.6-dihydro-(2H)-4-pyranyloxy)-3,5-dimethyl-8-phenyl]oct-7-enyl}-4, 6,7-trihydroxy-6-O-(tetradeca-6,12-dienoyl)-7-(1-methoxy-1-methyl)ethyl-2,8-dioxabicyclo[3.2.1]octane 3,4,5-tris-t-butyl ester (2B') and (1S,3S,4S,5R,6R, -7R)-1-}[4-(5,6-dihydro-(2H)-4-pyranyloxy)-3,5-di-methyl- 8-phenyl]oct-7-enyl}-4,6,7-trihydroxy-7-(1-methoxy- 1-methyl)ethyl-2,8-dioxabicyclo-[3.2.1]octane 3,4,5-tris-t-butyl ester (3B')

Step A

Preparation of (1S,3S,4S,5R,6R,7R)-1-{[4-(5.6-dihydro-(2H)-4-pyranyloxy)-3,5-dimethyl-8-phenyl] oct-7-enyl}-4,6, 7-trihydroxy-6-O-(tetradeca- 6,12-dienoyl)-7-(1-methoxy-1-methyl)ethyl- 2,8-dioxabicyclo[3.2.1]octane 3,4,5-tris-butyl ester (2B')

Pyridinium p-toluenesulfonate (4.3 mg, 5 mol %) was added to a solution of (1S,3S,4S,5R,6R,7R)- 1-[(4-hydroxy-3,5-dimethyl-8-phenyl)oct-7-enyl]-4,6,7-trihydroxy- 6-O-(tetradeca-6,12-dienoyl)-7-(1-methoxy-1-methyl)ethyl-2,8-dioxabicyclo[3.2.1]octane-3,4,5-tris-t-butyl ester (2B; 337 mg, 0.35 mmol) and 5,6-dihydro-4-methoxy-2H-pyran (388 uL, 10 eq) in dry dichloromethane (3 mL), and the mixture was stirred at room temperature overnight. The reaction mixture was diluted with dichloromethane and washed with aq. NaHCO$_3$ and brine, dried, and evaporated to dryness. The crude product was purified by preparative TLC (hexanes-ethyl acetate, 4:1; v/v) to give the title compound, which was used directly in the next experiment without further purification.

Step B

Preparation of (1S,3S,4S,5R,6R,7R)-1-}[4-(5.6-dihydro-(2H)-4-pyranyloxy)-3,5-dimethyl-8-phenyl] oct-7-enyl}-4,6, 7-trihydroxy-7-(1-methoxy- 1-methyl)ethyl-2,8-dioxabicyclo-[3.2.1] octane 3.4.5-tris-t-butyl ester (3B')

A solution of (1S,3S,4S,5R,6R,7R)-1-{[4-(5.6-dihydro-(2H)-4-pyranyloxy)-3,5-dimethyl-8-phenyl]oct-7-enyl}-4, 6,7-trihydroxy-6-O-(tetradeca-6,12-dienoyl)-7-(1-methoxy- 1-methyl)ethyl-2,8-dioxabi-cyclo-[3.2.1]-octane 3,4,5-tris-t-butyl ester (2B', from the previous experiment) in methanol (1.5 mL), THF (1.5 mL) and 5N NaOH (1.0 mL) was heated with stirring at 65° C. overnight, and neutralized with glacial acetic acid. The solution was concentrated to a small volume and partitioned between dichloromethane and brine. The organic layer was separated, dried, and evaporated to a residue which was treated with O-t-butyldiisopropylisourea (360 mg) in toluene (2 mL) at 65° C. overnight. The crude product was purified by preparative TLC (hexanes-ethyl acetate, 7:3; v/v) to give the title compound.

1H NMR (CDCl$_3$, 400 MHz): d 0.91–0.96 (m, CH$_3$-3'& CH$_3$-5'), 1.40 & 1.47 [2 s, (CH$_3$)$_2$CHOCH$_3$], 1.46, 1.47 1.59 (3 S, t-Bu), 2.21 (m, H-5"), 2.36 (d, J=5.5 Hz, C$_6$—OH), 3.28 [s, (CH$_3$)$_2$CHOCH$_3$], 3.83 (t, J=5.7 Hz, H-6"), 3.85–3.88 (m, H-4'), 3.94 (s, C$_4$—OH), 4.08 (d, J=1.8 Hz, H-7), 4.18 (d, J=2.1 Hz, H-2"), 4.62 (br s, H-3"), 4.86 (s, H-3), 4.96 (2 d, J=1.7 5.5 Hz, H-6), 6.13–6.20 (m, H-7'), 6.36 (d, J=15.8, H-8'), 7.17–7.34 (m, ArH).

EXAMPLE 454

Preparation of (1S,3S,4S,5R,6R,7R)-1-{[4-(5.6-dihydro-(2H)-4-pyranyloxy)-3,5-dimethyl-8-phenyl]-oct- 7-enyl}-4,6,7-trihydroxy-6-isopropylaminocarbonyl- 7-(1-methoxy-1-methyl)ethyl-2,8-dioxabicyclo[3.2.1]octane 3,4,5-tris-t-butyl ester (4B')

A solution of (1S,3S,4S,5R,6R,7R)-1-{[4-(5.6-dihydro-(2H)-4-pyranyloxy)-3,5-dimethyl-8-phenyl]oct-7-enyl}-4,6,7-trihydroxy-7-(1-methoxy-1-methyl)ethyl- 2,8-dioxabicyclo[3.2.1]octane 3,4,5-tris-t-butyl ester (3B', 46 mg) and carbonylimidazole (20 mg) in dry toluene (1.0 mL) was stirred at room temperature for 6 h. Isopropylamine 50 uL, 10 eq) was added, and the reaction mixture was again stirred for 3 d and concentrated to dryness. The crude product was purified by preparative TLC (hexanes-ethyl acetate, 7:3; v/v) to give the title compound. $^1$H NMR (CDCl$_3$, 400 MHz): d 0.92 & 0.96 (2 d, J=6.7 & 6.4 Hz, CH$_3$-3'& CH$_3$-5'), 1.07 & 1.08 [2 d, J=6.5 & 6.5 Hz, (CH$_3$)$_2$CHNH], 1.34 & 1.38 [2 s, (CH$_3$)$_2$CHOCH$_3$], 1.43, 1.45 & 1.68 (3 s, t-Bu), 2.27–2.31 (m, H-5"), 3.25 [s, (CH$_3$)2CHOCH$_3$], 3.73–3.79 [m, (CH$_3$)$_2$CHNH & H-4'], 3.86–3.90 (m, H-6"), 4.01 (s, C$_4$—OH), 4.17–4.19 (m, H-2"), 4.22 (d, J=1.4 Hz, H-7), 4.67 (br s, H-3"), 5.04 (s, H-3), 5.22 (d, J=8.0 Hz, NH), 6.14–6.19 (m, H-7'), 6.20 (d, J=1.3 Hz, H-6), 6.39 (d, J=25.8, H-8'), 7.18–7.36 (m, ArH).

EXAMPLE 455

Preparation of (1S,3S,4S,5R,6R,7R)-1-[(4-hydroxy-3,5-dimethyl-8-phenyl)oct-7-enyl]-4,6,7-trihydroxy-6-O-(isopropylaminocarbonyl)-2,8-dioxabicyclo-[3.2.1]octane 3,4,5-tricarboxylic acid (5B)

A solution of (1S,3S,4S,5R,6R,7R)-1-{[4-(5.6-dihydro-(2H)-4-pyranyloxy)-3,5-dimethyl-8-phenyl]]-oct- 7-enyl}-4,6,7-trihydroxy-6-isopropylaminocarbonyl- 7-(1-methoxy-1-methyl)ethyl-2,8-dioxabicyclo[3.2.1]octane 3,4,5-tris-t-butyl ester (4B', 25 mg) in dry dichloromethane (0.75 mL) and trifluoroacetic acid (0.25 mL) was kept at room temperature overnight and evaporated to dryness. Traces of trifluoroacetic acid were co-distilled with toluene. The crude product was purified by reversed-phase HPLC to give the title compound. $^1$H NMR (CD$_3$OD, 400 MHz): d 0.97 & 0.98 (2 d, J=6.7 & 6.5 Hz, CH$_3$-3'& CH$_3$-5'), 1.10 & 1.11 [2 d, J=6.0 & 6.2 Hz, (CH$_3$)$_2$CHNH], 3.69–3.72 (m, (CH$_3$)$_2$CHNH), 4.08 (d, J=1.6 Hz, H-7), 5.24 (s, H-3), 6.17 (br s, H-6), 6.22–6.29 (m, H-7'), 6.4.1 (d, J=15.8, H-8'), 7.14–7.37 (m, ArH).

EXAMPLE 456

IC-3,4,5-Tris-t-butyl Ester (1C)

A 10 mL pear shaped flask was equipped with a triangular stirring vane, rubber septum and nitrogen inlet. The flask was charged with 35 mg of IC followed by 1.50 mL of dry methylene chloride. The mixture was stirred at ambient temperature until dissolution was complete. The reaction was treated with 105 mg of freshly distilled O-t-butyl-N,N'-diisopropyl isourea. After two hours a white solid began to precipitate. After 10hr, the reaction mixture was poured into 40 mL of hexane. The turbid solution was filtered through Celite. The clear filtrate was stripped and pumped to an oil. The crude product was chromatographed on silica gel (10:1 methylene chloride/ethyl acetate). The combined fractions were evaporated to give IC-3,4,5-tris-t-butyl ester, 1C, as a pale brown residue. NMR (400 MHz, CDCl$_3$) d 7.23 (m, 4H), 7.17 (t, J=7.4 Hz, 4H), 7.09 (d, J=7.2 Hz, 2H), 5.89 (t, J=1.6 Hz, 1H), 5.31 (m, 2H), 4.97 (s, 1H), 4.85 (m, 1H), 4.02 (s, 1H), 3.94 (d, J=2.2 Hz, 1H), 2.73 (dd, J=13.7, 5.9 Hz, 1H), 2.54 (t, J=7.4 Hz, 1H), 2.36 (t, J=7.2 Hz, 1H), 2.28 (m, 2H), 2.02 (s, 3H), 1.91 (bt, J=7.7 Hz, 1H), 1.53 (s, 9H), 1.44 (s, 9H), 1.41 (s, 9H), 1.28 (m, 1.21 to 1.32, 8H), 0.92 (d, J=6.7 Hz, 3H), 0.81 (d, J=6.9 Hz, 3H).

EXAMPLE 457

IC$_7$-MME-3,4,5-tris-butyl Ester (2C)

A 15 mL pear shaped flask was equipped with a triangular stirring vane, a rubber septum and a nitrogen inlet. The flask was charged with 39 mg of IC-3,4,5-tris-t-butyl ester, 1C, followed by 1.5 mL of dry methylene chloride. The mixture was stirred until dissolution was complete. The solution was cooled to 5° C. and charged with 63 uL of 2-methoxypropene. The reaction was next charged with 278 uL of dry methylene chloride containing 547 ug of pyridinium p-toluenesulfonate (PPTS). The reaction was stirred at 5° C. for 21 hours until HPLC analysis indicated no starting material remained and one major product had formed. At the end of this time the reaction mixture was poured into a separatory funnel containing 40 mL of methylene chloride. The organic was washed once with 10 mL of saturated aqueous sodium bicarbonate. The organic was drawn off and dried over sodium sulfate. After 10 minutes the organic was filtered and stripped to a residue which was pumped under high vacuum. The residue was chromatographed over silica gel (10:1 methylene chloride/ethyl acetate; 1% triethylamine) and the fractions analyzed by HPLC. The fractions containing the product were collected. Removal of solvents gave IC-7-MME-tris-t-butyl ester, 2C, as a pale yellow oil. NMR (400 MHz, CD$_2$Cl$_2$) d 7.22 (m, 4H), 7.13 (m, 6H), 6.32 (d, J=1.1 Hz, 1H), 5.32 (m, overlapping CD$_2$Cl$_2$, 2H), 4.96'(s, 1H), 4.83 (m, broad, 1H, 4.12 (d, J=1.0 Hz, 1H), 3.95 (s, 1H), 3.19 (s, 3H), 2.76 (dd, J=13.1, 4.8 Hz, 1H), 2.55 (t, J=7.0 Hz, 2H), 2.34 (dd, J=7.8, 2.0 Hz, 1H), 3.30 (t, J=7.1 Hz, 1H, 2.25 (m, 2H), 2.03 (s, 3H), 1.61 (s, 9H), 1.42 (s, 9H), 1.39 (s, 9H), 1.35 (s, 3H), 1.26 (s, 3H), 0.93 (d, J=6.5 Hz, 3H), 0.84 (d, J=6.6 Hz, 3H).

EXAMPLE 458

IC-6-(4,5-Dihydro-4,5-dihydroxy)-7-MME-tris-t-butyl Ester (2C')

A 15 mL pear shaped flask was equipped with a triangular stirring vane, rubber stopper and nitrogen inlet. The flask was charged with 40 mg of IC-7-MME-tris-t-butyl ester, 2C. This was followed by 1.25 mL of acetone. The mixture was stirred until dissolution was complete. The flask was then charged with 313 uL of water. A slight turbidity resulted which was resolved after 10 minutes of stirring at 25° C. The flask was charged with 16 uL of a 0.08M solution of osmium tetroxide in t-butanol followed by 562 uL of acetone containing 5.14 mg of N-methyl-morpholine-N-oxide. The homogenous reaction was stirred at 25° C. for 22 hr. At this time HPLC analysis indicated no starting material remained and one major product had formed. The reaction solution was transferred to a separatory funnel containing 50 mL of isopropyl acetate. The organic was washed once with 5 mL of saturated aqueous sodium bisulfite solution and once with 5 mL of saturated aqueous sodium bicarbonate solution. The organic was dried over sodium sulfate, filtered, stripped and pumped to a residue. The crude product was chromatographed over silica gel (20:1 methylene chloride/ethyl acetate, 1% triethylamine). The fractions were analyzed by HPLC and those containing the product were collected. Removal of solvents gave IC-6-(4,5-dihydroxy-4,5-dihydro)-7-MME-tris-t-butyl ester, 2C', as a clear oil. NMR analysis indicated the diol 4 had been isolated as a pair of diastereomers. NMR (400 MHz, $CD_2Cl_2$) d 7.24 (t, J=7.1 Hz, 4H), 7.15 (m, 6H), 6.32 (d, J=1.2 Hz, 1H), 4.95 (s, 1H), 4.86 (vbs, 1H), 4.16 (d, J=1.5 Hz, 0.5H), 4.13 (d, J=1.5 Hz, 0.5H), 3.54 (m, 3.51 to 3.58, 2H), 3.21 (s, 3H), 3.08 (dd, J=6.4, 3.6 Hz, 0.5H), 2.75 (dd, J=13.5, 5.0 Hz, 1H), 2.45 (m, 2.27 to 2.68, 7H), 2.04 (s, 1.5H), 2.03 (s, 1.5H), 1.61 (s, 9H), 1.42 (s, 9H), 1.40 (s, 9H), 0.89 (d, J=7.0 Hz, 1.5H), 0.86'(d, J=6.8 Hz, 1.5H), 0.85 (d, J=7.1 Hz, 3H).

EXAMPLE 459

IC-6-Hydroxy-7-MME-3,4,5-tris-t-butyl Ester (3C)

A 10 mL pear shaped flask was equipped with a triangular stirring vane, rubber septum and nitrogen inlet. The flask was charged with 27 mg of IC-6-(4,5-dihydroxy-4,5-dihydro)-7-MME-tris-t-butyl ester, 2C', followed by 1.0 mL of dry DMF. The mixture was stirred at ambient temperature until dissolution was complete. The flask was charged with 5 mg of solid potassium t-butoxide. The mixture was stirred at 25° C., and within one hour the reaction became homogenous and assumed a yellow color. Stirring was continued for 14 hours. At the end of this time HPLC analysis indicated the disappearance of starting material and the appearance of a two new products. The reaction was partitioned between 40 mL of isopropyl acetate and 5 mL of pH 7 buffer. The layers were separated and the organic washed three more times with 5 mL portions of pH 7 buffer. The organic was dried over sodium sulfate, filtered, stripped and pumped to a residue. The crude product was chromatographed over silica gel (20:1 methylene chloride/ethyl acetate, 1% triethylamine) with the fractions analyzed by HPLC. The fractions containing the product having the greater retention time were collected. Removal of solvents gave IC-6-hydroxy-7-MME-3,4,5-tris-t-butyl ester, 3C, as a semi-solid. NMR (400 MHz, $CD_2Cl_2$) d 7.24 (t, J=7.3 Hz, broad triplet, 2H), 7.13 (m, b triplet overlapping vb singlet, 3H), 5.56 (s, 1H), 4.90 (s, broad, 1H, 4.83 (m, broad, 1H), 4.78 (s, 1H), 3.99 (t, J=1.8 Hz, 1H), 3.82 (s, 1H), 3.20 (s, 3H), 2.73 (dd, J=13.3, 5.1 Hz, 1H), 2.30 (dd, J=13.3, 9.6 Hz, 1H), 2.01 (s, 3H), 1.54 (s, 9H), 1.44 (s, 9H), 1.41 (s, 9H), 1.39 (s, 3H), 1.37 (s, 3H), 0.82 (d, J=6.8 Hz, 3H).

EXAMPLE 460

IC-6-Isopropyl carbamate-7-MME-3,4,5-tris-t-butyl Ester (4C)

IC-6-hydroxy-7-MME-3,4,5-tris-t-butyl ester (3C, 22 mg) was dissolved in 1 mL of dry toluene. A small amount of insoluble material was removed by passing the mixture through a 0.45 um syringe tip filter attached to a 1 mL gas tight syringe. A 10 ml pear shaped flask was equipped with a triangular stirring vane, reflux condenser and nitrogen inlet. The flask was charged with the above filtrate followed by 11 mg of carbonyl di-imidazole. The solution was stirred at 25° C. for 5 hours during which time a small amount of precipitate was noted. At the end of this time LC analysis indicated the almost total conversion of 5 to a new compound. The flask was charged with 62 uL of isopropyl amine. The precipitate immediately dissolved. Stirring was continued for 14 hours at 25° C. HPLC analysis at this time indicated the appearance of a small amount of a second new compound (integration ratio of 2nd/1st-1:14.6). An additional 31 uL of isopropyl amine were added and the flask placed in a 38° C. bath. Stirring was continued for an additional 6 hours. HPLC analysis indicated a significant change in the proportion of the new compounds (integration of 2nd/1st=:1:7.2). An additional 31 uL of isopropyl amine were added and stirring continued for 14 hours at 38° C. HPLC analysis again indicated a significant change in proportion (2nd/1st-1.2:1). Stirring was continued at 38° C. for another 14 hours. The ratio of new compounds was now 4.2:1HPLC also indicated that 5% to 10% of the original amount of the first new compound was still present. The reaction was continued for another 14 hours, at which time none of the first new compound remained. The reaction was poured into 40 mL of isopropyl acetate and washed once with 5 mL of pH 7 buffer. The organic was dried over sodium sulfate, filtered, stripped and pumped to a residue. The crude product was chromatographed over silica gel (3:1 methylene chloride/hexane, 1% triethylamine) with the fractions analyzed by HPLC. The fractions containing the new product were collected and all solvents removed to give an oil. NMR analysis indicted this oil to be a 65:35 mixture of 4C and 3C. The mixture was rechromatographed over silica gel with a different solvent system (4:1 hexane/ethyl acetate, 1% triethylamine). The fractions were collected to give IC-6-isopropyl carbamate-7-MME-3,4,5-tris-t-butyl ester, 4C, as an oil. NMR (400 MHz, $CD_2Cl_2$) d 7.26 (t, J=7.3 Hz, 2H), 7.17 (m, 3H), 6.18 (d, J=1.3 Hz, 1H), 4.98 (s, 1H, 4.85 (dt, J=3.6, 4.5 Hz, broad, 1H), 4.69 (d, J=7.8 Hz, broad, 1H), 4.13 (s, broad, 1H, 3.93 (s, 1H, 3.71 (oct, J=7.3 Hz, 1H), 3.22 (s, 3H), 2.74 (dd, J=13.4, 5.0 Hz, 1H), 2.32 (dd, J=13.5, 9.7 Hz, 1H), 2.04 (s, 3H), 1.61 (s, 9H), 1.41 (s, 9H), 1.39 (s, 9H), 1.36 (s, 3H), 1.31 (s, 3H), 1.26 (s, 3H), 1.10 (t, J=6.3 Hz, 6H), 0.84 (d, J=6.8 Hz, 3H).

EXAMPLE 461

IC-6-Isopropyl Carbamate (5C)

IC-6-isopropyl carbamate-7-MME-3,4,5-tris-t-butyl ester, 4C, was deprotected using the trifluoroacetic acid protocol to give after preparative HPLC to give the title compound as a glassy solid. NMR (400 MHz, $CD_3OD$) d 7.24 (t, J=7.5 Hz, 2H), 7.15 (m, 3H), 6.16 (d, J=1.2 Hz, 1H), 5.22 (s, 1H), 4.20 (quart, J=4.8 Hz, 1H), 4.05 (s, 1H, 3.70 (m, very broad, 2H), 3.44 (d, J=2.0 Hz, broad, 1H, 2.73 (dd, J=13.3, 5.3 Hz, 1H), 2.36 (dd, J=13.5, 8.9 Hz, 1H), 2.06 (s, 3H), 2.05 (m, 1H), 1.89 (m, 2H), 1.68 (m, 2H), 1.59 (m, 2H), 1.11 (t, J=6.0 Hz, 6H), 0.87 (d, J=6.8 Hz, 3H).

What is claimed is:

1. A compound of structural formula (I):

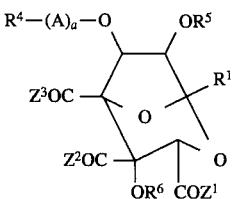

or a pharmaceutically acceptable salt thereof wherein
a is 0 or 1;

A is —C(O)—, —NR$^3$—C(O)—, or —OC(O)—;

R$^1$ is selected from the group consisting of:
(1) C$_{1-20}$alkyl,
(2) substituted C$_{1-20}$alkyl in which one or more of the carbons atoms is substituted with X$^3$;
(3) C$_{1-20}$alkyl wherein one or more of the carbons is replaced by —NR$^3$—, —O—, or —S(O)$_n$—;
(4) substituted C$_{1-20}$alkyl wherein one or more of the carbons is replaced by —NR$^3$—, —O— or —S(O)$_n$— and wherein one or more of the carbon atoms is substituted with X$^3$;
(5) aryl substituted with X and Y;
(6) heteroaryl substituted with X and Y;
(7) C$_{2-20}$alkenyl wherein alkenyl contains one or more double bonds;
(8) substituted C$_{2-20}$alkenyl wherein alkenyl contains one or more double bonds and wherein one or more of the carbons is substituted with X$^3$;
(9) C$_{2-20}$alkenyl wherein alkenyl contains one or more double bonds and one or more of the nonolefinic carbons is replaced by —NR$^3$—, —O— or —S(O)$_n$—;
(10) substituted C$_{2-20}$alkenyl wherein alkenyl contains one or more double bonds and one or more of the nonolefinic carbons is replaced by —NR$^3$—, —O— or —S(O)$_n$— and wherein one or more carbon atoms is substituted with X$^3$;
(11) C$_{3-10}$cycloalkyl; and
(12) substituted C$_{3-10}$cycloalkyl in which one or more of the substituents is selected from:
(a) halogen,
(b) hydroxy,
(c) R$^3$R$^3$N—,
(d) R$^2$O—,
(e) R$^2$O—,
(f) R$^3$—C(O)—O—,
(g) oxo,
(h) C$_{3-10}$cycloalkyl,
(i) aryl substituted with X and Y,
(j) heteroaryl substituted with X and Y,
(k) heterocycloalkyl,
(l) arylS(O)$_n$, wherein aryl is substituted with X and Y,
(m) R$^3$—C(O)—NR$^3$—,
(n) R$^3$R$^3$N—C(O)—,
(o) C$_{1-10}$alkylS(O)$_n$—,
(p) C$_{1-10}$alkyl,
(q) —CO$_2$H,
(r) -vinylidene,
(s) R$^3$—C(O)—,
(t) R$^2$O—C(O)—O—,
(u) R$^3$R$^3$N—C(O)—O—, and
(v) R$^2$O—C(O)—NR$^3$—;

each R$^2$ is independently selected from:
(1) C$_{1-10}$alkyl;
(2) aryl substituted with X and Y;
(3) arylC$_{1-4}$alkyl wherein aryl is substituted with X and Y;
(4) heteroaryl wherein heteroaryl is substituted with X and Y;
(5) heteroarylC$_{1-4}$alkyl- wherein heteroaryl is substituted with X and Y;
(6) heterocycloalkylC$_{1-4}$alkyl-;
(7) C$_{2-10}$alkenyl;
(8) arylC$_{2-10}$alkenyl wherein aryl is substituted with X and Y; and
(9) C$_{3-10}$alkynyl;

each R$^3$ is independently selected from:
(1) C$_{1-10}$alkyl;
(2) aryl substituted with X and Y;
(3) arylC$_{1-4}$alkyl wherein aryl is substituted with X and Y;
(4) heteroaryl wherein heteroaryl is substituted with X and Y;
(5) heteroarylC$_{1-4}$alkyl- wherein heteroaryl is substituted with X and Y;
(6) heterocycloalkylC$_{1-4}$alkyl-;
(7) C$_{2-10}$alkenyl;
(8) arylC$_{2-10}$alkenyl wherein aryl is substituted with X and Y;
(9) C$_{3-10}$alkynyl;
(10) hydrogen; and
(11) C$_{1-5}$alkyl substituted with X$^1$;

R$^4$ is selected from the group consisting of:
(1) C$_{1-20}$alkyl;
(2) substituted C$_{1-20}$alkyl in which one or more of the carbon atoms is substituted with X$^3$;
(3) C$_{1-20}$alkyl wherein one or more of the carbons is replaced by —NR$^3$—, —O—, or —S(O)$_n$—;
(4) substituted C$_{1-20}$alkyl wherein one or more of the carbons is replaced by —NR$^3$—, —O—, or —S(O)$_n$— and wherein one or more of the carbons is substituted with X$^3$;
(5) aryl substituted with X and Y;
(6) heteroaryl substituted with X and Y;
(7) C$_{2-20}$alkenyl wherein alkenyl contains one or more double bonds;
(8) substituted C$_{2-20}$alkenyl wherein alkenyl contains one or more double bonds and wherein one or more of the carbons is substituted with X$^3$;
(9) C$_{2-20}$alkenyl wherein alkenyl contains one or more double bonds and one or more of the nonolefinic carbons
is replaced by —NR$^3$—, —O— or —S(O)$_n$—;
(10) substituted C$_{2-20}$alkenyl wherein alkenyl contains one or more double bonds and one or more of the nonolefinic carbons is replaced by —NR$^3$—, —O— or —S(O)$_n$— and wherein one or more of the carbons is substituted with X$^3$;
(11) C$_{3-10}$cycloalkyl;
(12) substituted C$_{3-10}$cycloalkyl in which one or more of the carbon atoms is substituted with X$^3$; and
(13) hydrogen;

R$^5$ is selected from the group consisting of:
(1) hydrogen;
(2) C$_{1-10}$alkyl;
(3) aryl substituted with X and Y;
(4) arylC$_{1-4}$alkyl, wherein aryl is substituted with X and Y;
(5 R$^2$O—C(O)—;
(6) C$_{3-10}$cycloalkyl;
(7) R$^3$—C(O)—; and (8) R³R³N—C(O)—;

R⁶ and R⁶ᵃ are each independently selected from the group consisting of:
(1) $C_{1-20}$alkyl;
(2) substituted $C_{1-20}$alkyl in which one or more of the carbon atoms is substituted with $X^3$;
(3) $C_{1-20}$alkyl wherein one or more of the carbons is replaced by —NR³—, —O—, or —S(O)$_n$—;
(4) substituted $C_{1-20}$alkyl wherein one or more of the carbons is replaced by —NR³—, —O— or —S(O)$_n$— and wherein one or more carbon atoms is substituted with $X^3$;
(5) $C_{2-20}$alkenyl wherein alkenyl contains one or more double bonds:
(6) substituted $C_{2-20}$alkenyl wherein alkenyl contains one or more double bonds and wherein one or more of the carbons is substituted with $X^3$;
(7) $C_{2-20}$alkenyl wherein alkenyl contains one or more double bonds and one or more of the nonolefinic carbons is replaced by —NR³—, —O— or —S(O)$_n$—;
(8) substituted $C_{2-20}$alkenyl wherein alkenyl contains one or more double bonds and one or more of the nonolefinic carbons is replaced by —NR³—, —O— or —S(O)$_n$— and wherein one or more carbon atoms is substituted with $X^3$;
(9) $C_{2-20}$alkynyl wherein alkynyl contains one or more triple bonds;
(10) substituted $C_{2-20}$alkynyl wherein alkynyl contains one or more triple bonds and wherein one or more of the carbons is substituted with $X^3$;
(11) $C_{2-20}$alkynyl wherein alkynyl contains one or more triple bonds and one or more of the saturated carbons is replaced by —NR³—, —O— or —S(O)$_n$—;
(12) substituted $C_{2-20}$alkynyl wherein alkynyl contains one or more triple bonds and one or more of the saturated carbons is replaced by —NR³—, —O— or —S(O)$_n$— and wherein one or more carbon atoms is substituted with $X^3$;
(13) aryl substituted with X and Y;
(14) heteroaryl substituted with X and Y;
(15) $C_{3-5}$ cycloalkyl;
(16) substituted $C_{3-5}$ cycloalkyl in which one or more of the substituents is selected from:
(a) R³O—, and
(b) R³R³N—; and
(17) hydrogen;

aryl including X, Y substitution is:

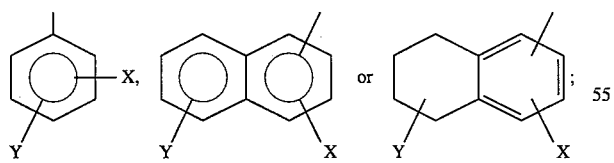

heteroaryl including X, Y substitution is selected from:

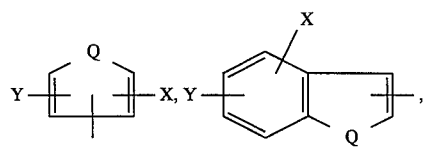

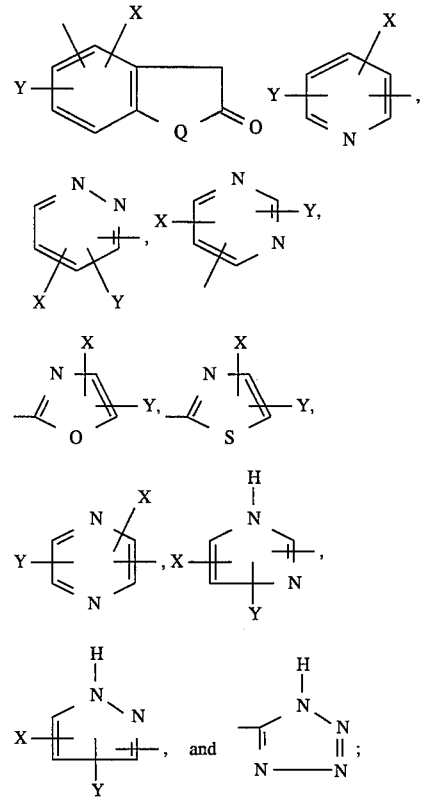

wherein
Q is —NR³, —O— or —S—;
heterocycloalkyl is selected from:

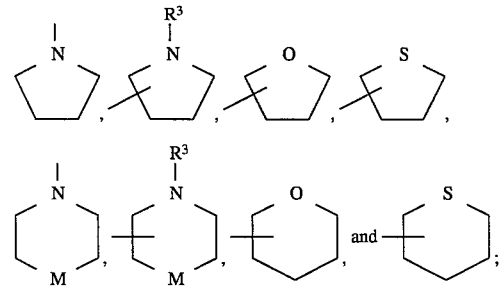

wherein:
M is —NR³, —O—, —S— or —CH₂—;
X and Y are each independently selected from:
(1) hydrogen;
(2) hydroxy;
(3) halogen;
(4) trifluoromethyl;
(5) $C_{1-10}$alkyl;
(6) aryl substituted with $X^1$ and $Y^1$;
(7) R²O—;
(8) arylcarbonyloxy—, wherein aryl is substituted with $X^1$ and $Y^1$;
(9) R³—C(O)—O—;
(10) —CO₂R²;
(11) —CO₂H;
(12) nitro; and
(13) —NR³R³;

$X^1$ and $Y^1$ are each independently selected from:
(1) hydrogen;

(2) hydroxy;
(3) halogen;
(4) trifluoromethyl;
(5) $C_{1-4}$alkyl;
(6) $R^2O$—;
(7) $R^3$—C(O)—O—;
(8) —$CO_2R^2$;
(9) —$CO_2H$; and
(10) nitro;

$X^3$ is independently selected at each occurrence from:
(1) halogen,
(2) hydroxy,
(3) $R^3R^3N$—,
(4) $R^2O$—,
(5) $R^2O$—C(O)—,
(6) $R^3$—C(O)—O—,
(7) oxo,
(8) $C_{3-10}$cycloalkyl,
(9) aryl substituted with X and Y,
(10) heteroaryl substituted with X and Y,
(11) heterocycloalkyl,
(12) arylS(O)$_n$—, wherein aryl is substituted with X and Y,
(13) $R^3$—C(O)—$NR^3$—,
(14) $R^3R^3N$—C(O)—,
(15) —$CO_2H$,
(16) -vinylidene,
(17) $R^3$—C(O)—O—,
(18) $R^2O$—C(O)—O—,
(19) $R^3R^3N$—C(O)—O—, and
(20) $R^2O$—C(O)—$NR^3$—;

n is 0, 1 or 2;

$Z^1$, $Z^2$ and $Z^3$ are each independently selected from:
(1) —$OR^{6a}$;
(2) —$SR^{6a}$; and
(3) —$NR^{6a}R^{6a}$;

provided that when $R^5$ and $R^6$ are H, and $Z^1$, $Z^2$ and $Z^3$ are each selected from:
(a) OH,
(b) $C_{1-20}$ alkoxy, and
(c) substituted $C_{1-20}$ alkoxy substituted with a member of the group consisting of:
(1) aryl, and
(2) aryl substituted with X and Y, then $R^1$ and $R^4$—(A)$_a$— are not both respectively:

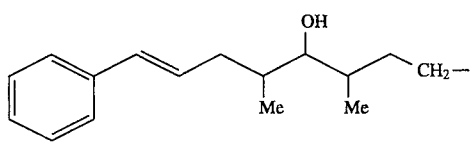 (i)

and

CH$_3$—CH=CH—(CH$_2$)$_4$—CH=CH—(CH$_2$)$_4$—C;

or

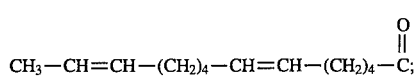 (ii)

and

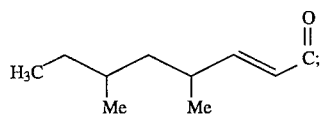

or

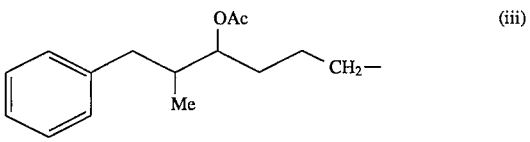 (iii)

and

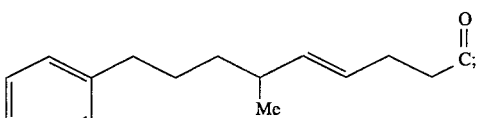

or

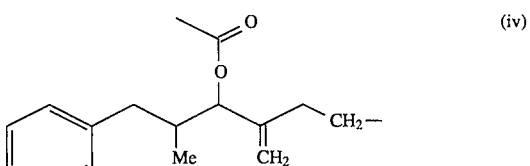 (iv)

and

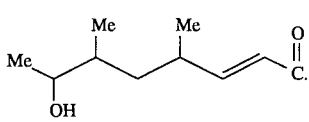

2. The compound of claim 1 or a pharmaceutically acceptable salt thereof wherein:
$R^1$ is selected from the group consisting of:
(1) $C_{1-20}$alkyl;
(2) substituted $C_{1-20}$alkyl in which one or more of the carbon atoms is substituted with $X^3$;
(3) $C_{1-20}$alkyl wherein one or more of the carbons is replaced by —$NR^3$—, —O—, or —S(O)$_n$—;
(4) substituted $C_{1-20}$alkyl wherein one or more of the carbons is replaced by —$NR^3$—, —O—, or —S(O)$_n$— and wherein one or more of the carbon atoms is substituted with $X^3$;
(5) aryl substituted with X and Y;
(6) heteroaryl substituted with X and Y;
(7) $C_{2-20}$alkenyl wherein alkenyl contains one, two or three double bonds;
(8) substituted $C_{2-20}$alkenyl wherein alkenyl contains one, two or three double bonds and wherein one or more of the carbons is substituted with $X^3$;
(9) $C_{2-20}$alkenyl wherein alkenyl contains one, two or three double bonds and one or more of the nonolefinic carbons is replaced by —$NR^3$—, —O—, or —S(O)$_n$—; and
(10) substituted $C_{2-20}$alkenyl wherein alkenyl contains one, two or three double bonds and one or more of the nonolefinic carbons is replaced by —$NR^3$—, —O—, or —S(O)$_n$— and wherein one or more of the carbons is substituted with $X^3$;

$R^4$ is selected from the group consisting of:
(1) $C_{1-20}$alkyl;

(2) substituted $C_{1-20}$alkyl in which one or more of the carbon atoms is substituted with $X^3$;
(3) $C_{1-20}$alkyl wherein one or more of the carbons is replaced by —$NR^3$—, —O—, or —$S(O)_n$—;
(4) substituted $C_{1-20}$alkyl wherein one or more of the carbons is replaced by —$NR^3$—, —O—or —$S(O)_n$— and wherein one or more carbon atoms is substituted with $X^3$;
(5) aryl substituted with X and Y;
(6) heteroaryl substituted with X and Y;
(7) $C_{2-20}$ alkenyl wherein alkenyl contains one, two or three double bonds;
(8) substituted $C_{2-20}$ alkenyl wherein alkenyl contains one, two or three double bonds and wherein one or more of the carbons is substituted with $X^3$;
(9) $C_{2-20}$alkenyl wherein alkenyl contains one, two or three double bonds and one or more of the nonolefinic carbons is replaced by —$NR^3$—, —O—or —$S(O)_n$—;
(10) substituted $C_{2-20}$alkenyl wherein alkenyl contains one, two or three double bonds and one or more of the nonolefinic carbons is replaced by —$NR^3$—, —O—or —$S(O)_n$— and wherein one or more carbon atoms is substituted with $X^3$; and
(11) hydrogen;

aryl including X, Y substitution is

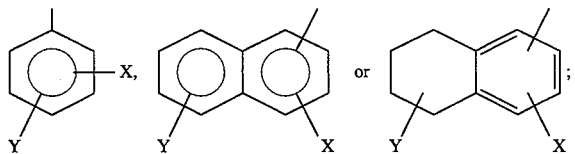

heteroaryl including X, Y substitution is selected from:

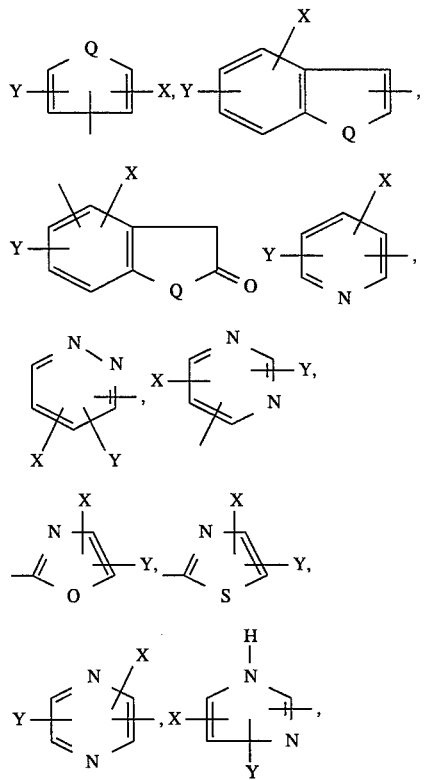

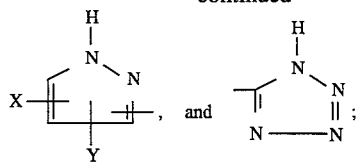

wherein:
Q is —$NR_3$, —O— or —S—;
heterocycloalkyl is selected from:

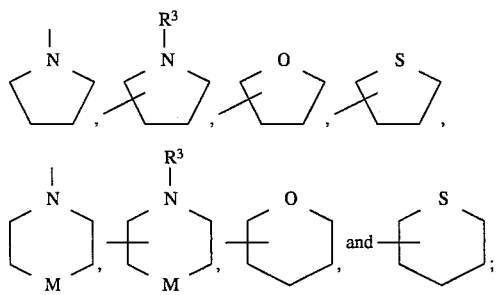

wherein:
M is —$NR^3$, —O—, —S— or —$CH_2$—;
and a, A, $R^2$, $R^3$, $R^5$, $R^6$, $R^{6a}$, X, Y, $X^1$, $Y^1$, $X^3$, n, $Z^1$, $Z^2$, and $Z^3$ are as defined in claim 1.

3. The compound of claim 1 or a pharmaceutically acceptable salt thereof wherein:
$R^1$ is selected from the group consisting of:
(1) $C_{1-20}$alkyl;
(2) substituted $C_{1-20}$alkyl in which one or more carbon atoms is substituted with $X^3$;
(3) $C_{1-20}$alkyl wherein one or more of the carbons is replaced by —$NR^3$—, —O—, or —$S(O)_n$—;
(4) substituted $C_{1-20}$alkyl wherein one or more of the carbons is replaced by —$NR^3$—, —O—, or —$S(O)_n$— and wherein one or more of the carbon atoms are substituted with $X^3$;
(5) aryl substituted with X and Y;
(6) heteroaryl substituted with X and Y;
(7) $C_{2-20}$alkenyl wherein alkenyl contains one, two or three double bonds;
(8) substituted $C_{2-20}$alkenyl wherein alkenyl contains one, two or three double bonds and wherein one or more of the carbons is substituted with $X^3$;
(9) $C_{2-20}$alkenyl wherein alkenyl contains one, two or three double bonds and one or more of the nonolefinic carbons is replaced by —$NR^3$—, —O—, or —$S(O)_n$—; and
(10) substituted $C_{2-20}$alkenyl wherein alkenyl contains one, two or three double bonds and one or more of the nonolefinic carbons is replaced by —$NR^3$—, —O—, or —$S(O)_n$— and wherein one or more of the carbons is substituted with $X^3$;

$R^4$ is selected from the group consisting of:
(1) $C_{1-20}$alkyl;
(2) substituted $C_{1-20}$alkyl in which one or more carbon atoms is substituted with $X^3$;
(3) $C_{1-20}$alkyl wherein one or more of the carbons is replaced by —$NR^3$—, —O—, or —$S(O)_n$—;
(4) substituted $C_{1-20}$alkyl wherein one or more of the carbons is replaced by —$NR^3$—, —O— or —$S(O)_n$— and wherein one or more carbon atoms is substituted with $X^3$;
(5) aryl substituted with X and Y;

(6) heteroaryl substituted with X and Y;
(7) $C_{2-20}$ alkenyl wherein alkenyl contains one, two or three double bonds;
(8) substituted $C_{2-20}$ alkenyl wherein alkenyl contains one, two or three double bonds and wherein one or more of the carbons is substituted with $X^3$;
(9) $C_{2-20}$alkenyl wherein alkenyl contains one, two or three double bonds and one or more of the non-olefinic carbons is replaced by $—NR^3—$, $—O—$ or $—S(O)_n—$;
(10) substituted $C_{2-20}$alkenyl wherein alkenyl contains one, two or three double bonds and one or more of the nonolefinic carbons is replaced by $—NR^3—$, $—O—$ or $—S(O)_n—$ and wherein one or more carbon atoms is substituted with $X^3$;
(11) hydrogen;

aryl is phenyl with X and Y substitution;
heteroaryl including X, Y substitution is selected from:

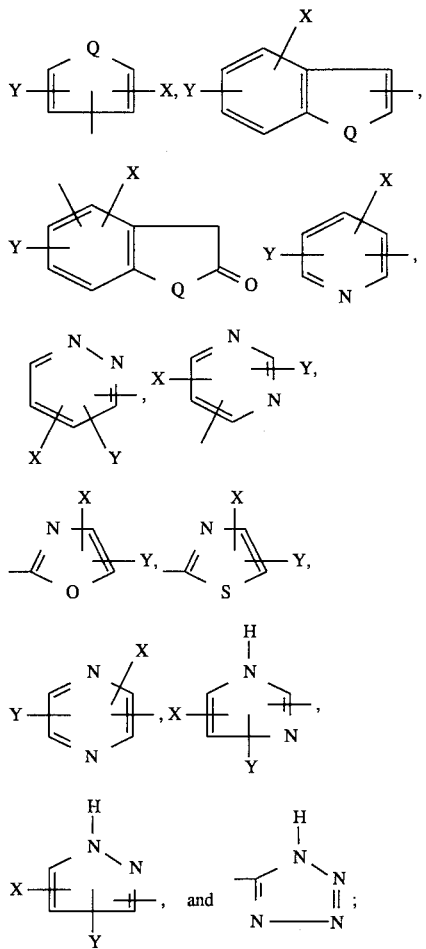

wherein:
Q is $—NR_3$, $—O—$ or $—S—$;
heterocycloalkyl is selected from:

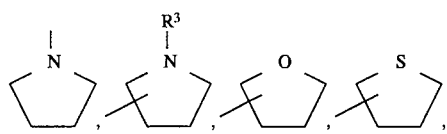

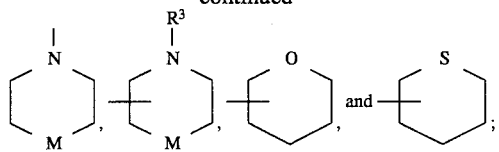

wherein:
M is $—NR^3$, $—O—$, $—S—$ or $—CH_2—$;
and a, A, $R^2$, $R^3$, $R^5$, $R^6$, $R^{6a}$, X, Y, $X^1$, $Y^1$, $X^3$, n, $Z^1$, $Z^2$, and $Z^3$ are as defined in claim 1.

4. The compound of claim 1 wherein:
$R^1$ is selected from the group consisting of:
(1) $C_{2-16}$alkyl;
(2) substituted $C_{2-16}$alkyl in which one or more substituents is selected from:
 (a) hydroxy,
 (b) $R^2O—$,
 (c) $R^2O—C(O)—$,
 (d) $R^3—C(O)—O—$,
 (e) oxo,
 (f) $C_{3-10}$cycloalkyl,
 (g) aryl substituted with X and Y,
 (h) $R^3R^3N—C(O)—$,
 (i) $—CO_2H$,
 (j) -vinylidene,
 (k) $R^3—C(O)—$,
 (l) $R^2O—C(O)—O—$, and
 (m) $R^3R^3N—C(O)—O—$;
(3) $C_{2-16}$alkyl wherein one of the carbons is replaced by $—NR^3—$, $—O—$, or $—S(O)_n—$;
(4) substituted $C_{2-16}$alkyl wherein one of the carbons is replaced by $—NR^3—$, $—O—$ or $—S(O)_n—$ and wherein one or more carbon substituents is selected from:
 (a) hydroxy,
 (c) $R^2O—$,
 (c) $R^2O—C(O)—$,
 (d) $R^3—C(O)—O—$,
 (e) oxo,
 (f) $C_{3-10}$cycloalkyl,
 (g) aryl substituted with X and Y,
 (h) $R^3R^3N—C(O)—$,
 (i) $—CO_2H$,
 (j) -vinylidene,
 (k) $R^3—C(O)—$,
 (l) $R^2O—C(O)—O—$, and
 (m) $R^3R^3N—C(O)—O—$;
(5) $C_{2-16}$alkenyl wherein alkenyl contains one, two or three double bonds;
(6) substituted $C_{2-16}$alkenyl wherein alkenyl contains one, two or three double bonds and wherein one or more of the carbons is substituted with:
 (a) hydroxy,
 (b) $R^2O—$,
 (c) $R^2O—C(O)—$,
 (d) $R^3—C(O)—O—$,
 (e) oxo,
 (f) $C_{3-10}$cycloalkyl,
 (g) aryl substituted with X and Y,
 (h) $R^3R^3N—C(O)—$,
 (i) $—CO_2H$,
 (j) -vinylidene,
 (k) $R^3—C(O)—$,
 (l) $R^2O—C(O)—O—$, and
 (m) $R^3R^3N—C(O)—O—$;
(7) $C_{2-16}$alkenyl wherein alkenyl contains one, two or three double bonds and one or more of the nonolefinic carbons is replaced by —NR$^3$—, —O— or —S(O)$_n$—; and (8) substituted C$_{2-16}$alkenyl wherein alkenyl contains one, two or three double bonds and one or more of the nonolefinic carbons is replaced by —NR$^3$, —O— or —S(O)$_n$— and wherein one or more carbons substituents is selected from:
  (a) hydroxy,
  (b) R$^2$O—,
  (c) R$^2$O—C(O)—,
  (d) R$^3$—C(O)—O—,
  (e) oxo,
  (f) C$_{3-10}$cycloalkyl,
  (g) aryl substituted with X and Y,
  (h) R$^3$R$^3$N—C(O)—,
  (i) —CO$_2$H,
  (j) -vinylidene,
  (k) R$^3$—C(O)—,
  (l) R$^2$O—C(O)—O—, and
  (m) R$^3$R$^3$N—C(O)—O—;

Each R$^2$ is independently selected from:
  (1) C$_{1-10}$alkyl;
  (2) aryl substituted with X and Y;
  (3) arylC$_{1-4}$alkyl wherein aryl is substituted with X and Y;
  (4) heteroaryl wherein heteroaryl is substituted with X and Y;
  (5) heteroarylC$_{1-4}$alkyl- wherein heteroaryl is substituted with X and Y;
  (6) heterocycloalkylC$_{1-4}$alkyl-;
  (7) C$_{2-10}$alkenyl; and
  (8) arylC$_{2-10}$alkenyl wherein aryl is substituted with X and Y;

Each R$^3$ is independently selected from:
  (1) C$_{1-10}$alkyl;
  (2) aryl substituted with X and Y;
  (3) arylC$_{1-4}$alkyl wherein aryl is substituted with X and Y;
  (4) heteroaryl wherein heteroaryl is substituted with X and Y;
  (5) heteroarylC$_{1-4}$alkyl- wherein heteroaryl is substituted with X and Y;
  (6) heterocycloalkylC$_{1-4}$alkyl-;
  (7) C$_{2-10}$alkenyl;
  (8) arylC$_{2-10}$alkenyl wherein aryl is substituted with X and Y; and
  (9) hydrogen;

R$^4$ is selected from the group consisting of:
  (1) C$_{1-20}$alkyl;
  (2) substituted C$_{1-20}$alkyl in which one or more substituents is selected from:
    (a) halogen,
    (b) hydroxy,
    (c) R$^3$R$^3$N—,
    (d) R$^2$O—,
    (e) R$^2$O—C(O)—,
    (f) R$^3$—C(O)—O—,
    (g) oxo,
    (h) C$_{3-10}$cycloalkyl,
    (i) aryl substituted with X and Y,
    (j) heteroaryl substituted with X and Y,
    (k) heterocycloalkyl,
    (l) arylS(O)$_n$, wherein aryl is substituted with X and Y,
    (m) R$^3$—C(O)—NR$^3$—,
    (n) R$^3$R$^3$N—C(O)—,
    (o) —CO$_2$H,
    (p) -vinylidene,
    (q) R$^3$—C(O)—,
    (r) R$^2$O—C(O)—O—,
    (s) R$^3$R$^3$N—C(O)—O—, and
    (t) R$^2$O—C(O)—NR$^3$—;
  (3) C$_{1-20}$alkyl wherein one or more of the carbons is replaced by —NR$^3$—, —O—, or —S(O)$_n$—;
  (4) substituted C$_{1-20}$alkyl wherein one or more of the carbons is replaced by —NR$^3$—, —O— or —S(O)$_n$— and wherein one or more carbon substituents is selected from:
    (a) halogen,
    (b) hydroxy,
    (c) R$^3$R$^3$N—,
    (d) R$^2$O—,
    (e) R$^2$O—C(O)—,
    (f) R$^3$—C(O)—O—,
    (g) oxo,
    (h) C$_{3-10}$cycloalkyl,
    (i) aryl substituted with X and Y,
    (j) heteroaryl substituted with X and Y,
    (k) heterocycloalkyl,
    (l) arylS(O)$_n$, wherein aryl is substituted with X and Y,
    (m) R$^3$—C(O)—NR$^3$—,
    (n) R$^3$R$^3$N—C(O)—,
    (o) —CO$_2$H,
    (p) -vinylidene,
    (q) R$^3$—C(O)—,
    (r) R$^2$O—C(O)—O—,
    (s) R$^3$R$^3$N—C(O)—O—, and
    (t) R$^2$O—C(O)—NR$^3$—;
  (5) aryl substituted with X and Y;
  (6) C$_{2-20}$ alkenyl wherein alkenyl contains one, two or three double bonds;
  (7) substituted C$_{2-20}$ alkenyl wherein alkenyl contains one, two or three double bonds and wherein one or more of the carbons is substituted with:
    (a) halogen,
    (b) hydroxy,
    (c) R$^3$R$^3$N—,
    (d) R$^2$O—,
    (e) R$^2$O—C(O)—,
    (f) R$^3$—C(O)—O—,
    (g) oxo,
    (h) C$_{3-10}$cycloalkyl,
    (i) aryl substituted with X and Y,
    (j) heteroaryl substituted with X and Y,
    (k) heterocycloalkyl,
    (l) arylS(O)$_n$, wherein aryl is substituted with X and Y,
    (m) R$^3$—C(O)—NR$^3$—,
  (n) R$^3$R$^3$N—C(O)—,
    (o) —CO$_2$H,
    (p) -vinylidene,
    (q) R$^3$—C(O)—,
    (r) R$^2$O—C(O)—O—,
    (s) R$^3$R$^3$NC(O)—O—, and
    (t) R$^2$O—C(O)—NR$^3$—; and
  (8) hydrogen;

R$^5$ is selected from the group consisting of:
  (1) hydrogen;
  (2) C$_{1-3}$alkyl; and
  (3) R$^2$—C(O)—;

R$^6$ is selected from the group consisting of:
  (1) C$_{1-20}$alkyl;
  (2) substituted C$_{1-20}$alkyl in which one or more substituents is selected from:

(a) halogen,
(b) hydroxy,
(c) $R^3R^3N—$,
(d) $R^2O—$,
(e) $R^2O—C(O)—$,
(f) $R^3—C(O)—O—$,
(g) oxo,
(h) $C_{3-10}$cycloalkyl,
(i) aryl substituted with X and Y,
(j) heteroaryl substituted with X and Y,
(k) heterocycloalkyl,
(l) $R^3—C(O)—NR^3—$,
(m) $R^3R^3N—C(O)—$,
(n) $—CO_2H$, and
(o) $R^2O—C(O)—NR^3—$;

(3) $C_{1-20}$alkyl wherein one or more of the carbons is replaced by $—NR^3—$, $—O—$, or $—S(O)_n—$;

(4) substituted $C_{1-20}$alkyl wherein one or more of the carbons is replaced by $—NR^3—$, $—O—$, or $—S(O)_n—$ and wherein one or more carbon substituents is selected from:
(a) halogen,
(b) hydroxy,
(c) $R^3R^3N—$,
(d) $R^2O—$,
(e) $R^2O—C(O)—$,
(f) $R^3—C(O)—O—$,
(g) oxo,
(h) $C_{3-10}$cycloalkyl,
(i) aryl substituted with X and Y,
(j) heteroaryl substituted with X and Y,
(k) heterocycloalkyl,
(l) $R^3—C(O)—NR^3—$,
(m) $R^3R^3N—C(O)—$,
(n) $—CO_2H$, and
(o) $R^2O—C(O)—NR^3—$;

(5) $C_{2-20}$alkenyl wherein alkenyl contains one or more double bonds;

(6) substituted $C_{2-20}$alkenyl wherein alkenyl contains one or more double bonds and wherein one or more of the carbons is substituted with:
(a) halogen,
(b) hydroxy,
(c) $R^3R^3N—$,
(d) $R^2O—$,
(e) $R^2O—C(O)—$,
(f) $R^3—C(O)—O—$,
(g) oxo,
(h) $C_{3-10}$cycloalkyl,
(i) aryl substituted with X and Y,
(j) heteroaryl substituted with X and Y,
(k) heterocycloalkyl,
(l) $R^3—C(O)—NR^3—$,
(m) $R^3R^3N—C(O)—$,
(n) $—CO_2H$, and
(o) $R^2O—C(O)—NR^3—$;

(7) $C_{2-20}$alkynyl wherein alkynyl contains one or more triple bonds;

(8) substituted $C_{2-20}$alkynyl wherein alkynyl contains one or more triple bonds and wherein one or more of the carbons is substituted with:
(a) halogen,
(b) hydroxy,
(c) $R^3R^3N—$,
(d) $R^2O—$,
(e) $R^2O—C(O)—$,
(f) $R^3—C(O)—O—$,
(g) oxo,
(h) $C_{3-10}$cycloalkyl,
(i) aryl substituted with X and Y,
(j) heteroaryl substituted with X and Y,
(k) heterocycloalkyl,
(l) $R^3—C(O)—NR^3—$,
(m) $R^3R^3N—C(O)—$,
(n) $—CO_2H$, and
(o) $R^2O—C(O)—NR^3—$;

(9) aryl substituted with X and Y
(10) Heteroaryl substituted with X and Y
(11) $C_{3-5}$ cycloalkyl
(12) substituted $C_{3-5}$ cycloalkyl in which one or more of the substituents is selected from:
(a) $R^3O—$, and
(b) $R^3R^3N—$; and
(13) hydrogen;

aryl is phenyl with X and Y substitution;

X and Y are each independently selected from:
(1) hydrogen;
(2) hydroxy;
(3) halogen;
(4) trifluoromethyl;
(5) $C_{1-10}$alkyl;
(6) aryl substituted with $X^1$ and $Y^1$;
(7) $R^2O—$;
(8) arylcarbonyloxy-, wherein aryl is substituted with $X^1$ and $Y^1$;
(9) $R^3—C(O)—O—$;
(10) $—CO_2R^2$;
(11) $—CO_2H$; and
(12) nitro;

$X^1$ and $Y^1$ are each independently selected from:
(1) hydrogen;
(2) hydroxy;
(3) halogen;
(4) trifluoromethyl;
(5) $C_{1-4}$alkyl;
(6) $R^2O—$;
(7) $R^3—C(O)—O—$;
(8) $—CO_2R^2$;
(10) $—CO_2H$; and
(11) nitro;

n is 0, 1 or 2;

$Z^1$, $Z^2$ and $Z^3$ are each independently selected from:
(1) $—OR^6$;
(2) $—SR^6$; and
(3) $—NR^6R^6$;

or a pharmaceutically acceptable salt.

5. The compound of claim 3 of the structural formula (II)

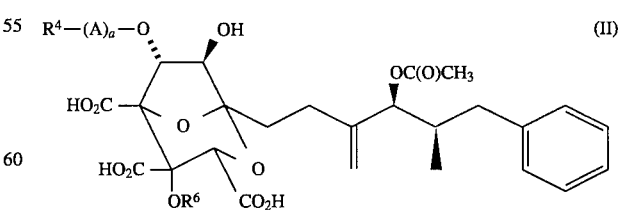

wherein:
$R^4—(A)$ and $R^6$ are selected from the group consisting of

|  | R⁴—(A)ₐ— | R⁶ |
|---|---|---|
| 5a | CH₃(CH₂)₆CO | H |
| 5b | CH₃CO | H |
| 5c | CH₃(CH₂)₁₀CO | H |
| 5d | CH₃(CH₂)₁₂CO | H |
| 5e | CH₃(CH₂)₅—CH=CH(CH₂)₇CO | H |
| 5f | CH₃(CH₂)₁₄CO | H |
| 5g | PhO(CH₂)₁₀CO | H |
| 5h | CH₃(CH₂)₆-p-C₆H₄—CO | H |
| 5i | Ph(CH₂)₁₀CO | H |
| 5j | Ph(CH₂)₃CO | H |
| 5k | 1-adamantylCH₂CO | H |
| 5l | CH₃(CH₂)₇NHCO | H |
| 5m | CH₃(CH₂)₉NHCO | H |
| 5n | CH₃(CH₂)₁₀NHCO | H |
| 5o | CH₃(CH₂)₁₁NHCO | H |
| 5p | CH₃(CH₂)₁₂NHCO | H |
| 5q | CH₃(CH₂)₁₃NHCO | H |
| 5r | CH₃(CH₂)₁₅NHCO | H |
| 5s | PhCH₂NHCO | H |
| 5t | 4-Ph—Ph—NHCO | H |
| 5u | PhO(CH₂)₁₁NHCO | H |
| 5v | CH₃(CH₂)₉N(CH₃)CO | H |
| 5w | CH₃(CH₂)₁₅N(CH₃)CO | H |
| 5x | CH₃(CH₂)₁₁OCO | H |
| 5y | PhO(CH₂)₁₁OCO | H |
| 5z | PhO(CH₂)₈ | H |
| 5a' | H | PhO(CH₂)₈ |
| 5b' | PhO(CH₂)₈ | PhO(CH₂)₈ |
| 5c' | PhO(CH₂)₁₁ | H |
| 5d' | H | PhO(CH₂)₁₁ |
| 5e' | PhO(CH₂)₁₁ | PhO(CH₂)₁₁ |
| 5f' | CH₃(CH₂)₁₃ | H |
| 5g' | CH₃(CH₂)₁₅ | H |
| 5h' | 2-Ph—C₆H₄—CH₂ | H |
| 5p' | CH₃CH₂CO | H |
| 5q' | CH₃(CH₂)₂CO | H |
| 5r' | (CH₃)₂CHCO | H |
| 5s' | (S)—CH₃CH₂CH(CH₃)CO | H |
| 5t' | CH₃O(CH₂)₃CO | H |
| 5u' | CH₃(CH₂)₃CO | H |
| 5v' | (CH₃)₂CHCH₂CO | H |
| 5w' | (CH₃)₂CH(CH₂)₂CO | H |
| 5x' | CH₃CH₂CH₂CH(CH₃)CO | H |
| 5y' | CH₃CH₂CH(CH₃)CH₂CO | H |
| 5z' | H₂N(CH₂)₅CO | H |
| 5a" | CH₃(CH₂)₈CH(CH₃)CO | H |
| 5b" | cyclohexyl-CH₂CO | H |
| 5c" | C₆H₅CH₂CO | H |
| 5d" | C₆H₅OCH₂CO | H |
| 5e" | C₆H₅CH₂CH₂CO | H |
| 5f" | C₆H₅OCH₂CH₂CO | H |
| 5g" | C₆H₅O(CH₂)₃CO | H |
| 5h" | 4-(CH₃CO)—C₆H₄(CH₂)₁₀CO | H |
| 5i" | E-C₆H₅CH=CHCO | H |
| 5j" | E-(3-CH₃O)C₆H₄CH=CHCO | H |
| 5k" | 4-(C₆H₅)—C₆H₄CO | H |
| 5l" | 4-(C₆H₅)—C₆H₄CH₂CO | H |
| 5m" | 4-(C₆H₅—O)—C₆H₄CH₂CO | H |
| 5n" | 3-(C₆H₅—O)—C₆H₄CH₂CO | H |
| 5o" | C₆H₅—CH₂CH(NH₂)CO | H |
| 5p" | Br(CH₂)₁₀CO | H |
| 5q" | 4-(CH₃O)C₆H₄O(CH₂)₁₀CO | H |
| 5r" | 3-((CH₃)₂N)C₆H₅O(CH₂)₁₀CO | H |
| 5s" | 4-((CH₃)₂N)C₆H₄S(CH₂)₁₀CO | H |
| 5t" | CH₃NHCO | H |
| 5u" | (CH₃)₂NCO | H |
| 5v" | CH₃CH₂NHCO | H |
| 5w" | (CH₃)₂NCH₂CH₂NHCO | H |
| 5x" | (CH₃)₂CHNHCH₂CH₂NHCO | H |
| 5y" | CH₃CH₂CH₂NHCO | H |
| 5z" | (CH₃)₂CHNHCO | H |
| 5a''' | cyclopropyl-NHCO | H |
| 5b''' | CH₃CH₂CH₂CH₂NHCO | H |
| 5c''' | (CH₃)₂CHCH₂NHCO | H |
| 5d''' | (R)-CH₃CH₂CH(CH₃)NHCO | H |
| 5e''' | (S)-CH₃CH₂CH(CH₃)NHCO | H |
| 5f''' | (CH₃(CH₂)₃)(CH₃(CH₂)₆)CHO(CH₂)₃NHCO | H |
| 5g''' | CH₃(CH₂)₁₁O(CH₂)₃NHCO | H |

-continued

| | $R^4-(A)_a-$ | $R^6$ |
|---|---|---|
| 5h''' | 4-$(CH_3O)C_6H_4CH_2NHCO$ | H |
| 5i''' | 4-$(CH_3SO_2)C_6H_4CH_2NHCO$ | H |
| 5j''' | $C_6H_5CH_2CH_2NHCO$ | H |
| 5k''' | $C_6H_5OCH_2CH_2NHCO$ | H |
| 5l''' | $C_6H_5O(CH_2)_8NHCO$ | H |
| 5m''' | adamantyl-$CH_2NHCO$ | H |
| 5n''' | $(CH_3)_2CHOCO$ | H |
| 5o''' | $CH_3(CH_2)_9OCO$ | H |
| 5p''' | $CH_2(CH_2)_3O(CH_2)_2O(CH_2)_2OCO$ | H |
| 5q''' | 3,4-$(CH_3O)_2C_6H_3O(CH_2)_{10}$ | H |
| 5r''' | $CH_3(CH_2)_2$ | H |
| 5s''' | H | $CH_3(CH_2)_2$ and |
| 5t''' | $CH_3(CH_2)_2$ | $CH_3(CH_2)_2$ |
| 5aa | cyclopropyl-CO— | H |
| 5ab | 1-methylcyclopropyl-CO— | H |
| 5ac | (3-$CF_3$)-$PhCH_2CO$— | H |
| 5ad | 4-pyridylthio-$CH_2CO$— | H |
| 5ae | 3-indolyl-$CH_2CO$— | H |
| 5af | furyl-$CH_2CO$— | H |
| 5ag | $Ph(CH_2)_4CO$— | H |
| 5ah | $(Ph)_2CHCH_2CO$ | H |
| 5ai | $CH_3(CH_2)_{11}$—O—$C_6H_4$—$CH_2CO$— | H |
| 5aj | PHCO— | H |
| 5ak | $PhO(CH_2)_{11}CO$— | H |
| 5al | $PhS(CH_2)_{10}CO$— | H |
| 5am | $PhS(O)(CH_2)_{10}CO$— | H |
| 5an | $PhS(O)_2(CH_2)_{10}CO$— | H |
| 5ao | $CH_3(CH_2)_4CO$— | H |
| 5ap | $CH_3C(O)(CH_2)_2CO$— | H |
| 5aq | $HO_2C$—$(CH_2)_2CO$— | H |
| 5ar | $H_2C=CHCO$— | H |
| 5as | $H_2C=C(CH_3)CO$— | H |
| 5at | $H_2N$—$(CH_2)_{10}CO$— | H |
| 5au | $H_2N$—$CH_2CO$— | H |
| 5av | $CH_3C(O)NHCH_2CO$— | H |
| 5aw | $CH_2=C(CH_3)CH_2CO$— | H |
| 5ax | $(CH_3)_2C=CHCO$— | H |
| 5ay | $CH_3CH=CHCO$— | H |
| 5az | $CH_2=CH$—$CH_2CO$— | H |
| 5ba | $(CH_3)_2CHCH(NH_2)CO$— | H |
| 5bb | $(CH_3)(NH_2)CHCO$— | H |
| 5bc | $CH_3C(O)$—NH—$CH(CH_3)CO$— | H |
| 5bd | cyclobutyl-CO— | H |
| 5be | $(CH_3)_3C$—CO— | H |
| 5bf | $CH_3$—O—CO— | H |
| 5ca | cyclopropyl-$CH_2NHCO$— | H |
| 5cb | 3-pyridinyl-$CH_2NHCO$— | H |
| 5cc | 1-imidazolyl-$(CH_2)_3NHCO$— | H |
| 5cd | N-morpholinyl-$(CH_2)_2NHCO$— | H |
| 5ce | 4-piperidinyl-$CH_2NHCO$— | H |
| 5cf | 2-tetrahydropyranyl-$CH_2NHCO$— | H |
| 5cg | cyclobutyl-NHCO— | H |
| 5ch | $CH_3$—O—NHCO— | H |
| 5ci | $CH_2=CHCH_2NHCO$— | H |
| 5cj | PhNHCO— | H |
| 5ck | furfuryl-NHCO— | H |
| 5cl | $(CH_3)CH$—NHCS— | H |
| 5da | H | $CH_3(CH_2)_{13}$— |
| 5db | $CH_3(CH_2)_{13}$— | $CH_3(CH_2)_{13}$— |
| 5dc | $CH_3(CH_2)_{11}$— | H |
| 5dd | H | $CH_3(CH_2)_{11}$— |
| 5de | $CH_3(CH_2)_{11}$— | $CH_3(CH_2)_{11}$— |
| 5df | $CH_3(CH_2)_9$— | H |
| 5dg | H | $CH_3(CH_2)_9$— |
| 5dh | $CH_3(CH_2)_9$— | $CH_3(CH_2)_9$— |
| 5di | $HO_2C$—$(CH_2)_{10}$— | H |
| 5dj | H | $HO_2C$—$(CH_2)_{10}$— |
| 5dk | $HO_2C$—$(CH_2)_{10}$— | $HO_2C$—$(CH_2)_{10}$— |
| 5dl | $CH_3(CH_2)_3$— | H |
| 5dm | $(CH_3)_2CHCH_2$— | H |
| 5dn | $CH_3(CH_2)_4$— | H |
| 5do | $(CH_3)_2CH(CH_2)_2$— | H. |

6. The compound of claim 3 of the structural formula (III)

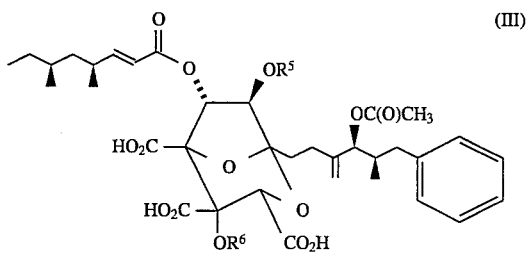

(III)

wherein:

$R^5$ and $R^6$ are selected from the group consisting of:

| | $R^5$ | $R^6$ |
|---|---|---|
| 5i' | COCH$_3$ | H |
| 5j' | COCH$_2$CH$_3$ | H |
| 5k' | COC(CH$_3$)$_3$ | H |
| 5l' | COPh | H |
| 5m' | COCH$_2$CH$_2$CH$_3$ | H |
| 5n' | CH$_3$ | H |
| 5o' | CH$_3$ | CH$_3$ |
| 5ea | H | CH$_2$CH$_3$ and |
| 5eb | CH$_3$ | CH$_3$. |

7. The compound of claim 3 of the structural formula (V):

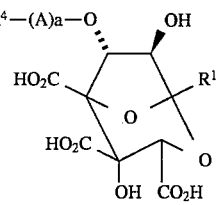

(V)

wherein $R^1$ and $R^4$—(A)$_a$ are selected from the group consisting of:

| | $R^1$ | $R^4$—(A)$_a$ |
|---|---|---|
| 7a | —(CH$_2$)$_2$C(CH$_2$)CH(CH$_3$CH$_2$CO$_2$)CH(CH$_3$)CH$_2$C$_6$H$_5$ | p$^1$ |
| 7b | —(CH$_2$)$_2$C(CH$_2$)CH(CH$_3$CH$_2$CH$_2$CO$_2$)CH(CH$_3$)CH$_2$C$_6$H$_5$ | p$^1$ |
| 7c | —(CH$_2$)$_2$C(CH$_2$)CH((CH$_3$)$_3$CCO$_2$)CH(CH$_3$)CH$_2$C$_6$H$_5$ | p$^1$ |
| 7d | —(CH$_2$)$_2$C(CH$_2$)CH(PhCO$_2$)CH(CH$_3$)CH$_2$C$_6$H$_5$ | p$^1$ |
| 7f | —(CH$_2$)$_2$C(CH$_2$)CH(CH$_3$CH$_2$CH$_2$NHCO$_2$)CH(CH$_3$)CH$_2$C$_6$H$_5$ | p$^1$ |
| 7g | —(CH$_2$)$_2$C(CH$_2$)CH(PhCH$_2$NHCO$_2$)CH(CH$_3$)CH$_2$C$_6$H$_5$ | p$^1$ |
| 7h | —(CH$_2$)$_2$C(CH$_2$)CH(PhNHCO$_2$)CH(CH$_3$)CH$_2$C$_6$H$_5$ | p$^1$ |
| 24b | —(CH$_2$)$_2$CH(CH$_3$)CH(OAc)CH(CH$_3$)CH$_2$Ph | p$^2$ |
| 25b | —(CH$_2$)$_2$CH(CH$_3$)CH$_2$CH(CH$_3$)CH$_2$Ph | p$^2$ |
| 26b | —(CH$_2$)$_2$CH(CH$_3$)CH(OAc)CH(CH$_3$)CH$_2$C$_6$H$_{11}$ | p$^2$ |
| 26c | —(CH$_2$)$_2$CH(CH$_3$)CH(OCH$_3$)CH(CH$_3$)CH$_2$C$_6$H$_5$ | p$^2$ |
| 29a | —(CH$_2$)$_2$COH(CH$_2$OH)CH(OH)CH(CH$_3$)CH$_2$Ph | p$^1$ |
| 30a | —(CH$_2$)$_2$CO$_2$H | p$^1$ |
| 31c | —(CH$_2$)$_2$C(=O)CH(OH)CH(CH$_3$)CH$_2$Ph | p$^1$ |
| 31d | —(CH$_2$)$_2$COCH$_2$OH | p$^1$ |
| 33a | —(CH$_2$)$_2$CH$_2$OH | p$^1$ |
| 39a | —(CH$_2$)$_2$CH$_2$OCO(CH$_2$)$_{10}$CH$_3$ | p$^1$ |
| 39b | —(CH$_2$)$_2$CH$_2$OCOC(CH$_3$)$_3$ | p$^1$ |
| 39c | —(CH$_2$)$_2$CH$_2$OCO(CH$_2$)$_3$CH$_3$ | p$^1$ |
| 39d | —(CH$_2$)$_2$CH$_2$OCOCH$_3$ | p$^1$ |
| 39e | —(CH$_2$)$_2$CH$_2$OCO(CH$_2$)$_3$Ph | p$^1$ |
| 39f | —(CH$_2$)$_2$CH$_2$OCOPh | p$^1$ |
| 39h | —(CH$_2$)$_2$CH$_2$OCONHPh | p$^1$ |
| 39i | —(CH$_2$)$_2$CH$_2$OCONHPh(2'-Et) | p$^1$ |
| 39j | —(CH$_2$)$_2$CH$_2$OCONH(CH$_2$)$_7$CH$_3$ | p$^1$ |
| 7aa | —(CH$_2$)$_2$CH(CH$_3$)CH(OAc)CH(CH$_3$)CH$_2$C$_6$H$_5$ | p$^2$ |
| 7ab | —(CH$_2$)$_2$CH(CH$_2$OAc)CH$_2$CH(CH$_3$)CH$_2$C$_6$H$_5$ | p$^2$ |
| 7ac | —(CH$_2$)$_2$C(CH$_2$)CH(OH)CH(CH$_3$)CH$_2$C$_6$H$_5$ | p$^1$ |
| 7ad | —(CH$_2$)$_2$CH(OH)(CH$_2$)$_3$Ph | p$^1$ |
| 7ae | —(CH$_2$)$_2$CH(OH)(CH$_2$)$_5$Ph | p$^1$ |
| 7af | —(CH$_2$)$_2$CH(OAc)(CH$_2$)$_5$Ph | p$^1$ |
| 7ag | —(CH$_2$)$_2$CH(OAc)(CH$_2$)$_3$Ph | p$^1$ |
| 7ah | —(CH$_2$)$_2$C(O)(CH$_2$)$_3$Ph | p$^1$ |
| 7ai | —(CH$_2$)$_2$C(O)(CH$_2$)$_5$Ph | p$^1$ |
| 7aj | —(CH$_2$)$_2$(1_methyl-1,2,3,4-tetrahydronaphthyl) | p$^1$ |
| 7ak | —(CH$_2$)$_2$C(CH$_2$)C(O)CH(CH$_3$)CH$_2$Ph | p$^1$ |
| 7al | —(CH$_2$)$_2$CH[(CH$_2$)$_4$CH$_3$]C(O)CH(CH$_3$)CH$_2$Ph | p$^1$ |
| 7am | —(CH$_2$)$_2$CH(CH$_2$Ph)C(O)CH(CH$_3$)CH$_2$Ph | p$^1$ |
| 7an | —(CH$_2$)$_2$C(O)OCH$_2$Ph | p$^1$ and |
| 7ao | —(CH$_2$)$_2$C(O)OCH$_3$ | p$^1$; | and wherein:

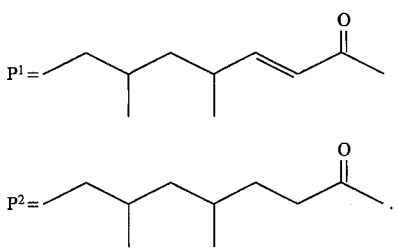

8. The compound of claim 3 of the structural formula (VII):

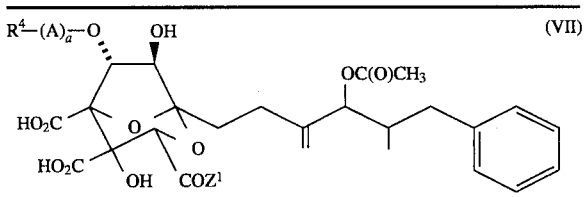

wherein $R^4-(A)_a-$ and $Z^1$ are selected from:

| | $R^4-(A)_a-$ | $Z^1$ |
|---|---|---|
| 40aa | $CH_3O(CH_2)_3(CO)-$ | $(CH_3)_2CHCH_2CH_2O$ |
| 40ab | $(CH_3)_2CHCH_2(CO)-$ | $(CH_3)_2CHCH_2CH_2O$ |
| 40ac | $CH_3(CH_2)_{10}(CO)-$ | $(CH_3)_2CHCH_2CH_2O$ |
| 40ad | $C_6H_5(CH_2)_3(CO)-$ | $(CH_3)_2CHCH_2CH_2O$ |
| 40ae | $C_6H_5O(CH_2)_{10}(CO)-$ | $(CH_3)_2CHCH_2CH_2O$ |
| 40af | $(CH_3)CH-NH(CO)-$ | $(CH_3)_2CHCH_2CH_2O$ |
| 40ag | $CH_3(CH_2)_9NH(CO)-$ | $(CH_3)_2CHCH_2CH_2O$ |
| 40ah | $C_6H_5O(CH_2)_8NH(CO)-$ | $(CH_3)_2CHCH_2CH_2O$ |
| 40ai | adamantyl-$CH_2NH(CO)-$ | $(CH_3)_2CHCH_2CH_2O$ |
| 40aj | $CH_3(CH_2)_9O(CO)-$ | $(CH_3)_2CHCH_2CH_2O$. |

9. A pharmaceutical composition comprising a nontoxic therapeutically effective amount of a compound of claim 1 and a pharmaceutically acceptable carrier.

10. A pharmaceutical composition comprising a nontoxic therapeutically effective amount of a compound of claim 1 in combination with a pharmaceutically acceptable nontoxic cationic polymer capable of binding bile acids in a non-reabsorbable form in the gastrointestinal tract and pharmaceutically acceptable carrier.

11. A pharmaceutical composition comprising a nontoxic therapeutically effective amount of a compound of claim 1 in combination with a nontoxic therapeutically effective amount of a cholesterol lowering agent selected from the group consisting of:

(a) HMG—CoA reductase inhibitor;

(b) HMG—CoA synthase inhibitor;

(c) Squalene expoxidase inhibitor;

(d) Probucol;

(e) Niacin;

(f) Gemfibrozil; and (g) Clofibrate.

12. The composition of claim 10 wherein the composition additionally comprises an HMG—CoA reductase inhibitor.

13. A composition of claim 11 wherein the HMG—CoA reductase inhibitor is selected from lovastatin, simvastatin, pravastatin and fluvastatin.

14. A method of treating hypercholesterolemia comprising the administration to a subject in need of such treatment a nontoxic therapeutically effective amount of the compound of claim 1.

15. A method of inhibiting squalene synthetase comprising the administration to a subject in need of such treatment a nontoxic therapeutically effective amount of a compound of claim 1.

16. A method of inhibiting fungal growth comprising applying to the area where growth is to be controlled an antifungally effective amount of a compound of claim 1.

17. A method for inhibiting fungal growth in a living organism in need of such treatment comprising the topical, oral, systemic, or parenteral administration of an antifungally effective amount of a compound of claim 1.

18. A compound of the structural formula (IV):

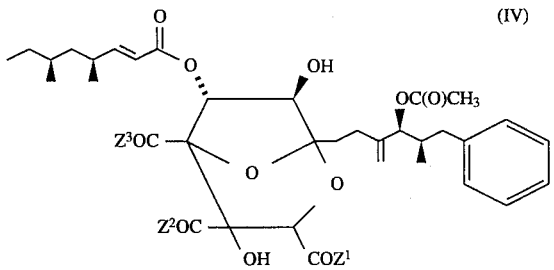

wherein $Z^1$, $Z^2$ and $Z^3$ are selected from the group consisting of:

| | $Z^1$ | $Z^2$ | $Z^3$ |
|---|---|---|---|
| 8a | $PhCH_2O$ | OH | OH |
| 8d | $Ph-(CH_2)_2O$ | OH | OH |
| 8i | $(CH_3)_2CHO-$ | OH | OH |
| 8j | $CH_3CH_2CH_2O$ | OH | OH |
| 8k | $(CH_3)_2CHCH_2O$ | OH | OH |
| 8m | $PhCH_2CH_2CH_2O$ | OH | OH |
| 8n | $CH_3CH(CH_3)CH_2CH_2O$ | OH | OH |
| 8p | $CH_3(CH_2)_4O$ | OH | OH |
| 14g | $(CH_3)_2CHCH_2CH_2O$ | $C_6H_5CH_2O$ | OH, and |
| 14p | $(CH_3)_2CHCH_2CH_2O$ | $CH_3O$ | OH. |

19. The compound of claim 1 selected from the group consisting of:

(a) (1S,3S,4S,5R,6R,7R)-1-[(4-hydroxy-3,5-dimethyl-8-phenyl)oct- 7-enyl]-3-isopentyloxycarbonyl-4-pivaloyloxymethyloxycarbonyl- 4,6,7-trihydroxy-6-O-(tetradeca- 6,12-dienoyl)-2,8-dioxabicyclo[3.2.1]-octane-5-carboxylic acid;

(b) (1S,3S,4S,5R,6R,7R)-1-[(4-hydroxy-3,5-dimethyl-8-phenyl)oct- 7-enyl]-4,6,7-trihydroxy-6-O-(isopropylaminocarbonyl)- 2,8-dioxabicyclo[3.2.1]-octane- 3,4,5-tricarboxylic acid;

(c) (1S,3S,4S,5R,6R,7R)-1-[(4)-acetoxy-5-methyl-6-phenylhexyl] -4,6,7-trihydroxy-6-O-(isopropyl-aminocarbonyl)- 2,8-dioxabicyclo[3.2.1]octane-3,4,5-tricarboxylic acid; and (d) (1S,3S,4S,5R, 6R,7R)-1-[(4)-acetoxy-5-methyl-6-phenyl] hexyl-3-isopentyloxycarbonyl-4,6,7-trihydroxy-4-pivaloxyloxymethyloxycarbonyl- 6-O-(6-methyl-9-phenyl- 4-nonenoyl)-2,8-dioxabicyclo[3.2.1] octane-5-carboxylic acid.

20. A compound of the structural formula (IV):

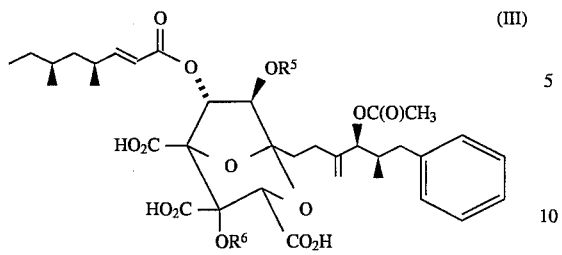

(III)

wherein $Z^1$, $Z^2$ and $Z^3$ are selected from the group consisting of:

| | $Z^1$ | $Z^2$ | $Z^3$ |
|---|---|---|---|
| 8e | $CH_2=CH-CH_2O-$ | OH | OH |
| 8h | $HC\equiv CCH_2O$ | OH | OH |
| 8l | $C_6H_{11}O-$ | OH | OH |
| 8o | $PhOCH_2CH_2O$ | OH | OH |
| 8q | $CH_3CH=CHCH_2O$ | OH | OH |
| 11a | $NH_2$ | tBuO | tBuO |
| 12a | $NH_2$ | OH | OH |
| 12b | $PhCH_2NH$ | OH | OH |
| 12c | $CH_3(CH_2)_6NH$ | OH | OH |
| 12d | $CH_3CH_2NH$ | OH | OH |
| 12e | $(CH_3)_2N$ | OH | OH |
| 12f | $Ph(CH_3)N$ | OH | OH |
| 12g | $O(CH_2CH_2)_2N$ | OH | OH |
| 18b | OH | OH | $NH_2$ |
| 22a | $PhCH_2O$ | $NH_2$ | OH |
| 8r | $(CH_3)_2CHOCH_2CH_2O$ | OH | OH |
| 8s | $CH_2=C(CH_3)CH_2CH_2O$ | OH | OH |
| 8x | $CH_3OCH_2CH(CH_3)O$ | OH | OH |
| 12h | $(CH_3)_2CHO(CH_2)_3NH-$ | OH | OH |
| 12i | $[(CH_2)_3N]-$ | OH | OH |
| 12j | $CH_3OCH_2CH_2NH-$ | OH | OH |
| 12k | $(CH_3)_2NCH_2CH_2NH-$ | OH | OH |
| 8y | $(CH_3)_2NCH_2CH_2O$ | OH | OH |
| 8z | $3-(CF_3)C_6H_4CH_2O$ | OH | OH |
| 8c' | 3-pyrrolidinyl-O | OH | OH |
| 12l | 2-pyridinyl-NH— | OH | OH |
| 12m | 3-pyridinyl-NH— | OH | OH |
| 12n | 4-pyrimidinyl-NH— | OH | OH |
| 12o | 5-quinolinyl-NH— | OH | OH |
| 8d' | $C_6H_5CH_2S-$ | OH | OH |
| 8e' | $4-(Cl)C_6H_4S-$ | OH | OH |
| 8f' | $(CH_3)_2CHCH_2CH_2S-$ | OH | OH |
| 8h' | $(CH_3)_3CCO_2CH_2O$ | OH | OH |
| 8i' | $(CH_3)_3C-O(CO)CH_2O$ | OH | OH |
| 8j' | $HO_2CCH_2O$ | OH | OH |
| 9b | $(CH_3)_3CCO_2CH_2O$ | $(CH_3)_3CCO_2CH_2O$ | $(CH_3)_3CCO_2CH_2O$ |
| 9c | $(CH_3)_2CHCH_2CH_2O$ | $(CH_3)_3CCO_2CH_2O$ | $(CH_3)_3CCO_2CH_2O$ |
| 9f | $(CH_3)_3CO(CO)CH_2O$ | $C_6H_5CH_2O$ | $C_6H_5CH_2O$ |
| 9g | $HO_2CCH_2O$ | $C_6H_5CH_2O$ | $C_6H_5CH_2O$ |
| 19c | $C_6H_5CH_2O$ | OH | $(CH_3)_3CCO_2CH_2O$ |
| 18c | OH | OH | $(CH_3)_3CCO_2CH_2O$ |
| 14b | $C_6H_5CH_2O$ | $(CH_3)_3CCO_2CH_2O$ | OH |
| 16c | OH | $(CH_3)_3CCO_2CH_2O$ | OH |
| 10e | OH | $(CH_3)_3CCO_2CH_2O$ | $(CH_3)_3CCO_2CH_2O$ |
| 19d | $(CH_3)_3CCO_2CH_2O$ | OH | $(CH_3)_3CCO_2CH_2O$ |
| 19e | $(CH_3)_2CHCH_2CH_2O$ | OH | $(CH_3)_3CCO_2CH_2O$ |
| 14c | $(CH_3)_3CCO_2CH_2O$ | $(CH_3)_3CCO_2CH_2O$ | OH |
| 8k' | $CH_3(CO)NHCH_2CH_2O$ | OH | OH |
| 8l' | 1-piperidinyl-$(CO)CH_2O$ | OH | OH |
| 12p | 1-pyrrolidinyl | OH | OH |
| 8m' | 1-morpholinyl-$(CO)CH_2O$ | OH | OH |
| 8n' | $H_2N(CO)CH_2O$ | OH | OH |
| 8o' | 1-pyrrolidinyl$(CO)CH_2O$ | OH | OH |
| 12q | 1-piperidinyl | OH | OH |
| 14d | $(CH_3)_2CHCH_2CH_2O$ | $(CH_3)_3CO(CO)CH_2O$ | OH |
| 14e | $(CH_3)_2CHCH_2CH_2O$ | $HO_2CCH_2O$ | OH |
| 14i | $(CH_3)_2CHCH_2CH_2O$ | $4-(Br)-C_6H_4(CO)CH_2O$ | OH |
| 14j | $(CH_3)_2CHCH_2CH_2O$ | allyl-O— | OH |
| 14k | $(CH_3)_2CHCH_2CH_2O$ | $CH_3OCH_2CH_2O$ | OH |
| 14l | $(CH_3)_2CHCH_2CH_2O$ | $C_6H_5OCH_2CH_2O$ | OH |
| 14o | $(CH_3)_2CHCH_2CH_2O$ | $CH_3CO_2CH_2O$ | OH |
| 16d | OH | $CH_3OCH_2CH_2O$ | OH |

-continued

|  | Z¹ | Z² | Z³ |
|---|---|---|---|
| 16e | OH | (CH$_3$)$_2$NCH$_2$CH$_2$O | OH |
| 8ad | HO(CH$_2$)$_6$O | OH | OH |
| 8ao | N-morpholino-(CH$_2$)$_2$O | OH | OH |
| 8ba | (CH$_3$)$_2$CH(CH$_2$)$_2$O | pyrrolidinyl-C(O)CH$_2$O | OH |
| 8bb | (CH$_3$)$_2$CH(CH$_2$)$_2$O | piperidinyl-C(O)CH$_2$O | OH |
| 8bc | (CH$_3$)$_2$CH(CH$_2$)$_2$O | OH | piperidinylC(O)CH$_2$O |
| 8bd | (CH$_3$)$_2$CH(CH$_2$)$_2$O | (CH$_3$)$_2$NC(O)CH$_2$O | OH |
| 8be | (CH$_3$)$_2$CH(CH$_2$)$_2$O | OH | (CH$_3$)$_2$NC(O)—CH$_2$O |
| 8bf | (CH$_3$)$_2$CH(CH$_2$)$_2$O | morpholinyl-C(O)CH$_2$O | OH |
| 8bg | (CH$_3$)$_2$CH(CH$_2$)$_2$O | [(CH$_3$)$_2$CH]$_2$NC(O)—CH$_2$O | OH |
| 8bh | (CH$_3$)$_2$CH(CH$_2$)$_2$O | (CH$_3$)C(O)OCH$_2$O | OH |
| 8bi | (CH$_3$)$_2$CH(CH$_2$)$_2$O | OH | (CH$_3$)C(O)O—CH$_2$O |
| 8bj | (CH$_3$)$_2$CH(CH$_2$)$_2$O | p-Br—C$_6$H$_4$—C(O)CH$_2$O | p-Br—C$_6$H$_4$—C(O)CH$_2$O |
| 8ca | HO(CH$_2$)$_2$NH | OH | OH |
| 8cb | furfuryl-NH | OH | OH |
| 8cc | 4-imidazolyl-(CH$_2$)$_2$NH | OH | OH |
| 8cd | Ph—CH$_2$CH(CO$_2$H)NH | OH | OH |
| 8ce | 3-indolyl-CH$_2$CH(CO$_2$H)NH | OH | OH |
| 8cf | (CH$_3$)$_3$COC(O)CH(CH$_3$)NH | OH | OH |
| 8cg | (CH$_3$)CH(OH)CH(CO$_2$H)NH | OH | OH |
| 8ch | H$_2$N(CH$_2$)$_4$CH(CO$_2$H)NH | OH | OH |
| 8ci | 1-(2-CO$_2$benzyl)-pyrrolidinyl | OH | OH |
| 8cj | benzyl-OC(O)NHC(O)—(CH$_2$)$_2$CH(CO$_2$benzyl)NH | OH | OH |
| 8ck | H$_2$NC(O)(CH$_2$)$_2$—CH(CO$_2$benzyl)NH | OH | OH |
| 8cl | HO$_2$C—CH(CH$_3$)NH | OH | OH |
| 8g' | [5,6,7,8-tetrahydronaphthalenyl-O-CH$_3$ structure] | OH | OH and |
| 8p' | [2,5-dimethoxyphenyl-CH$_2$-C(O)-O structure] | OH | OH. |